US011008312B2

(12) United States Patent
Bronner et al.

(10) Patent No.: US 11,008,312 B2
(45) **Date of Patent: *May 18, 2021**

(54) PYRIDAZINE DERIVATIVES AS RORC MODULATORS

(71) Applicant: Genentech, Inc., South San Francisco, CA (US)

(72) Inventors: Sarah M. Bronner, South San Francisco, CA (US); James J. Crawford, South San Francisco, CA (US); Andrew Cridland, Essex (GB); Patrick Cyr, Saint Constant (CA); Benjamin Fauber, Austin, TX (US); Emanuela Gancia, Essex (GB); Alberto Gobbi, South San Francisco, CA (US); Christopher Hurley, Essex (GB); Jonathan Killen, Essex (GB); Wendy Lee, South San Francisco, CA (US); Olivier Rene, South San Francisco, CA (US); Monique Bodil Van Niel, Essex (GB); Stuart Ward, Essex (GB); Paul Winship, Essex (GB); Jason Zbieg, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/398,795

(22) Filed: Apr. 30, 2019

(65) Prior Publication Data

US 2019/0263794 A1 Aug. 29, 2019

Related U.S. Application Data

(63) Continuation of application No. PCT/EP2017/077931, filed on Oct. 31, 2017.

(60) Provisional application No. 62/415,905, filed on Nov. 1, 2016.

(51) Int. Cl.

| | |
|---|---|
| *C07D 413/14* | (2006.01) |
| *C07D 403/14* | (2006.01) |
| *C07D 405/14* | (2006.01) |
| *C07D 409/14* | (2006.01) |
| *C07D 401/14* | (2006.01) |

(52) U.S. Cl.

CPC ......... *C07D 413/14* (2013.01); *C07D 401/14* (2013.01); *C07D 403/14* (2013.01); *C07D 405/14* (2013.01); *C07D 409/14* (2013.01)

(58) Field of Classification Search

CPC .. C07D 413/14; C07D 409/14; C07D 401/14; C07D 403/14; C07D 405/14; A61P 43/00; A61P 37/00; A61P 37/02; A61P 31/04; A61P 21/00; A61P 19/06; A61P 19/02; A61P 17/06; A61P 13/12; A61P 11/06; A61P 11/00; A61P 1/12; A61P 1/00; A61K 31/502; A61K 31/505

USPC ........................................................ 544/234

See application file for complete search history.

(56) References Cited

U.S. PATENT DOCUMENTS 10,487,068 B2 * 11/2019 Fauber .................... A61P 19/02
2015/0126491 A1 5/2015 Bodil van Niel et al.
2018/0222882 A1 * 8/2018 Fauber ................ C07D 401/14

FOREIGN PATENT DOCUMENTS

WO 2016/177686 A1 11/2016

OTHER PUBLICATIONS

International Preliminary Report on Patentability (IPRP) for PCT/EP2017/077931 dated May 7, 2019.
International Search Report for PCT/EP2017/077931 dated Jan. 11, 2018.

* cited by examiner

*Primary Examiner* — Taylor V Oh
(74) *Attorney, Agent, or Firm* — Brian L. Buckwalter

(57) ABSTRACT

Compounds of formula I:

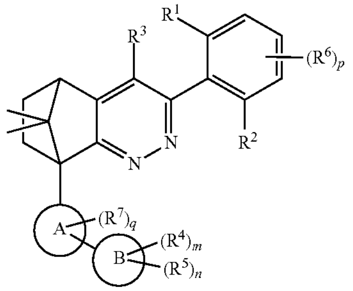

I or pharmaceutical salts thereof, wherein m, n, p, q A, B, $R_1$, $R^2$, $R^3$, $R^4$, $R^5$, $R^6$ and $R^7$ are as defined herein. Also disclosed are methods of making the compounds and using the compounds for treatment of inflammatory diseases such as arthritis.

9 Claims, No Drawings

Specification includes a Sequence Listing.

SEQUENCE LISTING

```
<160> NUMBER OF SEQ ID NOS: 1

<210> SEQ ID NO 1
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term biotin"

<400> SEQUENCE: 1

Cys Pro Ser Ser His Ser Ser Leu Thr Glu Arg Lys His Lys Ile Leu
1               5                   10                  15

His Arg Leu Leu Gln Glu Gly Ser Pro Ser
            20                  25
```

PYRIDAZINE DERIVATIVES AS RORC MODULATORS

CROSS REFERENCE TO RELATED APPLICATIONS

This application is a continuation of International Application No. PCT/EP2017/077931 having an international filing date of Oct. 31, 2017, the entire contents of which are incorporated herein by reference in its entirety, and which relates to and claims the benefit of priority under 35 U.S.C. § 119 to U.S. Provisional Application No. 62/415,905 filed Nov. 1, 2016, which is herein incorporated by reference in its entirety.

SEQUENCE LISTING

The instant application contains a Sequence Listing which has been submitted electronically in ASCII format and is hereby incorporated by reference in its entirety. Said ASCII copy, created on Apr. 22, 2019, is named P33796US1_SeqList.txt and is 749 bytes in size.

FIELD OF THE INVENTION

The invention pertains to compounds that modulate the function of retinoid-receptor related orphan receptor RORc (RORγ) and use of such compounds for treatment of autoimmune diseases.

BACKGROUND OF THE INVENTION

T helper 17 cells (Th17) are interleukin (IL)-17 secreting CD4+ T cells involved in pathogenesis of autoimmune diseases such as rheumatoid arthritis, irritable bowel disease, psoriasis, psoriatic arthritis and spondyloarthritis. The retinoic acid-related orphan receptor γ (RORγ or RORc) is recognized as a transcription factor necessary for Th17 cell differentiation. RORc is an orphan member of the nuclear hormone receptor subfamily that includes RORα (RORa) and RORβ (RORb). RORc controls gene transcription by binding to DNA as a monomer. Selective modulation of RORc has been proposed as a route to discovery and development of Th17 cell-associated autoimmune diseases.

There is accordingly a need for compounds that inhibit RORc for use in treatment of autoimmune diseases such as rheumatoid arthritis, irritable bowel disease, psoriasis, psoriatic arthritis and spondyloarthritis.

SUMMARY OF THE INVENTION

The invention provides compounds of formula I:

I

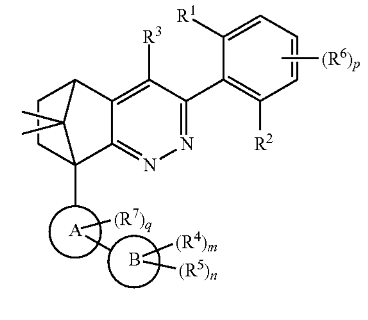

or pharmaceutical salts thereof, wherein:

A is hetereoaryl selected from:
- pyridinyl;
- pyrimidinyl;
- pyridazinyl; and
- pyrazinyl;

B is heteroaryl selected from:
- oxazolyl;
- isoxazolyl;
- thiazolyl;
- isothiazolyl;
- pyrrolyl;
- imidazolyl;
- pyridazolyl;
- triazolyl;
- oxadiazolyl;
- thiadiazolyl;
- pyridinyl;
- pyrimidinyl;
- pyrazinyl;
- pyridazinyl; or
- 2,3-dihydro-1H-imidazo[4,5-b]pyridinyl;

or B is piperidinyl;

m is: 0; 1; or 2;

n is: 0; or 1;

p is: 0; or 1;

q is: 0; or 1;

$R^1$ is:
- halo;

$R^2$ is:
- hydrogen;
- halo; or
- methoxy;

$R^3$ is:
- hydrogen;
- cyano;
- $C_{1-6}$alkyl; or
- halo;

$R^4$ is:
- $C_{1-6}$alkyl which may be unsubstituted or substituted one or more times with halo;
- $C_{2-6}$alkenyl;
- cyano;
- hydroxyl-$C_{1-6}$alkyl wherein the $C_{1-6}$alkyl moiety may be unsubstituted or substituted one or more times with halo;
- $C_{1-6}$alkoxy$C_{1-6}$alkyl wherein the $C_{1-6}$alkyl moieties may be unsubstituted or substituted one or more times with halo;
- oxo;
- hydroxy;
- $C_{1-6}$alkylsulfinyl;
- halo;

$R^5$ is:
- $-(CR^{a1}R^{a2})_p-NR^bR^c$;
- $-(CR^{a1}R^{a2})_p-SO_2-R^d$;
- $-(CR^{a1}R^{a2})_p-C(O)-R^e$;
- $-(CR^{a1}R^{a2})_p-NR^b-SO_2-R^d$;
- $-(CR^{a1}R^{a2})_p-NR^b-C(O)-R^e$;
- $-(CR^{a1}R^{a2})_p-NR^b-(CHR^c)_q-SO_2-R^d$;
- $-(CR^{a1}R^{a2})_p-NR^b-(CHR^c)_q-C(O)-R^e$;
- $-(CR^{a1}R^{a2})_p-CN$;
- $-C_{2-6}$alkenyl-CN;
- $-(CR^{a1}R^{a2})_p-Z$;
- $-(CR^{a1}R^{a2})_p-SO_2-Z$;
- $C_{1-6}$alkylsulfonimidamido; or
- $C_{1-6}$alkylsulfonimidoyl$C_{1-6}$alkyl;

$R^6$ is:

$C_{1-6}$alkyl;

halo; or hydroxyl;

$R^7$ is:

$C_{1-6}$alkyl;

$C_{1-6}$alkoxy;

halo; or hydroxyl;

Z is:

$C_{3-6}$cycloalkyl which may be unsubstituted or substituted once or twice with $R^f$;

a four or five membered heterocyclyl selected from azetidinyl, oxetanyl, thietanyl or tetrahydrothiophenyl, each of which may be unsubstituted or substituted once or twice with $R^f$;

$C_{1-6}$alkyl-heterocyclyl wherein the heterocyclyl is a four or five membered heterocyclyl selected from azetidinyl, oxetanyl, thietanyl or tetrahydrothiophenyl, each of which may be unsubstituted or substituted once or twice with $R^f$; or $C_{1-6}$alkylcarbonylamino$C_{1-6}$alkyl;

p is: 0; 1; 2; or 3 q is: 1; or 2;

$R^{a1}$ is:

hydrogen;

$C_{1-6}$alkyl which may be unsubstituted or substituted one or more times with halo;

$R^{a2}$ is:

hydrogen;

$C_{1-6}$alkyl which may be unsubstituted or substituted one or more times with halo; or hydroxyl;

or $R^{a1}$ and $R^{a2}$ may together form a $=CH_2$ group;

$R^b$ is:

hydrogen;

$C_{1-6}$alkyl which may be unsubstituted or substituted one or more times with halo; or hydroxyl-$C_{1-6}$alkyl wherein the $C_{1-6}$alkyl moiety may be unsubstituted or substituted one or more times with halo;

$R^c$ is:

hydrogen; or $C_{1-6}$alkyl which may be unsubstituted or substituted one or more times with halo;

$R^d$ is:

$C_{1-6}$alky which may be unsubstituted or substituted one or more times with halo;

$C_{3-6}$cycloalkyl;

$C_{3-6}$cycloalkyl-$C_{1-6}$alkyl;

hydroxy$C_{1-6}$alkyl; or $NR^bR^c$;

$R^e$ is:

$C_{1-6}$alkyl which may be unsubstituted or substituted one or more times with halo;

$C_{1-6}$alkoxy;

hydroxyl-$C_{1-6}$alkyl or hydroxyl; or $NR^bR^c$; and $R^f$ is: $C_{1-6}$alkyl which may be unsubstituted or substituted one or more times with halo; halo;

oxo;

cyano$C_{1-6}$alkyl;

hydroxy;

$-CH_2COOH$;

hydroxy$C_{1-6}$alkyl; or $C_{1-6}$alkylsulfonyl $C_{1-6}$alkyl;

and wherein the compound is selected from:

3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]oxetan-3-ol;

[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanamine;

N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide;

2,2,2-trifluoro-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]ethanamine;

[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methylurea;

(2S)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,2-diol;

(S)-cyclopropyl-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;

(R)-cyclopropyl-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;

(1R)-2,2-difluoro-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol;

(1S)-2,2-difluoro-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol (1S)-2-methyl-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-1-ol;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1R)-1-methylsulfonylethyl]oxazole;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1S)-1-methylsulfonylethyl]oxazole;

4-(isopropylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2S)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide;

(2R)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide;

N-(2-hydroxyethyl)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanenitrile;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(1S,8R)-5-(2,6-difluorophenyl)-11,11-dimethyl-1-[6-[1-(2-methylsulfonylethyl)pyrazol-4-yl]pyrazin-2-yl]-3,4-diazatricyclo[6.2.1.02,7]undeca-2(7),3,5-triene;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

N-[(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]methanesulfonamide;

[5-methyl-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;

5-methyl-4-(methylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

ethyl N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]carbamate;

[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanesulfonamide;

2-methyl-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]-N-[(2S)-2-hydroxypropyl]acetamide;

2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]-N-[(2R)-2-hydroxypropyl]acetamide;

4-(1-methyl-1-methylsulfonyl-ethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2R)-1,1-difluoro-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(2S)-1,1-difluoro-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(2R)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol;

2-hydroxy-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]acetamide;

(1S)-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,3-diol;

(1R)-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,3-diol;

4-(1-ethylsulfonyl-1-methyl-ethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

4-(1-cyclopropylsulfonyl-1-methyl-ethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

N-[(1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]methanesulfonamide;

(2S)-2-hydroxy-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]propanamide;

N-methyl-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide;

(E)-3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]prop-2-enenitrile;

3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

2,2,2-trifluoro-N-[(1S)-1-[2-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethyl]ethanamine;

(1S)-1-[2-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethanamine;

(2R)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

(2S)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol;

(1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol;

(1R)-1-[2-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethanamine;

2,2,2-trifluoro-N-[(1R)-1-[2-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethyl]ethanamine;

2-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]amino]ethanol;

(1S,8R)-5-(2,6-difluorophenyl)-1-[6-[1-(2-ethylsulfonylethyl)pyrazol-4-yl]pyrazin-2-yl]-11,11-dimethyl-3,4-diazatricyclo[6.2.1.02,7]undeca-2(7),3,5-triene;

N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

ethyl N-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]carbamate;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(1S,8R)-5-(2,6-difluorophenyl)-11,11-dimethyl-1-[6-[1-(2-methylsulfonylethyl)pyrazol-3-yl]pyrazin-2-yl]-3,4-diazatricyclo[6.2.1.02,7]undeca-2(7),3,5-triene;

(1S,8R)-5-(2,6-difluorophenyl)-1-[6-[1-(2-ethylsulfonylethyl)pyrazol-3-yl]pyrazin-2-yl]-11,11-dimethyl-3,4-diazatricyclo[6.2.1.02,7]undeca-2(7),3,5-triene;

2-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methylamino]acetamide;

(1R)-2,2,2-trifluoro-1-[5-methyl-2-[6-[(1R,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethanol;

(1S)-2,2,2-trifluoro-1-[5-methyl-2-[6-[(1R,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethanol;

(2R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(2S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(1S,8R)-5-(2,6-difluorophenyl)-11,11-dimethyl-1-[2-[6-(methylsulfonylmethyl)-3-pyridyl]pyrimidin-4-yl]-3,4-diazatricyclo[6.2.1.02,7]undeca-2(7),3,5-triene;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(1S,8R)-5-(2,6-difluorophenyl)-11,11-dimethyl-1-[6-[1-(2-methylsulfonylethyl)pyrazol-4-yl]-2-pyridyl]-3,4-diazatricyclo[6.2.1.02,7]undeca-2(7),3,5-triene;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1R)-1-ethylsulfonylethyl]oxazole;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1S)-1-ethylsulfonylethyl]oxazole;

4-[(1R)-1-cyclopropylsulfonylethyl]-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

4-[(1S)-1-cyclopropylsulfonylethyl]-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2R)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

(2S)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanenitrile;

(1S,8R)-5-(2,6-difluorophenyl)-11,11-dimethyl-1-[6-[1-(2-methylsulfonylethyl)pyrazol-3-yl]-2-pyridyl]-3,4-diazatricyclo[6.2.1.02,7]undeca-2(7),3,5-triene;

(2R)-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(2S)-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

2-methyl-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanenitrile;

2-[3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]oxetan-3-yl]acetonitrile N-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide;

(1S,8R)-1-[2-[6-[(amino-methyl-oxo-lambda6-sulfanylidene)amino]-3-pyridyl]pyrimidin-4-yl]-5-(2,6-difluorophenyl)-11,11-dimethyl-3,4-diazatricyclo[6.2.1.02,7]undeca-2(7),3,5-triene;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]butan-2-ol;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]butan-2-ol;

2-methyl-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethanesulfonamide;

N-[2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethyl]methanesulfonamide 3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanesulfonamide;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethanol;

N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]methanesulfonamide;

5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyridine-2-sulfonamide;

2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-pyridyl]propan-2-ol;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanol;

N-[(1S)-1-methyl-2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethyl]methanesulfonamide;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

imino-methyl-oxo-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]-lambda6-sulfane;

imino-methyl-oxo-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]-lambda6-sulfane;

(1S,8R)-5-(2,6-difluorophenyl)-1-[6-[1-(2-methoxyethyl)pyrazol-4-yl]pyrazin-2-yl]-11,11-dimethyl-3,4-diazatricyclo[6.2.1.02,7]undeca-2(7),3,5-triene;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridine-4-sulfonamide;

5-chloro-4-(methylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

4-(2-methylsulfonylethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2S)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

[5-(hydroxymethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;

(2S)-2-methyl-3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

(2R)-2-methyl-3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

N-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

(2R)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

N-[2-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethyl]methanesulfonamide;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]ethanol;

(2R)-1-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(2S)-1-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

2-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanol;

(2S)-1,1,1-trifluoro-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;

(2S)-1,1,1-trifluoro-3-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

N-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-pyridyl]methanesulfonamide;

(2R)-1,1,1-trifluoro-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;

5-chloro-4-(2-methylsulfonylethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

N-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]methanesulfonamide;

(2R)-1,1,1-trifluoro-3-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

N-[[5-methyl-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propan-2-ol;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propan-2-ol;

N-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]methanesulfonamide;

N-[6-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

N-[6-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-3-pyridyl]methanesulfonamide;

(2R)-1-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(2S)-1-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]cyclobutanol;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,3-diol;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]cyclobutanol;

3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]acetonitrile;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanamide;

N-(2-methylsulfonylethyl)-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridin-2-amine;

(2S)-2-hydroxy-N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]propanamide;

N-[[5-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methyl]methanesulfonamide;

1-[5-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]azetidin-3-ol;

N-[6-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridazin-3-yl]methanesulfonamide;
N-[6-methyl-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide;
N-[6-methyl-4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;
N-[3-methyl-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide;
N-[3-methyl-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;
N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;
(2S)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;
(2R)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;
2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]acetamide;
N-(2-hydroxyethyl)-2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]acetamide;
(1S,8R)-5-(2,6-difluorophenyl)-11,11-dimethyl-1-[6-(3-methyl-1H-pyrazol-4-yl)-2-pyridyl]-3,4-diazatricyclo[6.2.1.02,7]undeca-2(7),3,5-triene;
(1S,8R)-5-(2,6-difluorophenyl)-11,11-dimethyl-1-[6-[1-(methylsulfonylmethyl)pyrazol-4-yl]pyrazin-2-yl]-3,4-diazatricyclo[6.2.1.02,7]undeca-2(7),3,5-triene;
(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propane-1,2-diol;
(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-2-yl]propane-1,2-diol;
(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-2-yl]propane-1,2-diol;
N-(2-hydroxyethyl)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanamide;
2-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]acetamide;
N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-6-methyl-2-pyridyl]methanesulfonamide;
2-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]acetamide;
[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1H-pyrazol-3-yl]methanol;
N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-3-yl]methyl]methanesulfonamide;
(2S)-3-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;
(2R)-3-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;
(1S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethane-1,2-diol;
N-(2-methylsulfonylethyl)-5-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]pyrimidin-2-amine;
2-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]acetamide;
(1S)-1-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]ethane-1,2-diol;
(1R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethane-1,2-diol;
(1R)-1-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]ethane-1,2-diol;
N-[4-methyl-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;
(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-2-yl]propane-1,2-diol;
(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-2-yl]propane-1,2-diol;
(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-1-yl]propane-1,2-diol;
(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-1-yl]propane-1,2-diol;
(2S)-3-[5-methyl-4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;
(2S)-3-[3-methyl-4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;
N-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methanesulfonamide;
3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanamide;
(1S,8R)-5-(2,6-difluorophenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene;
2-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]acetamide;
2-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]acetamide;
(1S,8R)-5-(2,6-difluorophenyl)-11,11-dimethyl-1-[2-[1-(methylsulfonylmethyl)pyrazol-4-yl]pyrimidin-4-yl]-3,4-diazatricyclo[6.2.1.02,7]undeca-2(7),3,5-triene;
(2S)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol;

(2R)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol;

3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propanamide;

(2S)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-2-yl]propane-1,2-diol;

(2R)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-2-yl]propane-1,2-diol;

3-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]propanamide;

(1S,8R)-5-(2,6-difluorophenyl)-11,11-dimethyl-1-[6-[3-(2-methylsulfonylethyl)-1,2,4-triazol-1-yl]pyrazin-2-yl]-3,4-diazatricyclo[6.2.1.02,7]undeca-2(7),3,5-triene;

2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol;

N-[[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]methyl]methanesulfonamide;

2-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]propane-1,3-diol;

N-[[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-3-yl]methyl]methanesulfonamide;

N-(2-methylsulfonylethyl)-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-amine;

N-(2-methylsulfonylethyl)-5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-amine;

(2S)-1-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]propan-2-ol;

(2S)-1-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propan-2-ol;

(2S)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

(2R)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

(1S,8R)-5-(2,6-difluorophenyl)-11,11-dimethyl-1-[6-[1-(methylsulfonylmethyl)pyrazol-4-yl]-2-pyridyl]-3,4-diazatricyclo[6.2.1.02,7]undeca-2(7),3,5-triene;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazin-2-yl]methanesulfonamide;

N-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]ethanesulfonamide;

(2R)-3-[[5-[4-[(1S,8R)-5-(2,6-difluorophenyl)-11,11-dimethyl-3,4-diazatricyclo[6.2.1.02,7]undeca-2(7),3,5-trien-1-yl]-2-yl]pyrimidin-2-yl]amino]propane-1,2-diol;

(2S)-3-[[5-[4-[(1S,8R)-5-(2,6-difluorophenyl)-11,11-dimethyl-3,4-diazatricyclo[6.2.1.02,7]undeca-2(7),3,5-trien-1-yl]-2-yl]pyrimidin-2-yl]amino]propane-1,2-diol;

2-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]acetamide;

N-[4-methyl-5-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]pyrimidin-2-yl]methanesulfonamide;

N-[4-methyl-5-[4-[(1S,8R)-5-(2,6-difluorophenyl)-11,11-dimethyl-3,4-diazatricyclo[6.2.1.02,7]undeca-2(7),3,5-trien-1-yl]-2-yl]pyrimidin-2-yl]methanesulfonamide;

3-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propane-1,2-diol;

2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethanol;

3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-3-yl]propanamide;

3-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-3-yl]propanamide;

N-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]propane-2-sulfonamide;

N-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]methanesulfonamide;

(2R)-3-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]propane-1,2-diol;

(2S)-3-[[5-[6-[(1S,8R)-5-(2,6-difluorophenyl)-11,11-dimethyl-3,4-diazatricyclo[6.2.1.02,7]undeca-2(7),3,5-trien-1-ylpyrazin-2-yl]pyrazin-2-yl]pyrimidin-2-yl]amino]propane-1,2-diol;

(2R)-1-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propan-2-ol;

N-[4-methyl-5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

2-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]acetamide;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridylpyrazol-1-yl]-2-hydroxy-propanamide;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazin-2-yl]-2-hydroxy-propanamide;

(2S)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-1-yl]propane-1,2-diol;

(2R)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-1-yl]propane-1,2-diol;

(2R)-3-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-1-yl]propane-1,2-diol;

(2S)-3-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-1-yl]propane-1,2-diol;

(2R)-1-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propan-2-ol;
(2S)-1-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propan-2-ol;
3-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propanamide;
N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]methanesulfonamide;
(1S,8R)-5-(2,6-difluorophenyl)-11,11-dimethyl-1-[2-[1-(oxetan-3-yl)pyrazol-4-yl]pyrimidin-4-yl]-3,4-diazatricyclo[6.2.1.02,7]undeca-2(7),3,5-triene;
2-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,3-diol;
(1S,8R)-5-(2,6-difluorophenyl)-11,11-dimethyl-1-[2-[3-(methylsulfonylmethyl)-1,2,4-triazol-1-yl]pyrimidin-4-yl]-3,4-diazatricyclo[6.2.1.02,7]undeca-2(7),3,5-triene;
N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]ethanesulfonamide;
N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]propane-2-sulfonamide;
6-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,3-dihydroimidazo[4,5-b]pyridin-2-one;
(1S,8R)-1-[6-[5-(cyclopropylsulfonylmethyl)-4H-1,2,4-triazol-3-yl]-2-pyridyl]-5-(2,6-difluorophenyl)-11,11-dimethyl-3,4-diazatricyclo[6.2.1.02,7]undeca-2(7),3,5-triene;
(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]imidazol-1-yl]propane-1,2-diol;
(1S,8R)-5-(2,6-difluorophenyl)-11,11-dimethyl-1-[6-[3-(2-methylsulfonylethyl)-1,2,4-triazol-1-yl]-2-pyridyl]-3,4-diazatricyclo[6.2.1.02,7]undeca-2(7),3,5-triene;
(2S)-3-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol;
(2R)-3-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol;
(2R)-1-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]propan-2-ol; 2,2,2-trifluoroacetic acid;
(2R)-1-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]propan-2-ol; 2,2,2-trifluoroacetic acid;
(2S)-3-[4-[[6-[(1S,8R)-5-(2,6-difluorophenyl)-11,11-dimethyl-3,4-diazatricyclo[6.2.1.02,7]undeca-2(7),3,5-trien-1-yl]-2-pyridyl]amino]pyrazol-1-yl]propane-1,2-diol;
(2R)-3-[4-[[6-[(1S,8R)-5-(2,6-difluorophenyl)-11,11-dimethyl-3,4-diazatricyclo[6.2.1.02,7]undeca-2(7),3,5-trien-1-yl]-2-pyridyl]amino]pyrazol-1-yl]propane-1,2-diol;
3-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]propanamide;
3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]propanamide;
3-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]propanamide;
N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]propane-2-sulfonamide;
(1S,8R)-5-(2,6-difluorophenyl)-11,11-dimethyl-1-[6-[2-(methylsulfonylmethyl)pyrimidin-5-yl]pyrazin-2-yl]-3,4-diazatricyclo[6.2.1.02,7]undeca-2(7),3,5-triene;
(1S,8R)-5-(2,6-difluorophenyl)-11,11-dimethyl-1-[2-[2-(methylsulfonylmethyl)pyrimidin-5-yl]pyrimidin-4-yl]-3,4-diazatricyclo[6.2.1.02,7]undeca-2(7),3,5-triene;
(1S,8R)-5-(2,6-difluorophenyl)-11,11-dimethyl-1-[6-[2-(methylsulfonylmethyl)pyrimidin-5-yl]-2-pyridyl]-3,4-diazatricyclo[6.2.1.02,7]undeca-2(7),3,5-triene;
3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanenitrile;
(1S,8R)-5-(2,6-difluorophenyl)-1-[6-[5-(ethylsulfonylmethyl)-4H-1,2,4-triazol-3-yl]-2-pyridyl]-11,11-dimethyl-3,4-diazatricyclo[6.2.1.02,7]undeca-2(7),3,5-triene;
(1S,8R)-5-(2,6-difluorophenyl)-1-[6-[3-(isopropylsulfonylmethyl)-1H-1,2,4-triazol-5-yl]-2-pyridyl]-11,11-dimethyl-3,4-diazatricyclo[6.2.1.02,7]undeca-2,4,6-triene;
N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethanesulfonamide;
(1S,8R)-5-(2,6-difluorophenyl)-11,11-dimethyl-1-[6-[2-(methylsulfonylmethyl)-1,2,4-triazol-3-yl]-2-pyridyl]-3,4-diazatricyclo[6.2.1.02,7]undeca-2(7),3,5-triene;
(2R)-3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-1-yl]propane-1,2-diol;
(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]imidazol-1-yl]propane-1,2-diol;
5-(2-methylsulfonylethyl)-3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-oxadiazole;
3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-5-vinyl-1,2,4-oxadiazole;
(1S,8R)-5-(2,6-difluorophenyl)-11,11-dimethyl-1-[2-[1-(2-methylsulfonylethyl)-1,2,4-triazol-3-yl]pyrimidin-4-yl]-3,4-diazatricyclo[6.2.1.02,7]undeca-2(7),3,5-triene;
(1S,8R)-5-(2,6-difluorophenyl)-11,11-dimethyl-1-[6-[1-(2-methylsulfonylethyl)-1,2,4-triazol-3-yl]-2-pyridyl]-3,4-diazatricyclo[6.2.1.02,7]undeca-2(7),3,5-triene;
(1S,8R)-5-(2,6-difluorophenyl)-11,11-dimethyl-1-[6-[2-(2-methylsulfonylethyl)-1,2,4-triazol-3-yl]-2-pyridyl]-3,4-diazatricyclo[6.2.1.02,7]undeca-2(7),3,5-triene;
[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]urea;
(2R)-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol;
(3S)-3-[1-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,2,4-triazol-3-yl]thiolane 1,1-dioxide;
(3R)-3-[1-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,2,4-triazol-3-yl]thiolane 1,1-dioxide;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]cyclopropanesulfonamide;

(1S,8R)-5-(2,6-difluorophenyl)-11,11-dimethyl-1-[6-[5-[(1R)-1-ethylsulfonylethyl]-4H-1,2,4-triazol-3-yl]-2-pyridyl]-3,4-diazatricyclo[6.2.1.02,7]undeca-2(7),3,5-triene;

(1S,8R)-5-(2,6-difluorophenyl)-11,11-dimethyl-1-[6-[5-[(1S)-1-ethylsulfonylethyl]-4H-1,2,4-triazol-3-yl]-2-pyridyl]-3,4-diazatricyclo[6.2.1.02,7]undeca-2(7),3,5-triene;

2-hydroxy-N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]acetamide;

(1S,8R)-5-(2,6-difluorophenyl)-11,11-dimethyl-1-[2-[2-(methylsulfonylmethyl)-1,2,4-triazol-3-yl]pyrimidin-4-yl]-3,4-diazatricyclo[6.2.1.02,7]undeca-2(7),3,5-triene;

(1S)-1-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]ethane-1,2-diol;

(1S)-1-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethane-1,2-diol;

(1R)-1-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethane-1,2-diol;

2-(2-methylsulfonylethyl)-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,3,4-oxadiazole;

(1R)-1-[5-[6-[(1S,8R)-5-(2,6-difluorophenyl)-11,11-dimethyl-3,4-diazatricyclo[6.2.1.02,7]undeca-2(7), 3,5-trien-1-yl]-2-pyridyl]pyrimidin-2-yl]ethane-1,2-diol;

(1S)-1-[5-[4-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethane-1,2-diol;

(1R)-1-[5-[4-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethane-1,2-diol;

(1S,8R)-5-(2,6-difluorophenyl)-11,11-dimethyl-1-[2-[3-[(2S)-2-methylsulfonylpropyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-[(2R)-2-methylsulfonylpropyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[1-(2-methylsulfonylethyl)imidazol-4-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-(2-methylsulfonylethyl)imidazol-4-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-[2-(oxetan-3-ylsulfonyl)ethyl]-1,2,4-triazol-1-yl]pyrimidin-4-yl]-3,4-diazatricyclo[6.2.1.02,7]undeca-2(7),3,5-triene;

(1S,8R)-1-[2-[3-(cyclopropylmethylsulfonylmethyl)-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene;

(1S,8R)-5-(2,6-difluorophenyl)-11,11-dimethyl-1-[2-[2-(2-methylsulfonylethyl)pyrimidin-5-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[6-[2-(2-methylsulfonylethyl)pyrimidin-5-yl]-2-pyridyl]-3,4-diazatricyclo[6.2.1.02,7]undeca-2(7),3,5-triene;

N-methyl-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanamide;

(2S)-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol;

(1S,8R)-1-[2-[3-[2-(cyclopropylmethylsulfonyl)ethyl]-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene;

3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]oxetan-3-ol;

N-[5-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

(1S,8R)-5-(2,6-difluorophenyl)-11,11-dimethyl-1-(6-methylsulfonyl-2-pyridyl)-3,4-diazatricyclo[6.2.1.02,7]undeca-2(7),3,5-triene;

(1S,8R)-5-(2,6-difluorophenyl)-11,11-dimethyl-1-(2-methylsulfonylpyrimidin-4-yl)-3,4-diazatricyclo[6.2.1.02,7]undeca-2(7),3,5-triene;

(1S,8R)-5-(2,6-difluorophenyl)-11,11-dimethyl-1-[2-[1-(methylsulfonylmethyl)imidazol-4-yl]pyrimidin-4-yl]-3,4-diazatricyclo[6.2.1.02,7]undeca-2(7),3,5-triene (1S,8R)-5-(2,6-difluorophenyl)-11,11-dimethyl-1-[6-[1-(methylsulfonylmethyl)-1,2,4-triazol-3-yl]-2-pyridyl]-3,4-diazatricyclo[6.2.1.02,7]undeca-2(7),3,5-triene;

3-[[1-[4-[(1S,8R)-5-(2,6-difluorophenyl)-11,11-dimethyl-;3,4-diazatricyclo[6.2.1.02,7]undeca-2(7),3,5-trien-1-yl]pyrimidin-2-yl]-1,2,4-triazol-3-yl]methyl]thietane 1,1-dioxide;

3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]thietane 1,1-dioxide;

(1S,8R)-5-(2,6-difluorophenyl)-1-[2-[3-(2-ethylsulfonylethyl)-1,2,4-triazol-1-yl]pyrimidin-4-yl]-11,11-dimethyl-3,4-diazatricyclo[6.2.1.02,7]undeca-2(7),3,5-triene;

(1S,8R)-5-(2,6-difluorophenyl)-1-[2-[3-(2-isopropylsulfonylethyl)-1,2,4-triazol-1-yl]pyrimidin-4-yl]-11,11-dimethyl-3,4-diazatricyclo[6.2.1.02,7]undeca-2(7),3,5-triene;

(1S,8R)-1-[2-[3-(2-cyclopropylsulfonylethyl)-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene;

(1S,8R)-5-(2,6-difluorophenyl)-11,11-dimethyl-1-[2-(3-methylsulfinyl-1,2,4-triazol-1-yl)-1-oxido-pyrimidin-1-ium-4-yl]-3,4-diazatricyclo[6.2.1.02,7]undeca-2(7),3,5-triene;

(1S,8R)-5-(2,6-difluorophenyl)-11,11-dimethyl-1-[2-(3-methylsulfinyl-1,2,4-triazol-1-yl)pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-(3-methylsulfonyl-1,2,4-triazol-1-yl)pyrimidin-4-yl]-3,4-diazatricyclo[6.2.1.02,7]undeca-2(7),3,5-triene;

(2R)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-1-yl]propane-1,2-diol;

(1S,8R)-5-(2,6-difluorophenyl)-11,11-dimethyl-1-[2-[3-[(1R)-1-methyl-2-methylsulfonyl-ethyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-[(1S)-1-methyl-2-methylsulfonyl-ethyl]-1,2,4-triazol-1-yl]pyrimidin-4-yl]-3,4-diazatricyclo[6.2.1.02,7]undeca-2(7),3,5-triene;

(1R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol;

(1S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol;

(5R,8R)-3-(2,6-difluorophenyl)-9,9-dimethyl-8-(4-(3-(2-(methylsulfonyl)ethyl)-1H-1,2,4-triazol-1-yl)pyrimidin-2-yl)-5,6,7,8-tetrahydro-5,8-methanocinnoline;

(5R,8S)-3-(2,6-difluorophenyl)-9,9-dimethyl-8-(6-(3-vinyl-1H-1,2,4-triazol-1-yl)pyridin-2-yl)-5,6,7,8-tetrahydro-5,8-methanocinnoline;

imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;

imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;

(1S,8R)-5-(2,6-difluorophenyl)-11,11-dimethyl-1-[2-[3-(2-methylsulfonylethyl)-1,2,4-triazol-1-yl]-4-pyridyl]-3,4-diazatricyclo[6.2.1.02,7]undeca-2(7),3,5-triene;

(1S,8R)-5-(2,6-difluorophenyl)-11,11-dimethyl-1-[2-[3-(3-methylsulfonylpropyl)-1,2,4-triazol-1-yl]pyrimidin-4-yl]-3,4-diazatricyclo[6.2.1.02,7]undeca-2(7),3,5-triene;

(1S,8R)-6-chloro-5-(2,6-difluorophenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene;

(5R,8S)-3-(4-chloro-2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline;

(1S,8R)-6-chloro-5-(2,6-difluorophenyl)-11,11-dimethyl-1-[6-[3-(2-methylsulfonylethyl)-1,2,4-triazol-1-yl]-2-pyridyl]-3,4-diazatricyclo[6.2.1.02,7]undeca-2(7),3,5-triene;

(1S,8R)-5-(2,6-difluorophenyl)-11,11-dimethyl-1-[2-[3-[1-(methylsulfonylmethyl)cyclopropyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-[2-(3-methyloxetan-3-yl)ethyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[4-(2-methylsulfonylethyl)piperazin-1-yl]pyrimidin-4-yl]-3,4-diazatricyclo[6.2.1.02,7]undeca-2(7),3,5-triene;

4-((5R,8S)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnolin-3-yl)-3,5-difluorophenol;

1-(2-methylsulfonylethyl)-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyridin-2-one;

(5R,8S)-3-(2,6-difluorophenyl)-9,9-dimethyl-8-(4-(5-methyl-4H-1,2,4-triazol-3-yl)-6-(methylsulfonyl)pyridin-2-yl)-5,6,7,8-tetrahydro-5,8-methanocinnoline;

(5R,8S)-8-(6-(3-(difluoromethyl)-1H-1,2,4-triazol-1-yl)pyridin-2-yl)-3-(2,6-difluorophenyl)-9,9-dimethyl-5,6,7,8-tetrahydro-5,8-methanocinnoline;

(1S,8R)-5-(2,6-difluorophenyl)-11,11-dimethyl-1-[4-methyl-6-[3-(2-methylsulfonylethyl)-1,2,4-triazol-1-yl]-2-pyridyl]-3,4-diazatricyclo[6.2.1.02,7]undeca-2(7),3,5-triene;

3-[[1-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methyl]thietane 1,1-dioxide;

3-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methyl]thietane 1,1-dioxide;

3-[4-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide; and (5R,8S)-8-(2-(3-(difluoromethyl)-1H-1,2,4-triazol-1-yl)pyrimidin-4-yl)-3-(2,6-difluorophenyl)-9,9-dimethyl-5,6,7,8-tetrahydro-5,8-methanocinnoline.

(5R,8S)-8-(2-(3-(difluoromethyl)-1H-1,2,4-triazol-1-yl)pyrimidin-4-yl)-3-(2,6-difluorophenyl)-9,9-dimethyl-5,6,7,8-tetrahydro-5,8-methanocinnoline;

(1S,8R)-5-(2,6-difluorophenyl)-1-[6-methoxy-2-[3-(2-methylsulfonylethyl)-1,2,4-triazol-1-yl]pyrimidin-4-yl]-11,11-dimethyl-3,4-diazatricyclo[6.2.1.02,7]undeca-2(7),3,5-triene;

3-[[1-[4-methyl-6-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]thietane 1,1-dioxide;

1-(4-((5R,8S)-3-(2,6-difluorophenyl)-9,9-dimethyl-6,7-dihydro-5,8-methanocinnolin-8(5H)-yl)pyrimidin-2-yl)-N-methyl-1H-1,2,4-triazole-3-sulfonamide;

N,N-dimethyl-1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazole-3-sulfonamide;

(5R,8S)-3-(4-chloro-2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline;

(1R,8R)-5-(3-chloro-2,6-difluoro-phenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene;

5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidine-2-carboxylic acid;

(1R,8R)-5-(2,6-difluorophenyl)-11,11-dimethyl-1-[5-methyl-6-[3-(2-methylsulfonylethyl)-1,2,4-triazol-1-yl]-2-pyridyl]-3,4-diazatricyclo[6.2.1.02,7]undeca-2(7),3,5-triene;

(1R,8R)-5-(2,6-difluoro-3-methyl-phenyl)-11,11-dimethyl-1-[6-[3-(2-methylsulfonylethyl)-1,2,4-triazol-1-yl]-2-pyridyl]-3,4-diazatricyclo[6.2.1.02,7]undeca-2(7),3,5-triene;

2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]acetonitrile;

2,2-dimethyl-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanenitrile;

2-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]acetamide;

imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;

imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;

(1S,8R)-5-(2,6-difluorophenyl)-1-[2-[4-(2-methoxyethyl)-3-(2-methylsulfonylethyl)pyrazol-1-yl]pyrimidin-4-yl]-11,11-dimethyl-3,4-diazatricyclo[6.2.1.02,7]undeca-2(7),3,5-triene;

(1S,8R)-5-(2,6-difluorophenyl)-1-[2-[3-(2-methoxyethyl)-4-(2-methylsulfonylethyl)pyrazol-1-yl]pyrimidin-4-yl]-11,11-dimethyl-3,4-diazatricyclo[6.2.1.02,7]undeca-2(7),3,5-triene;

(1S,8R)-5-(2,6-difluorophenyl)-11,11-dimethyl-1-[2-[3-(oxetan-3-ylsulfonylmethyl)-1,2,4-triazol-1-yl]pyrimidin-4-yl]-3,4-diazatricyclo[6.2.1.02,7]undeca-2(7),3,5-triene (1S,8R)-5-(2,6-difluorophenyl)-11,11-dimethyl-1-[2-[3-(2-methylsulfonylethyl)pyrazol-1-yl]pyrimidin-4-yl]-3,4-diazatricyclo[6.2.1.02,7]undeca-2(7),3,5-triene;

imino-methyl-oxo-[[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]methyl]-lambda6-sulfane;

imino-methyl-oxo-[[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]methyl]-lambda6-sulfane;

N-[2-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonyl]ethyl]acetamide;

(1S,8R)-5-(2,6-difluorophenyl)-11,11-dimethyl-1-[2-[5-(2-methylsulfonylethyl)-1H-1,2,4-triazol-3-yl]pyrimidin-4-yl]-3,4-diazatricyclo[6.2.1.02,7]undeca-2(7),3,5-triene;

(5R)-5-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one;

(5S)-5-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one;

(1S,8R)-1-[5-bromo-2-[3-(2-methylsulfonylethyl)-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene;

(1S,8R)-5-(2,6-difluorophenyl)-11,11-dimethyl-1-[5-methyl-2-[3-(2-methylsulfonylethyl)-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-1-[5-methoxy-2-[3-(2-methylsulfonylethyl)-1,2,4-triazol-1-yl]pyrimidin-4-yl]-11,11-dimethyl-3,4-diazatricyclo[6.2.1.02,7]undeca-2(7),3,5-triene;

4-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]butanenitrile;

3-[6-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyridazin-3-yl]oxetan-3-ol;

N-[6-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyridazin-3-yl]methanesulfonamide;

3-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]oxetan-3-ol;

3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]oxetan-3-ol;

1-(2-methylsulfonylethyl)-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]piperazin-2-one;

2-amino-5-(4-((5R,8S)-3-(2,6-difluorophenyl)-9,9-dimethyl-6,7-dihydro-5,8-methanocinnolin-8(5H)-yl)pyrimidin-2-yl)nicotinonitrile;

N-(3-cyano-5-(4-((5R,8S)-3-(2,6-difluorophenyl)-9,9-dimethyl-6,7-dihydro-5,8-methanocinnolin-8(5H)-yl)pyrimidin-2-yl)pyridin-2-yl)methanesulfonamide;

6'-amino-6-((5R,8S)-3-(2,6-difluorophenyl)-9,9-dimethyl-6,7-dihydro-5,8-methanocinnolin-8(5H)-yl)-[2,3'-bipyridine]-5'-carbonitrile;

N-(5'-cyano-6-((5R,8S)-3-(2,6-difluorophenyl)-9,9-dimethyl-6,7-dihydro-5,8-methanocinnolin-8(5H)-yl)-[2,3'-bipyridin]-6'-yl)methanesulfonamide;

1-(2-methylsulfonylethyl)-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyridin-2-one;

1-(4-((5R,8S)-3-(2,6-difluorophenyl)-9,9-dimethyl-6,7-dihydro-5,8-methanocinnolin-8(5H)-yl)pyrimidin-2-yl)-1H-1,2,4-triazole-3-sulfonamide;

1-(4-((5R,8S)-3-(2,6-difluorophenyl)-9,9-dimethyl-6,7-dihydro-5,8-methanocinnolin-8(5H)-yl)pyrimidin-2-yl)-1H-pyrazole-3-sulfonamide;

(5R,8S)-8-(2-(3-(difluoromethyl)-1H-pyrazol-1-yl)pyrimidin-4-yl)-3-(2,6-difluorophenyl)-9,9-dimethyl-5,6,7,8-tetrahydro-5,8-methanocinnoline;

(1R)-2-methyl-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-1-ol;

N-[3-(hydroxymethyl)-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

(5R,8S)-3-(2,6-difluoro-4-(5-methyl-4H-1,2,4-triazol-3-yl)phenyl)-9,9-dimethyl-8-(6-(methylsulfonyl)pyridin-2-yl)-5,6,7,8-tetrahydro-5,8-methanocinnoline;

2-[3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]but-3-enylsulfonyl]ethanol;

(5R,8S)-3-(2-fluoro-6-methoxyphenyl)-9,9-dimethyl-8-(6-(3-(2-(methylsulfonyl)ethyl)-1H-1,2,4-triazol-1-yl)pyridin-2-yl)-5,6,7,8-tetrahydro-5,8-methanocinnoline;

2-[1,1-dioxo-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]thiolan-3-yl]acetic acid;

1-methyl-5-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one;

[3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]oxetan-3-yl]methanol;

1-fluoro-N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

1,1-difluoro-N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

(1R,2S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol;

(1S,2R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol; and (5R,8S)-3-(2-fluoro-6-methoxyphenyl)-9,9-dimethyl-8-(6-(3-(2-(methylsulfonyl)ethyl)-1H-1,2,4-triazol-1-yl)pyridin-2-yl)-5,6,7,8-tetrahydro-5,8-methanocinnoline.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise. In some instances dashes ("-") may be used interchangeably within definitions (for example, "alkoxyalkyl" omits the dash found in the equivalent term "alkoxyalkyl").

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy" means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylamino" means a group of the formula —R—C(O)—NR'— wherein R is alkyl and R' is hydrogen or alkyl.

"Alkylcarbonylalkyl" means a group of the formula —R—C(O)—R' wherein R is alkylene and R' is alkyl as defined herein.

"Alkylsulfonimidamido" means a group of the formula

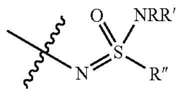

wherein R and R' are each independently hydrogen or alkyl, and R" is alkyl as defined herein.

"Alkylsulfonimidoylalkyl" means a group of the formula

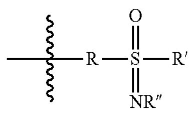

wherein R is alkylene, R' is alkyl, and R" is hydrogen or alkyl as defined herein.

"Alkoxyalkylcarbonyl" means a moiety of the formula —C(O)—R—R', wherein R is alkylene and R' is alkoxy as defined herein.

"Alkoxycarbonylalkyl" means a group of the formula —R—C(O)—R wherein R is alkylene and R' is alkoxy as defined herein.

"Alkoxycarbonylamino" means a moiety of the formula R—C(O)—NR'—, wherein R is alkoxy and R' is hydrogen or alkyl as defined herein.

"Alkoxycarbonylaminoalkyl" means a moiety of the formula R—C(O)—NR'—R"—, wherein R is alkoxy, R' is hydrogen or alkyl, and R" is alkylene as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —$SO_2$—R, wherein R is alkyl as defined herein.

"Alkylsulfonylalkyl means a moiety of the formula —R'—$SO_2$—R" where R' is alkylene and R" is alkyl as defined herein.

"Alkylsulfonylalkoxy" means a group of the formula —O—R—$SO_2$—R' wherein R is alkylene and R' is alkyl as defined herein.

"Amino means a moiety of the formula —NRR' wherein R and R' each independently is hydrogen or alkyl as defined herein. "Amino thus includes "alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"N-hydroxy-aminocarbonyl" means a group of the formula —C(O)—NR—OH wherein R is hydrogen or alkyl as defined herein.

"N-alkoxy-aminocarbonyl" means a group of the formula —C(O)—NR—R' wherein R is hydrogen or alkyl and R' is alkoxy as defined herein.

"Aminocarbonylaminoalkyl" means a group of the formula $R_2N$—C(O)—NR'—R"— wherein each R is independently hydrogen or alkyl, R' is hydrogen or alkyl, and R" is alkylene as defined herein.

"N-alkyl-aminocarbonyl means a group of the formula —C(O)—NH—R wherein R is alkyl as defined herein.

"N-hydroxy-N-alkylaminocarbonyl means a group of the formula —C(O)—NRR' wherein R is alkyl as defined herein and R' is hydroxy.

"N-alkoxy-N-alkylaminocarbonyl" means a group of the formula —C(O)—NRR' wherein R is alkyl and R' is alkoxy as defined herein.

"N,N-di-$C_{1-6}$alkyl-aminocarbonyl" means a group of the formula —C(O)—NRR' wherein R and R' are alkyl as defined herein.

"Aminosulfonyl" means a group of the formula —$SO_2$—$NH_2$.

"N-alkylaminosulfonyl" means a group of the formula —$SO_2$—NHR wherein R is alkyl as defined herein.

"N,N-dialkylaminosulfonyl" means a group of the formula —$SO_2$—NRR' wherein R and R' are alkyl as defined herein.

"Alkylsulfonylamino" means a group of the formula —NR'—$SO_2$—R wherein R id alkyl and R' is hydrogen or alkyl as defined herein.

"N-(alkylsulfonyl)-aminoalkyl" means a group of the formula —R—NH—$SO_2$—R' wherein R is alkylene and R' is alkyl as defined herein.

"N-(Alkylsulfonyl)aminocarbonyl" means a group of the formula —C(O)—NH—$SO_2$—R wherein wherein R is alkyl as defined herein.

"N-(Alkylsulfonyl)-N-alkylaminocarbonyl" means a group of the formula —C(O)—NR—$SO_2$—R' wherein R and R' are alkyl as defined herein.

"N-Alkoxyalkyl-aminocarbonyl" means a group of the formula —C(O)—NR—R'—OR" wherein R is hydrogen or alkyl, R' is alkylene, and R" is alkyl as defined herein.

"N-Hydroxyalkyl-aminocarbonyl" means a group of the formula —C(O)—NR—R'—OH" wherein R is hydrogen or alkyl and R' is alkylene as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein.

"Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, of which may be optionally substituted as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" "means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted as defined herein. Unless defined otherwise, cycloalkyl may be optionally substituted with one or more substituents, wherein each substituent is independently hydroxy, alkyl, alkoxy, halo, haloalkyl, amino, monoalkylamino, or dialkylamino. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkenyl" means a cycloalkyl as defined herein that includes at least one double bond or unsaturation. Exemplary cycloalkenyl include cyclohexenyl, cyclopentenyl, cyclobutenyl and the like.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Cycloalkylcarbonyl" means a moiety of the formula —C(O)—R, wherein R is cycloalkyl as defined herein.

"$C_{3-6}$cycloalkyl-$C_{1-6}$alkyl-carbonyl" means a moiety of the formula —C(O)—R, wherein R is cycloalkylalkyl as defined herein.

"Cyanoalkylcarbonyl" means a moiety of the formula —C(O)—R—R', wherein R is alkylene as defined herein and R' is cyano or nitrile.

"N-Cyano-aminocarbonyl" means a moiety of the formula —C(O)—NHR, wherein R is cyano or nitrile.

"N-Cyano-N-alkyl-aminocarbonyl" means a moiety of the formula —C(O)—NRR'—R, wherein R' is alkyl as defined herein and R is cyano or nitrile.

"Cycloalkylsulfonyl" means a group of the formula —$SO_2$—R wherein R is cycloalkyl as defined herein.

"Cycloalkylalkylsulfonyl" means a group of the formula —$SO_2$—R wherein R is cycloalkylalkyl as defined herein.

"Formyl" means a moiety of the formula —C(O)—H.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, each of which may be optionally substituted as defined herein.

Heteroarylalkyl" or "heteroaralkyl" means a group of the formula —R—R' wherein R is alkylene and R' is heteroaryl as defined herein.

"Heteroarylsulfonyl means a group of the formula —$SO_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, morpholinyl, thiomorpholinyl, azepinyl, pyrrolidinyl, azetidinyl, tetrahydropyranyl, tetrahydrofuranyl, oxetanyl and the like. Such heterocyclyl may be optionally substituted as defined herein.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkylcarbonyl" means a moiety of the formula —C(O)—R—R', wherein R is alkylene as defined herein and R' is hydroxy.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Oxo" means a group of the formula =O (i.e., an oxygen with a double bond). Thus, for example, a 1-oxo-ethyl group is an acetyl group.

"Alkoxy hydroxyalkyl" and "hydroxy alkoxyalkyl", which may be used interchangeably, means an alkyl as defined herein that is substituted at least once with hydroxy and at least once with alkoxy.

"Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —$SO_2$—NR'R" wherein R', R" and R'" each independently is hydrogen or alkyl.

"Optionally substituted" when used in association with an "aryl", phenyl", "heteroaryl"

"cycloalkyl" or "heterocyclyl" moiety means that such moiety may be unsubstituted (i.e., all open valencies are occupied by a hydrogen atom) or substituted with specific groups as related herein.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt. "Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions. "Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Arthritis" means a disease or condition that causes damage to joints of the body and pain associated with such joint damage. Arthritis includes rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions. "Respiratory disorder" refers to, without limitation, chronic obstructive pulmonary disease (COPD), asthma, bronchospasm, and the like. "Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature and chemical names used in this application are based on ChembioOffice™ by CambridgeSoft™. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes. One or more carbon atom(s) of a compound of the invention may be replaced by a silicon atom(s), and it is contemplated that one or more oxygen atom(s) of a compound of the invention may be replaced by a sulfur or selenium atom(s).

Compounds of the Invention

The invention provides compounds of formula I:

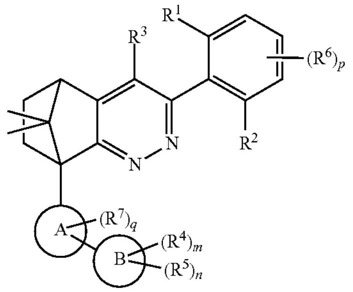

I or pharmaceutical salts thereof,
wherein:
A is hetereoaryl selected from:
pyridinyl;
pyrimidinyl;
pyridazinyl; and
pyrazinyl;
B is heteroaryl selected from:
oxazolyl;
isoxazolyl;
thiazolyl;
isothiazolyl;
pyrrolyl;
imidazolyl;
pyridazolyl;
triazolyl;
oxadiazolyl;
thiadiazolyl;
pyridinyl;
pyrimidinyl;
pyrazinyl;
pyridazinyl; or
2,3-dihydro-1H-imidazo[4,5-b]pyridinyl;
or B is piperidinyl;
m is: 0; 1; or 2;
n is: 0; or 1;
p is: 0; or 1;
q is: 0; or 1;
$R^1$ is:
halo;
$R^2$ is:
hydrogen;
halo; or
methoxy;
$R^3$ is:
hydrogen;
cyano;
$C_{1-6}$alkyl; or
halo;
$R^4$ is:
$C_{1-6}$alkyl which may be unsubstituted or substituted one or more times with halo;
$C_{2-6}$-alkenyl;
cyano;
hydroxyl-$C_{1-6}$alkyl wherein the $C_{1-6}$alkyl moiety may be unsubstituted or substituted one or more times with halo;
$C_{1-6}$alkoxy$C_{1-6}$alkyl wherein the $C_{1-6}$alkyl moieties may be unsubstituted or substituted one or more times with halo;
oxo;
hydroxy;
$C_{1-6}$alkylsulfinyl;
halo;
$R^5$ is:
$-(CR^{a1}R^{a2})_p-NR^bR^c$;
$-(CR^{a1}R^{a2})_p-SO_2-R^d$;
$-(CR^{a1}R^{a2})_p-C(O)-R^e$;
$-(CR^{a1}R^{a2})_p-NR^b-SO_2-R^d$;
$-(CR^{a1}R^{a2})_p-NR^b-C(O)-R^e$;
$-(CR^{a1}R^{a2})-NR^b-(CHR^c)_q-SO_2-R^d$;
$-(CR^{a1}R^{a2})_p-NR^b-(CHR^c)_q-C(O)-R^e$;
$-(CR^{a1}R^{a2})_p-CN$;
$-C_{2-6}$alkenyl-CN;
$-(CR^{a1}R^{a2})_p-Z$;
$-(CR^{a1}R^{a2})_p-SO_2-Z$;
$C_{1-6}$alkylsulfonimidamido; or
$C_{1-6}$alkylsulfonimidoyl$C_{1-6}$alkyl;
$R^6$ is:
$C_{1-6}$alkyl;
halo; or
hydroxyl;
$R^7$ is:
$C_{1-6}$alkyl;
$C_{1-6}$alkoxy;
halo; or
hydroxyl;
Z is:
$C_{3-6}$cycloalkyl which may be unsubstituted or substituted once or twice with $R^f$;
a four or five membered heterocyclyl selected from azetidinyl, oxetanyl, thietanyl or tetrahydrothiophenyl, each of which may be unsubstituted or substituted once or twice with $R^f$;
$C_{1-6}$alkyl-heterocyclyl wherein the heterocyclyl is a four or five membered heterocyclyl selected from azetidinyl, oxetanyl, thietanyl or tetrahydrothiophenyl, each of which may be unsubstituted or substituted once or twice with $R^f$; or
$C_{1-6}$alkylcarbonylamino$C_{1-6}$alkyl;
p is: 0; 1; 2; or 3
q is: 1; or 2;
$R^{a1}$ is:
hydrogen;
$C_{1-6}$alkyl which may be unsubstituted or substituted one or more times with halo;
$R^{a2}$ is:
hydrogen;
$C_{1-6}$alkyl which may be unsubstituted or substituted one or more times with halo; or
hydroxyl;
or $R^{a1}$ and $R^{a2}$ may together form a $=CH_2$ group;
$R^b$ is:
hydrogen;
$C_{1-6}$alkyl which may be unsubstituted or substituted one or more times with halo; or
hydroxyl-$C_{1-6}$alkyl wherein the $C_{1-6}$alkyl moiety may be unsubstituted or substituted one or more times with halo;

$R^c$ is:

hydrogen; or $C_{1-6}$alkyl which may be unsubstituted or substituted one or more times with halo;

$R^d$ is:

$C_{1-6}$alky which may be unsubstituted or substituted one or more times with halo;

$C_{3-6}$cycloalkyl;

$C_{3-6}$cycloalkyl-$C_{1-6}$alkyl;

hydroxy$C_{1-6}$alkyl; or $NR^bR^c$;

$R^e$ is:

$C_{1-6}$alkyl which may be unsubstituted or substituted one or more times with halo;

$C_{1-6}$alkoxy;

hydroxyl-$C_{1-6}$alkyl or hydroxyl; or $NR^bR^c$; and $R^f$ is: $C_{1-6}$alkyl which may be unsubstituted or substituted one or more times with halo;

halo;

oxo;

cyano$C_{1-6}$alkyl;

hydroxy;

—$CH_2COOH$;

hydroxy$C_{1-6}$alkyl; or $C_{1-6}$alkylsulfonyl$C_{1-6}$alkyl.

In certain embodiments, the compound is selected from:

3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]oxetan-3-ol;

[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanamine;

N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide;

2,2,2-trifluoro-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]ethanamine;

[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methylurea;

(2S)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,2-diol;

(S)-cyclopropyl-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;

(R)-cyclopropyl-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;

(1R)-2,2-difluoro-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol;

(1S)-2,2-difluoro-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol (1S)-2-methyl-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-1-ol;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1R)-1-methylsulfonylethyl]oxazole;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1S)-1-methylsulfonylethyl]oxazole;

4-(isopropylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2S)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide;

(2R)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide;

N-(2-hydroxyethyl)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanenitrile;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(1S,8R)-5-(2,6-difluorophenyl)-11,11-dimethyl-1-[6-[1-(2-methylsulfonylethyl)pyrazol-4-yl]pyrazin-2-yl]-3,4-diazatricyclo[6.2.1.02,7]undeca-2(7),3,5-triene;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

N-[(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]methanesulfonamide;

[5-methyl-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;

5-methyl-4-(methylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

ethyl N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]carbamate;

[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanesulfonamide;

2-methyl-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]-N-[(2S)-2-hydroxypropyl]acetamide;

2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]-N-[(2R)-2-hydroxypropyl]acetamide;

4-(1-methyl-1-methylsulfonyl-ethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2R)-1,1-difluoro-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(2S)-1,1-difluoro-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(2R)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol;

2-hydroxy-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]acetamide;

(1S)-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,3-diol;

(1R)-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,3-diol;

4-(1-ethylsulfonyl-1-methyl-ethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

4-(1-cyclopropylsulfonyl-1-methyl-ethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

N-[(1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]methanesulfonamide;

(2S)-2-hydroxy-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]propanamide;

N-methyl-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide;

(E)-3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]prop-2-enenitrile;

3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

2,2,2-trifluoro-N-[(1S)-1-[2-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethyl]ethanamine;

(1S)-1-[2-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethanamine;

(2R)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

(2S)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol;

(1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol;

(1R)-1-[2-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethanamine;

2,2,2-trifluoro-N-[(1R)-1-[2-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethyl]ethanamine;

2-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]amino]ethanol;

(1S,8R)-5-(2,6-difluorophenyl)-1-[6-[1-(2-ethylsulfonylethyl)pyrazol-4-yl]pyrazin-2-yl]-11,11-dimethyl-3,4-diazatricyclo[6.2.1.02,7]undeca-2(7),3,5-triene;

N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

ethyl N-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]carbamate;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(1S,8R)-5-(2,6-difluorophenyl)-11,11-dimethyl-1-[6-[1-(2-methylsulfonylethyl)pyrazol-3-yl]pyrazin-2-yl]-3,4-diazatricyclo[6.2.1.02,7]undeca-2(7),3,5-triene;

(1S,8R)-5-(2,6-difluorophenyl)-1-[6-[1-(2-ethylsulfonylethyl)pyrazol-3-yl]pyrazin-2-yl]-11,11-dimethyl-3,4-diazatricyclo[6.2.1.02,7]undeca-2(7),3,5-triene;

2-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methylamino]acetamide;

(1R)-2,2,2-trifluoro-1-[5-methyl-2-[6-[(1R,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethanol;

(1S)-2,2,2-trifluoro-1-[5-methyl-2-[6-[(1R,8R)-5-(2,6-difluorophenyl)-11,11-dimethyl-3,4-diazatricyclo[6.2.1.02,7]undeca-2(7), 3,5-trien-1-yl]pyrazin-2-yl]oxazol-4-yl]ethanol;

(2R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(2S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(1S,8R)-5-(2,6-difluorophenyl)-11,11-dimethyl-1-[2-[6-(methylsulfonylmethyl)-3-pyridyl]pyrimidin-4-yl]-3,4-diazatricyclo[6.2.1.02,7]undeca-2(7),3,5-triene;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(1S,8R)-5-(2,6-difluorophenyl)-11,11-dimethyl-1-[6-[1-(2-methylsulfonylethyl)pyrazol-4-yl]-2-pyridyl]-3,4-diazatricyclo[6.2.1.02,7]undeca-2(7),3,5-triene;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1R)-1-ethylsulfonylethyl]oxazole;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1S)-1-ethylsulfonylethyl]oxazole;

4-[(1R)-1-cyclopropylsulfonylethyl]-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

4-[(1S)-1-cyclopropylsulfonylethyl]-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2R)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

(2S)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanenitrile;

(1S,8R)-5-(2,6-difluorophenyl)-11,11-dimethyl-1-[6-[1-(2-methylsulfonylethyl)pyrazol-3-yl]-2-pyridyl]-3,4-diazatricyclo[6.2.1.02,7]undeca-2(7),3,5-triene;

(2R)-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(2S)-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

2-methyl-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanenitrile;

2-[3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]oxetan-3-yl]acetonitrile N-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide;

(1S,8R)-1-[2-[6-[(amino-methyl-oxo-lambda6-sulfanylidene)amino]-3-pyridyl]pyrimidin-4-yl]-5-(2,6-difluorophenyl)-11,11-dimethyl-3,4-diazatricyclo[6.2.1.02,7]undeca-2(7),3,5-triene;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]butan-2-ol;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]butan-2-ol;

2-methyl-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethanesulfonamide;

N-[2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethyl]methanesulfonamide 3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanesulfonamide;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethanol;

N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]methanesulfonamide;

5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyridine-2-sulfonamide;

2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-pyridyl]propan-2-ol;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanol;

N-[(1S)-1-methyl-2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethyl]methanesulfonamide;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

imino-methyl-oxo-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]-lambda6-sulfane;

imino-methyl-oxo-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]-lambda6-sulfane;

(1S,8R)-5-(2,6-difluorophenyl)-1-[6-[1-(2-methoxyethyl)pyrazol-4-yl]pyrazin-2-yl]-11,11-dimethyl-3,4-diazatricyclo[6.2.1.02,7]undeca-2(7),3,5-triene;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridine-4-sulfonamide;

5-chloro-4-(methylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

4-(2-methylsulfonylethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2S)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

[5-(hydroxymethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;

(2S)-2-methyl-3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

(2R)-2-methyl-3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

N-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

(2R)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

N-[2-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethyl]methanesulfonamide;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]ethanol;

(2R)-1-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(2S)-1-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

2-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanol;

(2S)-1,1,1-trifluoro-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;

(2S)-1,1,1-trifluoro-3-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

N-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-pyridyl]methanesulfonamide;

(2R)-1,1,1-trifluoro-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;

5-chloro-4-(2-methylsulfonylethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

N-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]methanesulfonamide;

(2R)-1,1,1-trifluoro-3-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

N-[[5-methyl-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propan-2-ol;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propan-2-ol;

N-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]methanesulfonamide;

N-[6-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

N-[6-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-3-pyridyl]methanesulfonamide;

(2R)-1-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(2S)-1-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]cyclobutanol;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,3-diol;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]cyclobutanol;

3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]acetonitrile;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanamide;

N-(2-methylsulfonylethyl)-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridin-2-amine;

(2S)-2-hydroxy-N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]propanamide;

N-[[5-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methyl]methanesulfonamide;

1-[5-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]azetidin-3-ol;

N-[6-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridazin-3-yl]methanesulfonamide;

N-[6-methyl-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide;

N-[6-methyl-4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

N-[3-methyl-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide;

N-[3-methyl-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

(2S)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;

(2R)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]acetamide;

N-(2-hydroxyethyl)-2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]acetamide;

(1S,8R)-5-(2,6-difluorophenyl)-11,11-dimethyl-1-[6-(3-methyl-1H-pyrazol-4-yl)-2-pyridyl]-3,4-diazatricyclo[6.2.1.02,7]undeca-2(7),3,5-triene;

(1S,8R)-5-(2,6-difluorophenyl)-11,11-dimethyl-1-[6-[1-(methylsulfonylmethyl)pyrazol-4-yl]pyrazin-2-yl]-3,4-diazatricyclo[6.2.1.02,7]undeca-2(7),3,5-triene;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propane-1,2-diol;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-2-yl]propane-1,2-diol;
(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-2-yl]propane-1,2-diol;
N-(2-hydroxyethyl)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanamide;
2-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]acetamide;
N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-6-methyl-2-pyridyl]methanesulfonamide;
2-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]acetamide;
[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1H-pyrazol-3-yl]methanol;
N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-3-yl]methyl]methanesulfonamide;
(2S)-3-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;
(2R)-3-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;
(1S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethane-1,2-diol;
N-(2-methylsulfonylethyl)-5-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]pyrimidin-2-amine;
2-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]acetamide;
(1S)-1-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]ethane-1,2-diol;
(1R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethane-1,2-diol;
(1R)-1-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]ethane-1,2-diol;
N-[4-methyl-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;
(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-2-yl]propane-1,2-diol;
(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-2-yl]propane-1,2-diol;
(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-1-yl]propane-1,2-diol;
(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-1-yl]propane-1,2-diol;
(2S)-3-[5-methyl-4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;
(2S)-3-[3-methyl-4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;
N-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methanesulfonamide;
3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanamide;
(1S,8R)-5-(2,6-difluorophenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene;
2-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]acetamide;
2-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]acetamide;
(1S,8R)-5-(2,6-difluorophenyl)-11,11-dimethyl-1-[2-[1-(methylsulfonylmethyl)pyrazol-4-yl]pyrimidin-4-yl]-3,4-diazatricyclo[6.2.1.02,7]undeca-2(7),3,5-triene;
(2S)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol;
(2R)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol;
3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propanamide;
(2S)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-2-yl]propane-1,2-diol;
(2R)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-2-yl]propane-1,2-diol;
3-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]propanamide;
(1S,8R)-5-(2,6-difluorophenyl)-11,11-dimethyl-1-[6-[3-(2-methylsulfonylethyl)-1,2,4-triazol-1-yl]pyrazin-2-yl]-3,4-diazatricyclo[6.2.1.02,7]undeca-2(7),3,5-triene;
2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol;
N-[[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]methyl]methanesulfonamide;
2-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]propane-1,3-diol;
N-[[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-3-yl]methyl]methanesulfonamide;
N-(2-methylsulfonylethyl)-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-amine;
N-(2-methylsulfonylethyl)-5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-amine;

(2S)-1-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]propan-2-ol;

(2S)-1-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propan-2-ol;

(2S)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

(2R)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

(1S,8R)-5-(2,6-difluorophenyl)-11,11-dimethyl-1-[6-[1-(methylsulfonylmethyl)pyrazol-4-yl]-2-pyridyl]-3,4-diazatricyclo[6.2.1.02,7]undeca-2(7),3,5-triene;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazin-2-yl]methanesulfonamide;

N-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]ethanesulfonamide;

(2R)-3-[[5-[4-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-pyrimidin-2-yl]amino]propane-1,2-diol;

(2S)-3-[[5-[4-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]propane-1,2-diol;

2-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]acetamide;

N-[4-methyl-5-[6-[(1S,8R)-5-(2,6-difluorophenyl)-11,11-dimethyl-3,4-diazatricyclo[6.2.1.02,7]undeca-2(7), 3,5-trien-1-yl]pyrazin-2-yl]pyrimidin-2-yl]methanesulfonamide;

N-[4-methyl-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]methanesulfonamide;

3-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propane-1,2-diol;

2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethanol;

3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-3-yl]propanamide;

3-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-3-yl]propanamide;

N-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]propane-2-sulfonamide;

N-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]methanesulfonamide;

(2R)-3-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]propane-1,2-diol;

(2S)-3-[[5-[6-[(1S,8R)-5-(2,6-difluorophenyl)-11,11-dimethyl-3,4-diazatricyclo[6.2.1.02,7]undeca-2(7),3,5-trien-1-ylpyrazin-2-yl]pyrazin-2-yl]pyrimidin-2-yl]amino]propane-1,2-diol;

(2R)-1-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propan-2-ol;

N-[4-methyl-5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

2-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]acetamide;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridylpyrazol-1-yl]-2-hydroxy-propanamide;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]-2-hydroxy-propanamide;

(2S)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-1-yl]propane-1,2-diol;

(2R)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-1-yl]propane-1,2-diol;

(2R)-3-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-1-yl]propane-1,2-diol;

(2S)-3-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-1-yl]propane-1,2-diol;

(2R)-1-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propan-2-ol;

(2S)-1-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propan-2-ol;

3-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propanamide;

N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]methanesulfonamide;

(1S,8R)-5-(2,6-difluorophenyl)-11,11-dimethyl-1-[2-[1-(oxetan-3-yl)pyrazol-4-yl]pyrimidin-4-yl]-3,4-diazatricyclo[6.2.1.02,7]undeca-2(7),3,5-triene;

2-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,3-diol;

(1S,8R)-5-(2,6-difluorophenyl)-11,11-dimethyl-1-[2-[3-(methylsulfonylmethyl)-1,2,4-triazol-1-yl]pyrimidin-4-yl]-3,4-diazatricyclo[6.2.1.02,7]undeca-2(7),3,5-triene;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]ethanesulfonamide;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]propane-2-sulfonamide;

6-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,3-dihydroimidazo[4,5-b]pyridin-2-one;

(1S,8R)-1-[6-[5-(cyclopropylsulfonylmethyl)-4H-1,2,4-triazol-3-yl]-2-pyridyl]-5-(2,6-difluorophenyl)-11,11-dimethyl-3,4-diazatricyclo[6.2.1.02,7]undeca-2(7),3,5-triene;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]imidazol-1-yl]propane-1,2-diol;

(1S,8R)-5-(2,6-difluorophenyl)-11,11-dimethyl-1-[6-[3-(2-methylsulfonylethyl)-1,2,4-triazol-1-yl]-2-pyridyl]-3,4-diazatricyclo[6.2.1.02,7]undeca-2(7),3,5-triene;
(2S)-3-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol;
(2R)-3-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol;
(2R)-1-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]propan-2-ol; 2,2,2-trifluoroacetic acid;
(2R)-1-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]propan-2-ol; 2,2,2-trifluoroacetic acid;
(2S)-3-[4-[[6-[(1S,8R)-5-(2,6-difluorophenyl)-11,11-dimethyl-3,4-diazatricyclo[6.2.1.02,7]undeca-2(7),3,5-trien-1-yl]-2-pyridyl]amino]pyrazol-1-yl]propane-1,2-diol;
(2R)-3-[4-[[6-[(1S,8R)-5-(2,6-difluorophenyl)-11,11-dimethyl-3,4-diazatricyclo[6.2.1.02,7]undeca-2(7),3,5-trien-1-yl]-2-pyridyl]amino]pyrazol-1-yl]propane-1,2-diol;
3-[5-[6-[(1S,8R)-5-(2,6-difluorophenyl)-11,11-dimethyl-3,4-diazatricyclo[6.2.1.02,7]undeca-2(7),3,5-trien-1-yl] pyrazin-2-yl]pyrimidin-2-yl]propanamide;
3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]propanamide;
3-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]propanamide;
N-[5-[6-[(1S,8R)-5-(2,6-difluorophenyl)-11,11-dimethyl-3,4-diazatricyclo[6.2.1.02,7]undeca-2(7),3,5-trien-1-yl] pyrazin-2-yl]pyrimidin-2-yl]propane-2-sulfonamide;
(1S,8R)-5-(2,6-difluorophenyl)-11,11-dimethyl-1-[6-[2-(methylsulfonylmethyl)pyrimidin-5-yl]pyrazin-2-yl]-3,4-diazatricyclo[6.2.1.02,7]undeca-2(7),3,5-triene;
(1S,8R)-5-(2,6-difluorophenyl)-11,11-dimethyl-1-[2-[2-(methylsulfonylmethyl)pyrimidin-5-yl]pyrimidin-4-yl]-3,4-diazatricyclo[6.2.1.02,7]undeca-2(7),3,5-triene;
(1S,8R)-5-(2,6-difluorophenyl)-11,11-dimethyl-1-[6-[2-(methylsulfonylmethyl)pyrimidin-5-yl]-2-pyridyl]-3,4-diazatricyclo[6.2.1.02,7]undeca-2(7),3,5-triene;
3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanenitrile;
(1S,8R)-5-(2,6-difluorophenyl)-1-[6-[5-(ethylsulfonylmethyl)-4H-1,2,4-triazol-3-yl]-2-pyridyl]-11,11-dimethyl-3,4-diazatricyclo[6.2.1.02,7]undeca-2(7),3,5-triene;
(1S,8R)-5-(2,6-difluorophenyl)-1-[6-[3-(isopropylsulfonylmethyl)-1H-1,2,4-triazol-5-yl]-2-pyridyl]-11,11-dimethyl-3,4-diazatricyclo[6.2.1.02,7]undeca-2,4,6-triene;
N-[5-[6-[(1S,8R)-5-(2,6-difluorophenyl)-11,11-dimethyl-3,4-diazatricyclo[6.2.1.02,7]undeca-2(7),3,5-trien-1-yl] pyrazin-2-yl]pyrimidin-2-yl]ethanesulfonamide;
(1S,8R)-5-(2,6-difluorophenyl)-11,11-dimethyl-1-[6-[2-(methylsulfonylmethyl)-1,2,4-triazol-3-yl]-2-pyridyl]-3,4-diazatricyclo[6.2.1.02,7]undeca-2(7),3,5-triene;
(2R)-3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-1-yl]propane-1,2-diol;
(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]imidazol-1-yl]propane-1,2-diol;
5-(2-methylsulfonylethyl)-3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-oxadiazole;
3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-5-vinyl-1,2,4-oxadiazole;
(1S,8R)-5-(2,6-difluorophenyl)-11,11-dimethyl-1-[2-[1-(2-methylsulfonylethyl)-1,2,4-triazol-3-yl]pyrimidin-4-yl]-3,4-diazatricyclo[6.2.1.02,7]undeca-2(7),3,5-triene;
(1S,8R)-5-(2,6-difluorophenyl)-11,11-dimethyl-1-[6-[1-(2-methylsulfonylethyl)-1,2,4-triazol-3-yl]-2-pyridyl]-3,4-diazatricyclo[6.2.1.02,7]undeca-2(7),3,5-triene;
(1S,8R)-5-(2,6-difluorophenyl)-11,11-dimethyl-1-[6-[2-(2-methylsulfonylethyl)-1,2,4-triazol-3-yl]-2-pyridyl]-3,4-diazatricyclo[6.2.1.02,7]undeca-2(7),3,5-triene;
[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]urea;
(2R)-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol;
(3S)-3-[1-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,2,4-triazol-3-yl]thiolane 1,1-dioxide;
(3R)-3-[1-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,2,4-triazol-3-yl]thiolane 1,1-dioxide;
N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]cyclopropanesulfonamide;
(1S,8R)-5-(2,6-difluorophenyl)-11,11-dimethyl-1-[6-[5-[(1R)-1-ethylsulfonylethyl]-4H-1,2,4-triazol-3-yl]-2-pyridyl]-3,4-diazatricyclo[6.2.1.02,7]undeca-2(7),3,5-triene;
(1S,8R)-5-(2,6-difluorophenyl)-11,11-dimethyl-1-[6-[5-[(1S)-1-ethylsulfonylethyl]-4H-1,2,4-triazol-3-yl]-2-pyridyl]-3,4-diazatricyclo[6.2.1.02,7]undeca-2(7),3,5-triene;
2-hydroxy-N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]acetamide;
(1S,8R)-5-(2,6-difluorophenyl)-11,11-dimethyl-1-[2-[2-(methylsulfonylmethyl)-1,2,4-triazol-3-yl]pyrimidin-4-yl]-3,4-diazatricyclo[6.2.1.02,7]undeca-2(7),3,5-triene;
(1S)-1-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]ethane-1,2-diol;
(1S)-1-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethane-1,2-diol;
(1R)-1-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethane-1,2-diol;
2-(2-methylsulfonylethyl)-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,3,4-oxadiazole;
(1R)-1-[5-[6-[(1S,8R)-5-(2,6-difluorophenyl)-11,11-dimethyl-3,4-diazatricyclo[6.2.1.02,7]undeca-2(7), 3,5-trien-1-yl]-2-pyridyl]pyrimidin-2-yl]ethane-1,2-diol;
(1S)-1-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]ethane-1,2-diol;

(1R)-1-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]ethane-1,2-diol;
(1S,8R)-5-(2,6-difluorophenyl)-11,11-dimethyl-1-[2-[3-[(2S)-2-methylsulfonylpropyl]-1,2,4-triazol-1-yl]pyrimidin-4-yl]-3,4-diazatricyclo[6.2.1.02,7]undeca-2(7),3,5-triene;
(1S,8R)-5-(2,6-difluorophenyl)-11,11-dimethyl-1-[2-[3-[(2R)-2-methylsulfonylpropyl]-1,2,4-triazol-1-yl]pyrimidin-4-yl]-3,4-diazatricyclo[6.2.1.02,7]undeca-2(7),3,5-triene;
(1S,8R)-5-(2,6-difluorophenyl)-11,11-dimethyl-1-[2-[1-(2-methylsulfonylethyl)imidazol-4-yl]pyrimidin-4-yl]-3,4-diazatricyclo[6.2.1.02,7]undeca-2(7),3,5-triene;
(1S,8R)-5-(2,6-difluorophenyl)-11,11-dimethyl-1-[2-[3-(2-methylsulfonylethyl)imidazol-4-yl]pyrimidin-4-yl]-3,4-diazatricyclo[6.2.1.02,7]undeca-2(7),3,5-triene;
(1S,8R)-5-(2,6-difluorophenyl)-11,11-dimethyl-1-[2-[3-[2-(oxetan-3-ylsulfonyl)ethyl]-1,2,4-triazol-1-yl]pyrimidin-4-yl]-3,4-diazatricyclo[6.2.1.02,7]undeca-2(7),3,5-triene;
(1S,8R)-1-[2-[3-(cyclopropylmethylsulfonylmethyl)-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene;
(1S,8R)-5-(2,6-difluorophenyl)-11,11-dimethyl-1-[2-[2-(2-methylsulfonylethyl)pyrimidin-5-yl]pyrimidin-4-yl]-3,4-diazatricyclo[6.2.1.02,7]undeca-2(7),3,5-triene;
(1S,8R)-5-(2,6-difluorophenyl)-11,11-dimethyl-1-[6-[2-(2-methylsulfonylethyl)pyrimidin-5-yl]-2-pyridyl]-3,4-diazatricyclo[6.2.1.02,7]undeca-2(7),3,5-triene;
N-methyl-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanamide;
(2S)-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol;
(1S,8R)-1-[2-[3-[2-(cyclopropylmethylsulfonyl)ethyl]-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene;
3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]oxetan-3-ol;
N-[5-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;
(1S,8R)-5-(2,6-difluorophenyl)-11,11-dimethyl-1-(6-methylsulfonyl-2-pyridyl)-3,4-diazatricyclo[6.2.1.02,7]undeca-2(7),3,5-triene;
(1S,8R)-5-(2,6-difluorophenyl)-11,11-dimethyl-1-(2-methylsulfonylpyrimidin-4-yl)-3,4-diazatricyclo[6.2.1.02,7]undeca-2(7),3,5-triene;
(1S,8R)-5-(2,6-difluorophenyl)-11,11-dimethyl-1-[2-[1-(methylsulfonylmethyl)imidazol-4-yl]pyrimidin-4-yl]-3,4-diazatricyclo[6.2.1.02,7]undeca-2(7),3,5-triene
(1S,8R)-5-(2,6-difluorophenyl)-11,11-dimethyl-1-[6-[1-(methylsulfonylmethyl)-1,2,4-triazol-3-yl]-2-pyridyl]-3,4-diazatricyclo[6.2.1.02,7]undeca-2(7),3,5-triene;
3-[[1-[4-[(1S,8R)-5-(2,6-difluorophenyl)-11,11-dimethyl-;3,4-diazatricyclo[6.2.1.02,7]undeca-2(7),3,5-trien-1-yl]pyrimidin-2-yl]-1,2,4-triazol-3-yl]methyl]thietane 1,1-dioxide;
3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]thietane 1,1-dioxide;
(1S,8R)-5-(2,6-difluorophenyl)-1-[2-[3-(2-ethylsulfonylethyl)-1,2,4-triazol-1-yl]pyrimidin-4-yl]-11,11-dimethyl-3,4-diazatricyclo[6.2.1.02,7]undeca-2(7),3,5-triene;
(1S,8R)-5-(2,6-difluorophenyl)-1-[2-[3-(2-isopropylsulfonylethyl)-1,2,4-triazol-1-yl]pyrimidin-4-yl]-11,11-dimethyl-3,4-diazatricyclo[6.2.1.02,7]undeca-2(7),3,5-triene;
(1S,8R)-1-[2-[3-(2-cyclopropylsulfonylethyl)-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene;
(1S,8R)-5-(2,6-difluorophenyl)-11,11-dimethyl-1-[2-(3-methylsulfinyl-1,2,4-triazol-1-yl)-1-oxido-pyrimidin-1-ium-4-yl]-3,4-diazatricyclo[6.2.1.02,7]undeca-2(7),3,5-triene;
(1S,8R)-5-(2,6-difluorophenyl)-11,11-dimethyl-1-[2-(3-methylsulfinyl-1,2,4-triazol-1-yl)pyrimidin-4-yl]-3,4-diazatricyclo[6.2.1.02,7]undeca-2(7),3,5-triene;
(1S,8R)-5-(2,6-difluorophenyl)-11,11-dimethyl-1-[2-(3-methylsulfonyl-1,2,4-triazol-1-yl)pyrimidin-4-yl]-3,4-diazatricyclo[6.2.1.02,7]undeca-2(7),3,5-triene;
(2R)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-1-yl]propane-1,2-diol;
(1S,8R)-5-(2,6-difluorophenyl)-11,11-dimethyl-1-[2-[3-[(1R)-1-methyl-2-methylsulfonyl-ethyl]-1,2,4-triazol-1-yl]pyrimidin-4-yl]-3,4-diazatricyclo[6.2.1.02,7]undeca-2(7),3,5-triene;
(1S,8R)-5-(2,6-difluorophenyl)-11,11-dimethyl-1-[2-[3-[(1S)-1-methyl-2-methylsulfonyl-ethyl]-1,2,4-triazol-1-yl]pyrimidin-4-yl]-3,4-diazatricyclo[6.2.1.02,7]undeca-2(7),3,5-triene;
(1R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol;
(1S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol;
(5R,8R)-3-(2,6-difluorophenyl)-9,9-dimethyl-8-(4-(3-(2-(methylsulfonyl)ethyl)-1H-1,2,4-triazol-1-yl)pyrimidin-2-yl)-5,6,7,8-tetrahydro-5,8-methanocinnoline;
(5R,8S)-3-(2,6-difluorophenyl)-9,9-dimethyl-8-(6-(3-vinyl-1H-1,2,4-triazol-1-yl)pyridin-2-yl)-5,6,7,8-tetrahydro-5,8-methanocinnoline;
imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;
imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;
(1S,8R)-5-(2,6-difluorophenyl)-11,11-dimethyl-1-[2-[3-(2-methylsulfonylethyl)-1,2,4-triazol-1-yl]-4-pyridyl]-3,4-diazatricyclo[6.2.1.02,7]undeca-2(7),3,5-triene;
(1S,8R)-5-(2,6-difluorophenyl)-11,11-dimethyl-1-[2-[3-(3-methylsulfonylpropyl)-1,2,4-triazol-1-yl]pyrimidin-4-yl]-3,4-diazatricyclo[6.2.1.02,7]undeca-2(7),3,5-triene;
(1S,8R)-6-chloro-5-(2,6-difluorophenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene;
(5R,8S)-3-(4-chloro-2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline;
(1S,8R)-6-chloro-5-(2,6-difluorophenyl)-11,11-dimethyl-1-[6-[3-(2-methylsulfonylethyl)-1,2,4-triazol-1-yl]-2-pyridyl]-3,4-diazatricyclo[6.2.1.02,7]undeca-2(7),3,5-triene;

(1S,8R)-5-(2,6-difluorophenyl)-11,11-dimethyl-1-[2-[3-[1-(methylsulfonylmethyl)cyclopropyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-[2-(3-methyloxetan-3-yl)ethyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[4-(2-methylsulfonylethyl)piperazin-1-yl]pyrimidin-4-yl]-3,4-diazatricyclo[6.2.1.02,7]undeca-2(7),3,5-triene;

4-((5R,8S)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnolin-3-yl)-3,5-difluorophenol;

1-(2-methylsulfonylethyl)-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyridin-2-one;

(5R,8S)-3-(2,6-difluorophenyl)-9,9-dimethyl-8-(4-(5-methyl-4H-1,2,4-triazol-3-yl)-6-(methylsulfonyl)pyridin-2-yl)-5,6,7,8-tetrahydro-5,8-methanocinnoline;

(5R,8S)-8-(6-(3-(difluoromethyl)-1H-1,2,4-triazol-1-yl)pyridin-2-yl)-3-(2,6-difluorophenyl)-9,9-dimethyl-5,6,7,8-tetrahydro-5,8-methanocinnoline;

(1S,8R)-5-(2,6-difluorophenyl)-11,11-dimethyl-1-[4-methyl-6-[3-(2-methylsulfonylethyl)-1,2,4-triazol-1-yl]-2-pyridyl]-3,4-diazatricyclo[6.2.1.02,7]undeca-2(7),3,5-triene;

3-[[1-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methyl]thietane 1,1-dioxide;

3-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methyl]thietane 1,1-dioxide;

3-[4-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide; and (5R,8S)-8-(2-(3-(difluoromethyl)-1H-1,2,4-triazol-1-yl)pyrimidin-4-yl)-3-(2,6-difluorophenyl)-9,9-dimethyl-5,6,7,8-tetrahydro-5,8-methanocinnoline.

(5R,8S)-8-(2-(3-(difluoromethyl)-1H-1,2,4-triazol-1-yl)pyrimidin-4-yl)-3-(2,6-difluorophenyl)-9,9-dimethyl-5,6,7,8-tetrahydro-5,8-methanocinnoline;

(1S,8R)-5-(2,6-difluorophenyl)-1-[6-methoxy-2-[3-(2-methylsulfonylethyl)-1,2,4-triazol-1-yl]pyrimidin-4-yl]-11,11-dimethyl-3,4-diazatricyclo[6.2.1.02,7]undeca-2(7),3,5-triene;

3-[[1-[4-methyl-6-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]thietane 1,1-dioxide;

1-(4-((5R,8S)-3-(2,6-difluorophenyl)-9,9-dimethyl-6,7-dihydro-5,8-methanocinnolin-8(5H)-yl)pyrimidin-2-yl)-N-methyl-1H-1,2,4-triazole-3-sulfonamide;

N,N-dimethyl-1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazole-3-sulfonamide;

(5R,8S)-3-(4-chloro-2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline;

(1R,8R)-5-(3-chloro-2,6-difluoro-phenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene;

5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidine-2-carboxylic acid;

(1R,8R)-5-(2,6-difluorophenyl)-11,11-dimethyl-1-[5-methyl-6-[3-(2-methylsulfonylethyl)-1,2,4-triazol-1-yl]-2-pyridyl]-3,4-diazatricyclo[6.2.1.02,7]undeca-2(7),3,5-triene;

(1R,8R)-5-(2,6-difluoro-3-methyl-phenyl)-11,11-dimethyl-1-[6-[3-(2-methylsulfonylethyl)-1,2,4-triazol-1-yl]-2-pyridyl]-3,4-diazatricyclo[6.2.1.02,7]undeca-2(7),3,5-triene;

2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]acetonitrile;

2,2-dimethyl-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanenitrile;

2-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]acetamide;

imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;

imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;

(1S,8R)-5-(2,6-difluorophenyl)-1-[2-[4-(2-methoxyethyl)-3-(2-methylsulfonylethyl)pyrazol-1-yl]pyrimidin-4-yl]-11,11-dimethyl-3,4-diazatricyclo[6.2.1.02,7]undeca-2(7),3,5-triene;

(1S,8R)-5-(2,6-difluorophenyl)-1-[2-[3-(2-methoxyethyl)-4-(2-methylsulfonylethyl)pyrazol-1-yl]pyrimidin-4-yl]-11,11-dimethyl-3,4-diazatricyclo[6.2.1.02,7]undeca-2(7),3,5-triene;

(1S,8R)-5-(2,6-difluorophenyl)-11,11-dimethyl-1-[2-[3-(oxetan-3-ylsulfonylmethyl)-1,2,4-triazol-1-yl]pyrimidin-4-yl]-3,4-diazatricyclo[6.2.1.02,7]undeca-2(7),3,5-triene (1S,8R)-5-(2,6-difluorophenyl)-11,11-dimethyl-1-[2-[3-(2-methylsulfonylethyl)pyrazol-1-yl]pyrimidin-4-yl]-3,4-diazatricyclo[6.2.1.02,7]undeca-2(7),3,5-triene;

imino-methyl-oxo-[[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]methyl]-lambda6-sulfane;

imino-methyl-oxo-[[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]methyl]-lambda6-sulfane;

N-[2-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonyl]ethyl]acetamide;

(1S,8R)-5-(2,6-difluorophenyl)-11,11-dimethyl-1-[2-[5-(2-methylsulfonylethyl)-1H-1,2,4-triazol-3-yl]pyrimidin-4-yl]-3,4-diazatricyclo[6.2.1.02,7]undeca-2(7),3,5-triene;

(5R)-5-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one;

(5S)-5-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one;

(1S,8R)-1-[5-bromo-2-[3-(2-methylsulfonylethyl)-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene;

(1S,8R)-5-(2,6-difluorophenyl)-11,11-dimethyl-1-[5-methyl-2-[3-(2-methylsulfonylethyl)-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-1-[5-methoxy-2-[3-(2-methylsulfonylethyl)-1,2,4-triazol-1-yl]pyrimidin-4-yl]-11,11-dimethyl-3,4-diazatricyclo[6.2.1.02,7]undeca-2(7),3,5-triene;

4-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]butanenitrile;

3-[6-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyridazin-3-yl]oxetan-3-ol;

N-[6-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyridazin-3-yl]methanesulfonamide;

3-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]oxetan-3-ol;

3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]oxetan-3-ol;

1-(2-methylsulfonylethyl)-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]piperazin-2-one;

2-amino-5-(4-((5R,8S)-3-(2,6-difluorophenyl)-9,9-dimethyl-6,7-dihydro-5,8-methanocinnolin-8(5H)-yl)pyrimidin-2-yl)nicotinonitrile;

N-(3-cyano-5-(4-((5R,8S)-3-(2,6-difluorophenyl)-9,9-dimethyl-6,7-dihydro-5,8-methanocinnolin-8(5H)-yl)pyrimidin-2-yl)pyridin-2-yl)methanesulfonamide;

6'-amino-6-((5R,8S)-3-(2,6-difluorophenyl)-9,9-dimethyl-6,7-dihydro-5,8-methanocinnolin-8(5H)-yl)-[2,3'-bipyridine]-5'-carbonitrile;

N-(5'-cyano-6-((5R,8S)-3-(2,6-difluorophenyl)-9,9-dimethyl-6,7-dihydro-5,8-methanocinnolin-8(5H)-yl)-[2,3'-bipyridin]-6'-yl)methanesulfonamide;

1-(2-methylsulfonylethyl)-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyridin-2-one;

1-(4-((5R,8S)-3-(2,6-difluorophenyl)-9,9-dimethyl-6,7-dihydro-5,8-methanocinnolin-8(5H)-yl)pyrimidin-2-yl)-1H-1,2,4-triazole-3-sulfonamide;

1-(4-((5R,8 S)-3-(2,6-difluorophenyl)-9,9-dimethyl-6,7-dihydro-5,8-methanocinnolin-8(5H)-yl)pyrimidin2-yl)-1H-pyrazole-3-sulfonamide;

(5R,8S)-8-(2-(3-(difluoromethyl)-1H-pyrazol-1-yl)pyrimidin-4-yl)-3-(2,6-difluorophenyl)-9,9-dimethyl-5,6,7,8-tetrahydro-5,8-methanocinnoline;

(1R)-2-methyl-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-1-ol;

N-[3-(hydroxymethyl)-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

(5R,8S)-3-(2,6-difluoro-4-(5-methyl-4H-1,2,4-triazol-3-yl)phenyl)-9,9-dimethyl-8-(6-(methylsulfonyl)pyridin-2-yl)-5,6,7,8-tetrahydro-5,8-methanocinnoline;

2-[3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]but-3-enylsulfonyl]ethanol;

(5R,8S)-3-(2-fluoro-6-methoxyphenyl)-9,9-dimethyl-8-(6-(3-(2-(methylsulfonyl)ethyl)-1H-1,2,4-triazol-1-yl)pyridin-2-yl)-5,6,7,8-tetrahydro-5,8-methanocinnoline;

2-[1,1-dioxo-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]thiolan-3-yl]acetic acid;

1-methyl-5-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one;

[3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]oxetan-3-yl]methanol;

1-fluoro-N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

1,1-difluoro-N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

(1R,2S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol;

(1S,2R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol; and (5R,8S)-3-(2-fluoro-6-methoxyphenyl)-9,9-dimethyl-8-(6-(3-(2-(methylsulfonyl)ethyl)-1H-1,2,4-triazol-1-yl)pyridin-2-yl)-5,6,7,8-tetrahydro-5,8-methanocinnoline.

In certain embodiments A is: pyridinyl; pyrimdinyl; or pyrazinyl.

In certain embodiments A is pyridinyl.

In certain embodiments A is pyrimidinyl.

In certain embodiments A is pyridazinyl.

In certain embodiments A is pyrazinyl.

In certain embodiments B is: oxazolyl; isoxazolyl; pyrrolyl; imidazolyl; pyridazolyl; triazolyl; or oxadiazolyl.

In certain embodiments B is: pyridinyl; pyrimidinyl; or pyrazinyl.

In certain embodiments B is oxazolyl.

In certain embodiments B is isoxazolyl.

In certain embodiments B is thiazolyl.

In certain embodiments B is isothiazolyl.

In certain embodiments B is pyrrolyl.

In certain embodiments B is imidazolyl.

In certain embodiments B is pyridazolyl.

In certain embodiments B is triazolyl; In certain embodiments B is oxadiazolyl.

In certain embodiments B is thiadiazolyl.

In certain embodiments B is pyridinyl; In certain embodiments B is pyrimidinyl.

In certain embodiments B is pyrazinyl.

In certain embodiments B is pyridazinyl.

In certain embodiments B is 2,3-dihydro-1H-imidazo[4,5-b]pyridinyl.

In certain embodiments B is piperidinyl.

In certain embodiments m is 0.

In certain embodiments m is 1.

In certain embodiments m is 2 In certain embodiments n is 0.

In certain embodiments n is 1.

In certain embodiments p is 0.

In certain embodiments p is 1.

In certain embodiments q is 0.

In certain embodiments q is 1.

In certain embodiments $R^1$ is halo.

In certain embodiments $R^2$ is hydrogen.

In certain embodiments $R^2$ is halo.

In certain embodiments $R^3$ is hydrogen.

In certain embodiments $R^3$ is cyano.

In certain embodiments $R^2$ is $C_{1-6}$alkyl.

In certain embodiments $R^2$ is halo.

In certain embodiments $R^4$ is $C_{1-6}$alkyl which may be unsubstituted or substituted one or more times with halo.

In certain embodiments $R^4$ is $C_{2-6}$alkenyl.

In certain embodiments $R^4$ is cyano.

In certain embodiments $R^4$ is hydroxyl-$C_{1-6}$alkyl wherein the $C_{1-6}$alkyl moiety may be unsubstituted or substituted one or more times with halo.

In certain embodiments $R^4$ is $C_{1-6}$alkoxy$C_{1-6}$alkyl wherein the $C_{1-6}$alkyl moieties may be unsubstituted or substituted one or more times with halo.

In certain embodiments $R^4$ is hydroxyl-$C_{1-6}$alkyl

In certain embodiments $R^4$ is oxo.

In certain embodiments $R^4$ is hydroxyl.

In certain embodiments $R^4$ is $C_{1-6}$alkylsulfinyl.

In certain embodiments $R^4$ is halo.

In certain embodiments $R^4$ is $C_{1-6}$alkyl.

In certain embodiments $R^4$ is $C_{2-6}$alkenyl.

In certain embodiments $R^4$ is cyano.

In certain embodiments $R^4$ is hydroxyl-$C_{1-6}$alkyl.

In certain embodiments $R^4$ is $C_{1-6}$alkoxy$C_{1-6}$alkyl.

In certain embodiments $R^5$ is —$(CR^{a1}R^{a2})_p$—$NR^bR^c$.

In certain embodiments $R^5$ is —$(CR^{a1}R^{a2})_p$—$SO_2$—$R^d$.

In certain embodiments R is —$(CR^{a1}R^{a2})_p$—C(O)—$R^e$.

In certain embodiments R is —$(CR^{a1}R^{a2})_p$—$NR^b$—$SO_2$—$R^d$.

In certain embodiments $R^5$ is —$(CR^{a1}R^{a2})_p$—$NR^b$—C(O)—$R^e$.

In certain embodiments $R^5$ is —$(CR^{a1}R^{a2})_p$—$NR^b$—$(CHR^c)_q$—$SO_2$—$R^d$.

In certain embodiments $R^5$ is —$(CR^{a1}R^{a2})_p$—$NR^b$—$(CHR^c)_q$—C(O)—$R^e$.

In certain embodiments R is —$(CR^{a1}R^{a2})_p$—CN.

In certain embodiments $R^5$ is —$C_{2-6}$alkenyl-CN.

In certain embodiments R is —$(CR^{a1}R^{a2})$—Z.

In certain embodiments R is —$(CR^{a1}R^{a2})$—$SO_2$—Z.

In certain embodiments $R^5$ is $C_{1-6}$alkylsulfonimidamido.

In certain embodiments $R^5$ is $C_{1-6}$alkylsulfonimidoyl$C_{1-6}$alkyl.

In certain embodiments R is —$(CH_2)_p$—$NR^bR^c$.

In certain embodiments R is —$(CH_2)_p$—$SO_2$—$R^d$.

In certain embodiments $R^5$ is —$(CH_2)_p$—C(O)—$R^e$.

In certain embodiments $R^5$ is —$(CH_{22})_p$—$NR^b$—$SO_2$—$R^d$.

In certain embodiments $R^5$ is —$(CH_2)_p$—$NR^b$—C(O)—$R^e$.

In certain embodiments $R^5$ is —$(CH_2)_p$—$NR^b$—$(CHR^c)_q$—SO—$R^d$.

In certain embodiments $R^5$ is —$(CH_2)_p$—$NR^b$—$(CHR^c)_q$—C(O)—$R^e$.

In certain embodiments R is —$(CH_2)_p$—CN.

In certain embodiments $R^5$ is —$(CH_2)_p$—Z.

In certain embodiments $R^5$ is —$(CH_2)_p$—$SO_2$—Z.

In certain embodiments $R^5$ is —$(CH_2)_p$—$SO_2$—$CH_3$.

In certain embodiments $R^5$ is —$NR^b$—$SO_2$—$R^d$.

In certain embodiments $R^5$ is —$NR^b$—C(O)—$R^e$.

In certain embodiments $R^5$ is —$NH_2$—$SO_2$—$CH_3$.

In certain embodiments $R^5$ is —$(CH_2)_p$—$SO_2$—$NH_2$.

In certain embodiments $R^6$ is $C_{1-6}$alkyl.

In certain embodiments $R^6$ is halo.

In certain embodiments $R^6$ is hydroxyl.

In certain embodiments $R^7$ is $C_{1-6}$alkyl.

In certain embodiments $R^7$ is $C_{1-6}$alkoxy.

In certain embodiments $R^7$ is halo.

In certain embodiments $R^7$ is hydroxyl.

In certain embodiments Z is $C_{3-6}$cycloalkyl which may be unsubstituted or substituted once or twice with $R^f$.

In certain embodiments Z is a four or five membered heterocyclyl selected from azetidinyl, oxetanyl, thietanyl or tetrahydrothiophenyl, each of which may be unsubstituted or substituted once or twice with $R^f$.

In certain embodiments Z is $C_{1-6}$alkyl-heterocyclyl wherein the heterocyclyl is a four or five membered heterocyclyl selected from azetidinyl, oxetanyl, thietanyl or tetrahydrothiophenyl, each of which may be unsubstituted or substituted once or twice with $R^f$.

In certain embodiments Z is $C_{1-6}$alkylcarbonylamino$C_{1-6}$alkyl.

In certain embodiments p is: 0; 1; or 2.

In certain embodiments p is: 0; or 1.

In certain embodiments p is 0.

In certain embodiments p is 1.

In certain embodiments p is 2.

In certain embodiments p is 3.

In certain embodiments q is 1.

In certain embodiments q is 2.

In certain embodiments $R^{a1}$ is hydrogen.

In certain embodiments $R^{a1}$ is $C_{1-6}$alkyl.

In certain embodiments $R^{a2}$ is hydrogen.

In certain embodiments $R^{a2}$ is $C_{1-6}$alkyl which may be unsubstituted or substituted one or more times with halo.

In certain embodiments $R^{a2}$ is hydroxyl.

In certain embodiments $R^b$ is hydrogen.

In certain embodiments $R^b$ is $C_{1-6}$alkyl which may be unsubstituted or substituted one or more times with halo.

In certain embodiments $R^b$ is hydroxyl-$C_{1-6}$alkyl wherein the $C_{1-6}$alkyl moiety may be unsubstituted or substituted one or more times with halo.

In certain embodiments $R^c$ is hydrogen.

In certain embodiments $R^c$ is $C_{1-6}$alkyl which may be unsubstituted or substituted one or more times with halo.

In certain embodiments $R^d$ is $C_{1-6}$alkyl.

In certain embodiments $R^d$ is $C_{3-6}$cycloalkyl.

In certain embodiments $R^d$ is $C_{3-6}$cycloalkyl-$C_{1-6}$alkyl.

In certain embodiments $R^d$ is hydroxy$C_{1-6}$alkyl.

In certain embodiments $R^d$ is $NR^bR^c$.

In certain embodiments $R^e$ is $C_{1-6}$alkyl.

In certain embodiments $R^e$ is $C_{1-6}$alkoxy.

In certain embodiments $R^e$ is hydroxyl-$C_{1-6}$alkyl.

In certain embodiments $R^e$ is hydroxyl.

In certain embodiments $R^e$ is $NR^bR^c$.

In certain embodiments $R^f$ is halo.

In certain embodiments $R^f$ is oxo.

In certain embodiments $R^f$ is cyano$C_{1-6}$alkyl.

In certain embodiments $R^f$ is hydroxyl.

In certain embodiments $R^f$ is $C_{1-6}$alkylsulfonyl$C_{1-6}$alkyl.

In certain embodiments the subject compounds are of formula II

II

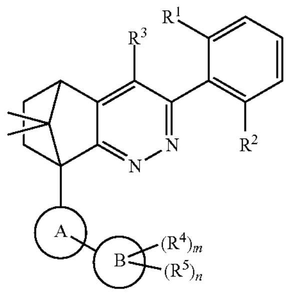

wherein A, B, m, n, $R^1$, $R^2$, $R^3$, $R^4$ and $R^5$ are as defined herein.

In certain embodiments the subject compounds are of formula IIIa

IIIa

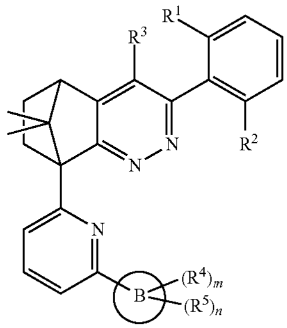

wherein B, m, n, $R^1$, $R^2$, $R^3$, $R^4$ and $R^5$ are as defined herein.

In certain embodiments the subject compounds are of formula IIIb

IIIb

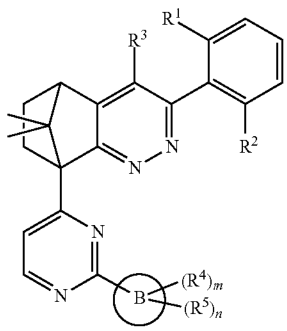

wherein B, m, n, $R^1$, $R^2$, $R^3$, $R^4$ and $R^5$ are as defined herein.

In certain embodiments the subject compounds are of formula IIIc

IIIc

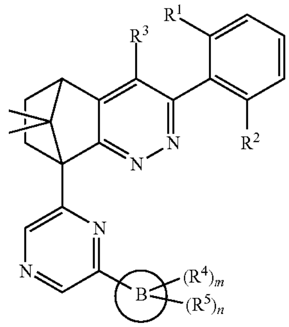

wherein B, m, n, $R^1$, $R^2$, $R^3$, $R^4$ and $R^5$ are as defined herein.

Methods

The invention also provides a method for treating a disease or condition mediated by or otherwise associated with the RORc receptor, the method comprising administering to a subject in need thereof an effective amount of a compound of the invention.

The disease may be arthritis such as rheumatoid arthritis, psoriatic arthritis, spondyloarthriti, ankylosing spondylitis, or osteoarthritis.

The disease may be asthma or COPD.

The disease may be psoriasis.

The disease may be muscular distrophy.

Representative compounds in accordance with the methods of the invention are shown in the experimental examples below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, for example 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. A particular manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets may contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Utility

The compounds of the invention are useful for treatment of immune disorders generally. The compounds may be used for treatment of arthritis, including rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

The compounds may be used for treatment of respiratory disorders such as chronic obstructive pulmonary disease (COPD), asthma, bronchospasm, and the like.

The compounds may be used for treatment of gastrointestinal disorder ("GI disorder") such as Irritable Bowel Syndrome (IBS), Inflammatory Bowel Disease (IBD), biliary colic and other biliary disorders, renal colic, diarrhea-dominant IBS, pain associated with GI distension, and the like.

The compounds may be used for treatment of pain conditions such as inflammatory pain; arthritic pain, surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

The compounds may be used for treatment of muscular sclerosis, Sjogren's disease, lupus, and pulmonary fibrosis.

GENERAL EXPERIMENTAL

LCMS Methods:

High Pressure Liquid Chromatography-Mass Spectrometry (LCMS) experiments to determine retention times (RT) and associated mass ions were performed using one of the following methods:

Method A: Compounds were analyzed using the following conditions: Experiments were performed on a Waters ZMD single quadrupole mass spectrometer linked to a Hewlett-Packard HP1100 LC system with UV diode array detector and 100 position autosampler. The spectrometer has an electrospray source operating in positive and negative ion mode. This system uses a Phenomenex Luna 3 μm C18(2) 30×4.6 mm column at ambient temperature and a 2.0 mL/min flow rate. The initial solvent system was 95% water containing 0.1% formic acid (solvent A) and 5% acetonitrile containing 0.1% formic acid (solvent B) for the first 0.5 min, followed by a gradient up to 5% solvent A and 95% solvent B over the next 4 min. This was maintained for 1 min before returning to 95% solvent A and 5% solvent B over the next 0.5 min. Total run time was 6 min.

Method B: Compounds were analysed using the following conditions: Experiments were performed on a Waters Micromass ZQ2000 quadrupole mass spectrometer linked to a Waters Acquity UPLC system with a PDA UV detector. The spectrometer has an electrospray source operating in positive and negative ion mode. This system uses an Acquity BEH C18 1.7 μm 100×2.1 mm column, maintained at 40° C. or an Acquity BEH Shield RP18 1.7 μm 100×2.1 mm column, maintained at 40° C. and a 0.4 mL/min flow rate. The initial solvent system was 95% water containing 0.1% formic acid (solvent A) and 5% acetonitrile containing 0.1% formic acid (solvent B) for the first 0.4 min followed by a gradient up to 5% solvent A and 95% solvent B over the next 5.6 min. This was maintained for 0.8 min before returning to 95% solvent A and 5% solvent B over the next 1.2 min. Total run time was 8 min.

Method C: Compounds were analysed using the following conditions: Experiments were performed on a Waters ZMD mass spectrometer linked to a Waters Acquity UPLC system with a PDA UV detector. The spectrometer has an electrospray source operating in positive and negative ion mode. This system uses an Acquity CSH C18 1.7 μm 50×2.1 mm column, maintained at 40° C. and a 1.0 mL/min flow rate. The initial solvent system was 97% water containing 0.1% formic acid (solvent A) and 3% acetonitrile containing 0.1% formic acid (solvent B) for the first 0.15 min followed by a gradient up to 1% solvent A and 99% solvent B over the next 1.85 min. This was maintained for 0.4 min before returning to 97% solvent A and 3% solvent B over the next 0.1 min. Total run time was 2.5 min.

NMR Methods:

$^1H$ NMR spectra were recorded at ambient temperature, or at 80° C. where indicated, using one of the following machines: Varian Unity Inova (400 MHz) spectrometer with a triple resonance 5 mm probe, Bruker Avance DRX 400 (400 MHz) spectrometer with a triple resonance 5 mm probe, a Bruker Avance DPX 300 (300 MHz) equipped with a standard 5 mm dual frequency probe for detection of $^1H$ and $^{13}C$, Bruker Fourier 300 MHz system equipped with a standard 5 mm $^1H/^{13}C$ probe, a Bruker AVIII (400 MHz) using a BBI Broad Band Inverse 5 mm probe, or a Bruker AVIII (500 MHz) using a QNP (Quad Nucleus detect) 5 mm probe. Chemical shifts are expressed in ppm relative to an internal standard, tetramethylsilane (ppm=0.00). The following abbreviations have been used: br=broad signal, s=singlet, d=doublet, dd=double doublet, t=triplet, td=triplet doublet, dddd=doublet doublet doublet doublet, q=quartet, m=multiplet, or any combination thereof.

Microwave Reactor:

Microwave reactions were carried out using a Biotage® Initiator® in vials appropriate to the scale of the reaction and at the temperature and time described in the experimental details.

Purification Equipment:

Purifications were carried out using pre-packed silica gel cartridges either on a Teledyne ISCO CombiFlash® or Biotage® Isolera Four® or using compressed air to apply external pressure. Solvents and gradients shown in the experimental details were used.

Reverse Phase High Pressure Liquid Chromatography (HPLC) was used to purify compounds where indicated. Separation using gradient elution on a Phenomenex Gemini C18 column (250×21.2 mm, 5 micron) as stationary phase and using mobile phase indicated, operating at a 18 mL/min flow rate using a Gilson UV/Vis-155 dual channel detector and Gilson GX-271 automated liquid handler. The desired fractions were freeze-dried, except where specified otherwise.

Mass Directed Auto-Purification (MDAP) was used to purify compounds where indicated. Separation using Agilent 1260 Infinity Purifications System, XSelect CSH Prep C18 5 μm, 21×250 mm as the stationary phase, maintained at RT and a 19 mL/min flow. The initial solvent system was 90% water containing 0.1% formic acid (solvent A) and 10% acetonitrile containing 0.1% formic acid (solvent B), followed by a gradient up to 5% solvent A and 95% solvent B, centred around a specific focused gradient, over 22 min. Product collection was triggered by an Agilent 6100 series single Quadrupole LC/MS. The desired fractions were concentrated in vacuo at 40° C. and the residue freeze-dried from MeCN-water (1:1), except where stated otherwise.

Phase separator cartridges are supplied by Biotage® as Isolute® phase separator cartridges.

LIST OF ABBREVIATIONS

AcOH Acetic acid
Atm. Atmosphere
BOC tert-Butyloxycarbonyl group
$CDCl_3$ Deuterated chloroform
$CH_3CN$ Acetonitrile
DavePhos 2-Dicyclohexylphosphino-2'-(N,N-dimethylamino)biphenyl
DCM Dichloromethane/methylene chloride
DMFDMA N,N-Dimethylformamide dimethyl acetal
DIPEA Di-iso-propylethylamine
DMF N,N-Dimethylformamide
DMSO Dimethyl sulfoxide
ES Electrospray
$Et_2O$ Diethyl ether
$Et_3N$ Triethylamine
EtOH Ethanol/Ethyl alcohol
EtOAc Ethyl acetate
$H_2O$ Water
$H_2SO_4$ Sulfuric acid
$HCO_2H$Formic acid
HCl Hydrochloric acid
HOBT 1-Hydroxybenzotriazole
HPLC High pressure liquid chromatography
IMS Industrial methylated spirit
KOH Potassium hydroxide
$K_2CO_3$ Potassium carbonate
LDA Lithium diisopropylamide
i-PrOH Isopropanol/isopropyl alcohol/propan-2-ol
LCMS Liquid Chromatograph/Mass Spectroscopy
LiOH Lithium hydroxide
$MgSO_4$ Magnesium sulphate
MeOH Methanol/Methyl alcohol
MW Microwaves
NaH Sodium hydride
NaCl Sodium chloride
NaOH Sodium hydroxide
$Na_2SO_4$ Sodium sulfate
$NaHCO_3$ Sodium bicarbonate/Sodium hydrogen carbonate
$NH_4Cl$ Ammonium chloride
$POCl_3$ Phosphorus oxychloride
$PhCH_3$ Toluene
RT Room temperature
sat. Saturated
SCX-2 Pre-packed Isolute® silica-based sorbent with a chemically bonded propylsulfonic acid functional group
TBDMS tert-Butyldimethylsilyl
TFA Trifluoroacetic acid
THF Tetrahydrofuran
aq. Aqueous
Ar Argon
Bu Butyl
EDCI N-(3-Dimethylaminopropyl)-N'-ethylcarbodiimide hydrochloride
FCC Flash column chromatography on silica
h hour(s)
MeCN Acetontrile
min minute(s)
NaHMDS Sodium hexamethyldisilazane/sodium bis(trimethylsilyl)amide
$Ph_3P$ Triphenylphosphine
$(Ph_3P)_4Pd$ Tetrakis(triphenylphosphine)palladium (0)
TBA Tetrabutylammonium
Tr Trityl

Intermediate A: (1R)-5-(2,6-Fluorophenyl)-11,11-dimethyl-3,4-diazatricyclo[6.2.1.02,7]undeca-2(7),3,5-triene-1-carboxylic Acid

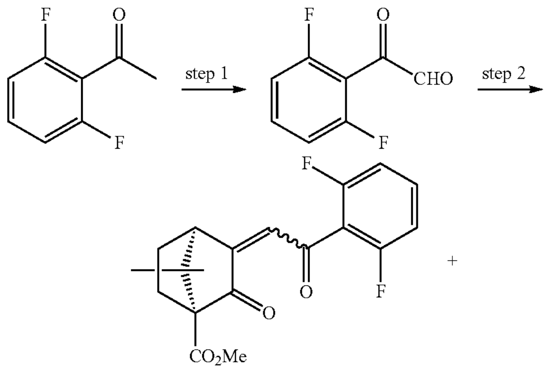

-continued

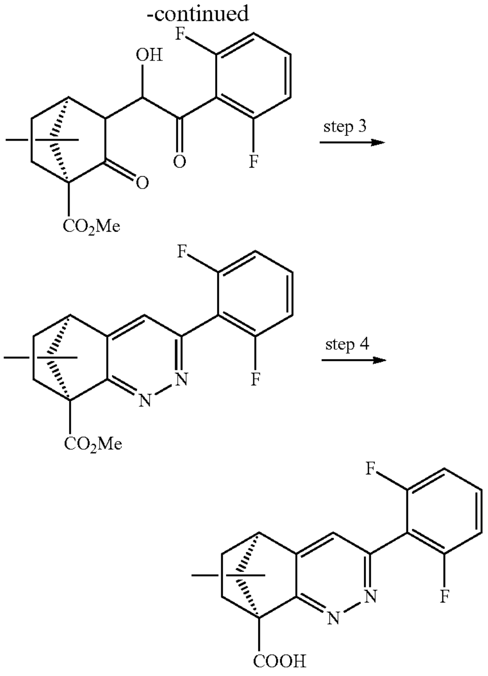

Step 1: 2-(2,6-Difluorophenyl)-2-oxoacetaldehyde

A mixture of selenium dioxide (111 g, 1000 mmol) in 1,4-dioxane/$H_2O$ (500 mL/20 mL) at 55° C. was stirred for 30 min and then added 1-(2,6-difluorophenyl)ethanone (156 g, 1000 mmol). The mixture was refluxed for 20 h. The reaction was cooled to RT and filtered. The filtrate was concentrated under reduced pressure. The residue was purified by fractional distillation collecting the fractions between 90-94° C., under vacuum (~1 mm mercury), to afford the title compound as yellow oil (98.5 g). $^1H$ NMR (500 MHz, DMSO-$d_6$): δ 9.48 (t, J=2.0 Hz, 1H), 7.79-7.76 (m, 1H), 7.33-7.29 (m, 2H); MS (ESI): $[M+H]^+$171.

Step 2: Methyl (1R)-3-[2-(2,6-difluorophenyl)-2-oxoethylidene]-7,7-dimethyl-2-oxobicyclo[2.2.1]heptane-1-carboxylate and (1R)-methyl 3-(2-(2,6-difluorophenyl)-1-hydroxy-2-oxoethyl)-7,7-dimethyl-2-oxobicyclo[2.2.1]heptane-1-carboxylate To a solution of (1R)-methyl 7,7-dimethyl-2-oxobicyclo[2.2.1]heptane-1-carboxylate (19.6 g, 100 mmol) in anhydrous THF (100 mL) at −78° C. under nitrogen was added LDA (75 mL, 2 M in THF) dropwise. The mixture was stirred at −78° C. for 1 h, and then 2-(2,6-difluorophenyl)-2-oxoacetaldehyde (20.4 g, 120 mmol) in THF (50 mL) was added. The mixture was stirred at −78° C. for 1 h and allowed to warm to RT. The reaction mixture was quenched with 1 N aqueous HCl and concentrated under reduced pressure. The residue was extracted with EtOAc (×3). The combined organic layers were concentrated under reduced pressure and the residue was purified by FCC (1: 30 EtOAc in petroleum ether) to afford the title compounds as yellow solids: methyl (1R)-3-[2-(2,6-difluorophenyl)-2-oxoethylidene]-7,7-dimethyl-2-oxobicyclo[2.2.1]heptane-1-carboxylate, (2.12 g), $^1H$ NMR (500 MHz, DMSO-$d_6$): δ 7.72-7.66 (m, 1H), 7.29-7.26 (m, 2H), 6.99 (s, 1H), 3.72 (s, 3H), 3.30-3.29 (m, 1H), 2.45-2.39 (m, 1H), 2.24-2.17 (m, 1H), 1.79-1.74 (m, 1H), 1.43-1.38 (m, 1H), 1.07 (s, 3H), 1.03 (s, 3H); MS (ESI): $[M+H]^+$ 349.1; (1R)-methyl 3-(2-(2,6-difluorophenyl)-1-hydroxy-2-oxoethyl)-7,7-dimethyl-2-oxobicyclo[2.2.1]heptane-1-carboxylate, (5.51 g), $^1H$ NMR (500 MHz, DMSO-$d_6$): δ 7.65-7.58 (m, 1H), 7.24-7.20 (m, 2H), 6.27 (d, J=7.5 Hz, 1H), 4.63-4.60 (m, 1H), 3.66 (s, 3H), 2.28-2.23 (m, 1H), 2.04-1.97 (m, 2H), 1.87-1.81 (m, 1H), 1.51-1.46 (m, 1H), 1.89 (s, 3H), 0.99 (s, 3H); MS (ESI): $[M+H]^+$ 367.1.

Step 3: Methyl (1R)-5-(2,6-fluorophenyl)-11,11-dimethyl-3,4-diazatricyclo[6.2.1.02,7]undeca-2(7),3,5-triene-1-carboxylate A mixture of methyl (1R)-3-[2-(2,6-difluorophenyl)-2-oxoethylidene]-7,7-dimethyl-2-oxobicyclo[2.2.1]heptane-1-carboxylate (2.09 g, 6.0 mmol) and hydrazine hydrochloride (4.08 g, 60 mmol) in butan-1-ol (100 mL) was heated at 135° C. for 20 h. The reaction mixture was concentrated under reduced pressure. The residue was dissolved in $H_2O$ and extracted with EtOAc (×3). The combined organic fractions were concentrated in vacuo and the residue was purified by FCC (3:1 petroleum ether/EtOAc) to afford the title compound as yellow solid (1.78 g). MS (ESI): $[M+H]^+$ 345.1.

Following the procedure as described above and starting with (1R)-methyl 3-(2-(2,6-difluorophenyl)-1-hydroxy-2-oxoethyl)-7,7-dimethyl-2-oxobicyclo[2.2.1]heptane-1-carboxylate (5.49 g, 15 mmol), the title compound was obtained as a yellow solid (4.39 g). MS (ESI): $[M+H]^+$ 345.1.

Step 4: (1R)-5-(2,6-Fluorophenyl)-11,11-dimethyl-3,4-diazatricyclo[6.2.1.02,7]undeca-2(7),3,5-triene-1-carboxylic Acid A mixture of the product from Step 3 (5.16 g, 15 mmol) and LiOH monohydrate (0.84 g, 63.5 mmol) in THF/$H_2O$ (50 mL/5 mL) was heated at 30° C. for 20 h. The reaction mixture was cooled to RT and concentrated in vacuo. The residue was dissolved in $H_2O$ and 1N aqueous HCl added slowly until pH 3 was achieved. The mixture was extracted with EtOAc (×3) and the combined organic fractions were concentrated in vacuo to afford the title compound as yellow solid (4.21 g). $^1H$ NMR (500 MHz, DMSO-$d_6$): δ 12.88 (s, 1H), 7.75 (s, 1H), 7.65-7.59 (m, 1H), 7.32-7.29 (m, 1H), 3.16-3.15 (m, 1H), 2.61-2.54 (m, 1H), 2.32-2.27 (m, 1H), 1.52-1.47 (m, 1H), 1.18-1.13 (m, overlap, 4H), 0.79 (s, 3H); MS (ESI): $[M+H]^+$ 331.1.

Intermediate B: Trifluoro-methanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyridin-2-yl ester

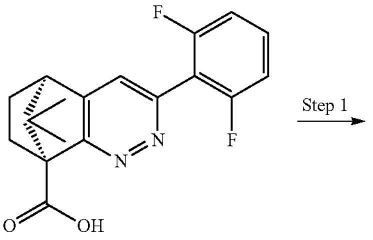

-continued

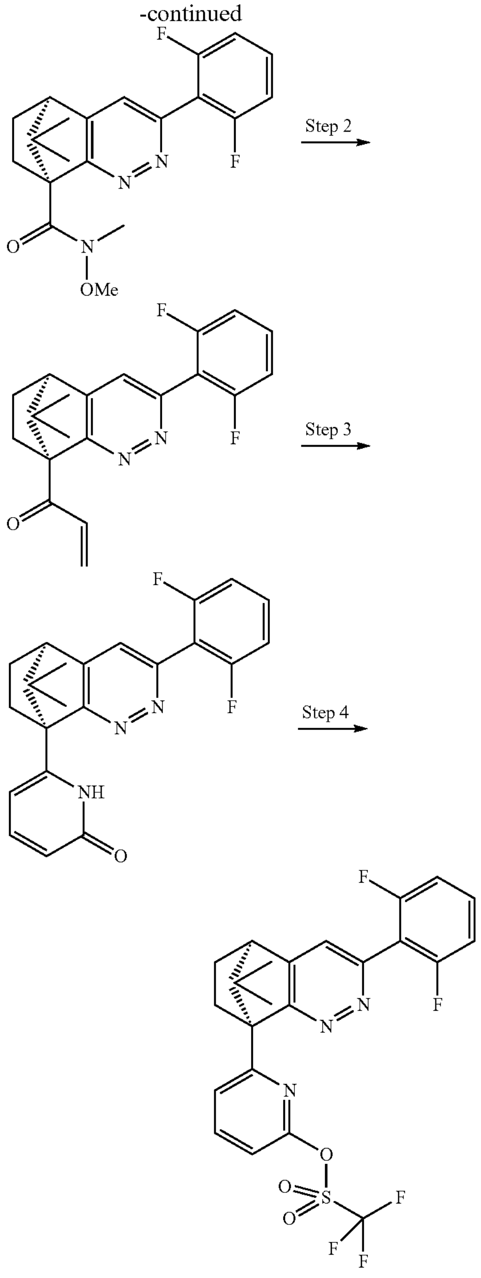

Step 1: (1R,8R)-5-(2,6-Difluoro-phenyl)-11,11-dimethyl-3,4-diaza-tricyclo[6.2.1.0*2,7*]undeca-2(7),3,5-triene-1-carboxylic Acid methoxy-methyl-amide A solution of (1R,8R)-5-(2,6-difluoro-phenyl)-11,11-dimethyl-3,4-diaza-tricyclo[6.2.1.0*2,7*]undeca-2(7),3,5-triene-1-carboxylic acid (3.75 g, 11.35 mmol) in DCM (150 mL) containing DMF (3 drops) was treated with oxalyl chloride (1.44 g, 11.35 mmol) and stirred for 2 h. The reaction was concentrated in vacuo, redissolved in DCM (150 mL) and N,O-dimethylhydroxylamine.hydrochloride (1.44 g, 14.76 mmol) and $Et_3N$ (4.71 mL, 34.05 mmol) were added and the reaction stirred for 18 h. The reaction was washed with aqueous 1N HCl, $NaHCO_3$, $H_2O$, brine, and then dried over ($Na_2SO_4$) and concentrated in vacuo. FCC (0-60% EtOAc-cyclohexane) gave the title compound as a yellow solid (3.69 g). $^1H$ NMR (300 MHz, $CDCl_3$): δ d 7.44-7.36 (m, 2H), 7.07-7.00 (m, 2H), 3.87 (s, 3H), 3.38 (s, 3H), 3.25-3.18 (m, 1H), 2.90 (d, J=4.2 Hz, 1H), 2.62 (ddd, J=3.9, 10.5, 12.9 Hz, 1H), 2.37-2.25 (m, 1H), 2.11-2.01 (m, 1H), 1.28 (s, 3H), 0.95 (s, 3H). LCMS (m/z, Method B) $ES^+$ 374.18 $[M+1]^+$.

Step 2: 1-[(1R,8R)-5-(2,6-Difluoro-phenyl)-11,11-dimethyl-3,4-diaza-tricyclo[6.2.1.0*2,7*]undeca-2(7),3,5-trien-1-yl]-propenone A solution of the product from step 1 (3.68 g, 9.86 mmol) in THF (100 mL) was stirred at 0° C. and treated dropwise with vinyl magnesium bromide (14.78 mL, 1.0 M THF). The reaction was stirred at RT for 1.5 h, quenched with aqueous $NH_4Cl$ and extracted into EtOAc, dried ($Na_2SO_4$), concentrated and purified by chromatography (0-50% EtOAc-cyclohexane) to give the title compound as a yellow solid. $^1H$ NMR (300 MHz, $CDCl_3$) δ 7.45-7.38 (m, 2H), 7.23-7.02 (m, 3H), 6.45 (dd, J=1.9, 17.0 Hz, 1H), 5.70 (dd, J=1.9, 10.3 Hz, 1H), 3.05 (d, J=4.1 Hz, 1H), 2.82 (ddd, J=4.1, 10.5, 13.0 Hz, 1H), 2.41-2.29 (m, 1H), 1.68-1.58 (m, 1H), 1.34-1.23 (m, 1H), 1.19 (s, 3H), 0.90 (s, 3H). LCMS (m/z, Method B) $ES^+$341.16 $[M+1]^+$.

Step 3: 6-[(1S,8R)-5-(2,6-Difluoro-phenyl)-11,11-dimethyl-3,4-diaza-tricyclo[6.2.1.0*2,7*]undeca-2(7),3,5-trien-1-yl]-1H-pyridin-2-one A mixture of the product from step 2 (1.61 g, 4.73 mmol), 1-carbamoylmethyl-pyridinium chloride (0.816 mg, 4.73 mmol) and $Et_3N$ (0.65 mL, 4.73 mmol) in MeOH (40 mL) was heated at reflux for 4 h. The cooled reaction was concentrated in vacuo, and $Ph_2O$ (5 mL) was added and the reaction heated to 200° C. for 15 min. The cooled reaction was extracted into EtOAc, washed with $H_2O$, brine, dried ($Na_2SO_4$), concentrated and purified by chromatography (0-10% 2M $NH_3$/MeOH-EtOAc) to give the title compound as a yellow solid (1.11 g). $^1H$ NMR (300 MHz, $CDCl_3$): δ 11.05-11.04 (m, 1H), 7.49-7.42 (m, 3H), 7.07 (dd, J=8.1, 8.1 Hz, 2H), 6.54 (dd, J=0.9, 9.2 Hz, 1H), 6.37 (dd, J=0.9, 7.0 Hz, 1H), 3.15 (d, J=4.1 Hz, 1H), 2.65 (ddd, J=3.8, 10.5, 12.9 Hz, 1H), 2.52-2.40 (m, 1H), 2.04 (s, 3H), 1.88-1.77 (m, 1H), 1.46-1.36 (m, 1H), 0.72 (s, 3H). LCMS (m/z, Method B) $ES^+$ 380.16 $[M+1]^+$.

Step 4: Trifluoro-methanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyridin-2-yl ester A solution of the product from step 3 (1.10 g, 2.9 mmol) in pyridine (10 mL) was stirred at 0° C. and treated dropwise with trifluoromethanesulfonic anhydride (976 ul, 5.8 mmol). The reaction was concentrated in vacuo after 1 h, partitioned between EtOAc-$H_2O$ and the extracts washed with $H_2O$, brine, dried ($Na_2SO_4$) concentrated and purified by chromatography (0-40% EtOAc-cyclohexane) to give the title compound as a yellow solid (1.22 g). $^1H$ NMR (300 MHz, $CDCl_3$): δ 8.06 (d, J=7.6 Hz, 1H), 7.93 (dd, J=7.8, 7.8 Hz, 1H), 7.48-7.38 (m, 2H), 7.14-7.02 (m, 3H), 3.29 (ddd, J=4.0, 10.6, 13.2 Hz, 1H), 3.14 (d, J=4.0 Hz, 1H), 2.53-2.41 (m, 1H), 1.72-1.55 (m, 1H), 1.41-1.25 (m, 1H), 1.12 (s, 3H), 0.69 (s, 3H). LCMS (m/z, Method B) ES 512.14 $[M+1]^+$.

Intermediate C: 6-[(5R,8S)-3-(2,6-difluorophenyl)-9,9-dimethyl-6,7-dihydro-5,8-methanocinnolin-8(5H)-yl]pyridine-2-carbonitrile

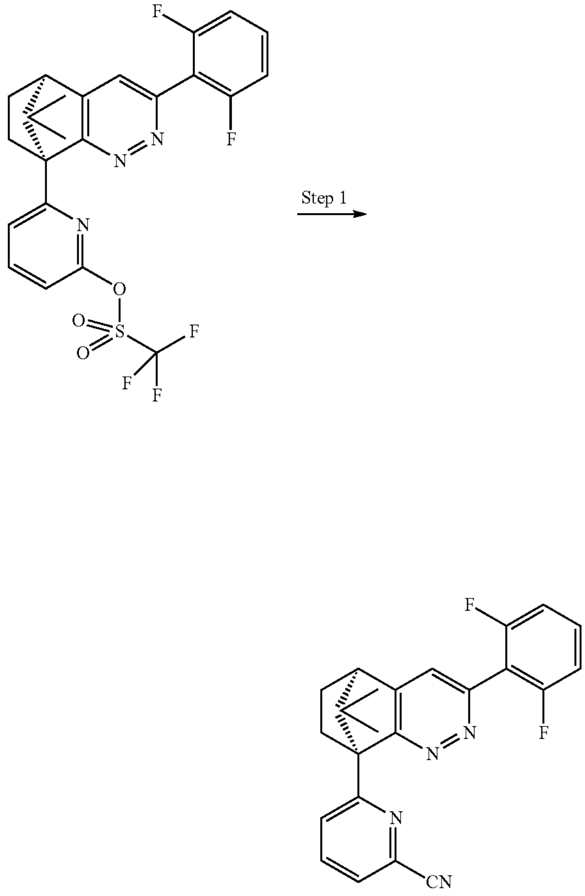

Step 1:6-[(5R,8S)-3-(2,6-difluorophenyl)-9,9-dimethyl-6,7-dihydro-5,8-methanocinnolin-8(5H)-yl] pyridine-2-carbonitrile A mixture of trifluoro-methanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyridin-2-yl ester (750 mg, 1.47 mmol), zinc cyanide (430 mg, 3.67 mmol) and $Pd(PPh_3)_4$(85 mg, 0.074 mmol) in DMF (10 mL) was purged with nitrogen and heated at 90° C. for 3 h. The cooled reaction was diluted with EtOAc and washed with $H_2O$, brine, dried ($Na_2SO_4$) concentrated and purified by chromatography (0-60% EtOAc-cyclohexane) to give the title compound as a yellow solid (652 mg). $^1H$ NMR (300 MHz, $CDCl_3$) δ 8.13 (dd, J=1.0, 8.1 Hz, 1H), 7.86 (dd, J=7.9, 7.9 Hz, 1H), 7.66 (dd, J=1.0, 7.6 Hz, 1H), 7.49-7.39 (m, 2H), 7.06 (dd, J=8.1, 8.1 Hz, 2H), 3.43-3.32 (m, 1H), 3.16 (d, J=4.1 Hz, 1H), 2.53-2.41 (m, 1H), 1.72-1.59 (m, 1H), 1.36 (dd, J=4.2, 22.0 Hz, 1H), 1.13 (s, 3H), 0.71 (s, 3H). LCMS (m/z, Method B) ES 389.24 $[M+1]^+$.

Intermediate D: 4-[(5R,8S)-3-(2,6-difluorophenyl)-9,9-dimethyl-6,7-dihydro-5,8-methanocinnolin-8(5H)-yl]pyrimidin-2-amine

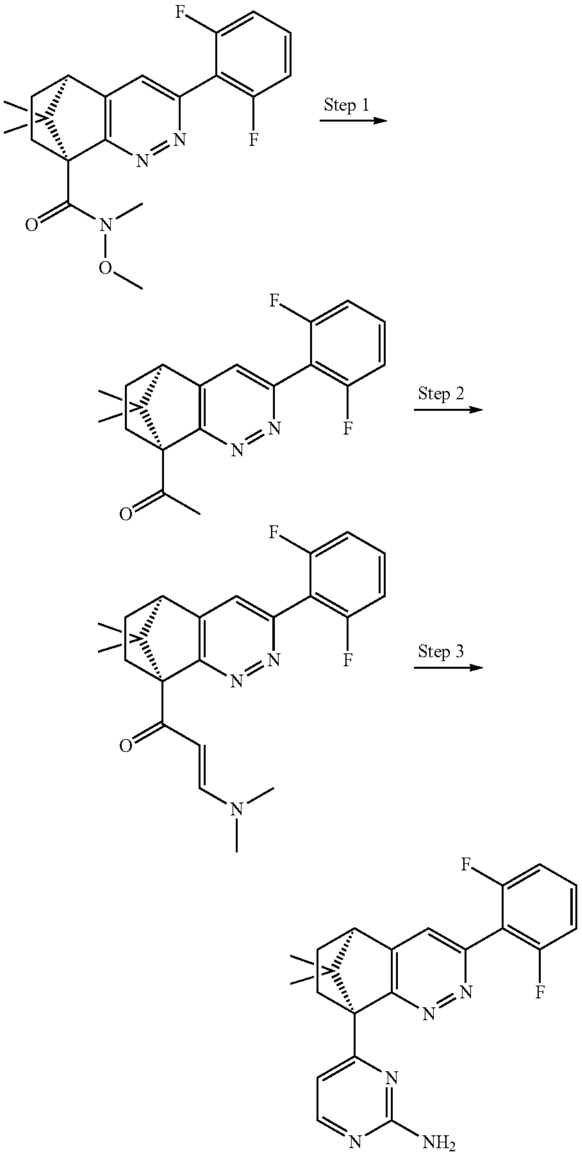

Step 1: 1-[(1R,8R)-5-(2,6-difluoro-phenyl)-11,11-dimethyl-3,4-diaza-tricyclo[6.2.1.0*2,7*]undeca-2(7),3,5-trien-1-yl]-ethanone A solution of (1R,8R)-5-(2,6-difluoro-phenyl)-11,11-dimethyl-3,4-diaza-tricyclo[6.2.1.0*2,7*]undeca-2(7),3,5-triene-1-carboxylic acid methoxy-methyl-amide (3.05 g, 8.17 mmol) in THF (50 mL) was stirred under $N_2$ and treated dropwise with methyl magnesium bromide (3.0 M $Et_2O$, 4.36 mL, 13.07 mmol). After 2 h, the reaction was quenched with aqueous $NH_4Cl$, extracted into EtOAc and washed with $H_2O$, brine, dried ($Na_2SO_4$) and concentrated in vacuo. Purification by chromatography (0-50% EtOAc-cyclohexane) gave the title compound as a yellow solid (2.11 g). $^1H$ NMR (300 MHz, $CDCl_3$) δ 7.45-7.38 (m, 2H), 7.05 (dd, J=8.1, 8.1 Hz, 2H), 3.01 (d, J=4.1 Hz, 1H), 2.72 (ddd, J=3.3, 10.3, 13.5 Hz, 1H), 2.66 (s, 3H), 2.39-2.27 (m, 1H), 1.70-1.58 (m, 1H), 1.27 (tt, J=5.7, 6.6 Hz, 1H), 1.20 (s, 3H), 0.91 (s, 3H).LCMS (m/z, Method B) $ES^+$ 329.11 $[M+1]^+$.

Step 2: (E)-1-[(1R,8R)-5-(2,6-Difluoro-phenyl)-11,11-dimethyl-3,4-diaza-tricyclo[6.2.1.0*2,7*]undeca-2(7),3,5-trien-1-yl]-3-dimethylamino-propenone A solution of the product from step 1 (520 mg, 1.58 mmol) in DMF-DMA (3 mL) was heated to 120° C. in a sealed tube for 18 h. The cooled reaction was concentrated in vacuo and purified by chromatography (50-100% EtOAc-cyclohexane) to give the title compound as a yellow solid (2.11 g). $^1H$ NMR (300 MHz, $CDCl_3$) δ 7.79 (d, J=12.4 Hz, 1H), 7.43-7.36 (m, 2H), 7.04 (dd, J=8.0, 8.0 Hz, 2H), 5.80 (d, J=12.4 Hz, 1H), 3.01-2.85 (m, 2H), 2.39-2.27 (m, 1H), 1.60 (s, 1H), 1.51 (qdd, J=4.7, 5.9, 5.9 Hz, 1H), 1.21 (s, 9H), 0.86 (s, 3H). LCMS (m/z, Method B) $ES^+$ 384.20 $[M+1]^+$.

Step 3: 4-[(5R,8S)-3-(2,6-difluorophenyl)-9,9-dimethyl-6,7-dihydro-5,8-methanocinnolin-8(5H)-yl] pyrimidin-2-amine A mixture of the product from step 2 (50 mg, 0.13 mmol), guanidine hydrochloride (15 mg, 0.156 mmol), $K_2CO_3$ (22 mg, 0.156 mmol) in EtOH (2 mL) was heated to reflux in a sealed tube for 18 h. The reaction was partitioned between $H_2O$-EtOAc, extracted and the organic phase washed with $H_2O$, brine, dried ($Na_2SO_4$) and concentrated in vacuo. Purification by chromatography (0-10% MeOH-DCM) and trituration with $Et_2O$ gave the title compound as a yellow solid (23 mg). $^1H$ NMR (400 MHz, DMSO-$d_6$): δ 8.23 (d, J=5.2 Hz, 1H), 7.73 (s, 1H), 7.63-7.54 (m, 1H), 7.27 (dd, J=8.1, 8.1 Hz, 2H), 6.75 (d, J=5.2 Hz, 1H), 6.50 (s, 2H), 3.19 (d, J=4.1 Hz, 1H), 3.04 (ddd, J=3.8, 10.5, 13.0 Hz, 1H), 2.39-2.28 (m, 1H), 1.45-1.36 (m, 1H), 1.21-1.12 (m, 1H), 1.00 (s, 3H), 0.69 (s, 3H). LCMS (m/z, Method B) $ES^+$ 380.2 $[M+1]^+$.

Intermediate E: 6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrazine-2-carboxylic Acid

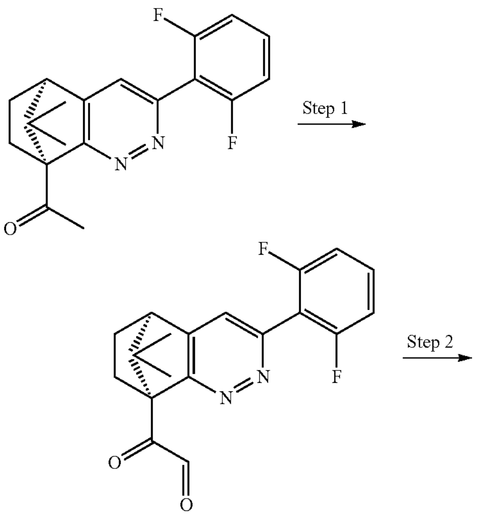

-continued

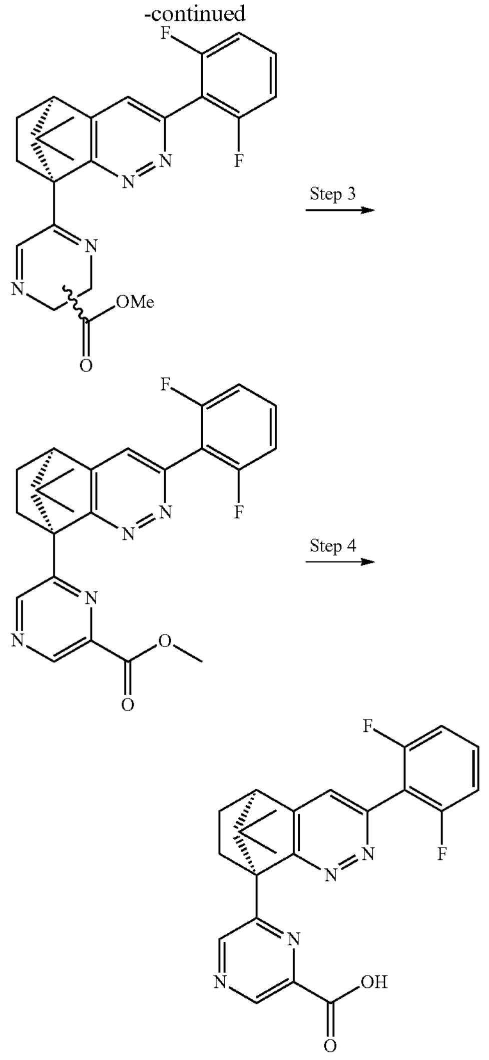

Step 1: [(1R,8R)-5-(2,6-Difluoro-phenyl)-11,11-dimethyl-3,4-diaza-tricyclo[6.2.1.0*2,7*]undeca-2(7),3,5-trien-1-yl]-oxo-acetaldehyde A mixture of 1-[(1R,8R)-5-(2,6-difluoro-phenyl)-11,11-dimethyl-3,4-diaza-tricyclo[6.2.1.0*2,7*]undeca-2(7),3,5-trien-1-yl]-ethanone (15.13 g, 46.13 mmol) and selenium dioxide (7.68 g, 69.19 mmol) in 1,4-dioxane (250 mL) and $H_2O$ (10 mL) was heated at 100° C. for 20 h. The cooled reaction was filtered and the filtrate evaporated and dissolved in EtOAc and filtered through a pad of silica eluting with 1.3 L of EtOAc. The filtrate was evaporated to give the title compound as a yellow foam (17.45 g) which was used directly in the next step.

Step 2: 5-[(1R,8R)-5-(2,6-Difluoro-phenyl)-11,11-dimethyl-3,4-diaza-tricyclo[6.2.1.0*2,7*]undeca 2(7),3,5-trien-1-yl]-2,3-dihydro-pyrazine-2-carboxylic acid methyl ester and 6-[(1R,8R)-5-(2,6-difluoro-phenyl)-11,11-dimethyl-3,4-diaza-tricyclo [6.2.1.0*2,7*]undeca-2(7),3,5-trien-1-yl]-2,3-dihydro-pyrazine-2-carboxylic Acid Methyl Ester Triethylamine (27.95 g, 276.8 mmol) was added to a suspension of the product from step 1 and 2,3-diaminopropionic acid methyl ester (17.63 g, 92.26 mmol) in MeOH (370 mL) and the reaction heated at 70° C. for 1 h. The cooled reaction was partitioned between EtOAc-$H_2O$ and the organic phase dried ($Na_2SO_4$) and concentrated in vacuo to give the title compounds which were used directly in the next step.

Step 3: 5-[(1R,8R)-5-(2,6-Difluoro-phenyl)-11,11-dimethyl-3,4-diaza-tricyclo[6.2.1.0*2,7*]undeca-2(7),3,5-trien-1-yl]-2,3-dihydro-pyrazine-2-carboxylic Acid Methyl Ester The residue from step 2 was dissolved in $PhCH_3$ (370 mL) and manganese dioxide (40.13 g, 461.3 mmol) was added and the reaction heated at reflux for 2 h. The cooled reaction was filtered, concentrated in vacuo and purified by chromatography (0-60% EtOAc-cyclohexane). Fractions containing the title compound were dissolved in $Et_2O$, allowed to crystallise and collected by filtration. Filtrate and mixed fractions were re-purified to give the title compound as a white solid (5.82 g). $^1H$ NMR (300 MHz, $CDCl_3$) δs, 1H), 9.26 (s, 1H), 7.50 (t, J=1.3 Hz, 1H), 7.42 (tt, J=6.7, 7.5 Hz, 1H), 7.06 (dd, J=8.0, 8.0 Hz, 2H), 4.04 (s, 3H), 3.44-3.33 (m, 1H), 3.19 (d, J=4.1 Hz, 1H), 2.55-2.42 (m, 1H), 1.81-1.70 (m, 1H), 1.45-1.34 (m, 1H), 1.14 (s, 3H), 0.79 (s, 3H).

Step 4: 6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrazine-2-carboxylic acid A solution of the product from step 3 (5.81 g, 13.77 mmol) and KOH (960 mg, 17.14 mmol) in $H_2O$ (5 mL) and MeOH (80 mL) was stirred for 0.5 h, evaporated in vacuo and the residue partitioned between $H_2O$-$Et_2O$. The aqueous phase was acidified with AcOH and extracted with EtOAc. The organic phases were dried ($Na_2SO_4$) concentrated in vacuo and azeotroped twice with $PhCH_3$ to give the title compound as a foam. $^1H$ NMR (300 MHz, $CDCl_3$) δ 9.37 (d, J=13.8 Hz, 1H), 7.53 (t, J=1.4 Hz, 1H), 7.43 (ddd, J=9.4, 9.4, 9.4 Hz, 2H), 7.07 (td, J=4.6, 17.2 Hz, 2H), 3.30-3.20 (m, 1H), 2.57-2.45 (m, 1H), 2.06 (d, J=10.8 Hz, 1H), 1.80 (ddd, J=4.0, 9.1, 13.0 Hz, 1H), 1.48-1.38 (m, 1H), 1.12 (s, 3H), 0.80 (s, 3H).

Intermediate F: 2-[(1R,8R)-5-(2,6-Difluoro-phenyl)-11,11-dimethyl-3,4-diaza-tricyclo[6.2.1.0*2,7*]undeca-2(7),3,5-trien-1-yl]-pyrimidine-4-carboxylic Acid

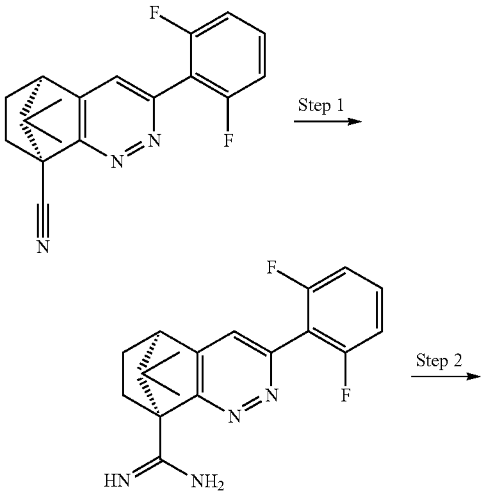

-continued

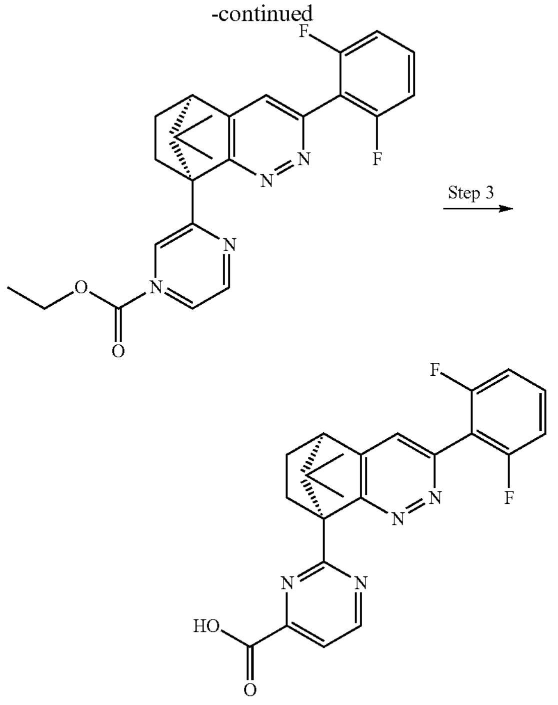

Step 1: (1R,8R)-5-(2,6-Difluoro-phenyl)-11,11-dimethyl-3,4-diaza-tricyclo[6.2.1.0*2,7*]undeca-2(7),3,5-triene-1-carboxamidine A suspension of $NH_4Cl$ (dried at 80° C. under vacuum prior to use, 352 mg, 6.58 mmol) in $PhCH_3$ (5 mL) at 0° C. was stirred under $N_2$ and treated dropwise with trimethylaluminium (2.0 M toluene, 2.63 mL, 5.26 mmol). After 1 h, a solution of (1R,8R)-5-(2,6-difluoro-phenyl)-11,11-dimethyl-3,4-diazatricyclo[6.2.1.0*2,7*]undeca-2(7),3,5-triene-1-carbonitrile (820 mg, 2.63 mmol) in hot toluene (15 mL) was added in one portion and the reaction heated at 80° C. for 18 h. The cooled reaction was quenched with MeOH (5 mL) and stirred for 1 h, filtered through Celite® using MeOH washings and the filtrate concentrated in vacuo. Purification using SCX-2 isolute cartridge and elution with MeOH followed by 2M $NH_3$-MeOH gave the title compound which was used directly in the next step.

Step 2: 2-[(1R,8R)-5-(2,6-Difluoro-phenyl)-11,11-dimethyl-3,4-diaza-tricyclo[6.2.1.0*2,7*]undeca-2(7),3,5-trien-1-yl]-pyrimidine-4-carboxylic acid ethyl ester (Intermediate S)

A mixture of the product from step 1 (314 mg, 0.956 mmol) and (E)-4-ethoxy-2-oxo-but-3-enoic acid ethyl ester (0.209 mL, 1.43 mmol) in EtOH (8 mL) was heated to reflux in a sealed tube for 48 h. A further 0.5 eq (E)-4-ethoxy-2-oxo-but-3-enoic acid ethyl ester was added and heating continued for 24 h. The cooled reaction was concentrated in vacuo and purified by chromatography (0-100% EtOAc-cyclohexane) to give the title compound as an orange residue (272 mg). $^1H$ NMR (300 MHz, $CDCl_3$): δ 9.07 (d, J=5.0 Hz, 1H), 7.89 (d, J=5.0 Hz, 1H), 7.43-7.34 (m, 2H), 7.05-6.98 (m, 2H), 4.51-4.41 (m, 2H), 3.22-3.11 (m, 2H), 2.48-2.36 (m, 1H), 1.97 (tt, J=5.0, 5.7 Hz, 1H), 1.42 (m, 4H), 1.13 (s, 3H), 1.04 (s, 3H). LCMS (m/z, Method B) $ES^+$ 437.23 $[M+1]^+$.

Step 3: 2-[(1R,8R)-5-(2,6-Difluoro-phenyl)-11,11-dimethyl-3,4-diaza-tricyclo[6.2.1.0*2,7*]undeca-2(7),3,5-trien-1-yl]-pyrimidine-4-carboxylic acid A solution of the product from step 2 (268 mg, 0.61 mmol) in EtOH (15 mL) was treated with lithium hydroxide solution (1 M, 1.84 mL, 1.84 mmol). After 0.5 h, the reaction was concentrated in vacuo and diluted with $H_2O$ and washed with EtOAc. The aqueous phase was acidified to pH 2-3 using 1 N HCl and the precipitate extracted into EtOAc and DCM. The combined organics were dried ($Na_2SO_4$) and concentrated in vacuo to give the title compound as a beige solid (195 mg). $^1H$ NMR (300 MHz, DMSO-$d_6$) δ 9.16 (d, J=4.9 Hz, 1H), 7.97 (d, J=4.9 Hz, 1H), 7.77 (s, 1H), 7.66-7.55 (m, 1H), 7.29 (m, 2H), 3.26 (d, J=4.9 Hz, 1H), 3.14-3.03 (m, 1H), 2.46-2.36 (m, 1H), 1.79-1.69 (m, 1H), 1.36-1.17 (m, 1H), 1.02 (s, 3H), 0.93 (s, 3H). LCMS (m/z, Method B) ES 409.19 $[M+1]^+$.

Intermediate G: (1S,8R)-1-(6-Bromo-pyrazin-2-yl)-5-(2,6-difluoro-phenyl)-11,11-dimethyl-3,4-diaza-tricyclo[6.2.1.0*2,7*]undeca-2(7),3,5-triene

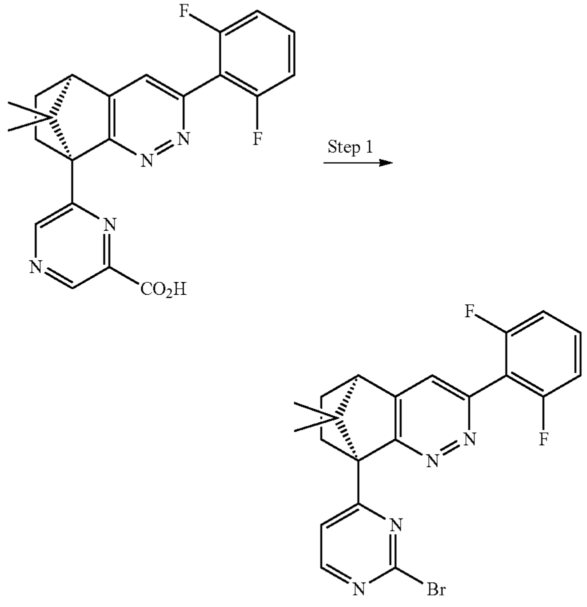

Step 1: (1S,8R)-1-(6-Bromo-pyrazin-2-yl)-5-(2,6-difluoro-phenyl)-11,11-dimethyl-3,4-diaza-tricyclo[6.2.1.0*2,7*]undeca-2(7),3,5-triene A suspension of 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyrazine-2-carboxylic acid (3.57 g, 8.75 mmol), potassium bromide (2.60 g, 21.9 mmol) and iodine pentoxide (5.84 g, 17.5 mmol) in $CH_3CN$ (50 mL) and $H_2O$ (50 mL) was heated at 40° C. for 24 h. The cooled mixture was diluted with $H_2O$ and extracted into EtOAc (3×). The combined extracts were washed with 10% sodium thiosulfate solution, brine, dried ($Na_2SO_4$) and concentrated in vacuo. Purification by chromatography (0-60% EtOAc-cyclohexane) afforded the title compound (2.28 g, 5.14 mmol) as an off white solid. $^1H$ NMR ($CDCl_3$, 300 MHz): δ 9.08 (s, 1H), 8.65 (s, 1H), 7.48 (t, J=1.4 Hz, 1H), 7.47-7.37 (m, 1H), 7.10-7.01 (m, 2H), 3.31-3.20 (m, 1H), 3.17 (d, J=4.1 Hz, 1H), 2.52-2.40 (m, 1H), 1.77-1.67 (m, 1H), 1.43-1.32 (m, 1H), 1.13 (s, 3H), 0.76 (s, 3H); LCMS (ESI) RT=4.14 min, M+H 443.0 and 445.0.

Intermediate H: 3-(2,2-Dimethyl-1,3-dioxan-5-yl)-4H-1,2,4-triazole

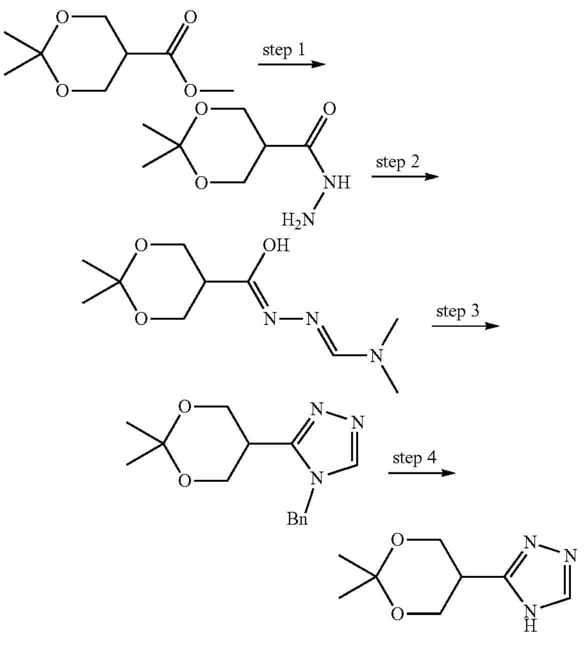

Step 1: 2.2-Dimethyl-1,3-dioxane-5-carbohydrazide

A mixture of methyl 2,2-dimethyl-1,3-dioxane-5-carboxylate (4.52 mL, 18.37 mmol) and $N_2H_4.H_2O$ (9.37 g, 184 mmol) was stirred at 25° C. for 16 h. The mixture was concentrated in vacuo to give the title compound as an oil (3.2 g). LCMS (m/z, Method C) $ES^+$ 175.1 $[M+1]^+$.

Step 2: (Z)—N—((E)-(Dimethylamino)methylene)-2,2-dimethyl-1,3-dioxane-5-carbohydrazonic Acid To a solution of the product from step 1 (3.2 g, 18.4 mmol) in MeCN (150 mL) was added DMF-DMA (4.83 mL, 36.7 mmol). The mixture was heated at 120° C. for 1 h, cooled, concentrated in vacuo and purified by FCC (0-10% MeOH/DCM) to give the title compound as a solid (4.0 g). LCMS (m/z, Method C) $ES^+$ 230.1 $[M+1]^+$.

Step 3: 4-Benzyl-3-(2,2-dimethyl-1,3-dioxan-5-yl)-4H-1,2,4-triazole

To a solution of the product from step 2 (4.0 g, 17.5 mmol) in MeCN (150 mL) was added AcOH (3 mL, 17.5 mmol) and benzylamine (2.0 g, 19.2 mmol). The mixture was heated at 120° C. for 16 h, cooled, concentrated in vacuo and purified by FCC (0-10% MeOH/DCM) to give the title compound as an oil (3.3 g). LCMS (m/z, Method C) $ES^+$ 274.1 $[M+1]^+$.

Step 4: 3-(2,2-Dimethyl-1,3-dioxan-5-yl)-4H-1,2,4-triazole

To a solution of the product from step 3 (3.3 g, 12.07 mmol) in MeOH (150 mL) was added Pd/C (500 mg), and then the mixture was stirred at RT under $H_2$ (1 atm) for 16 h. The mixture was filtered and the filtrate concentrated in vacuo, and then purified by FCC (0-10% MeOH/DCM) to give the title compound as a solid (1.08 g). LCMS (m/z, Method C) $ES^+$ 184.1 $[M+1]^+$. $^1H$ NMR (400 MHz, DMSO-$d_6$): δ 13.86-13.80 (m, 1H), 8.46 (s, 0.6H), 7.86 (s, 0.4H), 4.04-3.94 (m, 4H), 3.21-3.11 (m, 1H), 1.41 (s, 3.6H), 1.33 (s, 2.4H).

Intermediate I:
3-(2-(Methylsulfonyl)ethyl)-1H-1,2,4-triazole

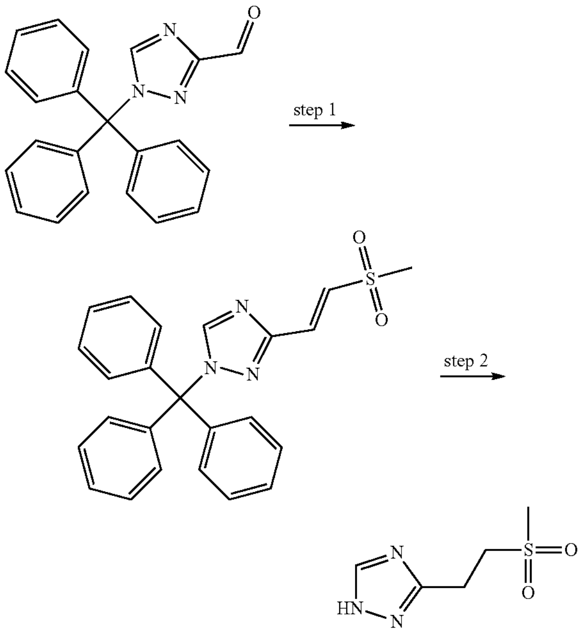

Step 1: (E)-3-(2-(Methylsulfonyl)vinyl)-1-trityl-1H-1,2,4-triazole

To a solution of diethyl methylsulfonylmethylphosphonate (5.09 g, 22.1 mmol) in THF (30 mL) at 0° C. was added t-BuOK (2.48 g, 22.1 mmol) and the mixture was stirred for 5 min. To the reaction was added 1-trityl-1,2,4-triazole-3-carbaldehyde (2.5 g, 7.37 mmol) and stirring continued at RT for 4 h. The mixture was treated with 1 N HCl to adjust to pH 6, extracted with EtOAc (×2), dried ($Na_2SO_4$) and concentrated in vacuo. The residue was purified by FCC (MeOH/DCM=0-10%) to afford the title compound as a solid (1.8 g). LCMS (m/z, Method C) $ES^+$ 243.1 [Trityl Fragment]$^+$.

Step 2:
3-(2-(Methylsulfonyl)ethyl)-1H-1,2,4-triazole

To a solution of the product from step 1 (1.3 g, 3.13 mmol) in MeOH (30 mL) was added Pd/C (500 mg), and the reaction stirred at 25° C. under $H_2$ (1 atm) for 48 h. The mixture was filtered, the filtrate concentrated in vacuo and purified by FCC (EtOAc/0-80% petroleum ether 40/60) to afford the title compound as a solid (468 mg). LCMS (m/z, Method C) $ES^+$ 176.1 $[M+1]^+$. $^1H$ NMR (400 MHz, DMSO-$d_6$): δ 13.83 (s, 1H), 8.47 (s, 0.6H), 7.87 (s, 0.4H), 3.56-3.42 (m, 2H), 3.20-3.03 (m, 2H), 3.01 (s, 3H).

Intermediate J:
3-(1H-1,2,4-Triazol-3-yl)propanamide

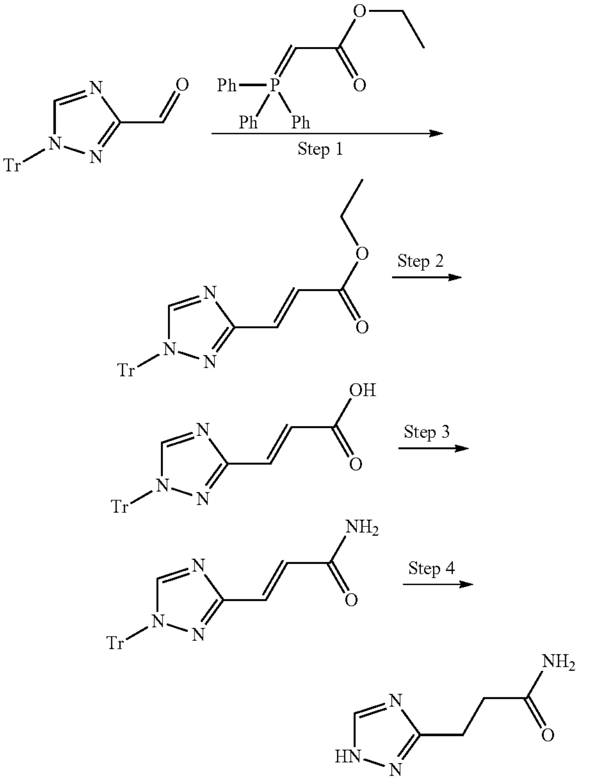

Step 1: Ethyl (E)-3-(1-trityl-1H-1,2,4-triazol-3-yl) acrylate

To a solution of 1-trityl-1,2,4-triazole-3-carbaldehyde (3.0 g, 8.87 mmol) in toluene (100 mL) was added (triphenylphosphoranylidene)-acetic acid ethylester (3.09 g, 8.87 mmol). The mixture was heated at 100° C. for 16 h, concentrated in vacuo and the residue was purified by FCC (0-20% EtOAc/petroleum ether 40/60) to give the title compound as a solid (4.0 g). LCMS (m/z, Method C) 2.19 min, $ES^+$ 243.1 [Trityl Fragment]$^+$.

Step 2: (E)-3-(1-Trityl-1H-1,2,4-triazol-3-yl)acrylic Acid

To a solution of the product from step 1 (4.0 g, 9.77 mmol) in EtOH (80 mL) was added $LiOH.H_2O$ (1.23 g, 29.31 mmol) in $H_2O$ (10 mL). Then the mixture was stirred at RT for 16 h and the solvents were removed in vacuo. AcOH was added to adjust to pH 7 and the reaction was concentrated in vacuo and purified by FCC (0-5% MeOH/DCM) to give the title compound as a solid (2.5 g). LCMS (m/z, Method C) 1.55 min, $ES^+$ 243.1 [Trityl Fragment]$^+$.

Step 3: (E)-3-(1-Trityl-1H-1,2,4-triazol-3-yl)acrylamide

To a solution of the product from step 2 (2.5 g, 6.55 mmol) in DMF (50 mL) was added HOBt (1.33 g, 9.83 mmol), N-(3-dimethylaminopropyl)-N'-ethylcarbodiimide hydrochloride (1.89 g, 9.83 mmol), $Et_3N$ (6.6 g, 65.54 mmol) and $NH_4Cl$ (3.5 g, 65.5 mmol). The mixture was stirred at RT for 16 h, diluted with water and extracted with EtOAc (×2). The combined organic layers were washed with water (×3) and brine, dried ($Na_2SO_4$) and concentrated in vacuo. The residue was purified by FCC (0-5% MeOH/DCM) to give the title compound as a solid (1.68 g). LCMS (m/z, Method C) 1.85 min, $ES^+$ 243.1 [Trityl Fragment]$^+$.

Step 4: 3-(1H-1,2,4-Triazol-3-yl)propanamide

To a solution of the product from step 3 (1.68 g, 4.42 mmol) in MeOH (100 mL) was added Pd/C (500 mg), and the mixture was stirred at RT under $H_2$ (1 atm) for 1 h. The mixture was filtered and the filtrate was concentrated in vacuo, EtOAc/Petroleum ether (1:10) was added and then sonicated for 5 min. The mixture was filtered and the filter cake was rinsed with EtOAc/Petroleum ether (1:10) and dried in vacuo to give the title compound as a solid (599.7 mg). LCMS (m/z, Method C) $ES^+$ 141.0 [M+1]$^+$. [M+H]$^+$. $^1$H NMR (400 MHz, DMSO-$d_6$): δ 13.56 (br s, 1H), 7.95 (s, 1H), 7.28 (s, 1H), 6.72 (s, 1H), 2.79 (t, J=7.6 Hz, 2H), 2.41 (t, J=7.6 Hz, 2H).

Intermediate K: 3-(1H-1,2,4-triazol-3-yl)oxetan-3-ol

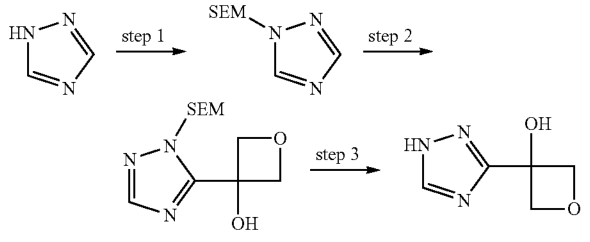

Step 1: 1-[[2-(trimethylsilyl)ethoxy]methyl]-1H-1,2,4-triazole

A solution of 1H-1,2,4-triazole (10.0 g, 145 mmol), NaH (4.92 g, 214 mmol) in THF (300 mL) was stirred for 1 h at 0° C. and then 2-(trimethylsilyl)ethoxymethyl chloride (24.3 g, 159 mmol) was added and stirring continued for another 2 h at RT. The solution was concentrated in vacuo and purified by FCC (20:1 DCM/MeOH) to afford the title compound (15 g). LCMS (m/z, Method C) $ES^+$ 200.0 [M+1]$^+$.

Step 2: 3-(1-[[2-(trimethylsilyl)ethoxy]methyl]-1H-1,2,4-triazol-3-yl)oxetan-3-ol A solution of the product from step 1 (5.00 g, 25.1 mmol) in THF (30.0 mL) was stirred for 5 min at −78° C. under $N_2$, then n-BuLi (2.5M in THF, 10.4 ml) was added dropwise. After 0.5 h, oxetan-3-one (1.99 g, 27.6 mmol) was added and stirring continued for 1 h. The solution was concentrated in vacuo and purified by FCC (DCM/MeOH, 20:1) to afford the title compound as an oil (7 g). LCMS (m/z, Method C) $ES^+$ 272.0 [M+1]$^+$.

Step 3: 3-(1H-1,2,4-triazol-3-yl)oxetan-3-ol

A solution of the product from step 2 (1.50 g, 5.5 mmol) and TFA (6.30 g, 55.3 mmol) in THF (30 mL) was stirred for 2 h. The reaction was concentrated in vacuo and purified by FCC (DCM/MeOH, 20:1) to afford the title compound as an oil (1.2 g). LCMS (m/z, Method C) $ES^+$ 142.0 [M+1]$^+$.

Intermediate L: 3-(1,1-Dioxo-thietan-3-ylmethyl)-1H-[1,2,4]triazole

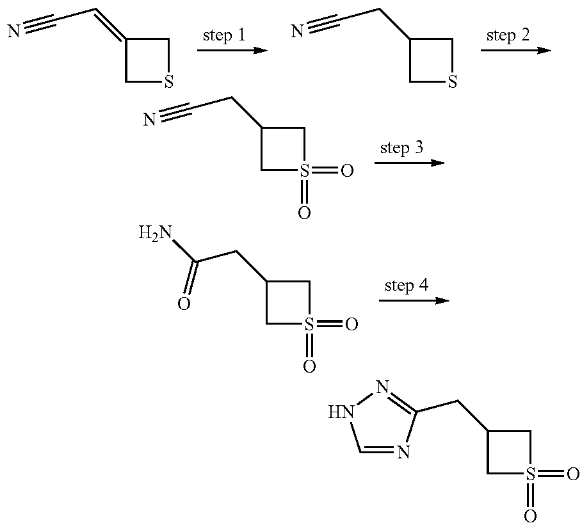

Step 1: Thietan-3-yl-acetonitrile

Sodium borohydride (2.53 g, 66.9 mmol) was added portionwise over 30 min to a solution of 2-(thietan-3-ylidene)acetonitrile (760 mg, 6.84 mmol) in MeOH (60 mL) at 0° C. After gas evolution had ceased the mixture was stirred at RT for 16 h. The mixture was concentrated in vacuo and the residue suspended in $Et_2O$. The insoluble material was removed by filtration. The filtrate was washed with water and brine, dried ($Na_2SO_4$) and concentrated in vacuo to leave an oil. FCC (0-25% EtOAc in cyclohexane) left the title compound as an oil (320 mg). $^1$H NMR (300 MHz, $CDCl_3$) δ 3.63-3.49 (m, 1H), 3.35 (dd, J=7.8, 15.0 Hz, 2H), 3.07 (dd, J=7.2, 14.2 Hz, 2H), 2.64 (t, J=6.4 Hz, 2H).

Step 2; (1,1-Dioxo-thietan-3-yl)-acetonitrile

A mixture of the product from step 1 (565 mg, 4.99 mmol), sulfamic acid (0.09 mL, 2 mmol) and hydrogen peroxide (30 wt % in water, 2.05 mL, 20 mmol) was heated at 80° C. for 30 min. The cooled mixture was diluted with water and extracted with EtOAc (×3). The combined extracts were washed with brine, dried ($Na_2SO_4$) and concentrated in vacuo to leave the title compound as a solid (374 mg). $^1$H NMR (300 MHz, DMSO-$d_6$) δ 4.37-4.29 (m, 2H), 4.03-3.95 (m, 2H), 2.97-2.90 (m, 3H).

Step 3: 2-(1,1-Dioxo-thietan-3-yl)-acetamide

A mixture of the title compound from step 2 (370 mg, 2.55 mmol) in EtOH (10 mL) and water (10 μL) was treated with hydrido(dimethylphosphinous acid-kP)[hydrogen bis(dimethylphosphinito-kP)]platinum(II) (14.11 mg, 0.0300 mmol) and heated at reflux for 16 h. The cooled mixture was concentrated in vacuo, triturated with IMS and dried in vacuo to leave the title compound as a solid (324 mg). $^1$H NMR (300 MHz, DMSO-$d_6$) δ 7.41 (br s, 1H), 6.92 (br s, 1H), 4.30-4.18 (m, 2H), 3.87-3.78 (m, 2H), 2.83-2.66 (m, 1H), 2.47 (d, J=7.6 Hz, 2H).

Step 4: 3-(1,1-Dioxo-thietan-3-ylmethyl)-1H-[1,2,4] triazole

A mixture of the title compound from step 3 (550 mg, 3.37 mmol) and DMF-DMA (0.90 mL, 6.7 mmol) in MeCN (5 mL) was heated at 60° C. for 30 min. The cooled mixture was concentrated in vacuo and redissolved in MeCN (5 mL), then AcOH (0.23 mL, 4.04 mmol) and hydrazine monohydrate (0.20 mL, 4.0 mmol) were added and the suspension heated at 60° C. for a further 1 h. The cooled mixture was concentrated in vacuo, dissolved in the minimum amount of hot methanol then left to stand at RT for 16 h. The precipitate was filtered, washed with MeOH and dried in vacuo to leave the title compound as a solid (429 mg). $^1$H NMR (300 MHz, DMSO-$d_6$) δ 13.75 (br s, 1H), 8.21 (br s, 1H), 4.32-4.21 (m, 2H), 3.98-3.87 (m, 2H), 3.05 (d, J=7.5 Hz, 2H), 2.97-2.81 (m, 1H).

Intermediate M: 3-(2-Methanesulfonyl-ethyl)-1H-[1,2,4]triazole

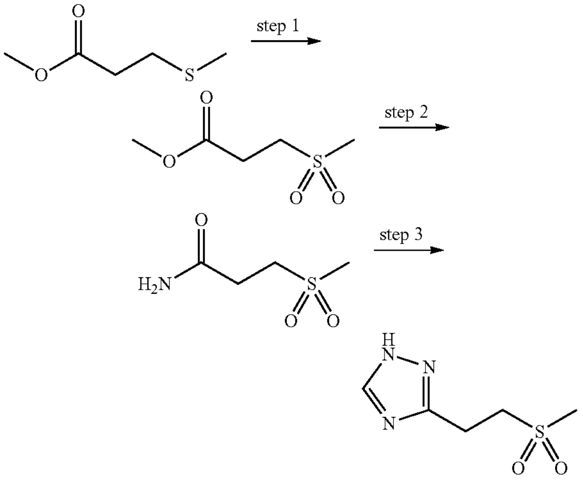

Step 1: 3-Methanesulfonyl-propionic Acid Methyl Ester

A mixture of sulfamic acid (32.62 g) in hydrogen peroxide (30 wt % in $H_2O_2$, 340 mL) was treated dropwise with methyl-3-(methylthio) propionate (123.0 g) at a rate to maintain the internal temperature at 80° C. The reaction was stirred for 0.5 h, cooled with an ice bath, diluted with water and extracted into EtOAc (×4). The combined extracts were washed with brine, dried ($Na_2SO_4$) and concentrated under vacuum to give a solid. A suspension of the title compound and 3-methanesulfonyl-propionic and 3-methanesulfonyl-propionic acid (93.1 mmol) in methanol (400 mL) at 0° C. was treated dropwise with thionyl chloride (37 mL, 510 mmol) to give a clear solution which was then heated at reflux for 0.5 h. The cooled mixture was concentrated in vacuo, triturated with MeOH and the solid collected by filtration and washed with cold MeOH to give the title compound as a solid (88.3 g). $^1$H NMR (300 MHz, DMSO-$d_6$) δ 3.64 (s, 3H), 3.39 (t, J=7.5 Hz, 2H), 3.00 (s, 3H), 2.78 (t, J=7.5 Hz, 2H).

Step 2: 3-Methanesulfonyl-propionamide

A suspension of the product from step 1 (87.5 g, 526.5 mmol) in 7N $NH_3$/MeOH (1 L) was stirred at ambient temperature for 5 h, concentrated to low volume in vacuo and the solid collected by filtration, washed with ice-cold MeOH to leave the title compound as a white solid (66.95 g). $^1$H NMR (300 MHz, DMSO-$d_6$) δ 7.45 (s, 1H), 6.96 (s, 1H), 3.29 (t, J=7.7 Hz, 2H), 2.97-2.96 (m, 3H), 2.53 (t, J=7.7 Hz, 2H).

Step 3: 3-(2-Methanesulfonyl-ethyl)-1H-[1,2,4]triazole

A suspension of the product from step 2 (63.3 g, 418.7 mmol) in $CH_3CN$ (510 mL) was treated with DMF-DMA (111.2 mL, 837.4 mmol) and heated at 60° C. for 1.25 hours. The cooled mixture was concentrated in vacuo and dissolved in $CH_3CN$ (630 mL), treated with AcOH (28.71 mL) then hydrazine monohydrate (24.49 mL). The suspension was heated at 60° C. for 1.25 hours, cooled and concentrated in vacuo. MeOH (75 mL) was added and the solid was collected by filtration, washed with ice-cold MeOH to leave the title compound as a solid (58.0 g). LCMS (m/z, Method C) $ES^+$ 176.1 $[M+1]^+$. $^1$H NMR (400 MHz, DMSO-$d_6$): δ 13.83 (s, 1H), 8.47 (s, 0.6H), 7.87 (s, 0.4H), 3.56-3.42 (m, 2H), 3.20-3.03 (m, 2H), 3.01 (s, 3H).

Intermediate N: [(5S,8S)-3-(2-fluorophenyl)-9,9-dimethyl-6,7-dihydro-5,8-methanocinnolin-8(5H)-yl]methanol

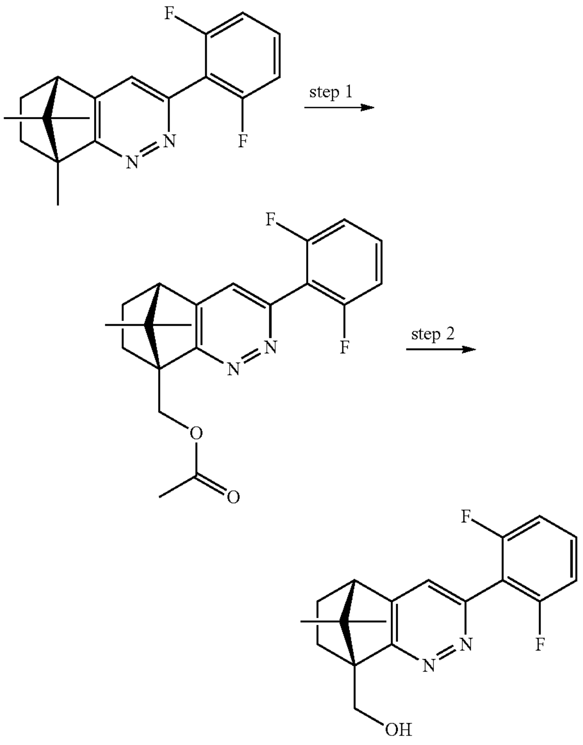

Step 1: Acetic acid (1S,8S)-5-(2,6-difluoro-phenyl)-11,11-dimethyl-3,4-diaza-tricyclo[6.2.1.0*2,7*]undeca-2(7),3,5-trien-1-ylmethyl Ester A mixture of (1R,8S)-5-(2,6-difluoro-phenyl)-1,11,11-trimethyl-3,4-diaza-tricyclo[6 0.2.1.0*2,7*]undeca-2(7),3,5-triene (19.23 g), $PhI(OAc)_2$ (24.88 g), $Pd(OAc)_2$ (765 mg, 10 mol %), AcOH (130 ml) and acetic anhydride (130 ml) were heated to 100° C. for 3 days. The reaction was filtered through Celite®, evaporated in vacuo, partitioned between $Et_2O$—$H_2O$, extracted, dried ($MgSO_4$) and concentrated to a brown oil. Purification by FCC (0-40% EtOAc-cyclohexane) to give the title compound as an oil. LCMS (m/z, Method A) 3.74 min, $ES^+$ 359 $[M+1]^+$.

Step 2: [(1S,8S)-5-(2,6-Difluoro-phenyl)-11,11-dimethyl-3,4-diaza-tricyclo[6.2.1.0*2,7*]undeca-2(7),3,5-trien-1-yl]-methanol To the product from step 1 (1.2 g, 3.35 mmol) was added to 7 ml of 1M KOH and MeOH (30 ml) and the reaction stirred at room temperature for 45 min, evaporated, partitioned between EtOAc-$H_2O$, dried ($NaSO_4$), filtered and evaporated in vacuo. Purification by FCC (10-70% EtOAc-cyclohexane) gave the title compound as a solid (952 mg). LCMS (m/z, Method A) 3.27 min, $ES^+$ 317 $[M+1]^+$.

Intermediate O: (1R,8R)-5-(2,6-Difluoro-phenyl)-11,11-dimethyl-3,4-diaza-tricyclo[6.2.1.0*2,7]undeca-2(7),3,5-triene-1-carboxylic Acid

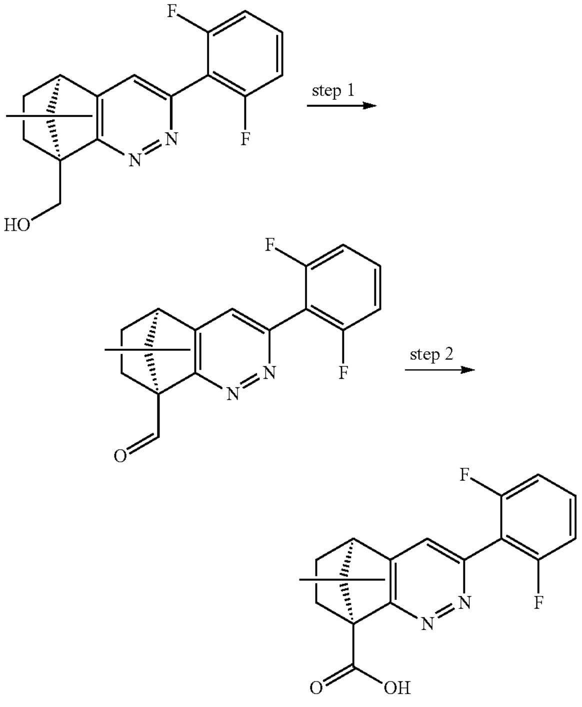

Step 1: (1R,8R)-5-(2,6-Difluoro-phenyl)-11,11-dimethyl-3,4-diaza-tricyclo[6.2.1.0*2,7*]undeca-2(7),3,5-triene-1-carbaldehyde Dess-Martin periodinane (40 g) was added in portions to an ice-cooled, stirred solution of [(1R,8R)-5-(2,6-difluoro-phenyl)-11,11-dimethyl-3,4-diaza-tricyclo[6.2.1.0*2,7*]undeca-2(7),3,5-trien-1-yl]-methanol (30 g) in DCM (450 mL) and stirred for 2 h. The resulting solution was washed with a 10% solution of sodium thiosulphate in sat. $NaHCO_3$ and the organic phase dried ($Na_2SO_4$), filtered and evaporated. The residue was dissolved in DCM and applied to a 6 cm pad of silica on a 10 cm sinter funnel and eluted with 1 L of EtOAc/cyclohexane (5:4) and the eluent evaporated to give an off-white solid which was dissolved in DCM and left to stand overnight. The resulting suspension was filtered to remove a small amount of insoluble solid and evaporated to give the title compound as an off-white solid (27.16 g). $^1H$ NMR (300 MHz, $CDCl_3$) δ 10.54 (s, 1H), 7.45-7.39 (m, 2H), 7.05 (m, 2H), 3.07 (d, J=4.1 Hz, 1H), 2.66 (ddd, J=4.1, 10.5, 12.9 Hz, 1H), 2.43-2.26 (m, 1H), 1.64-1.49 (m, 1H), 1.39-1.25 (m, 1H), 1.22 (s, 3H), 0.93 (s, 3H).

Step 2: (1R,8R)-5-(2,6-Difluoro-phenyl)-11,11-dimethyl-3,4-diaza-tricyclo[6.2.1.0*2,7*]undeca-2(7),3,5-triene-1-carboxylic Acid A solution of 80% sodium chlorite (9.44 g, 83.1 mmol) and sodium phosphate monobasic monohydrate (11.5 g) in $H_2O$ (90 mL) was added dropwise to a stirred, ice-cooled solution of the product from step 1 (15.61 g) in a mixture of 2-methyl-2-butene (31 mL), THF (80 mL) and t-butanol (310 mL). The cooling was removed and the reaction was stirred for a further 2 h and then evaporated in vacuo. The residue was dissolved in DCM/$H_2O$, acidified with AcOH, filtered through a phase separator and the filtrate evaporated and twice azeotroped with $PhCH_3$. The residue was triturated with $Et_2O$ and filtered to give the title compound as a white solid (14.55 g). $^1H$ NMR (300 MHz, $CDCl_3$) δ 7.54-7.42 (m, 2H), 7.08 (dd, J=8.1, 8.1 Hz, 2H), 3.10 (d, J=4.2 Hz, 1H), 2.78 (ddd, J=4.2, 10.6, 12.7 Hz, 1H), 2.56-2.43 (m, 1H), 1.84-1.74 (m, 1H), 1.45 (s, 3H), 1.42-1.27 (m, 1H), 0.81 (s, 3H). LCMS (m/z, Method A) $ES^+$331 [M+1]

Intermediate P: 6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrazine-2-carboxylic Acid

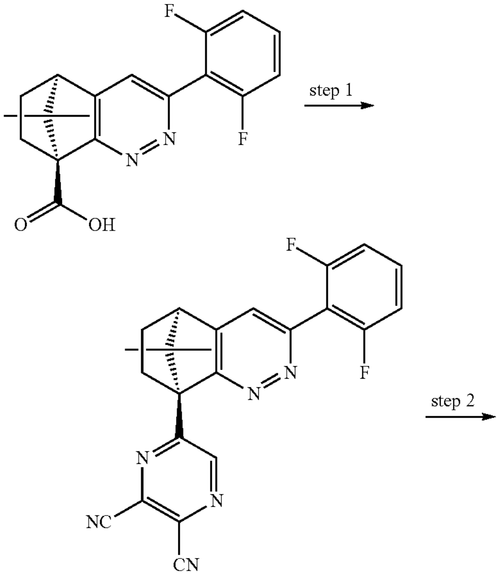

-continued

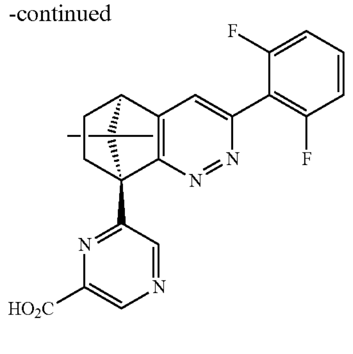

Step 1: 5-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrazine-2,3-dicarbonitrile A suspension of (1R,8R)-5-(2,6-difluoro-phenyl)-11,11-dimethyl-3,4-diaza-tricyclo[6.2.1.0*2,7*]undeca-2(7),3,5-triene-1-carboxylic acid (20.0 g) and 2,3-dicyanopyrazine (15.7 g) in water (150 mL) and MeCN (150 mL) was stirred at 70° C. and a solution of ammonium persulfate (55.3 g) in water (110 mL) added. The mixture was stirred for 5 min, then a solution of silver nitrate (4.10 g) in water (10 mL) was added and stirring continued at 70° C. for 2 h. After cooling, the mixture was extracted with DCM (×3). The combined extracts were dried ($Na_2SO_4$), filtered, evaporated in vacuo and the residue purified by FCC (20-100% DCM-cyclohexane then 0-20% EtOAc-cyclohexane). The title compound was triturated with $Et_2O$ to give a solid (16.8 g). $^1H$ NMR ($CDCl_3$, 300 MHz): δ 9.47 (s, 1H), 7.54 (t, J=1.3 Hz, 1H), 7.45 (tt, J=6.3, 8.5 Hz, 1H), 7.11-7.04 (m, 2H), 3.28-3.19 (m, 2H), 2.59-2.46 (m, 1H), 1.78 (ddd, J=4.1, 9.2, 13.2 Hz, 1H), 1.45 (ddd, J=4.0, 9.0, 12.9 Hz, 1H), 1.16 (s, 3H), 0.79 (s, 3H); LCMS (m/z) $ES^+$ 415.1 $[M+1]^+$.

Step 2: 6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrazine-2-carboxylic Acid A solution of the product from step 1 (16.8 g) in concentrated HCl (82 mL) and AcOH (410 mL) was heated with a block temperature of 106° C. under an air condenser fitted with a septum which was vented with a wide bore needle. Heating was continued for 20 h at 106° C., 125° C. for 22 h and 135° C. for 32 h. The reaction was cooled and concentrated in vacuo to give ~40 mL of a thick mobile oil. Water was added with stirring and after 1 h the solid was filtered, washed with water and dried at 50° C. under vacuum to give the title compound as a solid (14.6 g). $^1H$ NMR ($CDCl_3$, 300 MHz): δ 9.42 (s, 1H), 9.39 (s, 1H), 7.53 (s, 1H), 7.44 (tt, J=6.3, 8.4 Hz, 1H), 7.12-7.02 (m, 2H), 3.31-3.20 (m, 2H), 2.59-2.46 (m, 1H), 1.82 (ddd, J=4.0, 9.2, 13.1 Hz, 1H), 1.45 (ddd, J=3.9, 9.1, 12.9 Hz, 1H), 1.12 (s, 3H), 0.81 (s, 3H), OH signal missing; LCMS (m/z) $ES^+$ 409.1 $[M+1]^+$.

Intermediate P: [(1R,8R)-5-(2,6-difluoro-phenyl)-11,11-dimethyl-3,4-diaza-tricyclo[6.2.1.0*2,7*]undeca-2(7),3,5-trien-1-yl]-methanol

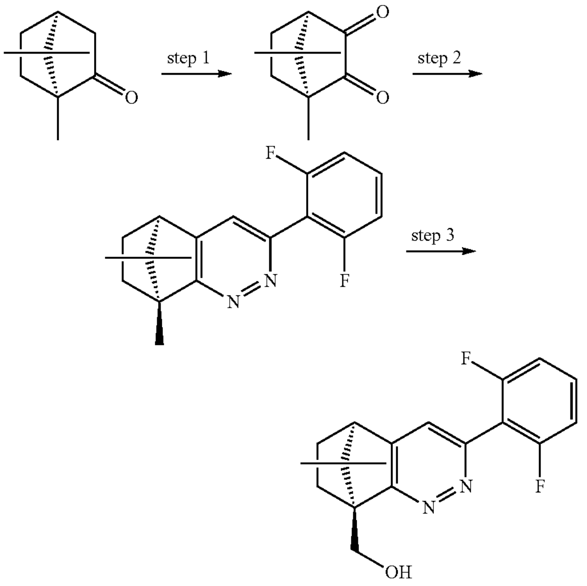

Step 1: (1S,4R)-1,7,7-Trimethyl-bicyclo[2.2.1]heptane-2,3-dione

To (S)-Camphor (2.0 kg) in $Ac_2O$ (2.0 L) was added $SeO_2$ (2.92 kg) and the solution was heated for 20 h at 130-140° C. The solution was diluted with t-butyl methyl ether (17 L), filtered and the filtrate was washed with 10% NaOH (4.0v, 2×). The organic phase was dried ($Na_2SO_4$), concentrated in vacuo and the solid slurried with n-hexane (2.0v) to give the title compound (1.89 kg).

Step 2: (1S,8R)-5-(2,6-difluoro-phenyl)-11,11-trimethyl-3,4-diaza-tricyclo[6.2.1.0*2,7*]undeca-2(7),3,5-triene To the product from step 1 (1.70 kg) in THF (17.0 L) was added 1-(2,6-difluorophenyl) ethanone (2.08 kg) and the mixture cooled to −50~−40° C. LiHMDS (13.30 L) was added dropwise at −50~−40° C. and then stirred at 5~15° C. for 20 h. The solution was diluted with t-butyl methyl ether (10v) and $NH_4Cl$(20% aq, 12v) and separated. The aqueous phase was extracted with t-butyl methyl ether (5v) and the organic phase was concentrated in vacuo. The residue was stirred in n-PrOH (17 L) and AcOH (1.84 kg) and $N_2H_4$.HOAc (4.51 kg) added at 8~15° C. and the reaction stirred for 20 h at 8-15° C. The solution was diluted with t-butyl methyl ether (10v) and $H_2O$ (4v), separated and the aqueous was extracted with EtOAc (3v).The organic phase was concentrated in vacuo and the solid slurried by TBME (2.0v) to give the title compound as a solid (1.40 kg). $^1H$ NMR (300 MHz, $CDCl_3$): δ 7.38 (tt, J=8.4, 6.2 Hz, 1H); 7.30 (s, 1H); 7.02 (t, J=7.9 Hz, 2H); 2.96 (d, J=4.3 Hz, 1H); 2.21-2.23 (m, 1H); 2.00-2.01 (m, 1H); 1.50 (s, 3H); 1.23-1.25 (m, 2H); 1.07 (s, 3H); 0.62 (s, 3H). LCMS (m/z, Method B) ES 301 $[M+1]^+$.

Step 3: [(1R,8R)-5-(2,6-difluoro-phenyl)-11,11-dimethyl-3,4-diaza-tricyclo[6.2.1.0*2,7*]undeca-2(7),3,5-trien-1-yl]-methanol The product from step 2 (1.40 kg), AcOH (21.0 L), $PhI(AcO)_2$ (5.25 kg) and $Pd(AcO)_2$ (209 g) were stirred at 105-110° C. for 48 h. The reaction mixture was concentrated to 1.5V under vacuum at 70±5° C. and the residue dissolved in MeOH (14 L). The pH of the solution was adjusted to pH=12 with 2M NaOH at 25-30° C. and the mixture was stirred at 25-30° C. for 2-4 h. The mixture was concentrated to 6V under vacuum at 40±5° C. and extracted with DCM (14 L, 10V then 7 L, 5V). The organic phase was concentrated at 40-50° C. under vacuum and the residue was purified by FCC (10-60% EtOAc in petroleum ether-) to give the title compound as a solid (501 g). MS (ESI): $[M+H]^+$ 317.0.

Intermediate Q: (1S,8R)-1-(6-Bromo-pyrazin-2-yl)-5-(2,6-difluoro-phenyl)-11,11-dimethyl-3,4-diaza-tricyclo[6.2.1.0*2,7*]undeca-2(7),3,5-triene

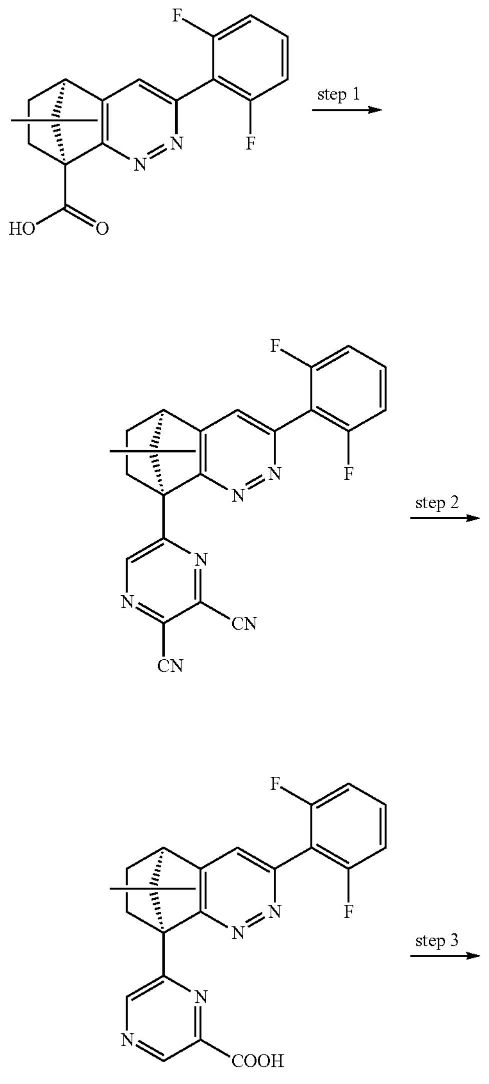

-continued

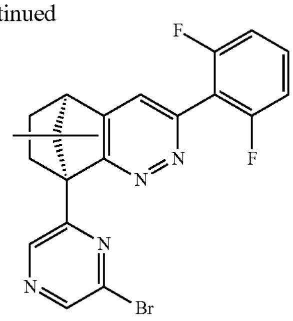

Step 1: 5-[(1S,8R)-5-(2,6-difluoro-phenyl)-11,11-dimethyl-3,4-diaza-tricyclo[6.2.1.0*2,7*]undeca-2(7),3,5-trien-1-yl]-pyrazine-2,3-dicarbonitrile A suspension of (1R,8R)-5-(2,6-difluoro-phenyl)-11,11-dimethyl-3,4-diaza-tricyclo[6.2.1.0*2,7*]undeca-2(7),3,5-triene-1-carboxylic acid (5.0 g, 15.2 mmol) in water (20 mL) and MeCN (15 mL) was heated to 70° C. A solution of $(NH_4)_2S_2O_8$(10.0 g, 43.9 mmol) in distilled water (40 mL) was added, followed by solid $AgNO_3$ (1.0 g, 5.88 mmol), added as a single portion. After 90 min, MeCN was added, then the reaction mixture was filtered, washing the cake with MeCN. The filtrate was washed with saturated brine solution (20 mL), then a solvent swap was performed to n-PrOH (total volume 20 mL). Crystallization was initiated by heating to 70° C. and adding water (20 mL) over 5 min, then cooling to 25° C., giving the title compound as a yellow solid after filtration and drying (4.30 g, 9.42 mmol); 1H NMR ($CDCl_3$, 300 MHz): δ 9.48 (s, 1H), 7.55 (t, J=1.3 Hz, 1H), 7.45 (tt, J=8.4, 6.2 Hz, 1H), 7.08 (m, 2H), 3.19-3.30 (m, 2H), 2.48-2.60 (m, 1H), 1.78 (ddd, J=13.4, 9.1, 4.1 Hz, 1H), 1.46 (ddd, J=13.4, 9.1, 4.1 Hz, 1H), 1.17 (s, 3H), 0.80 (s, 3H); LCMS (ESI, Method C) 1.34 min, $[M+H]^+$ 415.3.

b. Step 2: 6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrazine-2-carboxylic Acid A solution of 5-[(1S,8R)-5-(2,6-difluoro-phenyl)-11,11-dimethyl-3,4-diaza-tricyclo[6.2.1.0*2,7*]undeca-2(7),3,5-trien-1-yl]-pyrazine-2,3-dicarbonitrile (39 g, 94 mmol, 1.0 eq.) in conc. HCl (195 mL) and glacial AcOH (39 mL) was heated to 80° C. for 16 h, then 130° C. for 51 h. The reaction mixture was cooled to 10° C. and water (158 mL) was added. The pH was adjusted to ~3 with 10% NaOH solution and a precipitate obtained over 1 h at 5-10° C. The title compound was isolated as a beige solid after filtration, washing with water, and drying (36.5 g, 89.3 mmol); $^1H$ NMR (300 MHz, $CDCl_3$) δ 9.37 (d, J=13.8 Hz, 1H), 7.53 (t, J=1.4 Hz, 1H), 7.43 (ddd, J=9.4, 9.4, 9.4 Hz, 2H), 7.07 (td, J=4.6, 17.2 Hz, 2H), 3.30-3.20 (m, 1H), 2.57-2.45 (m, 1H), 2.06 (d, J=10.8 Hz, 1H), 1.80 (ddd, J=4.0, 9.1, 13.0 Hz, 1H), 1.48-1.38 (m, 1H), 1.12 (s, 3H), 0.80 (s, 3H); LCMS (ESI, Method B) 3.41 min, $[M+H]^+$ 407.1.

Step 3: (1S,8R)-1-(6-Bromo-pyrazin-2-yl)-5-(2,6-difluoro-phenyl)-11,11-dimethyl-3,4-diaza-tricyclo[6.2.1.0*2,7*]undeca-2(7),3,5-triene 6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrazine-2-carboxylic acid (185 g, 78.1% weight assay, 354 mmol, 1.0 equiv.) was added to a 2 L flask. Carefully, $AgNO_3$ (30.9 g, 177 mmol, 0.5 equiv) was added in one portion at 25° C., during the addition no exotherm was observed. NBS (31.5 g, 177 mmol, 0.5 equiv.) was then added portion-wise in a period of 5 min at 25° C. during which no exotherm was observed. Then 1850 mL of ACN/$H_2O$ (8.3 vol/1.7 vol) was added at 25° C. during which no exotherm was observed. A concentrated aqueous solution of hydrochloric acid (36% wt, 35.9 g, 177 mmol, 1.0 equiv.) was added at 25° C., a mild exotherm was observed and the temperature rose to 33° C. in a period of 3 min. The reaction mixture was heated to 60° C. over a period of 45 min, a mild exotherm was observed, the reaction temperature increased to 68° C. from 60° C. over a period of 20 min, and then the temperature dropped to 61° C. within 35 min and the reaction was stirred at this temperature. After 2 hours, NBS (31.5 g, 177 mmol, 0.5 equiv.) was added portion-wise at 60° C. in a period of 5 min. A mild exotherm was observed, the reaction temperature rose to 64° C. from 60° C., at the same time, a large amount of gas was generated and lasted for 10 min. After 2 hours, NBS (6.3 g, 35.4 mmol, 0.1 equiv.) was added portion-wise at 60° C. in a period of 30 seconds, a large amount of gas was generated and lasted for 1 min. After 1 hour, NBS (6.3 g, 35.4 mmol, 0.1 equiv.) was added portion-wise at 60° C. in a period of 30 seconds, a large amount of gas was generated and lasted for 1 min. The reaction mixture was then let to stir for 1.5 h and cooled to room temperature. The reaction was then filtered and the cake was washed with 185 mL of acetonitrile twice. The pH of the solution was then was then adjusted to 9, by adding an aqueous solution of 10 wt % NaOH (342 g) dropwise at 10-15° C. in a period of 30 min. The mixture was then stirred for 20 min. The phases were then separated and the organic layer was washed with a saturated aqueous solution of $Na_2S_2O_3$ aq (435 g). 1645 g of crude material in ACN was concentrated under vacuum at 45° C. to ~700 g, then n-PrOH (~406 g) was added. This process was repeated until the acetonitrile content was less than 2%. n-PrOH was added to the crude mixture at 80° C. until all components were soluble. Water (930 g) was added to this solution dropwise over the course of 2 h. This solution was then stirred at 80° C. for 0.5 h. The mixture was then gradually cooled to room temperature overnight. Then the solution was cooled to 5° C. and stirred for 1 h. The product was then filtered and washed with cold n-PrOH/water (1:1.5, 280 ml). The solid was then dried under vacuum to furnish 119 g of (1S,8R)-1-(6-Bromo-pyrazin-2-yl)-5-(2,6-difluoro-phenyl)-11,11-dimethyl-3,4-diaza-tricyclo[6.2.1.0*2,7*]undeca-2(7),3,5-triene in 74.2% yield.

$^1H$ NMR (300 MHz, $CDCl_3$) δ 9.09 (s, 1H), 8.66 (s, 1H), 7.49 (t, J=1.3 Hz, 1H), 7.43 (tt, J=8.4, 6.2 Hz, 1H), 7.07 (m, 2H), 3.27 (ddd, J=13.2, 10.4, 4.0 Hz, 1H), 3.19 (d, J=4.2 Hz, 1H), 2.47 (ddt, J=12.7, 10.7, 4.3 Hz, 1H), 1.72 (ddd, J=13.3, 9.1, 4.0 Hz, 1H), 1.38 (ddd, J=12.9, 8.9, 3.6 Hz, 1H), 1.13 (s, 3H), 0.77 (s, 3H); LCMS (ESI, method C) 1.55 min, $[M+H]^+$ 443.1 and 445.1.

Example 1: 3-(4-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrazol-1-yl)-propionamide

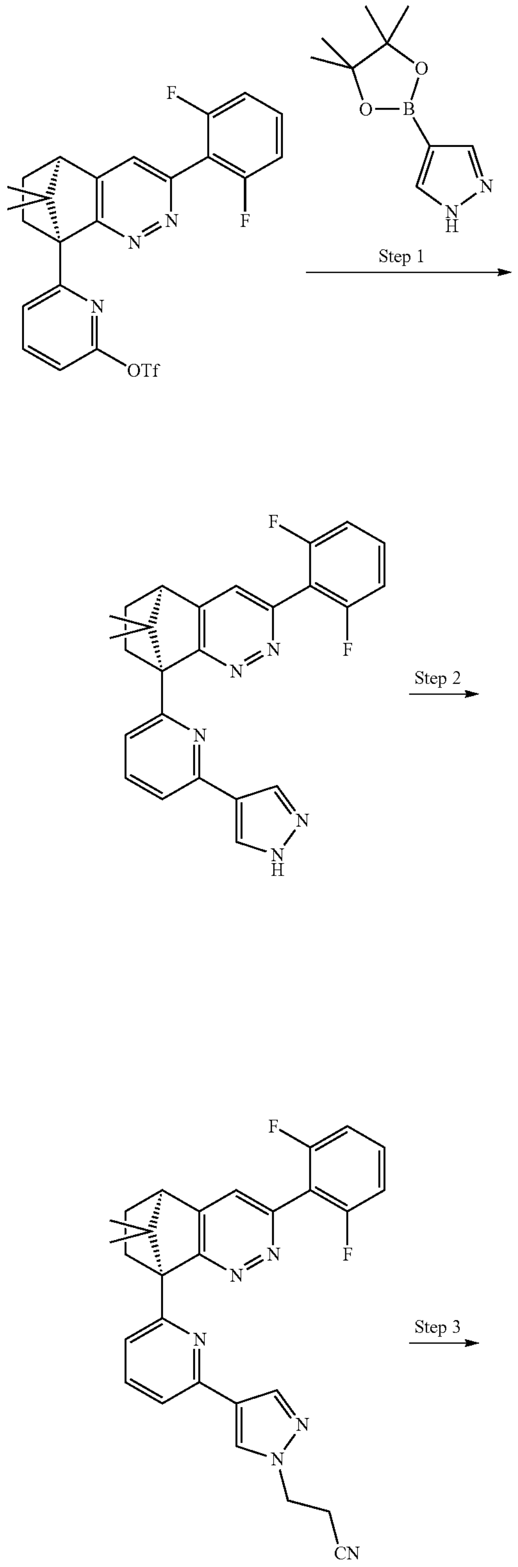

-continued

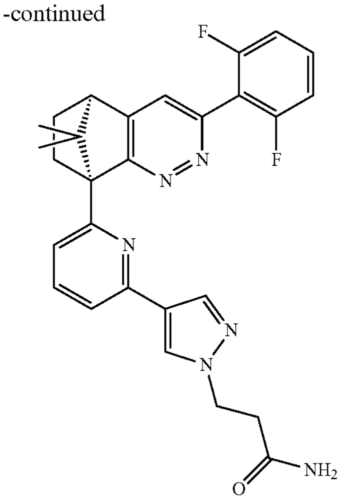

Step 1: (1S,8R)-5-(2,6-Difluoro-phenyl)-11,11-dimethyl-1-[6-(1H-pyrazol-4-yl)-pyridin-2-yl]-3,4-diaza-tricyclo[6.2.1.0*2,7*]undeca-2(7),3,5-triene A 20 mL microwave vial was charged with trifluoromethanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyridin-2-yl ester (1.0 g, 1.96 mmol), 4-pyrazole boronic acid pinacol ester (950 mg, 4.90 mmol), $(Ph_3P)_4Pd$ (230 mg, 200 μmol), DIPEA (1.03 mL, 5.88 mmol), toluene (8 mL) and IMS (8 mL), degassed, purged with Ar and heated at 150° C. using MW. The cooled mixture was diluted with EtOAc, washed with water and brine, dried ($Na_2SO_4$) and concentrated in vacuo. Purification by FCC (0-100% EtOAc in cyclohexane) gave the title compound as a solid (504 mg). $^1H$ NMR ($CDCl_3$, 400 MHz): δ 8.11 (br s, 2H), 7.74-7.67 (m, 2H), 7.44 (s, 1H), 7.43-7.35 (m, 2H), 7.08-7.00 (m, 2H), 3.46-3.38 (m, 1H), 3.12 (d, J=4.1 Hz, 1H), 2.50-2.40 (m, 1H), 1.74-1.65 (m, 1H), 1.39-1.30 (m, 1H), 1.15 (s, 3H), 0.75 (s, 3H). LCMS (m/z, Method B) $ES^+$430.1 $[M+1]^+$.

Step 2: 3-(4-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrazol-1-yl)-propionitrile A mixture of the product from step 1 (125 mg, 291 μmol), acrylonitrile (95 μL, 1.45 mmol) and 1,8-diazabicycloundec-7-ene (130 μL, 872 μmol) in MeCN (2 mL) was heated at 80° C. for 18 h. The cooled mixture was diluted with EtOAc, washed with water, brine, dried ($Na_2SO_4$) and concentrated in vacuo. Purification by FCC (0-100% EtOAc in cyclohexane) gave the title compound as a residue (135 mg). $^1H$ NMR ($CDCl_3$, 400 MHz): δ 8.07 (s, 1H), 8.03 (s, 1H), 7.75-7.67 (m, 2H), 7.45 (s, 1H), 7.44-7.37 (m, 2H), 7.09-7.00 (m, 2H), 4.46 (t, J=6.7 Hz, 2H), 3.47-3.37 (m, 1H), 3.13 (d, J=4.1 Hz, 1H), 3.02 (t, J=6.7 Hz, 2H), 2.51-2.42 (m, 1H), 1.73-1.65 (m, 1H), 1.39-1.31 (m, 1H), 1.15 (s, 3H), 0.76 (s, 3H). LCMS (m/z, Method B) ES 483.2 $[M+1]^+$.

Step 3: 3-(4-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrazol-1-yl)-propionamide A mixture of the product from step 2 (134 mg, 278 μmol) and hydrido(dimethylphosphinous acid-kP)[hydrogen bis(dimethylphosphinito-kP)]platinum (II) (5 mg, 12 μmol) in IMS (5 mL) and $H_2O$ (0.5 mL) was heated at reflux for 6 h. The cooled mixture was concentrated in vacuo and the residue purified by FCC (0-10% MeOH in DCM) to afford the title compound as a foam (115 mg). $^1H$ NMR ($CDCl_3$, 400 MHz): δ 8.02 (s, 1H), 7.99 (s, 1H), 7.71-7.67 (m, 2H), 7.47-7.35 (m, 3H), 7.08-7.00 (m, 2H), 5.89 (br s, 1H), 5.34 (br s, 1H), 4.50 (t, J=6.5 Hz, 2H), 3.46-3.38 (m, 1H), 3.13 (d, J=4.1 Hz, 1H), 2.86 (t, J=6.5 Hz, 2H), 2.50-2.41 (m, 1H), 1.72-1.64 (m, 1H), 1.39-1.31 (m, 1H), 1.15 (s, 3H), 0.75 (s, 3H). LCMS (m/z, Method B) $ES^+$ 501.2 $[M+1]^+$.

Example 2: (1S,8R)-5-(2,6-difluorophenyl)-1-[2-[3-(2-methanesulfonylethyl)-1H-1,2,4-triazol-1-yl]pyridin-4-yl]-11,11-dimethyl-3,4-diazatricyclo[6.2.1.0^[2,7]]undeca-2(7),3,5-triene

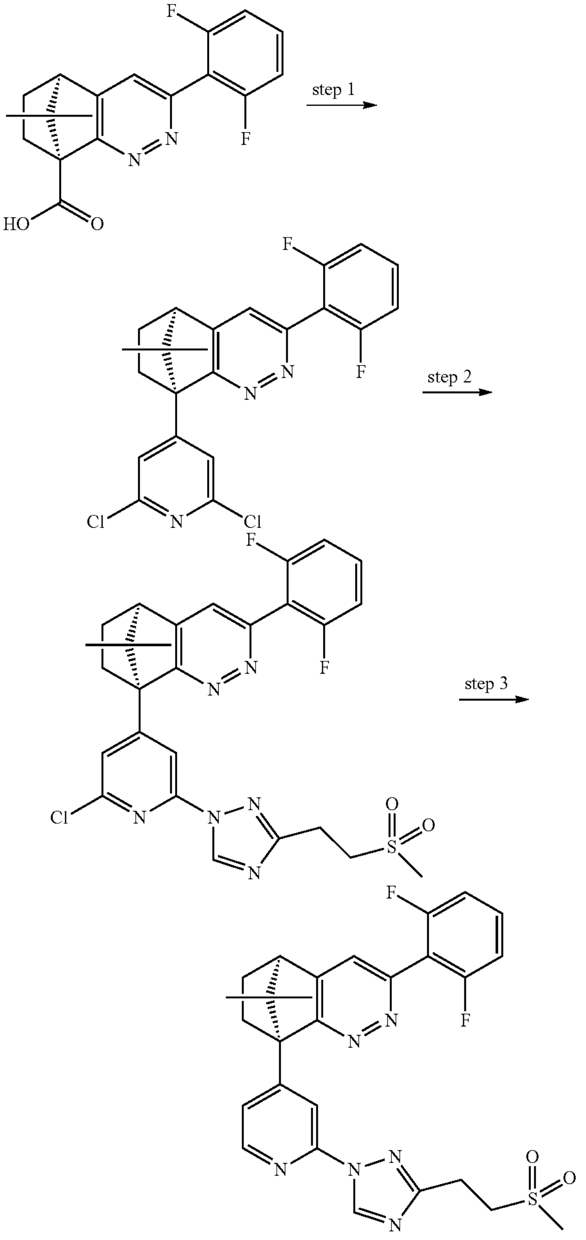

Step 1: (1S,8R)-1-(2,6-dichloropyridin-4-yl)-5-(2,6-difluorophenyl)-11,11-dimethyl-3,4-diazatricyclo [6.2.1.0^[2,7]]undeca-2(7),3,5-triene Under $N_2$, a solution of (1R,8R)-5-(2,6-difluorophenyl)-11,11-dimethyl-3,4-diazatricyclo[6.2.1.0^2,7]]undeca-2(7), 3,5-triene-1-carboxylic acid (1.00 g, 3.03 mmol), 2,6-dichloropyridine (1.78 g, 12.0 mmol) and silver nitrate (2.0 g, 11.8 mmol) in 10% aq. sulfuric acid (5 mL) was stirred for 3 h at 110° C. Then a freshly prepared solution of ammonium persulfate (2.76 g, 12.1 mmol) in water (5 mL) was added dropwise to the mixture during 15 min at 110° C. The resulting solution was stirred for 30 h at 110° C. The solids were collected by filtration and washed with DCM/MeOH (1:1). The filtrate was concentrated in vacuo and the crude product purified by FCC (EtOAc/petroleum ether, 2:3) to afford mixture of (1S,8R)-1-(2,6-dichloropyridin-4-yl)-5-(2,6-difluorophenyl)-11,11-dimethyl-3,4-diazatricyclo [6.2.1.0^2,7]]undeca-2(7),3,5-triene and (1S,8R)-1-(2,6-dichloropyridin-3-yl)-5-(2,6-difluorophenyl)-11,11-dimethyl-3,4-diazatricyclo[6.2.1.0^2,7]]undeca-2(7),3,5-triene as a solid (300 mg). LCMS (ESI) RT=4.01 min, $[M+H]^+$ 432.

Step 2: (1S,8R)-1-[2-chloro-6-[3-(2-methanesulfonylethyl)-1H-1,2,4-triazol-1-yl]pyridin-4-yl]-5-(2,6-difluorophenyl)-11,11-dimethyl-3,4-diazatricyclo [6.2.1.0^[2,7]]undeca-2(7),3,5-triene A solution of the products from step 1 (150 mg, 0.348 mmol), 3-(2-methanesulfonylethyl)-1H-1,2,4-triazole (68 mg, 0.386 mmol) and $K_2CO_3$ (96 mg, 0.695 mmol) in DMF (1 mL) was stirred for 20 h at 80° C. The reaction was purified by reversed-phase column with $MeCN/H_2O$ (5-60%) to afford the title compound as a solid (60 mg). (400 MHz, $CD_3OD$): δ 9.63 (s, 2H), 8.16 (s, 2H), 7.85 (s, 1H), 7.61 (t, J=8.5, 6.4 Hz, 1H), 7.22 (m, 2H), 3.72-3.63 (m, 4H), 3.46-3.33 (m, 5H), 3.21 (m, 1H), 3.05 (s, 6H), 2.65 (m, 1H), 1.77 (m, 1H), 1.49 (m, 1H), 1.18 (s, 3H), 0.85 (s, 3H). LCMS (ESI) RT=4.01 min, $[M+H]^+$ 571. (1S,8R)-1-[2,6-bis[3-(2-methanesulfonylethyl)-1H-1,2,4-triazol-1-yl]pyridin-4-yl]-5-(2,6-difluorophenyl)-11,11-dimethyl-3,4-diazatricyclo [6.2.1.0^2,7]]undeca-2(7),3,5-triene was also obtained as a white solid. LCMS (ESI) RT=4.01 min, $[M+H]^+$ 710.

Step 3: (1S. 8R)-5-(2,6-difluorophenyl)-1-[2-[3-(2-methanesulfonylethyl)-1H-12,4-triazol-1-yl]pyridin-4-yl]-11,11-dimethyl-3,4-diazatricyclo[6.2.1.0^[2,7]] undeca-2(7),3,5-triene A solution of the product from step 2 (60 mg, 0.11 mmol), AcOH (0.05 mL, 0.87 mmol), and Pd/C (10 mg) in EtOH (2 mL) was stirred under hydrogen for 10 h at 60° C. The reaction was purified by reversed-phase column with $MeCN/H_2O$ (5-60%) to afford the title compound as a solid (6.7 mg). (400 MHz, $CD_3OD$): δ 9.34 (s, 1H), 8.60 (d, J=5.2 Hz, 1H), 8.17 (d, J=1.5 Hz, 1H), 7.82 (s, 1H), 7.73-7.68 (m, 1H), 7.62-7.58 (m, 1H), 7.21 (t, J=8.1 Hz, 2H), 3.65 (dd, J=9.1, 6.7 Hz, 2H), 3.42-3.33 (m, 3H), 3.23-3.11 (m, 1H), 3.04 (s, 3H), 2.68-2.55 (m, 1H), 1.69 (m, H), 1.45 (m, 1H), 1.12 (s, 3H), 0.80 (s, 3H). LCMS (ESI) RT=4.01 min, $[M+H]^+$ 537.

Example 3: (1S,8R)-6-Chloro-5-(2,6-difluoro-phenyl)-1-{2-[3-(2-methanesulfonyl-ethyl)-[1,2,4]triazol-1-yl]-pyrimidin-4-yl}-11,11-dimethyl-3,4-diaza-tricyclo[6.2.1.0*2,7*]undeca-2(7),3,5-triene

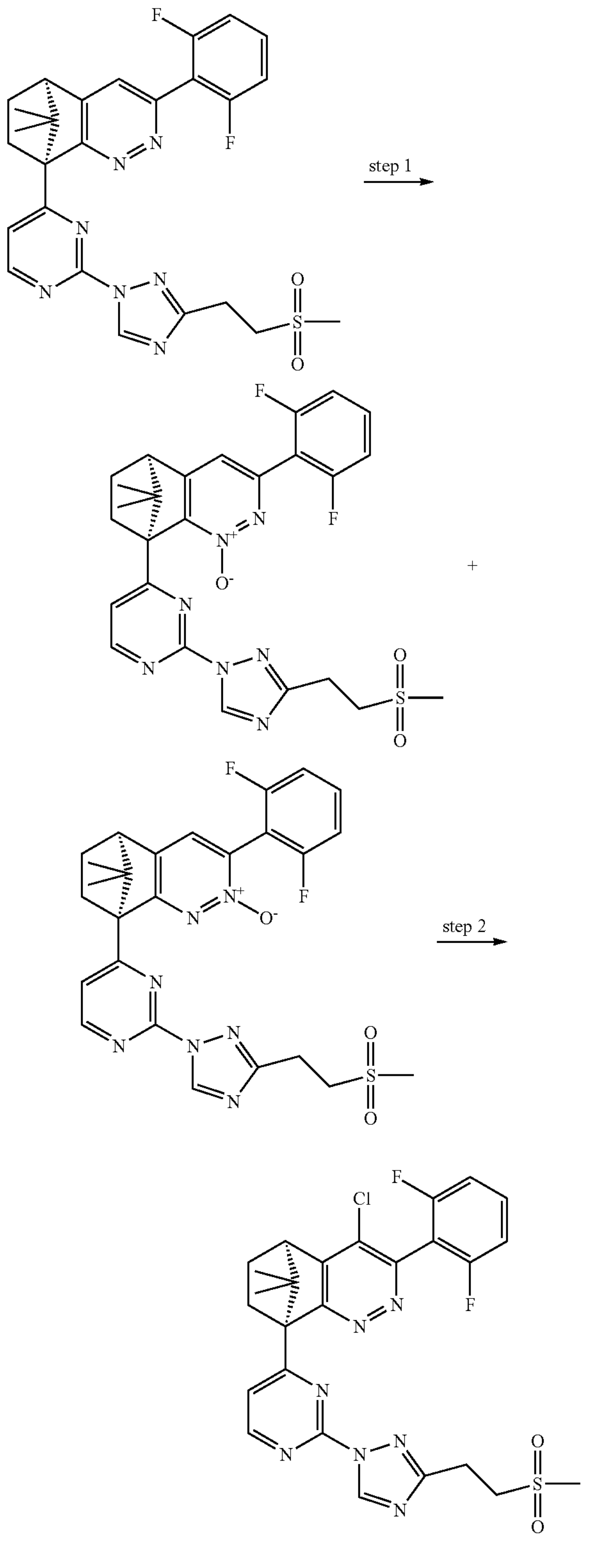

Step 1: (1S,8R)-5-(2,6-Difluoro-phenyl)-1-{2-[3-(2-methanesulfonyl-ethyl)-[1,2,4]triazol-1-yl]-pyrimidin-4-yl}-11,11-dimethyl-3,4-diaza-tricyclo[6.2.1.0*2,7*]undeca-2(7),3,5-triene 3-oxide and (1S,8R)-5-(2,6-difluoro-phenyl)-1-{2-[3-(2-methanesulfonyl-ethyl)-[1,2,4]triazol-1-yl]-pyrimidin-4-yl}-11,11-dimethyl-3,4-diaza-tricyclo[6.2.1.0*2,7*]undeca-2(7),3,5-triene 4-oxide A solution of (1S,8R)-5-(2,6-difluoro-phenyl)-1-{2-[3-(2-methanesulfonyl-ethyl)-[1,2,4]triazol-1-yl]-pyrimidin-4-yl}-11,11-dimethyl-3,4-diaza-tricyclo[6.2.1.0*2,7*]undeca-2(7),3,5-triene (69 mg, 0.30 mmol) in DCM (2 mL) was stirred at RT for 2.5 h. Aq NaOH solution (1M) was added, the organics passed through a hydrophobic frit and concentration in vacuo to give the title compounds as an oil (163 mg).

Step 2: (1S,8R)-6-Chloro-5-(2,6-difluoro-phenyl)-1-{2-[3-(2-methanesulfonyl-ethyl)-[1.2.4]triazol-1-yl]-pyrimidin-4-yl}-11,11-dimethyl-3,4-diaza-tricyclo[6.2.1.0*2,7*]undeca-2(7),3,5-triene To a mixture of DMF-toluene (1:1, 1 mL) was added $POCl_3$ (0.050 mL, 0.50 mmol) and the solution stirred at RT for 5 min. A solution of the products from step 1 (0.25 mmol) in DMF-toluene (1:1, 1 mL) was added and the solution stirred at RT for 45 min, at 50° C. for 2 h and at 75° C. for 16 h. The cooled solution was diluted with $H_2O$ and extracted with EtOAc. The organics were passed through a hydrophobic frit and concentrated under vacuum to leave an oil. FCC (50-100% THF in cyclohexane) and HPLC (30-60% MeCN in water, 0.1% $HCO_2H$, 18 min); concentration of the desired fractions in vacuo, followed by extraction with DCM (×2) gave an organic phase which was passed through a hydrophobic frit and concentrated in vacuo to leave a solid. The solid was freeze-dried from MeCN-water (1:1) to leave the title compound as a solid (12 mg). $^1H$ NMR ($CDCl_3$, 400 MHz): δ 9.18 (s, 1H), 8.87 (d, J=5.4 Hz, 1H), 7.95 (d, J=5.1 Hz, 1H), 7.54-7.45 (m, 1H), 7.08 (m, 2H), 3.63 (dd, J=6.6, 9.1 Hz, 2H), 3.49-3.45 (m, 3H), 3.33 (ddd, J=4.0, 10.4, 13.2 Hz, 1H), 2.98 (s, 3H), 2.60-2.52 (m, 1H), 1.82 (ddd, J=4.1, 9.1, 13.2 Hz, 1H), 1.50 (ddd, J=3.9, 9.2, 13.0 Hz, 1H), 1.23 (s, 3H), 0.83 (s, 3H). LCMS (ESI) RT=4.01 min, $[M+H]^+$ 572.1

Example 4: (1S,8R)-5-(2,6-Difluoro-phenyl)-1-{2-[3-(2-methanesulfonyl-ethyl)-[1,2,4]triazol-1-yl]-pyrimidin-4-yl}-11,11-dimethyl-3,4-diaza-tricyclo[6.2.1.0*2,7*]undeca-2(7),3,5-triene

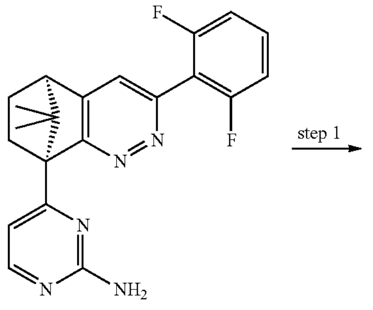

-continued

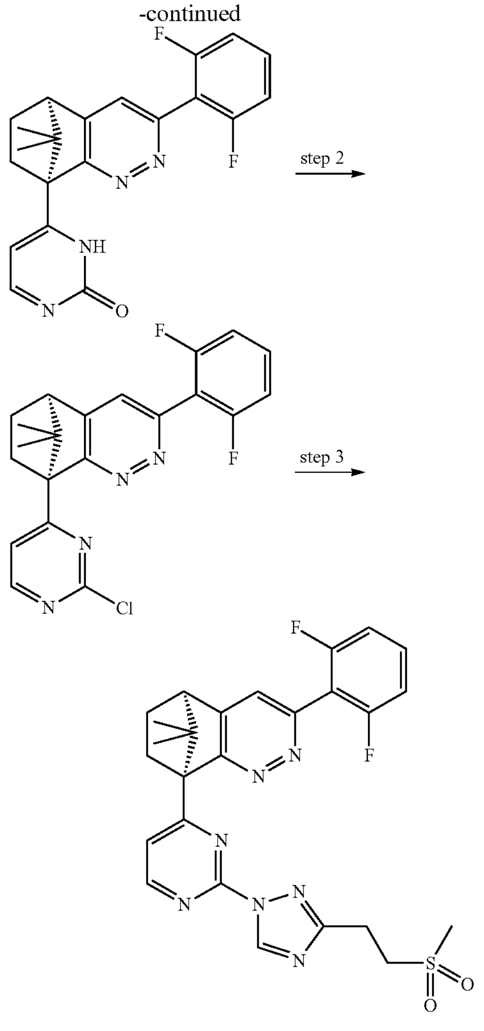

Step 1: 6-[(1S,8R)-5-(2,6-Difluoro-phenyl)-11,11-dimethyl-3,4-diaza-tricyclo[6.2.1.0*2,7*]undeca-2(7),3,5-trien-1-yl]-1H-pyrimidin-2-one A solution of 4-[(1S,8R)-5-(2,6-difluoro-phenyl)-11,11-dimethyl-3,4-diaza-tricyclo[6.2.1.0*2,7*]undeca-2(7),3,5-trien-1-yl]-pyrimidin-2-ylamine (9.55 g, 25.2 mmol) in AcOH (80 mL) and water (40 mL) at 0° C. was treated dropwise with a solution of sodium nitrite (3.47 g, 50.3 mmol) in water (10 mL). The mixture was stirred for 1 h at 0° C. then heated at 100° C. for 1 h, cooled, concentrated in vacuo and partitioned between DCM and an aq. sat. solution of $NaHCO_3$. The DCM phase was washed with $H_2O$ and brine, dried ($Na_2SO_4$) and concentrated in vacuo to afford the title compound as a solid (12.5 g). $^1H$ NMR (DMSO-$d_6$) δ 7.96 (d, J=6.5 Hz, 1H), 7.79 (s, 1H), 7.62 (m, 1H), 7.30 (m, 2H), 6.55 (d, J=6.5 Hz, 1H), 3.24 (d, J=4.0 Hz, 1H), 3.03 (m, 1H), 2.30-2.43 (m, 1H), 1.44 (ddd, J=12.6, 8.8, 3.8 Hz, 1H), 1.15-1.25 (m, 1H), 1.07 (s, 3H), 0.73 (s, 3H), LCMS (m/z, Method A) 3.01 min, $ES^+$ 381 $[M+1]^+$.

Step 2: (1S,8R)-1-(2-Chloro-pyrimidin-4-yl)-5-(2,6-difluoro-phenyl)-11,11-dimethyl-3,4-diaza-tricyclo[6.2.1.0*2,7*]undeca-2(7),3,5-triene A solution of the product from step 1 (13.3 g, 34.8 mmol) in $POCl_3$ (100 mL) was heated at 100° C. for 2.5 h. The cooled mixture was concentrated in vacuo and the residue partitioned between EtOAc and a sat. solution of $NaHCO_3$. The organic phase was washed with water, brine, dried ($Na_2SO_4$) and the solvent passed through a silica pad washing through with 5 volumes of EtOAc. The combined EtOAc was concentrated in vacuo and recrystallized from EtOAc to afford the title compound as a solid (6.18 g). The filtrate was concentrated and triturated with $Et_2O$ to afford a second crop of the title compound as a solid (3.35 g). $^1H$ NMR ($CDCl_3$) δ 8.65 (d, J=5.2 Hz, 1H), 7.95 (d, J=5.2 Hz, 1H), 7.50 (t, J=1.3 Hz, 1H), 7.43 (tt, J=8.4, 6.4 Hz, 1H), 7.07 (m, 2H), 3.31 (ddd, J=13.1, 10.6, 4.1 Hz, 1H), 3.18 (d, J=4.1 Hz, 1H), 2.49 (ddt, J=12.6, 10.6, 4.1 Hz, 1H), 1.69 (ddd, J=13.3, 9.1, 4.1 Hz, 1H), 1.39 (ddd, J=13.0, 8.8, 4.1 Hz, 1H), 1.19 (s, 3H), 0.72 (s, 3H); LCMS (ESI) m/z 399 $[M+H]^+$, 4.05 min.

Step 3: (1S,8R)-5-(2,6-Difluoro-phenyl)-1-{2-[3-(2-methanesulfonyl-ethyl)-[1,2,4]triazol-1-yl]-pyrimidin-4-yl}-11,11-dimethyl-3,4-diaza-tricyclo[6.2.1.0*2,7*]undeca-2(7),3,5-triene A mixture of the product from step 2 (1.0 g, 2.51 mmol), 3-(2-methanesulfonyl-ethyl)-1H-[1,2,4]triazole (571 mg, 3.26 mmol) and $K_2CO_3$ (468 mg, 3.39 mmol) in DMSO (6 mL) was heated at 50° C. for 24 h. The cooled reaction mixture was poured onto ice cold water and extracted into EtOAc (×3). The combined extracts were washed with water (×2), brine, dried ($Na_2SO_4$) and concentrated in vacuo. The residue was taken up in a minimum amount of IMS and stirred at RT for 16 h. The precipitate was collected by filtration, washed with IMS and dried at 50° C. in vacuo to leave the title compound as a solid (3.11 g). $^1H$ NMR (400 MHz, $CDCl_3$) δ 9.19 (s, 1H), 8.86 (d, J=5.2 Hz, 1H), 8.00 (d, J=5.2 Hz, 1H), 7.52 (t, J=1.2 Hz, 1H), 7.48-7.40 (m, 1H), 7.11-7.03 (m, 2H), 3.64 (dd, J=6.7, 9.2 Hz, 2H), 3.50-3.45 (m, 2H), 3.29 (ddd, J=4.0, 10.6, 13.1 Hz, 1H), 3.22 (d, J=4.0 Hz, 1H), 2.98 (s, 3H), 2.58-2.49 (m, 1H), 1.79 (ddd, J=4.1, 9.1, 13.1 Hz, 1H), 1.44 (ddd, J=3.9, 9.1, 12.8 Hz, 1H), 1.21 (s, 3H), 0.79 (s, 3H). LCMS (m/z, Method B) 3.92 min, $ES^+$ 538.2 $[M+1]^+$.

Example 5: N-(5-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrimidin-2-yl)-methanesulfonamide Sodium Salt

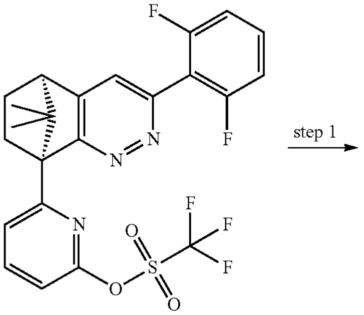

-continued

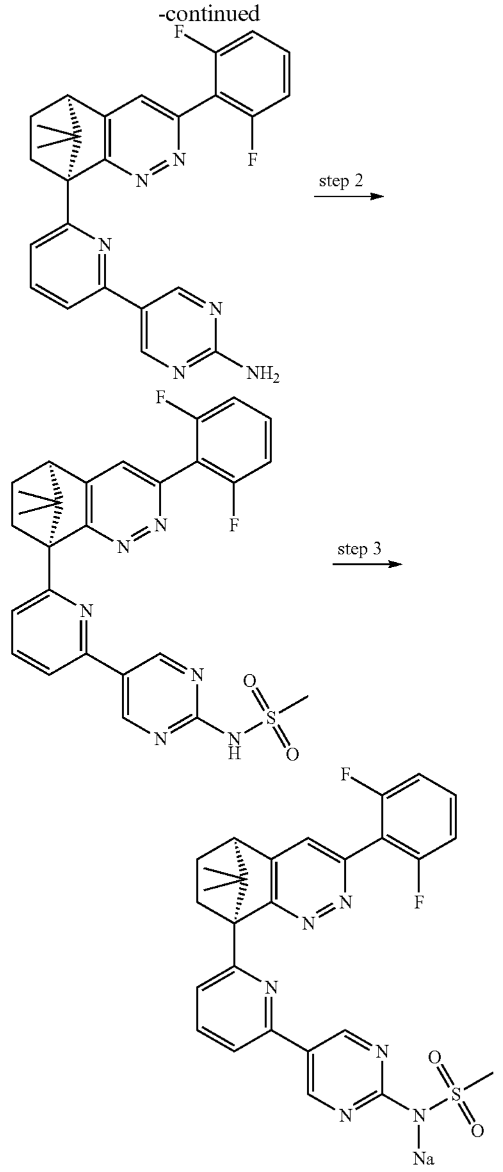

Step 1: 5-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrimidin-2-ylamine $N_2$ was bubbled through a mixture of dioxane-water (2:1, 300 mL) for 30 min. Separately, a flask was charged with trifluoro-methanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyridin-2-yl ester (51 g, 100 mmol), (2-aminopyrimidin-5-yl)boronic acid (14.5 g, 105 mmol), $(Ph_3P)_4Pd$ (576 mg, 0.50 mmol) and $K_2CO_3$ (41.3 g, 299 mmol), then evacuated and purged with $N_2$ thrice. The solvent was injected into the flask and the yellow solution stirred at 90° C. under $N_2$ for 1 h. The aqueous layer was removed via cannula, then the organics allowed to cool to RT over 1 h, then cooled to 0° C. The resulting precipitate was filtered and washed with EtOAc. The solid was dried under vacuum at 60° C. for 3 days to leave the title compounds as a white crystalline solid (36.3 g) The combined organics were concentrated in vacuo, slurried in hot (60° C.) EtOAc for 1 h, then cooled to 0° C. and filtered. The solid was washed with EtOAc then dried under vacuum at 60° C. for 3 days to leave additional title compound as an off-white solid (12.4 g). LCMS (Method C) 1.44 min, $ES^+$ 457 $[M+1]^+$.

Step 2: N-(5-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrimidin-2-yl)-methanesulfonamide To a suspension of the product from step 1 (44.1 g, 96.7 mmol) in dry 1,2-dimethoxyethane (500 mL) at RT was added sodium tert-butoxide (27.9 g, 290 mmol) in one portion (exotherm to 24° C.) and the resulting mixture stirred at RT for 5 min, then sonicated for 1 min. The mixture was poured into a pre-cooled (0° C.) solution of methanesulfonyl chloride (15 mL, 193 mmol) in dry 1,2-dimethoxyethane (100 mL) (CARE: exotherm to 35° C.). The suspension was stirred at RT for 10 min, then aq HCl solution (1 M) was added and the mixture concentrated in vacuo to remove most of the organics. The mixture was extracted with DCM (×2), then the combined organics passed through a hydrophobic frit and concentrated in vacuo to leave a solid. Flash chromatography (silica 420 g, 2-12% THF in DCM) gave clean fractions and mixed fractions. The clean fractions were concentrated in vacuo to give a solid that was suspended in MeCN and stirred at reflux for 1 h. The suspension was cooled to 0° C., filtered and dried in vacuo to leave the title compound as a solid (27.4 g). The mixed fractions were concentrated in vacuo to leave a foam that was dissolved in MeCN and stirred at RT for 15 min. The suspension was cooled to 0° C., then filtered and dried in vacuo to leave additional title compound as a white solid (9.04 g). LCMS (Method B) 4.61 min, $ES^+$ 535.2 $[M+1]^+$. $^1H$ NMR (400 MHz, $CDCl_3$) δ 10.85 (br s, 1H), 9.38 (s, 2H), 7.94 (dd, J=0.8, 7.9 Hz, 1H), 7.86 (t, J=7.8 Hz, 1H), 7.70 (dd, J=1.0, 7.8 Hz, 1H), 7.48 (s, 1H), 7.46-7.38 (m, 1H), 7.10-7.01 (m, 2H), 3.54 (s, 3H), 3.47 (ddd, J=4.0, 10.5, 13.1 Hz, 1H), 3.17 (d, J=4.0 Hz, 1H), 2.54-2.44 (m, 1H), 1.73 (ddd, J=4.0, 9.1, 13.1 Hz, 1H), 1.38 (ddd, J=3.8, 9.0, 12.6 Hz, 1H), 1.17 (s, 3H), 0.77 (s, 3H).

Step 3: N-(5-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrimidin-2-yl)-methanesulfonamide Sodium Salt To a suspension of the product from step 2 (36.5 g, 68.2 mmol) in MeOH (250 mL) was added aq. NaOH solution (1M, 68.2 mL) and the mixture stirred at RT for 30 min, then sonicated for 10 min and stirred at RT for 30 min. The mixture was filtered through Celite®, concentrated in vacuo and azeotroped with MeOH to leave a solid. This was suspended in hot (60° C.) EtOAc, then MeOH added until complete dissolution. The hot solution was stirred at 60° C. for 15 min, then allowed to cool to RT over 1 h and then cooled to 0° C. The solid was filtered, washed with cold (0° C.) EtOAc then dried in vacuo to leave the title compound as a solid (35.9 g). LCMS (Method B) 4.57 min, $ES^+$ 535.2 $[M+1]^+$. $^1H$ NMR (400 MHz, DMSO-$d_6$) □ 8.96 (s, 2H), 7.87 (t, J=7.8 Hz, 1H), 7.82-7.78 (m, 2H), 7.66-7.57 (m, 1H), 7.54 (dd, J=0.8, 7.6 Hz, 1H), 7.35-7.26 (m, 2H), 3.32-3.28 (m, 1H), 3.26 (d, J=4.0 Hz, 1H), 2.88 (s, 3H), 2.48-2.41 (m, 1H), 1.58 (ddd, J=4.0, 9.2, 13.1 Hz, 1H), 1.26 (ddd, J=3.8, 9.0, 12.6 Hz, 1H), 1.10 (s, 3H), 0.74 (s, 3H)

Example 6: (1S,8R)-5-(2,6-Difluoro-phenyl)-1-[2-(6-methanesulfonylmethyl-pyridin-3-yl)-pyrimidin-4-yl]-11,11-dimethyl-3,4-diaza-tricyclo[6.2.1.0*2,7*]undeca-2(7),3,5-triene

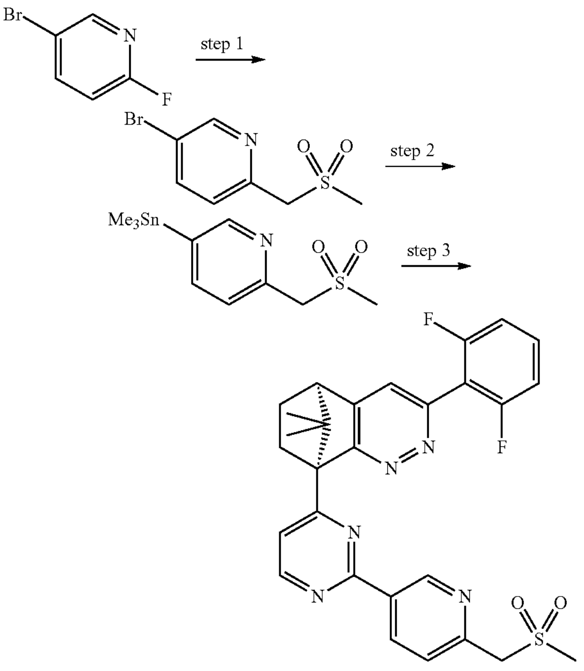

Step 1: 5-Bromo-2-methanesulfonylmethyl-pyridine

A solution of 5-bromo-2-fluoropyridine (2.00 g, 12.4 mmol) in dry THF (20 mL) was added dropwise to a solution at 17° C. under $N_2$ to NaHMDS (1M in THF, 57 mL, 57 mmol). The mixture was stired for 5 min, then dimethyl sulfone (4.00 g, 42.6 mmol) added. The solution was stirred at 17° C. for 1 h and at RT for 1 h. Sat. aq. $NH_4Cl$ solution was added and the mixture extracted with EtOAc. The organics were washed with water and brine, dried ($Na_2SO_4$), filtered and concentrated in vacuo to leave a residue. Trituration with EtOAc left the title compound as a solid (1.67 g). LCMS (Method A) 2.39 min, ES 250 and 252 $[M+1]^+$.

Step 2: 2-Methanesulfonylmethyl-5-trimethylstannanyl-pyridine

Ar was bubbled through a mixture of the product from step 1 (250 mg, 1.0 mmol), hexamethylditin (426 mg, 1.3 mmol) and $(Ph_3P)_4Pd$ (58 mg, 0.05 mmol) in toluene for 10 min, then the mixture stirred at 110° C. for 90 min. The cooled mixture was purified immediately by FCC (0-100% EtOAc in cyclohexane) to leave the title compound as an oil that solidified on standing (323 mg). LCMS (Method A) 3.12 min, $ES^+$ 334 and 336 $[M+1]^+$.

Step 3: (1S,8R)-5-(2,6-Difluoro-phenyl)-1-[2-(6-methanesulfonylmethyl-pyridin-3-yl)-pyrimidin-4-yl]-11,11-dimethyl-3,4-diaza-tricyclo[6.2.1.0*2,7*]undeca-2(7),3,5-triene Ar was bubbled through a mixture of the product from step 2 (150 mg, 0.45 mmol), (1S,8R)-1-(2-chloro-pyrimidin- 4-yl)-5-(2,6-difluoro-phenyl)-11,11-dimethyl-3,4-diaza-tricyclo[6.2.1.0*2,7*]undeca-2(7),3,5-triene (100 mg, 0.25 mmol) and $(Ph_3P)_4Pd$ (29 mg, 0.025 mmol) in dioxane, then the mixture stirred at 100° C. for 16 h. The cooled solution was diluted with EtOAc, washed with water and brine, dried ($Na_2SO_4$), filtered and concentrated in vacuo to leave a residue. FCC (0-100% EtOAc in cyclohexane, then 0-10% MeOH in DCM) gave a solid. MDAP, followed by trituration with $Et_2O$ and drying in vacuo at 50° C. gave the title compound as a solid (95 mg). LCMS (Method B) 4.40 min, ES 534.2 $[M+1]^+$. $^1H$ NMR (400 MHz, $CDCl_3$) δ 9.70 (dd, J=0.7, 2.2 Hz, 1H), 8.87 (d, J=5.2 Hz, 1H), 8.84 (dd, J=2.1, 8.1 Hz, 1H), 7.95 (d, J=5.2 Hz, 1H), 7.64 (dd, J=0.7, 8.2 Hz, 1H), 7.51 (t, J=1.4 Hz, 1H), 7.46-7.40 (m, 1H), 7.11-7.03 (m, 2H), 4.53 (s, 2H), 3.42 (ddd, J=4.1, 10.5, 13.1 Hz, 1H), 3.21 (d, J=4.1 Hz, 1H), 2.97 (s, 3H), 2.57-2.49 (m, 1H), 1.77 (ddd, J=4.0, 9.1, 13.1 Hz, 1H), 1.43 (ddd, J=3.9, 9.1, 12.8 Hz, 1H), 1.23 (s, 3H), 0.78 (s, 3H).

Example 7: N-(5-{4-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrimidin-2-yl}-pyridin-2-yl)-methanesulfoximine-amide

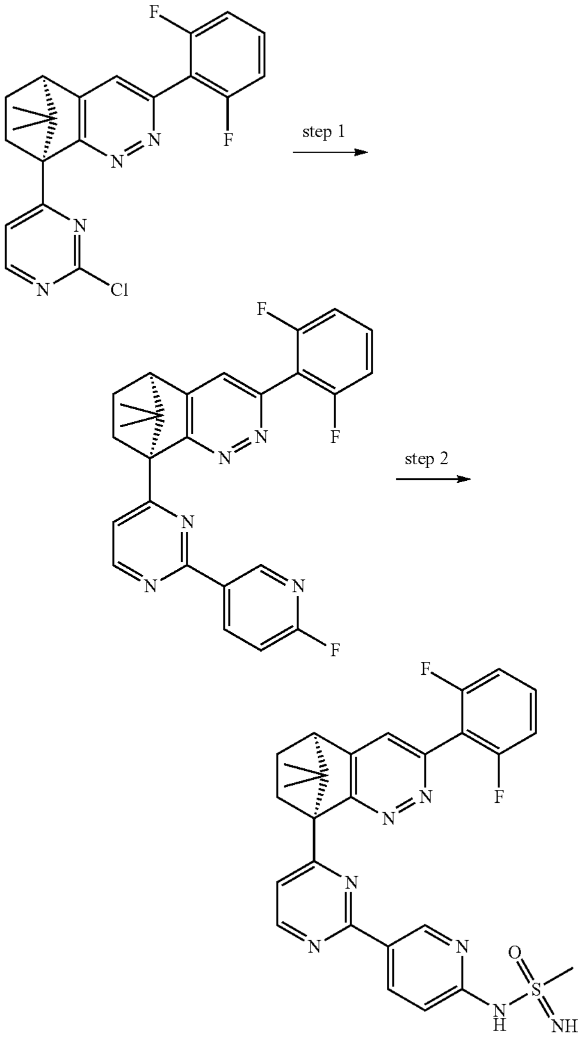

Step 1: (1S,8R)-5-(2,6-Difluoro-phenyl)-1-[2-(6-fluoro-pyridin-3-yl)-pyrimidin-4-yl]-11,11-dimethyl-3,4-diaza-tricyclo[6.2.1.0*2,7*]undeca-2(7),3,5-triene Following the procedure described in Example 1 step 1 and using 2-fluoropyridine-5-boronic acid pinacol ester (290 mg, 130 mmol) and (1S,8R)-1-(2-chloro-pyrimidin-4-yl)-5-(2,6-difluoro-phenyl)-11,11-dimethyl-3,4-diaza-tricyclo[6.2.1.0*2,7*]undeca-2(7),3,5-triene (400 mg, 1.00 mmol), gave the title compound as a foam (420 mg). LCMS (Method A) 4.24 min, $ES^+$ 460 $[M+1]^+$.

Step 2: N-(5-{4-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrimidin-2-yl}-pyridin-2-yl)-methanesulfoximine amide A mixture of methanesulfoximine amide (*RSC Advances*, 2015, 5(6), 4171. 17 mg, 0.18 mmol) and NaH (60% in mineral oil, 8 mg, 0.20 mmol) in dry DMSO (1 mL) was stirred at RT for 1 h, then a solution of the product from step 1 (75 mg, 0.16 mmol) in dry DMSO (0.5 mL) was added and the mixture stirred at RT for 1 h and at 50° C. for 6 h. The cooled mixture was suspended in sat. aq $NH_4Cl$ solution, then extracted with EtOAc (×2). The combined organics were washed with water and brine, then dried ($MgSO_4$), filtered and concentrated in vacuo to leave a residue. FCC (0-10% EtOAc in DCM, twice) and freeze-drying from MeCN-water gave the title compound as a solid (20.9 mg). LCMS (Method B) 3.52 min, $ES^+$ 534.2 $[M+1]^+$. $^1H$ NMR (400 MHz, DMSO-$d_6$) δ 9.17 (t, J=2.8 Hz, 1H), 8.90 (d, J=5.3 Hz, 1H), 8.46 (dd, J=2.4, 8.6 Hz, 1H), 7.84 (s, 1H), 7.65 (q, J=2.2 Hz, 1H), 7.64-7.58 (m, 1H), 7.35-7.27 (m, 2H), 7.11 (br s, 2H), 6.79 (d, J=8.6 Hz, 1H), 3.35 (s, 3H), 3.31 (d, J=2.3 Hz, 1H), 3.30-3.21 (m, 1H), 2.48-2.42 (m, 1H), 1.64 (ddd, J=3.8, 9.0, 12.9 Hz, 1H), 1.34-1.25 (m, 1H), 1.13 (s, 3H), 0.77 (apparent d, J=2.9 Hz, 3H).

Example 8: 5-{4-[(1S,8R)-5-(2,6-Difluoro-phenyl)-11,11-dimethyl-3,4-diaza-tricyclo[6.2.1.0*27*]undeca-2(7),3,5-trien-1-yl]-pyrimidin-2-yl}-pyridine-2-sulfonic Acid Amide

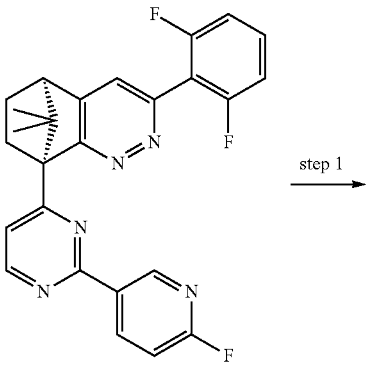

-continued

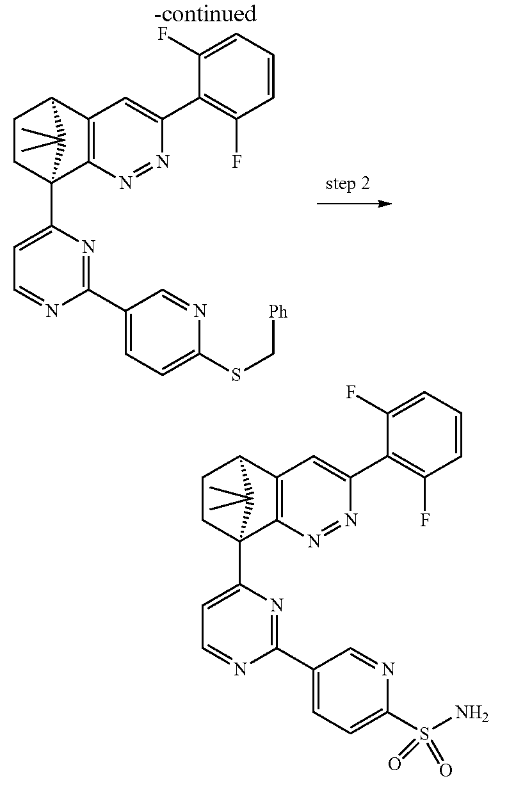

Step 1: (1S,8R)-1-[2-(6-Benzylsulfanyl-pyridin-3-yl)-pyrimidin-4-yl]-5-(2,6-difluoro-phenyl)-1,11-dimethyl-3,4-diaza-tricyclo[6.2.1.0*2,7*]undeca-2(7),3,5-triene A mixture of benzyl mercaptan (51 μM, 0.43 mmol) and NaH (60% in mineral oil, 19 mg, 0.47 mmol) in dry THF (1 mL) was stirred at 0° C. under Ar for 30 min, then a solution of (1S,8R)-5-(2,6-difluoro-phenyl)-1-[2-(6-fluoro-pyridin-3-yl)-pyrimidin-4-yl]-11,11-dimethyl-3,4-diaza-tricyclo[6.2.1.0*2,7*]undeca-2(7),3,5-triene (200 mg, 0.43 mmol) in dry THF (1 mL) was added and the mixture stirred at RT for 20 h. Water was added, then the mixture extracted with EtOAc (×3). The combined organics were washed with water and brine, then dried ($MgSO_4$), filtered and concentrated in vacuo to leave the title compound as a solid (240 mg). LCMS (Method A) 5.01 min, $ES^+$ 564 $[M+1]^+$.

Step 2: 5-{4-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrimidin-2-yl}-pyridine-2-sulfonic Acid Amide A suspension of the product from step 1 (120 mg, 0.21 mmol) and NCS (85 mg, 0.63 mmol) in AcOH (0.75 mL) and water (0.3 mL) was stirred at RT for 90 min. This mixture was added dropwise to a pre-cooled (0° C.) ammonia solution (33% in water, 8 mL) and the resulting solid filtered and washed with water and dried in vacuo to give crude product. FCC (0-80% EtOAc in DCM) gave a solid. The solid was slurried in EtOAc-cyclohexane (1:4), then filtered, washed with EtOAc-cyclohexane (1:4) and dried in vacuo to leave the title compound as a solid (50 mg). LCMS (Method B) 4.31 min, $ES^+$ 521.2 $[M+1]^+$. $^1H$ NMR (400 MHz, DMSO-$d_6$) δ 9.64 (dd, J=0.8, 2.1 Hz, 1H), 9.08 (d, J=5.2 Hz, 1H), 8.97 (dd, J=2.1, 8.2 Hz, 1H), 8.13 (dd, J=0.8, 8.2 Hz, 1H), 7.88 (d, J=5.2 Hz, 1H), 7.86 (s, 1H), 7.67-7.57 (m, 1H), 7.60 (br s, 2H), 7.35-7.26 (m, 2H), 3.34 (d, J=4.1 Hz, 1H), 3.31-3.26 (m, 1H), 2.53-2.44 (m, 1H), 1.68 (ddd, J=4.0, 9.0, 12.9 Hz, 1H), 1.32 (ddd, J=3.7, 9.0, 12.7 Hz, 1H), 1.15 (s, 3H), 0.78 (s, 3H).

Example 9: (1S,8R)-5-(2,6-Difluoro-phenyl)-1-[6-(4-methanesulfoximinylmethyl-oxazol-2-yl)-pyrazin-2-yl]-11,11-dimethyl-3,4-diaza-tricyclo[6.2.1.0*2,7*]undeca-2(7),3,5-triene

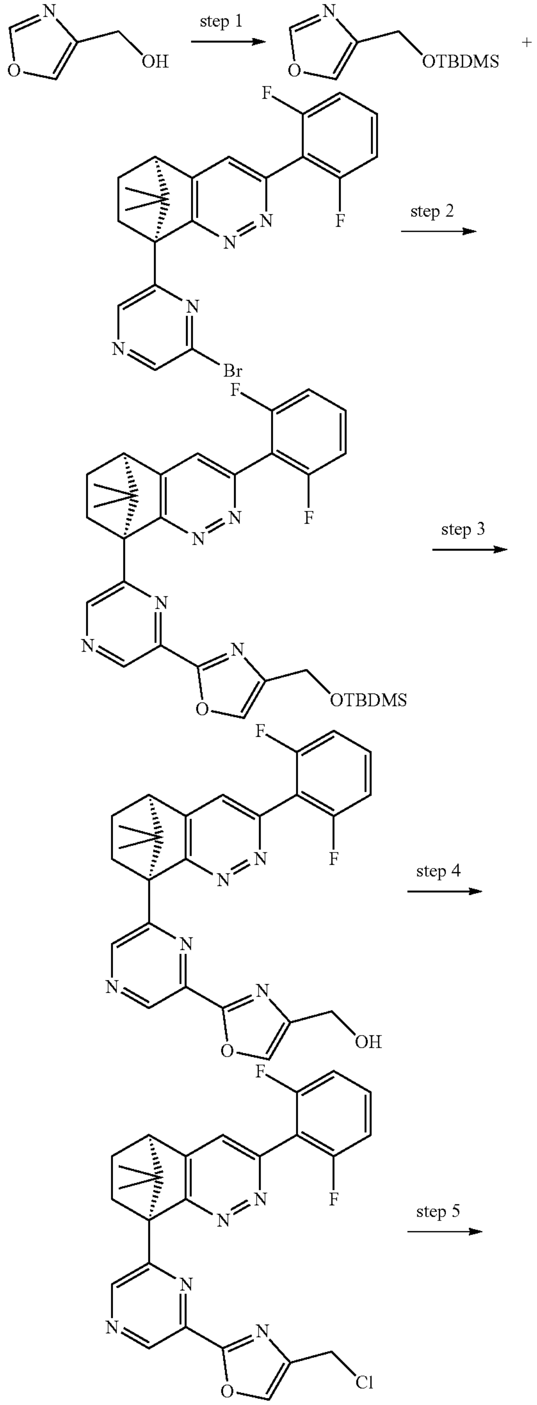

-continued

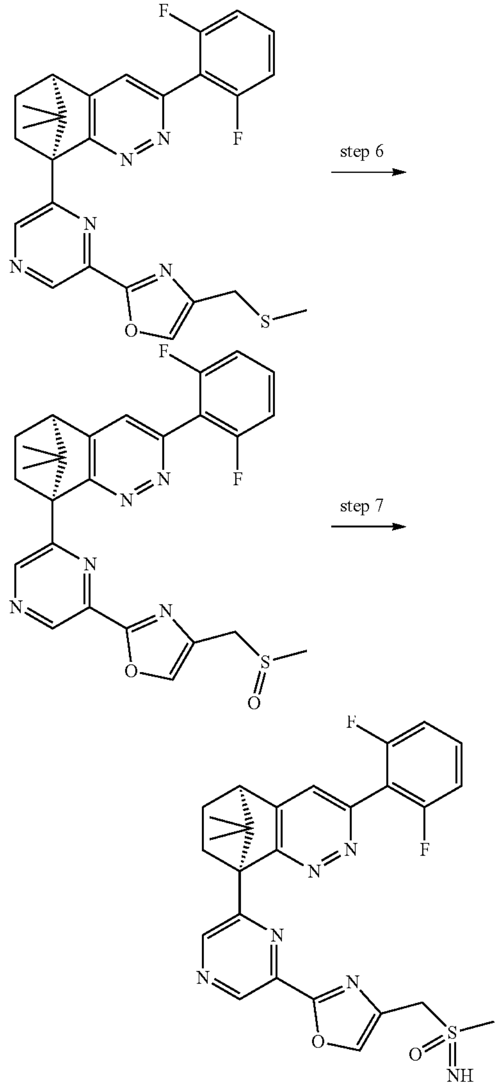

Step 2: 4-(tert-Butyl-dimethyl-silanyloxymethyl)-oxazole

A solution of oxazol-4-yl-methanol (773 mg, 7.80 mmol) (1.03 g, 4.83 TBDMS chloride (1.76 g, 11.7 mmol) and imidazole (1.12 g, 16.4 mmol) in DMF (20 mL) was stirred at RT for 16 h. The solution was concentrated in vacuo, suspended in water and extracted with $Et_2O$ (×2). The combined organics were washed with brine, dried ($Na_2SO_4$), filtered and concentrated in vacuo to leave the title compound as an oil (890 mg). LCMS (Method A) 4.16 min, $ES^+$ 214 $[M+1]^+$.

Step 2: (1S,8R)-1-{6-[4-(tert-Butyl-dimethyl-silanyloxymethyl)-oxazol-2-yl]-pyrazin-2-yl}-5-(2,6-difluoro-phenyl)-11,11-dimethyl-3,4-diaza-tricyclo[6.2.1.0*2,7*]undeca-2(7),3,5-triene A flask was charged with the product from step 1 (1.03 g, 4.83 mmol), (1S,8R)-1-(6-bromo-pyrazin-2-yl)-5-(2,6-difluoro-phenyl)-11,11-dimethyl-3,4-diaza-tricyclo[6.2.1.0*2,7*]undeca-2(7),3,5-triene (1.71 g, 3.86 mmol) and RuPhos Pd G2 (150 mg, 0.19 mmol), then sealed, evacuated and purged with $N_2$ twice. Degassed THF (25 ml) and tetramethylpiperidinezinc chloride lithium chloride complex (Rockwood, 0.65 M in THF, 7.4 mL, 4.83 mmol) were added sequentially, then solution stirred at 70° C. for 15 min. To the cooled solution was added aq. HCl solution (0.5 M, 50 mL), then the mixture extracted with EtOAc (×2). The combined organics were washed with brine, dried ($Na_2SO_4$), filtered and concentrated in vacuo to leave a gum. FCC (0-40% EtOAc in cyclohexane) gave the title compound as a foam (2.04 g). LCMS (Method A) 5.13 min, ES 576 $[M+1]^+$.

Step 3: (2-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrazin-2-yl}-oxazol-4-yl)-methanol To a solution of the product from step 2 (2.87 g, 4.99 mmol) in THF (50 mL) at 0° C. was added TBA fluoride (1M in THF, 10 mL, 10 mmol) and the solution stirred at 0° C. for 30 min. The solution was concentrated to 10 mL volume, then diluted with water and extracted with EtOAc (×2). The combined organics were washed with brine, dried ($Na_2SO_4$), filtered and concentrated in vacuo to leave a foam. FCC (50-100% EtOAc in cyclohexane) gave the title compound as a solid (2.20 g). LCMS (Method A) 3.34 min, ES 462 $[M+1]^+$.

Step 4: (1S,8R)-1-[6-(4-Chloromethyl-oxazol-2-yl)-pyrazin-2-yl]-5-(2,6-difluoro-phenyl)-11,11-dimethyl-3,4-diaza-tricyclo[6.2.1.0*2,7*]undeca-2(7),3,5-triene To a solution of the product from step 3 (1.15 g, 2.50 mmol) in DCM (25 mL) at 0° C. was added thionyl chloride (0.36 mL, 5.00 mmol) and the mixture stirred at RT for 30 min. The solution was concentrated in vacuo, dissolved in EtOAc and washed with water-sat. aq. $NaHCO_3$ solution (1:1). The aq. was extracted with EtOAc, then the combined organics washed with brine, dried ($Na_2SO_4$), filtered and concentrated in vacuo to leave the title compound as a foam (1.20 g). LCMS (Method A) 4.01 min, ES 480 $[M+1]^+$.

Step 5: (1S,8R)-5-(2,6-Difluoro-phenyl)-11,11-dimethyl-1-[6-(4-methylsulfanylmethyl-oxazol-2-yl)-pyrazin-2-yl]-3,4-diaza-tricyclo[6.2.1.0*2,7*]undeca-2(7),3,5-triene A solution of the product from step 4 (0.97 mmol) and sodium thiomethoxide (985 mg, 1.21 mmol) in DMF (2 mL) was stirred at RT for 16 h, then at 75° C. for 2 h. To the cooled solution was added sodium thiomethoxide (85 mg, 1.21 mmol) and the mixture stirred at 75° C. for 1 h. To the cooled solution was added sodium thiomethoxide (85 mg, 1.21 mmol) and the mixture stirred at 50° C. for 1 h. The cooled solution was concentrated in vacuo, suspended in water and extracted with EtOAc (×2). The combined organics were washed with brine, dried ($Na_2SO_4$), filtered and concentrated in vacuo to leave a gum. FCC (20-60% EtOAc in cyclohexane) gave the title compound as a gum (249 mg). LCMS (Method A) 4.04 min, $ES^+$ 492 $[M+1]^+$.

Step 6: (1S,8R)-5-(2,6-Difluoro-phenyl)-1-[6-(4-methanesulfinylmethyl-oxazol-2-yl)-pyrazin-2-yl]-11,11-dimethyl-3,4-diaza-tricyclo[6.2.1.0*2,7*]undeca-2(7),3,5-triene To a solution of the product from step 5 (155 mg, 0.315 mmol) in water (2 mL) and IMS (2 mL) at 0° C. was added sodium periodate (68 mg, 0.32 mmol) and the mixture stirred at RT for 30 min. IMS (2 mL) was added and the mixture stirred at RT for 2.5 h. The reaction was diluted with water and extracted with DCM (×3). The combined organics were passed through a hydrophobic frit and concentrated in vacuo to leave the title compound as a gum (151 mg). LCMS (Method A) 3.23 min, ES$^+$ 508 [M+1]$^+$.

Step 7: (1S,8R)-5-(2,6-Difluoro-phenyl)-1-[6-(4-methanesulfoximinylmethyl-oxazol-2-yl)-pyrazin-2-yl]-11,11-dimethyl-3,4-diaza-tricyclo[6.2.1.0*2,7*]undeca-2(7),3,5-triene To a suspension of the product from step 6 (151 mg, 0.297 mmol), trifluoroacetamide (67 mg, 0.595 mmol), rhodium acetate dimer (6.6 mg, 0.015 mmol) and magnesium oxide (48 mg, 1.19 mmol) in DCM (2 mL) at RT was added (diacetoxyiodo)benzene (144 mg, 0.446 mmol) and the suspension stirred at RT for 16 h. Trifluoroacetamide (67 mg, 0.595 mmol), rhodium acetate dimer (6.6 mg, 0.015 mmol), magnesium oxide (48 mg, 1.19 mmol) and (diacetoxyiodo)benzene (144 mg, 0.446 mmol) were added and the suspension stirred at RT for 24 h. The suspension was filtered through Celite® and the filter cake washed with DCM. The organics were concentrated in vacuo to leave a gum. The gum was dissolved in MeOH (10 mL) and $K_2CO_3$ (205 mg, 1.5 mmol) added and the suspension stirred at RT for 1 h. The mixture was concentrated in vacuo, suspended in water and extracted with DCM (×3). The combined organics were passed through a hydrophobic frit and concentrated in vacuo to leave a gum. FCC (2-7% MeOH in DCM) gave a gum. HPLC (30-45% MeCN in water, 0.1% $HCO_2H$, 18 min, x2) gave a solid. SFC separated the enantiomers to give the title compound as a solids (27.6 mg and 25.0 mg). LCMS (Method B) 3.74 min, ES$^+$ 523.3 [M+1]$^+$. $^1$H NMR (400 MHz, $CDCl_3$) δ 9.31 (s, 1H), 9.22 (s, 1H), 8.01 (s, 1H), 7.51 (t, J=1.3 Hz, 1H), 7.47-7.38 (m, 1H), 7.11-7.02 (m, 2H), 4.42 (s, 2H), 3.38 (ddd, J=4.0, 10.6, 13.1 Hz, 1H), 3.20 (d, J=4.1 Hz, 1H), 3.14 (s, 3H), 2.81 (br s, 1H), 2.55-2.45 (m, 1H), 1.79 (ddd, J=4.1, 9.1, 13.2 Hz, 1H), 1.41 (ddd, J=3.9, 9.1, 12.8 Hz, 1H), 1.17 (s, 3H), 0.83 (s, 3H).

Example 10: 3-(4-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrazin-2-yl}-pyrazol-1-yl)-cyclobutanol

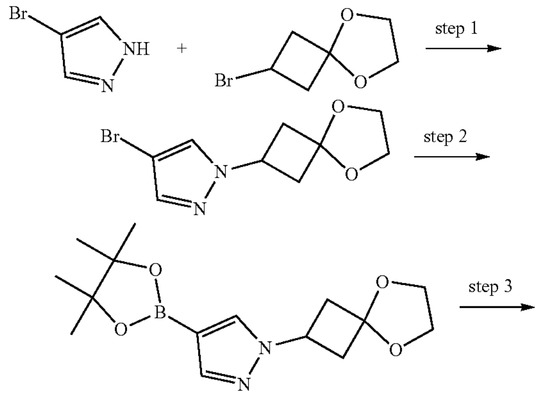

-continued

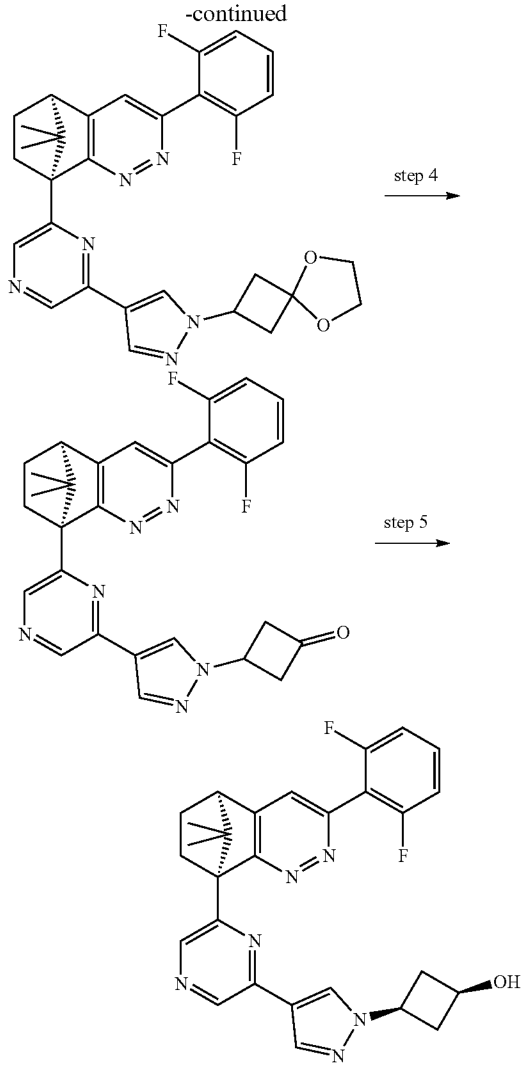

Step 1: 4-Bromo-1-(5,8-dioxa-spiro[3,4]oct-2-yl)-1H-pyrazole

A mixture of NaH (60% in mineral oil, 100 mg, 2.72 mmol) and 4-bromopyrazole (200 mg, 1.36 mmol) in DMF (1 mL) was stirred at RT for 10 min, then a solution of 2-bromo-5,8-dioxaspiro[3,4]octane (484 mg, 2.5 mmol) in DMF (0.5 mL) was added, and the mixture stirred at 100° C. for 2 h. The cooled mixture was diluted with EtOAc, washed with water (×3) and brine, dried ($Na_2SO_4$), filtered and concentrated in vacuo to leave a residue. FCC (0-50% EtOAc in cyclochexane) gave the title compound as a solid (207 mg). $^1$H NMR (300 MHz, $CDCl_3$) δ 7.51 (s, 1H), 7.48 (s, 1H), 4.63 (quin, J=7.9 Hz, 1H), 3.99-3.89 (m, 4H), 2.95-2.81 (m, 4H).

Step 2: 1-(5,8-Dioxa-spiro[3,4]oct-2-yl)-4-(4,4,5,5-tetramethyl-[1,3,2]dioxaborolan-2-yl)-1H-pyrazole Ar was bubbled through a mixture of the product from step 1 (205 mg, 0.79 mmol), bis(pinacolato)diboron (301 mg, 1.19 mmol), [1,1'-bis(diphenylphosphino)ferrocene]dichloropalladium(II), DCM complex (65 mg, 0.080 mmol) and potassium acetate (194 mg, 1.98 mmol) in 1,4-dioxane (6 mL), then the mixture stirred at 90° C. for 16 h. The cooled solution was diluted with EtOAc, washed with water (×2) and brine, dried ($Na_2SO_4$), filtered and concentrated in vacuo to leave a residue. FCC (0-60% EtOAc in cyclohexane) gave the title compound as a residue (147 mg). LCMS (Method A) 3.30 min, $ES^+$ 307 $[M+1]^+$.

Step 3: (1S,8R)-5-(2,6-Difluoro-phenyl)-1-{6-[1-(5,8-dioxa-spiro [3.4]oct-2-yl)-1H-pyrazol-4-yl]-pyrazin-2-yl}-11,11-dimethyl-3,4-diaza-tricyclo [6.2.1.0*2,7*]undeca-2(7),3,5-triene Following the procedure described in Example 1 step 1 and using the product from step 2 (142 mg, 0.464 mmol) and the product of Example 8, step 1 (200 mg, 0.451 mmol), gave the title compound as a residue (179 mg). LCMS (Method C) 1.21 min, ES 543 $[M+1]^+$.

Step 4: 3-(4-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrazin-2-yl}-pyrazol-1-yl)-cyclobutanone A solution of the product from step 3 (175 mg, 0.323 mmol) and hydrogen chloride (4M in dioxane, 0.81 mL, 3.23 mmol) in MeOH (3 mL) was stirred at RT for 90 min. The solution was concentrated in vacuo, then redissolved in acetone (5 mL) and conc. $H_2SO_4$ (2 drops) added. The mixture was stirred at RT for 16 h. Conc. $H_2SO_4$ (2 drops) was added and the mixture stirred at reflux for 3 h. The cooled solution was concentrated in vacuo and partitioned between EtOAc and sat aq. $NaHCO_3$ solution. The organics were washed with brine, dried ($Na_2SO_4$), filtered and concentrated in vacuo to leave a solid. FCC (0-100% EtOAc in cyclohexane) gave the title compound as a solid (121 mg). LCMS (Method C) 1.16 min, ES 499 $[M+1]^+$.

Step 5: 3-(4-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyrazin-2-yl}-pyrazol-1-yl)-cyclobutanol A mixture of the product from step 4 (115 mg, 0.231 mmol) and sodium borohydride (13 mg, 0.35 mmol) in EtOH-THF (1:1, 8 mL) was stirred at 0° C. for 15 min. The mixture was diluted with EtOAc, washed with water and brine, dried ($Na_2SO_4$), filtered and concentrated in vacuo to leave a residue. FCC (0-10% MeOH in DCM) gave the title compound as a foam (80 mg). LCMS (Method B) 4.18 min, $ES^+$ 501.4 $[M+1]^+$. $^1H$ NMR (400 MHz, $CDCl_3$) δ 8.90 (s, 1H), 8.71 (s, 1H), 8.10 (s, 1H), 8.03 (s, 1H), 7.49 (t, J=1.2 Hz, 1H), 7.46-7.37 (m, 1H), 7.10-7.02 (m, 2H), 4.52-4.43 (m, 1H), 4.31-4.21 (m, 1H), 3.34 (ddd, J=4.0, 10.5, 13.1 Hz, 1H), 3.18 (d, J=4.1 Hz, 1H), 3.08-2.99 (m, 2H), 2.89 (d, J=7.9 Hz, 1H), 2.62-2.43 (m, 3H), 1.74 (ddd, J=4.1, 9.1, 13.2 Hz, 1H), 1.39 (ddd, J=3.9, 9.0, 12.8 Hz, 1H), 1.14 (s, 3H), 0.81 (s, 3H).

Example 11: (S)-3-(4-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-[1,2,3]triazol-2-yl)-propane-1,2-diol

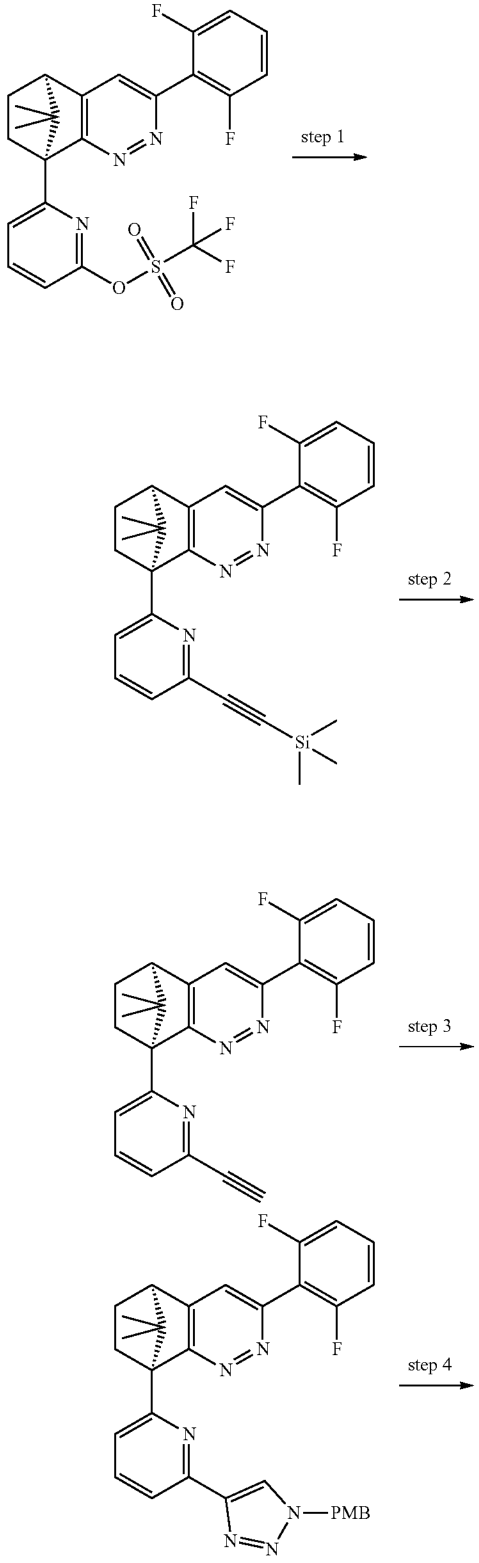

-continued

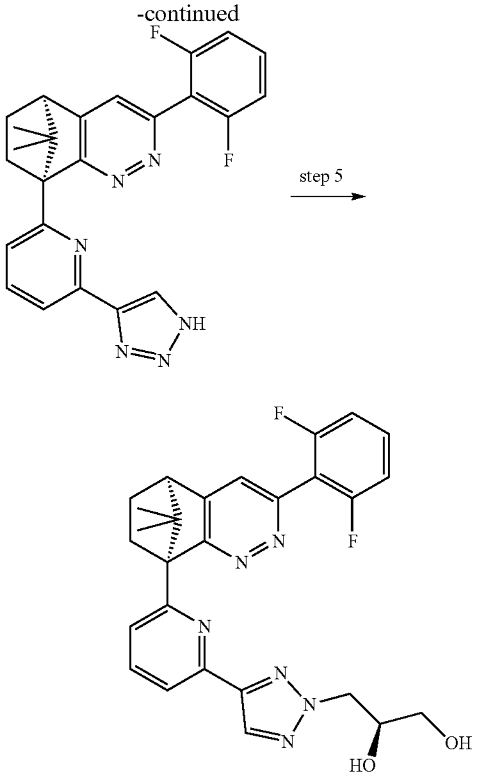

Step 1: (1S,8R)-5-(2,6-Difluoro-phenyl)-11,11-dimethyl-1-(6-trimethylsilanylethynyl-pyridin-2-yl)-3,4-diaza-tricyclo[6.2.1.0*2,7*]undeca-2(7),3,5-triene A flask was charged with trifluoro-methanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyridin-2-yl ester (750 mg, 1.47 mmol), diisopropylamine (7.0 mL) and copper(I) iodide (7.0 mg, 0.037 mmol) then sealed, evacuated and purged with Ar (×4). Dichlorobis(triphenylphosphine)palladium (26 mg, 0.037 mol) and trimethylsilylacetylene (0.62 mL, 4.38 mmol) were added and the solution stirred at 40° C. then at RT for 16 h. The reaction mixture was added to water, and then extracted with DCM (×3). The combined organics were washed with water and brine, dried ($MgSO_4$), filtered and concentrated in vacuo to leave a residue. FCC (cyclohexane-DCM, 1:1, then 0-10% EtOAc in DCM) gave the title compound as a residue (800 mg). LCMS (Method C) 1.53 min, $ES^+$ 460 $[M+1]^+$.

Step 2: (1S,8R)-5-(2,6-Difluoro-phenyl)-1-(6-ethynyl-pyridin-2-yl)-11,11-dimethyl-3,4-diaza-tricyclo[6.2.1.0*2,7*]undeca-2(7),3,5-triene A solution of the product from step 1(500 mg, 1.07 mmol), KOH (125 mg, 2.23 mmol) in MeOH-DCM (1:1, 8 mL) was stirred at RT for 1 h, then water added and the mixture extracted with DCM (×3). The combined organics were washed with water and brine, then passed through a hydrophobic frit and concentrated in vacuo to leave the title compound as a foam (>99%). LCMS (Method C) 1.27 min, $ES^+$388 $[M+1]^+$.

Step 3: (S. 8R)-5-(2,6-Difluoro-phenyl)-1-{6-[1-(4-methoxy-benzyl)-1H-[1123]triazol-4-yl]-pyridin-2-yl}-11,11-dimethyl-3,4-diaza-tricyclo[6.2.1.0*2,7*]undeca-2(7),3,5-triene A solution of the product from step 2 (210 mg, 0.54 mmol), 1-azidomethyl-4-methoxy-benzene (0.55 mmol) and copper(II) sulfate pentahydrate (27 mg, 0.090 mmol) in water (4 ml) and MeOH (6 mL) was stirred at 50° C. for 2.5 h. Water was added, then the mixture extracted with DCM (×2). The combined organics were washed with water and brine, then passed through a hydrophobic frit and concentrated in vacuo to give a residue. FCC (0-100% EtOAc in cyclohexane) gave the title compound as a solid (257 mg). LCMS (Method C) 1.33 min, $ES^+$ 551 $[M+1]^+$.

Step 4: (1S,8R)-5-(2,6-Difluoro-phenyl)-11,11-dimethyl-1-[6-(1H-[1,2,3]triazol-4-yl)-pyridin-2-yl]-34-diaza-tricyclo[6.2.1.0*2,7*]undeca-2(7),3,5-triene A solution of the product from step 3 (255 mg, 0.46 mmol) in TFA (5 mL) was stirred at 65° C. for 9 h and at RT for 15 h. The mixture was concentrated in vacuo, and the residue azeotroped with toluene (×3), and then DCM to leave a gum (>99%). LCMS (Method C) 1.14 min, $ES^+$ 431 $[M+1]^+$.

Step 5: (S)-3-(4-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-[1,2,3]triazol-2-yl)-propane-1,2-diol A mixture of the product from step 4 (0.23 mmol), (S)-(−)-glycidol (26 μL, 0.39 mmol) and $K_2CO_3$ (159 mmol, 1.15 mmol) in DMF (3 mL) was stirred at 80° C. for 3 h. The reaction mixture was diluted with DCM, washed with water (×2) and brine, and then passed through a hydrophobic frit and concentrated in vacuo to leave a residue. FCC (0-100% EtOAc in cyclohexane, then 0-10% MeOH in DCM) gave a residue. MDAP gave the title compound as a solid (22 mg). LCMS (Method B) 4.27 min, $ES^+$ 505.3 $[M+1]^+$. $^1H$ NMR (400 MHz, DMSO-$d_6$) δ 8.22 (s, 1H), 7.97 (t, J=7.8 Hz, 1H), 7.89 (dd, J=1.0, 7.7 Hz, 1H), 7.81 (s, 1H), 7.66 (dd, J=1.0, 7.8 Hz, 1H), 7.66-7.57 (m, 1H), 7.35-7.27 (m, 2H), 5.06 (d, J=5.8 Hz, 1H), 4.83 (t, J=5.7 Hz, 1H), 4.59 (dd, J=4.1, 13.5 Hz, 1H), 4.38 (dd, J=8.3, 13.5 Hz, 1H), 4.11-4.03 (m, 1H), 3.50-3.38 (m, 2H), 3.37-3.29 (m, 1H), 3.27 (d, J=3.9 Hz, 1H), 2.48-2.39 (m, 1H), 1.59 (ddd, J=4.0, 9.1, 13.0 Hz, 1H), 1.27 (ddd, J=3.8, 9.0, 12.7 Hz, 1H), 1.08 (s, 3H), 0.75 (s, 3H).

Example 12: N-(5-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrazin-2-yl)-methanesulfonamide

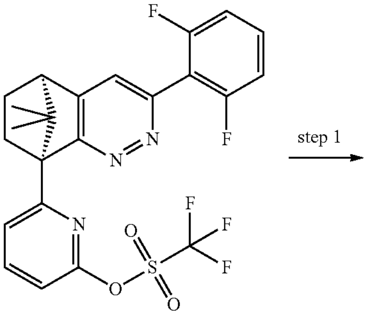

-continued

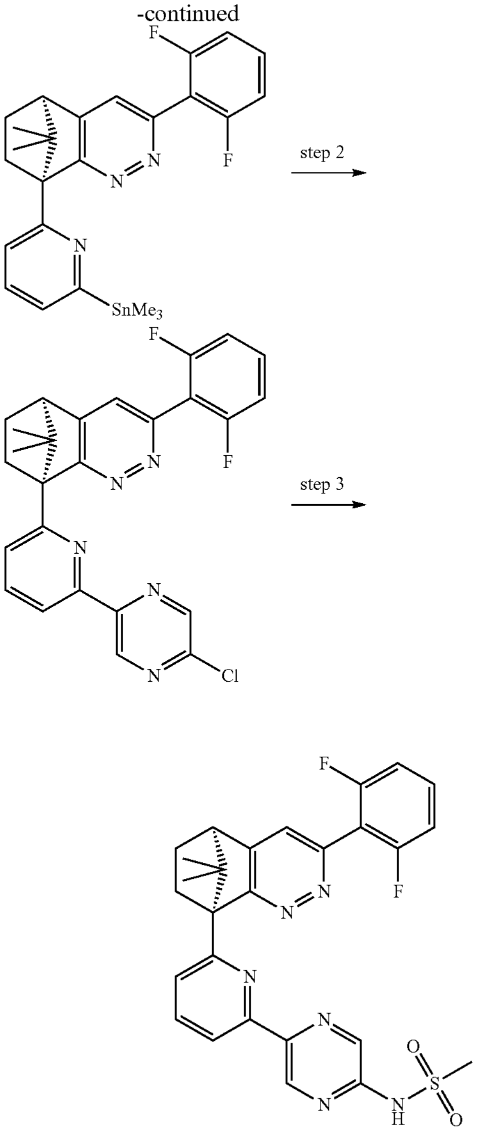

Step 1: (1S,8R)-5-(2,6-Difluoro-phenyl)-11,11-dimethyl-1-(6-trimethylstannanyl-pyridin-2-yl)-3,4-diaza-tricyclo[6.2.1.0*2,7*]undeca-2(7),3,5-triene $N_2$ was bubbled through a mixture of dioxane (5 mL) and toluene (1 mL) for 30 min. Separately, a flask was charged with the product trifluoro-methanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyridin-2-yl ester (256 mg, 0.50 mmol), hexamethylditin (180 mg, 0.55 mmol), lithium chloride (64 mg, 1.5 mmol) and $(Ph_3P)_4Pd$ (29 mg, 0.025 mmol), then sealed evacuated and purged with $N_2$ thrice. The solution was injected into the flask and the solution stirred at 100° C. for 1 h. The cooled solution was diluted with sat. aq. $NH_4Cl$ solution, then extracted with EtOAc (x2). The combined organics were filtered through Celite and concentrated in vacuo to leave a gum. FCC (alumina, 10-50% EtOAc in cyclohexane) gave the title compound as a gum (197 mg). LCMS (Method A) 2.90 min, $ES^+$ 524-533 $[M+1]^+$.

Step 2: (1S,8R)-1-[6-(5-Chloro-pyrazin-2-yl)-pyridin-2-yl]-5-(2,6-difluoro-phenyl)-11,11-dimethyl-3,4-diaza-tricyclo[6.2.1.0*2,7*]undeca-2(7),3,5-triene $N_2$ was bubbled through a solution of the product from step 1 (0.37 mmol) in toluene for 30 min. Separately, a flask was charged with 2-bromo-5-chloropyrazine (108 mg, 0.56 mmol), $(Ph_3P)_4Pd$ (21.5 mg, 0.19 mmol) and copper(I) iodide (7.1 mg, 0.037 mmol), then sealed evacuated and purged with $N_2$ thrice. The toluene solution was injected in to the flask and the solution stirred at 100° C. for 3 h 15 min. The cooled solution was concentrated in vacuo to ~½ volume. FCC (5-40% EtOAc in cyclohexane) gave the title compound as a solid (97 mg). LCMS (Method A) 4.66 min, ES 476 $[M+1]^+$.

Step 3: N-(5-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrazin-2-yl)-methanesulfonamide $N_2$ was bubbled through dry THF (1 mL) for 15 min. Separately, a vial was charged with the product from step 2 (97 mg, 0.20 mmol), methanesulfonamide (29 mg, 0.31 mmol), $^t$BuBrettPhos (20 mg, 0.041 mmol), allyl palladium chloride dimer (3.7 mg, 0.010 mmol), cesium carbonate (133 mg, 0.041 mmol) and 3 Å MS (25 mg), sealed then evacuated and purged with $N_2$ (x3). The THF was injected into the vial and the suspension stirred at 60° C. for 30 min. The cooled solution was diluted with EtOAc and filtered through Celite®. The filter cake was washed with EtAOc, then the combined organics washed with water and brine, dried ($Na_2SO_4$), filtered and concentrated in vacuo to leave a film. FCC (25-75% EtOAc in cyclohexane) gave a solid. HPLC (50-70% MeCN in water, 0.1% $HCO_2H$, 20 min) gave the title compound as a solid (20.9 mg). LCMS (Method B) 4.79 min, $ES^+$ 535.3 $[M+1]^+$. $^1H$ NMR (400 MHz, $CDCl_3$) δ 9.32 (s, 1H), 8.60 (br s, 1H), 8.42 (d, J=1.2 Hz, 1H), 8.16 (dd, J=1.9, 6.7 Hz, 1H), 7.89-7.82 (m, 2H), 7.52 (s, 1H), 7.46-7.38 (m, 1H), 7.10-7.02 (m, 2H), 3.46 (ddd, J=3.8, 10.6, 13.1 Hz, 1H), 3.33 (s, 3H), 3.19 (d, J=3.9 Hz, 1H), 2.54-2.45 (m, 1H), 1.81 (ddd, J=4.0, 9.1, 13.1 Hz, 1H), 1.40 (ddd, J=3.7, 9.0, 12.6 Hz, 1H), 1.14 (s, 3H), 0.82 (s, 3H).

Example 13: 3-(5-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrimidin-2-yl)-propionamide

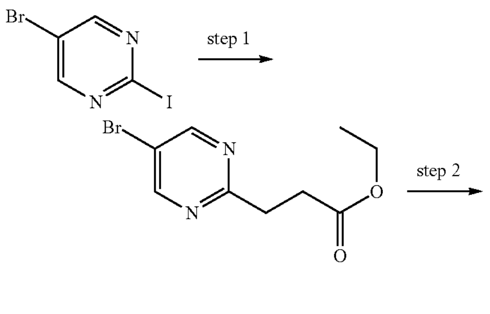

-continued

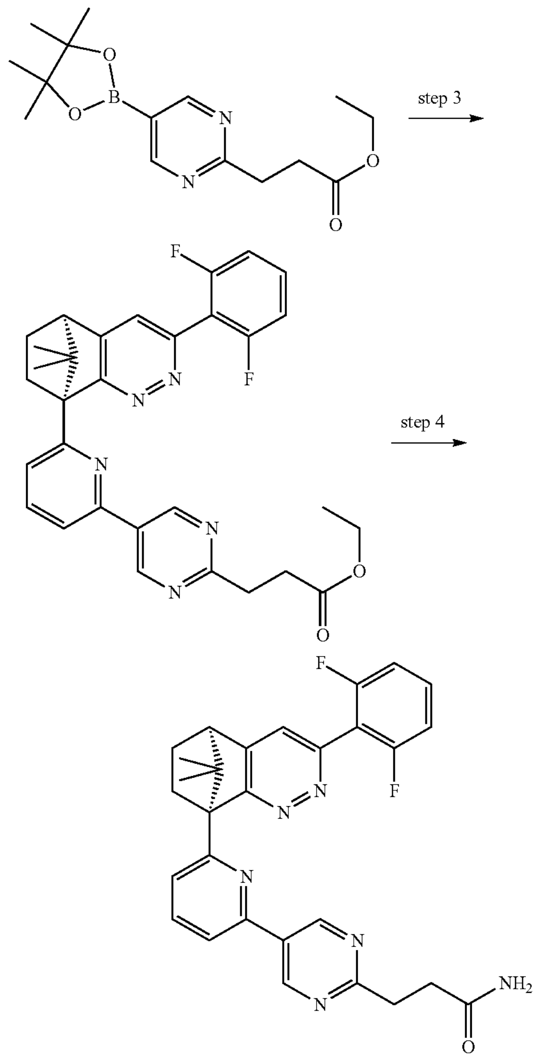

Step 1: 3-(5-Bromo-pyrimidin-2-yl)-propionic Acid Ethyl Ester

A solution of 5-bromo-2-iodopyrimidine (2.0 g, 8.3 mmol), 3-ethoxy-3-oxopropylzinc bromide (0.5M in THF, 16.6 mmol, 8.3 mmol) and $(Ph_3P)_4Pd$ (958 mg, 0.83 mmol) in dry THF (40 mL) was stirred at RT for 16 h. The reaction was quenched with water-sat. aq. $NH_4Cl$ solution (1:1) then extracted with EtOAc. The organics were washed with brine, dried ($MgSO_4$), filtered and concentrated in vacuo to leave a residue. FCC (0-30% EtOAc in cyclohexane) gave the title compound as an oil (750 mg). LCMS (Method C) 0.97 min, ES 259 and 261 $[M+1]^+$.

Step 2: 3-[5-(4,4,5,5-Tetramethyl-[1,3,2]dioxaborolan-2-yl)-pyrimidin-2-yl]-propionic Acid Ethyl Ester Following the procedure described in Example 10 step 2 and using the product from step 1 (750 mg, 2.85 mmol), gave the title compound as an oil (>99%). LCMS (Method C) 0.65 min, ES 225 $[M-C_6H_{10}+1]$.

Step 3: 3-(5-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrimidin-2-yl)-propionic Acid Ethyl Ester Following the procedure described in Example 1 step 1 and using the product from step 2 (178 mg, 0.58 mmol) and trifluoro-methanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyridin-2-yl ester (200 mg, 0.39 mmol), gave the title compound as a residue (>99%). LCMS (Method C) 1.33 min, $ES^+$ 542 $[M+1]^+$.

Step 4: 3-(5-{6-[(1S,8R)-5-(2,6-Difluoro-phenyl)-11,11-dimethyl-3,4-diaza-tricyclo[6.2.1.0*2,7*]undeca-2(7),3,5-trien-1-yl]-pyridin-2-yl}-pyrimidin-2-yl)-propionamide A solution of the product from step 3(0.39 mmol), aqueous ammonia solution (33%, 1.5 mL) in dioxane (3 mL) was stirred at 70° C. for 5 days. The cooled solution was concentrated in vacuo then applied to an SCX-2 cartridge and washed with MeOH. The product was eluted with methanolic ammonia (2M); concentration in vacuo left a residue. MDAP gave a solid (45 mg). LCMS (Method B) 4.08 min, $ES^+$ 513.3 $[M+1]^+$. $^1H$ NMR (400 MHz, DMSO-$d_6$) δ 9.40 (s, 2H), 8.11 (dd, J=0.9, 7.9 Hz, 1H), 8.04 (t, J=7.8 Hz, 1H), 7.81 (s, 1H), 7.74 (dd, J=0.8, 7.7 Hz, 1H), 7.66-7.58 (m, 1H), 7.39 (br s, 1H), 7.35-7.27 (m, 2H), 6.78 (br s, 1H), 3.38-3.34 (m, 1H), 3.29 (d, J=4.0 Hz, 1H), 3.17 (t, J=7.5 Hz, 2H), 2.65 (t, J=7.5 Hz, 2H), 2.48-2.41 (m, 1H), 1.60 (ddd, J=4.0, 9.1, 13.0 Hz, 1H), 1.26 (ddd, J=3.8, 9.1, 12.7 Hz, 1H), 1.09 (s, 3H), 0.74 (s, 3H).

Example 14: (1S,8R)-5-(2,6-Difluoro-phenyl)-1-[6-(2-methanesulfonylmethyl-pyrimidin-5-yl)-pyridin-2-yl]-11,11-dimethyl-3,4-diaza-tricyclo[6.2.1.0*2,7*]undeca-2(7),3,5-triene

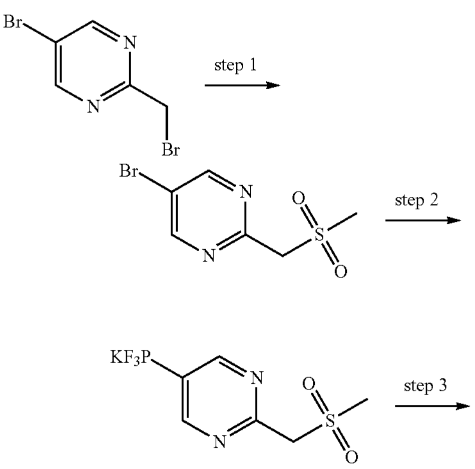

-continued

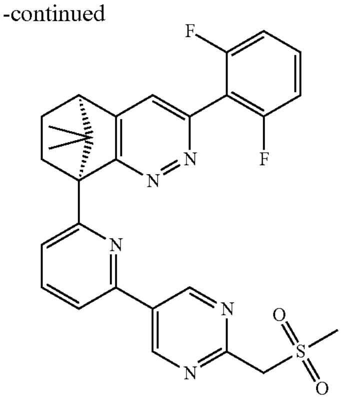

Step 1: 5-Bromo-2-methanesulfonylmethyl-pyrimidine

A suspension of 5-bromo-2-(bromomethyl)pyrimidine (504 mg, 2.0 mmol) and methanesulfinic acid, sodium salt (306 mg, 3.0 mmol) in DMF (2 mL) was stirred at RT for 16 h. The suspension was concentrated in vacuo, suspended in water and extracted with DCM (×2). The combined organics were passed through a hydrophobic frit and concentrated in vacuo to leave the title compound as a solid (>99%). LCMS (Method C) 0.60 min, $ES^+$ 251 and 253 $[M+1]^+$.

Step 2: potassium (2-methanesulfonylmethyl-pyrimidin-5-yl)trifluoroborate $N_2$ was bubbled through dioxane (4 mL) for 15 min. Separately, a flask was charged with the product from step 1 (370 mg, 1.47 mmol), $(Ph_3P)_4Pd$ (170 mg, 0.15 mmol), bis(pinacolato)diboron (468 mg, 1.74 mmol) and potassium acetate (434 mg, 4.42 mmol), then sealed, evacuated and purged with $N_2$ thrice. The solvent was injected into the flask and the mixture stirred at 105° C. for 2.5 h. The cooled suspension was filtered through Celite® and the filter cake washed with EtOAc. The combined organics were concentrated in vacuo to leave a solid. The solid was suspended in water (3 mL) and MeOH (3 mL), then potassium hydrogen fluoride (287 mg, 3.68 mmol) added and the mixture stirred at RT for 30 min. The organics were removed in vacuo, then the aqueous diluted with water and MeCN, then freeze-dried to leave a solid. The solid was suspended in acetone (×5), and the organics decanted. The combined organics were concentrated in vacuo, then triturated with acetone-$Et_2O$ to leave the title compound as a solid (352 mg). LCMS (Method C) 0.32 min, ES-239 $[M]^-$.

Step 3: (1S,8R)-5-(2,6-Difluoro-phenyl)-1-[6-(2-methanesulfonylmethyl-pyrimidin-5-yl)-pyridin-2-yl]-11,11-dimethyl-3,4-diaza-tricyclo[6.2.1.0*2,7*]undeca-2(7),3,5-triene $N_2$ was bubbled through dry THF (2 mL) for 15 min. Separately, a vial was charged with the product from step 2 (120 mg, 0.43 mmol), trifluoro-methanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyridin-2-yl ester (221 mg, 0.43 mmol), SPhos Pd G2 (16 mg, 0.022 mmol) and potassium phosphate tribasic (92 mg, 0.43 mmol), then sealed evacuated and purged with $N_2$ thrice. The solvent was injected into the vial and the mixture stirred at 70° C. for 3 h. The cooled solution was diluted with water and extracted with DCM (×2). The combined organics were passed through a hydrophobic frit and concentrated in vacuo to leave a gum. FCC (25-100% EtOAc in cyclohexane) gave a gum. HPLC (45-65% MeCN in water, 0.1% $HCO_2H$, 18 min) gave a solid (47 mg). LCMS (Method B) 4.54 min, $ES^+$ 534.3 $[M+1]^+$. $^1H$ NMR (400 MHz, $CDCl_3$) δ 9.45 (s, 2H), 7.98 (dd, J=0.9, 7.9 Hz, 1H), 7.90 (t, J=7.8 Hz, 1H), 7.76 (dd, J=0.9, 7.7 Hz, 1H), 7.49 (t, J=1.2 Hz, 1H), 7.46-7.38 (m, 1H), 7.10-7.02 (m, 2H), 4.71 (s, 2H), 3.45 (ddd, J=4.0, 10.6, 13.1 Hz, 1H), 3.19-3.17 (m, 4H), 2.54-2.45 (m, 1H), 1.74 (ddd, J=4.1, 9.2, 13.2 Hz, 1H), 1.40 (ddd, J=3.9, 9.0, 12.7 Hz, 1H), 1.16 (s, 3H), 0.78 (s, 3H).

Example 15: (1S,8R)-5-(2,6-Difluoro-phenyl)-1-{6-[2-(2-methanesulfonyl-ethyl)-pyrimidin-5-yl]-pyridin-2-yl}-11,11-dimethyl-3,4-diaza-tricyclo[6.2.1.0*2,7*]undeca-2(7),3,5-triene

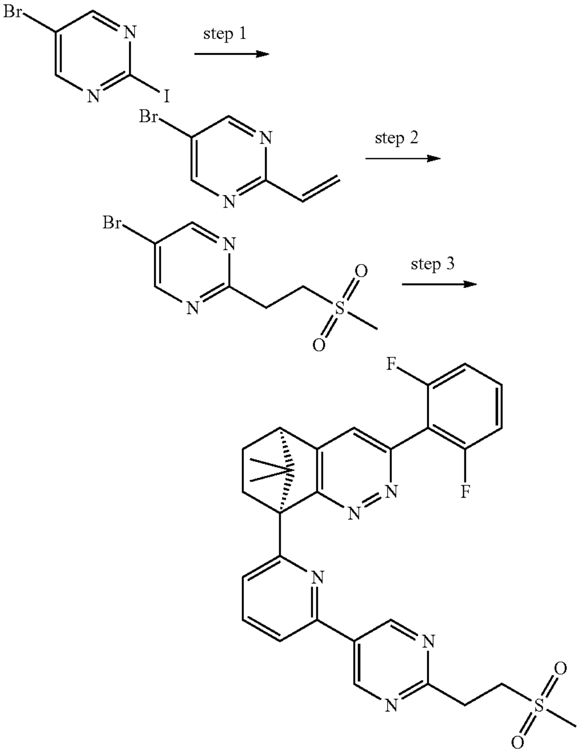

Step 1: 5-Bromo-2-vinylpyrimidine

A suspension of 5-bromo-2-iodopyrimidine (2.81 g, 9.86 mmol), vinyl boronic acid pinacol ester (1.98 mL, 11.7 mmol) and cesium carbonate (6.30 g, 19.5 mmol) in dioxane (39 mL) and water (14 mL) was degassed by sparging with Ar. [1,1'-Bis(diphenylphosphino)ferrocene]dichloropalladium(II), complex with DCM (364 mg, 486 μmol) was added and the reaction heated to 100° C. for 4 h. The reaction mixture was concentrated in vacuo to remove the dioxane, then partitioned between EtOAc and water. The aqueous layer was extracted EtOAc (×2), then the combined organic layers dried ($MgSO_4$), filtered and concentrated in vacuo. FCC (2-16% EtOAc in toluene) provided the title compound as an oil (0.850 g). $^1H$ NMR ($CDCl_3$, 300 MHz): δ 8.74 (s, 2H), 6.83 (dd, J=17.4, 10.5 Hz, 1H), 6.62 (dd, J=17.4, 1.8 Hz, 1H), 5.76 (dd, J=10.5, 1.8 Hz, 1H).

Step 2: 5-Bromo-2-(2-methanesulfonyl-ethyl)-pyrimidine

The product from step 1 (0.85 g, 4.60 mmol), methanesulfinic acid sodium salt (0.542 g, 5.33 mmol), AcOH (23 mL) and EtOH (23 mL) were stirred at 78° C. for 5 h, at which time methane sulfinic acid sodium salt (1.16 g, 11.4 mmol) was added and the reaction stirred at 78° C. for a further 5 h. The mixture was concentrated in vacuo to leave a residue. FCC (25-100% EtOAc in cyclohexane) gave the title compound as an oil which solidified to a crystalline solid (0.834 g). $^1$H NMR ($CDCl_3$, 300 MHz): δ 8.74 (s, 2H), 3.58-3.66 (m, 2H), 3.45-3.54 (m, 2H), 2.96 (s, 3H).

Step 3: (1S,8R)-5-(2,6-Difluoro-phenyl)-1-{6-[2-(2-methanesulfonyl-ethyl)-pyrimidin-5-yl]-pyridin-2-yl}-11,11-dimethyl-3,4-diaza-tricyclo[6.2.1.0*2,7*]undeca-2(7),3,5-triene The product from step 2 (156 mg, 587 μmol), (1S,8R)-5-(2,6-difluoro-phenyl)-11,11-dimethyl-1-(6-trimethylstannanyl-pyridin-2-yl)-3,4-diaza-tricyclo[6.2.1.0*2,7*]undeca-2(7),3,5-triene (587 μmol) and copper(I) iodide (22 mg, 117 μmol) in toluene (6 mL) were sparged with Ar. $(Ph_3P)_4Pd$ (68 mg, 59 mol) was added and the reaction mixture stirred at 100° C. for 16 h. The reaction mixture was then diluted with EtOAc, filtered through Celite, then concentrated in vacuo. FCC (1-7% MeOH in DCM) gave an oil (114 mg). MDAP (gradient of 20-80% MeCN/$H_2O$ with 0.1% HCOOH on Waters Sunfire C18 150×19 mm id 10 um) gave the title compound as a solid (13 mg). $^1$H NMR (DMSO-$d_6$, 400 MHz): δ 9.46 (s, 2H), 8.14 (d, J=7.6 Hz, 1H), 8.06 (t, J=7.6 Hz, 1H), 7.82 (s, 1H), 7.76 (d, J=7.2 Hz, 1H), 7.62 (tt, J=8.4, 6.6 Hz, 1H), 7.31 (m, 2H), 3.40-3.46 (m, 2H), 3.28-3.33 (m, 2H), 3.07 (s, 3H), 2.41-2.50 (m, 1H), 1.57-1.66 (m, 2H), 1.22-1.32 (m, 2H), 1.09 (s, 3H), 0.75 (s, 3H); LCMS (Method B) 4.57 min, 5 ES$^+$ 548.3 [M+1]$^+$.

Example 16: (1S,8R)-5-(2,6-Difluoro-phenyl)-1-{6-[3-(1,1-dioxo-1 lambda*6*-thietan-3-ylmethyl)-[1.2.4]triazol-1-yl]-4-methyl-pyridin-2-yl}-11,11-dimethyl-3,4-diaza-tricyclo[6.2.1.0*2,7*]undeca-2(7),3,5-triene

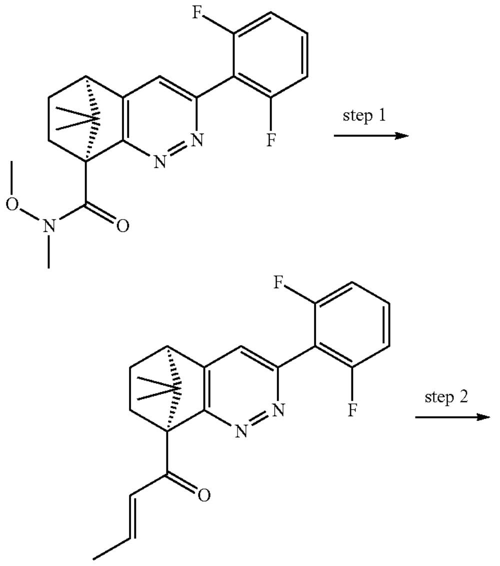

-continued

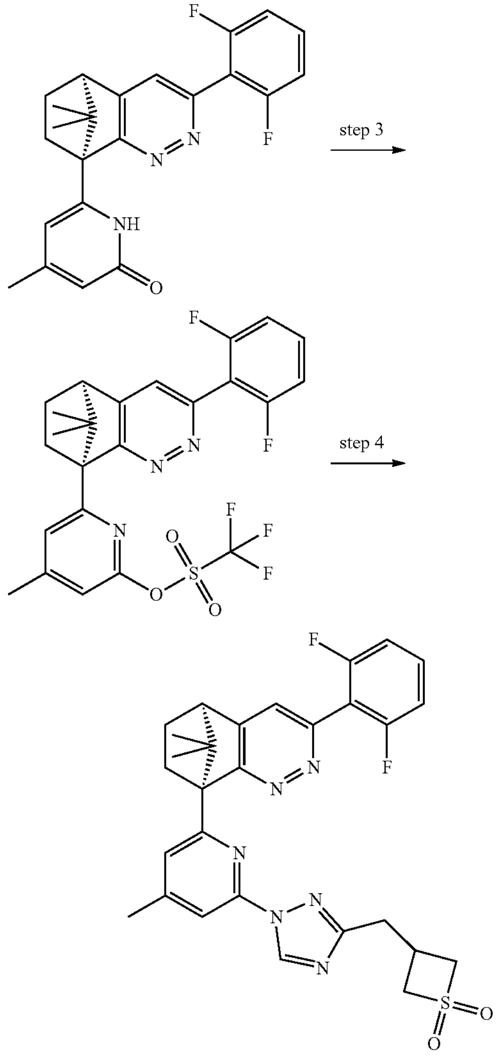

Step 1: (E)-1-[(1R,8R)-5-(2,6-Difluoro-phenyl)-11,11-dimethyl-3,4-diaza-tricyclo[6.2.1.0*2,7*]undeca-2(7),3,5-trien-1-yl]-but-2-en-1-one Following the procedure described for trifluoro-methanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyridin-2-yl ester, step 2 and using 1-propenyl magnesium bromide, gave the title compound as a solid (69%). LCMS (Method A) 3.85 min, ES$^+$ 355 [M+1]$^+$.

Step 2: 6-[(1S,8R)-5-(2,6-Difluoro-phenyl)-11,11-dimethyl-3,4-diaza-tricyclo[6.2.1.0*2,7*]undeca-2(7),3,5-trien-1-yl]-4-methyl-1H-pyridin-2-one Following the procedure described for trifluoro-methanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-pyridin-2-yl ester, step 3 and using the product from step 1, gave the title compound as a foam. LCMS (Method C) 1.02 min, ES$^+$ 394 [M+1]$^+$.

Step 3: Trifluoro-methanesulfonic acid 6-[(1S,8R)-5-(2,6-difluoro-phenyl)-11,11-dimethyl-3,4-diaza-tricyclo[6.2.1.0*2,7*]undeca-2(7),3,5-trien-1-yl]-4-methyl-pyridin-2-yl ester Following the procedure described for trifluoro-methane-sulfonic acid 6-[(1S,8R)-5-(2,6-difluoro-phenyl)-11,11-di-methyl-3,4-diaza-tricyclo[6.2.1.0*2,7*]undeca-2(7),3,5-trien-1-yl]-pyridin-2-yl ester, step 4 and using the product from step 2, gave the title compound as a solid (86%). LCMS (Method C) 1.47 min, $ES^+$ 526 $[M+1]^+$.

Step 4: (1S,8R)-5-(2,6-Difluoro-phenyl)-1-{6-[3-(1,1-dioxo-1lambda*6*-thietan-3-ylmethyl)-1,2,4]tri-azol-1-yl]-4-methyl-pyridin-2-yl}-11,11-dimethyl-3,4-diaza-tricyclo[6.2.1.0*2,7*]undeca-2(7),3,5-triene A mixture of the product from step 3 (150. mg, 0.290 mmol), Intermediate L (69 mg, 0.37 mmol), potassium phosphate tribasic (121 mg, 0.57 mmol) and $^t$BuXPhos Pd G3 (11 mg, 0.010 mmol) in 1,4-dioxane (3 mL) was degassed, purged with argon and heated at 100° C. for 16 h. The cooled mixture was diluted with EtOAc, washed with water and brine, dried ($Na_2SO_4$) and concentrated in vacuo to leave a residue. FCC (0-100% THF in cyclohexane, then 0-10% MeOH in DCM) gave a foam. MDAP then HPLC (50-98% MeCN in water, 0.1% $HCO_2H$, 20 min) gave the title compound as a solid (21 mg). LCMS (Method B) 4.79 min, $ES^+$ 563.1 $[M+1]^+$. $^1H$ NMR (400 MHz, $CDCl_3$) δ 9.06 (s, 1H), 7.74 (s, 1H), 7.61 (s, 1H), 7.48 (s, 1H), 7.46-7.38 (m, 1H), 7.10-7.02 (m, 2H), 4.35-4.29 (m, 2H), 4.11-4.04 (m, 2H), 3.29 (ddd, J=3.9, 10.6, 13.0 Hz, 1H), 3.24 (d, J=7.5 Hz, 2H), 3.16 (d, J=4.1 Hz, 1H), 3.15-3.08 (m, 1H), 2.51 (s, 3H), 2.49-2.43 (m, 1H), 1.72 (ddd, J=4.0, 9.1, 13.1 Hz, 1H), 1.38 (ddd, J=3.8, 9.1, 12.7 Hz, 1H), 1.15 (s, 3H), 0.77 (s, 3H).

Example 17: (1S,8R)-5-(2,6-Difluoro-phenyl)-1-{2-[3-(2-methanesulfonyl-ethyl)-[12,4]triazol-1-yl]-6-methoxy-pyrimidin-4-yl}-11,11-dimethyl-3,4-diaza-tricyclo[6.2.1.0*2,7*]undeca-2(7),3,5-triene

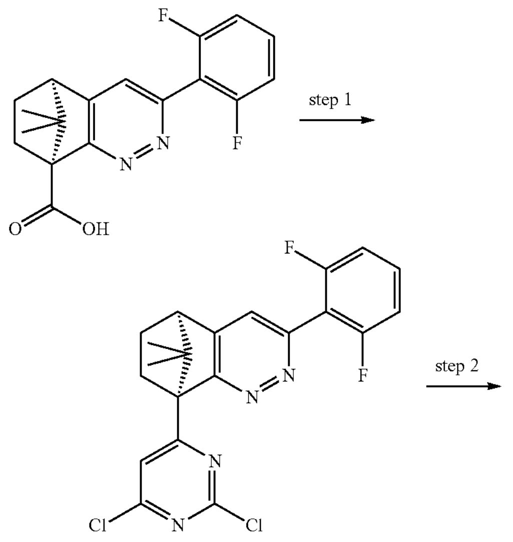

-continued

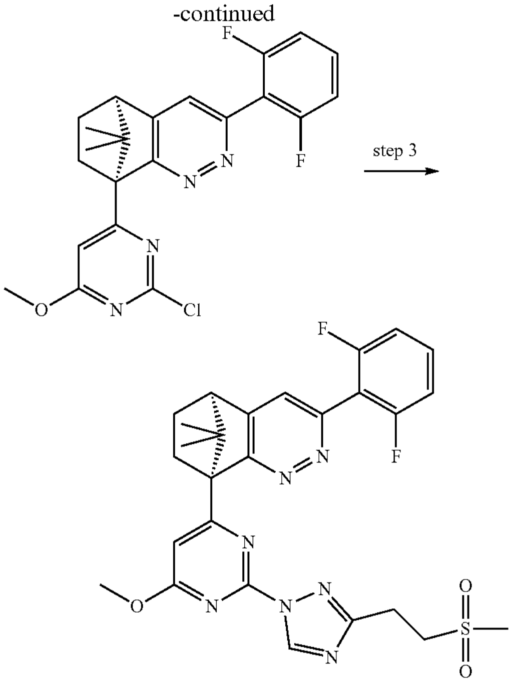

Step 1: (1S,8R)-1-(2,6-Dichloro-pyrimidin-4-yl)-5-(2,6-difluoro-phenyl)-11,11-dimethyl-3,4-diaza-tri-cyclo[6.2.1.0*2,7*]undeca-2(7),3,5-triene A mixture of Intermediate A (400 mg, 1.21 mmol), 2,4-dichloropyrimidine (451 mg, 3.03 mmol), ammonium persulfate (1.38 g, 6.05 mmol) and silver nitrate (411 mg, 2.42 mmol) in MeCN (6 mL) and water (6 mL) was stirred at 70° C. for 45 min. The mixture was diluted with EtOAc, washed with water, dried ($MgSO_4$) and concentrated in vacuo to leave a residue. FCC (15-25% EtOAc in cyclo-hexane) gave the title compound as a solid (100 mg). LCMS (Method C) 1.63 min, $ES^+$ 433 $[M+1]^+$.

Step 2: (1S,8R)-1-(2-Chloro-6-methoxy-pyrimidin-4-yl)-5-(2,6-difluoro-phenyl)-11,11-dimethyl-3,4-diaza-tricyclo[6.2.1.0*2,7*]undeca-2(7),3,5-triene A solution of the product from step 1 (195 mg, 0.450 mmol) and sodium methoxide solution (25% in MeOH; 0.08 mL, 0.59 mmol) in MeOH (10 mL) was added at RT. Concentration in vacuo removed some of the MeOH, then to the resulting suspension was added water. The precipitate was filtered, washed with MeOH/water and dried in vacuo to leave the title compound as a solid (quant.). LCMS (Method C) 1.62 min, $ES^+$ 425 $[M+1]^+$.

Step 3: (1S,8R)-5-(2,6-Difluoro-phenyl)-1-{2-[3-(2-methanesulfonyl-ethyl)-[1,2,4]triazol-1-yl]-6-methoxy-pyrimidin-4-yl}-11,11-dimethyl-3,4-diaza-tricyclo[6.2.1.0*2,7*]undeca-2(7),3,5-triene Following the procedure described in Example 4 step 3 and using Intermediate M and the product from step 2, gave the title compound as a solid (22%). LCMS (Method B) 4.24 min, $ES^+$ 568.1 $[M+1]^+$. $^1H$ NMR (400 MHz, DMSO-$d_6$) δ 9.45 (s, 1H), 7.83 (s, 1H), 7.67-7.58 (m, 1H), 7.35-7.27 (m, 2H), 7.25 (s, 1H), 4.10 (s, 3H), 3.59 (dd, J=6.6, 9.4 Hz, 2H), 3.29 (d, J=4.0 Hz, 1H), 3.26-3.16 (m, 3H), 3.08 (s, 3H), 2.48-2.39 (m, 1H), 1.59 (ddd, J=3.9, 9.1, 13.0 Hz, 1H), 1.28 (ddd, J=3.8, 9.1, 12.7 Hz, 1H), 1.13 (s, 3H), 0.75 (s, 3H).

Example 18: (1S,8R)-5-(2,6-Difluoro-phenyl)-1-{2-[3-(1,1-dioxo-1lambda*6*-thietan-3-ylmethyl)-[1,2,4]triazol-1-yl]-6-methyl-pyrimidin-4-yl}-11,11-dimethyl-3,4-diaza-tricyclo[6.2.1.0*2,7*]undeca-2(7),3,5-triene

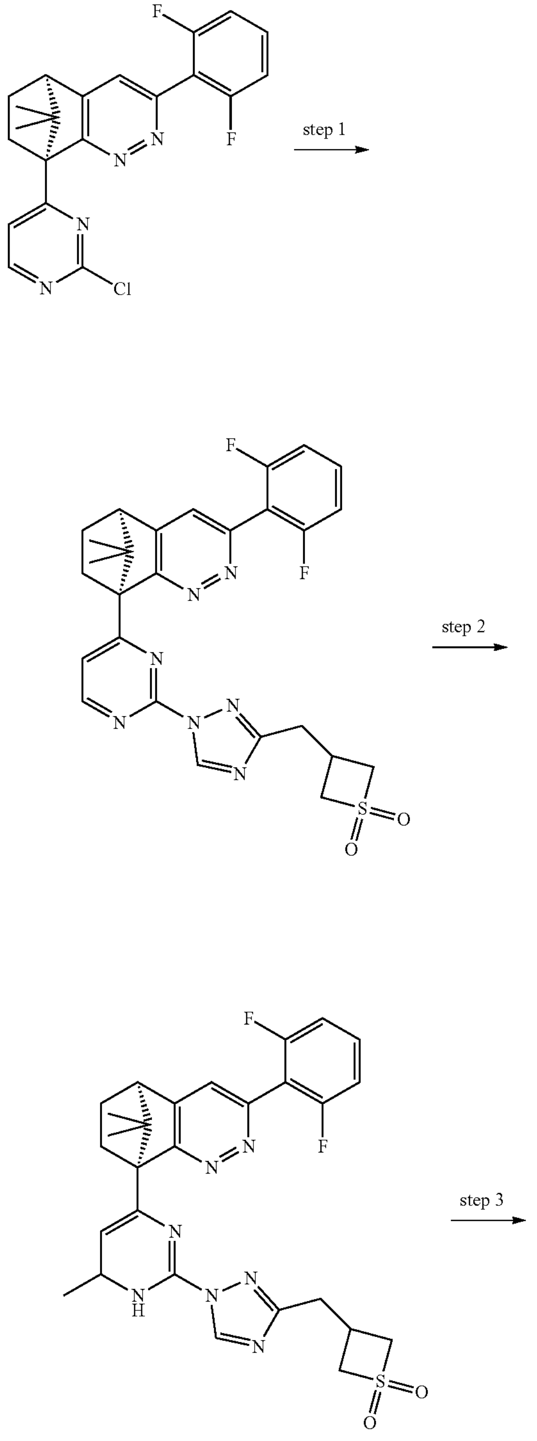

-continued

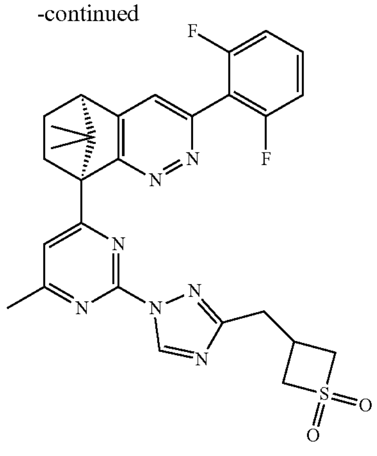

Step 1: (1S,8R)-5-(2,6-Difluoro-phenyl)-1-{2-[3-(1,1-dioxo-1 lambda*6*-thietan-3-ylmethyl)-[1.2.4]triazol-1-yl]-pyrimidin-4-yl}-11,11-dimethyl-3,4-diaza-tricyclo[6.2.1.0*2,7*]undeca-2(7),3,5-triene Following the procedure described in Example 4, step 3 and using 3-(1,1-dioxo-thietan-3-ylmethyl)-1H-[1,2,4]triazole gave the title compound as a solid. LCMS (Method C) 1.12 min, $ES^+$ 550 $[M+1]^+$. $^1H$ NMR (400 MHz, $CDCl_3$) δ 9.18 (s, 1H), 8.86 (d, J=5.2 Hz, 1H), 8.01 (d, J=5.2 Hz, 1H), 7.52 (t, J=1.3 Hz, 1H), 7.48-7.40 (m, 1H), 7.11-7.03 (m, 2H), 4.34-4.26 (m, 2H), 4.13-4.06 (m, 2H), 3.33-3.09 (m, 5H), 2.59-2.49 (m, 1H), 1.79 (ddd, J=4.1, 9.1, 13.1 Hz, 1H), 1.44 (ddd, J=3.9, 9.1, 12.9 Hz, 1H), 1.22 (s, 3H), 0.79 (s, 3H).

Step 2: (1S,8R)-5-(2,6-Difluoro-phenyl)-1-{2-[3-(1.1-dioxo-1lambda*6*-thietan-3-ylmethyl)-[1.2.4]triazol-1-yl]-6-methyl-6-dihydro-pyrimidin-4-yl}-11,11-dimethyl-3,4-diaza-tricyclo[6.2.1.0*2,7*]undeca-2(7),3,5-triene To a stirred solution of the product from step 1 (185 mg, 0.34 mmol) in dry THF (4 mL) at RT was added methylmagnesium bromide (3M in THF, 0.34 mL, 1.0 mmol) dropwise. The mixture was stirred at RT for 15 min then quenched with water. The aqueous phase was extracted with EtOAc (×2) and the combined extracts dried ($MgSO_4$), filtered and concentrated in vacuo to give the title compound as a residue (160 mg). LCMS (Method C) 1.39 min, ES 566 $[M+1]^+$.

Step 3: (1S,8R)-5-(2,6-Difluoro-phenyl)-1-{2-[3-(1,1-dioxo-1 lambda*6*-thietan-3-ylmethyl)-[1,2,4]triazol-1-yl]-6-methyl-pyrimidin-4-yl}-11,11-dimethyl-3,4-diaza-tricyclo[6.2.1.0*2,7*]undeca-2(7),3,5-triene A stirred solution of the product from step 2 (160 mg, 0.28 mmol) in THF (4 mL) was treated with 2,3-dichloro-5,6-dicyano-p-benzoquinone (64 mg, 0.28 mmol) at RT for 1 h. The reaction was quenched with water and extracted into EtOAc. The combined extracts were washed with water and brine solution, then dried ($MgSO_4$), filtered and concentrated in vacuo and give a residue. MDAP gave the title compound as a solid (12.8 mg). LCMS (Method B) 4.20 min, $ES^+$ 564.1 $[M+1]^+$. $^1H$ NMR (400 MHz, $CDCl_3$) δ 9.17 (s, 1H), 7.88 (s, 1H), 7.52 (t, J=1.3 Hz, 1H), 7.48-7.39 (m, 1H), 7.11-7.03 (m, 2H), 4.32-4.26 (m, 2H), 4.13-4.05 (m, 2H), 3.30 (d, J=7.3 Hz, 2H), 3.27 (ddd, J=3.9, 10.3, 12.9 Hz, 1H), 3.20 (d, J=4.0 Hz, 1H), 3.19-3.10 (m, 1H), 2.72 (s, 3H), 2.57-2.48 (m, 1H), 1.76 (ddd, J=4.1, 9.1, 13.1 Hz, 1H), 1.43 (ddd, J=3.9, 9.0, 12.7 Hz, 1H), 1.22 (s, 3H), 0.77 (s, 3H).

Example 19: (1S,8R)-5-(2,6-Difluoro-phenyl)-1-{2-[3-(2-methanesulfonyl-ethyl)-[1,2,4]triazol-1-yl]-pyrimidin-4-yl}-11,11-dimethyl-3,4-diaza-tricyclo[6.2.1.0*2,7*]undeca-2(7),3,5-triene

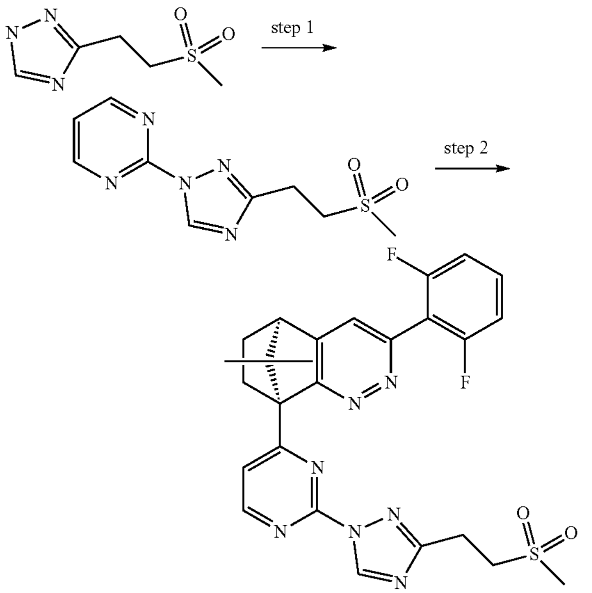

Step 1: 2-[3-(2-Methanesulfonyl-ethyl)-[1,2,4]triazol-1-yl]-pyrimidine

2-Chloropyrimidine (1.0 g, 8.73 mmol), 3-(2-methylsulfonylethyl)-1H-1,2,4-triazole (1.91 g, 10.9 mmol), $K_2CO_3$ (1.57 g, 11.4 mmol) and MeCN (29 mL) were heated to 70° C. for 18 h. The solvent was removed in vacuo, the solid placed in a Soxhlet extractor and refluxed with chloroform (250 mL) for 3 h to give the title compound as a mixture of isomers (1:14:3 ratio). The isomer ratio was improved by chromatography (80-100% THF/cHex then 1-10% MeOH/DCM) to provide the title compound as a white solid (ratio 1:18:0) (0.98 g, 3.88 mmol); $^1$H NMR (300 MHz, $CDCl_3$) δ 8.83 (d, J=4.8 Hz, 2H), 7.36 (t, J=4.8 Hz, 1H), 3.59-3.64 (m, 2H), 3.43-3.48 (m, 2H), 2.96 (s, 3H); LCMS (ESI, Method C) RT=0.68 min, $[M+H]^+$ 254.1.

Step 2: (1S,8R)-5-(2,6-Difluoro-phenyl)-1-{2-[3-(2-methanesulfonyl-ethyl)-[1,2,4]triazol-1-yl]-pyrimidin-4-yl}-11,11-dimethyl-3,4-diaza-tricyclo[6.2.1.0*2,7*]undeca-2(7),3,5-triene A mixture of (1R,8R)-5-(2,6-difluoro-phenyl)-11,11-dimethyl-3,4-diaza-tricyclo[6.2.1.0*2,7*]undeca-2(7),3,5-triene-1-carboxylic acid (204 mg, 0.62 mmol), 2-[3-(2-methylsulfonylethyl)-1,2,4-triazol-1-yl]pyrimidine (468.1 mg, 1.85 mmol) and silver nitrate (52 mg, 0.31 mmol) in MeCN (2 mL) and water (2 mL) was heated to 70° C., then ammonium persulfate (562 mg, 2.46 mmol) in water (0.8 mL) were added. After 90 min, the reaction mixture was concentrated then partitioned between chloroform (50 mL) and $H_2O$ (50 mL). The aqueous layer was extracted with chloroform (2×50 mL). The combined organic layers were washed with brine, passed through a phase-separator cartridge and purified by column chromatography (50-100% THF/cHex) to provide the title compound as a beige foam (80 mg; 92:8 ratio of isomers by HPLC); $^1$H NMR (400 MHz, $CDCl_3$) δ 9.19 (s, 1H), 8.86 (d, J=5.2 Hz, 1H), 8.00 (d, J=5.2 Hz, 1H), 7.52 (t, J=1.2 Hz, 1H), 7.48-7.40 (m, 1H), 7.11-7.03 (m, 2H), 3.64 (dd, J=6.7, 9.2 Hz, 2H), 3.50-3.45 (m, 2H), 3.29 (ddd, J=4.0, 10.6, 13.1 Hz, 1H), 3.22 (d, J=4.0 Hz, 1H), 2.98 (s, 3H), 2.58-2.49 (m, 1H), 1.79 (ddd, J=4.1, 9.1, 13.1 Hz, 1H), 1.44 (ddd, J=3.9, 9.1, 12.8 Hz, 1H), 1.21 (s, 3H), 0.79 (s, 3H). LCMS (Method B) RT=3.88 min, [M+H]+ 538.0.

Example 20: (1S,8R)-5-(2,6-Difluoro-phenyl)-1-{2-[3-(2-methanesulfonyl-ethyl)-[1,2,4]triazol-1-yl]-pyrimidin-4-yl}-11,11-dimethyl-3,4-diaza-tricyclo[6.2.1.0*2,7*]undeca-2(7),3,5-triene

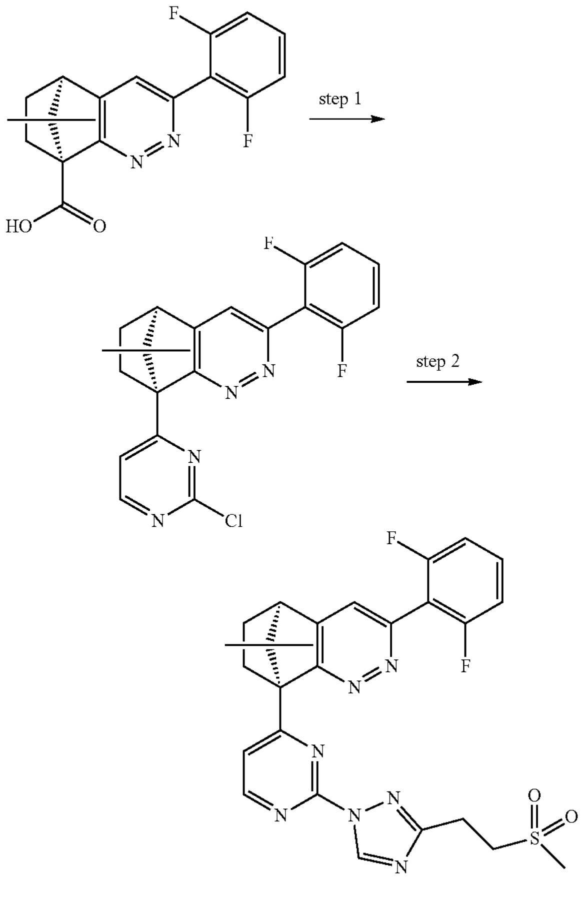

Step 1: (1S,8R)-1-(2-Chloro-pyrimidin-4-yl)-5-(2,6-difluoro-phenyl)-11,11-dimethyl-3,4-diaza-tricyclo[6.2.1.0*2,7*]undeca-2(7),3,5-triene A mixture of (1R,8R)-5-(2,6-difluorophenyl)-11,11-dimethyl-3,4-diazatricyclo[6.2.1.0*[2,7]]undeca-2(7),3,5-triene-1-carboxylic acid (1.20 g, 3.63 mmol), 2-chloropyrimidine (1.04 g, 9.08 mmol) and silver nitrate (1.23 g, 7.27 mmol in $CH_3CN$ (6 mL) was was stirred at 70° C. and a freshly prepared solution of ammonium persulfate (2.49 g, 10.9 mmol) in water (24 mL) was added in one portion. The resulting mixture was stirred for 20 min at 70° C., cooled with stirring at 0° C. for 5 min. The solids were collected by filtration and washed with acetonitrile/water 1:3 followed by water to afford the title compound as a solid (0.85 g, >20:1 isomeric purity by NMR); $^1$H NMR (300 MHz, $CDCl_3$) δ 8.65 (d, J=5.2 Hz, 1H), 7.95 (d, J=5.2 Hz, 1H), 7.50 (t, J=1.4 Hz, 1H), 7.43 (tt, J=8.4, 6.2 Hz, 1H), 7.09 (app. t, J=8.0 Hz, 2H), 3.31 (ddd, J=13.2, 10.5, 4.0 Hz, 1H), 3.18 (d, J=4.1 Hz, 1H), 2.49 (ddt, J=12.6, 10.7, 4.4 Hz, 1H), 1.69 (ddd, J=13.4, 9.1, 4.2 Hz, 1H), 1.39 (ddd, J=13.0, 8.8 3.7 Hz, 1H), 1.19 (s, 3H), 0.72 (s, 3H); LCMS (ESI, Method A) RT=1.5 min, $[M+H]^+$ 399.3.

Step 2: (1S,8R)-5-(2,6-Difluoro-phenyl)-1-{2-[3-(2-methanesulfonyl-ethyl)-[2,4]triazol-1-yl]-pyrimidin-4-yl}-11,11-dimethyl-3,4-diaza-tricyclo[6.2.1.0*2,7*]undeca-2(7),3,5-triene A mixture of the product from step 1 (310 mg, 0.780 mmol), 3-(2-methanesulfonylethyl)-1H-1,2,4-triazole (170 mg, 0.970 mmol) and $K_2CO_3$ (161 mg, 1.17 mmol) in DMSO (2 mL) was stirred for 2 h at 70° C. The reaction was cooled, diluted with EtOAc (40 ml),washed with water (40 ml), concentrated in vacuo and the crude product purified by FCC (0-5% MeOH/EtOAc) to afford the title compound as a solid (245 mg); $^1$H NMR (400 MHz, $CDCl_3$) δ 9.19 (s, 1H), 8.86 (d, J=5.2 Hz, 1H), 8.00 (d, J=5.2 Hz, 1H), 7.52 (t, J=1.2 Hz, 1H), 7.48-7.40 (m, 1H), 7.11-7.03 (m, 2H), 3.64 (dd, J=6.7, 9.2 Hz, 2H), 3.50-3.45 (m, 2H), 3.29 (ddd, J=4.0, 10.6, 13.1 Hz, 1H), 3.22 (d, J=4.0 Hz, 1H), 2.98 (s, 3H), 2.58-2.49 (m, 1H), 1.79 (ddd, J=4.1, 9.1, 13.1 Hz, 1H), 1.44 (ddd, J=3.9, 9.1, 12.8 Hz, 1H), 1.21 (s, 3H), 0.79 (s, 3H); LCMS (Method B) RT=3.88 min, [M+H]+ 538.0.

Example 21: (5R,8S)-8-(2-(3-(difluoromethyl)-1H-1,2,4-triazol-1-yl)pyrimidin-4-yl)-3-(2,6-difluorophenyl)-9,9-dimethyl-5,6,7,8-tetrahydro-5,8-methanocinnoline

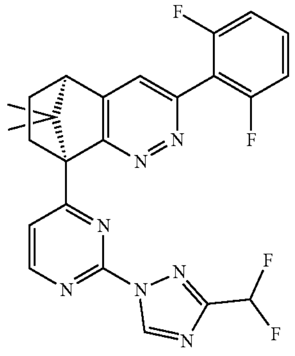 [SMILES: CC1(C)[C@H]2CC[C@]1(c1ccnc(-n3cnc(C(F)F)n3)n1)c1nnc(-c3c(F)cccc3F)cc12]

To a solution of (5R,8S)-8-(2-chloropyrimidin-4-yl)-3-(2,6-difluorophenyl)-9,9-dimethyl-5,6,7,8-tetrahydro-5,8-methanocinnoline (Intermediate R, 50 mg, 0.12 mmol) in DMSO (0.50 mL) was added $K_2CO_3$ (35 mg, 0.25 mmol) and 3-(difluoromethyl)-1H-1,2,4-triazole (30 mg, 0.25 mmol). The mixture was stirred at 110° C. for 15 h under a nitrogen atmosphere. The mixture was then diluted in DCM (10 mL), filtered through Celite® and concentrated in vacuo. The crude residue was purified by reverse phase chromatography (acetonitrile 30-70%/0.1% ammonium hydroxide in water) to give the title compound (37 mg) as a white solid. $^1$H NMR (400 MHz, DMSO-d6) δ 9.67 (s, 1H), 9.04 (d, J=5.2 Hz, 1H), 7.93 (d, J=5.2 Hz, 1H), 7.86 (s, 1H), 7.63 (tt, J=8.5, 6.5 Hz, 1H), 7.37-7.26 (m, 2H), 7.29 (d, J=54.0 Hz, 1H), 3.36-3.24 (m, 2H), 2.50-2.41 (m, 1H), 1.68-1.59 (m, 1H), 1.35-1.25 (m, 1H), 1.12 (s, 3H), 0.74 (s, 3H). LCMS M/Z (M+H) 482.

Example 22 and 23: 1-(4-((5R,8S)-3-(2,6-difluorophenyl)-9,9-dimethyl-6,7-dihydro-5,8-methanocinnolin-8(5H)-yl)pyrimidin-2-yl)-N-methyl-1H-1,2,4-triazole-3-sulfonamide and 1-(4-((5R,8S)-3-(2,6-difluorophenyl)-9,9-dimethyl-6,7-dihydro-5,8-methanocinnolin-8 (5H)-yl)pyrimidin-2-yl)-N,N-dimethyl-1H-1,2,4-triazole-3-sulfonamide

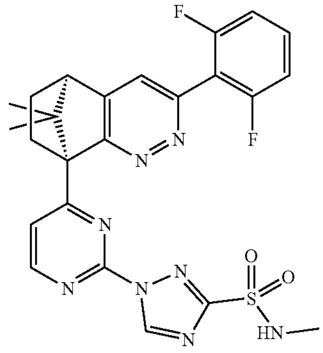

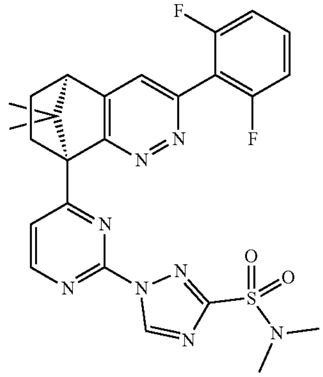

To a solution of 1-(4-((5R,8S)-3-(2,6-difluorophenyl)-9,9-dimethyl-6,7-dihydro-5,8-methanocinnolin-8(5H)-yl)pyrimidin-2-yl)-1H-1,2,4-triazole-3-sulfonamide (77 mg, 0.15 mmol) in DMF (0.75 mL) was added sodium hydride 60 mass % (12 mg, 0.30 mmol) in one portion followed by iodomethane (43 mg, 0.30 mmol). The mixture was stirred at room temperature for 4 h. Then, MeOH (1 mL) was added followed by DCM (10 mL). The solution was filtered through Celite® and concentrated in vacuo. The crude residue was purified by reverse phase chromatography (acetonitrile 5-70%/0.1% ammonium hydroxide in water) to give 1-(4-((5R,8S)-3-(2,6-difluorophenyl)-9,9-dimethyl-6,7-dihydro-5,8-methanocinnolin-8(5H)-yl)pyrimidin-2-yl)-N-methyl-1H-1,2,4-triazole-3-sulfonamide (Example 22, 1.2 mg) as a white solid and 1-(4-((5R,8S)-3-(2,6-difluorophenyl)-9,9-dimethyl-6,7-dihydro-5,8-methanocinnolin-8 (5H)-yl)pyrimidin-2-yl)-N,N-dimethyl-1H-1,2,4-triazole-3-sulfonamide (Example 23, 20 mg) as a white solid. Example 23: LCMS M/Z (M+H) 525. Example 23: $^1$H NMR (400

MHz, DMSO-d6) δ 9.76 (s, 1H), 9.07 (d, J=5.3 Hz, 1H), 7.97 (d, J=5.3 Hz, 1H), 7.86 (s, 1H), 7.68-7.57 (m, 1H), 7.37-7.22 (m, 2H), 3.36-3.24 (m, 2H), 2.90 (s, 6H), 2.57-2.41 (m, 1H), 1.70-1.59 (m, 1H), 1.35-1.25 (m, 1H), 1.14 (s, 3H), 0.75 (s, 3H). LCMS M/Z (M+H) 539.

Example 24: (5R,8S)-3-(2,6-difluorophenyl)-9,9-dimethyl-8-(2-(3-(methylsulfinyl)-1H-1,2,4-triazol-1-yl)pyrimidin-4-yl)-5,6,7,8-tetrahydro-5,8-methanocinnoline

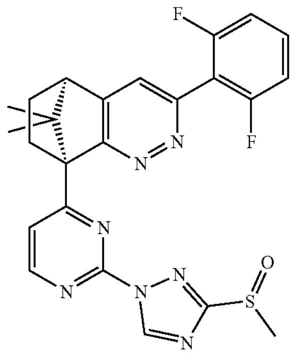 [SMILES: CS(=O)c1ncn(-c2nccc([C@@]34CC[C@@H](c5cc(-c6c(F)cccc6F)nnc53)C4(C)C)n2)n1]

To a solution of (5R,8S)-8-(2-chloropyrimidin-4-yl)-3-(2,6-difluorophenyl)-9,9-dimethyl-5,6,7,8-tetrahydro-5,8-methanocinnoline (Intermediate R, 100 mg, 0.251 mmol) in DMSO (0.84 mL) was added N,N-diisopropylethylamine (81 mg, 0.63 mmol) and 3-(methylsulfinyl)-1H-1,2,4-triazole (111 mg, 0.752 mmol). The mixture was stirred at 150° C. for 20 min in a microwave under a nitrogen atmosphere. The mixture was then diluted in DCM (10 mL), filtered through Celite® and concentrated in vacuo. The crude residue was purified by reverse phase chromatography (acetonitrile 30-70%/0.1% formic acid in water) to give the title compound (70 mg) as a white solid. $^1$H NMR (400 MHz, $CDCl_3$) δ 9.36 (d, J=1.5 Hz, 1H), 8.89 (d, J=5.2 Hz, 1H), 8.09 (dd, J=5.2, 2.7 Hz, 1H), 7.53 (d, J=1.4 Hz, 1H), 7.44 (tt, J=8.3, 6.3 Hz, 1H), 7.07 (t, J=8.0 Hz, 2H), 3.37-3.26 (m, 1H), 3.23 (d, J=4.0 Hz, 1H), 3.13 (s, 3H), 2.59-2.49 (m, 1H), 1.85-1.74 (m, 1H), 1.50-1.40 (m, 1H), 1.23 (d, J=1.7 Hz, 3H), 0.79 (s, 3H). LCMS M/Z (M+H) 494.

Example 25: (5R,8S)-3-(2,6-difluorophenyl)-9,9-dimethyl-8-(2-(3-(methylsulfonyl)-1H-1,2,4-triazol-1-yl)pyrimidin-4-yl)-5,6,7,8-tetrahydro-5,8-methanocinnoline

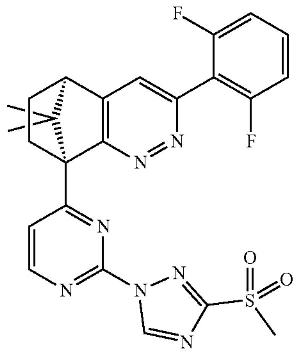 [SMILES: CC1(C)[C@H]2CC[C@]1(c1ccnc(-n3cnc(S(C)(=O)=O)n3)n1)c1nnc(-c3c(F)cccc3F)cc12]

To a solution of (5R,8S)-3-(2,6-difluorophenyl)-9,9-dimethyl-8-(2-(3-(methylsulfinyl)-1H-1,2,4-triazol-1-yl)pyrimidin-4-yl)-5,6,7,8-tetrahydro-5,8-methanocinnoline (70 mg, 0.14 mmol) in DCM (1.4 mL) was added 3-chloroperoxybenzoic acid 77 mass % (32 mg, 0.14 mmol) in one portion at 0° C. The mixture was stirred at 0° C. for 20 min. Then, the reaction mixture was slowly warmed up to room temperature and stirred at this temperature for 15 h. The mixture was then diluted in DCM (10 mL), filtered through Celite® and concentrated in vacuo. The crude residue was purified by reverse phase chromatography (acetonitrile 20-60%/0.1% ammonium hydroxide in water) to give the title compound (15 mg) as a white solid. $^1$H NMR (400 MHz, DMSO-d6) δ 9.81 (s, 1H), 9.07 (d, J=5.2 Hz, 1H), 7.98 (d, J=5.1 Hz, 1H), 7.87 (s, 1H), 7.63 (tt, J=8.4, 6.5 Hz, 1H), 7.31 (t, J=8.1 Hz, 2H), 3.39-3.26 (m, 3H), 3.31 (s, 3H), 1.69-1.60 (m, 1H), 1.36-1.27 (m, 1H), 1.13 (s, 3H), 0.74 (s, 3H). LCMS M/Z (M+H) 510.

Example 26: (5R,8S)-3-(2,6-difluorophenyl)-9,9-dimethyl-8-(6-(methylsulfonyl)pyridin-2-yl)-5,6,7,8-tetrahydro-5,8-methanocinnoline

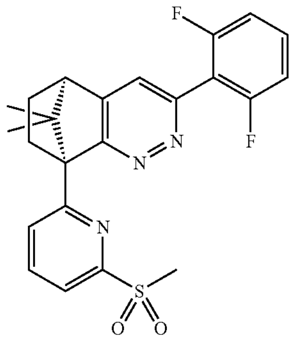 [SMILES: CC1(C)[C@H]2CC[C@]1(c1cccc(S(C)(=O)=O)n1)c1nnc(-c3c(F)cccc3F)cc12]

Step 1: (5R,8S)-3-(2,6-difluorophenyl)-9,9-dimethyl-8-(6-(methylthio)pyridin-2-yl)-5,6,7,8-tetrahydro-5,8-methanocinnoline

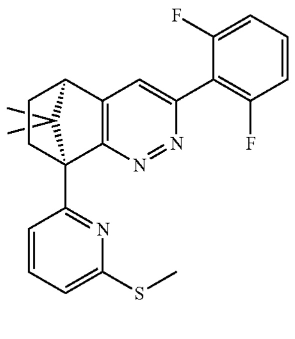 [SMILES: CSc1cccc([C@@]23CC[C@@H](c4cc(-c5c(F)cccc5F)nnc42)C3(C)C)n1]

To a solution of 6-((5R,8S)-3-(2,6-difluorophenyl)-9,9-dimethyl-6,7-dihydro-5,8-methanocinnolin-8(5H)-yl)pyridin-2-yl trifluoromethanesulfonate (Intermediate B, 250 mg, 0.489 mmol), N,N-diisopropylethylamine (69 mg, 0.54 mmol), 4,5-bis(diphenylphosphino)-9,9-dimethylxanthene (28 mg, 0.049 mmol) and tris(diebnzylideneacetone)dipalladium (0) (45 mg, 0.049 mmol) in dioxane (3.3 mL) was added sodium thiomethoxide 16% in water (642 mg, 1.47 mmol). The mixture was stirred at 120° C. for 5 min in a microwave under a nitrogen atmosphere. The reaction mixture was then cooled to room temperature, dichloromethane (35 mL) and sat. $NaHCO_3$ aqueous solution (35 mL) were added and the two phases were separated. The aqueous layer was extracted with DCM (2×20 mL). The combined organic layers were dried over anhydrous $MgSO_4$, filtered and concentrated in vacuo. The crude residue was purified by silica gel chromatography (iPrOAc/Heptane=1:5) to afford the title compound (98 mg) as a white solid. $^1H$ NMR (400 MHz, $CDCl_3$) δ 7.63-7.48 (m, 2H), 7.44 (t, J=1.4 Hz, 1H), 7.43-7.35 (m, 1H), 7.14 (dd, J=7.8, 1.0 Hz, 1H), 7.09-7.01 (m, 2H), 3.47-3.35 (m, 1H), 3.11 (d, J=4.1 Hz, 1H), 2.59 (s, 3H), 2.48-2.40 (m, 1H), 1.70-1.60 (m, 1H), 1.38-1.29 (m, 1H), 1.13 (s, 3H), 0.71 (s, 3H). LCMS M/Z (M+H) 410.

Step 2: (5R,8S)-3-(2,6-difluorophenyl)-9,9-dimethyl-8-(6-(methylsulfonyl)pyridin-2-yl)-5,6,7,8-tetrahydro-5,8-methanocinnoline

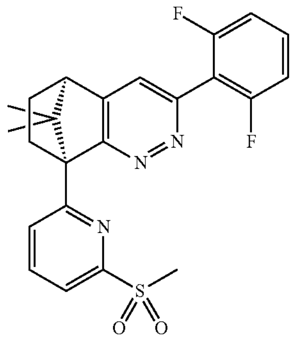 [SMILES: CC1(C)[C@H]2CC[C@]1(c1cccc(S(C)(=O)=O)n1)c1nnc(-c3c(F)cccc3F)cc12]

To a solution of (5R,8S)-3-(2,6-difluorophenyl)-9,9-dimethyl-8-(6-(methylthio)pyridin-2-yl)-5,6,7,8-tetrahydro-5,8-methanocinnoline (96 mg, 0.23 mmol) in DCM (2.3 mL) was added 3-chloroperoxybenzoic acid 77 mass % (105 mg, 0.469 mmol) in one portion at 0° C. The mixture was stirred at 0° C. for 20 min. Then, the reaction mixture was slowly warmed up to room temperature and stirred at this temperature for 15 h. The mixture was then diluted in DCM (10 mL), filtered through Celite® and concentrated in vacuo. The crude residue was purified by reverse phase chromatography (acetonitrile 20-60%/0.1% ammonium hydroxide in water) to give the title compound (53 mg) as a white solid. $^1H$ NMR (400 MHz, DMSO-d6) δ 8.25 (t, J=7.8 Hz, 1H), 8.04 (t, J=8.3 Hz, 2H), 7.85 (s, 1H), 7.69-7.58 (m, 1H), 7.32 (t, J=8.1 Hz, 2H), 3.34 (s, 3H), 3.30 (d, J=4.0 Hz, 1H), 3.27-3.15 (m, 1H), 2.50-2.39 (m, 1H), 1.68-1.55 (m, 1H), 1.24-1.30 (m, 1H), 1.06 (s, 3H), 0.70 (s, 3H). LCMS M/Z (M+H) 442.

Example 27: (5R,8R)-3-(2,6-difluorophenyl)-9,9-dimethyl-8-(4-(3-(2-(methylsulfonyl)ethyl)-1H-1,2,4-triazol-1-yl)pyrimidin-2-yl)-5,6,7,8-tetrahydro-5,8-methanocinnoline

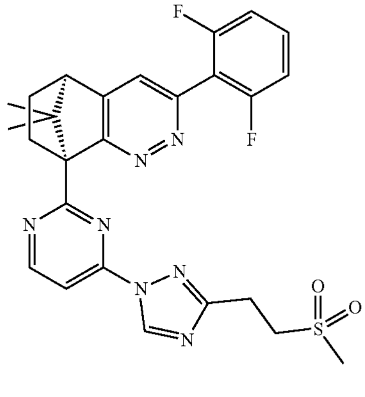 [SMILES: CC1(C)[C@H]2CC[C@]1(c1nccc(-n3cnc(CCS(C)(=O)=O)n3)n1)c1nnc(-c3c(F)cccc3F)cc12]

Step 1: 2-((5R,8R)-3-(2,6-difluorophenyl)-9,9-dimethyl-6,7-dihydro-5 8-methanocinnolin-8(5H)-yl) pyrimidin-4-ol

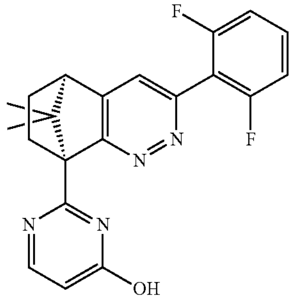 [SMILES: CC1(C)[C@H]2CC[C@]1(c1nccc(O)n1)c1nnc(-c3c(F)cccc3F)cc12]

To a solution of (5R,8R)-3-(2,6-difluorophenyl)-9,9-dimethyl-6,7-dihydro-5,8-methanocinnoline-8(5H)-carboximidamide (Intermediate S, 733 mg, 2.32 mmol) in EtOH (17. mL) was added ethyl 3-ethoxyacrylate (492 mg, 3.35 mmol). The reaction mixture was stirred at 78° C. for 24 h. The reaction was cooled to room temperature, ethyl 3-ethoxyacrylate (164 mg, 1.12 mmol) was added and the mixture was stirred at 78° C. for another 24 h. The mixture was cooled to room temperature and concentrated in vacuo. The crude residue was purified by silica gel chromatography (iPrOAc/Heptane=1:5 to 1:0) to afford the title compound (454 mg) as a white solid. $^1H$ NMR (400 MHz, $CDCl_3$) δ12.68 (s, 1H), 7.97 (d, J=6.7 Hz, 1H), 7.52 (s, 1H), 7.50-7.39 (m, 1H), 7.13-7.02 (m, 2H), 6.39 (d, J=6.7 Hz, 1H), 3.11 (d, J=4.1 Hz, 1H), 2.99-2.88 (m, 1H), 2.58-2.47 (m, 1H), 1.85-1.75 (m, 1H), 1.45 (s, 3H), 1.44-1.26 (m, 1H), 0.71 (s, 3H). LCMS M/Z (M+H) 381.

Step 2: (5R,8R)-3-(2,6-difluorophenyl)-9,9-dimethyl-8-(4-(3-(2-(methylsulfonyl)ethyl)-1H-1,2,4-triazol-1-yl)pyrimidin-2-yl)-5,6,7,8-tetrahydro-5,8-methanocinnoline

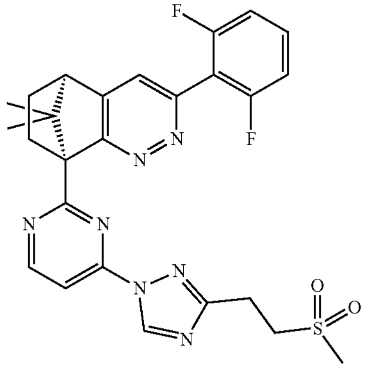 [SMILES: CC1(C)[C@H]2CC[C@]1(c1nccc(-n3cnc(CCS(C)(=O)=O)n3)n1)c1nnc(-c3c(F)cccc3F)cc12]

To a solution of 2-((5R,8R)-3-(2,6-difluorophenyl)-9,9-dimethyl-6,7-dihydro-5,8-methanocinnolin-8(5H)-yl)pyrimidin-4-ol (50 mg, 0.13 mmol) and N,N-diisopropylethylamine (21 mg, 0.16 mmol), in DCM (0.66 mL) was added trifluoromethanesulfonic anhydride (41 mg, 0.14 mmol) at 0° C. The reaction mixture was stirred at 0° C. for 15 min, warmed up to room temperature and stirred at this temperature for an additional 30 min. The mixture concentrated in vacuo and then re-dissolved in dioxane (0.54 mL). To this solution was added 3-(2-(methylsulfonyl)ethyl)-1H-1,2,4-triazole (Intermediate M, 24 mg, 0.14 mmol), potassium phosphate tribasic (47 mg, 0.21 mmol) and [(2-Di-tert-butylphosphino-2',4',6'-triisopropyl-1,1'-biphenyl)-2-(2'-amino-1,1'-biphenyl)]palladium(II) methanesulfonate (4.4 mg, 0.0054 mmol). The reaction mixture was stirred at 50° C. for 4 h. The mixture was cooled to room temperature, diluted in DCM (10 mL), filtered through Celite and concentrated in vacuo. The crude residue was purified by reverse phase chromatography (acetonitrile 20-60%/0.1% ammonium hydroxide in water) to give the title compound (14 mg) as a beige solid. $^1$H NMR (400 MHz, DMSO-d6) δ 9.39 (s, 1H), 9.10 (d, J=5.5 Hz, 1H), 7.85 (d, J=5.5 Hz, 1H), 7.79 (s, 1H), 7.67-7.55 (m, 1H), 7.29 (t, J=8.1 Hz, 2H), 3.65-3.56 (m, 2H), 3.30-3.21 (m, 3H), 3.21-3.11 (m, 1H), 3.07 (s, 3H), 2.45-2.36 (m, 1H), 1.82-1.72 (m, 1H), 1.32-1.22 (m, 1H), 1.07 (s, 3H), 0.94 (s, 3H). LCMS M/Z (M+H) 538.

Example 28 and 29: (5R,8S)-3-(3-chloro-2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline and (5R,8S)-3-(4-chloro-2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline

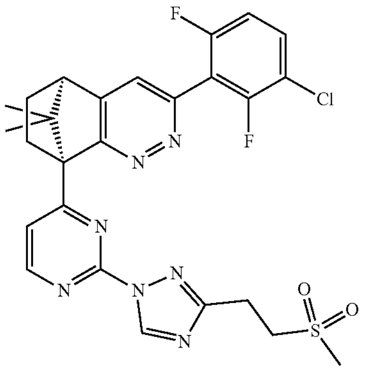

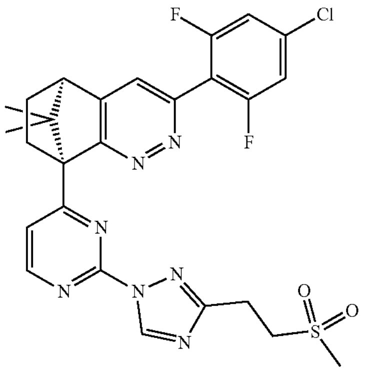

To a solution of (5R,8S)-3-(2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline (Example 4, 200 mg, 0.372 mmol) and bis(pinacolato) diboron (142 mg, 0.558 mmol) in cyclopentyl methyl ether (2.5 mL) was added (1,5-cyclooctadiene)(methoxy)iridium (I) dimer (38 mg, 0.056 mmol) and 4,4'-di-tert-butyl-2,2'-bipyridine (31 mg, 0.11 mmol). The reaction mixture was sparged with nitrogen for 2 min and then stirred at 100° C. for 15 h under a nitrogen atmosphere. The mixture concentrated in vacuo and then re-dissolved in MeOH (1.0 mL) and water (1.0 mL). To this solution was added cupric chloride (162 mg, 1.21 mmol) and the reaction mixture was stirred at 80° C. for 5 h under a nitrogen atmosphere. The reaction mixture was then cooled to room temperature, diluted in dichloromethane (25 mL) and water (25 mL) was added. The two phases were separated and the aqueous layer was extracted with DCM (3×). The combined organic layers were dried over anhydrous $MgSO_4$, filtered and concentrated in vacuo. The crude residue was purified by SFC (Pyridyl amide 150×30.0 mm I.D., 5 μm; 5-60% of 0.1% ammonium hydroxide in MeOH/Supercritical $CO_2$) to give (5R,8S)-3-(3-chloro-2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline (Example 28, 1.6 mg, first peak) as a beige solid and (5R,8S)-3-(4-chloro-2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline (Example 29, 1.3 mg second peak) as a beige solid. Example 28: LCMS M/Z (M+H) 573. Example 29: $^1$H NMR (400 MHz, $CDCl_3$) δ 9.18 (s, 1H), 8.86 (d, J=5.2 Hz, 1H), 7.98 (d, J=5.2 Hz, 1H), 7.49 (d, J=1.5 Hz, 1H), 7.12 (d, J=7.5 Hz, 2H), 3.67-3.58 (m, 2H), 3.47 (dd, J=9.4, 6.4 Hz, 2H), 3.33-3.24 (m, 1H), 3.22 (d, J=4.1 Hz, 1H), 2.97 (s, 3H), 2.59-2.47 (m, 1H), 1.85-1.71 (m, 1H), 1.50-1.35 (m, 1H), 1.21 (s, 3H), 0.78 (s, 3H). LCMS M/Z (M+H) 573.

Example 30 and 31: 3-((5R,8S)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnolin-3-yl)-2,4-difluorophenol and 4-((5R,8S)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnolin-3-yl)-3,5-difluorophenol

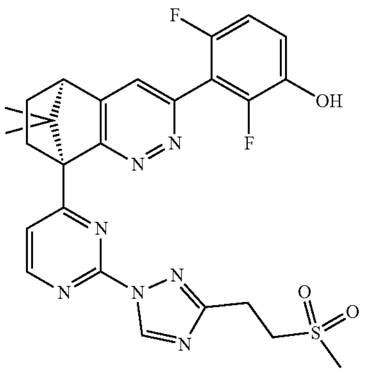

-continued

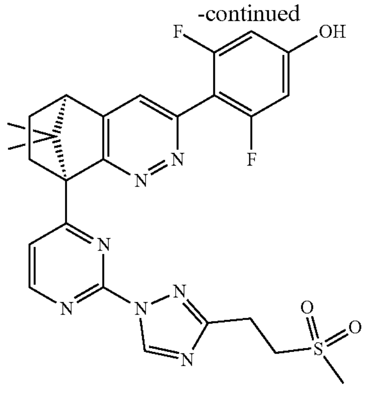

To a solution of (5R,8S)-3-(2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline (Intermediate S, 45 mg, 0.084 mmol) and bis(pinacolato) diboron (42 mg, 0.17 mmol) in cyclopentyl methyl ether (0.56 mL) was added (1,5-cyclooctadiene)(methoxy)iridium (I) dimer (8.5 mg, 0.013 mmol) and 4,4'-di-tert-butyl-2,2'-bipyridine (6.9 mg, 0.025 mmol). The reaction mixture was sparged with nitrogen for 2 min and then stirred at 100° C. for 15 h under a nitrogen atmosphere. The mixture concentrated in vacuo and then re-dissolved in acetone (0.23 mL) and water (0.14 mL). To this solution was slowly added potassium peroxymonosulfate (46 mg, 0.075 mmol) over 3 min and the reaction mixture was vigorously stirred at room temperature for 15 min. To the reaction mixture was added aqueous $Na_2S_2O_5$ 1 M (20 mL) and the solution was extracted with DCM (3×). The combined organic layers were dried over anhydrous $MgSO_4$, filtered and concentrated in vacuo. The crude residue was purified by SFC (Pyridyl amide 150×30.0 mm I.D., 5 μm; 5-60% of 0.1% ammonium hydroxide in MeOH/Supercritical $CO_2$) to give 3-((5R,8S)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnolin-3-yl)-2,4-difluorophenol (Example 30, 1.1 mg, first peak) as a pale yellow solid and 4-((5R,8S)-9,9-dimethyl-8-(2-(3-(2-(methylsulfonyl)ethyl)-H-1,2,4-triazol-1-yl)pyrimidin-4-yl)-5,6,7,8-tetrahydro-5,8-methanocinnolin-3-yl)-3,5-difluorophenol (Example 31, 1.0 mg, second peak) as a white solid. Example 30: LCMS M/Z (M+H) 554. Example 31: LCMS M/Z (M+H) 554.

Example 32: (5R,8S)-8-(6-(3-(difluoromethyl)-1H-1,2,4-triazol-1-yl)pyridin-2-yl)-3-(2,6-difluorophenyl)-9,9-dimethyl-5,6,7,8-tetrahydro-5,8-methanocinnoline

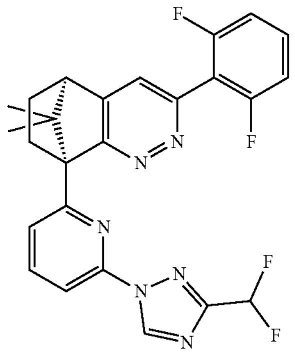 [SMILES: CC1(C)[C@H]2CC[C@]1(c1cccc(-n3cnc(C(F)F)n3)n1)c1nnc(-c3c(F)cccc3F)cc12]

To a solution of 6-((5R,8S)-3-(2,6-difluorophenyl)-9,9-dimethyl-6,7-dihydro-5,8-methanocinnolin-8(5H)-yl)pyridin-2-yl trifluoromethanesulfonate (Intermediate B, 50 mg, 0.098 mmol) in dioxane (0.49 mL) was added 3-(difluoromethyl)-1H-1,2,4-triazole (24 mg, 0.20 mmol), potassium phosphate tribasic (43 mg, 0.20 mmol) and [(2-Di-tert-butylphosphino-2',4',6'-triisopropyl-1,1'-biphenyl)-2-(2'-amino-1,1'-biphenyl)] palladium(II) methanesulfonate (4.8 mg, 0.0059 mmol). The reaction mixture was stirred at 90° C. for 18 h. The mixture was cooled to room temperature, diluted in DCM (10 mL), filtered through Celite® and concentrated in vacuo. The crude residue was purified by reverse phase chromatography (acetonitrile 30-70%/0.1% ammonium hydroxide in water) to give the title compound (7.1 mg) as a white solid. $^1H$ NMR (400 MHz, DMSO-d6) δ 9.59 (s, 1H), 8.19 (t, J=7.9 Hz, 1H), 7.89 (d, J=8.0 Hz, 1H), 7.86-7.80 (m, 2H), 7.62 (tt, J=8.5, 6.6 Hz, 1H), 7.31 (t, J=8.1 Hz, 2H), 7.27 (t, J=53.0 Hz, 1H), 3.46-3.38 (m, 1H), 3.32-3.21 (m, 2H), 1.63-1.54 (m, 1H), 1.33-1.22 (m, 1H), 1.08 (s, 3H), 0.71 (s, 3H). LCMS M/Z (M+H) 481.

Example 33: N-(5-(6-((5R,8S)-3-(2,6-difluorophenyl)-9,9-dimethyl-6,7-dihydro-5,8-methanocinnolin-8(5H)-yl)pyridin-2-yl)pyrimidin-2-yl)acetamide

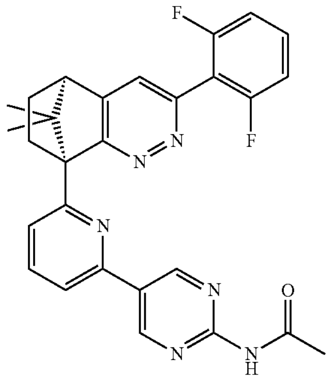 [SMILES: CC(=O)Nc1ncc(-c2cccc([C@@]34CC[C@@H](c5cc(-c6c(F)cccc6F)nnc53)C4(C)C)n2)cn1]

To a solution of 5-(6-((5R,8S)-3-(2,6-difluorophenyl)-9,9-dimethyl-6,7-dihydro-5,8-methanocinnolin-8(5H)-yl)pyridin-2-yl)pyrimidin-2-amine (30 mg, 0.066 mmol) in DCM (0.66 mL) was added NN-diisopropylethylamine (34 mg, 0.26 mmol) followed by acetyl bromide (24 mg, 0.20 mmol) at 0° C. The reaction mixture was stirred at 0° C. for 20 min and slowly warmed up to room temperature over 1 h. The mixture was then concentrated in vacuo and re-dissolved in THF (0.21 mL). To this solution was added sodium hydroxide 1 M in water (0.21 mL) and the reaction mixture was stirred at room temperature for 1 h. A saturated aqueous solution of $NH_4Cl$ (0.5 mL) was added and the mixture was concentrated in vacuo. The mixture was dissolved in DCM (10 mL), filtered through Celite® and concentrated in vacuo again. The crude residue was purified by reverse phase chromatography (acetonitrile 20-60%/0.1% ammonium hydroxide in water) to give the title compound (5.6 mg, 15%) as a beige solid. $^1H$ NMR (400 MHz, DMSO-d6) δ 1H NMR (400 MHz, DMSO-d6) δ 8.83 (d, J=4.9 Hz, 2H), 7.95 (t, J=7.9 Hz, 1H), 7.73 (s, 1H), 7.67-7.51 (m, 3H), 7.43 (t, J=4.9 Hz, 1H), 7.35-7.22 (m, 2H), 3.41-3.25 (m, 1H), 3.13 (d, J=4.0 Hz, 1H), 2.77-2.68 (m, 1H), 2.26 (s, 3H), 1.43-1.34 (m, 1H), 1.19-1.08 (m, 1H), 0.74 (s, 3H), 0.46 (s, 3H). LCMS M/Z (M+H) 499.

Example 34: 5-(6-((5R,8S)-3-(2,6-difluorophenyl)-9,9-dimethyl-6,7-dihydro-5,8-methanocinnolin-8(5H)-yl)pyridin-2-yl)pyrimidine-2-carboxylic Acid

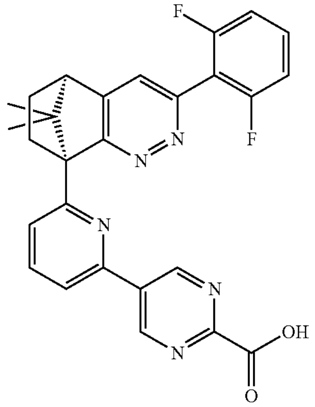 [SMILES: CC1(C)[C@H]2CC[C@]1(c1cccc(-c3cnc(C(=O)O)nc3)n1)c1nnc(-c3c(F)cccc3F)cc12]

To a solution of 6-((5R,8S)-3-(2,6-difluorophenyl)-9,9-dimethyl-6,7-dihydro-5,8-methanocinnolin-8(5H)-yl)pyridin-2-yl trifluoromethanesulfonate (Intermediate B, 125 mg, 0.244 mmol) in dioxane (1.6 mL) was added methyl 5-(4,4,5,5,-tetramethyl-1,3,2-dioxaborolan-2-yl)pyrimidine-2-carboxylate (101 mg, 0.367 mmol), potassium phosphate tribasic (145 mg, 0.611 mmol) and [(2-Di-tert-butylphosphino-2',4',6'-triisopropyl-1,1'-biphenyl)-2-(2'-amino-1,1'-biphenyl)] palladium(II) methanesulfonate (14 mg, 0.017 mmol). The reaction mixture was stirred at 90° C. for 4 h. The mixture was cooled to room temperature and [(2-Di-tert-butylphosphino-2',4',6'-triisopropyl-1,1'-biphenyl)-2-(2'-amino-1,1'-biphenyl)] palladium(II) methanesulfonate (14 mg, 0.017 mmol) was added, after which the reaction mixture was stirred at 90° C. for 16 h. The mixture was cooled to room temperature and an aqueous solution of sodium hydroxide 1 M (0.50 mL) was added and the reaction mixture was stirred at room temperature for 1 h. To the reaction mixture was added an aqueous solution of hydrogen chloride 1 N (20 mL) and DCM (20 mL). The two phases were separated and the aqueous layer was extracted with DCM (2×). The combined organic layers were washed with brine, dried over anh. $MgSO_4$, filtered and concentrated in vacuo. The crude residue was purified by reverse phase chromatography (acetonitrile 5-50%/0.1% ammonium hydroxide in water) to give the title compound (5.5 mg) as a beige solid. $^1$H NMR (400 MHz, DMSO-d6) δ 9.52 (s, 2H), 8.18 (d, J=7.8 Hz, 1H), 8.07 (t, J=7.8 Hz, 1H), 7.84-7.75 (m, 2H), 7.68-7.56 (m, 1H), 7.31 (t, J=8.1 Hz, 2H), 6.65 (s, 1H), 3.39-3.28 (m, 2H), 2.49-2.41 (m, 1H), 1.68-1.55 (m, 1H), 1.33-1.23 (m, 1H), 1.11 (s, 3H), 0.75 (s, 3H). LCMS M/Z (M+H) 486.

Example 35 and 36: (5R,8S)-3-(2,6-difluorophenyl)-9,9-dimethyl-8-(5-methyl-6-(3-(2-(methylsulfonyl)ethyl)-1H-1,2,4-triazol-1-yl)pyridin-2-yl)-5,6,7,8-tetrahydro-5,8-methanocinnoline and (5R,8S)-3-(2,6-difluoro-3-methylphenyl)-9,9-dimethyl-8-(6-(3-(2-(methylsulfonyl)ethyl)-1H-1,2,4-triazol-1-yl)pyridin-2-yl)-5,678-tetrahydro-5,8-methanocinnoline

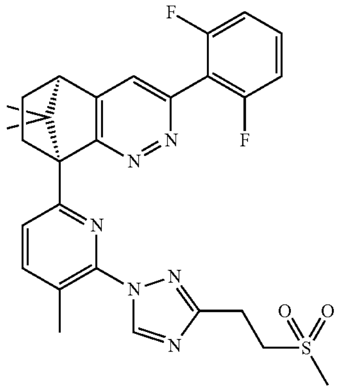

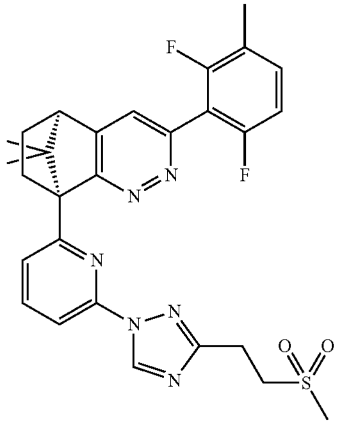

Step 1: (5R,8S)-8-(6-chloropyridin-2-yl)-3-(2,6-difluorophenyl)-9,9-dimethyl-5,6,7,8-tetrahydro-5,8-methanocinnoline

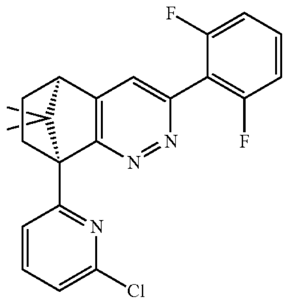 [SMILES: CC1(C)[C@H]2CC[C@]1(c1cccc(Cl)n1)c1nnc(-c3c(F)cccc3F)cc12]

To a solution of (5R,8R)-3-(2,6-difluorophenyl)-9,9-dimethyl-6,7-dihydro-5,8-methanocinnoline-8(5H)-carboxylic acid (Intermediate A, 2.00 g, 6.06 mmol) and silver nitrate (4.12 g, 24.2 mmol) in an aqueous solution of sulfuric acid 10 mass % (15 mL) under a nitrogen atmosphere was added 2-chloropyridine (2.75 g, 24.2 mmol). The reaction mixture was stirred at 100° C. for 1 h. A freshly prepared solution of ammonium persulfate (5.58 g, 24.2 mmol) in water (10 mL) was added dropwise over 5 min at 110° C. and the reaction mixture was stirred at that temperature for 72 h. The mixture was cooled to room temperature, diluted with water (50 mL) and basified to pH=13 with an aqueous solution of NaOH 3 N. The aqueous solution was extracted with a DCM:MeOH (9:1) mixture (3×). The combined organic layers were washed with brine, dried over anh. $MgSO_4$, filtered and concentrated in vacuo. The crude residue was purified by silica gel chromatography (iPrOAc/Heptane=1:1 to 1:0) to afford the title compound (840 mgas a pale yellow solid. $^1$H NMR (400 MHz, $CDCl_3$) δ 7.83 (d, J=7.9 Hz, 1H), 7.72-7.65 (m, 1H), 7.47-7.45 (m, 1H), 7.45-7.36 (m, 1H), 7.27 (d, J=7.3 Hz, 1H), 7.10-6.99 (m, 2H), 3.40-3.30 (m, 1H), 3.13 (d, J=4.1 Hz, 1H), 2.52-2.37 (m, 1H), 1.71-1.61 (m, 1H), 1.39-1.26 (m, 1H), 1.13 (s, 3H), 0.70 (s, 3H). LCMS M/Z (M+H) 398.

Step 2: (5R,8S)-8-(6-chloro-5-iodopyridin-2-yl)-3-(2,6-difluorophenyl)-9,9-dimethyl-5,6,7,8-tetrahydro-5,8-methanocinnoline and (5R,8S)-8-(6-chloropyridin-2-yl)-3-(2,6-difluoro-3-iodophenyl)-9,9-dimethyl-5,6,7,8-tetrahydro-5,8-methanocinnoline

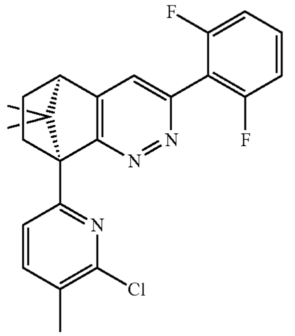

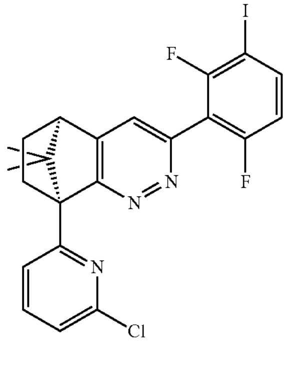

To a solution of (5R,8S)-8-(6-chloropyridin-2-yl)-3-(2,6-difluorophenyl)-9,9-dimethyl-5,6,7,8-tetrahydro-5,8-methanocinnoline (315 mg, 0.792 mmol) in THF (7.9 mL) under a nitrogen atmosphere was added 2-2,2,6,6-tetramethylpiperidine (257 mg, 1.82 mmol) followed by a freshly prepared solution of n-butyllithium 0.42 M in THF (5.3 mL) dropwise at −78° C. The reaction mixture was stirred at −78° C. for 1 h. A solution of iodine (181 mg, 0.713 mmol) in THF (3 mL) was then added dropwise and the solution was stirred at −78° C. another 10 min. Water (1 mL) was added and the solution was warmed up at room temperature. To the mixture was added brine (60 mL) and iPrOAc (50 mL) and the two phases were separated. The aqueous layer was extracted with iPrOAc (2×40 mL). The combined organic layers were dried over anhydrous $MgSO_4$, filtered and concentrated in vacuo. The crude residue was purified by silica gel chromatography (iPrOAc/Heptane=1:6) to afford a 5:1 mixture of (5R,8S)-8-(6-chloro-5-iodopyridin-2-yl)-3-(2,6-difluorophenyl)-9,9-dimethyl-5,6,7,8-tetrahydro-5,8-methanocinnoline and (5R,8S)-8-(6-chloropyridin-2-yl)-3-(2,6-difluoro-3-iodophenyl)-9,9-dimethyl-5,6,7,8-tetrahydro-5,8-methanocinnoline (145 mgas a white solid. (5R,8S)-8-(6-chloro-5-iodopyridin-2-yl)-3-(2,6-difluorophenyl)-9,9-dimethyl-5,6,7,8-tetrahydro-5,8-methanocinnoline: $^1$H NMR (400 MHz, $CDCl_3$) δ 8.15 (d, J=8.1 Hz, 1H), 7.60 (d, J=8.0 Hz, 1H), 7.45 (d, J=1.6 Hz, 1H), 7.44-7.35 (m, 1H), 7.10-7.00 (m, 2H), 3.34-3.24 (m, 1H), 3.13 (d, J=4.1 Hz, 1H), 2.51-2.38 (m, 1H), 1.70-1.59 (m, 1H), 1.39-1.28 (m, 1H), 1.13 (s, 3H), 0.69 (s, 3H). LCMS M/Z (M+H) 524.

Step 3: (5R,8S)-3-(2,6-difluorophenyl)-9,9-dimethyl-8-(5-methyl-6-(3-(2-(methylsulfonyl)ethyl)-1H-1,2,4-triazol-1-yl)pyridin-2-yl)-5,6,7,8-tetrahydro-5,8-methanocinnoline and (5R,8S)-3-(2,6-difluoro-3-methylphenyl)-9,9-dimethyl-8-(6-(3-(2-(methylsulfonyl)ethyl)-1H-1,2,4-triazol-1-yl)pyridin-2-yl)-5,6,7,8-tetrahydro-5,8-methanocinnoline

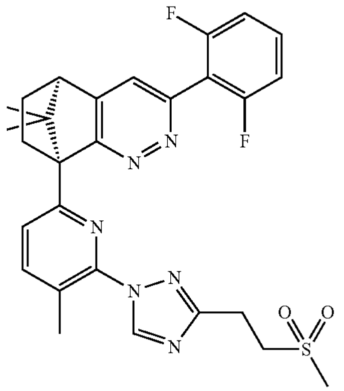

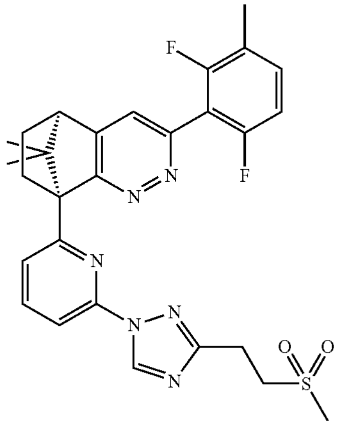

To a 5:1 mixture of (5R,8S)-8-(6-chloro-5-iodopyridin-2-yl)-3-(2,6-difluorophenyl)-9,9-dimethyl-5,6,7,8-tetrahydro-5,8-methanocinnoline and (5R,8S)-8-(6-chloropyridin-2-yl)-3-(2,6-difluoro-3-iodophenyl)-9,9-dimethyl-5,6,7,8-tetrahydro-5,8-methanocinnoline (40 mg, 0.076 mmol) in THF (0.76 mL) under a nitrogen atmosphere was added n-butyllithium 2.5 M in Hexanes (0.040 mL) dropwise at −78° C. The reaction mixture was stirred at −78° C. for 10 min and iodomethane (22 mg, 0.15 mmol) was added dropwise. The reaction mixture was stirred at −78° C. for 30 min and the solution was slowly warmed up to room temperature for 1 h. The mixture was quenched with MeOH (1 mL) and concentrated in vacuo. To the resulting residue was added 3-(2-methylsulfonylethyl)-1H-1,2,4-triazole (Intermediate M, 20 mg, 0.11 mmol), [(2-Di-tert-butylphosphino-2',4',6'-triisopropyl-1,1'-biphenyl)-2-(2'-amino-1,1'-biphenyl)] palladium(II) methanesulfonate (3.8 mg, 0.0046 mmol), potassium phosphate tribasic (33 mg, 0.15 mmol) in dioxane (0.51 mL). The reaction mixture was stirred at 100° C. for 15 h under a nitrogen atmosphere. The mixture was cooled to room temperature, diluted in DCM (10 mL), filtered through Celite and concentrated in vacuo. The crude residue was purified by reverse phase chromatography (acetonitrile 30-70%/0.1% ammonium hydroxide in water) to give (5R,8S)-3-(2,6-difluorophenyl)-9,9-dimethyl-8-(5-methyl-6-(3-(2-(methylsulfonyl)ethyl)-1H-1,2,4-triazol-1-yl)pyridin-2-yl)-5,6,7,8-tetrahydro-5,8-methanocinnoline (Example 35, 3.3 mg, first peak) as a yellow solid and (5R,8S)-3-(2,6-difluoro-3-methylphenyl)-9,9-dimethyl-8-(6-(3-(2-(methylsulfonyl)ethyl)-1H-1,2,4-triazol-1-yl)pyridin-2-yl)-5,6,7,8-tetrahydro-5,8-methanocinnoline (Example 36, 2.0 mg, second peak) as a beige solid. Example 35: $^1$H NMR (400 MHz, DMSO-d6) δ 9.04 (s, 1H), 8.01 (d, J=8.0 Hz, 1H), 7.81 (s, 1H), 7.73 (d, J=8.0 Hz, 1H), 7.63 (tt, J=8.5, 6.5 Hz, 1H), 7.31 (t, J=8.1 Hz, 2H), 3.60 (dd, J=9.5, 6.6 Hz, 2H), 3.32-3.25 (m, 2H), 3.25-3.18 (m, 2H), 3.15-3.08 (m, 1H), 3.06 (s, 4H), 2.48 (s, 3H), 1.54 (td, J=9.6, 9.1, 5.0 Hz, 1H), 1.04 (s, 3H), 0.71 (s, 3H). LCMS M/Z (M+H) 551. Example 36: LCMS M/Z (M+H) 551.

Example 37: 2-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)acetonitrile

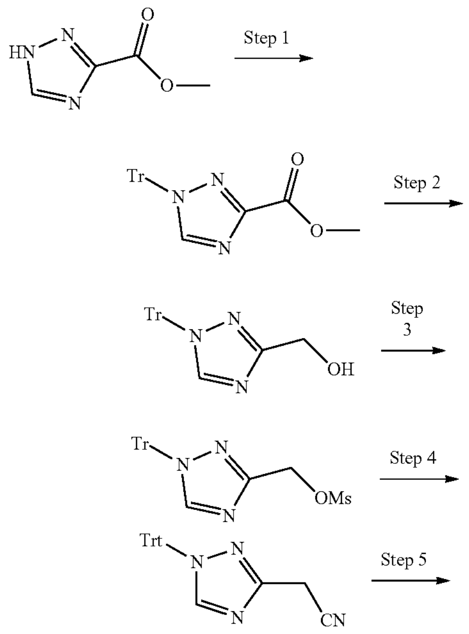

-continued

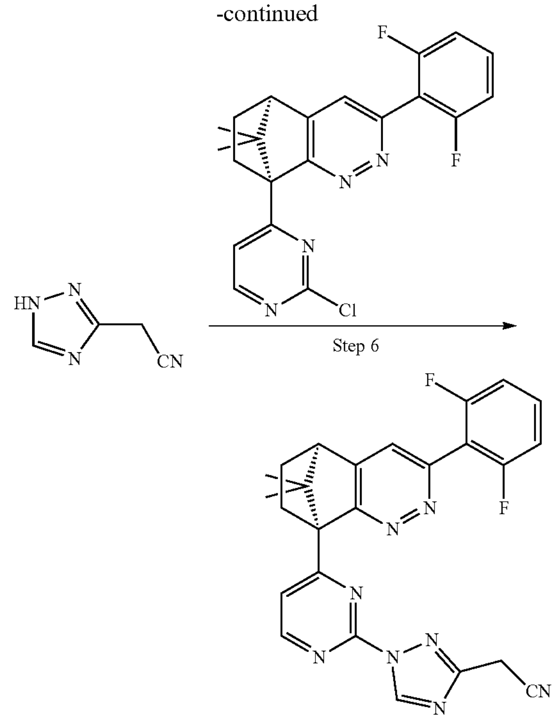

Step 1: Methyl 1-trityl-1H-1,2,4-triazole-3-carboxylate

To a cooled (0° C.) solution of methyl 1H-1,2,4-triazole-3-carboxylate (36 g, 283.2 mmol, 1.0 equiv) in pyridine(300 mL) was added triphenylmethyl chloride (85 g, 304.9 mmol, 1.1 equiv) and the suspension was stirred for 90 min at room temperature. Then the suspension was then heated at 100° C. and refluxed for 2 h. The clear solution was cooled to room temperature and concentrated under vacuum. Isopropanol (500 mL) was added to the residue and the solid was filtered and washed with 3×300 mL $H_2O$. The solid was dried in an oven under reduced pressure to afford 85 g of the title compound as a white solid. LCMS $ES^+$ 243 $[M+H]^+$ (Trityl fragment).

Step 2: (1-Trityl-1H-1,2,4-triazol-3-yl)methanol

A solution of methyl 1-(triphenylmethyl)-1H-1,2,4-triazole-3-carboxylate (26 g, 70.4 mmol, 1.0 equiv) in 300 mL THF was added 2M LiAlH4 in THF (50 mL) dropwise in 30 minutes with stirring at 0° C. The reaction was then increased to room temperature naturally and quenched by the addition of 4.3 mL of NaOH saturated solution. The mixture was diluted with 100 mL THF dried over anhydrous magnesium sulfate. The solids were filtered out and recrystallized from diethyl ether. The solids were collected by filtration, washed with ether and dried in an oven. This resulted in 15 g of the title compound as a white solid. LCMS $ES^+$ 243 $[M+H]^+$ (Trityl fragment).

Step 3: (1-Trityl-1H-1,2,4-triazol-3-yl)methyl methanesulfonate

A solution of [1-(triphenylmethyl)-1H-1,2,4-triazol-3-yl] methanol (5 g, 14.6 mmol, 1.0 equiv) in 20 mL DCM was added TEA (1.5 g, 14.8 mmol, 1.0 equiv) and methanesulfonyl methanesulfonate (3.8 g, 21.8 mmol, 1.5 equiv). The resulting solution was stirred for 30 min at 25° C. The resulting mixture was concentrated under vacuum and applied onto a silica gel column eluting with DCM/MeOH (95:5) to afford 5 g of the title compound as white solid crystal. LCMS ES+ 243 [M+H]+(Trityl fragment).

Step 4: 2-(1-Trityl-1H-1,24-triazol-3-yl)acetonitrile

A mixed solution of [1-(triphenylmethyl)-1H-1,2,4-triazol-3-yl]methyl methanesulfonate (5 g, 11.9 mmol, 1.000 equiv) in 5 mL $CH_3CN$ and 4 mL THF was added trimethylsilanecarbonitrile (2 g, 20.2 mmol, 1.7 equiv) and a solution of 1M TBAF in THF (17.2 mL). The resulting solution was stirred for 30 min at 80° C. After completion, the solution was concentrated under vacuum and the residue was applied onto a silica gel column with DCM/MeOH (10:1) to afford 2.7 g of the title compound as a white solid. LCMS $ES^+$ 243 $[M+H]^+$ (Trityl fragment).

Step 5: 2-(1H-1,2,4-Triazol-3-yl)acetonitrile

A solution of 2-[1-(triphenylmethyl)-1H-1,2,4-triazol-3-yl]acetonitrile (2.7 g, 7.7 mmol, 1.0 equiv) was dissolved in a solution of 4M HCl in 1,4-dioxane (10 mL). The resulting mixture was stirred for 60 min at room temperature. After completion, the solution was concentrated under vacuum and the residue was washed with 50 mL of diethyl ether. The solid was dried in an oven under reduced pressure. This resulted in 800 mg of the title compound as a white solid. LCMS $ES^+$ 109 $[M+H]^+$.

Step 6: 2-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)acetonitrile A solution of (5R,8S)-8-(2-chloropyrimidin-4-yl)-3-(2,6-difluorophenyl)-9,9-dimethyl-5,6,7,8-tetrahydro-5,8-methanocinnoline (200 mg, 0.5 mmol, 1.0 equiv), 2-(1H-1,2,4-triazol-3-yl)acetonitrile (108.5 mg, 1.0 mmol, 2.0 equiv) and potassium carbonate (208 mg, 1.5 mmol, 3.0 equiv) in DMSO (10 mL) was stirred for 3 h at 80° C. After completion, the solution was diluted with sat. aq. $NH_4Cl$ (50 mL) extracted with 40 mL of EtOAc for 3 times and the organic layers combined. The resulting mixture was washed with 2×25 mL brine and dried over anhydrous sodium sulfate and concentrated under vacuum. The residue was applied onto a silica gel column eluting with DCM/MeOH (20:1) and finally purified by Prep-HPLC with the following conditions (2#-AnalyseHPLC-SHIMADZU(HPLC-10)): Column, SunFire Prep C18 OBD Column, 19*150 mm 5 um 10 nm; mobile phase, Water (0.05% $NH_3H2O$) and ACN (25% ACN up to 43% in 12 min); Detector, UV 254/220 nm to afford 12.7 mg (5%) of the title compound as a white solid. $^1H$ NMR (400 MHz, $CDCl_3$): δ: 9.25 (s, 1H), 8.89 (d, J=5.2 Hz, 1H), 8.07 (d, J=5.2 Hz, 1H), 7.58-7.40 (m, 2H), 7.10 (t, J=8.0 Hz, 2H), 4.06 (s, 2H), 3.38-3.22 (m, 1H), 3.20 (s, 1H), 2.57-2.51 (m, 1H), 1.82-1.77 (m, 1H), 1.48-1.41 (m, 1H), 1.24 (s, 3H), 0.80 (s, 3H); LCMS $ES^+$ 471 $[M+H]^+$.

Example 38: 3-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)-2,2-dimethylpropanenitrile

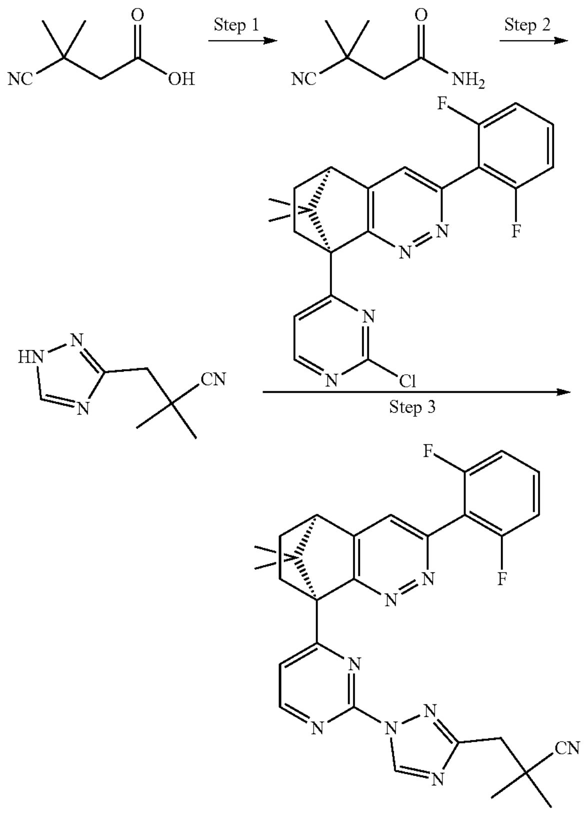

Step 1: 3-Cyano-3-methylbutanamide

Under nitrogen, a solution of 3-cyano-3,3-dimethylpropanoic acid (2 g, 15.7 mmol, 1.0 equiv) and oxalyl chloride (2.5 g, 19.7 mmol, 1.3 equiv) in DCM (20 mL) was added a drop of DMF at room temperature and the resulting solution was stirred for 3 h at 25° C. Then the solution was quenched with excessive amount of ammonium hydroxide (in 5 mL DCM). After completion, the resulting mixture was diluted with 50 mL of DCM and washed with 3×25 mL of brine. The organic layer was dried over anhydrous sodium sulfate and concentrated under vacuum to afford 1.5 g of the title compound as a yellow solid. LCMS $ES^+$ 127 $[M+H]^+$.

Step 2: 2,2-Dimethyl-3-(1H-1,2,4-triazol-3-yl)propanenitrile

A solution of 3-cyano-3,3-dimethylpropanamide (1 g, 7.9 mmol, 1.0 equiv) in acetonitrile (10 mL) was treated with DMFdimethyl acetal (1.5 g, 12.6 mmol, 1.6 equiv). and heated at 60° C. for 1.25 hours. The cooled mixture was concentrated under vacuum and taken up in acetonitrile (10 mL). The solution was treated with AcOH (800 mg, 13.3 mmol, 1.7 equiv) followed by hydrazine monohydrate (600 mg, 12.0 mmol, 1.5 equiv) instantly giving a white precipitate. The suspension was heated at 60° C. for 1.25 hours in which time all solid has dissolved to leave a pale pink solution. The cooled mixture was concentrated under vacuum to leave a viscous pink syrup. The residue was applied onto a silica gel column eluting with DCM/MeOH (10:1) to afford 900 mg of the title compound as a pink solid. LCMS $ES^+$ 151 $[M+H]^+$.

Step 3: 3-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)-2,2-dimethylpropanenitrile A solution of (5R,8S)-8-(2-chloropyrimidin-4-yl)-3-(2,6-difluorophenyl)-9,9-dimethyl-5,6,7,8-tetrahydro-5,8-methanocinnoline (200 mg, 0.5 mmol, 1.0 equiv), 2,2-dimethyl-3-(1H-1,2,4-triazol-3-yl)propanenitrile (150 mg, 1.0 mmol, 2.0 equiv) and potassium carbonate (138 mg, 1.0 mmol, 2.0 equiv) in DMSO (5 mL) was stirred for 8 h at 80° C. After completion, the solution was diluted with 50 mL of water and extracted with 3×50 mL of EtOAc. Then the organic layers ware combined and washed with 3×50 mL of brine. The organic layer was dried over anhydrous sodium sulfate and concentrated under vacuum. The residue was applied onto a silica gel column eluting with DCM/MeOH (95:5) to afford 50.1 mg of the title compound as a white solid. $^1H$ NMR (300 MHz, $CDCl_3$): δ: 9.21 (s, 1H) 8.88 (d, J=5.2 Hz, 1H), 7.98 (d, J=5.2 Hz, 1H), 7.63 (t, J=1.3 Hz, 1H), 7.55-7.43 (m, 1H), 7.11 (t, J=8.1 Hz, 2H), 3.39-3.26 (m, 2H), 3.19 (s, 2H), 2.65-2.50 (m, 1H), 1.88-1.72 (m, 1H), 1.53 (s, 6H), 1.52-1.38 (m, 1H), 1.25 (s, 3H), 0.80 (s, 3H); LCMS $ES^+$ 513 $[M+H]^+$.

Example 39: 2-(3-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-1-yl)acetamide

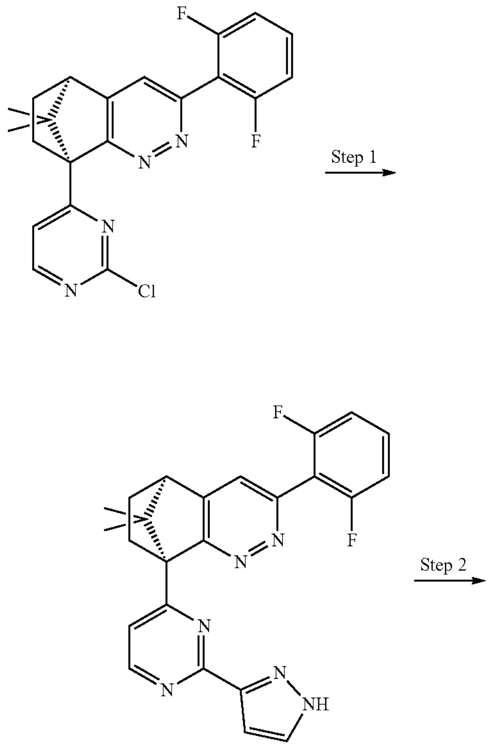

-continued

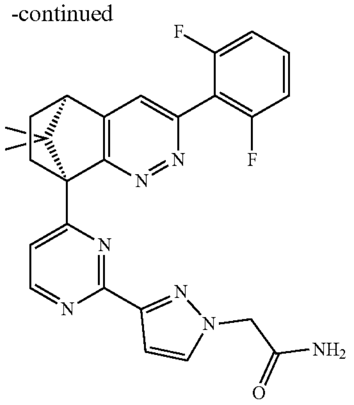

Step 1: (5R,8S)-8-(2-(1H-Pyrazol-3-yl)pyrimidin-4-yl)-3-(2,6-difluorophenyl)-9,9-dimethyl-5,6,7,8-tetrahydro-5,8-methanocinnoline Under nitrogen, a solution of (5R,8S)-8-(2-chloropyrimidin-4-yl)-3-(2,6-difluorophenyl)-9,9-dimethyl-5,6,7,8-tetrahydro-5,8-methanocinnoline (200 mg, 0.5 mmol, 1.0 equiv), 3-(tetramethyl-1,3,2-dioxaborolan-2-yl)-1H-pyrazole (180 mg, 0.9 mmol, 1.9 equiv), $Pd(PPh_3)_2Cl_2$ (75 mg, 0.1 mmol, 0.2 equiv), CsF (160 mg, 1.1 mmol, 2.1 equiv) in 1,4-dioxane (10 mL) and water (10 mL) was stirred for 4 h at 100° C. After completion, the solution was diluted with 50 mL of water and extracted with 3×50 mL of EtOAc. Then the organic layers ware combined and washed with 3×50 mL of brine. The organic layer was dried over anhydrous sodium sulfate and concentrated under vacuum. The residue was applied onto a silica gel column eluting with DCM/MeOH (20:1) to afford 180 mg (83%) of the title compound as an off-white solid. LCMS $ES^+$ 431 $[M+H]^+$.

Step 2: 2-(3-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-1-yl)acetamide A solution of (5R,8S)-8-(2-(1H-pyrazol-3-yl)pyrimidin-4-yl)-3-(2,6-difluorophenyl)-9,9-dimethyl-5,6,7,8-tetrahydro-5,8-methanocinnoline (150 mg, 0.4 mmol, 1.0 equiv), 2-chloroacetamide (96 mg, 1.0 mmol, 3 equiv) and potassium carbonate (96 mg, 0.7 mmol, 2.0 equiv), in DMF (10 mL) was stirred for 8 h at 85° C. After completion, the solution was diluted with 50 mL of water and extracted with 3×50 mL of EtOAc. Then the organic layers ware combined and washed with 3×50 mL of brine. The organic layer was dried over anhydrous sodium sulfate and concentrated under vacuum. The residue was applied onto a silica gel column eluting with DCM/MeOH (95:5) to afford 100 mg crude product. Then the crude was purified by Prep-HPLC with the following conditions (2#-Analyse HPLC-SHIMADZU (HPLC-10)): Column, XBridge Shield RP18 OBD Column, 5 um, 19*150 mm; mobile phase, Water (0.05% $NH_3H_2O$) and ACN (20% ACN up to 35% in 13 min); Detector, UV 220 nm to afford 42.2 mg (25%) of the title compound as a white solid. $^1H$ NMR (300 MHz, $CD_3OD$): δ: 8.85 (d, J=5.3 Hz, 1H), 7.84-7.79 (m, 2H), 7.78-7.70 (m, 1H), 7.63-7.53 (m, 1H), 7.27-7.15 (m, 2H), 7.08 (s, 1H), 5.02 (s, 2H), 3.55-3.50 (m, 1H), 3.36-3.30 (m, 1H), 2.62-2.58 (m, 1H), 1.72-1.64 (m, 1H), 1.46-1.42 (m, 1H), 1.19 (s, 3H), 0.85 (s, 3H); LCMS $ES^+$ 488 $[M+H]^+$.

Examples 40 and 41: (2-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)ethyl)(imino)(methyl)-λ$^6$-sulfanone Stereoisomer A and (2-(1-(4-((5R,8S)-3-(2,6-difluorophenyl)-9,9-dimethyl-6,7-dihydro-5,8-methanocinnolin-8(5H)-yl)pyrimidin-2-yl)-1H-12,4-triazol-3-yl)ethyl)(imino)(methyl)-λ$^6$-sulfanone Stereoisomer B

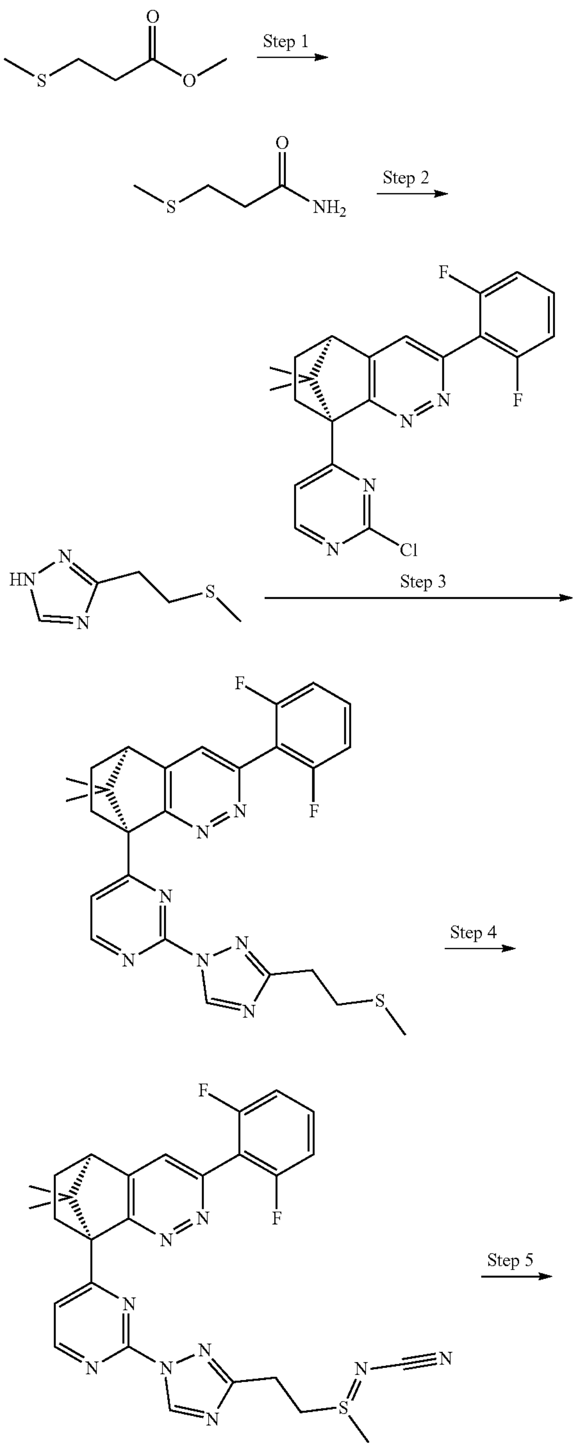

-continued

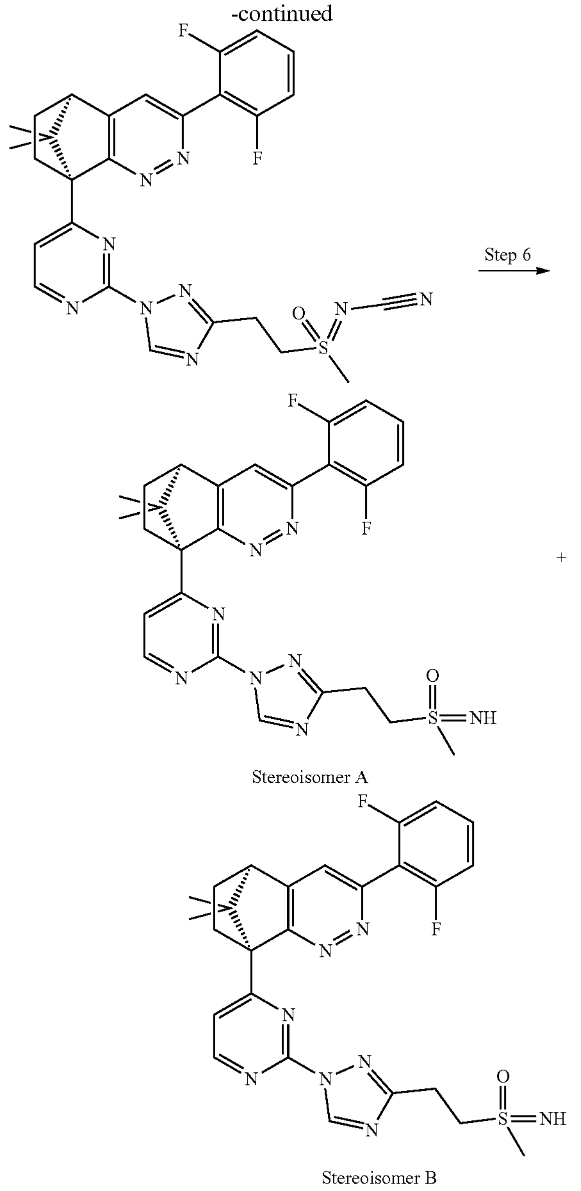

Step 1: 3-(Methylthio)propanamide

A solution of methyl 3-(methylsulfanyl)propanoate (8 g, 59.61 mmol, 1.00 equiv) in methanol (saturated with ammonia, 100 mL) was stirred for 10 h at 40° C. After completion, the solution was concentrated under vacuum. The residue was applied onto a silica gel column eluting with DCM/MeOH (10:1) to afford 6 g of the title compound as a white solid. LCMS ES$^+$ 120 $[M+H]^+$.

Step 2: 3-(2-(Methylthio)ethyl)-1H-1,2,4-triazole

A solution of 3-(methylsulfanyl)propanamide (4 g, 33.56 mmol, 1.00 equiv) in acetonitrile (10 mL) was treated with DMFdimethyl acetal (8 g, 67.13 mmol, 2.00 equiv) and heated at 60° C. for 1.25 hours. The cooled mixture was concentrated under vacuum and taken up in acetonitrile (15 mL). The solution was treated with acetic acid (5 mL, 87.25 mmol, 2.60 equiv) followed by hydrazine monohydrate (7 mL, 144.02 mmol, 4.29 equiv) instantly giving a white precipitate. The suspension was heated at 60° C. for 1.25 hours in which time all solid has dissolved to leave a pale pink solution. The cooled mixture was concentrated under vacuum to leave a viscous pink syrup. The residue was applied onto a silica gel column eluting with DCM/MeOH (10:1) to afford 2.1 g of the title compound as an orange oil. LCMS $ES^+$ 144 $[M+H]^+$.

Step 3: (5R,8S)-3-(2,6-Difluorophenyl)-9,9-dimethyl-8-(2-(3-(2-(methylthio)ethyl)-1H-1,2,4-triazol-1-yl)pyrimidin-4-yl)-5,6,7,8-tetrahydro-5,8-methanocinnoline A solution of (5R,8S)-8-(2-chloropyrimidin-4-yl)-3-(2,6-difluorophenyl)-9,9-dimethyl-5,6,7,8-tetrahydro-5,8-methanocinnoline (200 mg, 0.50 mmol, 1.00 equiv), 3-[2-(methylsulfanyl)ethyl]-1H-1,2,4-triazole (108 mg, 0.75 mmol, 1.50 equiv), potassium carbonate (103 mg, 0.74 mmol, 1.48 equiv) in DMSO (5 mL) was stirred for 3 h at 75° C. After completion, the solution was diluted with 30 mL of water and extracted with 3×50 mL of EtOAc. Then the organic layers was combined and washed with 3×50 mL of brine. The mixture was dried over anhydrous sodium sulfate and concentrated under vacuum. The residue was applied onto a silica gel column eluting with DCM/MeOH (15:1) to afford 130 mg (51%) of the title compound as a white solid. LCMS $ES^+$ 506 $[M+H]^+$.

Step 4: N—((E)-(2-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)ethyl)(methyl)-$\lambda^4$-sulfanylidene)cyanamide A solution of (5R,8S)-3-(2,6-difluorophenyl)-9,9-dimethyl-8-(2-(3-(2-(methylthio)ethyl)-1H-1,2,4-triazol-1-yl)pyrimidin-4-yl)-5,6,7,8-tetrahydro-5,8-methanocinnoline (410 mg, 0.81 mmol, 1.00 equiv), aminoformonitrile (35 mg, 0.83 mmol, 1.02 equiv), (acetyloxy)(phenyl)-1^[3]-iodanyl acetate (262 mg, 0.81 mmol, 1.00 equiv) in THF (6 mL) was stirred for 2 h at 25° C. After completion, the solution was diluted with 30 mL of water and extracted with 3×50 mL of EtOAc. Then the organic layers was combined and washed with 3×50 mL of brine. The organic layer was dried over anhydrous sodium sulfate and concentrated under vacuum. The residue was applied onto a silica gel column eluting with DCM/MeOH (16:1) to afford 280 mg (63%) of the title compound as a white solid. LCMS $ES^+$ 546 $[M+H]^+$.

Step 5: N-((2-(1-(4-((5R,8S)-3-(2,6-difluorophenyl)-9,9-dimethyl-6,7-dihydro-5,8-methanocinnolin-8(5H)-yl)pyrimidin-2-yl)-1H-1,2,4-triazol-3-yl)ethyl)(methyl)(oxo)-$\lambda^6$-sulfanylidene)cyanamide A solution of N—((E)-(2-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)ethyl)(methyl)-$\lambda^4$-sulfanylidene)cyanamide (200.00 mg, 0.36 mmol, 1.00 equiv), $KMnO_4$ (231.72 mg, 1.46 mmol, 4.00 equiv), $NaIO_4$ (313.62 mg, 1.46 mmol, 4.00 equiv) in methanol (6 mL) and water(1 mL) was stirred for 2 h at 25° C. The cooled mixture was concentrated under vacuum to afford 160 mg (77%) of the title compound as a white solid. LCMS $ES^+$ 562 $[M+H]^+$.

Step 6: 2-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)ethyl)(imino)(methyl)-$\lambda^6$-sulfanone Stereoisomer A and (2-(1-(4-((5R,8S)-3-(2,6-difluorophenyl)-9,9-dimethyl-6,7-dihydro-5,8-methanocinnolin-8(5H)-yl)pyrimidin-2-yl)-1H-1,2,4-triazol-3-yl)ethyl)(imino)(methyl)-$\lambda^6$-sulfanone Stereoisomer B A solution of N-((2-(1-(4-((5R,8S)-3-(2,6-difluorophenyl)-9,9-dimethyl-6,7-dihydro-5,8-methanocinnolin-8(5H)-yl)pyrimidin-2-yl)-1H-1,2,4-triazol-3-yl)ethyl)(methyl)(oxo)-$\lambda^6$-sulfanylidene)cyanamide (200 mg, 0.35 mmol, 1.00 equiv), trifluoroacetic anhydride (5 mL, 35.97 mmol, 101.37 equiv) in DCM (6 mL) was stirred for 2 h at 25° C. The cooled mixture was concentrated under vacuum and taken up in MeOH (4 mL). The solution was treated with ethyldiisopropylamine (1 mL, 6.05 mmol, 17.05 equiv) and heated at 40° C. for 3 h. After completion, the solution was diluted with 30 mL of water and extracted with 3×50 mL of EtOAc. Then the organic layers was combined and washed with 3×50 mL of brine. The mixture was dried over anhydrous sodium sulfate and concentrated under vacuum. The residue was applied onto a silica gel column eluting with DCM/MeOH (13:1) to afford the title compounds.

2-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)ethyl)(imino)(methyl)-$\lambda^6$-sulfanone Stereoisomer A as a white solid (11.6 mg). $^1$H NMR (400 MHz, $CD_3OD$): δ: 8.96 (s, 1H), 8.94 (d, J=5.2 Hz, 1H), 7.91 (d, J=5.2 Hz, 1H), 7.82 (t, J=1.1 Hz, 1H), 7.62-7.58 (m, 1H), 7.23-7.21 (t, J=8.1 Hz, 2H), 3.78-3.76 (m, 2H), 3.49-3.33 (m, 4H), 3.12 (s, 3H), 2.63-2.60 (m, 1H), 1.73-1.72 (m, 1H), 1.45-1.43 (m, 1H), 1.25 (s, 3H), 0.88 (s, 3H); LCMS $ES^+$ 537 $[M+H]^+$.

2-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)ethyl)(imino)(methyl)-$\lambda^6$-sulfanone Stereoisomer B as a white solid (8.7 mg, 5%). $^1$H NMR (400 MHz, $CD_3OD$): δ: 8.96 (s, 1H), 8.94 (d, J=5.2 Hz, 1H), 7.91 (d, J=5.2 Hz, 1H), 7.82 (t, J=1.1 Hz, 1H), 7.62-7.58 (m, 1H), 7.23-7.18 (t, J=8.1 Hz, 2H), 3.83-3.76 (m, 2H), 3.49-3.33 (m, 4H), 3.15 (s, 3H), 2.64-2.61 (m, 1H), 1.76-1.71 (m, 1H), 1.48-1.38 (m, 1H), 1.21 (s, 3H), 0.87 (s, 3H); LCMS $ES^+$ 537 $[M+H]^+$.

Example 42: (5R,8S)-3-(2,6-Difluorophenyl)-9,9-dimethyl-8-(2-(methylsulfonyl)pyrimidin-4-yl)-5,6,7,8-tetrahydro-5,8-methanocinnoline

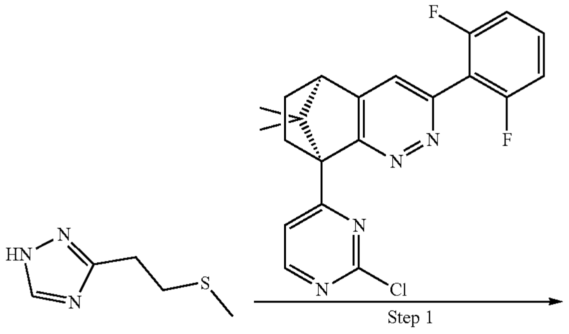

-continued

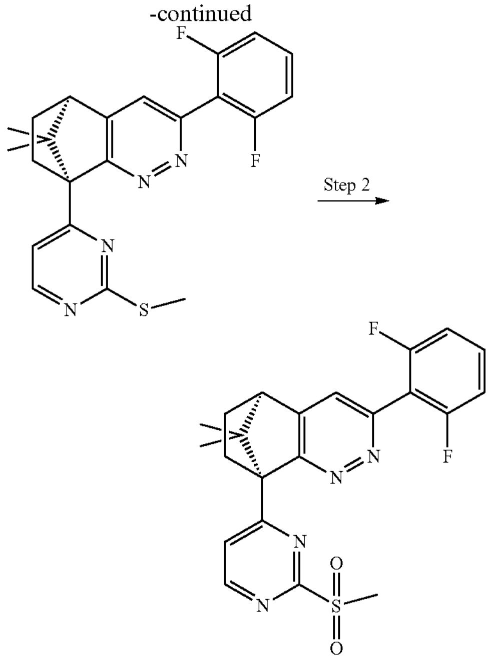

Step 1: (5R,8S)-3-(2,6-Difluorophenyl)-9,9-dimethyl-8-(2-(methylthio)pyrimidin-4-yl)-5,6,7,8-tetrahydro-5,8-methanocinnoline Under nitrogen, a solution of (5R,8S)-8-(2-chloropyrimidin-4-yl)-3-(2,6-difluorophenyl)-9,9-dimethyl-5,6,7,8-tetrahydro-5,8-methanocinnoline (86 mg, 0.60 mmol, 1.00 equiv), 3-[2-(methylsulfanyl)ethyl]-1H-1,2,4-triazole (46 mg, 0.32 mmol, 1.5 equiv), $Pd_2(dba)_3.CHCl_3$ (52 mg, 0.05 mmol, 0.08 equiv), XantPhos (58 mg, 0.10 mmol, 0.16 equiv), $Cs_2CO_3$ (326 mg, 1.00 mmol, 1.66 equiv) in 1,4-dioxane (8 mL) was stirred for 2 h at 100° C. After completion, the solution was diluted with 30 mL of water and extracted with 3×50 mL of EtOAc. Then the organic layers was combined and washed with 3×50 mL of brine. The mixture was dried over anhydrous sodium sulfate and concentrated under vacuum. The residue was applied onto a silica gel column eluting with DCM/MeOH (14:1) to afford 40 mg of the title compound as a white solid. LCMS $ES^+$ 411 $[M+H]^+$.

Step 2: (5R,8S)-3-(2,6-difluorophenyl)-9,9-dimethyl-8-(2-(methylsulfonyl)pyrimidin-4-yl)-5,6,7,8-tetrahydro-5,8-methanocinnoline A solution of (5R,8S)-3-(2,6-difluorophenyl)-9,9-dimethyl-8-(2-(methylthio)pyrimidin-4-yl)-5,6,7,8-tetrahydro-5,8-methanocinnoline (20 mg, 0.04 mmol, 1.00 equiv), $NaIO_4$ (43 mg, 0.20 mmol, 4.12 equiv), $KMnO_4$ (32 mg, 0.22 mmol, 4.15 equiv) in methanol (5 mL) and water(1 mL) was stirred for 2 h at 25° C. After completion, the solution was diluted with 30 mL of water and extracted with 3×50 mL of EtOAc. Then the organic layers was combined and washed with 3×50 mL of brine. The mixture was dried over anhydrous sodium sulfate and concentrated under vacuum. The residue was applied onto a silica gel column eluting with DCM/MeOH to afford 7.8 mg of the title compound as a white solid. $^1H$ NMR (400 MHz, $CD_3OD$): δ: 9.06 (d, J=5.2 Hz, 1H), 8.16 (d, J=5.2 Hz, 1H), 7.81 (s, 1H), 7.62-7.56 (m, 1H), 7.23-7.17 (m, 2H), 3.45 (s, 3H), 3.40-3.33 (m, 2H), 2.62-2.57 (m, 1H), 1.76-1.71 (m, 1H), 1.48-1.42 (m, 1H), 1.20 (s, 3H), 0.84 (s, 3H); LCMS $ES^+$ 443$[M+H]^+$.

Examples 43 and 44: (5R,8S)-3-(2,6-Difluorophenyl)-9,9-dimethyl-8-(2-(1-(2-(methylsulfonyl)ethyl)-1H-imidazol-4-yl)pyrimidin-4-yl)-5,6,7,8-tetrahydro-5,8-methanocinnoline and (5R,8S)-3-(2,6-Difluorophenyl)-9,9-dimethyl-8-(2-(1-(2-(methylsulfonyl)ethyl)-1H-imidazol-5-yl)pyrimidin-4-yl)-5,6,7,8-tetrahydro-5,8-methanocinnoline

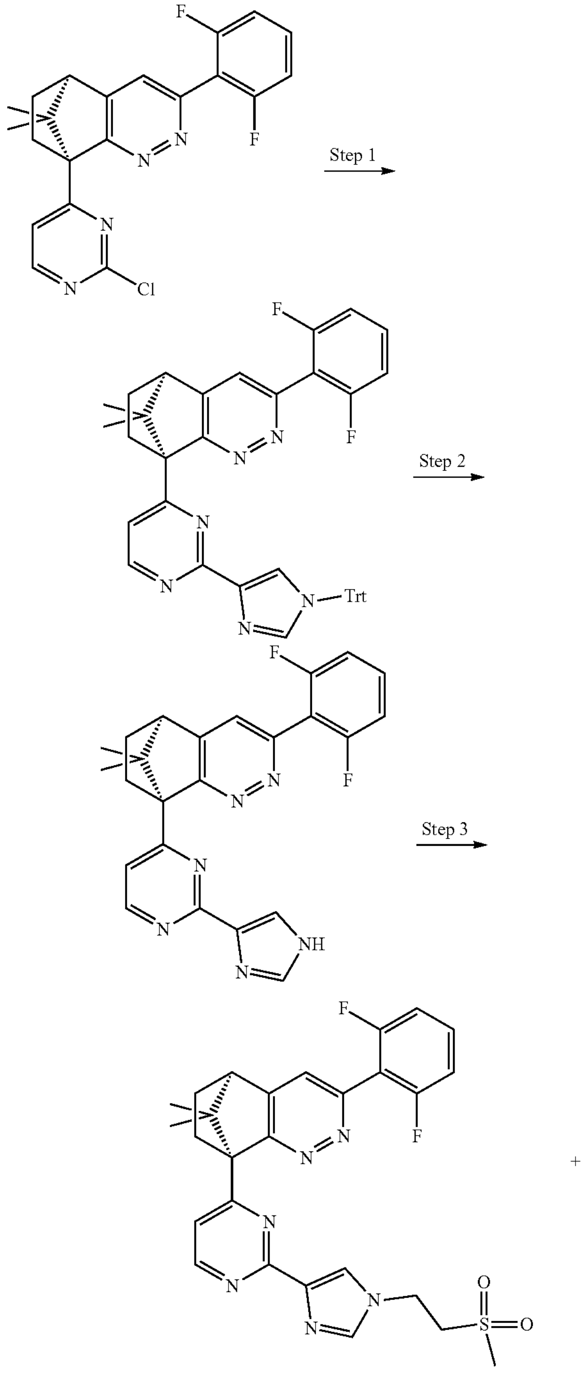

-continued

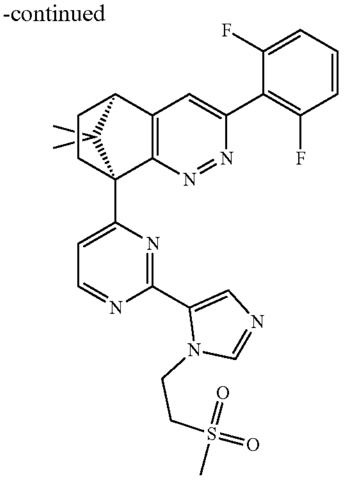

Step 1: (5R,8S)-3-(2,6-Difluorophenyl)-9,9-dimethyl-8-(2-(1-trityl-1H-imidazol-4-yl)pyrimidin-4-yl)-5,6,7,8-tetrahydro-5,8-methanocinnoline Under nitrogen, a solution of (5R,8S)-8-(2-chloropyrimidin-4-yl)-3-(2,6-difluorophenyl)-9,9-dimethyl-5,6,7,8-tetrahydro-5,8-methanocinnoline (1 g, 2.5 mmol, 1.0 equiv), 4-(tributylstannyl)-1-(triphenylmethyl)-1H-imidazole (1.2 g, 2.0 mmol, 0.8 equiv), $Pd(PPh_3)_2C1_2$ (175.5 mg, 0.3 mmol, 0.1 equiv), 1,4-dioxane (18 mL) was stirred for 24 h at 105° C. After completion, the solution was diluted with 100 mL of water and extracted with 3×100 mL of EtOAc. Then the organic layers was combined and washed with 3×50 mL of brine. The mixture was dried over anhydrous sodium sulfate and concentrated under vacuum. The residue was applied onto a silica gel column with EtOAc/petroleum ether (1:3) to afford 1 g of the title compound as a light yellow solid. LCMS $ES^+$ 673 $[M+H]^+$.

Step 2: (5R,8S)-8-(2-(1H-Imidazol-4-yl)pyrimidin-4-yl)-3-(2,6-difluorophenyl)-9,9-dimethyl-5,6,7,8-tetrahydro-5,8-methanocinnoline Under hydrogen chloride, a solution of (5R,8S)-3-(2,6-difluorophenyl)-9,9-dimethyl-8-(2-(1-trityl-1H-imidazol-4-yl)pyrimidin-4-yl)-5,6,7,8-tetrahydro-5,8-methanocinnoline (1 g, 1.5 mmol, 1.0 equiv) in 1,4-dioxane (20 mL) was stirred for 30 min at 25° C. After completion, the solution was diluted with 100 mL of sat. eq. sodium bicarbonate and extracted with 3×100 mL of EtOAc and washed with 3×50 mL of brine. The mixture was dried over anhydrous sodium sulfate and concentrated under vacuum. The residue was applied onto a reversed-phase column eluting with acetonitrile/water(25:75) to afford 380 mg of the title compound as a white solid. LCMS $ES^+$ 431 $[M+H]^+$.

Step 3: (5R,8S)-3-(2,6-Difluorophenyl)-9,9-dimethyl-8-(2-(1-(2-(methylsulfonyl)ethyl)-1H-imidazol-4-yl)pyrimidin-4-yl)-5,6,7,8-tetrahydro-5,8-methanocinnoline and (5R,8S)-3-(2,6-Difluorophenyl)-9,9-dimethyl-8-(2-(1-(2-(methylsulfonyl)ethyl)-1H-imidazol-5-yl)pyrimidin-4-yl)-5,6,7,8-tetrahydro-5,8-methanocinnoline A solution of (1S,8R)-5-(2,6-difluorophenyl)-1-[2-(1H-imidazol-4-yl)pyrimidin-4-yl]-11,11-dimethyl-3,4-diazatricyclo[6.2.1.0^[2,7]]undeca-2(7),3,5-triene (300 mg, 0.7 mmol, 1.0 equiv), methanesulfonylethene (111 mg, 1.046 mmol, 1.500 equiv) and potassium carbonate (145 mg, 1.049 mmol, 1.5 equiv) in DMF(10 mL) was stirred for 2 h at 25° C. After completion, the solution was diluted with 100 mL of water and extracted with 3×100 mL of EtOAc and washed with 3×50 mL of brine. The mixture was dried over anhydrous sodium sulfate and concentrated under vacuum. The residue was applied onto a silica gel column eluting with DCM/MeOH (10:1) to afford a crude product. Then the crude product was purified by Prep-HPLC with the following conditions: Column, XBridge Shield RP18 OBD Column, 5 um, 19*150 mm; mobile phase, Waters(0.05% $NH_3H_2O$) and $CH_3CN$ (20.0% $CH_3CN$ up to 45.0% in 7 min); Detector, UV 220 nm to afford the title compounds.

(5R,8S)-3-(2,6-Difluorophenyl)-9,9-dimethyl-8-(2-(1-(2-(methylsulfonyl)ethyl)-1H-imidazol-4-yl)pyrimidin-4-yl)-5,6,7,8-tetrahydro-5,8-methanocinnoline (58.3 mg) as a white solid. $^1H$ NMR (400 MHz, $CDCl_3$): δ: 8.82 (d, J=5.3 Hz, 1H), 8.10 (s, 1H), 7.91 (d, J=1.4 Hz, 1H), 7.78 (d, J=5.2 Hz, 1H), 7.51 (s, 1H), 7.49-7.41 (m, 1H), 7.11-7.05 (m, 2H), 4.69 (t, J=6.6 Hz, 2H), 3.63 (t, J=6.6 Hz, 2H), 3.54-3.43 (m, 1H), 3.19 (d, J=4.1 Hz, 1H), 2.84 (s, 3H), 2.50-2.42 (m, 1H), 1.79-1.72 (m, 1H), 1.42-1.35 (m, 1H), 1.19 (s, 3H), 0.77 (s, 3H); LCMS $ES^+$ 537 $[M+H]^+$.

(5R,8S)-3-(2,6-Difluorophenyl)-9,9-dimethyl-8-(2-(1-(2-(methylsulfonyl)ethyl)-1H-imidazol-5-yl)pyrimidin-4-yl)-5,6,7,8-tetrahydro-5,8-methanocinnoline (22.8 mg) as a white solid. $^1H$ NMR (400 MHz, $CDCl_3$): δ: 8.77 (d, J=5.2 Hz, 1H), 8.12 (s, 1H), 8.00 (s, 1H), 7.77-7.65 (m, 1H), 7.51 (s, 1H), 7.49-7.41 (m, 1H), 7.09 (t, J=7.9, 4.4 Hz, 2H), 5.09 (t, J=6.5 Hz, 2H), 3.68 (t, J=6.5 Hz, 2H), 3.30-3.18 (m, 2H), 2.77 (s, 3H), 2.59-2.45 (m, 1H), 1.83-1.73 (m, 1H), 1.50-1.40 (m, 1H), 1.20 (s, 3H), 0.82 (s, 3H); LCMS $ES^+$ 537 $[M+H]^+$.

Example 45: (5R,8)-3-(2,6-Difluorophenyl)-9,9-dimethyl-8-(2-(1-((methylsulfonyl)methyl)-1H-imidazol-4-yl)pyrimidin-4-yl)-5,6,7,8-tetrahydro-5,8-methanocinnoline

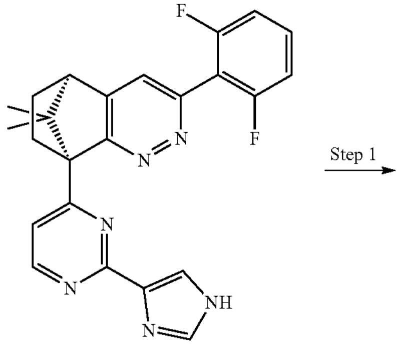

-continued

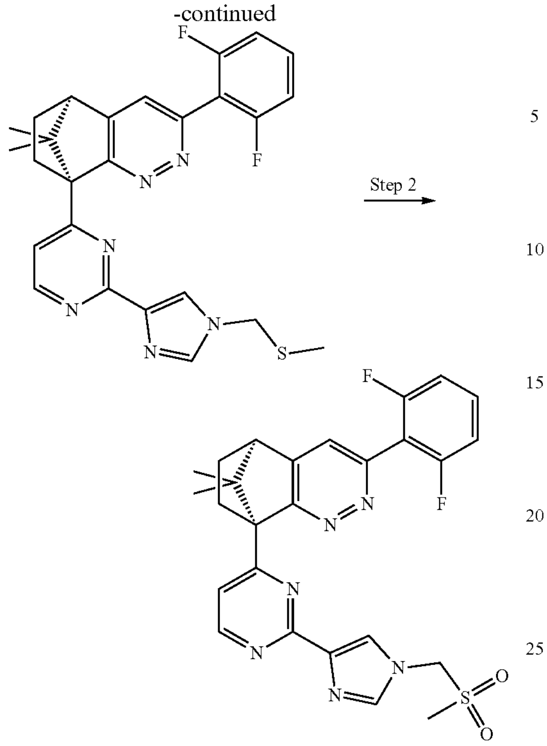

Step 1: (5R,8S)-3-(2,6-Difluorophenyl)-9,9-dimethyl-8-(2-(1-((methylthio)methyl)-1H-imidazol-4-yl)pyrimidin-4-yl)-5,6,7,8-tetrahydro-5,8-methanocinnoline A solution of (5R,8S)-8-(2-(1H-imidazol-4-yl)pyrimidin-4-yl)-3-(2,6-difluorophenyl)-9,9-dimethyl-5,6,7,8-tetrahydro-5,8-methanocinnoline (260 mg, 0.6 mmol, 1.0 equiv), chloro(methylsulfanyl)methane (116 mg, 1.2 mmol, 2.0 equiv) and potassium carbonate (165.5 mg, 1.2 mmol, 2.0 equiv) in DMF(10 mL) was stirred for 12 h at 25° C. After completion, the solution was diluted with 100 mL of water and extracted with 3×100 mL of EtOAc and washed with 3×50 mL of brine. The organic layer was dried over anhydrous sodium sulfate and concentrated under vacuum. The residue was applied onto a reversed-phase column eluting with water/acetonitrile (60:40) to afford 120 mg of the title compounds as a brown oil. LCMS $ES^+$ 491 $[M+H]^+$.

Step 2: (5R,8S)-3-(2,6-Difluorophenyl)-9,9-dimethyl-8-(2-(1-((methylsulfonyl)methyl)-1H-imidazol-4-yl)pyrimidin-4-yl)-5,6,7,8-tetrahydro-5,8-methanocinnoline A solution of (5R,8S)-3-(2,6-difluorophenyl)-9,9-dimethyl-8-(2-(1-((methylthio)methyl)-1H-imidazol-4-yl)pyrimidin-4-yl)-5,6,7,8-tetrahydro-5,8-methanocinnoline (100 mg, 0.2 mmol, 1.0 equiv), $KMnO_4$ (60 mg, 0.4 mmol, 1.9 equiv), $NaIO_4$ (80 mg, 0.4 mmol, 1.8 equiv) in methanol (15 mL) and water (3 mL) was stirred for 60 min at 25° C. After completion, the solution was diluted with 100 mL of sat. eq. sodium bicarbonate and extracted with 3×100 mL of EtOAc and washed with 3×50 mL of brine. The organic layer was dried over anhydrous sodium sulfate and concentrated under vacuum. The residue was applied onto a reversed-phase column eluting with acetonitrile/water(60:40) to afford 25.5 mg of the title compound as a white solid. $^1H$ NMR (400 MHz, $CD_3OD$): δ: 8.88 (d, J=5.3 Hz, 1H), 8.08 (s, 1H), 8.00 (s, 1H), 7.80 (s, 1H), 7.70-7.64 (m, 1H), 7.59-7.53 (m, 1H), 7.21 (t, J=8.1 Hz, 2H), 6.48 (d, J=14.2 Hz, 1H), 6.35 (d, J=14.2 Hz, 1H), 3.38-3.32 (m, 2H), 2.93 (s, 3H), 2.68-2.55 (m, 1H), 1.73-1.65 (m, 1H), 1.44-1.36 (m, 1H), 1.19 (s, 3H), 0.86 (s, 3H); LCMS $ES^+$ 491 $[M+H]^+$.

Example 46: (5R,8S)-3-(2,6-Difluorophenyl)-8-(2-(4-(2-methoxyethyl)-3-(2-(methylsulfonyl)ethyl)-1H-pyrazol-1-yl)pyrimidin-4-yl)-9,9-dimethyl-5,6,7,8-tetrahydro-5,8-methanocinnoline

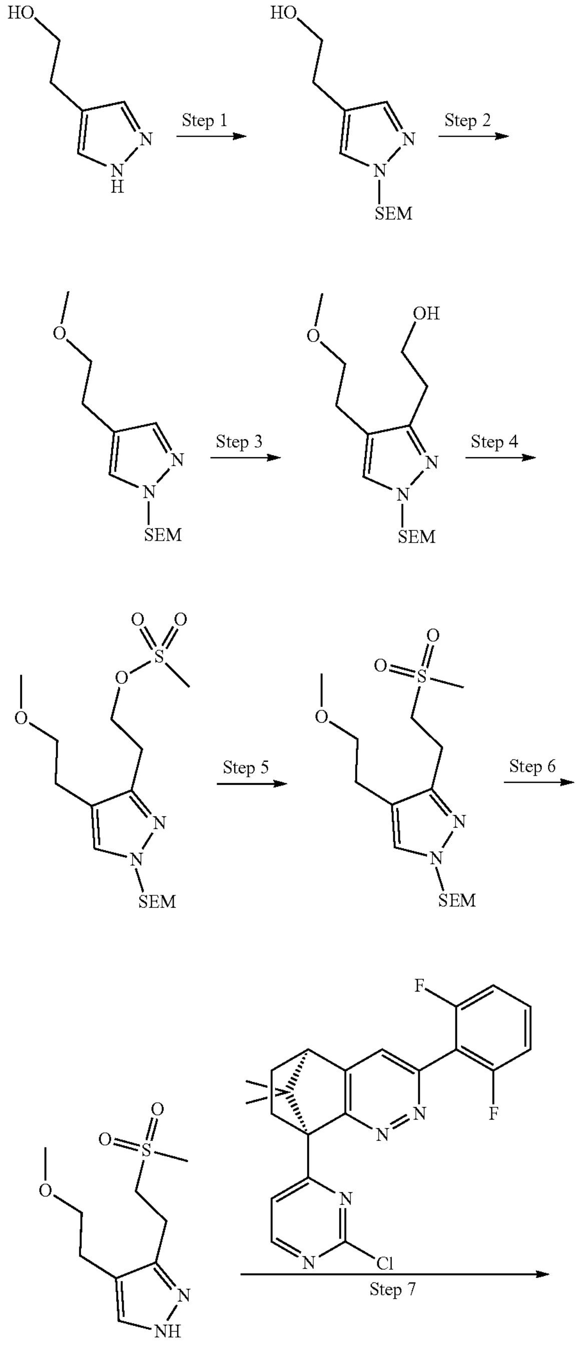

-continued

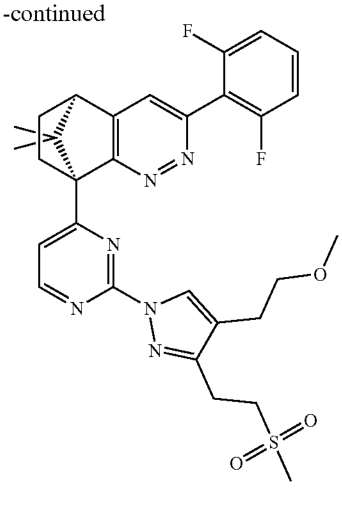

Step 1: 2-(1-((2-(Trimethylsilyl)ethoxy)methyl)-1H-pyrazol-4-yl)ethan-1-ol

A solution of 2-(1H-pyrazol-4-yl)ethan-1-ol (3.00 g, 26.75 mmol, 1.00 equiv), SEM-Cl (7.00 mL, 43.18 mmol, 1.61 equiv) and $Cs_2CO_3$ (13.00 g, 39.89 mmol, 1.49 equiv) in NN-dimethylformamide (20 mL) was stirred for 3 h at room temperature. When LCMS indicated most of starting material was converted into the desired product, the resulting solution was concentrated and diluted with 150 mL of dichloromethane, washed with 3×50 mL of brine, dried over anhydrous sodium sulfate and concentrated under vacuum. The residue was purified by a silica gel column eluting with DCM/MeOH (10:1) to afford 2.6 g of the title compound as yellow oil.

Step 2: 4-(2-Methoxyethyl)-1-((2-(trimethylsilyl)ethoxy)methyl)-1H-pyrazole

A solution of 2-(1-[[2-(trimethylsilyl)ethoxy]methyl]-1H-pyrazol-4-yl)ethan-1-ol (2.6 g, 10.72 mmol, 1.00 equiv) and sodium hydride (645 mg, 26.88 mmol, 2.506 equiv) in THF (20 mL) was stirred for 10 min at 0° C. Then $CH_3I$ (0.93 mL, 14.93 mmol, 1.39 equiv) was allowed to react, with stirring, for an additional 60 min at room temperature. When LCMS indicated most of starting material was converted into the desired product, the resulting solution was concentrated and diluted with 150 mL of dichloromethane, washed with 3×50 mL of brine, dried over anhydrous sodium sulfate and concentrated under vacuum. The residue was purified by a silica gel column eluting with DCM/MeOH (10:1) to afford 2.0 g of the title compound as yellow oil.

Step 3: 2-(4-(2-Methoxyethyl)-1-((2-(trimethylsilyl)ethoxy)methyl)-1H-pyrazol-3-yl)ethan-1-ol A solution of 4-(2-methoxyethyl)-1-[[2-(trimethylsilyl)ethoxy]methyl]-1H-pyrazole (1 g, 3.90 mmol, 1.00 equiv), n-BuLi (2 mL, 6.24 mmol, 1.60 equiv) in THF (20 mL) was stirred for 2 h at −78° C. The resulting solution was allowed to react, with stirring, for an additional 30 min while the temperature was maintained at −10° C. Then oxirane (6 mL, 13.62 mmol, 3.49 equiv) was added to the system. The resulting solution was allowed to react, with stirring, for an additional 2 h at room temperature. The reaction was then quenched by the addition of sat.aq. ammonium chloride. The resulting solution was concentrated and diluted with 150 mL of dichloromethane, washed with 3×50 mL of brine, dried over anhydrous sodium sulfate and concentrated under vacuum. The residue was purified by a silica gel column eluting with DCM/MeOH (10:1) to afford 500 mg of the title compound as yellow oil.

Step 4: 2-(4-(2-Methoxyethyl)-1-((2-(trimethylsilyl)ethoxy)methyl)-1H-pyrazol-3-yl)ethyl methanesulfonate A solution of 2-[4-(2-methoxyethyl)-1-[[2-(trimethylsilyl)ethoxy]methyl]-1H-pyrazol-3-yl]ethan-1-ol (550 mg, 1.83 mmol, 1.00 equiv), methanesulfonyl methanesulfonate (381 mg, 2.23 mmol, 1.20 equiv) and TEA (0.5 mL) in dichloromethane (10 mL) was stirred for 60 min at room temperature. When LCMS indicated most of starting material was converted into the desired product, the resulting solution was concentrated and diluted with 150 mL of dichloromethane, washed with 3×50 mL of brine, dried over anhydrous sodium sulfate and concentrated under vacuum. The residue was purified by a silica gel column eluting with DCM/MeOH (10:1) to afford 700 mg (crude) of the title compound as yellow oil.

Step 5: 4-(2-Methoxyethyl)-3-(2-(methylsulfonyl)ethyl)-1-((2-(trimethylsilyl)ethoxy)methyl)-1H-pyrazole A solution of sodium methanesulfinate (560 mg, 5.48 mmol, 3.00 equiv) and 2-[4-(2-methoxyethyl)-1-[[2-(trimethylsilyl)ethoxy]methyl]-1H-pyrazol-3-yl]ethyl methanesulfonate (691 mg, 1.82 mmol, 1.00 equiv) in DMF(10 mL) was stirred for 5 h. After completion, the solution was diluted with 50 mL of water and extracted with 3×50 mL of EtOAc. Then the organic layers was combined and washed with 3×50 mL of brine. The organic layer was dried over anhydrous sodium sulfate and concentrated under vacuum. The residue was applied onto a silica gel column eluting with DCM/MeOH (10:1) to afford 176 mg of the title compound as a yellow oil.

Step 6: 4-(2-Methoxyethyl)-3-(2-(methylsulfonyl)ethyl)-1H-pyrazole

A solution of 3-(2-methanesulfonylethyl)-4-(2-methoxyethyl)-1-[[2-(trimethylsilyl)ethoxy]methyl]-1H-pyrazole (176 mg, 0.48 mmol, 1.00 equiv) and trifluoroacetic acid (2 mL, 26.92 mmol, 55.46 equiv) in dichloromethane (4 mL) was stirred for 3 h at room temperature. After completion, the resulting mixture was concentrated under vacuum to afford 250 mg (crude) of the title compound as a brown solid.

Step 7: (5R,8S)-3-(2,6-Difluorophenyl)-8-(2-(4-(2-methoxyethyl)-3-(2-(methylsulfonyl)ethyl)-1H-pyrazol-1-yl)pyrimidin-4-yl)-9,9-dimethyl-5,6,7,8-tetrahydro-5,8-methanocinnoline A solution of (5R,8S)-8-(2-chloropyrimidin-4-yl)-3-(2,6-difluorophenyl)-9,9-dimethyl-5,6,7,8-tetrahydro-5,8-methanocinnoline (257 mg, 0.64 mmol, 1.49 equiv), 3-(2-methanesulfonylethyl)-4-(2-methoxyethyl)-1H-pyrazole (100 mg, 0.43 mmol, 1.00 equiv) and potassium carbonate (237 mg, 1.71 mmol, 3.98 equiv) in DMSO (5 mL) was stirred for 12 h at 100° C. After completion, the solution was diluted with 50 mL of water and extracted with 3×50 mL of EtOAc.

Then the organic layers was combined and washed with 3×50 mL of brine. The organic layer was dried over anhydrous sodium sulfate and concentrated under vacuum. The residue was purified by Prep-HPLC with the following conditions: Column: X Bridge C18, 19*150 mm, 5 um; Mobile Phase A:Water/0.05% TFA, Mobile Phase B: ACN; Flow rate: 20 mL/min; Gradient: 30% B to 70% B in 10 min; 254 nm to afford 57.5 mg of the title compound as a white solid. $^{1}$H NMR (300 MHz, Methanol-d4): δ: 8.86 (d, J=5.2 Hz, 1H), 8.52 (s, 1H), 7.85 (s, 1H), 7.75-7.71 (m, 1H), 7.64-7.55 (m, 1H), 7.18 (q, J=8.1, 6.1 Hz, 3H), 3.71-3.59 (m, 4H), 3.57-3.19 (m, 7H), 3.08 (s, 3H), 2.88-2.77 (m, 2H), 2.70-2.52 (m, 1H), 1.78-1.68 (m, 1H), 1.47-1.45 (m, 1H), 1.21 (s, 3H), 0.88 (s, 3H); LCMS ES$^{+}$ 595 [M+H]$^{+}$.

Example 47: (5R,8S)-3-(2,6-Difluorophenyl)-8-(2-(3-(2-methoxyethyl)-4-(2-(methylsulfonyl)ethyl)-1H-pyrazol-1-yl)pyrimidin-4-yl)-9,9-dimethyl-5,6,7,8-tetrahydro-5,8-methanocinnoline

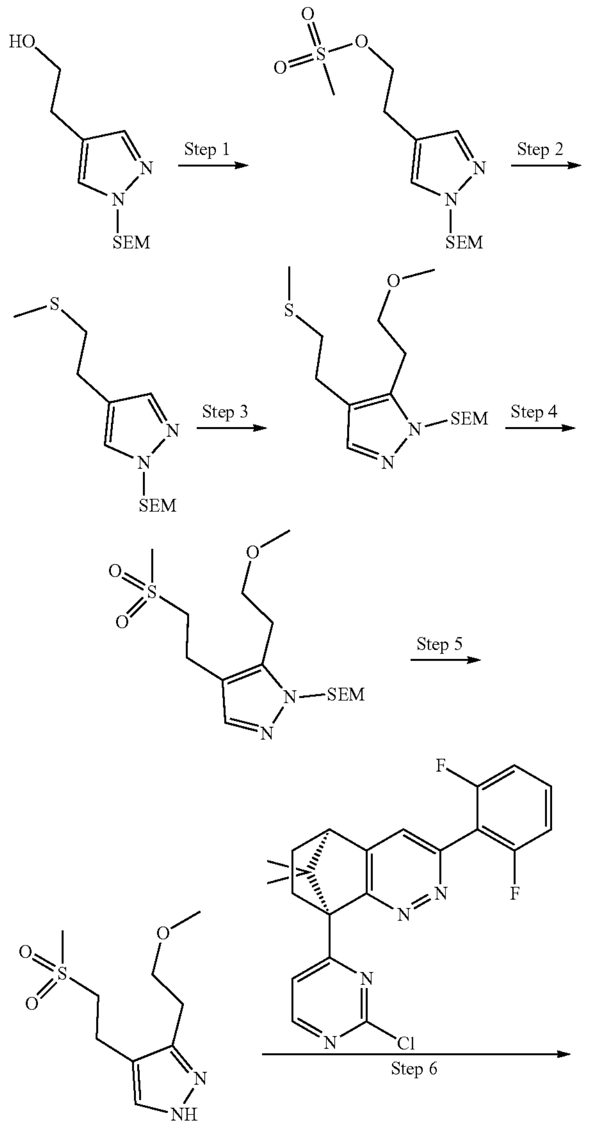

-continued

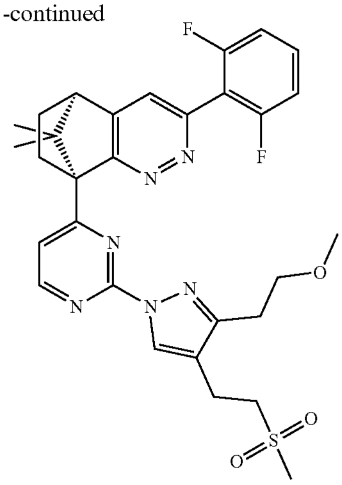

Step 1: 2-(1-((2-(Trimethylsilyl)ethoxy)methyl)-1H-pyrazol-4-yl)ethyl methanesulfonate A solution of 2-(1-[[2-(trimethylsilyl)ethoxy]methyl]-1H-pyrazol-4-yl)ethan-1-ol (6.53 g, 26.94 mmol, 1.00 equiv), methanesulfonyl methanesulfonate (7 g, 40.18 mmol, 1.49 equiv) and TEA (7 mL, 50.36 mmol, 1.86 equiv) in dichloromethane (50 mL) was stirred for 3 h at room temperature. When LCMS indicated most of starting material was converted into the desired product, the resulting solution was concentrated and diluted with 150 mL of dichloromethane and washed with 3×50 mL of brine and dried over anhydrous sodium sulfate and concentrated under vacuum. The residue was purified by a silica gel column eluting with DCM/MeOH (10:1) to afford 3.6 g of the title compound as a yellow oil.

Step 2: 4-(2-(Methylthio)ethyl)-1-((2-(trimethylsilyl)ethoxy)methyl)-1H-pyrazole A solution of 2-(1-[[2-(trimethylsilyl)ethoxy]methyl]-1H-pyrazol-4-yl)ethyl methanesulfonate (3.6 g, 11.233 mmol, 1.00 equiv) and (methylsulfanyl)sodium (945 mg, 13.48 mmol, 1.20 equiv) in DMF(30 mL) was stirred for 5 h at 80° C. When LCMS indicated most of starting material was converted into the desired product, the resulting solution was concentrated and diluted with 150 mL of dichloromethane, washed with 3×50 mL of brine, dried over anhydrous sodium sulfate and concentrated under vacuum. The residue was purified by a silica gel column eluting with DCM/MeOH (10:1) to afford 2.2 g of the title compound as yellow oil.

Step 3: 5-(2-Methoxyethyl)-4-(2-(methylthio)ethyl)-1-((2-(trimethylsilyl)ethoxy)methyl)-1H-pyrazole A solution of 4-[2-(methylsulfanyl)ethyl]-1-[[2-(trimethylsilyl)ethoxy]methyl]-1H-pyrazole (700 mg, 2.56 mmol, 1.00 equiv) and n-BuLi (1.54 mL, 4.80 mmol, 1.87 equiv) in THF (20 mL) was stirred for 1.5 h at −78° C. The resulting solution was allowed to react, with stirring, for an additional 60 min while the temperature was maintained at −10° C. Then oxirane (2.3 mL, 5.22 mmol, 2.03 equiv) was added to the system. The resulting solution was allowed to react, with stirring, for an additional 3 h while the temperature was maintained at −10° C. Then $CH_3I$ (0.3 mL, 4.81 mmol, 1.87 equiv) was added to the system. After completion, the solution was quenched by the addition of sat. aq. ammonium chloride. The resulting solution was diluted with 200 mL of EtOAc and washed with 3×80 mL of water. The organic layer was dried over anhydrous sodium sulfate and concentrated under vacuum. The residue was applied onto a silica gel column eluting with DCM/MeOH (10: 1) to afford 250 mg the title compound as yellow oil.

Step 4: 5-(2-Methoxyethyl)-4-(2-(methylsulfonyl) ethyl)-1-((2-(trimethylsilyl)ethoxy)methyl)-1H-pyrazole A solution of 3-(2-methoxyethyl)-4-[2-(methylsulfanyl) ethyl]-1-[[2-(trimethylsilyl)ethoxy]methyl]-1H-pyrazole (240 mg, 0.72 mmol, 1.00 equiv) and m-CPBA (375 mg, 2.17 mmol, 2.99 equiv) in dichloromethane (10 mL) was stirred for 3 h at room temperature. When LCMS indicated most of starting material was converted into the desired product, the resulting solution was concentrated and diluted with 150 mL of dichloromethane, washed with 3×50 mL of brine, dried over anhydrous sodium sulfate and concentrated under vacuum. The residue was purified by a silica gel column eluting with DCM/MeOH (10:1) to afford 200 mg of the title compound as light yellow oil.

Step 5: 3-(2-Methoxyethyl)-4-(2-(methylsulfonyl) ethyl)-1H-pyrazole

A solution of 4-(2-methanesulfonylethyl)-3-(2-methoxyethyl)-1-[[2-(trimethylsilyl)ethoxy]methyl]-1H-pyrazole (200 mg, 0.55 mmol, 1.00 equiv) and trifluoroacetic acid (2 mL) in dichloromethane (4 mL) was stirred for 6 h at room temperature. The resulting mixture was concentrated under vacuum to afford 325 mg (crude) of the title compound as brown oil.

Step 6: (5R,8S)-3-(2,6-Difluorophenyl)-8-(2-(3-(2-methoxyethyl)-4-(2-(methylsulfonyl)ethyl)-1H-pyrazol-1-yl)pyrimidin-4-yl)-9,9-dimethyl-5,6,7,8-tetrahydro-5,8-methanocinnoline A solution of 4-(2-methanesulfonylethyl)-3-(2-methoxyethyl)-1H-pyrazole (230 mg, 0.99 mmol, 1.00 equiv), (5R,8S)-8-(2-chloropyrimidin-4-yl)-3-(2,6-difluorophenyl)-9,9-dimethyl-5,6,7,8-tetrahydro-5,8-methanocinnoline (691 mg, 1.73 mmol, 1.75 equiv) and potassium carbonate (280 mg, 2.02 mmol, 2.04 equiv) in DMSO (4 mL) was stirred for 24 h at 100° C. The resulting solution was diluted with 50 mL of water and extracted with 3×50 mL of EtOAc. Then the organic layers combined and washed with 3×50 mL of water. The organic layer was dried over anhydrous sodium sulfate and concentrated under vacuum. The residue was applied onto a silica gel column eluting with DCM/MeOH (10:1). The crude product was purified by Prep-HPLC with the following conditions: Column: X Bridge C18, 19*150 mm, 5 um; Mobile Phase A:Water/0.05% TFA, Mobile Phase B: ACN; Flow rate: 20 mL/min; Gradient: 30% B to 70% B in 10 min; 254 nm to afford 20.0 mg of the title compound as a white solid. $^1$H NMR (300 MHz, $CD_3OD$): δ: 8.85 (d, J=5.1 Hz, 1H), 8.57 (s, 1H), 7.78-7.75 (m, 1H), 7.70-7.68 (m, 1H), 7.60-7.51 (m, 1H), 7.19-7.13 (m, 2H), 3.77 (t, J=6.5 Hz, 2H), 3.49-3.40 (m, 3H), 3.38-3.30 (m, 5H), 3.15-2.91 (m, 6H), 2.69-2.51 (m, 1H), 1.70-1.64 (m, 1H), 1.44-1.38 (m, 1H), 1.20 (s, 3H), 0.86 (s, 3H); LCMS ES$^+$ 595 [M+H]$^+$.

Example 48: (5R,8R)-8-(2-(3-(2-((Cyclopropylmethyl)sulfonyl)ethyl)-1H-1,2,4-triazol-1-yl)pyrimidin-4-yl)-3-(2,6-difluorophenyl)-9,9-dimethyl-5,6,7,8-tetrahydro-5,8-methanocinnoline

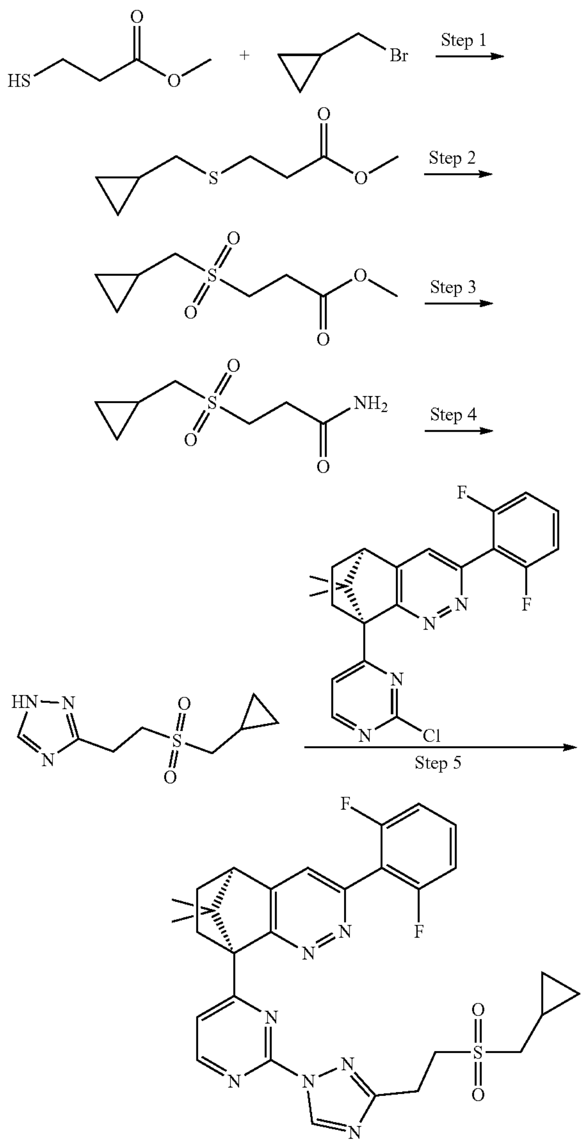

Step 1: Methyl 3-((cyclopropylmethyl)thio)propanoate

A solution of methyl 3-sulfanylpropanoate (3.3 g, 27.5 mmol, 1.0 equiv), (bromomethyl)cyclopropane (4 g, 29.6 mmol, 1.1 equiv), cesium carbonate (18 g, 55.2 mmol, 2.0 equiv) in DMF(20 mL) was stirred for 2 h at room temperature. After completion, the solution was diluted with 50 mL of water and extracted with 3×50 mL of EtOAc. Then the organic layers was combined and washed with 3×50 mL of brine. The mixture was dried over anhydrous sodium sulfate and concentrated under vacuum to afford 2.0 g of the title compound as a brown oil. LCMS ES$^+$ 175 [M+H]$^+$.

Step 2: Methyl 3-((cyclopropylmethyl)sulfonyl)propanoate

A solution of methyl 3-[(cyclopropylmethyl)sulfanyl]propanoate (2 g, 11.5 mmol, 1.0 equiv), 3-chloroperoxybenzoic acid (8.3 g, 48.1 mmol, 4.2 equiv) in dichloromethane (20 mL) was stirred for 5 h at 25° C. After completion, the solution was diluted with 50 mL of water and extracted with 3×50 mL of EtOAc. Then the organic layers were combined and washed with 3×50 mL of brine. The mixture was dried over anhydrous sodium sulfate and concentrated under vacuum to afford 1.5 g of the title compound as a brown oil. LCMS $ES^+$ 207 $[M+H]^+$.

Step 3: 3-((Cyclopropylmethyl)sulfonyl)propanamide

A solution of methyl 3-(cyclopropylmethane)sulfonylpropanoate (2 g, 9.7 mmol, 1.0 equiv) in MeOH (30 mL, saturated with ammonia) was stirred for 5 h at 40° C. After completion, the solution was concentrated under vacuum to afford 1.8 g (95%) of 3-(cyclopropylmethylsulfonyl)propanamide as a white solid. LCMS $ES^+$ 192 $[M+H]^+$.

Step 4: 3-(2-((Cyclopropylmethyl)sulfonyl)ethyl)-1H-1,2,4-triazole

A solution of 3-(cyclopropylmethane)sulfonylpropanamide (2 g, 10.5 mmol, 1.0 equiv) in acetonitrile (10 mL) was treated with DMFdimethyl acetal (3 mL, 22.4 mmol, 2.1 equiv) and heated at 60° C. for 1.25 hours. The cooled mixture was concentrated under vacuum and taken up in acetonitrile (15 mL). The solution was treated with AcOH (0.3 mL, 5.24 mmol, 0.5 equiv) followed by hydrazine monohydrate (0.7 mL, 14.4 mmol, 1.4 equiv) instantly giving a white precipitate. The suspension was heated at 60° C. for 1.25 hours in which time all solid has dissolved to leave a pale pink solution. The cooled mixture was concentrated under vacuum to leave viscous pink syrup. The residue was applied onto a silica gel column eluting with DCM/MeOH (10:1) to afford. 600 mg of the title compound as a pink solid. LCMS $ES^+$ 192 $[M+H]^+$.

Step 5: (5R,8R)-8-(2-(3-(2-((Cyclopropylmethyl) sulfonyl)ethyl)-1H-1,2,4-triazol-1-yl)pyrimidin-4-yl)-3-(2,6-difluorophenyl)-9,9-dimethyl-5.6.78-tetra-hydro-5,8-methanocinnoline Under nitrogen, a solution of (5R,8R)-8-(2-chloropyrimidin-4-yl)-3-(2,6-difluorophenyl)-9,9-dimethyl-5,6,7,8-tetrahydro-5,8-methanocinnoline (200 mg, 0.5 mmol, 1.0 equiv), 3-[2-(cyclopropylmethane)sulfonylethyl]-1H-1,2,4-triazole (130 mg, 0.6 mmol, 1.2 equiv), $Pd_2(dba)_3.CHCl_3$ (52 mg, 0.05 mmol, 0.1 equiv), XantPhos (58 mg, 0.1 mmol, 0.2 equiv) and cesium carbonate (326 mg, 1.0 mmol, 2.0 equiv) in 1,4-dioxane (5 mL) was stirred for 3 h at 110° C. After completion, the solution was diluted with 30 mL of water and extracted with 3×50 mL of EtOAc. Then the organic layers was combined and washed with 3×50 mL of brine. The mixture was dried over anhydrous sodium sulfate and concentrated under vacuum. The residue was applied onto a silica gel column eluting with DCM/MeOH (12:1) to afford 67 mg of the title compound as a white solid. $^1H$ NMR (400 MHz, DMSO-$d_6$): δ: 9.47 (s, 1H), 9.00 (d, J=5.2 Hz, 1H), 7.89-7.83 (m, 2H), 7.64 (m, 1H), 7.32 (t, J=8.1 Hz, 2H), 3.64-3.55 (m, 2H), 3.33 (m, 5H), 2.45 (m, 2H), 1.63 (m, 1H), 1.31 (m, 1H), 1.12 (s, 3H), 1.11-1.02 (m, 1H), 0.75 (s, 3H), 0.68-0.57 (m, 2H), 0.44-0.35 (m, 2H); LCMS $ES^+$ 578 $[M+H]^+$.

Example 49: (5R,8S)-8-(2-(3-(((Cyclopropylmethyl) sulfonyl)methyl)-1H-1,2,4-triazol-1-yl)pyrimidin-4-yl)-3-(2,6-difluorophenyl)-9,9-dimethyl-5,6,7,8-tetrahydro-5,8-methanocinnoline

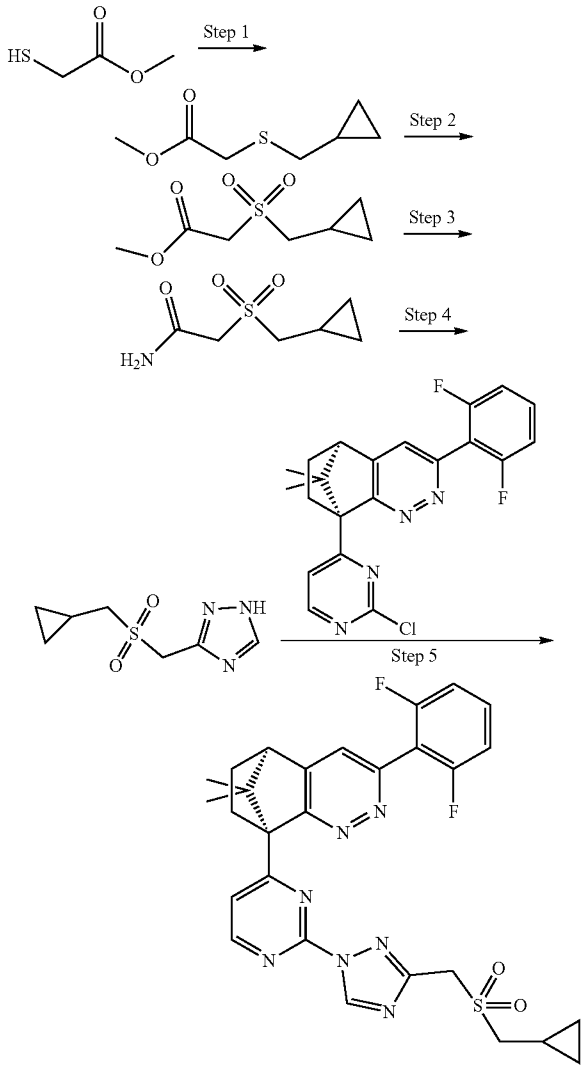

Step 1: Methyl 2-((cyclopropylmethyl)thio)acetate

A solution of methyl 2-sulfanylacetate (1 g, 9.4 mmol, 1.0 equiv), (bromomethyl)cyclopropane (1.4 g, 10.4 mmol, 1.1 equiv) and cesium carbonate (6.1 g, 18.7 mmol, 2.0 equiv) in DMF(6 mL) was stirred for 12 hours at room temperature. After completion, the solution was diluted with 30 mL of water and extracted with 3×50 mL of EtOAc. Then the organic layers was combined and washed with 3×50 mL of brine. The mixture was dried over anhydrous sodium sulfate and concentrated under vacuum. The residue was applied onto a silica gel column with EtOAc/petroleum ether (10:1) to afford 1.1 g of the title compound as colorless oil. LCMS $ES^+$ 161 $[M+H]^+$.

Step 2: Methyl 2-((cyclopropylmethyl)sulfonyl)acetate

A solution of methyl 2-[(cyclopropylmethyl)sulfanyl]acetate (200 mg, 1.2 mmol, 1.0 equiv) and 3-chloroperoxybenzoic acid (432 mg, 2.5 mmol, 2.0 equiv) in dichloromethane (5 mL) was stirred for 10 min at 0° C. After completion, the solution was then quenched by the addition of sat.aq.sodium hydrogen sulfite (2 mL). Then the resulting solution was extracted with 2×25 mL of DCM. The organic layers were combined, dried over anhydrous sodium sulfate and concentrated under vacuum. The residue was applied onto a silica gel column eluting with EtOAc/petroleum ether (5:1) to afford 220 mg of the title compound as colorless oil. LCMS ES$^+$ 193 [M+H]$^+$.

Step 3: 2-((Cyclopropylmethyl)sulfonyl)acetamide

A solution of methyl 2-(cyclopropylmethane)sulfonylacetate (200 mg, 1.0 mmol, 1.0 equiv) in MeOH (20 mL, saturated with ammonia) was stirred for 3 h at 50° C. After completion, the solution was concentrated under vacuum to afford 150 mg of the title compound as an orange solid. LCMS ES$^+$ 178 [M+H]$^+$.

Step 4: 3-(((Cyclopropylmethyl)sulfonyl)methyl)-1H-1,2,4-triazole

A solution of 2-(cyclopropylmethane)sulfonylacetamide (5 g, 28.2 mmol, 1.0 equiv) in acetonitrile (20 mL) was treated with DMFdimethyl acetal (6.7 g, 56.2 mmol, 2.1 equiv) and heated at 60° C. for 1.25 hours. The cooled mixture was concentrated under vacuum and taken up in acetonitrile (20 mL). The solution was treated with AcOH (3.4 g, 56.6 mmol, 2.0 equiv) followed by hydrazine monohydrate (2.8 g, 55.9 mmol, 2.0 equiv) instantly giving a white precipitate. The suspension was heated at 60° C. for 1.25 hours in which time all solid has dissolved to leave a pale pink solution. The cooled mixture was concentrated under vacuum to leave viscous pink syrup. The residue was applied onto a silica gel column eluting with DCM/MeOH (10:1) to afford 2.0 g of the title compound as a yellow green solid. LCMS ES$^+$ 202 [M+H]$^+$.

Step 5: (5R,8S)-8-(2-(3-(((Cyclopropylmethyl)sulfonyl)methyl)-1H-1,2,4-triazol-1-yl)pyrimidin-4-yl)-3-(2,6-difluorophenyl)-9,9-dimethyl-5,6,7,8-tetrahydro-5,8-methanocinnoline Under nitrogen, a solution of (5R,8S)-8-(2-chloropyrimidin-4-yl)-3-(2,6-difluorophenyl)-9,9-dimethyl-5,6,7,8-tetrahydro-5,8-methanocinnoline (101 mg, 0.5 mmol, 1.0 equiv), $Pd_2(dba)_3$'$CHCl_3$ (104 mg, 0.1 mmol, 0.2 equiv), XantPhos (58 mg, 0.1 mmol, 0.2 equiv) and cesium carbonate (324 mg, 1.0 mmol, 2.0 equiv) in 1,4-dioxane (2 mL) was stirred for 3 h at 110° C. After completion, the solution was diluted with 30 mL of water and extracted with 3×50 mL of EtOAc. Then the organic layers was combined and washed with 3×50 mL of brine. The organic layer was dried over anhydrous sodium sulfate and concentrated under vacuum. The residue was applied onto a reversed-phase column eluting with water/acetonitrile (60:40) to afford 53.6 mg of the title compound as a white solid. $^1$H NMR (300 MHz, DMSO-d$_6$): δ: 9.57 (d, J=2.5 Hz, 1H), 9.03 (dd, J=5.3, 2.6 Hz, 1H), 7.91-7.86 (m, 2H), 7.68-7.58 (m, 1H), 7.34-7.29 (m, 2H), 4.76 (d, J=2.6 Hz, 2H), 3.29 (m, 3H), 2.46 (d, J=11.6 Hz, 2H), 1.65 (m, 1H), 1.40-1.12 (m, 2H), 1.10 (s, 3H), 0.75 (s, 3H), 0.68-0.65 (m, 2H), 0.49 (m, 2H); LCMS ES$^+$ 564 [M+H]$^+$.

Example 50: 3-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)oxetan-3-ol

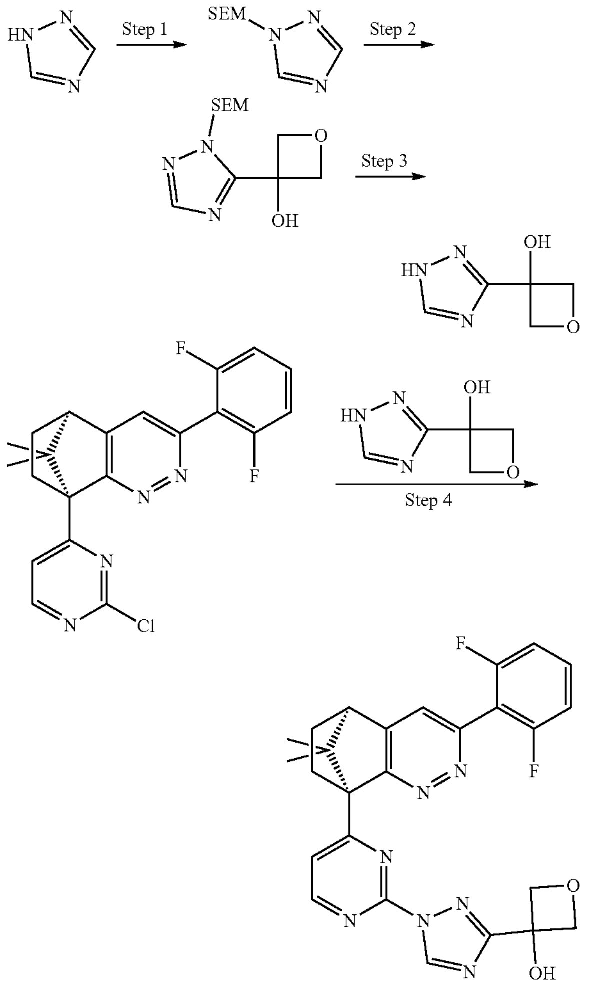

Step 1: 1-((2-(Trimethylsilyl)ethoxy)methyl)-1H-1,2,4-triazole

A solution of 1H-1,2,4-triazole (10.0 g, 144.8 mmol, 1.000 equiv), NaH (4.9 g, 213.9 mmol, 1.2 equiv) in THF (300 mL) was stirred for 1 h at 0° C. Then 2-(trimethylsilyl)ethoxymethyl chloride (24.3 g, 159.3 mmol, 1.1 equiv) was added to the mixture. The resulting solution was stirred for 2 h at 25° C. After completion, the mixture was concentrated under vacuum and applied onto a silica gel column eluting with DCM/MeOH (20:1) to afford 15 g of the title compound as colorless oil.

Step 2: 3-(1-((2-(Trimethylsilyl)ethoxy)methyl)-1H-1,2,4-triazol-5-yl)oxetan-3-ol Under nitrogen, a solution of 1-[[2-(trimethylsilyl)ethoxy]methyl]-1H-1,2,4-triazole (5.00 g, 25.085 mmol, 1.000 equiv) in THF (30 mL) was stirred for 10 min at −78° C. Then n-BuLi (2.5M in hexane) (10 mL, 26.1 mmol, 1.0 equiv) was added at −78° C. After 30 min, oxetan-3-one (1.99 g, 27.6 mmol, 1.1 equiv) was added at −78° C. and stirred for 1 h at −78° C. After completion, the reaction was quenched with sat. eq. ammonium chloride (50 mL) and extracted with 3×50 mL of EtOAc. Then the organic layers were combined and washed with 3×50 mL of brine. The organic layer was dried over anhydrous sodium sulfate and concentrated under vacuum. The residue was applied onto a silica gel column eluting with DCM/MeOH (20:1) to afford 7 g (crude) of the title compound as a colorless oil.

Step 3: 3-(1H-1,2,4-Triazol-3-yl)oxetan-3-ol

A solution of 3-(1-[[2-(trimethylsilyl)ethoxy]methyl]-1H-1,2,4-triazol-3-yl)oxetan-3-ol (1.50 g, 5.5 mmol, 1.0 equiv), trifluoroacetic acid (6.30 g, 55.3 mmol, 10.0 equiv) in THF (50 mL) was stirred for 2 h at 25° C. After completion, the resulting mixture was concentrated under vacuum. The residue was applied onto a silica gel column eluting with DCM/MeOH (20:1) to afford 1.2 g (crude) of the title compound as a colorless oil.

Step 4: 3-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)oxetan-3-ol Under nitrogen, a solution of (5R,8S)-8-(2-chloropyrimidin-4-yl)-3-(2,6-difluorophenyl)-9,9-dimethyl-5,6,7,8-tetrahydro-5,8-methanocinnoline (300.0 mg, 0.75 mmol, 1.0 equiv), 3-(1H-1,2,4-triazol-3-yl)oxetan-3-ol (212.3 mg, 1.5 mmol, 2.0 equiv), $Pd_2(dba)_3CHCl_3$ (77.9 mg, 0.075 mmol, 0.1 equiv), XantPhos (87.0 mg, 0.15 mmol, 0.2 equiv), cesium carbonate (490.2 mg, 1.5 mmol, 2.0 equiv) in 1,4-dioxane (6 mL) was irradiated with microwave radiation for 1.5 h at 110° C. After completion, the solution was diluted with 50 mL of water and extracted with 3×50 mL of EtOAc. Then the organic layers was combined and washed with 3×50 mL of brine. The organic layer was dried over anhydrous sodium sulfate and concentrated under vacuum. The residue was applied onto a silica gel column eluting with DCM/MeOH (15:1) to afford 78.5 mg of the title compound as a white solid. $^1H$ NMR (300 MHz, $CD_3OD$): δ: 9.48 (s, 1H), 8.97 (d, J=5.2 Hz, 1H), 7.93 (d, J=5.3 Hz, 1H), 7.82 (t, J=1.2 Hz, 1H), 7.69-7.52 (m, 1H), 7.29-7.13 (m, 2H), 5.17 (d, J=6.9 Hz, 2H), 4.90 (m, 2H), 3.55-3.34 (m, 2H), 2.68-2.60 (m, 1H), 1.79-1.55 (m, 1H), 1.45-1.35 (m, 1H), 1.23 (s, 3H), 0.89 (s, 3H); LCMS $ES^+$ 504 $[M+H]^+$.

Example 50: (5R,8S)-8-(2,6-Bis(3-(2-(methylsulfonyl)ethyl)-1H-1,2,4-triazol-1-yl)pyridin-4-yl)-3-(2,6-difluorophenyl)-9,9-dimethyl-5,6,7,8-tetrahydro-5,8-methanocinnoline

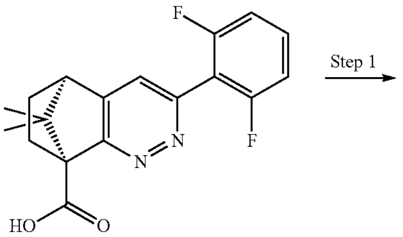

-continued

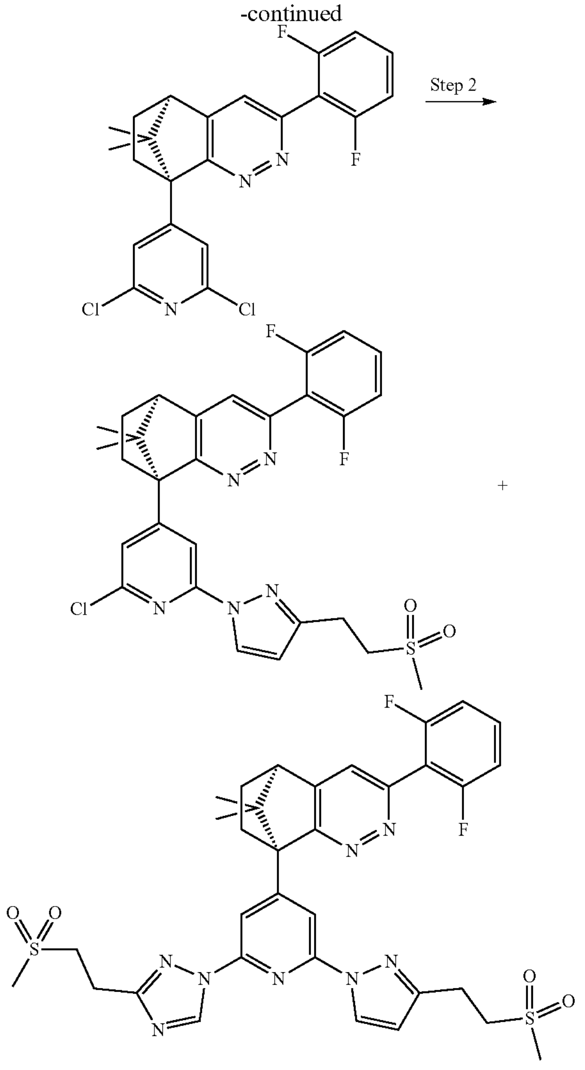

Step 1: (5R,8S)-8-(2,6-Dichloropyridin-4-yl)-3-(2,6-difluorophenyl)-9,9-dimethyl-5,6,7,8-tetrahydro-5,8-methanocinnoline Under nitrogen, a solution of (5R,8R)-3-(2,6-difluorophenyl)-9,9-dimethyl-6,7-dihydro-5,8-methanocinnoline-8(5H)-carboxylic acid (1.00 g, 3.03 mmol, 1.0 equiv), 2,6-dichloropyridine (1.78 g, 12.03 mmol, 3.97 equiv) and silver nitrate (2.0 g, 11.77 mmol, 3.89 equiv) in 10% sulfuric acid aq. Solution (5 mL) was stirred for 3 h at 110° C. Then a freshly prepared solution of ammonium persulfate (2.76 g, 12.10 mmol, 4.00 equiv) in water (5 mL) was added drop wise to the mixture during 15 min at 110° C. The resulting solution was stirred for 30 h at 110° C. (The precipitates formed during this period, and most product was contained in the solids, the major part in solvent was starting material). After completion, the solids were collected by filtration (the original solvent was removed, which contained almost only starting material), and then was dissolved in 100 mL of DCM/MeOH (1:1) (only the product can be dissolved and the unknown impurities remained as insoluble solids). After filtration, the solids were filtered out to remove insoluble impurities. The filtrate was collected and concentrated under vacuum. The crude product (with 70-80% purity) was purified by silica gel chromatography eluting with EtOAc/petroleum ether (2:3) to afford 300 mg mixture of the title compound and (5R,8S)-8-(2,6-dichloropyridin-3-yl)-3-(2,6-difluorophenyl)-9,9-dimethyl-5,6,7,8-tetrahydro-5,8-methanocinnoline as yellow solids. Small amount of each isomer was separated and identified by $^1$H NMR. LCMS ES$^+$ 432 [M+H]$^+$.

Step 2: (5R,8S)-8-(2,6-Bis(3-(2-(methylsulfonyl)ethyl)-1H-1,2,4-triazol-1-yl)pyridin-4-yl)-3-(2,6-difluorophenyl)-9,9-dimethyl-5,6,7,8-tetrahydro-5,8-methanocinnoline A solution of (5R,8S)-8-(2,6-dichloropyridin-4-yl)-3-(2,6-difluorophenyl)-9,9-dimethyl-5,6,7,8-tetrahydro-5,8-methanocinnoline (150 mg, 0.348 mmol, 1.0 equiv), 3-(2-methanesulfonylethyl)-1H-1,2,4-triazole (68 mg, 0.386 mmol, 1.1 equiv) and potassium carbonate (96 mg, 0.695 mmol, 2.0 equiv) in N, N-dimethylformamide (1 mL) was stirred for 20 h at 80° C. After completion, the result system was purified by reversed-phase column with water: acetonitrile (5%-60%) to afford 60 mg of (5R,8S)-8-(2-chloro-6-(3-(2-(methylsulfonyl)ethyl)-1H-1,2,4-triazol-1-yl)pyridin-4-yl)-3-(2,6-difluorophenyl)-9,9-dimethyl-5,6,7,8-tetrahydro-5,8-methanocinnoline as a yellow solid (LCMS ES$^+$ 571 [M+H]$^+$) and 9.4 mg of the title compound as a white solid. $^1$H NMR (400 MHz, $CD_3OD$): 9.63 (s, 2H), 8.16 (s, 2H), 7.85 (s, 1H), 7.61 (t, J=8.5, 6.4 Hz, 1H), 7.22 (t, J=8.1 Hz, 2H), 3.72-3.63 (m, 4H), 3.46-3.33 (m, 5H), 3.21 (m, 1H), 3.05 (s, 6H), 2.65 (m, 1H), 1.77 (m, 1H), 1.49 (m, 1H), 1.18 (s, 3H), 0.85 (s, 3H); LCMS ES$^+$710 [M+H]$^+$.

Example 51: (5R,8S)-3-(2,6-Difluorophenyl)-9,9-dimethyl-8-(2-(3-(2-(methylsulfonyl)ethyl)-1H-1,2,4-triazol-1-yl)pyridin-4-yl)-5,6,7,8-tetrahydro-5,8-methanocinnoline

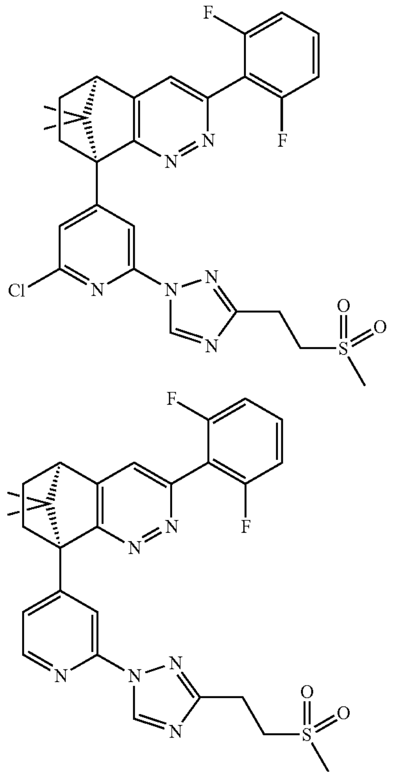

Under Hydrogen, a solution of (5R,8S)-8-(2-chloro-6-(3-(2-(methylsulfonyl)ethyl)-1H-1,2,4-triazol-1-yl)pyridin-4-yl)-3-(2,6-difluorophenyl)-9,9-dimethyl-5,6,7,8-tetrahydro-5,8-methanocinnoline (60 mg, 0.11 mmol, 1.0 equiv), AcOH (0.05 mL, 0.87 mmol, 8.0 equiv), and palladium on activated carbon (10 mg) in ethanol (2 mL) was stirred for 10 h at 60° C. After completion, the result system was purified by reversed-phase column with water: acetonitrile (5%-60%) to afford 6.7 mg of the title compound as a white solid. $^1$H NMR (400 MHz, $CD_3OD$): 9.34 (s, 1H), 8.60 (d, J=5.2 Hz, 1H), 8.17 (d, J=1.5 Hz, 1H), 7.82 (s, 1H), 7.73-7.68 (m, 1H), 7.62-7.58 (m, 1H), 7.21 (t, J=8.1 Hz, 2H), 3.65 (dd, J=9.1, 6.7 Hz, 2H), 3.42-3.33 (m, 3H), 3.23-3.11 (m, 1H), 3.04 (s, 3H), 2.68-2.55 (m, 1H), 1.69 (m, H), 1.45 (m, 1H), 1.12 (s, 3H), 0.80 (s, 3H); LCMS ES$^+$ 537 [M+H]$^+$.

Example 52: (5R,8S)-3-(2,6-Difluorophenyl)-9,9-dimethyl-8-(2-(2-(3-((oxetan-3-ylsulfonyl)methyl)-1H-1,2,4-triazol-1-yl)pyrimidin-4-yl)-567.8-tetrahydro-5,8-methanocinnoline

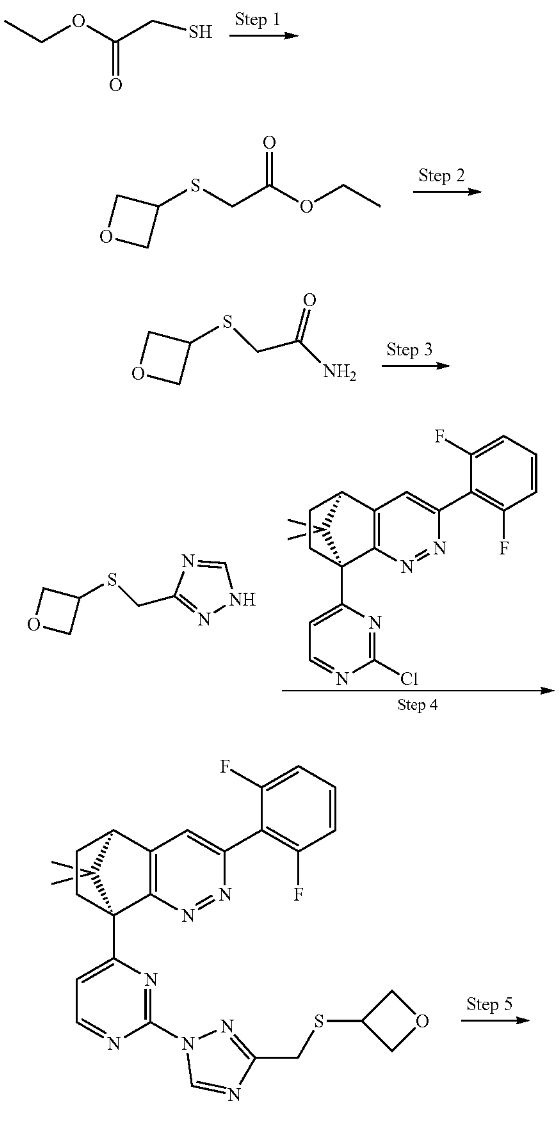

-continued

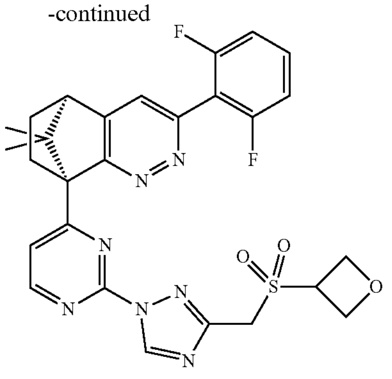

Step 1: Ethyl 2-(oxetan-3-ylthio)acetate

A solution of ethyl 2-sulfanylacetate (3 g, 24.96 mmol, 1.00 equiv), 3-iodooxetane (5.5 g, 29.89 mmol, 1.19 equiv), potassium carbonate (6.9 g, 49.92 mmol, 2.00 equiv) in DMF(10 mL) was stirred for 6 h at 25° C. After completion, the solution was diluted with 50 mL of water and extracted with 3x50 mL of EtOAc. Then the organic layers was combined and washed with 3x50 mL of brine. The organic layer was dried over anhydrous sodium sulfate and concentrated under vacuum to afford 3.6 g of the title compound as a brown oil.

Step 2: 2-(Oxetan-3-ylthio)acetamide

Under ammonia, a solution of ethyl 2-(oxetan-3-ylsulfanyl)acetate (2 g, 11.34 mmol, 1.00 equiv) in methanol (saturated with ammonia, 30 mL) was stirred for 6 h at 40° C. The cooled mixture was concentrated under vacuum to leave a viscous pink syrup. The residue was applied onto a silica gel column eluting with DCM/MeOH (10:1) to afford 1.4 g of the title compound as a white solid. LCMS $ES^+$ 148 $[M+H]^+$.

Step 3: 3-((Oxetan-3-ylthio)methyl)-1H-1,2,4-triazole

A solution of 2-(oxetan-3-ylsulfanyl)acetamide (500 mg, 3.39 mmol, 1.00 equiv) in acetonitrile (10 mL) was treated with DMFdimethyl acetal (810 mg, 6.79 mmol, 2.00 equiv) and heated at 60° C. for 1.25 hours. The cooled mixture was concentrated under vacuum and taken up in acetonitrile (15 mL). The solution was treated with AcOH (244 mg, 4.06 mmol, 1.19 equiv) followed by hydrazine monohydrate (200 mg, 3.99 mmol, 1.17 equiv) instantly giving a white precipitate. The suspension was heated at 60° C. for 1.25 hours in which time all solid has dissolved to leave a pale pink solution. The cooled mixture was concentrated under vacuum to leave a viscous pink syrup. The residue was applied onto a silica gel column eluting with DCM/MeOH (10:1) to afford 363 mg of 3-[(oxetan-3-ylsulfanyl)methyl]-1H-1,2,4-triazole as an orange oil. LCMS $ES^+$ 172 $[M+H]^+$.

Step 4: (5R,8S)-3-(2,6-Difluorophenyl)-9,9-dimethyl-8-(2-(3-((oxetan-3-ylthio)methyl)-1H-1,2,4-triazol-1-yl)pyrimidin-4-yl)-5,6,7,8-tetrahydro-5,8-methanocinnoline A solution of 3-[(oxetan-3-ylsulfanyl)methyl]-1H-1,2,4-triazole (108 mg, 0.63 mmol, 1.00 equiv), (1S,8R)-1-(2-chloropyrimidin-4-yl)-5-(2,6-difluorophenyl)-11,11-dimethyl-3,4-diazatricyclo[6.2.1.0^2,7]undeca-2(7),3,5-triene (300 mg, 0.75 mmol, 1.19 equiv), potassium carbonate 5 (173 mg, 1.25 mmol, 1.98 equiv) in DMF(6 mL) was stirred for 2 h at 75° C. After completion, the solution was diluted with 30 mL of water and extracted with 3x50 mL of EtOAc. Then the organic layers was combined and washed with 3x50 mL of brine. The organic layer was dried over anhydrous sodium sulfate and concentrated under vacuum. The residue was applied onto a silica gel column eluting with DCM/MeOH (13:1) to afford 203 mg (65%) of the title compound as a white solid. LCMS $ES^+$ 534 $[M+H]^+$.

Step 5: (5R,8S)-3-(2,6-Difluorophenyl)-9,9-dimethyl-8-(2-(3-((oxetan-3-ylsulfonyl)methyl)-1H-1,2,4-triazol-1-yl)pyrimidin-4-yl)-5,6,7,8-tetrahydro-5,8-methanocinnoline A solution of (5R,8S)-8-(2-chloropyrimidin-4-yl)-3-(2,6-difluorophenyl)-9,9-dimethyl-5,6,7,8-tetrahydro-5,8-methanocinnoline (200 mg, 0.37 mmol, 1.00 equiv), NaIO4 (237 mg, 1.10 mmol, 2.95 equiv), KMnO4 (321 mg, 2.03 mmol, 5.419 equiv) in methanol (6 mL) and water(1 mL) was stirred for 2 h at 25° C. After completion, the solution was diluted with 30 mL of water and extracted with 3x50 mL of EtOAc. Then the organic layers was combined and washed with 3x50 mL of brine. The mixture was dried over anhydrous sodium sulfate and concentrated under vacuum. The residue was applied onto a silica gel column eluting with DCM/MeOH (14:1) to afford 20.1 mg (9%) of the title compound as a white solid. $^1H$ NMR (400 MHz, CD3OD): δ: 9.48 (s, 1H), 8.97 (d, J=5.2 Hz, 1H), 7.95 (d, J=5.3 Hz, 1H), 7.82 (s, 1H), 7.62-7.58 (m, 1H), 7.23-7.19 (m, 2H), 5.06-5.01 (m, 1H), 4.96-4.84 (t, J=7.4 Hz, 2H), 4.83-4.73 (s, 2H), 4.71 (s, 1H), 3.47-3.38 (m, 3H), 2.62-2.62 (m, 1H), 1.75-1.73 (m, 1H), 1.48-1.44 (m, 1H), 1.22 (s, 3H), 0.89 (s, 3H); LCMS $ES^+$ 566 $[M+H]^+$.

Example 53: (5R,8S)-3-(2,6-Difluorophenyl)-9,9-dimethyl-8-(2-(3-(2-(methylsulfonyl)ethyl)-1H-pyrazol-1-yl)pyrimidin-4-yl)-5,6,7,8-tetrahydro-5,8-methanocinnoline

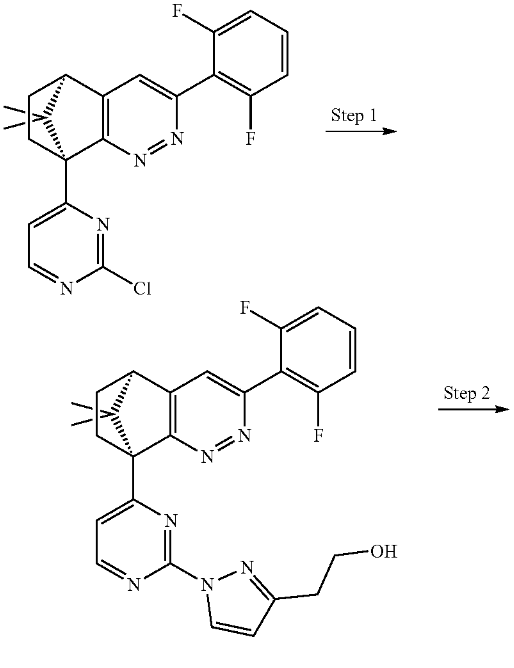

-continued

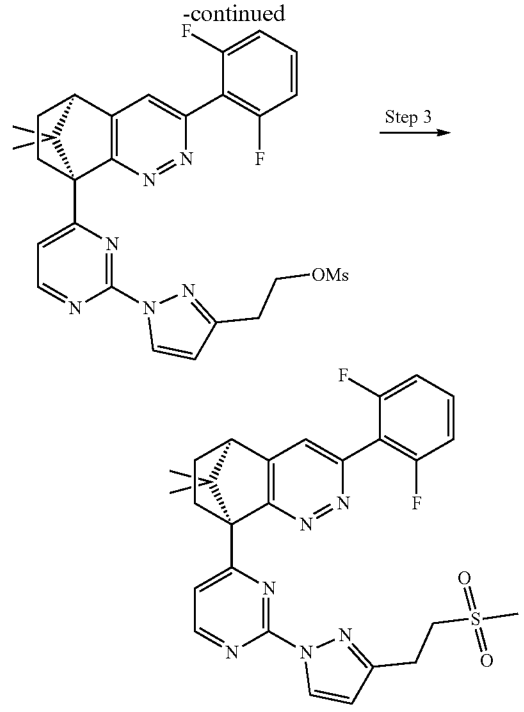

Step 1: 2-(1-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-3-yl)ethan-1-ol A solution of (5R,8S)-8-(2-chloropyrimidin-4-yl)-3-(2,6-difluorophenyl)-9,9-dimethyl-5,6,7,8-tetrahydro-5,8-methanocinnoline (90 mg, 0.80 mmol, 1.60 equiv), potassium carbonate (220 mg, 1.59 mmol, 3.17 equiv) in DMSO (5 mL) was stirred for 6 h at 80° C. After completion, the solution was diluted with 25 mL of water and extracted with 3x25 mL of EtOAc. Then the organic layers was combined and washed with 3x15 mL of brine. The mixture was dried over anhydrous sodium sulfate and concentrated under vacuum. The residue was applied onto a silica gel column eluting with DCM/MeOH (10:1). This resulted in 210 mg of the title compound an off-white solid. LCMS ES$^+$ 475 $[M+H]^+$.

Step 2: 2-(1-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-3-yl)ethyl methanesulfonate A solution of 2-(1-(4-((5R,8S)-3-(2,6-difluorophenyl)-9,9-dimethyl-6,7-dihydro-5,8-methanocinnolin-8(5H)-yl)pyrimidin-2-yl)-1H-pyrazol-3-yl)ethanol (210 mg, 0.44 mmol, 1.0 equiv), TEA (90 mg, 0.89 mmol, 2.01 equiv), methanesulfonic anhydride (116 mg, 0.67 mmol, 1.51 equiv) in dichloromethane (10 mL) was stirred for 30 min at 25° C. After completion, the resulting mixture was concentrated under vacuum. The residue was applied onto a silica gel column with DCM/MeOH (10:1). This resulted in 240 mg of the title compound as a white solid.

Step 3: (5R,8S)-3-(2,6-Difluorophenyl)-9,9-dimethyl-8-(2-(3-(2-(methylsulfonyl)ethyl)-1H-pyrazol-1-yl)pyrimidin-4-yl)-5,6,7,8-tetrahydro-5,8-methanocinnoline A solution of 2-(1-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-3-yl)ethyl methanesulfonate (240 mg, 0.44 mmol, 1.0 equiv), potassium iodide (11 mg, 0.07 mmol, 0.15 equiv), sodium methanesulfinate (110 mg, 1.08 mmol, 2.48 equiv) in DMF(5 mL) was stirred for 3 h at 85° C. After completion, the solution was diluted with 50 mL of water and extracted with 3x50 mL of EtOAc. Then the organic layers was combined and washed with 3x50 mL of brine. The mixture was dried over anhydrous sodium sulfate and concentrated under vacuum. The residue was applied onto a silica gel column eluting with DCM/MeOH (from 100:0 to 95:5). The crude product was purified by Prep-HPLC with the following conditions: Column, XBridge Prep F-Phenyl OBD Column, 19� 100 mm 5 um 13 nm; mobile phase, Water (10 MMOL/L $NH_4HCO_3$) and methanol-(45% methanol-up to 65% in 15 min); Detector, UV 220 nm to afford 121.6 mg (52%) of the title compound as an off-white solid. $^1$H NMR (300 MHz, $CD_3OD$): δ: 8.88 (d, J=5.2 Hz, 1H), 8.67 (d, J=2.7 Hz, 1H), 7.85-7.73 (m, 2H), 7.68-7.52 (m, 1H), 7.28-7.13 (m, 2H), 6.58 (d, J=2.7 Hz, 1H), 3.69-3.57 (m, 2H), 3.53-3.24 (m, 4H), 3.03 (s, 3H), 2.70-2.52 (m, 1H), 1.75-1.68 (m, 1H), 1.48-1.41 (m, 1H), 1.21 (s, 3H), 0.87 (s, 3H); LCMS ES$^+$ 537 $[M+H]^+$.

Examples 54 and 55: ((4-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-1-yl)methyl)(imino)(methyl)-$\lambda^6$-sulfanone Stereoisomer A and ((4-(4-((5R,8S)-3-(2,6-difluorophenyl)-9,9-dimethyl-6,7-dihydro-5,8-methanocinnolin-8(5H)-yl)pyrimidin-2-yl)-1H-pyrazol-1-yl)methyl)(imino)(methyl)-$\lambda^6$-sulfanone Stereoisomer B

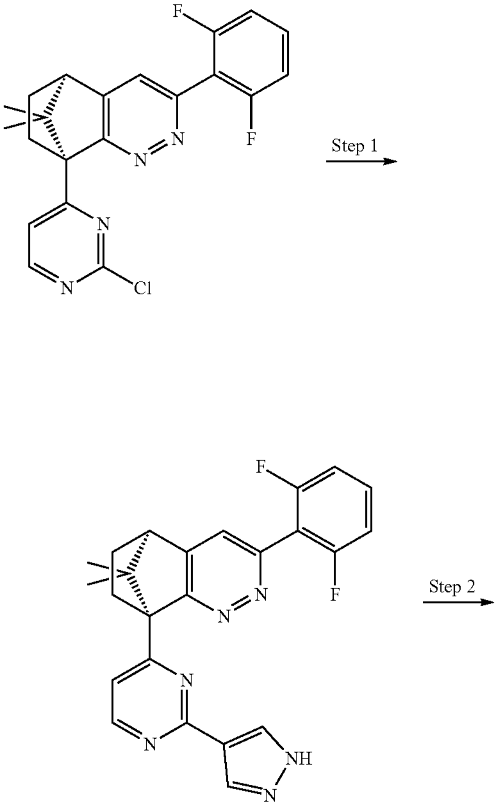

-continued

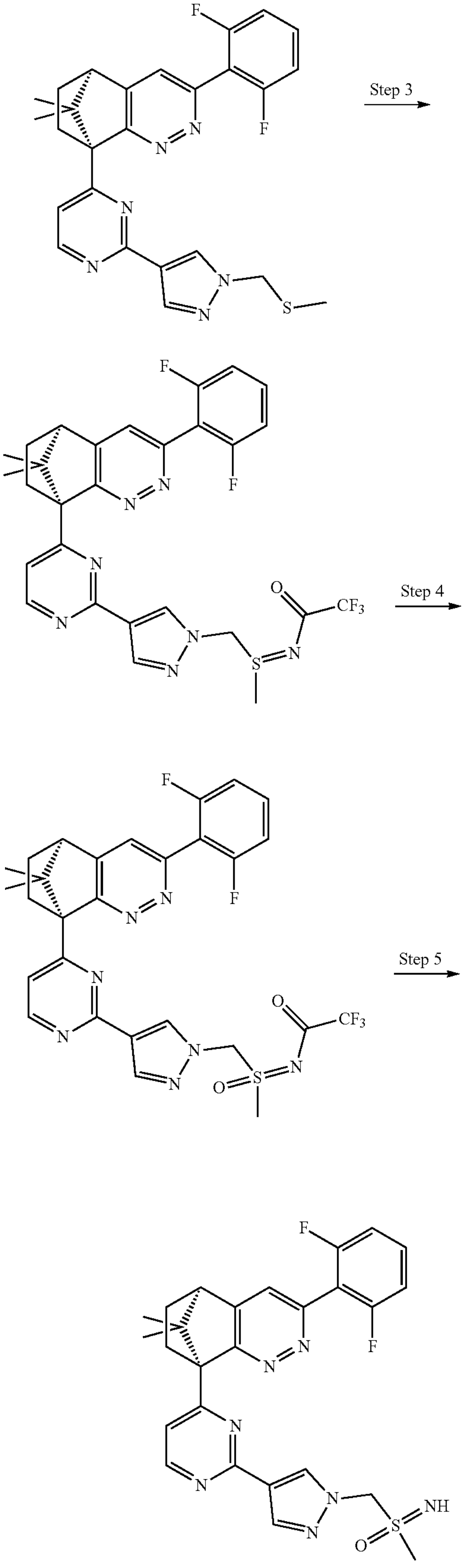

Stereoisomer A

-continued

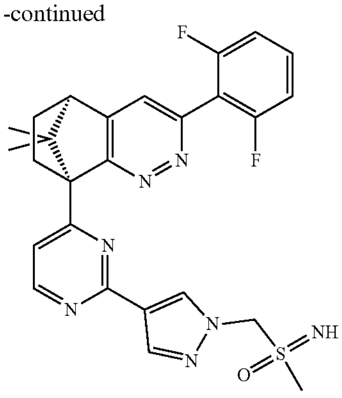

Stereoisomer B

Step 1: (5R,8S)-8-(2-(1H-Pyrazol-4-yl)pyrimidin-4-yl)-3-(2,6-difluorophenyl)-9,9-dimethyl-5,6,7,8-tetrahydro-5,8-methanocinnoline A solution of (5R,8S)-8-(2-chloropyrimidin-4-yl)-3-(2,6-difluorophenyl)-9,9-dimethyl-5,6,7,8-tetrahydro-5,8-methanocinnoline (300 mg, 0.75 mmol, 1.0 equiv), 4-(tetramethyl-1,3,2-dioxaborolan-2-yl)-1H-pyrazole (175 mg, 0.9 mmol, 1.2 equiv), $Pd(PPh_3)_2Cl_2$ (70 mg, 0.1 mmol, 0.13 equiv), and CsF (152 mg, 1.0 mmol, 1.3 equiv) in ethanol (3 mL) and water (0.5 mL) was stirred for 2 h at 110° C. After completion, the residue was applied onto a reversed-phase column eluting with acetonitrile/water(40:60) to afford 150 mg of the title compound as a light yellow solid. LCMS $ES^+$ 431 $[M+H]^+$.

Step 2: (5R,8S)-3-(2,6-Difluorophenyl)-9,9-dimethyl-8-(2-(1-((methylthio)methyl)-1H-pyrazol-4-yl)pyrimidin-4-yl)-5,6,7,8-tetrahydro-5,8-methanocinnoline A solution of (5R,8S)-8-(2-(1H-pyrazol-4-yl)pyrimidin-4-yl)-3-(2,6-difluorophenyl)-9,9-dimethyl-5,6,7,8-tetrahydro-5,8-methanocinnoline (150 mg, 0.35 mmol, 1.0 equiv), chloro(methylsulfanyl)methane (50 mg, 0.52 mmol, 1.5 equiv), $Cs_2CO_3$ (225 mg, 0.7 mmol, 2 equiv), DMF(1 mL) was stirred for 30 h at 80° C. After completion, the residue was applied onto a reversed-phase column eluting with acetonitrile/water(60:40) to afford 100 mg of the title compound as a yellow solid. LCMS $ES^+$ 491 $[M+H]^+$.

Step 3: N—((Z)-((4-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-1-yl)methyl)(methyl)-$\lambda^4$-sulfanylidene)-2,2,2-trifluoroacetamide A solution of (5R,8S)-3-(2,6-difluorophenyl)-9,9-dimethyl-8-(2-(1-((methylthio)methyl)-1H-pyrazol-4-yl)pyrimidin-4-yl)-5,6,7,8-tetrahydro-5,8-methanocinnoline (100 mg, 0.2 mmol, 1.0 equiv), trifluoroacetamide (23 mg, 0.2 mmol, 1 equiv), $Rh_2(OAc)_4$ (18 mg, 0.04 mmol, 0.2 equiv), MgO (16 mg, 0.4 mmol, 2 equiv), iodobenzene diacetate (66 mg, 0.2 mmol, 1.0 equiv) in dichloromethane (2 mL) was stirred overnight at room temperature. After completion, the solids were filtered out and the filtrate was concentrated under vacuum to afford 120 mg (crude) of the title compound as yellow oil. LCMS $ES^+$ 602 $[M+H]^+$.

Step 4: N-(((4-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-1-yl)methyl)(oxo)-$\lambda^6$-sulfanylidene)-2,2,2-trifluoroacetamide A solution of N—((Z)-((4-(4-((5R,8S)-3-(2,6-difluorophenyl)-9,9-dimethyl-6,7-dihydro-5,8-methanocinnolin-8(5H)-yl)pyrimidin-2-yl)-1H-pyrazol-1-yl)methyl)(methyl)-$\lambda^4$-sulfanylidene)-2,2,2-trifluoroacetamide (120 mg, 0.2 mmol, 1.0 equiv), $NaIO_4$ (86 mg, 0.4 mmol, 2.0 equiv), $KMnO_4$ (63 mg, 0.44 mmol, 2 equiv) in methanol (2 mL) and water (2 mL) was stirred for 2 h at room temperature. After completion, the solution was diluted with 30 mL of water and extracted with 3×50 mL of dichloromethane. Then the organic layers was combined and washed with 3×50 mL of brine. The organic layer was dried over anhydrous sodium sulfate and concentrated under vacuum. The residue was afforded 100 mg of the title compound as yellow oil. LCMS $ES^+$ 618 $[M+H]^+$.

Step 5: ((4-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-1-yl)methyl)(imino)(methyl)-$\lambda^6$-sulfanone Stereoisomer A and ((4-(4-((5R,8S)-3-(2,6-difluorophenyl)-9,9-dimethyl-6,7-dihydro-5,8-methanocinnolin-8(5H)-yl)pyrimidin-2-yl)-1H-pyrazol-1-yl)methyl)(imino)(methyl)-$\lambda^6$-sulfanone Stereoisomer B A solution of N-(((4-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-1-yl)methyl)(methyl)(oxo)-$\lambda^6$-sulfanylidene)-2,2,2-trifluoroacetamide (100 mg, 0.16 mmol, 1 equiv), potassium carbonate (45 mg, 0.33 mmol, 2 equiv) in methanol (1 mL) was stirred for 2 h at room temperature. After completion, the residue was applied onto a reversed-phase column eluting with water/acetonitrile (50:50) to afford 50 mg crude product. The crude product was purified by Chiral-Prep-HPLC: (Column: CHIRALPAK IA, 2.12*15 cm, 5 um; Mobile Phase A:Hex-HPLC, Mobile Phase B: MeOH:EtOH=1:1-HPLC; Flow rate: 20 mL/min; Gradient: 50 B to 50 B in 14 min; 220/254 nm; RT1:9.08; RT2:11.85) to afford the title compounds.

((4-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-1-yl)methyl)(imino)(methyl)-$\lambda^6$-sulfanone Stereoisomer A: 6.3 mg as a white solid. $^1$H NMR (400 MHz, Methanol-$d_4$): δ: 8.79 (d, J=5.3 Hz, 1H), 8.54 (s, 1H), 8.33 (s, 1H), 7.79 (d, J=1.2 Hz, 1H), 7.68-7.54 (m, 2H), 7.26-7.15 (m, 2H), 5.76 (d, J=14.4 Hz, 1H), 5.58 (d, J=14.4 Hz, 1H), 3.49-3.35 (m, 2H), 3.06 (s, 3H), 2.60-2.50 (m, 1H), 1.70-1.60 (m, 1H), 1.50-1.40 (m, 1H), 1.20 (s, 3H), 0.87 (s, 3H); LCMS $ES^+$ 522 $[M+H]^+$.

((4-(4-((5R,8S)-3-(2,6-Difluorophenyl)-9,9-dimethyl-6,7-dihydro-5,8-methanocinnolin-8(5H)-yl)pyrimidin-2-yl)-1H-pyrazol-1-yl)methyl)(imino)(methyl)-$\lambda^6$-sulfanone Stereoisomer B: 6.7 mg as a white solid. $^1$H NMR (400 MHz, Methanol-$d_4$): δ: 8.79 (d, J=5.3 Hz, 1H), 8.54 (s, 1H), 8.33 (s, 1H), 7.79 (t, J=1.1 Hz, 1H), 7.71-7.52 (m, 2H), 7.26-7.15 (m, 2H), 5.77 (d, J=14.4 Hz, 1H), 5.58 (d, J=14.3 Hz, 1H), 3.50-3.39 (m, 2H), 3.06 (s, 3H), 2.59-2.50 (m, 1H), 1.69-1.59 (m, 1H), 1.43-1.38 (m, 1H), 1.31 (t, J=7.3 Hz, 1H), 1.20 (s, 3H), 0.87 (s, 3H); LCMS $ES^+$ 522 $[M+H]^+$.

Example 56: (5R,8S)-3-(2,6-Difluorophenyl)-9,9-dimethyl-8-(2-(3-(1-((methylsulfonyl)methyl)cyclopropyl)-1H-1,2,4-triazol-1-yl)pyrimidin-4-yl)-5,6,7,8-tetrahydro-5,8-methanocinnoline

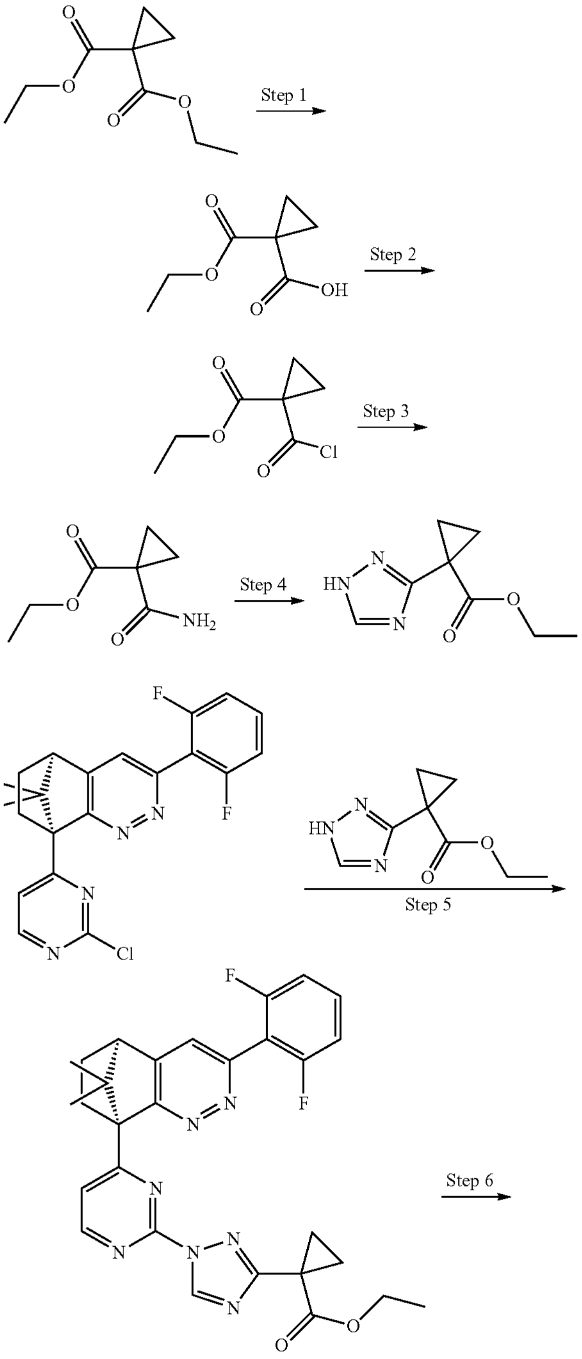

-continued

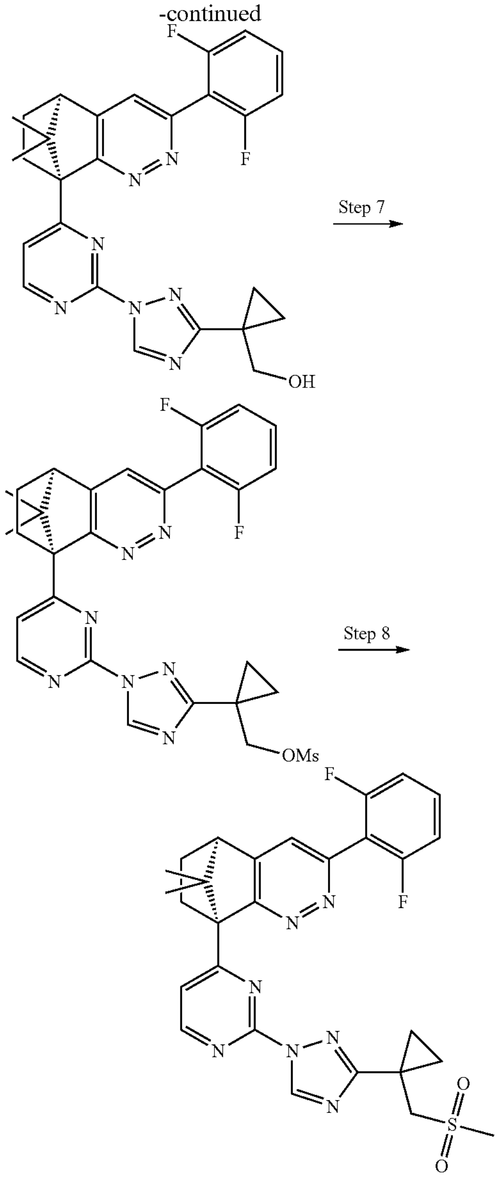

Step 1: 1-(Ethoxycarbonyl)cyclopropane-1-carboxylic Acid

A solution of 1,1-diethyl cyclopropane-1,1-dicarboxylate (10.00 g, 53.70 mmol, 1.00 equiv), sodium hydroxide (2.15 g, 53.75 mmol, 1.00 equiv) in ethanol (50 mL) was stirred for 12 h at 25° C. After completion, the solids were collected by filtration and re-crystallized from ethanol. This resulted in 6 g of the title compound as a white solid.

Step 2: Ethyl 1-(chlorocarbonyl)cyclopropane-1-carboxylate

A solution of 1-(ethoxycarbonyl)cyclopropane-1-carboxylic acid (6.00 g, 37.94 mmol, 1.00 equiv), thionyl chloride (50 mL) was stirred for 2 h at 60° C. After completion, the resulting mixture was concentrated under vacuum to afford (90%) of the title compound as a light yellow solid.

Step 3: Ethyl 1-carbamoylcyclopropane-1-carboxylate

A solution of 1-(carbonochloridoyl)cyclopropane-1-carboxylate (6.00 g, 33.98 mmol, 1.00 equiv) in dichloromethane (60 mL) was added drop wise to ammonia (150 mL). The resulting solution was stirred for 10 min at 25° C. After completion, the resulting solution was extracted with 3×150 mL of dichloromethane and washed with sat. aq. sodium chloride. The organic layer was dried over anhydrous sodium sulfate and concentrated under vacuum to afford 5 g of the title compound as a white solid.

Step 4: Ethyl 1-(1H-1,2,4-triazol-3-yl)cyclopropane-1-carboxylate

A solution of ethyl 1-carbamoylcyclopropane-1-carboxylate (5.00 g, 31.81 mmol, 1.00 equiv) in acetonitrile (10 mL) was treated with DMFdimethyl acetal (7.50 g, 62.94 mmol, 1.98 equiv) and heated at 60° C. for 1.25 hours. The cooled mixture was concentrated under vacuum and taken up in acetonitrile (15 mL). The solution was treated with AcOH (2.29 g, 38.13 mmol, 1.20 equiv) followed by hydrazine hydrate (1.91 g, 38.15 mmol, 1.20 equiv) instantly giving a white precipitate. The suspension was heated at 60° C. for 1.25 hours in which time all solid has dissolved to leave a pale pink solution. The cooled mixture was concentrated under vacuum to leave a viscous pink syrup. The residue was applied onto a silica gel column eluting with DCM/MeOH (10:1) to afford 3 g (52%) of the title compound as a white solid.

Step 5: Ethyl 1-(1-(4-((5R,8S)-3-(2,6-difluorophenyl)-9,9-dimethyl-6,7-dihydro-5,8-methanocinnolin-8(5H)-yl)pyrimidin-2-yl)-1H-1,2,4-triazol-3-yl)cyclopropane-1-carboxylate A solution of (5R,8S)-8-(2-chloropyrimidin-4-yl)-3-(2,6-difluorophenyl)-9,9-dimethyl-5,6,7,8-tetrahydro-5,8-methanocinnoline (400.00 mg, 1.00 mmol, 1.00 equiv), ethyl 1-(1H-1,2,4-triazol-3-yl)cyclopropane-1-carboxylate (218.06 mg, 1.20 mmol, 1.20 equiv), Cs2CO3 (653.54 mg, 2.00 mmol, 2.00 equiv) in DMSO (10 mL) was stirred for 1 h at 80° C. After completion, the solution was diluted with 100 mL of water and extracted with 3×100 mL of EtOAc. Then the organic layers was combined and washed with 3×50 mL of brine. The organic layer was dried over anhydrous sodium sulfate and concentrated under vacuum. The residue was applied onto a silica gel column eluting with DCM/MeOH (20:1) to afford 450 mg of the title compound as colorless oil.

Step 6: (1-(1-(4-((5R,8S)-3-(2,6-Difluorophenyl)-9,9-dimethyl-6,7-dihydro-5 8-methanocinnolin-8(5H)-yl)pyrimidin- 2-yl)-1H-1,2,4-triazol-3-yl)cyclopropyl)methanol A solution of ethyl 1-(1-(4-((5R,8S)-3-(2,6-difluorophenyl)-9,9-dimethyl-6,7-dihydro-5,8-methanocinnolin-8(5H)-yl)pyrimidin-2-yl)-1H-1,2,4-triazol-3-yl)cyclopropane-1-carboxylate (400.00 mg, 0.74 mmol, 1.00 equiv in THF (20 mL) was stirred for at 0° C. Then diisobutylaluminium hydride (1.05 g, 7.4 mmol, 10 equiv, in THF 4 mL) was added drop wise to the system. Then the resulting solution was stirred for another 2 h at 0° C. After completion, the reaction was quenched with sat. eq. ammonium chloride (5 mL) and the solids were filtered out. The residue was dissolved into dichloromethane and applied onto a silica gel column eluting with DCM/MeOH (20:1) to afford 200 mg of the title compound as a white solid Step 7: (1-(1-(4-((5R,8S)-3-(2,6-Difluorophenyl)-9,9-dimethyl-6,7-dihydro-5 8-methanocinnolin-8(5H)-yl)pyrimidin- 2-yl)-1H-1,2,4-triazol-3-yl)cyclopropyl)methyl methanesulfonate A solution of (1-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)cyclopropyl)methanol (200.00 mg, 0.40 mmol, 1.000 equiv), triethanolamine (80.70 mg, 0.80 mmol, 2.00 equiv) in dichloromethane (10 mL) was stirred for 5 min at 0° C. Then mesyl chloride (91.36 mg, 0.80 mmol, 2.00 equiv) was added drop wise to the system, and the resulting solution was stirred for 30 min at 25° C. After completion, the solution was diluted with 100 mL of dichloromethane and washed with 3×15 mL of brine. The organic layer was dried over anhydrous sodium sulfate and concentrated under vacuum to afford 200 mg of the title compound as colorless crude oil.

Step 8: (5R,8S)-3-(2,6-Difluorophenyl)-9,9-dimethyl-8-(2-(3-(1-((methylsulfonyl)methyl)cyclopropyl)-1H-1,2,4-triazol-1-yl)pyrimidin-4-yl)-5,6,7,8-tetrahydro-5,8-methanocinnoline A solution of (1-(1-(4-((5R,8S)-3-(2,6-difluorophenyl)-9,9-dimethyl-6,7-dihydro-5,8-methanocinnolin-8(5H)-yl)pyrimidin-2-yl)-1H-1,2,4-triazol-3-yl)cyclopropyl)methyl methanesulfonate (200.00 mg, 0.35 mmol, 1.00 equiv), methanesulfonylsodium (70.45 mg, 0.69 mmol, 2.00 equiv), KI (5.73 mg, 0.035 mmol, 0.10 equiv) in DMF(10 mL) was stirred for 5 h at 60° C. After completion, the solution was diluted with 80 mL of water and extracted with 3×80 mL of EtOAc. Then the organic layers was combined and washed with 3×500 mL of brine. The organic layer was dried over anhydrous sodium sulfate and concentrated under vacuum. The residue was applied onto a silica gel column eluting with DCM/MeOH (20:1) to afford 15.7 mg of the title compound as a white solid. $^1$H NMR (400 MHz, $CDCl_3$-d): δ: 9.15 (s, 1H), 8.86 (d, J=5.2 Hz, 1H), 7.99 (d, J=5.2 Hz, 1H), 7.58 (s, 1H), 7.50-7.42 (m, 1H), 7.17-7.05 (m, 2H), 3.87-3.73 (m, 2H), 3.35-3.23 (m, 2H), 3.02 (s, 3H), 2.63-2.50 (m, 1H), 1.80-1.75 (m, 1H), 1.66 (t, J=3.8 Hz, 2H), 1.49-1.41 (m, 3H), 1.24 (s, 3H), 0.81 (s, 3H); LCMS $ES^+$ 564 $[M+H]^+$.

Example 57: (5R,8S)-3-(2,6-Difluorophenyl)-9,9-dimethyl-8-(2-(3-(2-(3-methyloxetan-3-yl)ethyl)-1H-1,2,4-triazol-1-yl)pyrimidin-4-yl)-5,6,7,8-tetrahydro-5,8-methanocinnoline

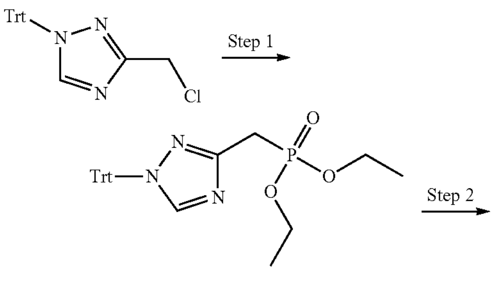

-continued

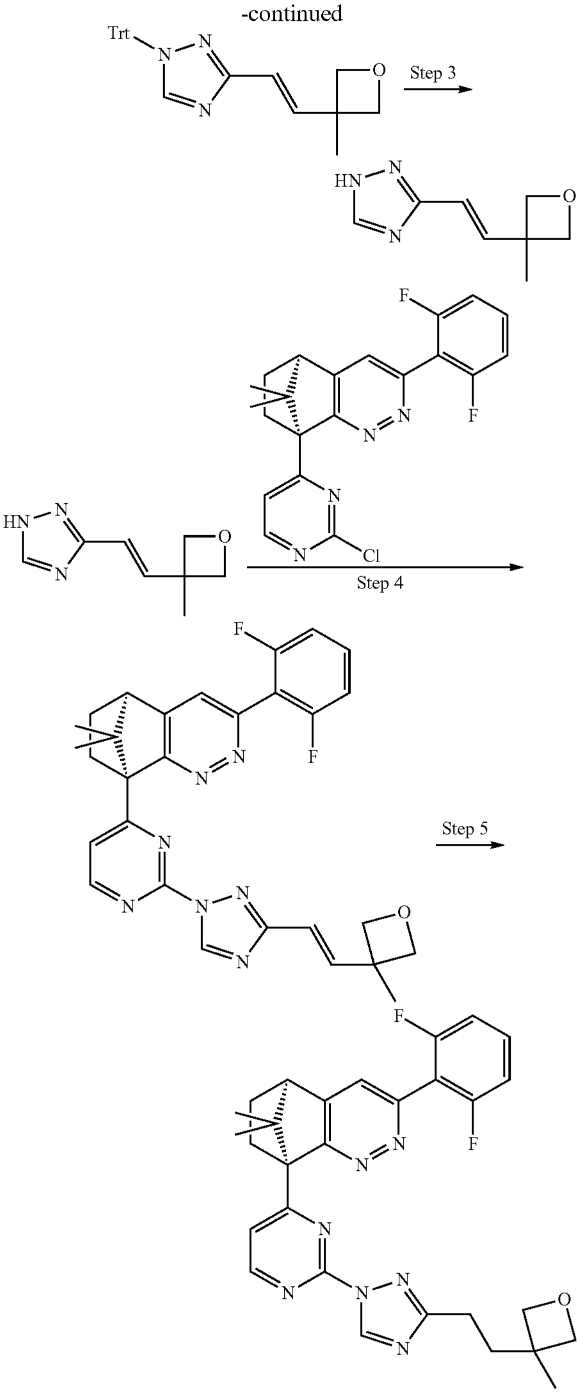

Step 1: Diethyl ((1-trityl-1H-1,2,4-triazol-3-yl)methyl)phosphonate

A solution of 3-(chloromethyl)-1-(triphenylmethyl)-1H-1,2,4-triazole (500 mg, 1.39 mmol, 1.00 equiv) in triethyl phosphite (10 mL) was stirred for 3 h at 135° C. After completion, the solution was diluted with 100 mL of water and extracted with 3×100 mL of EtOAc and washed with 3×50 mL of brine. The organic layer was dried over anhydrous sodium sulfate and concentrated under vacuum to afford 400 mg (crude) of the title compound as a yellow solid. LCMS $ES^+$ 461 $[M+H]^+$.

Step 2: (E)-3-(2-(3-Methyloxetan-3-yl)vinyl)-1-trityl-1H-1,2,4-triazole

A solution of [[1-(triphenylmethyl)-1H-1,2,4-triazol-3-yl] methyl]phosphonate (450 mg, 0.975 mmol, 1.00 equiv), 3-methyloxetane-3-carbaldehyde (146 mg, 1.46 mmol, 1.49 equiv), t-BuOK (218.6 mg, 2.0 mmol, 2.0 equiv) in DMF(5 mL) was stirred for 2 h at 80° C. After completion, the solution was diluted with 50 mL of water and extracted with 3×50 mL of EtOAc and washed with 3×25 mL of brine. The organic layer was dried over anhydrous sodium sulfate and concentrated under vacuum. The residue was applied onto a silica gel column eluting with DCM/MeOH (20:1) to the title compound as yellow oil. LCMS $ES^+$ 407 $[M+H]^+$.

Step 3: (E)-3-(2-(3-Methyloxetan-3-yl)vinyl)-1H-1,2,4-triazole

A solution of 3-[(E)-2-(3-methyloxetan-3-yl)ethenyl]-1-(triphenylmethyl)-1H-1,2,4-triazole (400 mg, 0.98 mmol, 1.00 equiv) in trifluoroacetic acid (5 mL) and dichloromethane (20 mL) was stirred for 2 h at 25° C. The residue was applied onto a silica gel column eluting with DCM/MeOH (20:1) to afford 200 mg of the title compound as white oil. LCMS $ES^+$ 165 $[M+H]^+$.

Step 4: (5R,8S)-3-(2,6-Difluorophenyl)-9,9-dimethyl-8-(2-(3-((E)-2-(3-methyloxetan-3-yl)vinyl)-1H-1,2,4-triazol-1-yl)pyrimidin-4-yl)-567.8-tetrahydro-5,8-methanocinnoline A solution of (5R,8S)-8-(2-chloropyrimidin-4-yl)-3-(2,6-difluorophenyl)-9,9-dimethyl-5,6,7,8-tetrahydro-5,8-methanocinnoline (500 mg, 1.25 mmol, 1.00 equiv), 3-[(E)-2-(3-methyloxetan-3-yl)ethenyl]-1H-1,2,4-triazole (208 mg, 1.25 mmol, 1.04 equiv), potassium carbonate (345 mg, 2.49 mmol, 2.0 equiv) in DMSO (5 mL) was stirred for 2 h at 75° C. After completion, the solution was diluted with 50 mL of water and extracted with 3×50 mL of EtOAc and washed with 3×25 mL of brine. The organic layer was dried over anhydrous sodium sulfate and concentrated under vacuum. The residue was applied onto a silica gel column eluting with DCM/MeOH (20:1) to afford 160 mg of the title compound as a brown oil. LCMS $ES^+$ 527 $[M+H]^+$.

Step 5: (5R,8S)-3-(2,6-Difluorophenyl)-9,9-dimethyl-8-(2-(3-(2-(3-methyloxetan-3-yl)ethyl)-1H-1,2,4-triazol-1-yl)pyrimidin-4-yl)-5,6,7,8-tetrahydro-5,8-methanocinnoline Under hydrogen, a solution of (5R,8S)-3-(2,6-difluorophenyl)-9,9-dimethyl-8-(2-(3-((E)-2-(3-methyloxetan-3-yl)vinyl)-1H-1,2,4-triazol-1-yl)pyrimidin-4-yl)-5,6,7,8-tetrahydro-5,8-methanocinnoline (160 mg, 0.30 mmol, 1.00 equiv), palladium carbon (3.2 mg, 0.03 mmol, 0.09 equiv) in ethanol (5 mL) was stirred for 12 h at 55° C. After completion, the reaction was quenched with sat. eq. ammonium chloride (50 mL) and extracted with 3×50 mL of EtOAc. Then the organic layers was combined and washed with 3×50 mL of brine. The organic layer was dried over anhydrous sodium sulfate and concentrated under vacuum. The crude product was purified by Prep-HPLC with the following conditions (2#-AnalyseHPLC-SHIMADZU(HPLC-10)): Column, SunFire Prep C18 OBD Column, 19×150 mm 5 um 10 nm; mobile phase, Waters(0.1% FA) and ACN (30.0% ACN up to 47.0% in 15 min); Detector, UV 254/220 nm to afford 8.6 mg (5%) of the title compound as a white solid. $^1H$ NMR (400 MHz, $CD_3OD$): δ: 8.64 (dd, J=5.1, 1.0 Hz, 1H), 8.40 (d, J=4.6 Hz, 1H), 7.78 (d, J=1.4 Hz, 1H), 7.60-7.50 (m, 1H), 7.48 (dd, J=5.2, 2.2 Hz, 1H), 7.20-7.10 (t, J=8.0 Hz, 2H), 4.47-4.35 (m, 2H), 4.21 (dd, J=12.8, 2.0 Hz, 1H), 4.06-4.01 (m, 1H), 3.39-3.33 (m, 1H), 3.32-3.17 (m, 1H), 3.14-3.02 (m, 2H), 2.59-2.52 (m, 1H), 2.19-2.12 (m, 1H), 1.99-1.92 (m, 1H), 1.69-1.63 (m, 1H), 1.40-1.35 (m, 1H), 1.25 (d, J=4.8 Hz, 3H), 1.14 (s, 3H), 0.83 (s, 3H); LCMS $ES^+$ 529 $[M+H]^+$.

Example 58: N-(2-(((1-(6-((5R,8S)-3-(2,6-Difluorophenyl)-9,9-dimethyl-6,7-dihydro-5,8-methanocinnolin-8(5H)-yl)pyridin-2-yl)-1H-1,2,4-triazol-3-yl) methyl)sulfonyl)ethyl)acetamide

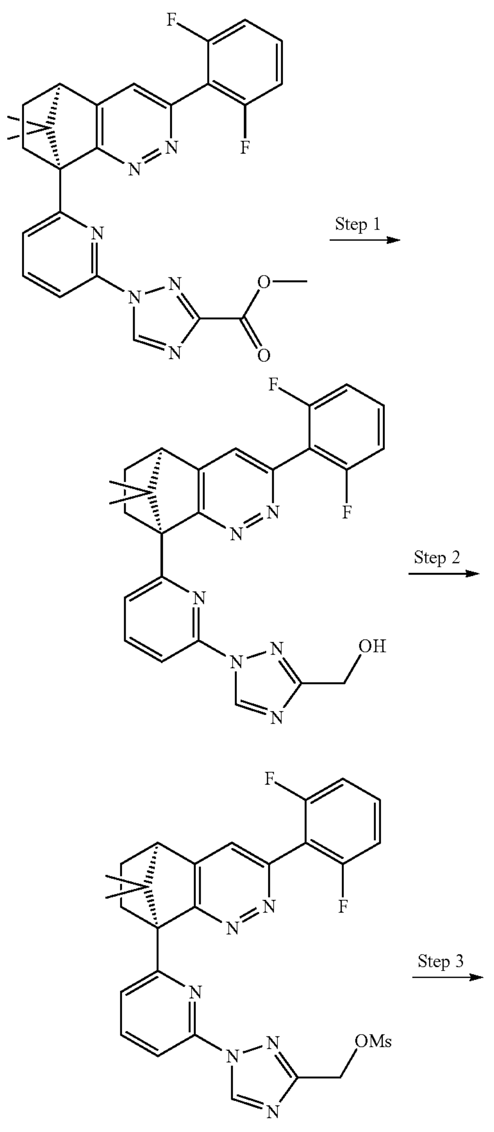

-continued

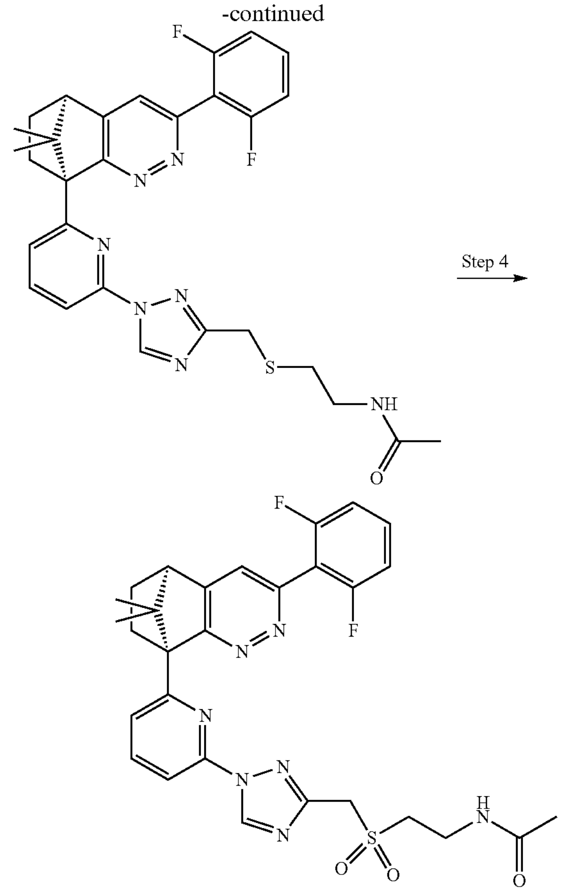

Step 1: (1-(6-((5R,8S)-3-(2,6-Difluorophenyl)-9,9-dimethyl-6,7-dihydro-5,8-methanocinnolin-8(5H)-yl)pyridin-2-yl)-1H-1,2,4-triazol-3-yl)methanol Under nitrogen, a solution of methyl 1-(6-((5R,8S)-3-(2,6-difluorophenyl)-9,9-dimethyl-6,7-dihydro-5,8-methanocinnolin-8(5H)-yl)pyridin-2-yl)-1H-1,2,4-triazole-3-carboxylate (200 mg, 0.40 mmol, 1.00 equiv), DIBAL-H (230 mg, 1.61 mmol, 3.95 equiv, 1.0 M in n-hexane) in THF (5 mL) was stirred for 15 min at 0° C. After completion, the resulting solution was quenched with 20 mL of sat.aq. ammonium chloride and extracted with 3x50 mL of EtOAc. Then the organic layers was combined and washed with 3x25 mL of brine. The organic layer was dried over anhydrous sodium sulfate and concentrated under vacuum. The residue was applied onto a silica gel column eluting with DCM/MeOH (10:1) to afford 100 mg of the title compound as a yellow solid.

Step 2: (1-(6-((5R,8S)-3-(2,6-Difluorophenyl)-9,9-dimethyl-6,7-dihydro-5,8-methanocinnolin-8(5H)-yl)pyridin-2-yl)-1H-1,2,4-triazol-3-yl)methyl methanesulfonate A solution of (1-(6-((5R,8S)-3-(2,6-difluorophenyl)-9,9-dimethyl-6,7-dihydro-5,8-methanocinnolin-8(5H)-yl)pyridin-2-yl)-1H-1,2,4-triazol-3-yl)methanol (300 mg, 0.65 mmol, 1.00 equiv), methanesulfonyl methanesulfonate (136 mg, 0.78 mmol, 1.19 equiv) and DIEA (0.16 mL, 0.97 mmol, 1.48 equiv) in dichloromethane (20 mL) was stirred for 50 min at room temperature. The resulting mixture was concentrated under vacuum to afford 700 mg (crude) of the title compound as yellow oil.

Step 3: N-(2-(((1-(6-((5R,8S)-3-(2,6-Difluorophenyl)-9,9-dimethyl-6,7-dihydro-5,8-methanocinnolin-8(5H)-yl)pyridin-2-yl)-1H-1,2,4-triazol-3-yl)methyl)thio)ethyl)acetamide Under nitrogen, a solution of (1-(6-((5R,8S)-3-(2,6-difluorophenyl)-9,9-dimethyl-6,7-dihydro-5,8-methanocinnolin-8(5H)-yl)pyridin-2-yl)-1H-1,2,4-triazol-3-yl)methyl methanesulfonate (350 mg, 0.65 mmol, 1.00 equiv), N-(2-sulfanylethyl)acetamide (155 mg, 1.30 mmol, 2.00 equiv), $Cs_2CO_3$ (424 mg, 1.30 mmol, 2.00 equiv) in dimethylformamide (10 mL) was stirred for 12 h at room temperature. After completion, the solution was diluted with 50 mL of water and extracted with 3x50 mL of EtOAc. Then the organic layers was combined and washed with 3x50 mL of brine. The organic layer was dried over anhydrous sodium sulfate and concentrated under vacuum. The residue was applied onto a silica gel column eluting DCM/MeOH (10:1) to afford 280 mg of the title compound as a light yellow solid.

Step 4: N-(2-(((1-(6-((5R,8S)-3-(2,6-Difluorophenyl)-9,9-dimethyl-6,7-dihydro-5,8-methanocinnolin-8(5H)-yl)pyridin-2-yl)-1H-1,2,4-triazol-3-yl)methyl)sulfonyl)ethyl)acetamide A solution of N-(2-(((1-(6-((5R,8S)-3-(2,6-difluorophenyl)-9,9-dimethyl-6,7-dihydro-5,8-methanocinnolin-8(5H)-yl)pyridin-2-yl)-1H-1,2,4-triazol-3-yl)methyl)thio)ethyl)acetamide (150 mg, 0.26 mmol, 1.00 equiv), $KMnO_4$ (84 mg, 0.53 mmol, 1.99 equiv) and $NaIO_4$ (114 mg, 0.53 mmol, 1.99 equiv) in methanol (10 mL) and water(2 mL) was stirred for 30 min at room temperature. After completion, the solution was diluted with 100 mL of water and extracted with 3x100 mL of EtOAc and washed with 3x50 mL of brine. The mixture was dried over anhydrous sodium sulfate and concentrated under vacuum. The residue was applied onto a silica gel column eluting with DCM/MeOH (10:1) to afford 60.1 mg of the title compound as a white solid. $^1H$ NMR (300 MHz, DMSO-d6): δ: 9.48 (s, 1H), 8.26-8.14 (m, 2H), 7.93-7.77 (m, 3H), 7.67-7.60 (m, 1H), 7.34-7.27 (m, 2H), 4.84 (s, 2H), 3.59-3.33 (m, 5H), 3.31-3.29 (m, 1H), 2.48-2.38 (m, 1H), 1.83 (s, 3H), 1.67-1.52 (m, 1H), 1.33-1.21 (m, 1H), 1.10 (s, 3H), 0.72 (s, 3H); LCMS $ES^+$ 594 $[M+H]^+$.

Example 59: (5R,8S)-3-(2,6-Difluorophenyl)-9,9-dimethyl-8-(2-(5-(2-(methylsulfonyl)ethyl)-1H-1,2,4-triazol-3-yl)pyrimidin-4-yl)-5,6,7,8-tetrahydro-5,8-methanocinnoline

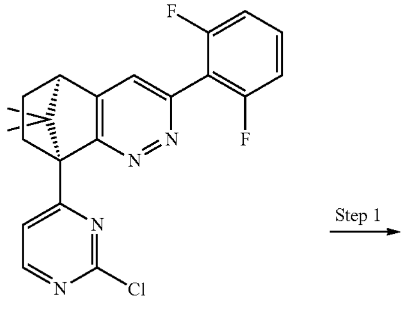

-continued

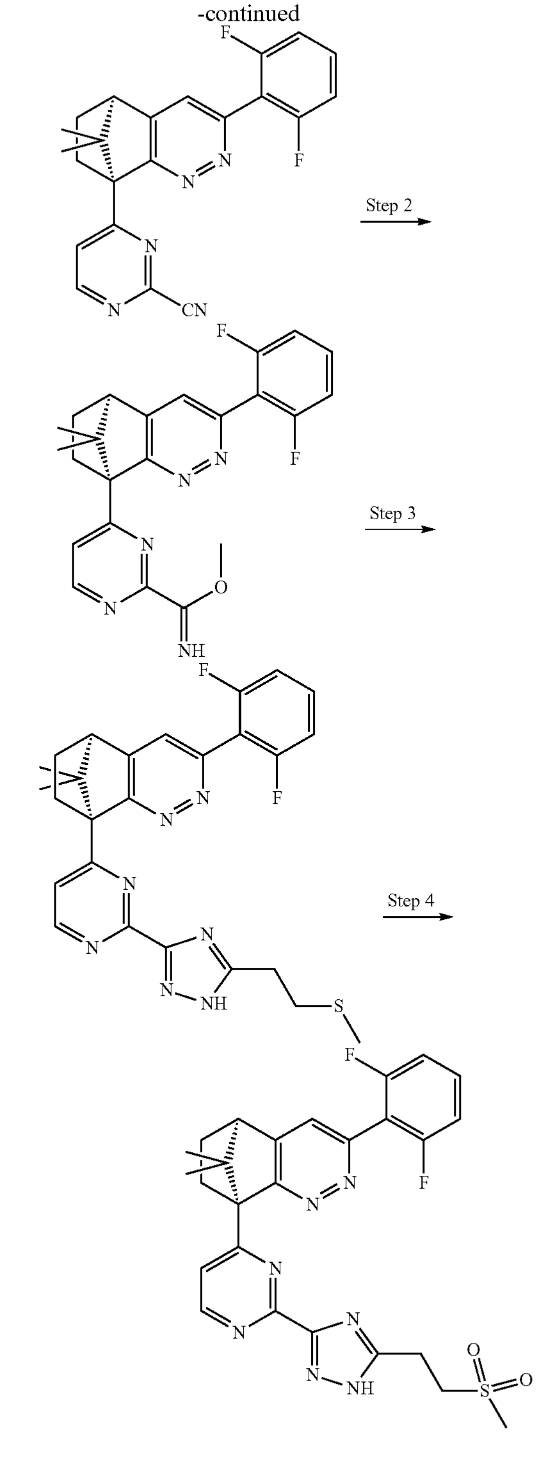

Step 1: 4-((5R,8S)-3-(2,6-Difluorophenyl)-9,9-dimethyl-6,7-dihydro-5,8-methanocinnolin-8(5H)-yl) pyrimidine-2-carbonitrile A solution of (5R,8S)-8-(2-chloropyrimidin-4-yl)-3-(2,6-difluorophenyl)-9,9-dimethyl-5,6,7,8-tetrahydro-5,8-methanocinnoline (500.00 mg, 1.25 mmol, 1.00 equiv), NaCN (67.58 mg, 1.38 mmol, 1.10 equiv) in DMSO (10 mL) was stirred for 12 h at 80° C. After completion, the reaction was quenched with sat. eq ferrous sulfate (100 m L) and extracted with 3×100 mL of EtOAc. Then the organic layers ware combined and washed with 3×50 mL of brine and dried over anhydrous sodium sulfate. The organic layer was concentrated under vacuum to afford 400 mg of the title compound as a yellow solid.

Step 2: Methyl 4-((5R,8S)-3-(2,6-difluorophenyl)-9,9-dimethyl-6,7-dihydro-5,8-methanocinnolin-8(5H)-yl)pyrimidine-2-carbimidate A solution of 4-((5R,8S)-3-(2,6-Difluorophenyl)-9,9-dimethyl-6,7-dihydro-5,8-methanocinnolin-8(5H)-yl)pyrimidine-2-carbonitrile (130.00 mg, 0.33 mmol, 1.00 equiv), sodium methanolate (18.07 mg, 0.33 mmol, 1.00 equiv) in methanol (3 mL) was stirred for 5 h at 25° C. After completion, the resulting mixture was concentrated under vacuum at 0° C. to afford 130 mg (crude) of the title compound as a yellow solid.

Step 3: (5R,8S)-3-(2,6-Difluorophenyl)-9,9-dimethyl-8-(2-(5-(2-(methylthio)ethyl)-1H-1,2,4-triazol-3-yl)pyrimidin-4-yl)-5,6,7,8-tetrahydro-5,8-methanocinnolin A solution of methyl 4-((5R,8S)-3-(2,6-difluorophenyl)-9,9-dimethyl-6,7-dihydro-5,8-methanocinnolin-8(5H)-yl) pyrimidine-2-carbimidate (150.00 mg, 0.36 mmol, 1.00 equiv), 3-(methylsulfanyl)propanehydrazide (95.53 mg, 0.71 mmol, 2.00 equiv) in propan-2-ol (4 mL) was irradiated with microwave radiation for 3 h at 130° C. After completion, the resulting mixture was concentrated under vacuum and applied onto a silica gel column eluting with DCM/MeOH (20:1) to afford 80 mg of the title compound as yellow oil.

Step 4: (5R,8S)-3-(2,6-Difluorophenyl)-9,9-dimethyl-8-(2-(5-(2-(methylsulfonyl)ethyl)-1H-1,2,4-triazol-3-yl)pyrimidin-4-yl)-5,6,7,8-tetrahydro-5,8-methanocinnoline A solution of ((5R,8S)-3-(2,6-Difluorophenyl)-9,9-dimethyl-8-(2-(5-(2-(methylthio)ethyl)-1H-1,2,4-triazol-3-yl) pyrimidin-4-yl)-5,6,7,8-tetrahydro-5,8-methanocinnoline (100.00 mg, 0.20 mmol, 1.00 equiv), $KMnO_4$ (125.00 mg, 0.80 mmol, 4.00 equiv), $NaIO_4$ (169.18 mg, 0.80 mmol, 4.00 equiv) in methanol (10 mL) and water(5 mL) was stirred for 3 h at 25° C. After completion, the solids were filtered out. The filtrate was collected and applied onto a silica gel column with DCM/MeOH (20:1) to afford 30 mg (28%) of the title compound as white solid. $^1H$ NMR (300 MHz, Methanol-d4): δ: 8.99 (d, J=5.3 Hz, 1H), 7.92-7.85 (m, 1H), 7.80 (s, 1H) 7.65-7.55 (m, 1H), 7.21 (t, J=8.1 Hz, 2H), 3.78-3.64 (m, 3H), 3.40-3.34 (m, 3H), 3.05 (s, 3H), 2.65-2.56 (m, 1H), 1.74-1.59 (m, 1H), 1.45-1.38 (m, 1H), 1.18 (s, 3H), 0.84 (s, 3H); LCMS $ES^+$ 538 $[M+H]^+$.

Examples 60 and 61: 5-((((1-(6-((5R,8S)-3-(2,6-Difluorophenyl)-9,9-dimethyl-6,7-dihydro-5,8-methanocinnolin-8(5H)-yl)pyridin-2-yl)-1H-1,2,4-triazol-3-yl)methyl)sulfonyl)methyl)pyrrolidin-2-one Stereoisomer A and 5-((((1-(6-((5R,8S)-3-(2,6-difluorophenyl)-9,9-dimethyl-6,7-dihydro-5 8-methanocinnolin-8(5H)-yl)pyridin-2-yl)-1H-1,2,4-triazol-3-yl)methyl)sulfonyl)methyl)pyrrolidin-2-one Stereoisomer B

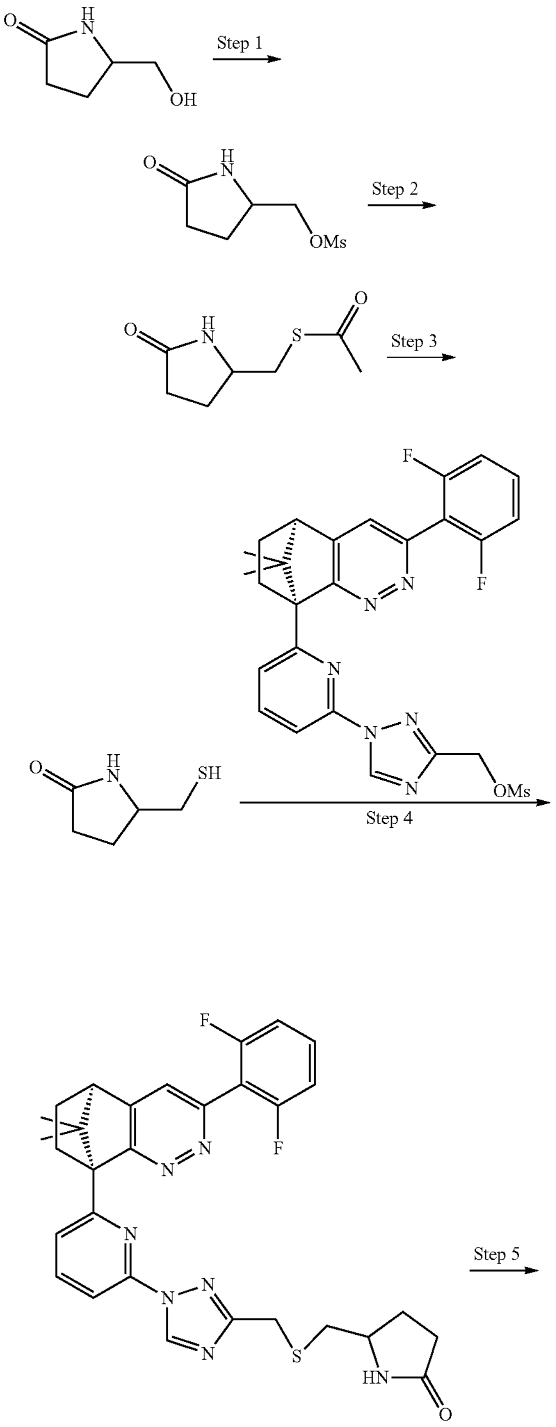

-continued

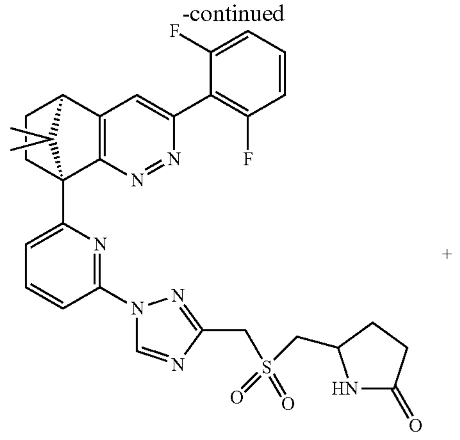

Stereoisomer A

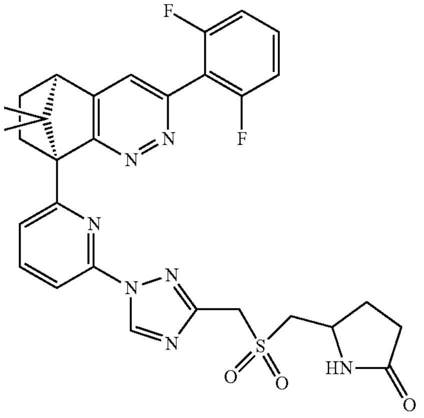

Stereoisomer B

Step 1: (5-Oxopyrrolidin-2-yl)methyl methanesulfonate

A solution of 1-(hydroxymethyl)pyrrolidin-2-one (2 g, 17.37 mmol, 1.00 equiv), methanesulfonyl methanesulfonate (3.6 g, 20.66 mmol, 1.19 equiv) and TEA (4.7 mL, 33.81 mmol, 1.94 equiv) in dichloromethane (40 mL, 629.20 mmol, 36.22 equiv) was stirred for 4 h at room temperature. When LCMS indicated most of starting materials were converted into the desired product, the resulting mixture was concentrated under vacuum. The residue was applied onto a silica gel column eluting with DCM/MeOH (10:1). This resulted in 1.8 g of the title compound as a yellow solid.

Step 2: S-((5-Oxopyrrolidin-2-yl)methyl) ethanethioate

A solution of 1-(potassiosulfanyl)ethan-1-one (975 mg, 8.54 mmol, 1.00 equiv) and (5-oxopyrrolidin-2-yl)methyl methanesulfonate (1.1 g, 5.69 mmol, 0.67 equiv) in DMF(30 mL) was stirred for 12 h at 50° C. When LCMS indicated most of starting materials were converted into the desired product, the resulting mixture was concentrated under vacuum. The residue was applied onto a silica gel column eluting with DCM/MeOH (10:1). This resulted in 725 mg of the title compound as a brown solid.

Step 3: 5-(Mercaptomethyl)pyrrolidin-2-one

A solution of 5-[(acetylsulfanyl)methyl]pyrrolidin-2-one (400 mg, 2.31 mmol, 1.00 equiv) and sodium methylate (150 mg, 2.78 mmol, 1.20 equiv) in methanol (10 mL, 246.99 mmol, 106.96 equiv) was stirred for 30 min at room temperature. The pH value of the solution was adjusted to 6.0 with HCl in 1,4-dioxane (4M). The resulting mixture was concentrated under vacuum to afford 500 mg (crude) of the title compound as a brown solid.

Step 4: 5-((((1-(6-((5R,8S)-3-(2,6-difluorophenyl)-9,9-dimethyl-6,7-dihydro-5,8-methanocinnolin-8(5H)-yl)pyridin-2-yl)-1H-1,2,4-triazol-3-yl)methyl)thio)methyl)pyrrolidin-2-one Under nitrogen, a solution of (1-(6-((5R,8S)-3-(2,6-difluorophenyl)-9,9-dimethyl-6,7-dihydro-5,8-methanocinnolin-8(5H)-yl)pyridin-2-yl)-1H-1,2,4-triazol-3-yl)methyl methanesulfonate (150 mg, 0.27 mmol, 1.00 equiv), 5-(sulfanylmethyl)pyrrolidin-2-one (40 mg, 0.30 mmol, 1.09 equiv) and $Cs_2CO_3$ (182 mg, 0.55 mmol, 2.00 equiv) in DMF(5 mL) was stirred for 30 min at room temperature. After completion, the resulting mixture was concentrated under vacuum. The residue was applied onto a silica gel column eluting with DCM/MeOH (10:1) to afford 200 mg (crude) of the title compound as a light yellow solid.

Step 5: 5-((((1-(6-((5R,8S)-3-(2,6-Difluorophenyl)-9,9-dimethyl-6,7-dihydro-5,8-methanocinnolin-8(5H)-yl)pyridin-2-yl)-1H-1,2,4-triazol-3-yl)methyl)sulfonyl)methyl)pyrrolidin-2-one Stereoisomer A and 5-((((1-(6-((5R,8S)-3-(2,6-difluorophenyl)-9,9-dimethyl-6,7-dihydro-5,8-methanocinnolin-8(5H)-yl)pyridin-2-yl)-1H-1,2,4-triazol-3-yl)methyl)sulfonyl)methyl)pyrrolidin-2-one Stereoisomer B A solution of 5-((((1-(6-((5R,8S)-3-(2,6-difluorophenyl)-9,9-dimethyl-6,7-dihydro-5,8-methanocinnolin-8(5H)-yl)pyridin-2-yl)-1H-1,2,4-triazol-3-yl)methyl)thio)methyl)pyrrolidin-2-one (200 mg, 0.35 mmol, 1.00 equiv), $KMnO_4$ (165 mg, 1.04 mmol, 2.99 equiv) and $NaIO_4$ (225 mg, 1.05 mmol, 3.02 equiv) in methanol (5 mL) and water(1 mL) was stirred for 30 min at room temperature. After completion, the resulting mixture was concentrated under vacuum. The product was purified by HPLC and chiral-HPLC with following condition: Column: X Bridge C18, 19*150 mm, 5 um; Mobile Phase A:Water/0.05% TFA, Mobile Phase B: ACN; Flow rate: 20 mL/min; Gradient: 30% B to 70% B in 10 min; 254 nm. This resulted in the title compounds.

5-((((1-(6-((5R,8S)-3-(2,6-Difluorophenyl)-9,9-dimethyl-6,7-dihydro-5,8-methanocinnolin-8(5H)-yl)pyridin-2-yl)-1H-1,2,4-triazol-3-yl)methyl)thio)methyl)pyrrolidin-2-one Stereoisomer A as a white solid 29.9 mg. $^1$H NMR (400 MHz, Chloroform-d): δ: 9.15 (s, 1H), 7.99 (t, J=7.8 Hz, 1H), 7.93-7.88 (m, 2H), 7.64 (s, 1H), 7.54-7.49 (m, 1H), 7.12 (t, J=8.1 Hz, 2H), 6.40 (s, 1H), 4.57 (d, J=2.0 Hz, 2H), 4.39-4.27 (m, 1H), 3.57 (dd, J=14.0, 2.6 Hz, 1H), 3.42 (dd, J=14.0, 9.8 Hz, 1H), 3.36-3.23 (m, 2H), 2.58-2.43 (m, 2H), 2.41-2.38 (m, 2H), 1.95-1.90 (m, 1H), 1.82-1.73 (m, 1H), 1.50-1.41 (m, 1H), 1.18 (s, 3H), 0.81 (s, 3H); LCMS $ES^+$ 606 $[M+H]^+$.

5-((((1-(6-((5R,8S)-3-(2,6-Difluorophenyl)-9,9-dimethyl-6,7-dihydro-5,8-methanocinnolin-8(5H)-yl)pyridin-2-yl)-1H-1,2,4-triazol-3-yl)methyl)thio)methyl)pyrrolidin-2-one Stereoisomer B as a white solid 26.6 mg. %). $^1$H NMR (400 MHz, Chloroform-d): δ: 9.15 (s, 1H), 8.02 (t, J=7.9 Hz, 1H), 7.93-7.88 (m, 2H), 7.73 (s, 1H), 7.58-7.50 (m, 1H), 7.15 (t, J=8.2 Hz, 2H), 6.42 (s, 1H), 4.57 (d, J=2.3 Hz, 2H), 4.39-4.27 (m, 1H), 3.56 (dd, J=14.0, 2.6 Hz, 1H), 3.51-3.29 (m, 3H), 2.64-2.58 (m, 1H), 2.56-2.42 (m, 1H), 2.40-2.28 (m, 2H), 1.98-1.84 (m, 1H), 1.84-1.74 (m, 1H), 1.50-1.41 (m, 1H), 1.21 (s, 3H), 0.83 (s, 3H); LCMS $ES^+$ 606 $[M+H]^+$.

Example 62: (5R,8S)-8-(5-Bromo-2-(3-(2-(methylsulfonyl)ethyl)-1H-1,24-triazol-1-yl)pyrimidin-4-yl)-3-(2,6-difluorophenyl)-9,9-dimethyl-5,6,7,8-tetrahydro-5,8-methanocinnoline

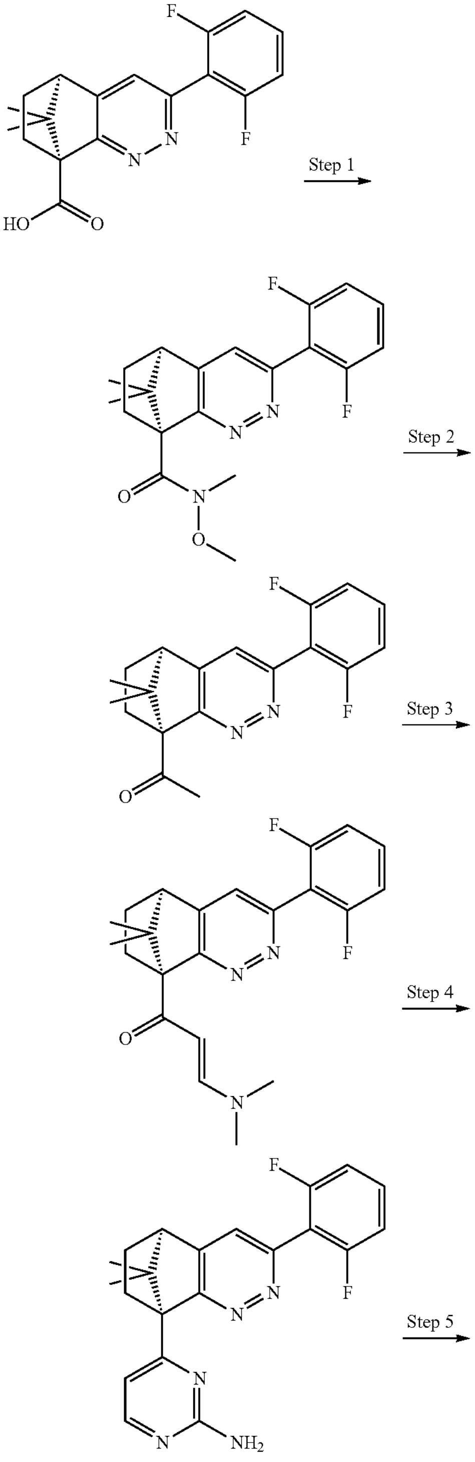

-continued

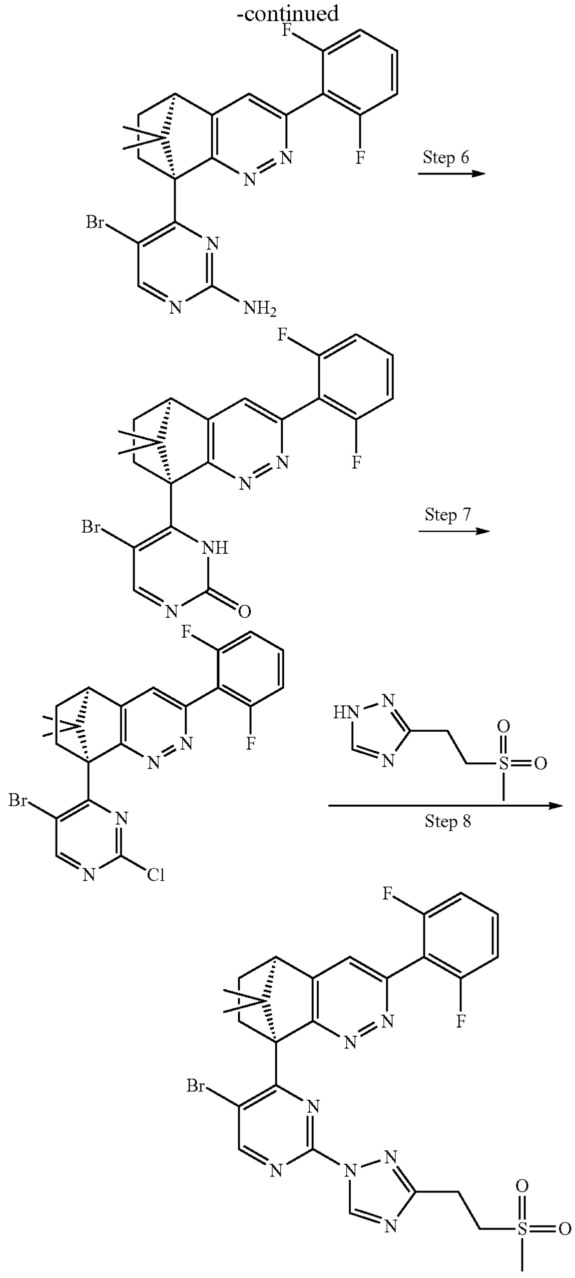

Step 1: (5R,8R)-3-(2,6-Difluorophenyl)-N-methoxy-N,9,9-trimethyl-6,7-dihydro-5,8-methanocinnoline-8(5H)-carboxamide A solution of (5R,8R)-3-(2,6-difluorophenyl)-9,9-dimethyl-6,7-dihydro-5,8-methanocinnoline-8(5H)-carboxylic acid (3.3 g, 9.99 mmol, 1.00 equiv), $(COCl)_2$ (2.54 g, 20.01 mmol, 2.00 equiv), triethylamine (2.5 g, 24.71 mmol, 2.47 equiv), methoxy(methyl)amine hydrochloride (1.5 g, 15.37 mmol, 1.53 equiv) in dichloromethane (20 mL) and DMF (0.5 mL) was stirred for 3 h at 25° C. After completion, the solution was diluted with 50 mL of water and extracted with 3×50 mL of EtOAc and washed with 3×25 mL of brine. The organic layer was dried over anhydrous sodium sulfate and concentrated under vacuum to afford 2.6 g of the title compound as a yellow solid. LCMS $ES^+$ 374 $[M+H]^+$.

Step 2: 1-((5R,8R)-3-(2,6-Difluorophenyl)-9,9-dimethyl-6,7-dihydro-5,8-methanocinnolin-8(5H)-yl)ethan-1-one A solution of (5R,8R)-3-(2,6-Difluorophenyl)-N-methoxy-N,9,9-trimethyl-6,7-dihydro-5,8-methanocinnoline-8(5H)-carboxamide (2.5 g, 6.70 mmol, 1.00 equiv), MeMgBr (1.6 g, 13.42 mmol, 2.00 equiv) in THF (20 mL) was stirred for 15 min at 0° C. then with stirring, for an additional 1 h at 25° C. After completion, the reaction was then quenched by the addition of sat. aq. $NH_4Cl$ (50 mL) and extracted with 3×50 mL of EtOAc. Then the organic layers were combined and washed with 3×25 mL of brine. The organic layer was dried over anhydrous sodium sulfate and concentrated under vacuum. The residue was applied onto a silica gel column eluting with EtOAc/petroleum ether (1:3) to afford 1.9 g (crude) of the title compound as a gray solid. LCMS $ES^+$ 329 $[M+H]^+$.

Step 3: (E)-1-((5R,8R)-3-(2,6-Difluorophenyl)-9,9-dimethyl-6,7-dihydro-5,8-methanocinnolin-8(5H)-yl)-3-(dimethylamino)prop-2-en-1-one A solution of 1-((5R,8R)-3-(2,6-difluorophenyl)-9,9-dimethyl-6,7-dihydro-5,8-methanocinnolin-8(5H)-yl)ethan-1-one (1.9 g, 5.78 mmol, 1.00 equiv) in DMF-DMA (20 mL) was stirred for 24 h at 125° C. After completion, the solution was diluted with 50 mL of water and extracted with 3×50 mL of EtOAc and washed with 3×25 mL of brine. The organic layer was dried over anhydrous sodium sulfate and concentrated under vacuum to afford 1.8 g of the title compound as an orange solid. LCMS $ES^+$ 384 $[M+H]^+$.

Step 4: 4-((5R,8S)-3-(2,6-Difluorophenyl)-9,9-dimethyl-6,7-dihydro-5,8-methanocinnolin-8(5H)-yl)pyrimidin-2-amine A solution of (E)-1-((5R,8R)-3-(2,6-Difluorophenyl)-9,9-dimethyl-6,7-dihydro-5,8-methanocinnolin-8(5H)-yl)-3-(dimethylamino)prop-2-en-1-one (1.8 g, 4.69 mmol, 1.00 equiv), guanidine hydrochloride (1.1 g, 11.51 mmol, 2.45 equiv), potassium carbonate (1.6 g, 11.57 mmol, 2.46 equiv) in ethanol (20 mL) was stirred for 40 h at 110° C. After completion, the solution was diluted with 50 mL of water and extracted with 3×50 mL of EtOAc. Then the organic layers ware combined and washed with 3×25 mL of brine. The organic layer was dried over anhydrous sodium sulfate and concentrated under vacuum to afford 1.9 g (crude) the title compound as a yellow solid. LCMS $ES^+$ 380 $[M+H]^+$.

Step 5: 5-Bromo-4-((5R,8S)-3-(2,6-difluorophenyl)-9,9-dimethyl-6,7-dihydro-5,8-methanocinnolin-8(5H)-yl)pyrimidin-2-amine A solution of 4-((5R,8S)-3-(2,6-difluorophenyl)-9,9-dimethyl-6,7-dihydro-5,8-methanocinnolin-8(5H)-yl)pyrimidin-2-amine (1.4 g, 3.69 mmol, 1.00 equiv), NBS (800 mg, 4.49 mmol, 1.21 equiv), AIBN (300 mg, 1.82 mmol, 0.49 equiv) in DMF(10 mL) was stirred for 30 h at 25° C. After completion, the solution was diluted with 50 mL of water and extracted with 3×50 mL of EtOAc. Then the organic layers ware combined and washed with 3×25 mL of brine. The organic layer was dried over anhydrous sodium sulfate and concentrated under vacuum to afford 1 g of the title compound as a gray solid. LCMS $ES^+$ 458 $[M+H]^+$.

Step 6: 5-Bromo-6-((5R,8S)-3-(2,6-Difluorophenyl)-9,9-dimethyl-6,7-dihydro-5 8-methanocinnolin-8(5H)-yl)pyrimidin-2(1H)-one A solution of 5-bromo-4-((5R,8S)-3-(2,6-difluorophenyl)-9,9-dimethyl-6,7-dihydro-5,8-methanocinnolin-8(5H)-yl)pyrimidin-2-amine (400 mg, 0.87 mmol, 1.00 equiv), $NaNO_2$ (180 mg, 2.61 mmol, 2.98 equiv) in HOAc (10 mL) and water(3 mL) was stirred for 12 h at room temperature. After completion, the pH value of the solution was adjusted to 6 with sodium hydroxide. the solution was diluted with 100 mL of water and extracted with 3×100 mL of EtOAc and washed with 3×50 mL of brine. The mixture was dried over anhydrous sodium sulfate and concentrated under vacuum. This resulted in 210 mg of the title compound as brown oil. LCMS $ES^+$ 459 $[M+H]^+$.

Step 7: (5R,8S)-8-(5-Bromo-2-chloropyrimidin-4-yl)-3-(2,6-difluorophenyl)-9,9-dimethyl-5,6,7,8-tetrahydro-5,8-methanocinnoline A solution of 5-bromo-6-((5R,8S)-3-(2,6-Difluorophenyl)-9,9-dimethyl-6,7-dihydro-5,8-methanocinnolin-8(5H)-yl)pyrimidin-2(1H)-one (500 mg, 1.08 mmol, 1.00 equiv), $POCl_3$ (6 mL) was stirred for 5 h at 110° C. After completion, the solution was diluted with 100 mL of water and extracted with 3×100 mL of EtOAc. Then the organic layers ware combined and washed with 3×50 mL of brine. The organic layer was dried over anhydrous sodium sulfate and concentrated under vacuum to afford 230 mg of the title compound as a yellow solid. LCMS $ES^+$ 478 $[M+H]^+$.

Step 8: (5R,8S)-8-(5-Bromo-2-(3-(2-(methylsulfonyl)ethyl)-1H-1,24-triazol-1-yl)pyrimidin-4-yl)-3-(2,6-difluorophenyl)-9,9-dimethyl-5,6,7,8-tetrahydro-5,8-methanocinnoline A solution of (5R,8S)-8-(5-Bromo-2-chloropyrimidin-4-yl)-3-(2,6-difluorophenyl)-9,9-dimethyl-5,6,7,8-tetrahydro-5,8-methanocinnoline (200 mg, 0.42 mmol, 1.00 equiv), 3-(2-methanesulfonylethyl)-1H-1,2,4-triazole (88 mg, 0.50 mmol, 1.20 equiv), potassium carbonate (115 mg, 0.83 mmol, 1.98 equiv) in DMF(3 mL) was stirred for 2 h at 70° C. After completion, the reaction was quenched with sat. eq. ammonium chloride (50 mL) and extracted with 3×50 mL of EtOAc. Then the organic layers were combined and washed with 3×50 mL of brine. The organic layer was dried over anhydrous sodium sulfate and concentrated under vacuum. The residue was applied onto a silica gel column eluting with DCM/MeOH (10:1) to afford 77.1 mg of the title compound as a white solid. $^1H$ NMR (300 MHz, $CDCl_3$): δ: 9.06 (s, 1H), 8.96 (s, 1H), 7.60 (s, 1H), 7.50-7.31 (m, 1H), 7.15-7.00 (m, 2H), 3.70-3.62 (m, 2H), 3.53-3.39 (m, 2H), 3.11 (s, 1H), 2.95 (m, 3H), 2.90-2.85 (m, 1H), 2.69-2.55 (m, 1H), 2.05-1.98 (m, 1H), 1.58-1.49 (m, 1H), 1.40 (s, 3H), 1.16 (s, 3H); LCMS $ES^+$ 616 $[M+H]^+$.

Example 63: (5R,8S)-3-(2,6-Difluorophenyl)-9,9-dimethyl-8-(5-methyl-2-(3-(2-(methylsulfonyl)ethyl)-1H-1,2,4-triazol-1-yl)pyrimidin-4-yl)-5,6,7,8-tetrahydro-5,8-methanocinnoline

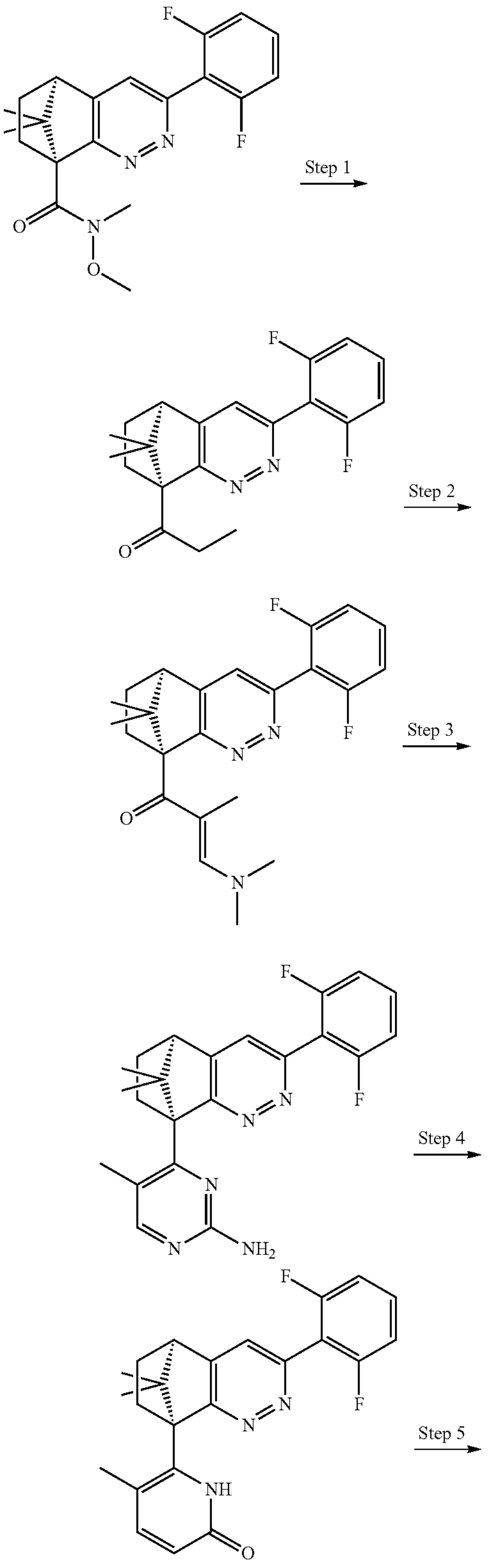

-continued

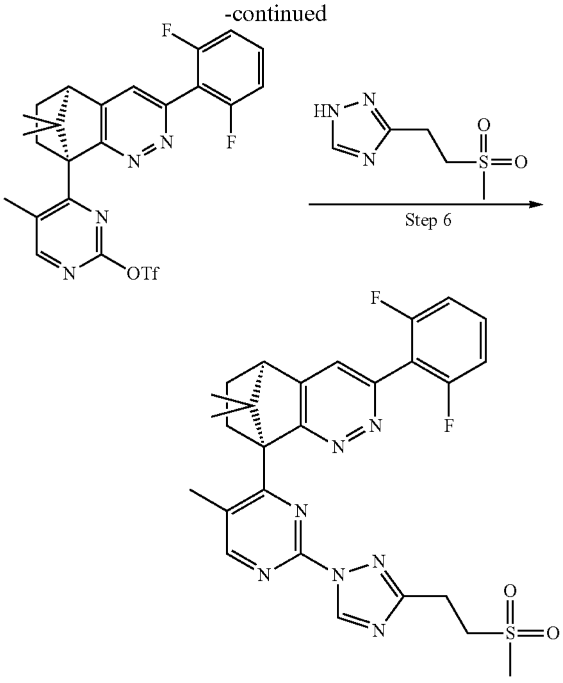

Step 1: 1-((5R,8R)-3-(2,6-Difluorophenyl)-9,9-dimethyl-6,7-dihydro-5 8-methanocinnolin-8(5H)-yl) propan-1-one Under nitrogen, a solution of ((5R,8R)-3-(2,6-difluorophenyl)-N-methoxy-N,9,9-trimethyl-6,7-dihydro-5,8-methanocinnoline-8(5H)-carboxamide (2 g, 5.3 mmol, 1.0 equiv), EtMgBr (6 mL, 45.5 mmol, 8.5 equiv) in THF (15 mL) was stirred for 15 min at 0° C. Then the resulting solution was stirred 1 hour at room temperature. After completion, the reaction was then quenched by the addition of sat.aq. $NH_4Cl$. The solution was diluted with 30 mL of water and extracted with 3×50 mL of dichloromethane. Then the organic layers was combined and washed with 3×50 mL of brine to afford 1.4 g of the title compound as a yellow solid. LCMS $ES^+$ 343 $[M+H]^+$.

Step 2: (E)-1-((5R,8R)-3-(2,6-Difluorophenyl)-9,9-dimethyl-6,7-dihydro-5,8-methanocinnolin-8(5H)-yl)-3-(dimethylamino)-2-methylprop-2-en-1-one A solution of 1-((5R,8R)-3-(2,6-Difluorophenyl)-9,9-dimethyl-6,7-dihydro-5,8-methanocinnolin-8(5H)-yl)propan-1-one (1.4 g, 4.1 mmol, 1.0 equiv) in DMF-DMA (15 mL) was stirred for 24 h at 130° C. After completion, the resulting mixture was concentrated under vacuum to afford 1.5 g of the title compound as a gray solid. LCMS $ES^+$ 398 $[M+H]^+$.

Step 3: 4-((5R,8S)-3-(2,6-Difluorophenyl)-9,9-dimethyl-6,7-dihydro-5 8-methanocinnolin-8(5H)-yl)-5-methylpyrimidin-2-amine A solution E)-1-((5R,8R)-3-(2,6-difluorophenyl)-9,9-dimethyl-6,7-dihydro-5,8-methanocinnolin-8(5H)-yl)-3-(dimethylamino)-2-methylprop-2-en-1-one (1.5 g, 3.8 mmol, 1.0 equiv), guanidine hydrochloride (900 mg, 9.4 mmol, 2.5 equiv), potassium carbonate (1.3 g, 9.4 mmol, 2.5 equiv) in ethanol (20 mL) was stirred for 30 h at 110° C. After completion, the solution was diluted with 100 mL of water and extracted with 2×100 mL of EtOAc and washed with 3×50 mL of brine. Then the organic layers was combined and dried over anhydrous sodium sulfate and concentrated under vacuum. The residue was applied onto a silica gel column eluting with EtOAc/petroleum ether (45:55) to afford 900 mg of the title compound as a yellow solid. LCMS $ES^+$ 394 $[M+H]^+$.

Step 4: 6-((5R,8S)-3-(2,6-Difluorophenyl)-9,9-dimethyl-6,7-dihydro-5,8-methanocinnolin-8(5H)-yl)-5-methylpyridin-2(1H)-one A solution of 4-((5R,8S)-3-(2,6-Difluorophenyl)-9,9-dimethyl-6,7-dihydro-5,8-methanocinnolin-8(5H)-yl)-5-methylpyrimidin-2-amine (900 mg, 2.3 mmol, 1.0 equiv), NaNO2 (474 mg, 6.9 mmol, 3.0 equiv) in AcOH (10 mL) and water(2 mL) was stirred for 1 h at 0° C. Then the resulting solution was stirred, for 12 h at room temperature. After completion, the pH value of the solution was adjusted to 6 with sat.aq. sodium hydroxide. The solution was diluted with 100 mL of water and extracted with 3×100 mL of EtOAc and washed with 3×50 mL of brine. Then the organic layers was combined and dried over anhydrous sodium sulfate and concentrated under vacuum to afford 400 mg of the title compound as a yellow solid. LCMS $ES^+$ 395 $[M+H]^+$.

Step 5: 4-((5R,8S)-3-(2,6-Difluorophenyl)-9,9-dimethyl-6,7-dihydro-5,8-methanocinnolin-8(5H)-yl)-5-methylpyrimidin-2-yl trifluoromethanesulfonate A solution of 6-((5R,8S)-3-(2,6-difluorophenyl)-9,9-dimethyl-6,7-dihydro-5,8-methanocinnolin-8(5H)-yl)-5-methylpyridin-2(1H)-one (200 mg, 0.5 mmol, 1.0 equiv), $Tf_2O$ (215 mg, 0.8 mmol, 1.5 equiv), pyridine (162 mg, 2.0 mmol, 4.0 equiv) in dichloromethane (10 mL) was stirred for 10 min at 0° C. Then the resulting solution was stirred for 2 h at room temperature. After completion, the solution was diluted 150 mL of dichloromethane and washed with 3×50 mL of brine. The organic layers was dried over anhydrous sodium sulfate and concentrated under vacuum to afford 220 mg of the title compound as a brown oil. EtOAc/petroleum ether (45:55) to afford 900 mg of the title compound as a yellow solid. LCMS $ES^+$ 527 $[M+H]^+$.

Step 6: (5R,8S)-3-(2,6-Difluorophenyl)-9,9-dimethyl-8-(5-methyl-2-(3-(2-(methylsulfonyl)ethyl)-1H-1,2,4-triazol-1-yl)pyrimidin-4-yl)-5,6,7,8-tetrahydro-5,8-methanocinnoline Under nitrogen, a solution of 4-((5R,8S)-3-(2,6-Difluorophenyl)-9,9-dimethyl-6,7-dihydro-5,8-methanocinnolin-8(5H)-yl)-5-methylpyrimidin-2-yl trifluoromethanesulfonate (200 mg, 0.380 mmol, 1.000 equiv), 3-(2-methanesulfonylethyl)-1H-1,2,4-triazole (80 mg, 0.5 mmol, 1.2 equiv), $K_3PO_4$ (161 mg, 0.76 mmol, 2 equiv), t-BuXPhos Pd-G3 (60 mg, 0.08 mmol, 0.2 equiv), t-BuXPhos (32 mg, 0.08 mmol, 0.2 equiv) in 1,4-dioxane (8 mL) was stirred for 2 h at 110° C. After completion, the solution was diluted with 100 mL of water and extracted with 3×100 mL of EtOAc and washed with 3×50 mL of brine. Then the organic layers was combined and dried over anhydrous sodium sulfate and concentrated under vacuum. The residue was applied onto a silica gel column eluting with water/CH3CN (65:35) to afford 62.3 mg of the title compound as a white solid. $^1H$ NMR (400 MHz, $CDCl_3$): δ: 9.09 (s, 1H), 8.69 (s, 1H), 7.55 (s, 1H), 7.50-7.30 (m, 1H), 7.15-7.05 (m, 2H), 3.70-3.55 (m, 2H), 3.51-3.42 (m, 2H), 3.12 (d, J=4.0 Hz, 1H), 2.98 (s, 3H), 2.67 (s, 4H), 2.50 (d, J=11.8 Hz, 1H), 2.33 (s, 1H), 1.45 (m, 4H), 1.16 (s, 3H); LCMS ES$^+$ 552 [M+H]$^+$.

Example 64: (5R,8S)-3-(2,6-Difluorophenyl)-8-(5-methoxy-2-(3-(2-(methylsulfonyl)ethyl)-1H-1,2,4-triazol-1-yl)pyrimidin-4-yl)-9,9-dimethyl-5,6,7,8-tetrahydro-5,8-methanocinnoline

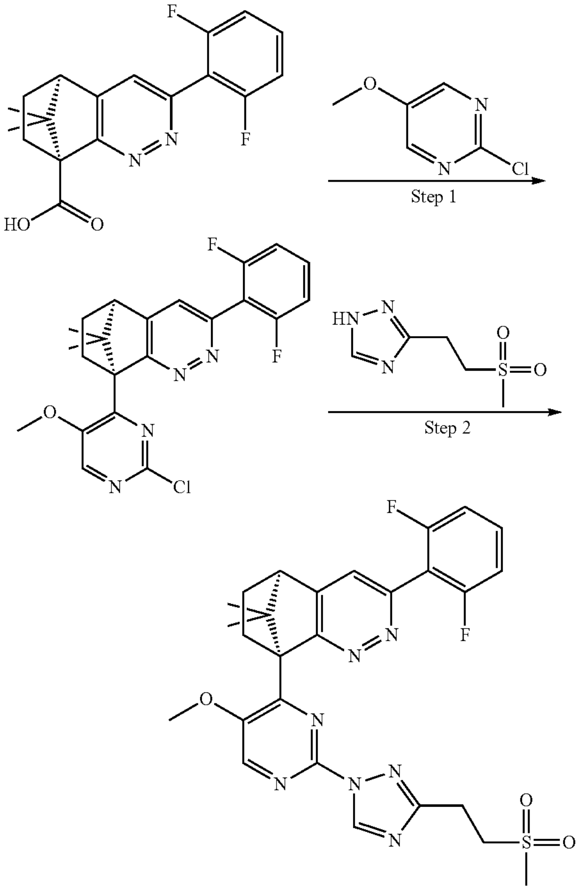

Step 1: (5R,8)-8-(2-Chloro-5-methoxypyrimidin-4-yl)-3-(2,6-difluorophenyl)-9,9-dimethyl-5,6,7,8-tetrahydro-5,8-methanocinnoline A solution of (5R,8R)-3-(2,6-difluorophenyl)-9,9-dimethyl-6,7-dihydro-5,8-methanocinnoline-8(5H)-carboxylic acid (1 g, 3.02 mmol, 1.00 equiv), 2-chloro-5-methoxypyrimidine (880 mg, 6.08 mmol, 2.01 equiv), $AgNO_3$ (120 mg, 0.71 mmol, 0.23 equiv) in CH3CN (10 mL) and water(10 mL) was stirred for 10 min at 25° C. Then $(NH_4)_2S_2O_8$(1.4 g, 6.13 mmol, 2.02 equiv) was added to the system, and the mixture was stirred for 10 h at 25° C. After completion, the solution was diluted with 100 mL of water and extracted with 3×100 mL of EtOAc and washed with 3×50 mL of brine. The organic layer was dried over anhydrous sodium sulfate and concentrated under vacuum to afford 390 mg of the title compound as a yellow solid. LCMS ES$^+$ 429 [M+H]$^+$.

Step 2: (5R,8S)-3-(2,6-Difluorophenyl)-8-(5-methoxy-2-(3-(2-(methylsulfonyl)ethyl)-1H-1,2,4-triazol-1-yl)pyrimidin-4-yl)-9,9-dimethyl-5,6,7,8-tetrahydro-5,8-methanocinnoline A solution of (5R,8S)-8-(2-Chloro-5-methoxypyrimidin-4-yl)-3-(2,6-difluorophenyl)-9,9-dimethyl-5,6,7,8-tetrahydro-5,8-methanocinnoline (200 mg, 0.46 mmol, 1.00 equiv), 3-(2-methanesulfonylethyl)-1H-1,2,4-triazole (122 mg, 0.69 mmol, 1.49 equiv), potassium carbonate (129 mg, 0.933 mmol, 2.01 equiv) in DMSO (6 mL) was stirred for 20 h at 90° C. After completion, the solution was diluted with 50 mL of water and extracted with 3×50 mL of EtOAc. Then the organic layers ware combined and washed with 3×25 mL of brine. The organic layer was dried over anhydrous sodium sulfate and concentrated under vacuum. The residue was applied onto a silica gel column eluting with water:CH3CN (5%-60%) to afford 56.5 mg of the title compound as a white solid. $^1$H NMR (400 MHz, $CD_3OD$): δ: 9.05 (s, 1H), 8.51 (s, 1H), 7.54 (s, 1H), 7.51-7.39 (m, 1H), 7.15-7.08 (m 2H), 4.00 (s, 3H), 3.64 (dd, J=9.5, 6.3 Hz, 2H), 3.47 (dd, J=9.3, 6.4 Hz, 2H), 3.15 (d, J=4.1 Hz, 1H), 2.98 (s, 3H), 2.96-2.91 (m, 1H), 2.49-2.43 (m, 1H), 2.25-2.15 (m, 1H), 1.46-1.41 (m, 1H), 1.33 (s, 3H), 1.05 (s, 3H); LCMS ES$^+$ 568 [M+H]$^+$.

Example 65: (5R,8S)-3-(2,6-Difluorophenyl)-9,9-dimethyl-8-(2-(4-(2-(methylsulfonyl)ethyl)piperazin-1-yl)pyrimidin-4-yl)-5,6,7,8-tetrahydro-5 8-methanocinnoline

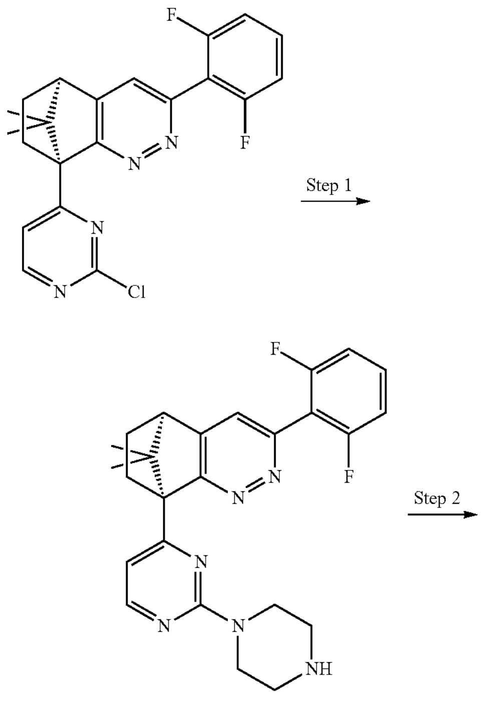

-continued

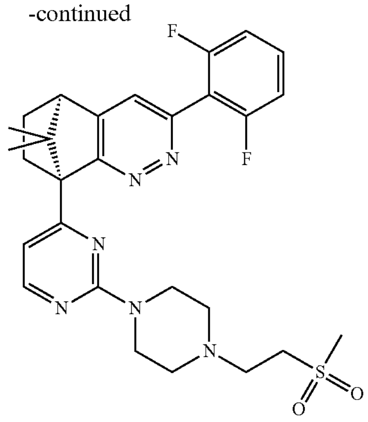

Step 1: (5R,8S)-3-(2,6-Difluorophenyl)-9,9-dimethyl-8-(2-(piperazin-1-yl)pyrimidin-4-yl)-56,7,8-tetrahydro-5,8-methanocinnoline A solution of (5R,8S)-8-(2-chloropyrimidin-4-yl)-3-(2,6-difluorophenyl)-9,9-dimethyl-5,6,7,8-tetrahydro-5,8-methanocinnoline (200 mg, 0.50 mmol, 1.00 equiv) potassium carbonate (145 mg, 1.05 mmol, 2.09 equiv), piperazine (55 mg, 0.64 mmol, 1.27 equiv) in DMF(3 mL) was stirred for 2 h at 75° C. After completion, the solution was diluted with 30 mL of water and extracted with 3x30 mL of EtOAc. Then the organic layers was combined and washed with 3x15 mL of brine. The mixture was dried over anhydrous sodium sulfate and concentrated under vacuum. The residue was applied onto a silica gel column eluting with DCM/MeOH (9:1) to afford 140 mg of the title compound as a yellow solid.

Step 2: (5R,8S)-3-(2,6-Difluorophenyl)-9,9-dimethyl-8-(2-(4-(2-(methylsulfonyl)ethyl)piperazin-1-yl)pyrimidin-4-yl)-5,6,7,8-tetrahydro-5,8-methanocinnoline A solution of (5R,8S)-3-(2,6-difluorophenyl)-9,9-dimethyl-8-(2-(piperazin-1-yl)pyrimidin-4-yl)-5,6,7,8-tetrahydro-5,8-methanocinnoline (130 mg, 0.29 mmol, 1.00 equiv), potassium carbonate (80 mg, 0.58 mmol, 2.0 equiv), methanesulfonylethene (34 mg, 0.32 mmol, 1.10 equiv) in methanol (1 mL) and 1,4-dioxane (4 mL) was stirred for 5 h at 80° C. After completion, the solution was diluted with 30 mL of water and extracted with 3x30 mL of EtOAc. Then the organic layers was combined and washed with 3x15 mL of brine. The mixture was dried over anhydrous sodium sulfate and concentrated under vacuum. The residue was applied onto a silica gel column eluting with DCM/MeOH (15:1) to afford (37%) of the title compound as a white solid. $^{1}$H NMR 300 MHz, CDC13): δ: 8.35 (s, 1H), 7.46-7.38 (m, 2H), 7.12-7.02 (m, 3H), 3.87 (s, 4H), 3.22-3.08 (m, 7H), 2.96 (s, 2H), 2.60 (s, 4H), 2.45-2.38 (m, 1H), 1.68-1.59 (m, 1H), 1.37-1.32 (m, 1H), 1.13 (s, 3H), 0.76 (s, 3H); LCMS ES$^+$ 555 [M+H]$^+$ Example 66: 4-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)butanenitrile

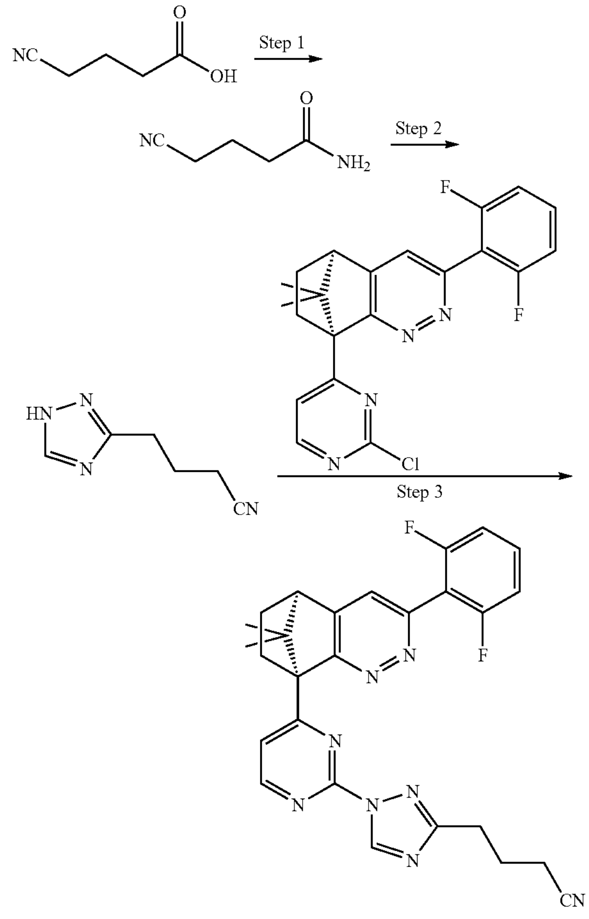

Step 1: 4-Cyanobutanamide

A solution of 4-cyanobutanoic acid (1.00 g, 8.84 mmol, 1.00 equiv), oxalyl chloride (2244.20 mg, 17.68 mmol, 2.00 equiv), ammonia (3.01 g, 88.39 mmol, 10.00 equiv) in dichloromethane (100 mL) was stirred for 1 h at 25° C. After completion, the solution was diluted with 50 mL of water and extracted with 3x50 mL of EtOAc. Then the organic layers was combined and washed with 3x50 mL of brine. The organic layer was dried over anhydrous sodium sulfate and concentrated under vacuum to afford as 600 mg of the title compound a white solid. LCMS ES$^+$ 113 [M+H]$^+$.

Step 2: 4-(1H-1,2,4-Triazol-3-yl)butanenitrile

A solution of 4-cyanobutanamide (1 g, 8.91 mmol, 1.00 equiv), DMFdimethyl acetal (2.10 g, 17.62 mmol, 1.97 equiv) was stirred for 2 h at 60° C. The cooled mixture was concentrated under vacuum and taken up in acetonitrile (15 mL). The solution was treated with AcOH ((800 mg, 13.322 mmol, 1.494 equiv) followed by hydrazine monohydrate (700 mg, 13.983 mmol, 1.568 equiv) instantly giving a white precipitate. The suspension was heated at 60° C. for 1.25 hours in which time all solid has dissolved to leave a pale pink solution. The cooled mixture was concentrated under vacuum to leave a viscous pink syrup. The residue was applied onto a silica gel column eluting with DCM/MeOH (10:1) to afford 650 mg of the title compound as an orange oil. LCMS $ES^+$ 137 $[M+H]^+$.

Step 3: 4-(1-(4-((5R,8S)-3-(2,6-Difluorophenyl)-9,9-dimethyl-6,7-dihydro-5,8-methanocinnolin-8(5H)-yl)pyrimidin-2-yl)-1H-1,2,4-triazol-3-yl)butanenitrile A solution of 4-(1H-1,2,4-triazol-3-yl)butanenitrile (100 mg, 0.73 mmol, 1.00 equiv), (5R,8S)-8-(2-chloropyrimidin-4-yl)-3-(2,6-difluorophenyl)-9,9-dimethyl-5,6,7,8-tetrahydro-5,8-methanocinnoline (250 mg, 0.62 mmol, 0.85 equiv), potassium carbonate (200 mg, 1.44 mmol, 1.97 equiv) in DMSO (10 mL) was stirred for 4 h at 75° C. After completion, the solution was diluted with 30 mL of water and extracted with 3×50 mL of EtOAc. Then the organic layers was combined and washed with 3×50 mL of brine. The mixture was dried over anhydrous sodium sulfate and concentrated under vacuum. The residue was applied onto a silica gel column eluting with DCM/MeOH (12:1) to afford 48.3 mg of the title compound as a white solid. $^1H$ NMR (400 MHz, $CD_3OD$): δ: 9.37 (s, 1H), 8.92 (d, J=5.2 Hz, 1H), 7.88 (d, J=5.2 Hz, 1H), 7.79 (s, 1H), 7.59-7.55 (m, 1H), 7.22-7.16 (m, 2H), 3.35-3.31 (m, 1H), 3.31-3.30 (m, 1H), 3.03 (t, J=7.3 Hz, 2H), 2.63-2.60 (m, 3H), 2.20-2.16 (m, 2H), 1.74-1.72 (m, 1H), 1.45-1.43 (m, 1H), 1.19 (s, 3H), 0.85 (s, 3H); LCMS $ES^+$ 499 $[M+H]^+$.

Example 67: 3-(6-(6-((5R,8S)-3-(2,6-Difluorophenyl)-9,9-dimethyl-6,7-dihydro-5,8-methanocinnolin-8(5H)-yl)pyridin-2-yl)pyridazin-3-yl)oxetan-3-ol

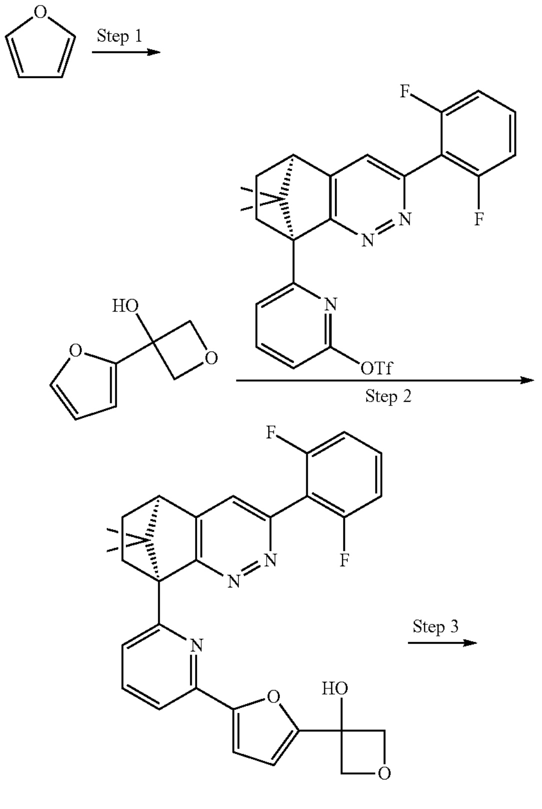

-continued

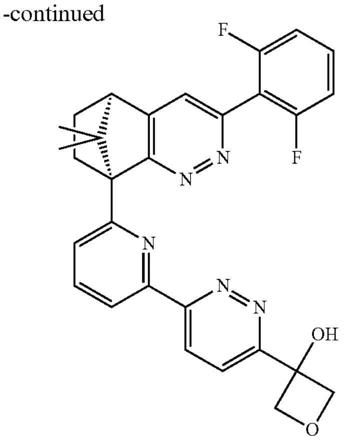

Step 1: 3-(Furan-2-yl)oxetan-3-ol

Under nitrogen, a solution of furan (5 g, 73.5 mmol, 1.0 equiv), tetramethylethylenediamine (17.5 g, 150.60 mmol, 2.05 equiv), in THF (100 mL) was stirred for 10 min at −78° C., then n-BuLi (59 mL, 2.5M in THF, 2.0 equiv) was added into the system at −78° C. After 30 min, oxetan-3-one (5.5 g, 76.32 mmol, 1.04 equiv) was added to the system and the resulting solution was stirred for 3 h at room temperature. After completion, the resulting mixture was quenching with methanol and concentrated under vacuum. The residue was applied onto a silica gel column eluting with EtOAc/petroleum ether (2:3) to afford 7 g of the title compound as a brown oil.

Step 2: 3-(5-(6-((5R,8S)-3-(2,6-Difluorophenyl)-9,9-dimethyl-6,7-dihydro-5,8-methanocinnolin-8(5H)-yl)pyridin-2-yl)furan-2-yl)oxetan-3-ol Under nitrogen, a solution of 6-((5R,8S)-3-(2,6-difluorophenyl)-9,9-dimethyl-6,7-dihydro-5,8-methanocinnolin-8(5H)-yl)pyridin-2-yl trifluoromethanesulfonate (500 mg, 0.98 mmol, 1.0 equiv), potassium carbonate (275 mg, 2.0 mmol, 2.0 equiv), 3-(furan-2-yl)oxetan-3-ol (2.75 g, 20 mmol, 20.1 equiv), Pd(PPh3)$_2$Cl2 (140 mg, 0.2 mmol, 0.2 equiv) in DMF(3 mL) was irradiated with microwave radiation for 1 h at 100° C. After completion, the solution was diluted with 50 mL of water and extracted with 3×50 mL of EtOAc. Then the organic layers ware combined and washed with 3×50 mL of brine. The organic layer was dried over anhydrous sodium sulfate and concentrated under vacuum. The residue was applied onto a silica gel column eluting with EtOAc/petroleum ether (3:7) to afford 100 mg of the title compound as a brown oil.

Step 3: 3-(6-(6-((5R,8S)-3-(2,6-Difluorophenyl)-9,9-dimethyl-6,7-dihydro-5,8-methanocinnolin-8(5H)-yl)pyridin-2-yl)pyridazin-3-yl)oxetan-3-ol A solution of 3-(5-(6-((5R,8S)-3-(2,6-difluorophenyl)-9,9-dimethyl-6,7-dihydro-5,8-methanocinnolin-8(5H)-yl) pyridin-2-yl)furan-2-yl)oxetan-3-ol (100 mg, 0.199 mmol, 1.0 equiv) in THF (5 mL) and water(0.5 mL) was stirred at −35° C. for 10 min, then NBS (39 mg, 0.219 mmol, 1.099 equiv) was added to the system at −35° C. After 1 h, hydrazine (1.8 mL, 1.685 mmol, 8.451 equiv, 1 M in THF) 5 was added to the system and the resulting was stirred for 3 h at 25° C. After completion, the resulting mixture was concentrated under vacuum. The crude product (70 mg) was purified by Flash-Prep-HPLC with the following conditions (IntelFlash-1): Column, silica gel; mobile phase, Water (0.05% NH3H2O):ACN=77:23 increasing to Water (0.05% NH3H2O):ACN=40:60 within 7.5 min; Detector, UV 254 nm to afford 35.1 mg (34%) of the title compound as a white solid. $^1$H NMR (300 MHz, CDCl3): δ: 8.81 (d, J=9 Hz, 1H), 8.63-8.60 (m, 1H), 8.28 (d, J=9 Hz. 1H), 8.01-7.94 (m, 2H), 7.50 (s, 1H), 7.45-7.40 (m, 1H), 7.09-7.04 (m, 2H), 5.19 (d, J=7.2 Hz, 2H), 4.81 (d, J=7.5 Hz, 2H), 3.49-3.44 (m, 1H), 3.20 (d, J=3.9 Hz, 1H), 2.52-2.45 (m, 1H), 1.83-1.74 (m, 2H), 1.45-1.40 (m, 1H), 1.16 (s, 3H), 0.78 (s, 3H); LCMS ES$^+$ 514 [M+H]$^+$.

Example 68: N-(6-(6-((5R,8S)-3-(2,6-Difluorophenyl)-9,9-dimethyl-6,7-dihydro-5,8-methanocinnolin-8(5H)-yl)pyridin-2-yl)pyridazin-3-yl)methanesulfonamide

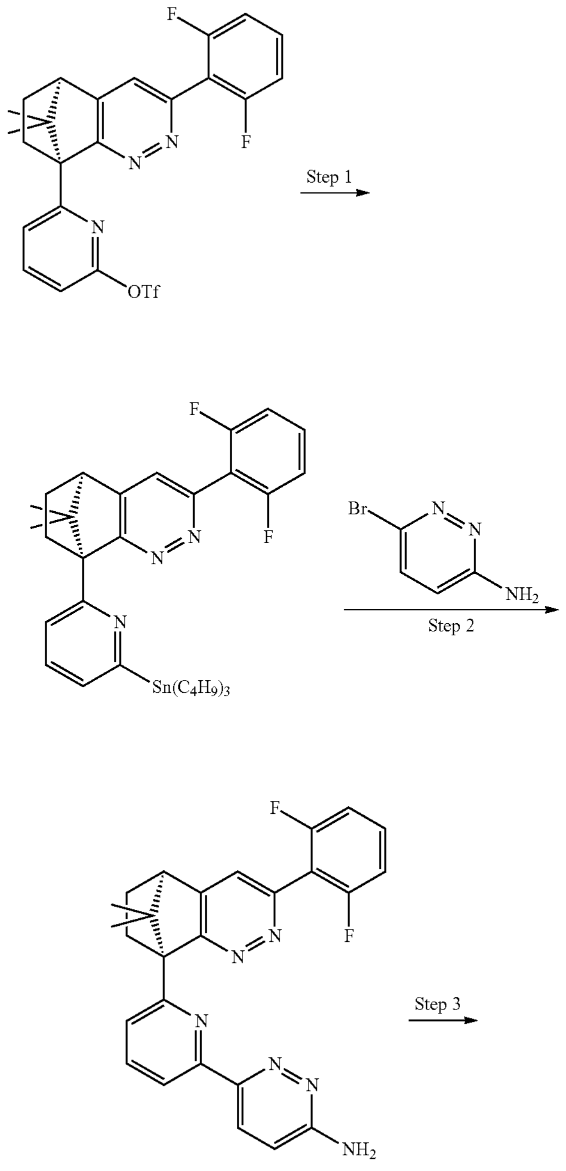

-continued

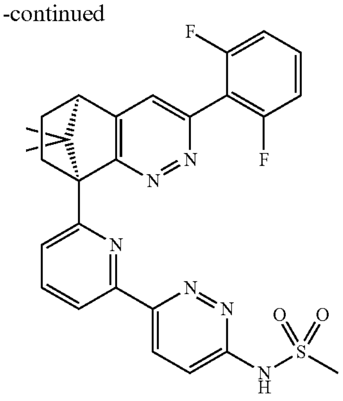

Step 1: (5R,8S)-3-(2,6-Difluorophenyl)-9,9-dimethyl-8-(6-(tributylstannyl)pyridin-2-yl)-5,6,7,8-tetrahydro-5,8-methanocinnoline Under nitrogen, a solution of 6-((5R,8S)-3-(2,6-difluorophenyl)-9,9-dimethyl-6,7-dihydro-5,8-methanocinnolin-8(5H)-yl)pyridin-2-yl trifluoromethanesulfonate (1.00 g, 1.96 mmol, 1.00 equiv), Hexa-n-butylditin (1.13 g, 1.95 mmol, 1.00 equiv), Pd(PPh3)$_4$ (225.93 mg, 0.20 mmol, 0.10 equiv), LiCl (164.00 mg, 4.00 mmol, 2.00 equiv) in toluene (10 mL) was stirred for 4 h at 100° C. After completion, the reaction was quenched with sat. eq. potassium fluoride and extracted with 3×150 mL of EtOAc. The organic layers were combined and washed with 3×50 mL of brine. The organic layer was dried over anhydrous sodium sulfate and concentrated under vacuum. The residue was applied onto a neutral alumina column with petroleum ether/EtOAc (4:1) to afford 300 mg of the title compound as a colorless oil.

Step 2: 6-(6-((5R,8S)-3-(2,6-Difluorophenyl)-9,9-dimethyl-6,7-dihydro-5,8-methanocinnolin-8(5H)-yl)pyridin-2-yl)pyridazin-3-amine Under nitrogen, a solution of (5R,8S)-3-(2,6-difluorophenyl)-9,9-dimethyl-8-(6-(tributylstannyl)pyridin-2-yl)-5,6,7,8-tetrahydro-5,8-methanocinnoline (200.00 mg, 0.31 mmol, 1.00 equiv), 6-bromopyridazin-3-amine (106.67 mg, 0.61 mmol, 2.00 equiv), Pd(PPh3)2Cl2 (43.03 mg, 0.06 mmol, 0.20 equiv) in DMF(4 mL) was stirred for 2 h at 120° C. After completion, the solution was diluted with 50 mL of water and extracted with 3×50 mL of EtOAc. Then the organic layers ware combined and washed with 3×50 mL of brine. The organic layer was dried over anhydrous sodium sulfate and concentrated under vacuum. The residue was applied onto a silica gel column eluting with DCM/MeOH (20: 1) to afford 50 mg (36%) of the title compound as a yellow solid.

Step 3: N-(6-(6-((5R,8S)-3-(2,6-Difluorophenyl)-9,9-dimethyl-6,7-dihydro-5,8-methanocinnolin-8(5H)-yl)pyridin-2-yl)pyridazin-3-yl)methane sulfonamide A solution of 6-(6-((5R,8S)-3-(2,6-Difluorophenyl)-9,9-dimethyl-6,7-dihydro-5,8-methanocinnolin-8(5H)-yl)pyridin-2-yl)pyridazin-3-amine (30.00 mg, 0.07 mmol, 1.00 equiv), methanesulfonyl methanesulfonate (57.24 mg, 0.35 mmol, 5.00 equiv), triethanolamine (33.25 mg, 0.35 mmol, 5.00 equiv) in dichloromethane (10 mL) was stirred for 12 h at 25° C. After completion, the resulting mixture was concentrated under vacuum. Then the residue was dissolved in THF (10 mL) and aq. sodium hydroxide (5N, 2 mL) was added to the system. After 1 hour, the pH value of the solution was adjusted to 7 with hydrogen chloride (6N). Then the resulting mixture was concentrated under vacuum. The residue was applied onto a silica gel column with DCM/MeOH (20:1) to afford 11.4 mg of the title compound as a white solid. $^1$H NMR (300 MHz, Methanol-d4): δ: 8.64 (d, J=9.7 Hz, 1H), 8.29 (d, J=7.9 Hz, 1H), 8.02 (t, J=7.9 Hz, 1H), 7.96-7.74 (m, 3H), 7.62-7.58 (m, 1H), 7.28-7.12 (m, 2H), 3.59-3.51 (m, 1H), 3.31-3.29 (m, 1H), 3.14 (s, 3H), 2.69-2.51 (m, 1H), 1.78-1.71 (m, 1H), 1.42-1.34 (m, 1H), 1.15 (s, 3H), 0.85 (s, 3H); LCMS ES$^+$ 535 [M+H]$^+$.

Example 69: 3-(5-(6-((5R,8S)-3-(2,6-Difluorophenyl)-9,9-dimethyl-6,7-dihydro-5,8-methanocinnolin-8(5H)-yl)pyridin-2-yl)pyrimidin-2-yl)oxetan-3-ol

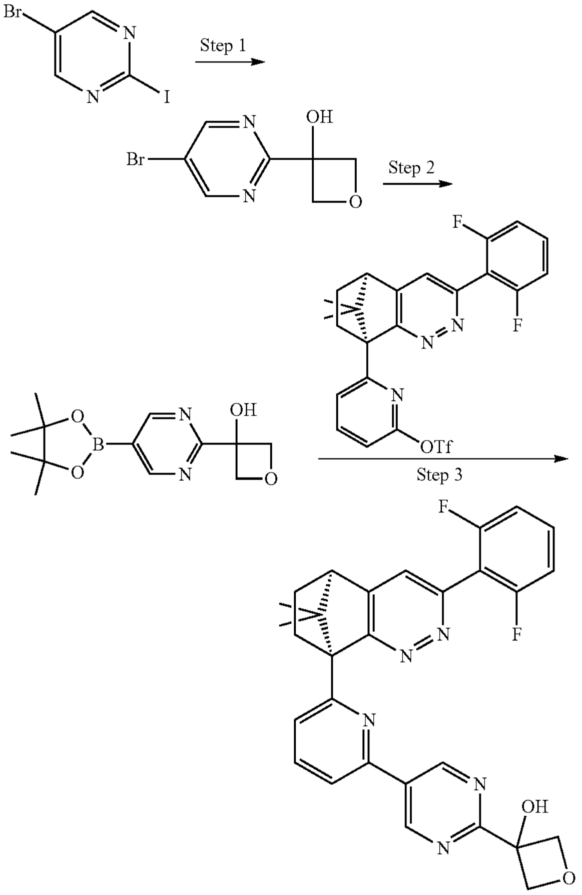

Step 1: 3-(5-Bromopyrimidin-2-yl)oxetan-3-ol

Under nitrogen, a solution of 5-bromo-2-iodopyrimidine (2 g, 7.02 mmol, 1.00 equiv) in toluene (30 mL) was stirred for 10 min at −78° C. Then n-butyllithium (2.5M in hexane) (2.95 mL, 31.31 mmol, 4.461 equiv) was added into the system at −78° C. After 30 min, oxetan-3-one (554 mg, 7.68 mmol, 1.09 equiv) was added into the system at −78° C. and stirred for 2 h at −78° C. After completion, the reaction was quenched with sat. eq. ammonium chloride (50 mL) and extracted with 3×50 mL of EtOAc. Then the organic layers was combined and washed with 3×50 mL of brine. The mixture was dried over anhydrous sodium sulfate and concentrated under vacuum. The residue was applied onto a silica gel column eluting with DCM/MeOH (25:1) to afford 1.1 g of the title compound as a brown oil. LCMS ES$^+$ 231 [M+H]$^+$.

Step 2: 3-(5-(4.4.5.5-Tetramethyl-1.32-dioxaborolan-2-yl)pyrimidin-2-yl)oxetan-3-ol Under nitrogen, a solution of 3-(5-bromopyrimidin-2-yl) oxetan-3-ol (750 mg, 3.24 mmol, 1.00 equiv), 4,4,5,5-tetramethyl-2-(tetramethyl-1,3,2-dioxaborolan-2-yl)-1,3,2-dioxaborolane (8.2 g, 32.29 mmol, 9.94 equiv), Pd(dppf)$C1_2$ dichloromethane (265 mg, 0.32 mmol, 0.10 equiv), KOAc (940 mg, 9.57 mmol, 2.95 equiv) in 1,4-dioxane (10 mL) was stirred for 2 h at 66° C. After completion, the solution was diluted with 30 mL of water and extracted with 3×50 mL of EtOAc. Then the organic layers was combined and washed with 3×50 mL of brine. The organic layer was dried over anhydrous sodium sulfate and concentrated under vacuum. The residue was applied onto a silica gel column eluting with DCM/MeOH (12:1) to afford 300 mg of the title compound as a white solid. LCMS ES$^+$ 279 [M+H]$^+$.

Step 3: 3-(5-(6-((5R,8S)-3-(2,6-Difluorophenyl)-9, 9-dimethyl-6,7-dihydro-5 8-methanocinnolin-8(5H)-yl)pyridin-2-yl)pyrimidin-2-yl)oxetan-3-ol Under nitrogen, a solution of 3-[5-(tetramethyl-1,3,2-dioxaborolan-2-yl)pyrimidin-2-yl]oxetan-3-ol (150 mg, 0.53 mmol, 1.00 equiv), 6-((5R,8S)-3-(2,6-difluorophenyl)-9,9-dimethyl-6,7-dihydro-5,8-methanocinnolin-8(5H)-yl) pyridin-2-yl trifluoromethanesulfonate (215 mg, 0.42 mmol, 0.77 equiv), $Pd(PPh_3)_2Cl_2$ (38 mg, 0.05 mmol, 0.10 equiv), CsF (164 mg, 1.08 mmol, 2.00 equiv) in ethanol (5 mL) and water(1 mL) was stirred for 2 h at 110° C. After completion, the solution was diluted with 30 mL of water and extracted with 3×50 mL of EtOAc. Then the organic layers was combined and washed with 3×50 mL of brine. The organic layer was dried over anhydrous sodium sulfate and concentrated under vacuum. The residue was applied onto a silica gel column eluting with DCM/MeOH (13:1) to afford 33.1 mg of the title compound as a white solid. $^1$H NMR (400 MHz, $CD_3OD$): δ: 9.52 (s, 2H), 8.11-8.03 (m, 2H), 7.96 (s, 1H), 7.83-7.81 (m, 1H), 7.66-7.62 (m, 1H), 7.26-7.22 (m, 2H), 5.19-5.18 (m, 2H), 4.92-4.90 (m, 2H), 3.52-3.49 (m, 1H), 3.42 (d, J=4.1 Hz, 1H), 2.64-2.63 (m, 1H), 1.76-1.73 (m, 1H), 1.48-1.46 (m, 1H), 1.18 (s, 3H), 0.88 (s, 3H); LCMS ES$^+$ 514 [M+H]$^+$.

Example 70: 3-(4-((5R,8S)-3-(2,6-Difluorophenyl)-9,9-dimethyl-6,7-dihydro-5,8-methanocinnolin-8(5H)-yl)-[2,5'-bipyrimidin]-2'-yl)oxetan-3-ol

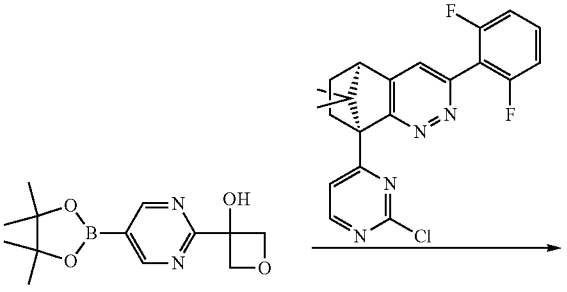

-continued

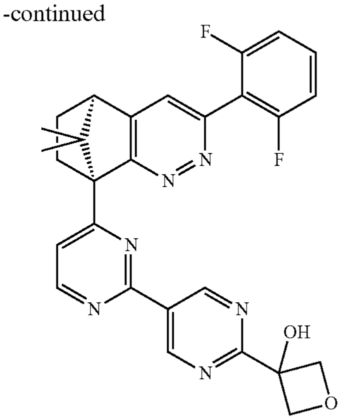

Under nitrogen, a solution of 3-[5-(tetramethyl-1,3,2-dioxaborolan-2-yl)pyrimidin-2-yl]oxetan-3-ol (150 mg, 0.53 mmol, 1.00 equiv), (5R,8S)-8-(2-chloropyrimidin-4-yl)-3-(2,6-difluorophenyl)-9,9-dimethyl-5,6,7,8-tetrahydro-5,8-methanocinnoline (216 mg, 0.54 mmol, 1.00 equiv), $Pd(PPh_3)_2Cl_2$ (38 mg, 0.05 mmol, 0.10 equiv), CsF (165 mg, 1.08 mmol, 2.01 equiv) in ethanol (6 mL) and water(1 mL) was stirred for 2 h at 110° C. After completion, the solution was diluted with 30 mL of water and extracted with 3×50 mL of EtOAc. Then the organic layers was combined and washed with 3×50 mL of brine. The organic layer was dried over anhydrous sodium sulfate and concentrated under vacuum. The residue was applied onto a silica gel column eluting with DCM/MeOH (12:1) to afford 51.1 mg of the title compound as a white solid. $^1H$ NMR (400 MHz, $CD_3OD$): δ: 9.83 (s, 2H), 9.01 (d, J=5.3 Hz, 1H), 7.89 (d, J=5.3 Hz, 1H), 7.81 (s, 1H), 7.62-7.57 (m, 1H), 7.22-7.18 (m, 2H), 5.20-4.92 (m, 2H), 4.91-4.88 (m, 2H), 3.51-3.46 (m, 1H), 3.38 (d, J=4.1 Hz, 1H), 2.66-2.60 (m, 1H), 1.77-1.72 (m, 1H), 1.49-1.45 (m, 1H), 1.23 (s, 3H), 0.89 (s, 3H); LCMS $ES^+$ 515 $[M+H]^+$.

Example 71: 4-(4-((5R,8S)-3-(2,6-Difluorophenyl)-9,9-dimethyl-6,7-dihydro-5,8-methanocinnolin-8(5H)-yl)pyrimidin-2-yl)-1-(2-(methylsulfonyl)ethyl)piperazin-2-one

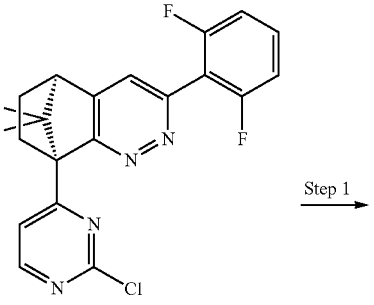

-continued

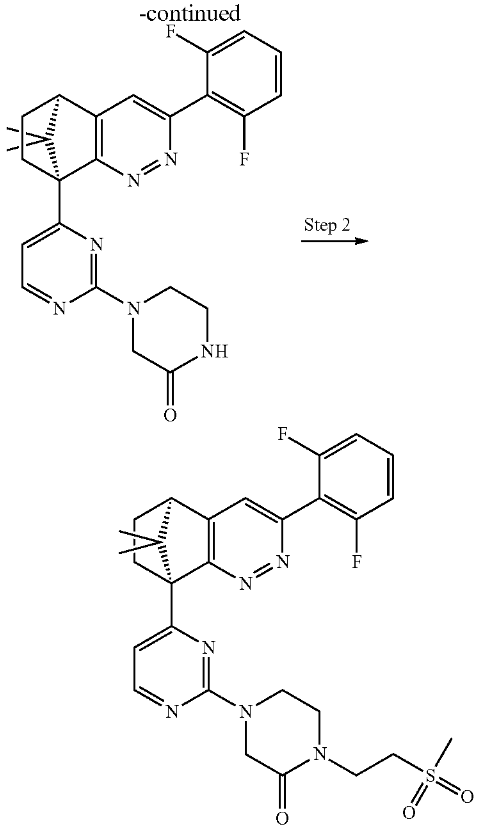

Step 1: 4-(4-((5R,8S)-3-(2,6-Difluorophenyl)-9,9-dimethyl-6,7-dihydro-5,8-methanocinnolin-8(5H)-yl)pyrimidin-2-yl)piperazin-2-one A solution of (5R,8S)-8-(2-chloropyrimidin-4-yl)-3-(2,6-difluorophenyl)-9,9-dimethyl-5,6,7,8-tetrahydro-5,8-methanocinnoline (500 mg, 1.25 mmol, 1.00 equiv), piperazin-2-one (251.2 mg, 2.50 mmol, 2.01 equiv), potassium carbonate (347 mg, 2.51 mmol, 2.00 equiv) in DMSO (5 mL) was stirred for 60 min at 80° C. After completion, the solution was diluted with 50 mL of water and extracted with 3×50 mL of EtOAc and washed with 3×25 mL of brine. The organic layer was dried over anhydrous sodium sulfate and concentrated under vacuum. The residue was applied onto a silica gel column eluting with DCM/MeOH (10:1) to afford 550 mg of the title compound as a white solid. LCMS $ES^+$ 462 $[M+H]^+$.

Step 2: 4-(4-((5R,8S)-3-(2,6-Difluorophenyl)-9,9-dimethyl-6,7-dihydro-5,8-methanocinnolin-8(5H)-yl)pyrimidin-2-yl)-1-(2-(methylsulfonyl)ethyl)piperazin-2-one A solution of 4-(4-((5R,8S)-3-(2,6-difluorophenyl)-9,9-dimethyl-6,7-dihydro-5,8-methanocinnolin-8(5H)-yl)pyrimidin-2-yl)piperazin-2-one (200 mg, 0.43 mmol, 1.00 equiv), 1-chloro-2-methanesulfonylethane (61 mg, 0.428 mmol, 1.0 equiv), t-BuOK (120 mg, 1.06 mmol, 2.47 equiv) in THF (10 mL) was stirred for 120 min at 80° C. After completion, the solution was diluted with 50 mL of water and extracted with 3×50 mL of EtOAc and washed with 3×25 mL of brine. The organic layer was dried over anhydrous sodium sulfate and concentrated under vacuum. The crude product was purified by Prep-HPLC with the following conditions (2#-AnalyseHPLC-SHIMADZU(HPLC-10)): Column, SunFire Prep C18 OBD Column, 19×150 mm 5 um 10 nm; mobile phase, Water (0.05% $NH_3H_2O$) and ACN (25.0% ACN up to 53.0% in 7 min); Detector, UV 254/220 nm to afford 15.8 mg (6%) of the title compound as a white solid. $^1$H NMR (400 MHz, DMSO): δ: 8.47 (s, 1H), 7.79 (s, 1H), 7.70-7.65 (m, 1H), 7.40-7.25 (m, 2H), 7.02 (d, J=2.4 Hz, 1H), 4.40-4.28 (m, 2H), 4.08-3.95 (m, 2H), 3.84-3.75 (m, 2H), 3.61-3.52 (m, 1H), 3.48-3.40 (m, 1H), 3.28-3.21 (m, 1H), 3.10-2.90 (m, 4H), 2.70-2.50 (M, 2H), 2.45-2.35 (s, 1H), 1.60-145 (m, 1H), 1.42-1.23 (m, 1H), 1.11 (s, 3H), 0.85 (s, 3H); LCMS ES$^+$ 568 [M+H]$^+$.

Example 72: 2-amino-5-(4-((5R,8S)-3-(2,6-difluorophenyl)-9,9-dimethyl-6,7-dihydro-5,8-methanocinnolin-8(5H)-yl)pyrimidin-2-yl)nicotinonitrile

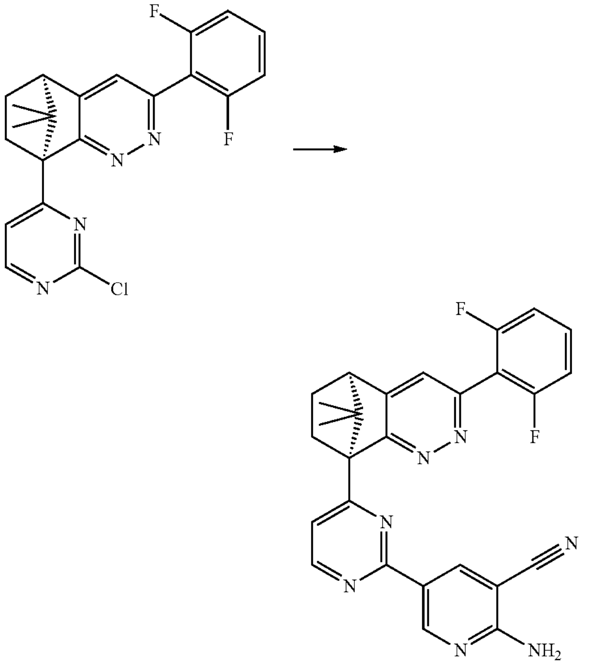 [SMILES: CC1(C)[C@H]2CC[C@]1(c1ccnc(Cl)n1)c1nnc(-c3c(F)cccc3F)cc12 ; CC1(C)[C@H]2CC[C@]1(c1ccnc(-c3cnc(N)c(C#N)c3)n1)c1nnc(-c3c(F)cccc3F)cc12]

In a vial was placed 2-amino-5-bromo-pyridine-3-carbonitrile (150 mg, 0.758 mmol), 4,4,5,5-tetramethyl-2-(4,4,5,5-tetramethyl-1,3,2-dioxaborolan-2-yl)-1,3,2-dioxaborolane (288 mg, 1.14 mmol), [1,1'-bis(diphenylphosphino)ferrocene]dichloropalladium(II) (11.7 mg, 0.015 mmol), and potassium acetate (149 mg, 0.515 mmol. Degassed ACN (9.5 mL) was added, and the reaction mixture was vacuum purged and back-filled with $N_2$ (3×). The vial was capped, and the reaction mixture was microwaved at 150° C. for 30 min and then cooled to room temperature. To the reaction mixture was then added (5R,8S)-8-(2-chloropyrimidin-4-yl)-3-(2,6-difluorophenyl)-9,9-dimethyl-5,6,7,8-tetrahydro-5,8-methanocinnoline (201 mg, 0.504 mmol), sodium carbonate (137 mg, 1.29 mmol), potassium acetate (74.3 mg, 0.757 mmol), [1,1'-bis(diphenylphosphino)ferrocene]dichloropalladium(II) (11.7 mg, 0.015 mmol), and water (3.8 mL). The vial was recapped, and the reaction mixture was microwaved at 120° C. for 30 min and then filtered through a pad of Celite® to rid Pd solid. The Celite® pad was rinsed well with iPrOAc, and the filtrate was diluted with iPrOAc.

The biphasic solution was separated. The organic layer was washed with water and brine, dried over anhydrous $Na_2SO_4$, filtered and concentrated under reduced pressure. The crude product was purified by silica gel chromatography eluted with methanol/isopropyl acetate followed by reverse phase prep-HPLC to give 120.4 mg of the title compound as a white solid. $^1$H NMR (DMSO-$d_6$, 400 MHz): δ 9.21 (d, J=2.3 Hz, 1H), 8.89 (d, J=5.2 Hz, 1H), 8.69 (d, J=2.3 Hz, 1H), 7.83 (s, 1H), 7.69-7.57 (m, 2H), 7.47 (s, 2H), 7.35-7.26 (m, 2H), 3.38-3.23 (m, 2H), 2.49-2.41 (m, 1H), 1.65-1.56 (m, 1H), 1.33-1.24 (m, 1H), 1.11 (s, 3H), 0.74 (s, 3H); LCMS ES$^+$ 482.1 [M+1]$^+$.

Example 73: N-(3-cyano-5-(4-((5R,8S)-3-(2,6-difluorophenyl)-9,9-dimethyl-6,7-dihydro-5,8-methanocinnolin-8(5H)-yl)pyrimidin-2-yl)pyridin-2-yl) methanesulfonamide

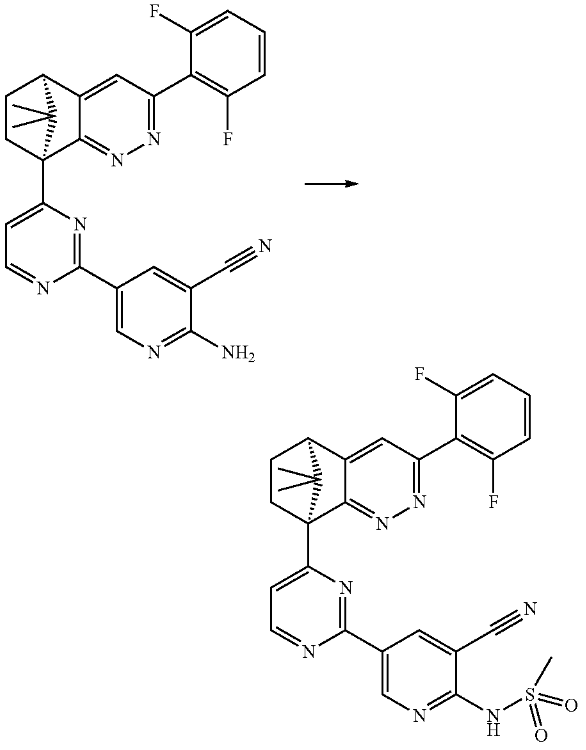 [SMILES: CC1(C)[C@H]2CC[C@]1(c1cccc(-c3cnc(N)c(C#N)c3)n1)c1nnc(-c3c(F)cccc3F)cc12 ; CC1(C)[C@H]2CC[C@]1(c1cccc(-c3cnc(NS(C)(=O)=O)c(C#N)c3)n1)c1nnc(-c3c(F)cccc3F)cc12]

To a stirred solution of 2-amino-5-(4-((5R,8S)-3-(2,6-difluorophenyl)-9,9-dimethyl-6,7-dihydro-5,8-methanocinnolin-8(5H)-yl)pyrimidin-2-yl)nicotinonitrile (45 mg, 0.093 mmol) in anhydrous 1,2-dimethoxyethane (9.3 mL) at 0° C. was added sodium tert-pentoxide (22 mg, 0.187 mmol), and the resultant yellow reaction mixture was stirred at 0° C. for 15 min. A solution of methanesulfonyl chloride (13 mg, 0.112 mmol) in anhydrous 1,2-dimethoxyethane (1 mL) was added, and the reaction mixture was stirred at room temperature for 15 min and then was diluted with iPrOAc. The organic layer was washed with saturated sodium bicarbonate, water, and brine, dried over anhydrous $Na_2SO_4$, filtered and concentrated under reduced pressure. The crude product was purified by silica gel chromatography eluted with methanol/isopropyl acetate followed by reverse phase prep-HPLC to give 23.7 mg of the title compound as a white solid. $^1$H NMR (DMSO-$d_6$, 400 MHz): δ 11.81 (s, 1H), 9.27 (s, 1H), 8.93 (d, J=5.2 Hz, 1H), 8.85-8.75 (m, 1H), 7.84 (s, 1H), 7.71 (d, J=5.2 Hz, 1H), 7.67-7.57 (m, 1H), 7.36-7.26 (m, 2H), 3.50-3.40 (m, 1H), 3.15 (s, 3H), 2.49-2.40 (m, 2H), 1.66-1.56 (m, 1H), 1.34-1.25 (m, 1H), 1.13 (s, 3H), 0.74 (s, 3H); LCMS $ES^+$ 560.1 $[M+1]^+$.

Example 74: 6'-amino-6-((5R,8S)-3-(2,6-difluorophenyl)-9,9-dimethyl-6,7-dihydro-5 8-methanocinnolin-8(5H)-yl)-[2,3'-bipyridine]-5'-carbonitrile

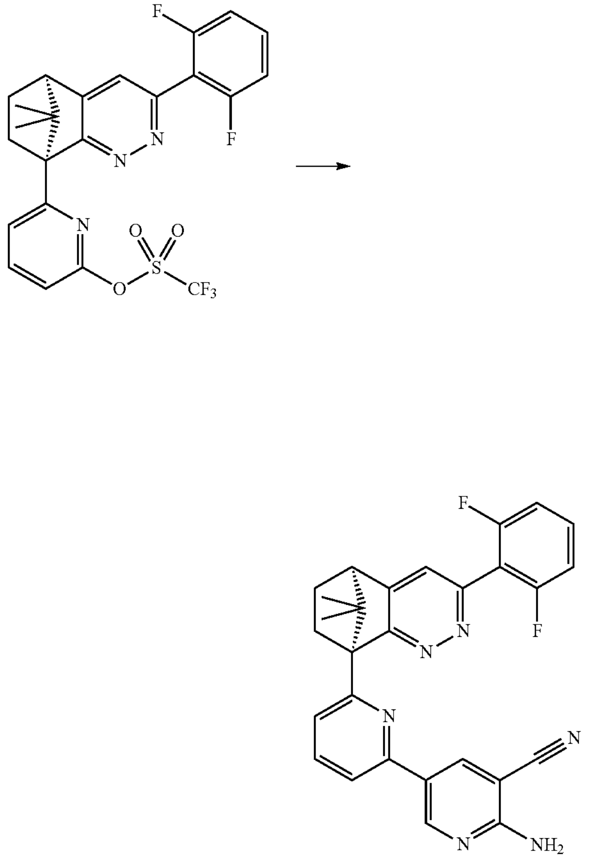

Following the procedure as described for Example 72, the title compound was prepared using 6-((5R,8S)-3-(2,6-difluorophenyl)-9,9-dimethyl-6,7-dihydro-5,8-methanocinnolin-8(5H)-yl)pyridin-2-yl trifluoromethanesulfonate in place of (5R,8S)-8-(2-chloropyrimidin-4-yl)-3-(2,6-difluorophenyl)-9,9-dimethyl-5,6,7,8-tetrahydro-5,8-methanocinnoline. $^1H$ NMR (DMSO-$d_6$, 400 MHz): δ 9.02 (d, J=2.4 Hz, 1H), 8.57 (d, J=2.3 Hz, 1H), 7.96-7.89 (m, 2H), 7.80 (s, 1H), 7.66-7.55 (m, 2H), 7.34-7.26 (m, 2H), 7.21 (s, 2H), 3.35-3.24 (m, 2H), 2.50-2.39 (m, 1H), 1.62-1.52 (m, 1H), 1.30-1.20 (m, 1H), 1.07 (s, 3H), 0.72 (s, 3H); LCMS ES 481.2 [M+1]+.

Example 75: N-(5'-cyano-6-((5R,8S)-3-(2,6-difluorophenyl)-9,9-dimethyl-6,7-dihydro-5,8-methanocinnolin-8(5H)-yl)-2,3'-bipyridinyl-6'-yl)methanesulfonamide

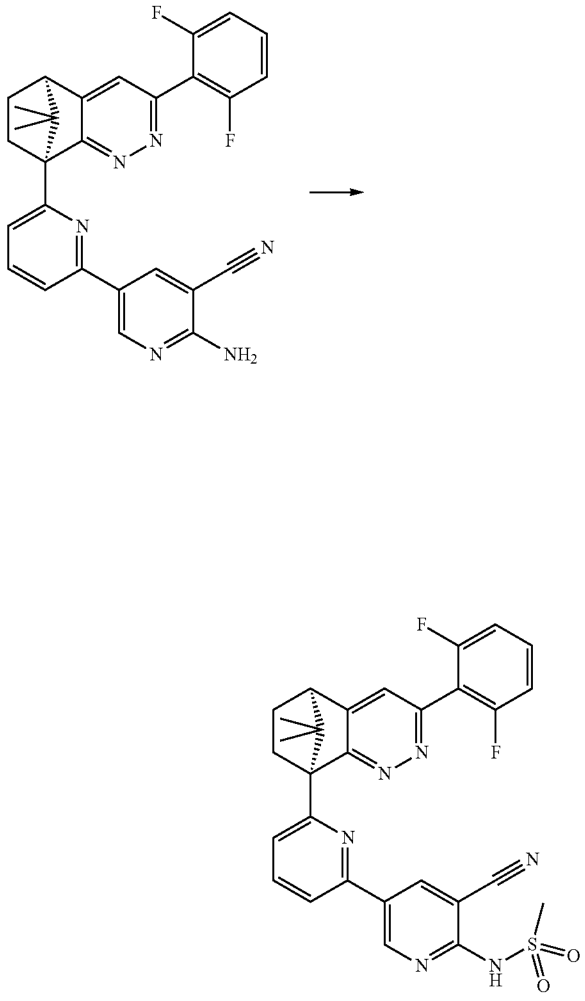

Following the procedure as described for Example 73, the title compound was prepared using 6'-amino-6-((5R,8S)-3-(2,6-difluorophenyl)-9,9-dimethyl-6,7-dihydro-5,8-methanocinnolin-8(5H)-yl)-[2,3'-bipyridine]-5'-carbonitrile in place of 2-amino-5-(4-((5R,8S)-3-(2,6-difluorophenyl)-9,9-dimethyl-6,7-dihydro-5,8-methanocinnolin-8(5H)-yl)pyrimidin-2-yl)nicotinonitrile. $^1H$ NMR (DMSO-$d_6$, 400 MHz): δ 11.38 (s, 1H), 9.28 (s, 1H), 8.96 (s, 1H), 8.11-7.97 (m, 2H), 7.81 (t, J=1.1 Hz, 1H), 7.70 (dd, J=7.5, 1.0 Hz, 1H), 7.67-7.57 (m, 1H), 7.35-7.26 (m, 2H), 3.45-3.30 (m, 4H), 3.29 (d, J=4.0 Hz, 1H), 2.50-2.39 (m, 1H), 1.64-1.53 (m, 1H), 1.32-1.22 (m, 1H), 1.08 (s, 3H), 0.73 (s, 3H); LCMS $ES^+$ 559.1 $[M+1]^+$.

Example 76: 4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1-(2-methylsulfonylethyl)pyridin-2-one

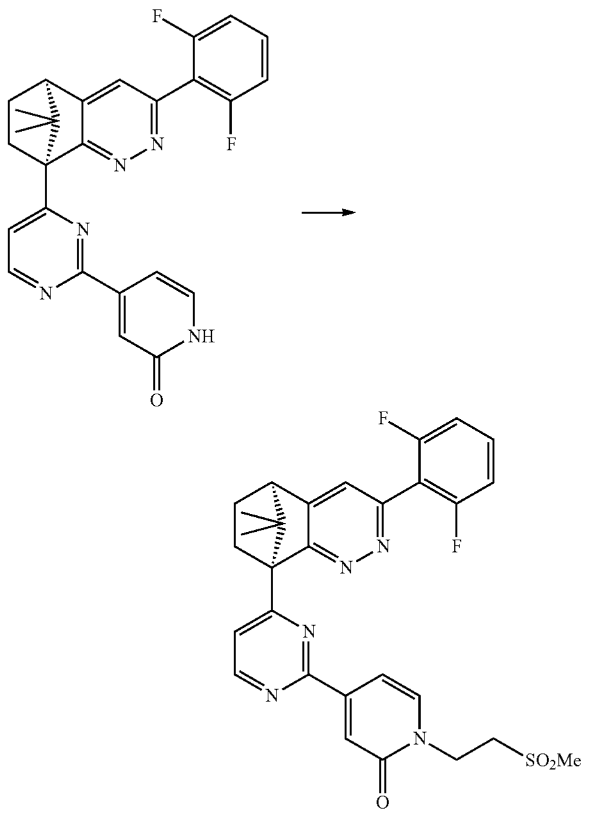 [SMILES: CC1(C)[C@H]2CC[C@]1(c1ccnc(-c3cc[nH]c(=O)c3)n1)c1nnc(-c3c(F)cccc3F)cc12 ; CC1(C)[C@H]2CC[C@]1(c1ccnc(-c3ccn(CCS(C)(=O)=O)c(=O)c3)n1)c1nnc(-c3c(F)cccc3F)cc12]

To a vial holding 4-[4-[(8R)-5-(2,6-difluorophenyl)-11,11-dimethyl-3,4-diazatricyclo[6.2.1.02,7]undeca-2(7),3,5-trien-1-yl]pyrimidin-2-yl]-1H-pyridin-2-one (21.5 mg, 0.0470 mmol) was added $Cs_2CO_3$ (30.6 mg, 0.0944 mmol) and then a solution of 1-methylsulfonylethylene (7.5 mg, 0.0705 mmol) in DMF (1.0 mL). The mixture was stirred at room temperature for 16 h, and then was diluted with 1 mL water and 1 mL 10% MeOH in DCM. The biphasic solution was separated, and the aqueous layer was extracted with 10% MeOH in DCM (2×1 mL). The combined organics were dried over anhydrous $Na_2SO_4$, filtered and concentrated under reduced pressure. For purification, the crude residue was combined with crude residue resulting from a small batch test reaction using the same procedure (5.0 mg, 0.011 mmol, 0.058 mmol total). The combined crude residue was purified by reverse phase preparative HPLC (acetonitrile 20-60%/0.1% formic acid in water) to give the title compound as a white solid (25.2 mg). $^1$H NMR (DMSO-$d_6$, 400 MHz): δ 9.04 (d, J=5.2 Hz, 1H), 7.96-7.82 (m, 3H), 7.62 (ddd, J=8.4, 6.3, 1.9 Hz, 1H), 7.41 (d, J=1.9 Hz, 1H), 7.31 (t, J=8.1 Hz, 2H), 7.17 (dd, J=7.1, 1.9 Hz, 1H), 4.36 (t, J=6.8 Hz, 2H), 3.61 (t, J=6.8 Hz, 2H), 3.34 (d, J=6.1 Hz, 2H), 3.27-3.19 (m, 1H), 3.07 (s, 3H), 1.65 (ddd, J=12.9, 9.1, 4.1 Hz, 1H), 1.30 (ddd, J=12.8, 9.1, 3.9 Hz, 1H), 1.12 (s, 3H), 0.76 (s, 3H); LCMS ES 564.1 $[M+1]^+$.

Example 77 (5R,8S)-3-(2,6-difluorophenyl)-9,9-dimethyl-8-(6-(3-vinyl-1H-1,2,4-triazol-1-yl)pyridin-2-yl)-5,6,7,8-tetrahydro-5,8-methanocinnoline

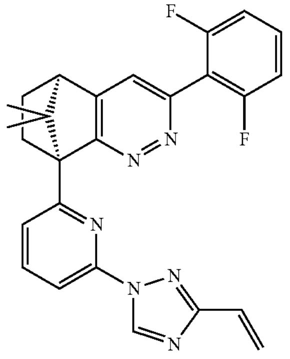 [SMILES: C=Cc1ncn(-c2cccc([C@@]34CC[C@@H](c5cc(-c6c(F)cccc6F)nnc53)C4(C)C)n2)n1]

To a solution of (5R,8S)-3-(2,6-difluorophenyl)-9,9-dimethyl-8-(6-(3-(2-(methylsulfonyl)ethyl)-1H-1,2,4-triazol-1-yl)pyridin-2-yl)-5,6,7,8-tetrahydro-5,8-methanocinnoline (25 mg, 0.047 mmol) in MeOH (0.23 mL) was added sodium methoxide 5.25 M (0.018 mL). The reaction mixture was stirred at 65° C. for 4 h. The mixture was cooled to room temperature, diluted in DCM (10 mL), filtered through celite and concentrated in vacuo. The crude residue was purified by reverse phase chromatography (acetonitrile 30-70%/0.1% formic acid in water) to give the title compound (14 mg, 64%) as a white solid. $^1$H NMR (400 MHz, DMSO-d6) δ 9.35 (s, 1H), 8.15 (t, J=8.0 Hz, 1H), 7.86-7.79 (m, 2H), 7.76 (d, J=7.6 Hz, 1H), 7.68-7.56 (m, 1H), 7.31 (t, J=8.1 Hz, 2H), 6.83 (dd, J=17.4, 10.9 Hz, 1H), 6.28 (dd, J=17.6, 1.8 Hz, 1H), 5.65 (dd, J=11.0, 1.8 Hz, 1H), 3.45-3.21 (m, 2H), 2.47-2.40 (m, 1H), 1.63-1.54 (m, 1H), 1.34-1.23 (m, 1H), 1.08 (s, H), 0.71 (s, 3H). LCMS M/Z (M+H) 457.

Example 78: (5R,8S)-4-chloro-3-(2,6-difluorophenyl)-9,9-dimethyl-8-(6-(3-(2-(methylsulfonyl)ethyl)-1H-1,2,4-triazol-1-yl)pyridin-2-yl)-5,6,7,8-tetrahydro-5,8-methanocinnoline

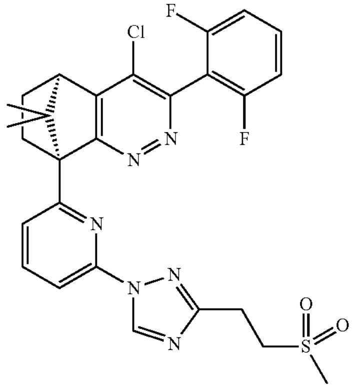 [SMILES: CC1(C)[C@H]2CC[C@]1(c1cccc(-n3cnc(CCS(C)(=O)=O)n3)n1)c1nnc(-c3c(F)cccc3F)c(Cl)c12]

To a solution of (5R,8S)-3-(2,6-difluorophenyl)-9,9-dimethyl-8-(6-(3-(2-(methylsulfonyl)ethyl)-1H-1,2,4-triazol-1-yl)pyridin-2-yl)-5,6,7,8-tetrahydro-5,8-methanocinnoline (50 mg, 0.093 mmol) in DCE (0.46 mL) was added 3-chloroperoxybenzoic acid 77 mass % (23 mg, 0.10 mmol) in one portion at 0° C. The mixture was stirred at 0° C. for 10 min. Then, the reaction mixture was slowly warmed up to room temperature and stirred at this temperature for 2 h. Then, phosphoryl chloride (86 mg, 0.56 mmol) was added and the reaction mixture was stirred at 88° C. for 20 h. The mixture was cooled to room temperature and diluted in DCM (30 mL) and sat. $NaHCO_3$ (35 mL). The two phases were separated and the organic layer was washed with brine, dried over anh. $MgSO_4$, filtered and concentrated in vacuo. The crude residue was purified by reverse phase chromatography (acetonitrile 30-70%/0.1% ammonium hydroxide in water) to give the title compound 12 mg as a white solid. $^1H$ NMR (400 MHz, DMSO-d6) δ 9.35 (s, 1H), 8.16 (t, J=8.0 Hz, 1H), 7.83 (d, J=8.0 Hz, 1H), 7.75 (d, J=7.7 Hz, 1H), 7.73-7.64 (m, 1H), 7.36 (td, J=8.8, 3.8 Hz, 2H), 3.65-3.56 (m, 2H), 3.48 (d, J=4.0 Hz, 1H), 3.47-3.35 (m, 1H), 3.29-3.18 (m, 3H), 3.07 (s, 3H), 1.70-1.60 (m, 1H), 1.39-1.29 (m, 1H), 1.09 (s, 3H), 0.76 (s, 3H). LCMS M/Z (M+H) 572.

The above compounds, together with additional compounds made using the above procedure, are shown in Table 1 below, together with RORc $IC_{50}$ (micromolar) data for selected compounds determined using the assays described below Table 1.

TABLE 1

| | Structure | Name | $IC_{50}$ |
|---|---|---|---|
| 1 | 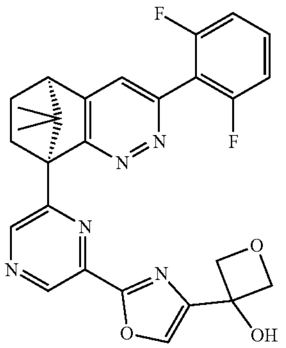 [SMILES: CC1(C)[C@H]2CC[C@]1(c1cncc(-c3nc(C4(O)COC4)co3)n1)c1nnc(-c3c(F)cccc3F)cc12] | 3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]oxetan-3-ol | 0.010 |
| 2 | 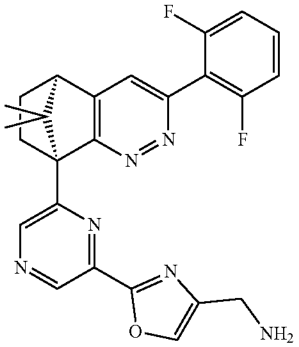 [SMILES: CC1(C)[C@H]2CC[C@]1(c1cncc(-c3nc(CN)co3)n1)c1nnc(-c3c(F)cccc3F)cc12] | [2-[6-[(1S,8R)-5-(2,6-difluorophenyl)-11,11-dimethyl-3,4-diazatricyclo[6.2.1.02.7]undec-2(7),3,5-trien-1-yl]pyrazin-2-yl]oxazol-4-yl] methanamine | 0.021 |
| 3 | 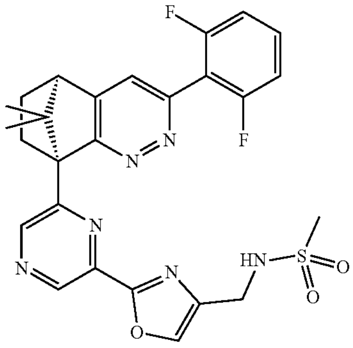 [SMILES: CC1(C)[C@H]2CC[C@]1(c1cncc(-c3nc(CNS(C)(=O)=O)co3)n1)c1nnc(-c3c(F)cccc3F)cc12] | N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide | 0.0063 |

TABLE 1-continued

| | Structure | Name | $IC_{50}$ |
|---|---|---|---|
| 4 | 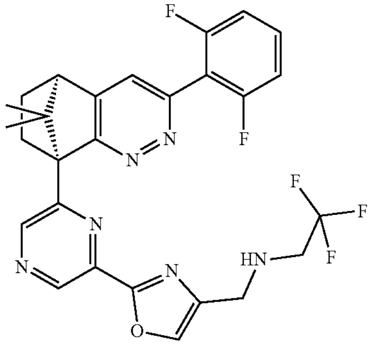 [SMILES: CC1(C)[C@H]2CC[C@]1(c1cncc(-c3nc(CNCC(F)(F)F)co3)n1)c1nnc(-c3c(F)cccc3F)cc12] | 2,2,2-trifluoro-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]ethanamine | 0.0061 |
| 5 | 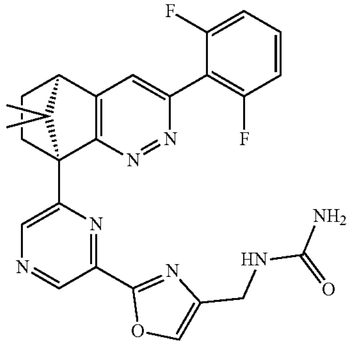 [SMILES: CC1(C)[C@H]2CC[C@]1(c1cncc(-c3nc(CNC(N)=O)co3)n1)c1nnc(-c3c(F)cccc3F)cc12] | [2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methylurea | 0.0087 |
| 6 | 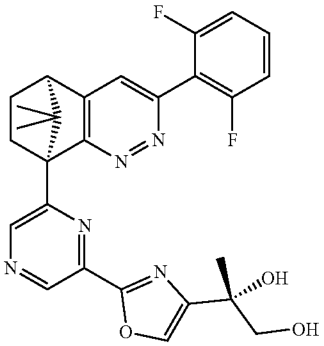 [SMILES: CC1(C)[C@H]2CC[C@]1(c1cncc(-c3nc([C@](C)(O)CO)co3)n1)c1nnc(-c3c(F)cccc3F)cc12] | (2S)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,2-diol | 0.012 |
| 7 | 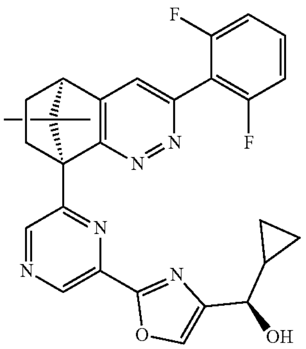 [SMILES: CC1(C)[C@H]2CC[C@]1(c1cncc(-c3nc([C@H](O)C4CC4)co3)n1)c1nnc(-c3c(F)cccc3F)cc12] | (S)-cyclopropyl-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl] methanol | 0.0064 |

TABLE 1-continued

| | Structure | Name | $IC_{50}$ |
|---|---|---|---|
| 8 | 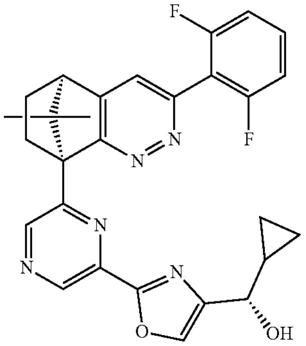 [SMILES: CC1(C)[C@H]2CC[C@]1(c1cncc(-c3nc([C@@H](O)C4CC4)co3)n1)c1nnc(-c3c(F)cccc3F)cc12] | (R)-cyclopropyl-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol | 0.0077 |
| 9 | 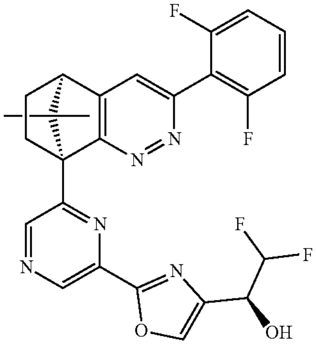 [SMILES: CC1(C)[C@H]2CC[C@]1(c1cncc(-c3nc([C@H](O)C(F)F)co3)n1)c1nnc(-c3c(F)cccc3F)cc12] | (1R)-2,2-difluoro-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol | 0.0063 |
| 10 | 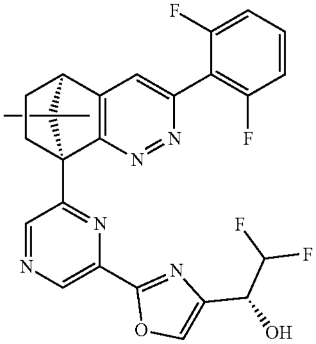 [SMILES: CC1(C)[C@H]2CC[C@]1(c1cncc(-c3nc([C@@H](O)C(F)F)co3)n1)c1nnc(-c3c(F)cccc3F)cc12] | (1S)-2,2-difluoro-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol | 0.0058 |
| 11 | 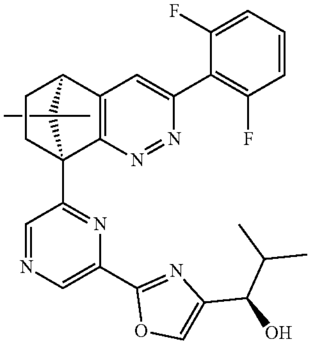 [SMILES: CC(C)[C@@H](O)c1coc(-c2cncc([C@@]34CC[C@@H](c5cc(-c6c(F)cccc6F)nnc53)C4(C)C)n2)n1] | (1S)-2-methyl-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-1-ol | 0.0051 |

TABLE 1-continued

| | Structure | Name | $IC_{50}$ |
|---|---|---|---|
| 12 | 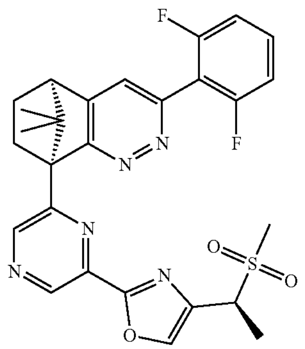 [SMILES: C[C@@H](c1coc(-c2cncc([C@@]34CC[C@@H](c5cc(-c6c(F)cccc6F)nnc53)C4(C)C)n2)n1)S(C)(=O)=O] | 2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1R)-1-methylsulfonylethyl]oxazole | 0.0097 |
| 13 | 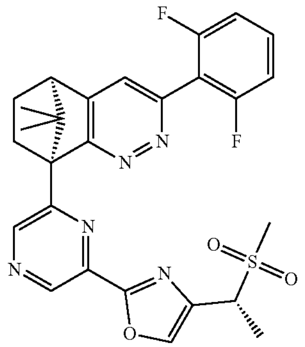 [SMILES: C[C@H](c1coc(-c2cncc([C@@]34CC[C@@H](c5cc(-c6c(F)cccc6F)nnc53)C4(C)C)n2)n1)S(C)(=O)=O] | 2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1S)-1-methylsulfonylethyl]oxazole | 0.0088 |
| 14 | 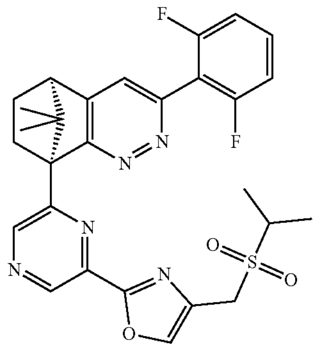 [SMILES: CC(C)S(=O)(=O)Cc1coc(-c2cncc([C@@]34CC[C@@H](c5cc(-c6c(F)cccc6F)nnc53)C4(C)C)n2)n1] | 4-(isopropylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole | 0.007 |
| 15 | 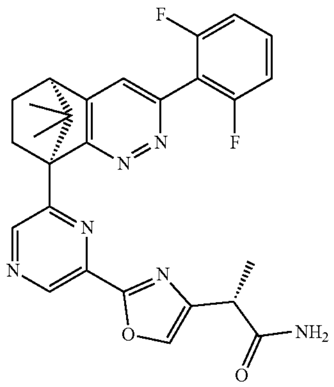 [SMILES: C[C@H](C(N)=O)c1coc(-c2cncc([C@@]34CC[C@@H](c5cc(-c6c(F)cccc6F)nnc53)C4(C)C)n2)n1] | (2S)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide | 0.010 |

TABLE 1-continued

| | Structure | Name | $IC_{50}$ |
|---|---|---|---|
| 16 | 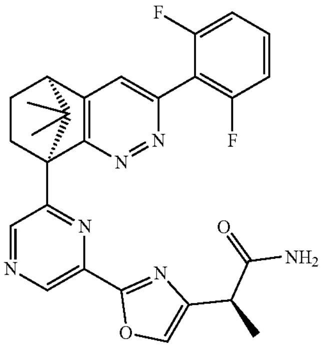 [SMILES: C[C@H](C(N)=O)c1coc(-c2cncc([C@@]34CC[C@@H](c5cc(-c6c(F)cccc6F)nnc53)C4(C)C)n2)n1] | (2R)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide | 0.0096 |
| 17 | 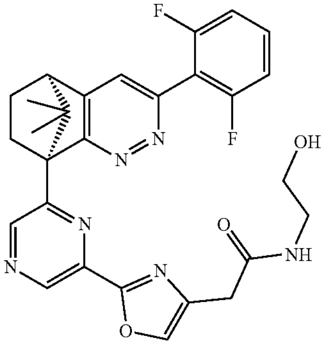 [SMILES: CC1(C)[C@H]2CC[C@]1(c1cncc(-c3nc(CC(=O)NCCO)co3)n1)c1nnc(-c3c(F)cccc3F)cc12] | N-(2-hydroxyethyl)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide | 0.014 |
| 18 | 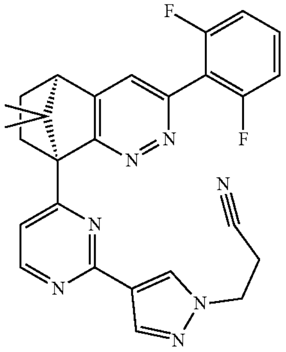 [SMILES: CC1(C)[C@H]2CC[C@]1(c1ccnc(-c3cnn(CCC#N)c3)n1)c1nnc(-c3c(F)cccc3F)cc12] | 3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanenitrile | 0.0030 |
| 19 | 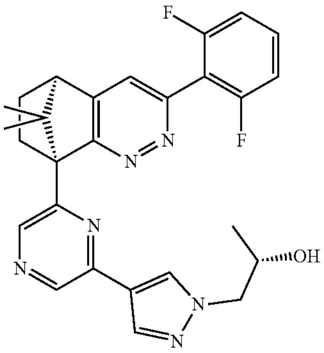 [SMILES: C[C@H](O)Cn1cc(-c2cncc([C@@]34CC[C@@H](c5cc(-c6c(F)cccc6F)nnc53)C4(C)C)n2)cn1] | (2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol | 0.0040 |

TABLE 1-continued

| | Structure | Name | $IC_{50}$ |
|---|---|---|---|
| 20 | 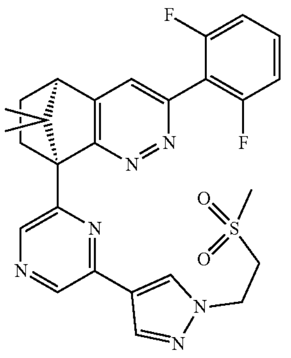 [SMILES: CC1(C)[C@H]2CC[C@]1(c1cncc(-c3cnn(CCS(C)(=O)=O)c3)n1)c1nnc(-c3c(F)cccc3F)cc12] | (1S,8R)-5-(2,6-difluorophenyl)-11,11-dimethyl-1-[6-[1-(2-methylsulfonylethyl)pyrazol-4-yl]pyrazin-2-yl]-3,4-diazatricyclo[6.2.1.02,7]undeca-2(7),3,5-triene | 0.0051 |
| 21 | 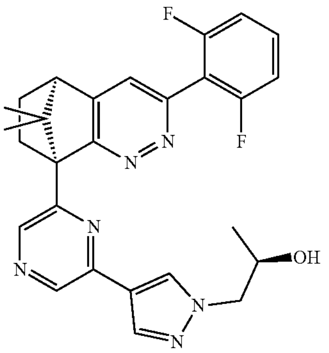 [SMILES: C[C@@H](O)Cn1cc(-c2cncc([C@@]34CC[C@@H](c5cc(-c6c(F)cccc6F)nnc53)C4(C)C)n2)cn1] | (2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol | 0.0065 |
| 22 | 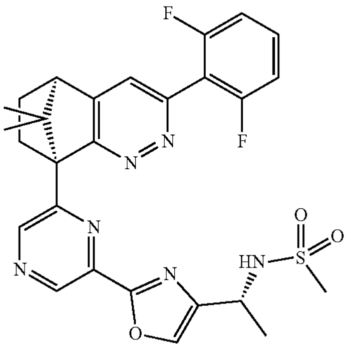 [SMILES: C[C@@H](NS(C)(=O)=O)c1coc(-c2cncc([C@@]34CC[C@@H](c5cc(-c6c(F)cccc6F)nnc53)C4(C)C)n2)n1] | N-[(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]methanesulfonamide | 0.0074 |
| 23 | 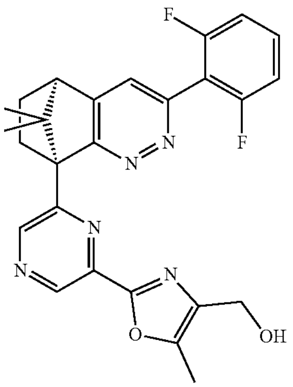 [SMILES: Cc1oc(-c2cncc([C@@]34CC[C@@H](c5cc(-c6c(F)cccc6F)nnc53)C4(C)C)n2)nc1CO] | [5-methyl-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol | 0.0091 |

TABLE 1-continued

| | Structure | Name | $IC_{50}$ |
|---|---|---|---|
| 24 | 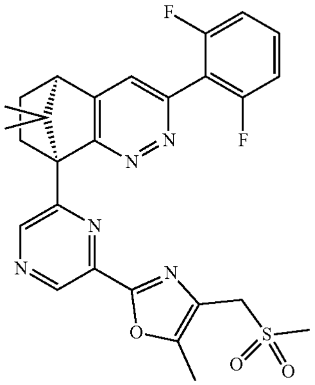 | 5-methyl-4-(methylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole | 0.014 |
| 25 | 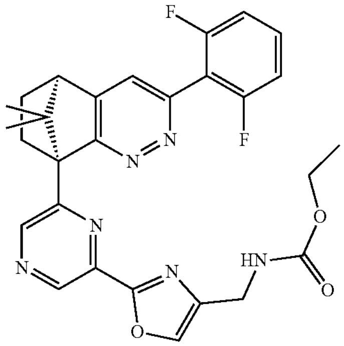 [SMILES: CCOC(=O)NCc1coc(-c2cncc([C@@]34CC[C@@H](c5cc(-c6c(F)cccc6F)nnc53)C4(C)C)n2)n1] | ethyl N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]carbamate | 0.0056 |
| 26 | 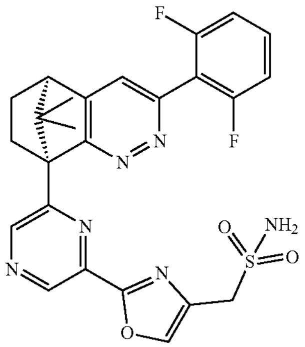 [SMILES: CC1(C)[C@H]2CC[C@]1(c1cncc(-c3nc(CS(N)(=O)=O)co3)n1)c1nnc(-c3c(F)cccc3F)cc12] | [2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanesulfonamide | 0.0064 |
| 27 | 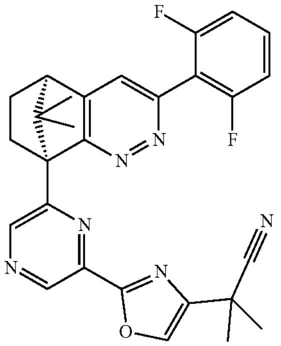 [SMILES: CC(C)(C#N)c1coc(-c2cncc([C@@]34CC[C@@H](c5cc(-c6c(F)cccc6F)nnc53)C4(C)C)n2)n1] | 2-methyl-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile | 0.0036 |

TABLE 1-continued

| | Structure | Name | $IC_{50}$ |
|---|---|---|---|
| 28 | 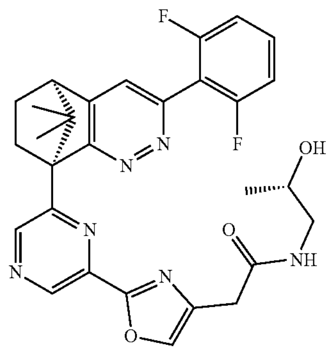 [SMILES: C[C@H](O)CNC(=O)Cc1coc(-c2cncc([C@@]34CC[C@@H](c5cc(-c6c(F)cccc6F)nnc53)C4(C)C)n2)n1] | 2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]-N-[(2S)-2-hydroxypropyl]acetamide | 0.013 |
| 29 | 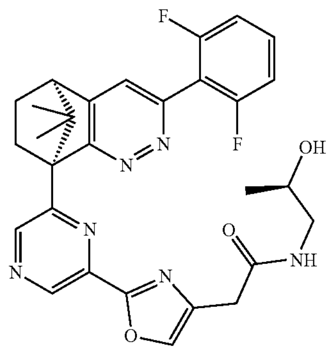 [SMILES: C[C@@H](O)CNC(=O)Cc1coc(-c2cncc([C@@]34CC[C@@H](c5cc(-c6c(F)cccc6F)nnc53)C4(C)C)n2)n1] | 2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]-N-[(2R)-2-hydroxypropyl]acetamide | 0.013 |
| 30 | 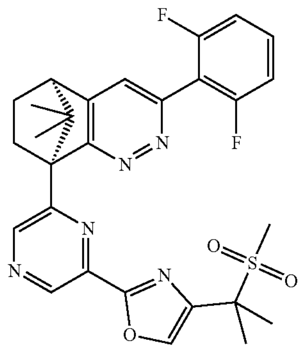 [SMILES: CC1(C)[C@H]2CC[C@]1(c1cncc(-c3nc(C(C)(C)S(C)(=O)=O)co3)n1)c1nnc(-c3c(F)cccc3F)cc12] | 4-(1-methyl-1-methylsulfonyl-ethyl)-2-[6-[1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole | 0.0092 |
| 31 | 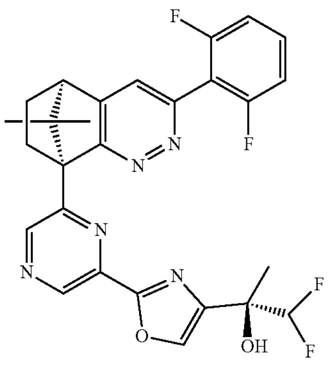 [SMILES: CC1(C)[C@H]2CC[C@]1(c1cncc(-c3nc([C@@](C)(O)C(F)F)co3)n1)c1nnc(-c3c(F)cccc3F)cc12] | (2R)-1,1-difluoro-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol | 0.0059 |

TABLE 1-continued

| | Structure | Name | $IC_{50}$ |
| --- | --- | --- | --- |
| 32 | 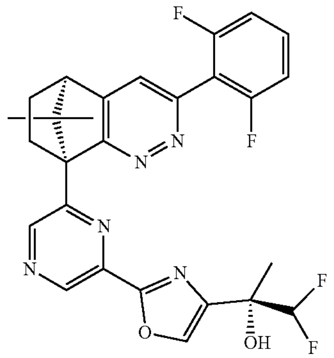 [SMILES: CC1(C)[C@H]2CC[C@]1(c1cncc(-c3nc([C@](C)(O)C(F)F)co3)n1)c1nnc(-c3c(F)cccc3F)cc12] | (2S)-1,1-difluoro-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol | 0.0060 |
| 33 | 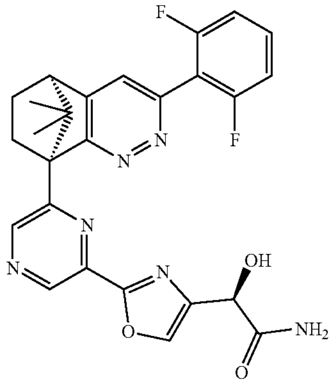 [SMILES: CC1(C)[C@H]2CC[C@]1(c1cncc(-c3nc([C@@H](O)C(N)=O)co3)n1)c1nnc(-c3c(F)cccc3F)cc12] | (2R)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide | 0.021 |
| 34 | 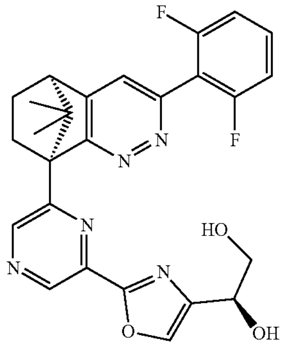 [SMILES: CC1(C)[C@H]2CC[C@]1(c1cncc(-c3nc([C@H](O)CO)co3)n1)c1nnc(-c3c(F)cccc3F)cc12] | (1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol | 0.013 |
| 35 | 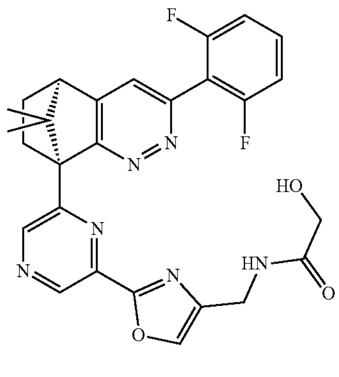 [SMILES: CC1(C)[C@H]2CC[C@]1(c1cncc(-c3nc(CNC(=O)CO)co3)n1)c1nnc(-c3c(F)cccc3F)cc12] | 2-hydroxy-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]acetamide | 0.017 |

TABLE 1-continued

| | Structure | Name | $IC_{50}$ |
|---|---|---|---|
| 36 | 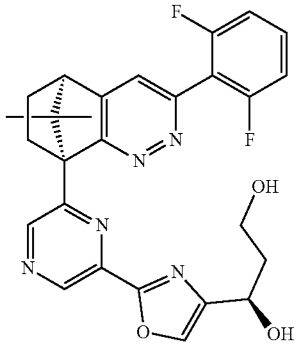 [SMILES: CC1(C)[C@H]2CC[C@]1(c1cncc(-c3nc([C@H](O)CCO)co3)n1)c1nnc(-c3c(F)cccc3F)cc12] | (1S)-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,3-diol | 0.017 |
| 37 | 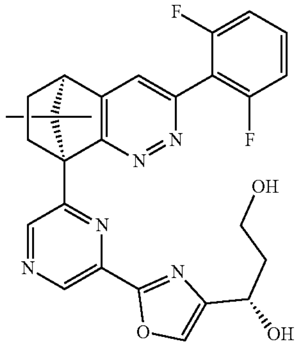 [SMILES: CC1(C)[C@H]2CC[C@]1(c1cncc(-c3nc([C@@H](O)CCO)co3)n1)c1nnc(-c3c(F)cccc3F)cc12] | (1R)-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,3-diol | 0.017 |
| 38 | 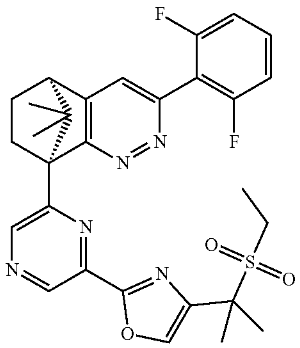 [SMILES: CCS(=O)(=O)C(C)(C)c1coc(-c2cncc([C@@]34CC[C@@H](c5cc(-c6c(F)cccc6F)nnc53)C4(C)C)n2)n1] | 4-(1-ethylsulfonyl-1-methyl-ethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole | 0.0095 |
| 39 | 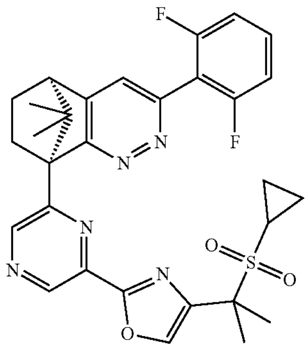 [SMILES: CC1(C)[C@H]2CC[C@]1(c1cncc(-c3nc(C(C)(C)S(=O)(=O)C4CC4)co3)n1)c1nnc(-c3c(F)cccc3F)cc12] | 4-(1-cyclopropylsulfonyl-1-methyl-ethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole | 0.012 |

TABLE 1-continued

| | Structure | Name | $IC_{50}$ |
|---|---|---|---|
| 40 | 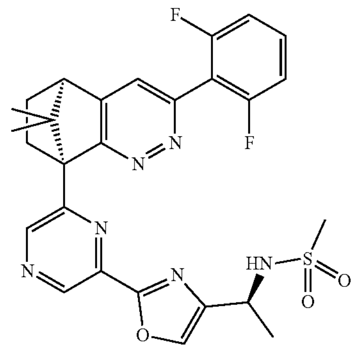 [SMILES: C[C@H](NS(C)(=O)=O)c1coc(-c2cncc([C@@]34CC[C@@H](c5cc(-c6c(F)cccc6F)nnc53)C4(C)C)n2)n1] | N-[(1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]methanesulfonamide | 0.012 |
| 41 | 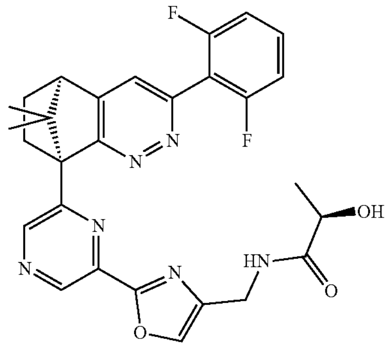 [SMILES: C[C@@H](O)C(=O)NCc1coc(-c2cncc([C@@]34CC[C@@H](c5cc(-c6c(F)cccc6F)nnc53)C4(C)C)n2)n1] | (2S)-2-hydroxy-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]propanamide | 0.027 |
| 42 | 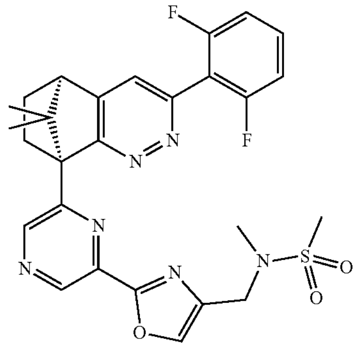 [SMILES: CN(Cc1coc(-c2cncc([C@@]34CC[C@@H](c5cc(-c6c(F)cccc6F)nnc53)C4(C)C)n2)n1)S(C)(=O)=O] | N-methyl-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide | 0.018 |
| 43 | 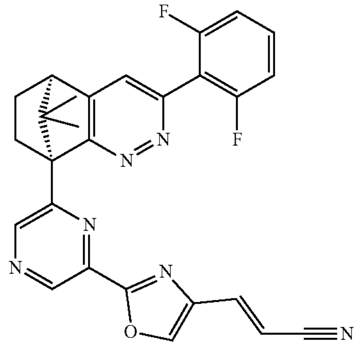 [SMILES: CC1(C)[C@H]2CC[C@]1(c1cncc(-c3nc(/C=C/C#N)co3)n1)c1nnc(-c3c(F)cccc3F)cc12] | (E)-3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]prop-2-enenitrile | 0.011 |

TABLE 1-continued

| | Structure | Name | $IC_{50}$ |
|---|---|---|---|
| 44 | 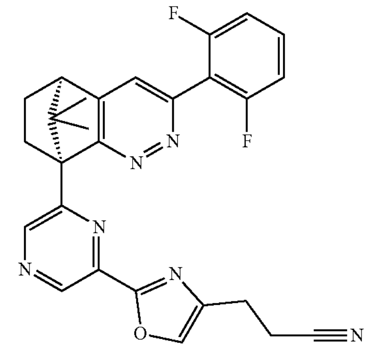 [SMILES: CC1(C)[C@H]2CC[C@]1(c1cncc(-c3nc(CCC#N)co3)n1)c1nnc(-c3c(F)cccc3F)cc12] | 3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile | 0.012 |
| 45 | 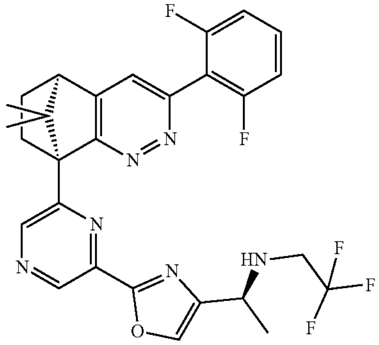 [SMILES: C[C@H](NCC(F)(F)F)c1coc(-c2cncc([C@@]34CC[C@@H](c5cc(-c6c(F)cccc6F)nnc53)C4(C)C)n2)n1] | 2,2,2-trifluoro-N-[(1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]ethanamine | 0.019 |
| 46 | 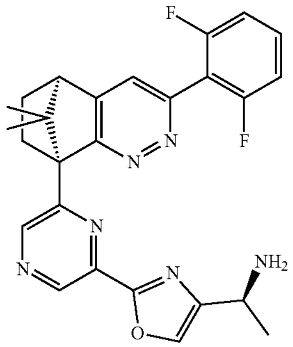 [SMILES: C[C@H](N)c1coc(-c2cncc([C@@]34CC[C@@H](c5cc(-c6c(F)cccc6F)nnc53)C4(C)C)n2)n1] | (1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanamine | 0.055 |
| 47 | 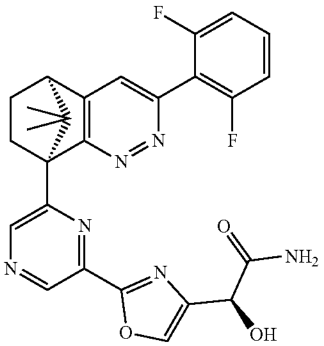 [SMILES: CC1(C)[C@H]2CC[C@]1(c1cncc(-c3nc([C@H](O)C(N)=O)co3)n1)c1nnc(-c3c(F)cccc3F)cc12] | (2R)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide | 0.034 |

TABLE 1-continued

| | Structure | Name | IC$_{50}$ |
|---|---|---|---|
| 48 | 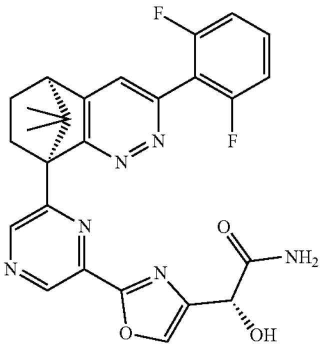 [SMILES: CC1(C)[C@H]2CC[C@]1(c1cncc(-c3nc([C@@H](O)C(N)=O)co3)n1)c1nnc(-c3c(F)cccc3F)cc12] | (2S)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide | 0.038 |
| 49 | 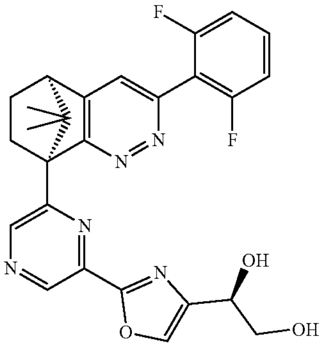 [SMILES: CC1(C)[C@H]2CC[C@]1(c1cncc(-c3nc([C@@H](O)CO)co3)n1)c1nnc(-c3c(F)cccc3F)cc12] | (1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol | 0.019 |
| 50 | 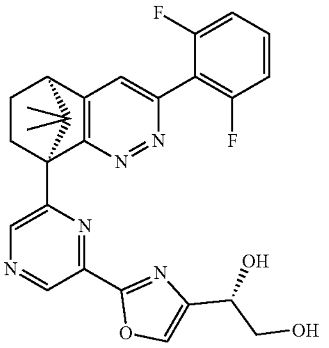 [SMILES: CC1(C)[C@H]2CC[C@]1(c1cncc(-c3nc([C@H](O)CO)co3)n1)c1nnc(-c3c(F)cccc3F)cc12] | (1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol | 0.019 |
| 51 | 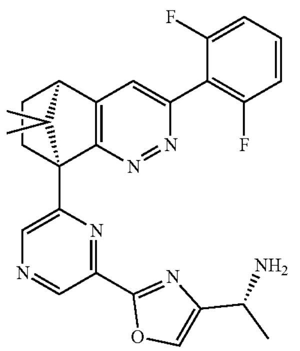 [SMILES: C[C@@H](N)c1coc(-c2cncc([C@@]34CC[C@@H](c5cc(-c6c(F)cccc6F)nnc53)C4(C)C)n2)n1] | (1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanamine | 0.015 |

TABLE 1-continued

| | Structure | Name | $IC_{50}$ |
|---|---|---|---|
| 52 | 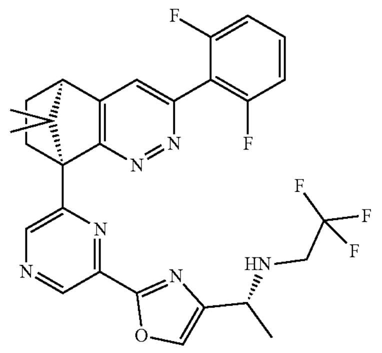 [SMILES: C[C@@H](NCC(F)(F)F)c1coc(-c2cncc([C@@]34CC[C@@H](c5cc(-c6c(F)cccc6F)nnc53)C4(C)C)n2)n1] | 2,2,2-trifluoro-N-[(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]ethanamine | 0.0054 |
| 53 | 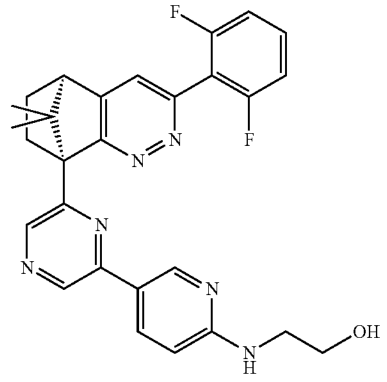 [SMILES: CC1(C)[C@H]2CC[C@]1(c1cncc(-c3ccc(NCCO)nc3)n1)c1nnc(-c3c(F)cccc3F)cc12] | 2-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]amino]ethanol | 0.0050 |
| 54 | 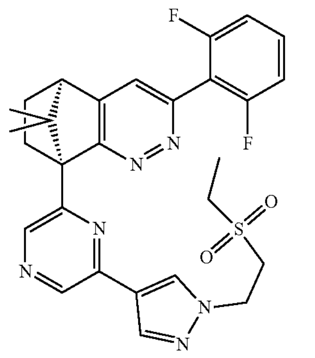 [SMILES: CCS(=O)(=O)CCn1cc(-c2cncc([C@@]34CC[C@@H](c5cc(-c6c(F)cccc6F)nnc53)C4(C)C)n2)cn1] | (1S,8R)-5-(2,6-difluorophenyl)-1-[6-[1-(2-ethylsulfonylethyl)pyrazol-4-yl]pyrazin-2-yl]-11,11-dimethyl-3,4-diazatricyclo[6.2.1.02,7]undeca-2(7),3,5-triene | 0.0042 |
| 55 | 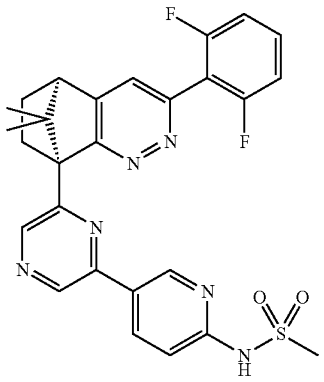 | N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide | 0.0057 |

TABLE 1-continued

| | Structure | Name | $IC_{50}$ |
|---|---|---|---|
| 56 | 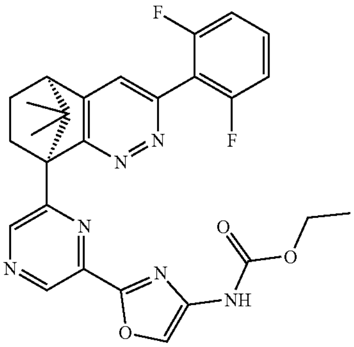 [SMILES: CCOC(=O)Nc1coc(-c2cncc([C@@]34CC[C@@H](c5cc(-c6c(F)cccc6F)nnc53)C4(C)C)n2)n1] | ethyl N-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]carbamate | 0.0081 |
| 57 | 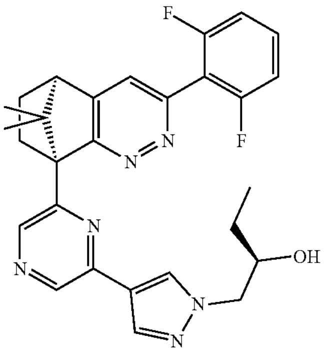 [SMILES: CC[C@@H](O)Cn1cc(-c2cncc([C@@]34CC[C@@H](c5cc(-c6c(F)cccc6F)nnc53)C4(C)C)n2)cn1] | (2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol | 0.0045 |
| 58 | 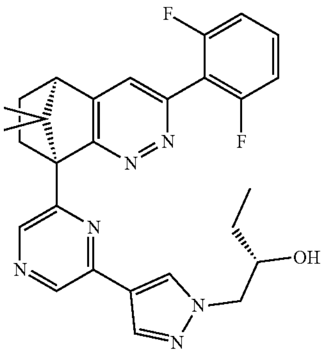 [SMILES: CC[C@H](O)Cn1cc(-c2cncc([C@@]34CC[C@@H](c5cc(-c6c(F)cccc6F)nnc53)C4(C)C)n2)cn1] | (2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol | 0.0045 |
| 59 | 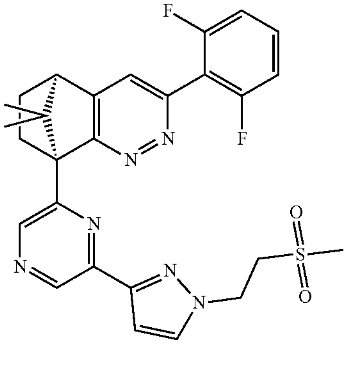 | (1S,8R)-5-(2,6-difluorophenyl)-11,11-dimethyl-1-[6-[1-(2-methylsulfonylethyl)pyrazol-3-yl]pyrazin-2-yl]-3,4-diazatricyclo[6.2.1.02,7]undeca-2(7),3,5-triene | 0.0046 |

TABLE 1-continued

| | Structure | Name | $IC_{50}$ |
|---|---|---|---|
| 60 | 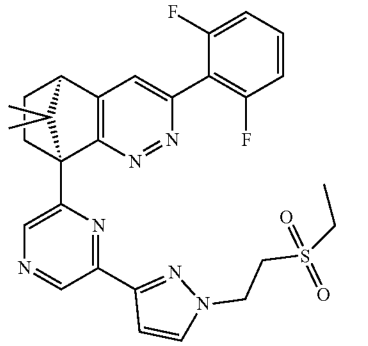 [SMILES: CCS(=O)(=O)CCn1ccc(-c2cncc([C@@]34CC[C@@H](c5cc(-c6c(F)cccc6F)nnc53)C4(C)C)n2)n1] | (1S,8R)-5-(2,6-difluorophenyl)-1-[6-[1-(2-ethylsulfonylethyl)pyrazol-3-yl]pyrazin-2-yl]-11,11-dimethyl-3,4-diazatricyclo[6.2.1.02,7]undeca-2(7),3,5-triene | 0.0064 |
| 61 | 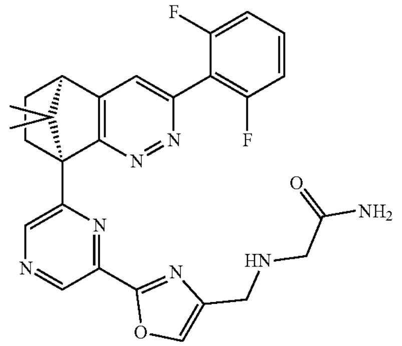 [SMILES: CC1(C)[C@H]2CC[C@]1(c1cncc(-c3nc(CNCC(N)=O)co3)n1)c1nnc(-c3c(F)cccc3F)cc12] | 2-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methylamino]acetamide | 0.014 |
| 62 | 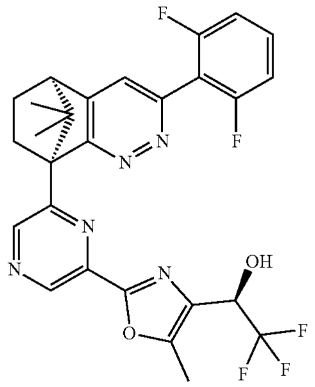 [SMILES: Cc1oc(-c2cncc([C@@]34CC[C@@H](c5cc(-c6c(F)cccc6F)nnc53)C4(C)C)n2)nc1[C@@H](O)C(F)(F)F] | (1R)-2,2,2-trifluoro-1-[5-methyl-2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol | 0.0091 |
| 63 | 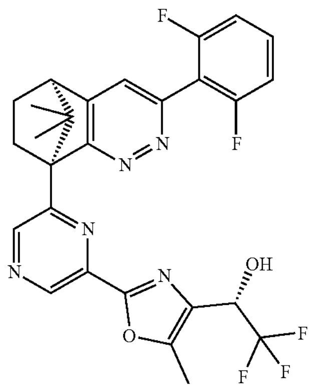 [SMILES: Cc1oc(-c2cncc([C@@]34CC[C@@H](c5cc(-c6c(F)cccc6F)nnc53)C4(C)C)n2)nc1[C@H](O)C(F)(F)F] | (1S)-2,2,2-trifluoro-1-[5-methyl-2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol | 0.0084 |

TABLE 1-continued

| | Structure | Name | $IC_{50}$ |
|---|---|---|---|
| 64 | 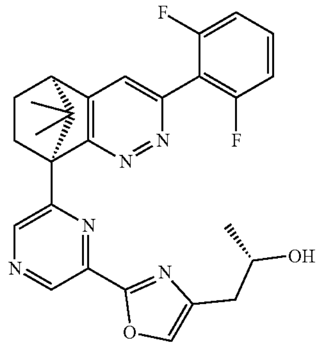 [SMILES: C[C@H](O)Cc1coc(-c2cncc([C@@]34CC[C@@H](c5cc(-c6c(F)cccc6F)nnc53)C4(C)C)n2)n1] | (2R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol | 0.0074 |
| 65 | 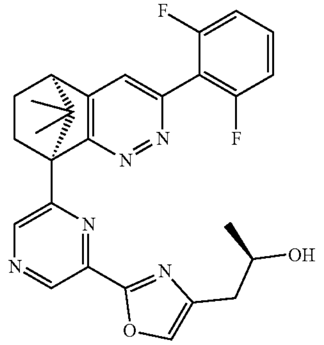 [SMILES: C[C@@H](O)Cc1coc(-c2cncc([C@@]34CC[C@@H](c5cc(-c6c(F)cccc6F)nnc53)C4(C)C)n2)n1] | (2S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol | 0.0076 |
| 66 | 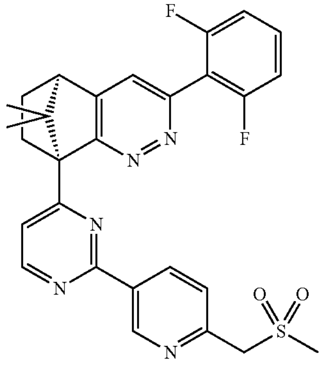 | (1S,8R)-5-(2,6-difluorophenyl)-11,11-dimethyl-1-[2-[6-(methylsulfonylmethyl)-3-pyridyl]pyrimidin-4-yl]-3,4-diazatricyclo[6.2.1.02,7]undeca-2(7),3,5-triene | 0.0080 |
| 67 | 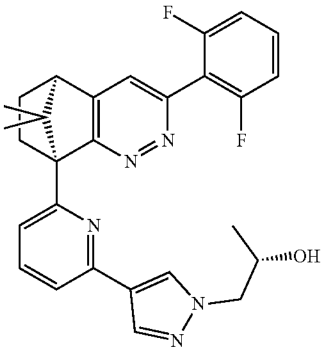 [SMILES: C[C@H](O)Cn1cc(-c2cccc([C@@]34CC[C@@H](c5cc(-c6c(F)cccc6F)nnc53)C4(C)C)n2)cn1] | (2R)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol | 0.0037 |

TABLE 1-continued

| | Structure | Name | $IC_{50}$ |
|---|---|---|---|
| 68 | 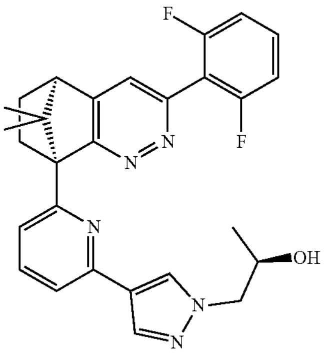 [SMILES: C[C@@H](O)Cn1cc(-c2cccc([C@@]34CC[C@@H](c5cc(-c6c(F)cccc6F)nnc53)C4(C)C)n2)cn1] | (2S)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol | 0.0030 |
| 69 | 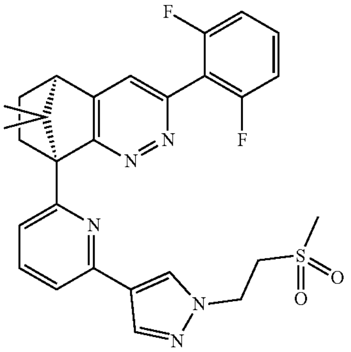 [SMILES: CC1(C)[C@H]2CC[C@]1(c1cccc(-c3cnn(CCS(C)(=O)=O)c3)n1)c1nnc(-c3c(F)cccc3F)cc12] | (1S,8R)-5-(2,6-difluorophenyl)-11,11-dimethyl-1-[6-[1-(2-methylsulfonylethyl)pyrazol-4-yl]-2-pyridyl]-3,4-diazatricyclo[6.2.1.02,7]undeca-2(7),3,5-triene | 0.0032 |
| 70 | 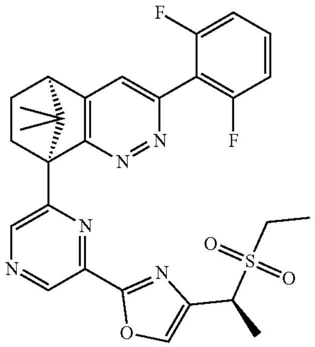 [SMILES: CCS(=O)(=O)[C@@H](C)c1coc(-c2cncc([C@@]34CC[C@@H](c5cc(-c6c(F)cccc6F)nnc53)C4(C)C)n2)n1] | 2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1R)-1-ethylsulfonylethyl]oxazole | 0.0058 |
| 71 | 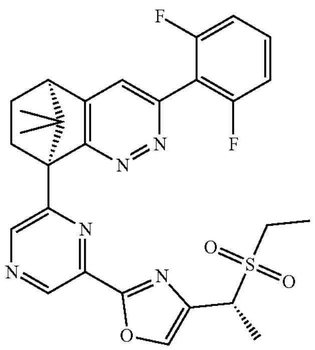 [SMILES: CCS(=O)(=O)[C@H](C)c1coc(-c2cncc([C@@]34CC[C@@H](c5cc(-c6c(F)cccc6F)nnc53)C4(C)C)n2)n1] | 2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1S)-1-ethylsulfonylethyl]oxazole | 0.0070 |

TABLE 1-continued

| | Structure | Name | $IC_{50}$ |
|---|---|---|---|
| 72 | 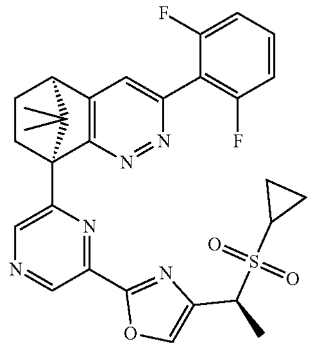 [SMILES: C[C@@H](c1coc(-c2cncc([C@@]34CC[C@@H](c5cc(-c6c(F)cccc6F)nnc53)C4(C)C)n2)n1)S(=O)(=O)C1CC1] | 4-[(1R)-1-cyclopropylsulfonylethyl]-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole | 0.0071 |
| 73 | 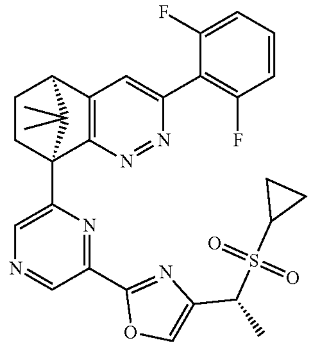 [SMILES: C[C@H](c1coc(-c2cncc([C@@]34CC[C@@H](c5cc(-c6c(F)cccc6F)nnc53)C4(C)C)n2)n1)S(=O)(=O)C1CC1] | 4-[(1S)-1-cyclopropylsulfonylethyl]-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole | 0.0073 |
| 74 | 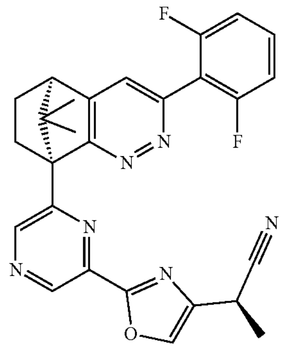 [SMILES: C[C@H](C#N)c1coc(-c2cncc([C@@]34CC[C@@H](c5cc(-c6c(F)cccc6F)nnc53)C4(C)C)n2)n1] | (2R)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile | 0.0056 |
| 75 | 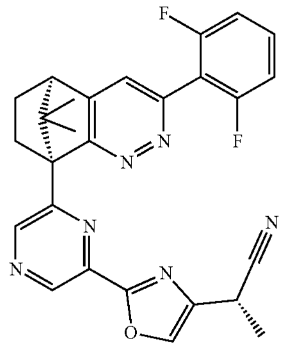 [SMILES: C[C@@H](C#N)c1coc(-c2cncc([C@@]34CC[C@@H](c5cc(-c6c(F)cccc6F)nnc53)C4(C)C)n2)n1] | (2S)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile | 0.0070 |

TABLE 1-continued

| | Structure | Name | $IC_{50}$ |
|---|---|---|---|
| 76 | 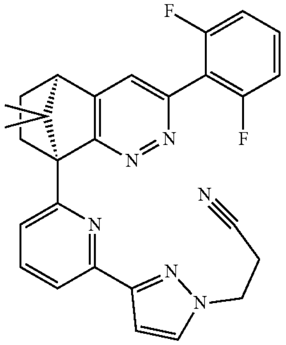 [SMILES: CC1(C)[C@H]2CC[C@]1(c1cccc(-c3ccn(CCC#N)n3)n1)c1nnc(-c3c(F)cccc3F)cc12] | 3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanenitrile | 0.0054 |
| 77 | 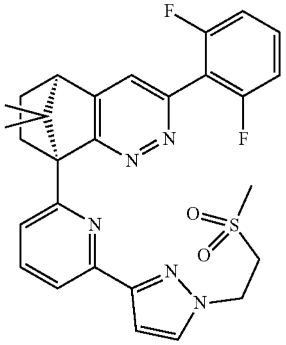 [SMILES: CC1(C)[C@H]2CC[C@]1(c1cccc(-c3ccn(CCS(C)(=O)=O)n3)n1)c1nnc(-c3c(F)cccc3F)cc12] | (1S,8R)-5-(2,6-difluorophenyl)-11,11-dimethyl-1-[6-[1-(2-methylsulfonylethyl)pyrazol-3-yl]-2-pyridyl]-3,4-diazatricyclo[6.2.1.02,7]undeca-2(7),3,5-triene | 0.0061 |
| 78 | 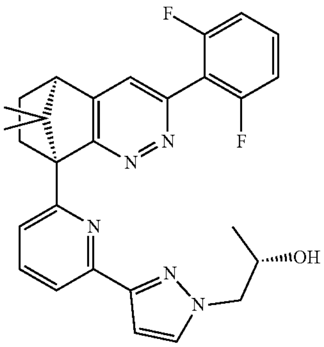 [SMILES: C[C@H](O)Cn1ccc(-c2cccc([C@@]34CC[C@@H](c5cc(-c6c(F)cccc6F)nnc53)C4(C)C)n2)n1] | (2R)-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol | 0.0067 |
| 79 | 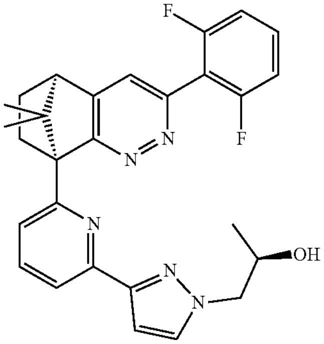 [SMILES: C[C@@H](O)Cn1ccc(-c2cccc([C@@]34CC[C@@H](c5cc(-c6c(F)cccc6F)nnc53)C4(C)C)n2)n1] | (2S)-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol | 0.0066 |

TABLE 1-continued

| | Structure | Name | $IC_{50}$ |
|---|---|---|---|
| 80 | 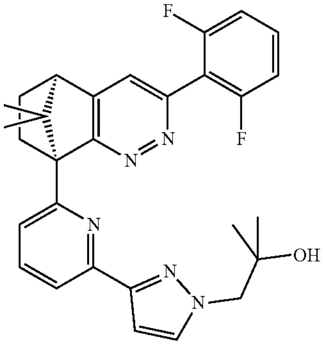 [SMILES: CC(C)(O)Cn1ccc(-c2cccc([C@@]34CC[C@@H](c5cc(-c6c(F)cccc6F)nnc53)C4(C)C)n2)n1] | 2-methyl-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol | 0.0073 |
| 81 | 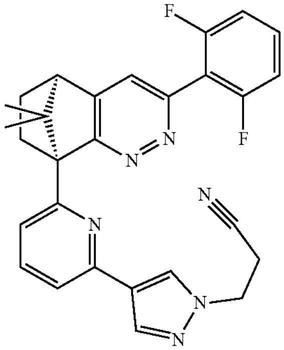 [SMILES: CC1(C)[C@H]2CC[C@]1(c1cccc(-c3cnn(CCC#N)c3)n1)c1nnc(-c3c(F)cccc3F)cc12] | 3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanenitrile | 0.0035 |
| 82 | 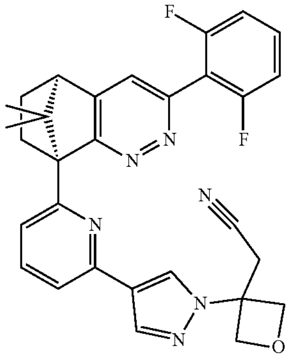 [SMILES: CC1(C)[C@H]2CC[C@]1(c1cccc(-c3cnn(C4(CC#N)COC4)c3)n1)c1nnc(-c3c(F)cccc3F)cc12] | 2-[3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]oxetan-3-yl]acetonitrile | 0.0046 |
| 83 | 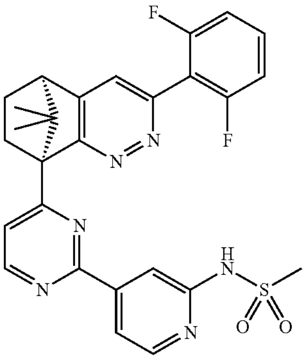 [SMILES: CC1(C)[C@H]2CC[C@]1(c1ccnc(-c3ccnc(NS(C)(=O)=O)c3)n1)c1nnc(-c3c(F)cccc3F)cc12] | N-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide | 0.034 |

TABLE 1-continued

| | Structure | Name | $IC_{50}$ |
|---|---|---|---|
| 84 | 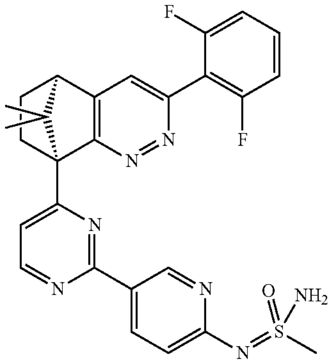 | (1S,8R)-1-[2-[6-[(amino-methyl-oxo-lambda6-sulfanylidene)amino]-3-pyridyl]pyrimidin-4-yl]-5-(2,6-difluorophenyl)-11,11-dimethyl-3,4-diazatricyclo[6.2.1.02,7]undeca-2(7),3,5-triene | 0.011 |
| 85 | 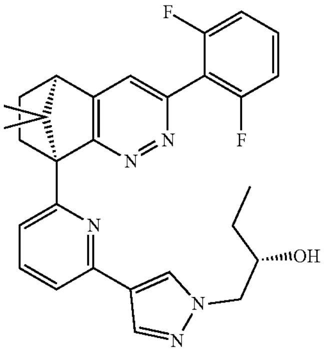 [SMILES: CC[C@H](O)Cn1cc(-c2cccc([C@@]34CC[C@@H](c5cc(-c6c(F)cccc6F)nnc53)C4(C)C)n2)cn1] | (2R)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]butan-2-ol | 0.0069 |
| 86 | 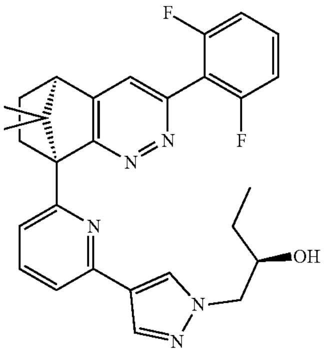 [SMILES: CC[C@@H](O)Cn1cc(-c2cccc([C@@]34CC[C@@H](c5cc(-c6c(F)cccc6F)nnc53)C4(C)C)n2)cn1] | (2S)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]butan-2-ol | 0.0068 |
| 87 | 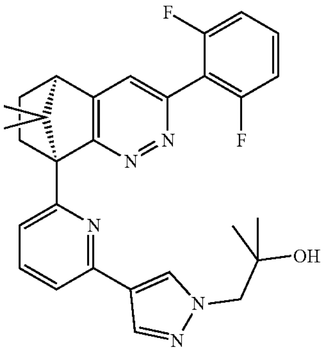 [SMILES: CC(C)(O)Cn1cc(-c2cccc([C@@]34CC[C@@H](c5cc(-c6c(F)cccc6F)nnc53)C4(C)C)n2)cn1] | 2-methyl-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol | 0.0090 |

TABLE 1-continued

| | Structure | Name | $IC_{50}$ |
|---|---|---|---|
| 88 | 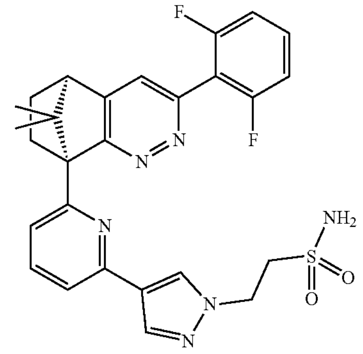 [SMILES: CC1(C)[C@H]2CC[C@]1(c1cccc(-c3cnn(CCS(N)(=O)=O)c3)n1)c1nnc(-c3c(F)cccc3F)cc12] | 2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethanesulfonamide | 0.0074 |
| 89 | 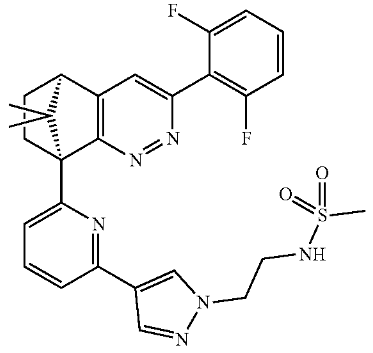 | N-[2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethyl]methanesulfonamide | 0.0079 |
| 90 | 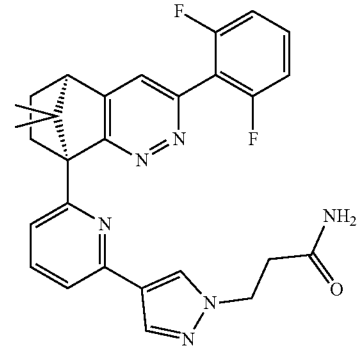 [SMILES: CC1(C)[C@H]2CC[C@]1(c1cccc(-c3cnn(CCC(N)=O)c3)n1)c1nnc(-c3c(F)cccc3F)cc12] | 3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide | 0.0077 |
| 91 | 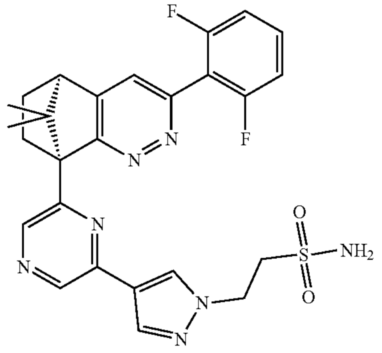 [SMILES: CC1(C)[C@H]2CC[C@]1(c1cncc(-c3cnn(CCS(N)(=O)=O)c3)n1)c1nnc(-c3c(F)cccc3F)cc12] | 2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanesulfonamide | 0.011 |

TABLE 1-continued

| | Structure | Name | $IC_{50}$ |
|---|---|---|---|
| 92 | 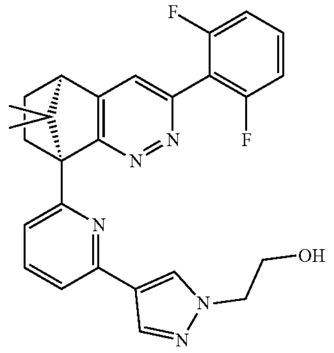 [SMILES: CC1(C)[C@H]2CC[C@]1(c1cccc(-c3cnn(CCO)c3)n1)c1nnc(-c3c(F)cccc3F)cc12] | 2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethanol | 0.0071 |
| 93 | 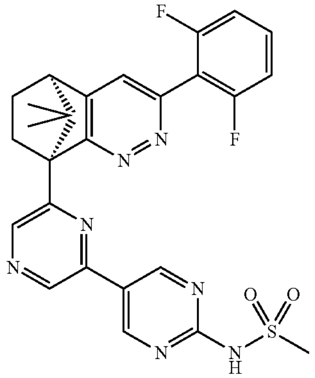 | N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]methanesulfonamide | 0.012 |
| 94 | 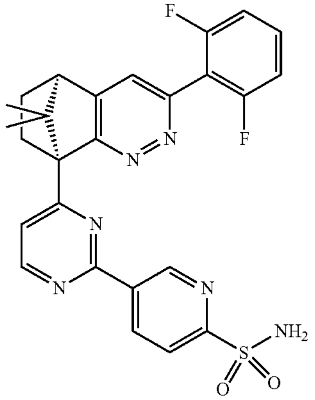 [SMILES: CC1(C)[C@H]2CC[C@]1(c1ccnc(-c3ccc(S(N)(=O)=O)nc3)n1)c1nnc(-c3c(F)cccc3F)cc12] | 5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyridine-2-sulfonamide | 0.0091 |
| 95 | 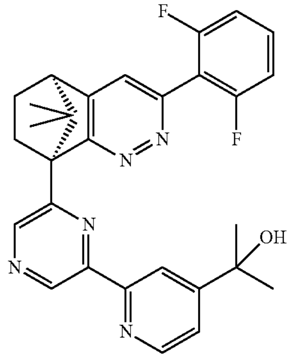 | 2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-pyridyl]propan-2-ol | 0.021 |

TABLE 1-continued

| | Structure | Name | $IC_{50}$ |
|---|---|---|---|
| 96 | 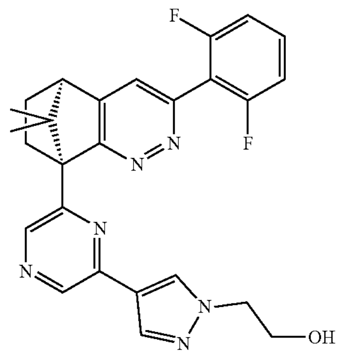 [SMILES: CC1(C)[C@H]2CC[C@]1(c1cncc(-c3cnn(CCO)c3)n1)c1nnc(-c3c(F)cccc3F)cc12] | 2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanol | 0.0083 |
| 97 | 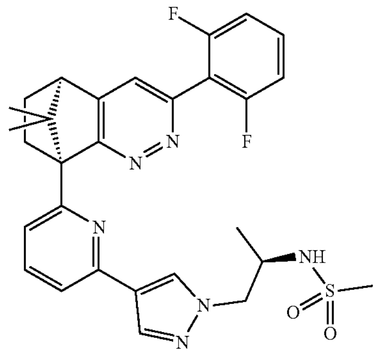 | N-[(1S)-1-methyl-2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethyl]methanesulfonamide | 0.0065 |
| 98 | 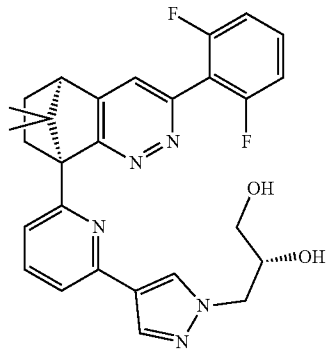 [SMILES: CC1(C)[C@H]2CC[C@]1(c1cccc(-c3cnn(C[C@@H](O)CO)c3)n1)c1nnc(-c3c(F)cccc3F)cc12] | (2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol | 0.0085 |
| 99 | 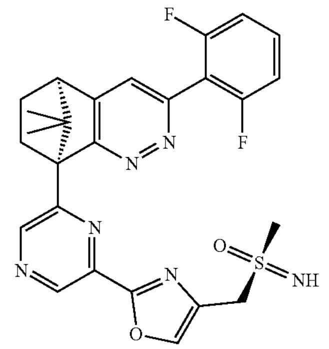 [SMILES: CC1(C)[C@H]2CC[C@]1(c1cncc(-c3nc(C[S@@](C)(=N)=O)co3)n1)c1nnc(-c3c(F)cccc3F)cc12] | imino-methyl-oxo-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl-lambda6-sulfane | 0.020 |

TABLE 1-continued

| | Structure | Name | $IC_{50}$ |
|---|---|---|---|
| 100 | 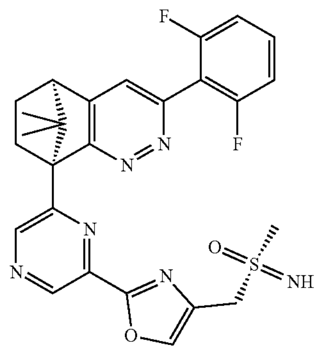 [SMILES: CC1(C)[C@H]2CC[C@]1(c1cncc(-c3nc(C[S@](C)(=N)=O)co3)n1)c1nnc(-c3c(F)cccc3F)cc12] | imino-methyl-oxo-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]-lambda6-sulfane | 0.034 |
| 101 | 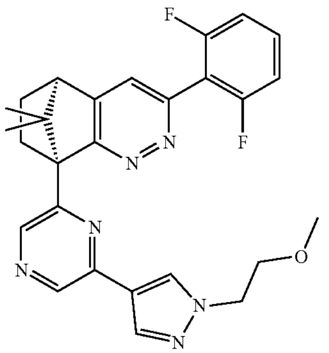 | (1S,8R)-5-(2,6-difluorophenyl)-1-[6-[1-(2-methoxyethyl)pyrazol-4-yl]pyrazin-2-yl]-11,11-dimethyl-3,4-diazatricyclo[6.2.1.02,7]undeca-2(7),3,5-triene | 0.0054 |
| 102 | 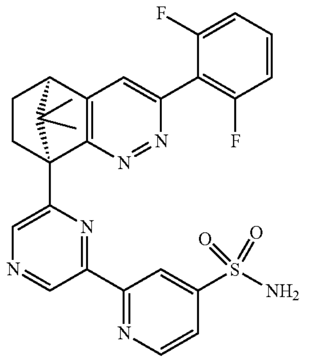 [SMILES: CC1(C)[C@H]2CC[C@]1(c1cncc(-c3cc(S(N)(=O)=O)ccn3)n1)c1nnc(-c3c(F)cccc3F)cc12] | 2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridine-4-sulfonamide | 0.019 |
| 103 | 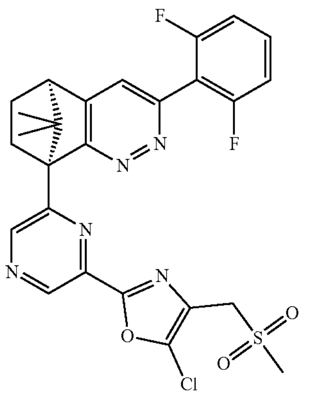 [SMILES: CC1(C)[C@H]2CC[C@]1(c1cncc(-c3nc(CS(C)(=O)=O)c(Cl)o3)n1)c1nnc(-c3c(F)cccc3F)cc12] | 5-chloro-4-(methylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole | 0.022 |

TABLE 1-continued

| | Structure | Name | $IC_{50}$ |
|---|---|---|---|
| 104 | 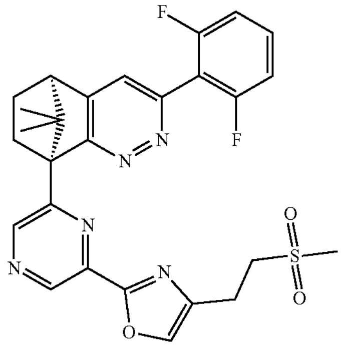 [SMILES: CC1(C)[C@H]2CC[C@]1(c1cncc(-c3nc(CCS(C)(=O)=O)co3)n1)c1nnc(-c3c(F)cccc3F)cc12] | 4-(2-methylsulfonylethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole | 0.015 |
| 105 | 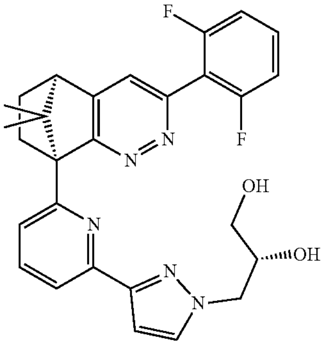 [SMILES: CC1(C)[C@H]2CC[C@]1(c1cccc(-c3ccn(C[C@@H](O)CO)n3)n1)c1nnc(-c3c(F)cccc3F)cc12] | (2S)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol | 0.012 |
| 106 | 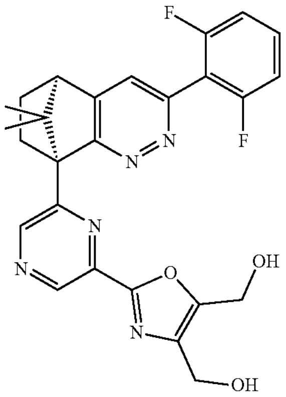 [SMILES: CC1(C)[C@H]2CC[C@]1(c1cncc(-c3nc(CO)c(CO)o3)n1)c1nnc(-c3c(F)cccc3F)cc12] | [5-(hydroxymethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol | 0.025 |
| 107 | 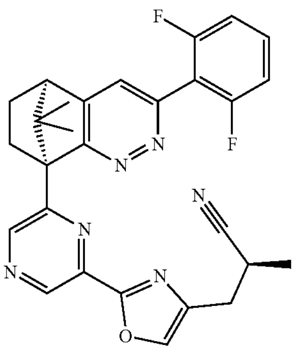 [SMILES: C[C@H](C#N)Cc1coc(-c2cncc([C@@]34CC[C@@H](c5cc(-c6c(F)cccc6F)nnc53)C4(C)C)n2)n1] | (2S)-2-methyl-3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile | 0.0086 |

TABLE 1-continued

| | Structure | Name | $IC_{50}$ |
|---|---|---|---|
| 108 | 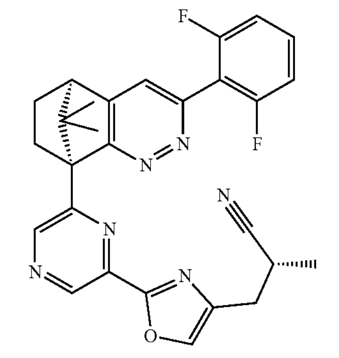 [SMILES: C[C@@H](C#N)Cc1coc(-c2cncc([C@@]34CC[C@@H](c5cc(-c6c(F)cccc6F)nnc53)C4(C)C)n2)n1] | (2R)-2-methyl-3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile | 0.0093 |
| 109 | 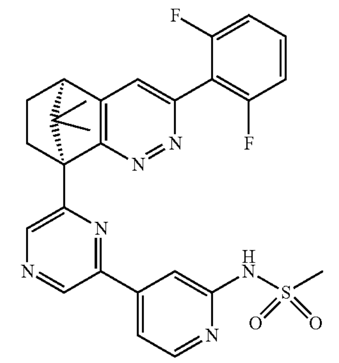 [SMILES: CC1(C)[C@H]2CC[C@]1(c1cncc(-c3ccnc(NS(C)(=O)=O)c3)n1)c1nnc(-c3c(F)cccc3F)cc12] | N-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide | 0.029 |
| 110 | 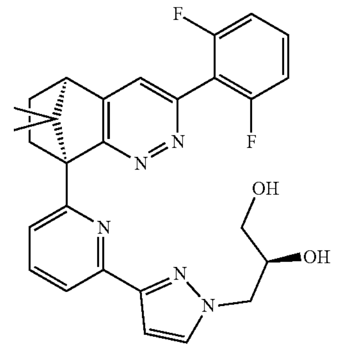 [SMILES: CC1(C)[C@H]2CC[C@]1(c1cccc(-c3ccn(C[C@H](O)CO)n3)n1)c1nnc(-c3c(F)cccc3F)cc12] | (2R)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol | 0.013 |
| 111 | 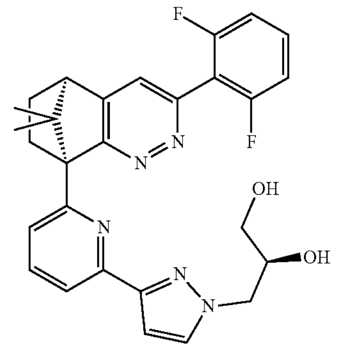 [SMILES: CC1(C)[C@H]2CC[C@]1(c1cccc(-c3ccn(C[C@H](O)CO)n3)n1)c1nnc(-c3c(F)cccc3F)cc12] | (2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol | 0.0078 |

TABLE 1-continued

| | Structure | Name | IC50 |
|---|---|---|---|
| 112 | 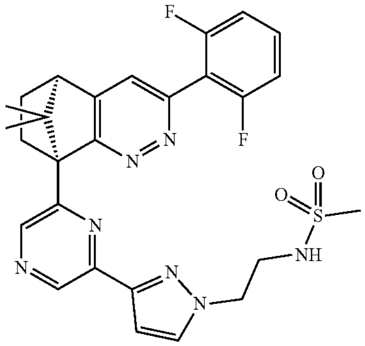 | N-[2-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethyl]methanesulfonamide | 0.010 |
| 113 | 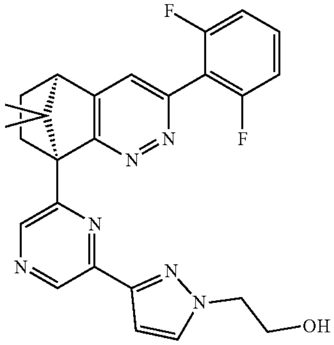 [SMILES: CC1(C)[C@H]2CC[C@]1(c1cncc(-c3ccn(CCO)n3)n1)c1nnc(-c3c(F)cccc3F)cc12] | 2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]ethanol | 0.022 |
| 114 | 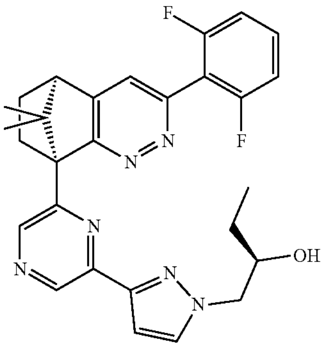 [SMILES: CC[C@@H](O)Cn1ccc(-c2cncc([C@@]34CC[C@@H](c5cc(-c6c(F)cccc6F)nnc53)C4(C)C)n2)n1] | (2R)-1-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol | 0.014 |
| 115 | 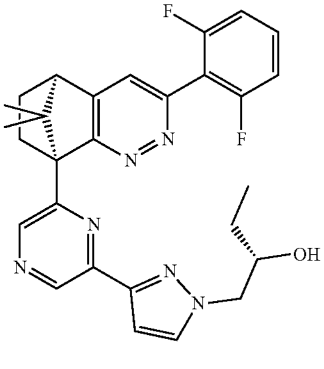 [SMILES: CC[C@H](O)Cn1ccc(-c2cncc([C@@]34CC[C@@H](c5cc(-c6c(F)cccc6F)nnc53)C4(C)C)n2)n1] | (2S)-1-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol | 0.019 |

TABLE 1-continued

| | Structure | Name | $IC_{50}$ |
|---|---|---|---|
| 116 | 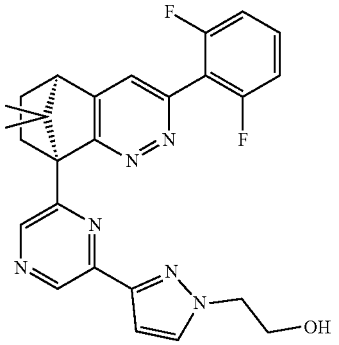 [SMILES: CC1(C)[C@H]2CC[C@]1(c1cncc(-c3ccn(CCO)n3)n1)c1nnc(-c3c(F)cccc3F)cc12] | 2-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanol | 0.016 |
| 117 | 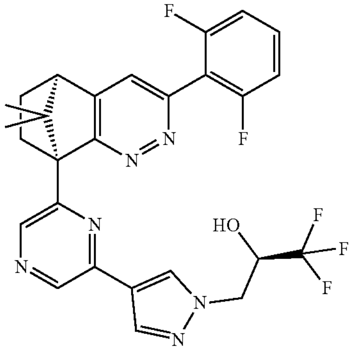 [SMILES: CC1(C)[C@H]2CC[C@]1(c1cncc(-c3cnn(C[C@@H](O)C(F)(F)F)c3)n1)c1nnc(-c3c(F)cccc3F)cc12] | (2S)-1,1,1-trifluoro-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol | 0.013 |
| 118 | 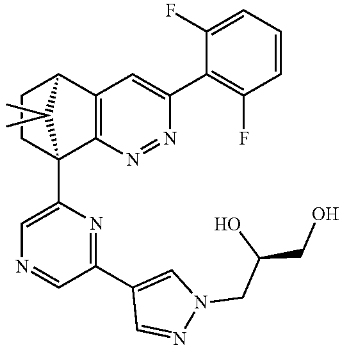 [SMILES: CC1(C)[C@H]2CC[C@]1(c1cncc(-c3cnn(C[C@@H](O)CO)c3)n1)c1nnc(-c3c(F)cccc3F)cc12] | (2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol | 0.0082 |
| 119 | 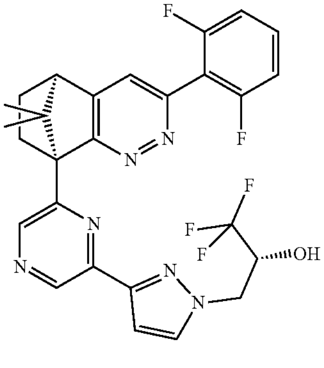 [SMILES: CC1(C)[C@H]2CC[C@]1(c1cncc(-c3ccn(C[C@@H](O)C(F)(F)F)n3)n1)c1nnc(-c3c(F)cccc3F)cc12] | (2S)-1,1,1-trifluoro-3-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol | 0.011 |

TABLE 1-continued

| | Structure | Name | $IC_{50}$ |
|---|---|---|---|
| 120 | 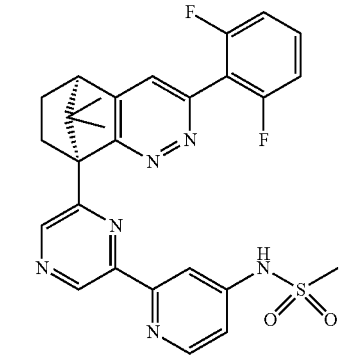 [SMILES: CC1(C)[C@H]2CC[C@]1(c1cncc(-c3cc(NS(C)(=O)=O)ccn3)n1)c1nnc(-c3c(F)cccc3F)cc12] | N-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-pyridyl]methanesulfonamide | 0.025 |
| 121 | 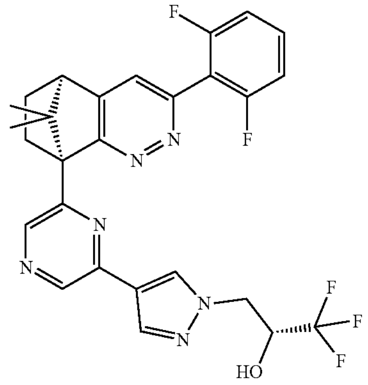 [SMILES: CC1(C)[C@H]2CC[C@]1(c1cncc(-c3cnn(C[C@@H](O)C(F)(F)F)c3)n1)c1nnc(-c3c(F)cccc3F)cc12] | (2R)-1,1,1-trifluoro-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol | 0.0077 |
| 122 | 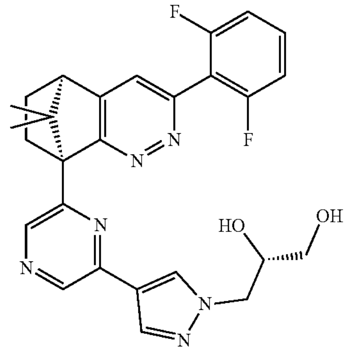 [SMILES: CC1(C)[C@H]2CC[C@]1(c1cncc(-c3cnn(C[C@H](O)CO)c3)n1)c1nnc(-c3c(F)cccc3F)cc12] | (2R)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol | 0.0050 |
| 123 | 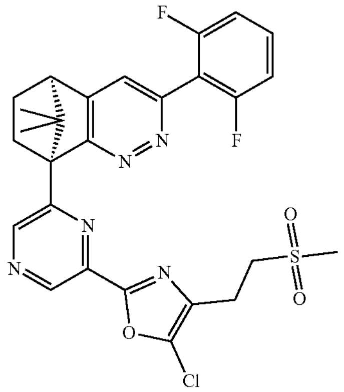 [SMILES: CC1(C)[C@H]2CC[C@]1(c1cncc(-c3nc(CCS(C)(=O)=O)c(Cl)o3)n1)c1nnc(-c3c(F)cccc3F)cc12] | 5-chloro-4-(2-methylsulfonylethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole | 0.0069 |

TABLE 1-continued

| | Structure | Name | $IC_{50}$ |
|---|---|---|---|
| 124 | 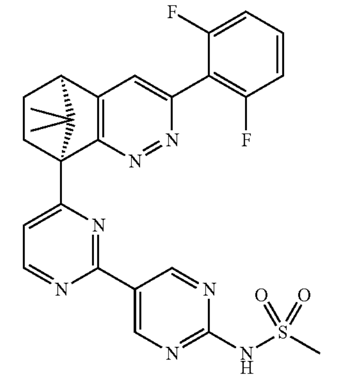 [SMILES: CC1(C)[C@H]2CC[C@]1(c1ccnc(-c3cnc(NS(C)(=O)=O)nc3)n1)c1nnc(-c3c(F)cccc3F)cc12] | N-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]methanesulfonamide | 0.014 |
| 125 | 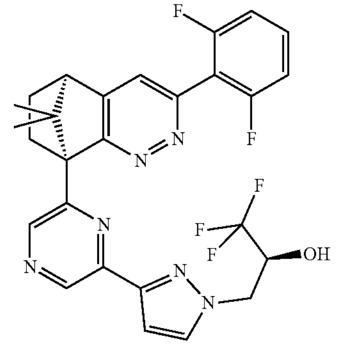 [SMILES: CC1(C)[C@H]2CC[C@]1(c1cncc(-c3ccn(C[C@H](O)C(F)(F)F)n3)n1)c1nnc(-c3c(F)cccc3F)cc12] | (2R)-1,1,1-trifluoro-3-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol | 0.0059 |
| 126 | 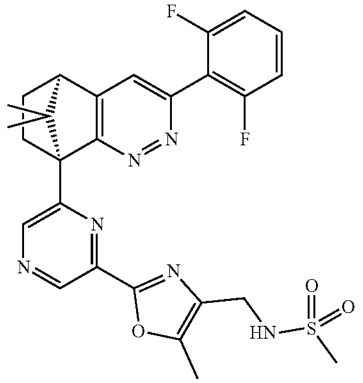 [SMILES: Cc1oc(-c2cncc([C@@]34CC[C@@H](c5cc(-c6c(F)cccc6F)nnc53)C4(C)C)n2)nc1CNS(C)(=O)=O] | N-[[5-methyl-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide | 0.0082 |
| 127 | 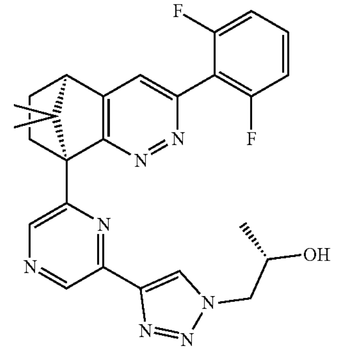 [SMILES: C[C@H](O)Cn1cc(-c2cncc([C@@]34CC[C@@H](c5cc(-c6c(F)cccc6F)nnc53)C4(C)C)n2)nn1] | (2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propan-2-ol | 0.024 |

TABLE 1-continued

| | Structure | Name | $IC_{50}$ |
|---|---|---|---|
| 128 | 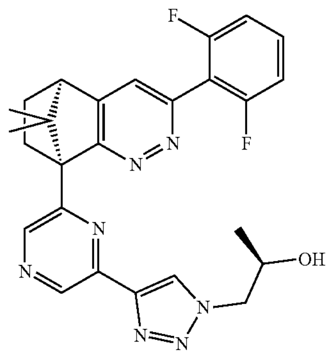 [SMILES: C[C@@H](O)Cn1cc(-c2cncc([C@@]34CC[C@@H](c5cc(-c6c(F)cccc6F)nnc53)C4(C)C)n2)nn1] | (2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propan-2-ol | 0.027 |
| 129 | 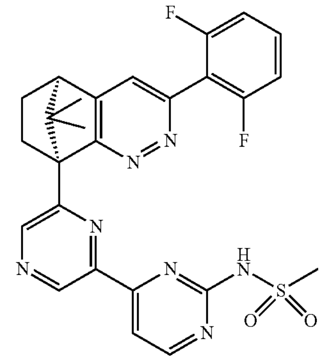 [SMILES: CC1(C)[C@H]2CC[C@]1(c1cncc(-c3ccnc(NS(C)(=O)=O)n3)n1)c1nnc(-c3c(F)cccc3F)cc12] | N-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]methanesulfonamide | 0.040 |
| 130 | 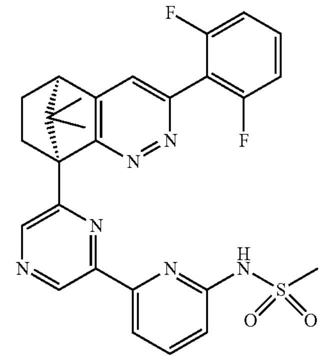 [SMILES: CC1(C)[C@H]2CC[C@]1(c1cncc(-c3cccc(NS(C)(=O)=O)n3)n1)c1nnc(-c3c(F)cccc3F)cc12] | N-[6-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide | 0.031 |
| 131 | 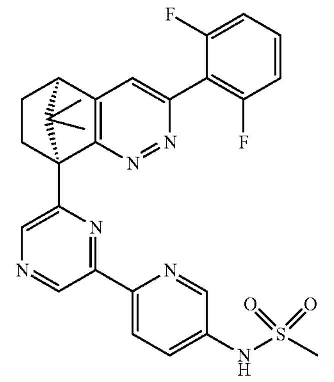 [SMILES: CC1(C)[C@H]2CC[C@]1(c1cncc(-c3ccc(NS(C)(=O)=O)cn3)n1)c1nnc(-c3c(F)cccc3F)cc12] | N-[6-[6-[1S,8R)-5-(2,6-difluorophenyl)-11,11-dimethyl-3,4-diazatricyclo[6.2.1.02,7]undeca-2(7),3,5-trien-1-yl]pyrazin-2-yl]-3-pyridyl]methanesulfonamide | 0.017 |

TABLE 1-continued

| | Structure | Name | $IC_{50}$ |
|---|---|---|---|
| 132 | 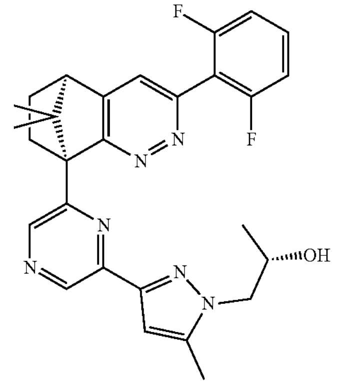 [SMILES: Cc1cc(-c2cncc([C@@]34CC[C@@H](c5cc(-c6c(F)cccc6F)nnc53)C4(C)C)n2)nn1C[C@H](C)O] | (2R)-1-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol | 0.018 |
| 133 | 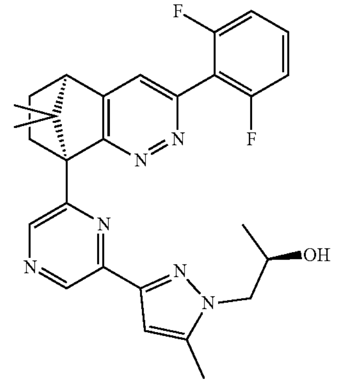 [SMILES: Cc1cc(-c2cncc([C@@]34CC[C@@H](c5cc(-c6c(F)cccc6F)nnc53)C4(C)C)n2)nn1C[C@@H](C)O] | (2S)-1-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol | 0.021 |
| 134 | 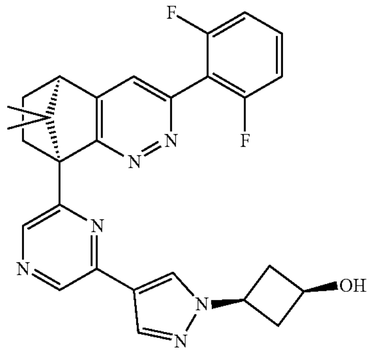 [SMILES: CC1(C)[C@H]2CC[C@]1(c1cncc(-c3cnn([C@H]4C[C@@H](O)C4)c3)n1)c1nnc(-c3c(F)cccc3F)cc12] | 3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]cyclobutanol | 0.0085 |
| 135 | 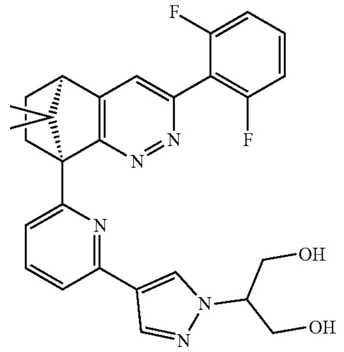 [SMILES: CC1(C)[C@H]2CC[C@]1(c1cccc(-c3cnn(C(CO)CO)c3)n1)c1nnc(-c3c(F)cccc3F)cc12] | 2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,3-diol | 0.0075 |

TABLE 1-continued

| | Structure | Name | $IC_{50}$ |
|---|---|---|---|
| 136 | 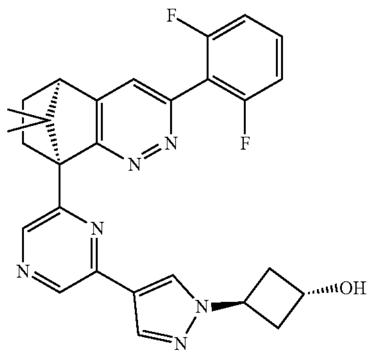 [SMILES: CC1(C)[C@H]2CC[C@]1(c1cncc(-c3cnn([C@H]4C[C@H](O)C4)c3)n1)c1nnc(-c3c(F)cccc3F)cc12] | 3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]cyclobutanol | 0.0069 |
| 137 | 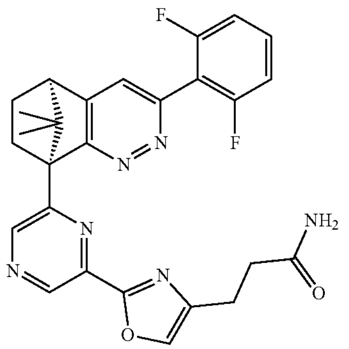 [SMILES: CC1(C)[C@H]2CC[C@]1(c1cncc(-c3nc(CCC(N)=O)co3)n1)c1nnc(-c3c(F)cccc3F)cc12] | 3-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide | 0.0088 |
| 138 | 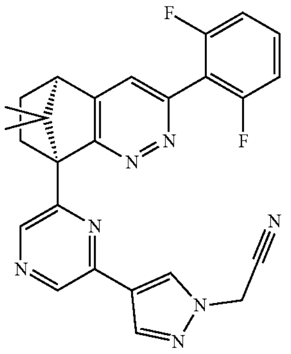 [SMILES: CC1(C)[C@H]2CC[C@]1(c1cncc(-c3cnn(CC#N)c3)n1)c1nnc(-c3c(F)cccc3F)cc12] | 2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]acetonitrile | 0.0057 |
| 139 | 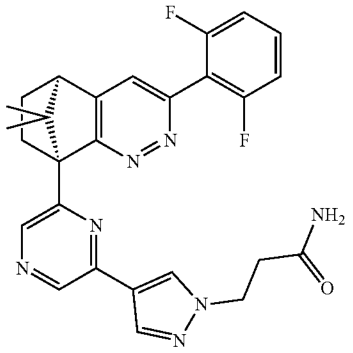 [SMILES: CC1(C)[C@H]2CC[C@]1(c1cncc(-c3cnn(CCC(N)=O)c3)n1)c1nnc(-c3c(F)cccc3F)cc12] | 3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanamide | 0.0051 |

TABLE 1-continued

| | Structure | Name | IC50 |
|---|---|---|---|
| 140 | 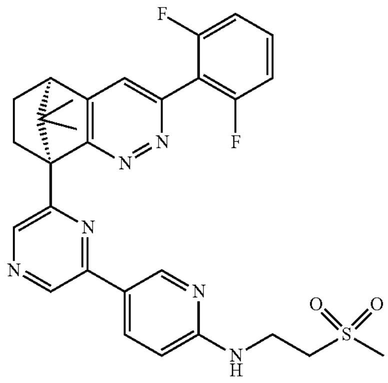 [SMILES: CC1(C)[C@H]2CC[C@]1(c1cncc(-c3ccc(NCCS(C)(=O)=O)nc3)n1)c1nnc(-c3c(F)cccc3F)cc12] | N-(2-methylsulfonylethyl)-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridin-2-amine | 0.0068 |
| 141 | 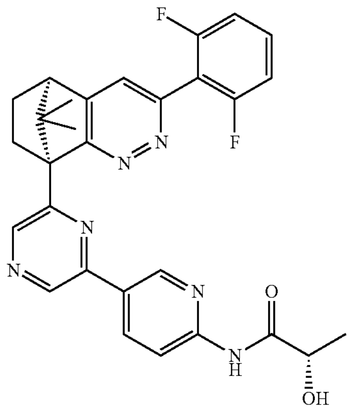 [SMILES: C[C@H](O)C(=O)Nc1ccc(-c2cncc([C@@]34CC[C@@H](c5cc(-c6c(F)cccc6F)nnc53)C4(C)C)n2)cn1] | (2S)-2-hydroxy-N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]propanamide | 0.0053 |
| 142 | 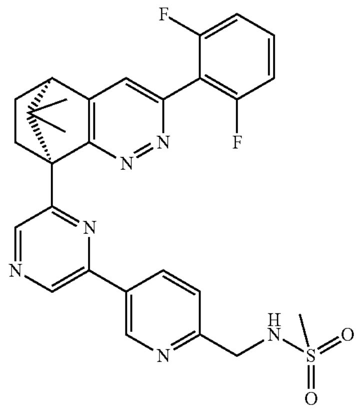 [SMILES: CC1(C)[C@H]2CC[C@]1(c1cncc(-c3ccc(CNS(C)(=O)=O)nc3)n1)c1nnc(-c3c(F)cccc3F)cc12] | N-[[5-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methyl]methanesulfonamide | 0.0031 |
| 143 | 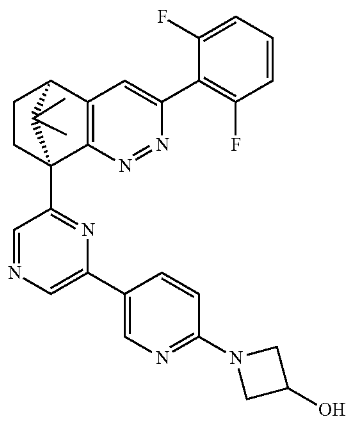 [SMILES: CC1(C)[C@H]2CC[C@]1(c1cncc(-c3ccc(N4CC(O)C4)nc3)n1)c1nnc(-c3c(F)cccc3F)cc12] | 1-[5-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]azetidin-3-ol | 0.0083 |

TABLE 1-continued

| | Structure | Name | $IC_{50}$ |
|---|---|---|---|
| 144 | 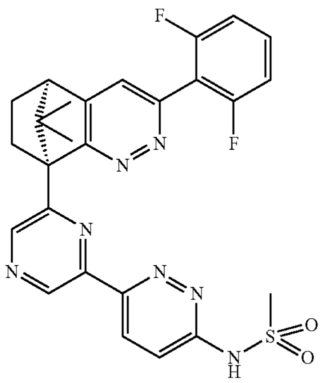 [SMILES: CC1(C)[C@H]2CC[C@]1(c1cncc(-c3ccc(NS(C)(=O)=O)nn3)n1)c1nnc(-c3c(F)cccc3F)cc12] | N-[6-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridazin-3-yl]methanesulfonamide | 0.014 |
| 145 | 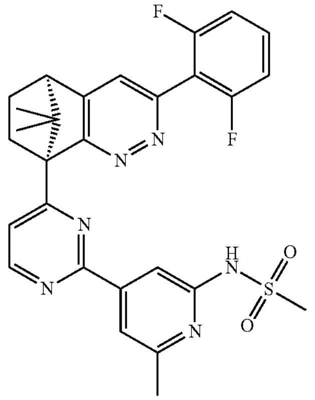 [SMILES: Cc1cc(-c2nccc([C@@]34CC[C@@H](c5cc(-c6c(F)cccc6F)nnc53)C4(C)C)n2)cc(NS(C)(=O)=O)n1] | N-[6-methyl-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide | 0.028 |
| 146 | 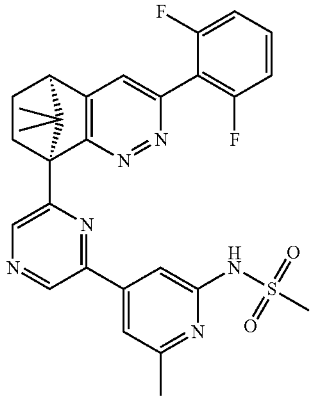 [SMILES: Cc1cc(-c2cncc([C@@]34CC[C@@H](c5cc(-c6c(F)cccc6F)nnc53)C4(C)C)n2)cc(NS(C)(=O)=O)n1] | N-[6-methyl-4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide | 0.028 |
| 147 | 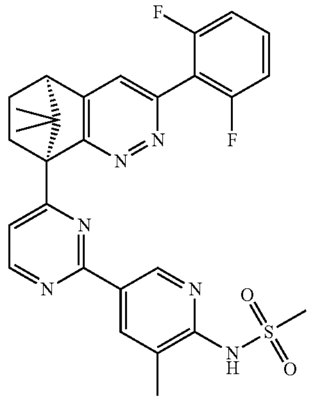 [SMILES: Cc1cc(-c2nccc([C@@]34CC[C@@H](c5cc(-c6c(F)cccc6F)nnc53)C4(C)C)n2)cnc1NS(C)(=O)=O] | N-[3-methyl-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide | 0.014 |

TABLE 1-continued

| | Structure | Name | IC50 |
|---|---|---|---|
| 148 | 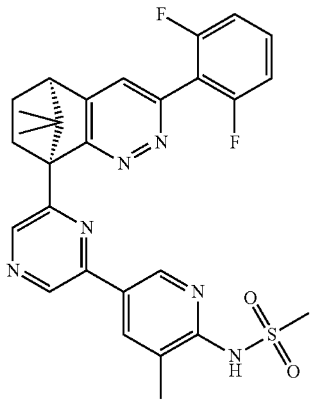 [SMILES: Cc1cc(-c2cncc([C@@]34CC[C@@H](c5cc(-c6c(F)cccc6F)nnc53)C4(C)C)n2)cnc1NS(C)(=O)=O] | N-[3-mehtyl-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide | 0.014 |
| 149 | 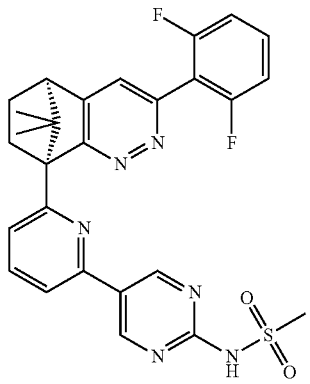 [SMILES: CC1(C)[C@H]2CC[C@]1(c1cccc(-c3cnc(NS(C)(=O)=O)nc3)n1)c1nnc(-c3c(F)cccc3F)cc12] | N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide | 0.0042 |
| 150 | 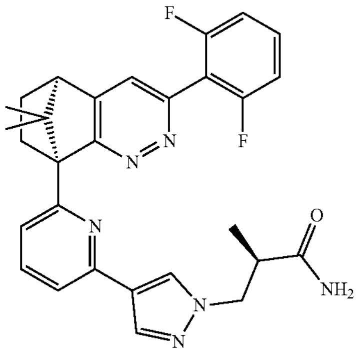 [SMILES: C[C@H](Cn1cc(-c2cccc([C@@]34CC[C@@H](c5cc(-c6c(F)cccc6F)nnc53)C4(C)C)n2)cn1)C(N)=O] | (2S)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide | 0.0042 |
| 151 | 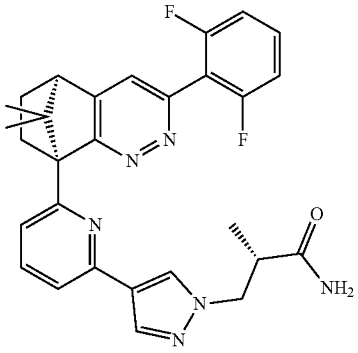 [SMILES: C[C@@H](Cn1cc(-c2cccc([C@@]34CC[C@@H](c5cc(-c6c(F)cccc6F)nnc53)C4(C)C)n2)cn1)C(N)=O] | (2R)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide | 0.0042 |

TABLE 1-continued

| | Structure | Name | IC50 |
|---|---|---|---|
| 152 | 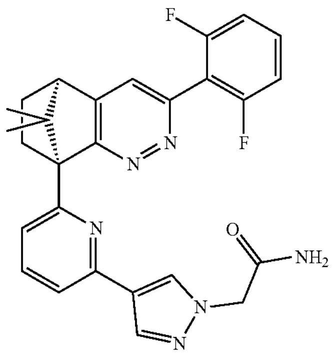 [SMILES: CC1(C)[C@H]2CC[C@]1(c1cccc(-c3cnn(CC(N)=O)c3)n1)c1nnc(-c3c(F)cccc3F)cc12] | 2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]acetamide | 0.0033 |
| 153 | 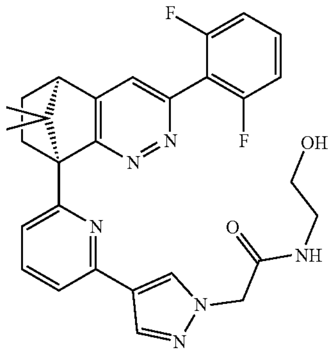 [SMILES: CC1(C)[C@H]2CC[C@]1(c1cccc(-c3cnn(CC(=O)NCCO)c3)n1)c1nnc(-c3c(F)cccc3F)cc12] | N-(2-hydroxyethyl)-2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]acetamide | 0.0052 |
| 154 | 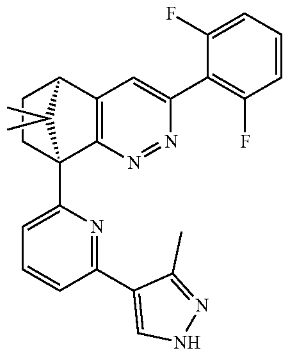 [SMILES: Cc1n[nH]cc1-c1cccc([C@@]23CC[C@@H](c4cc(-c5c(F)cccc5F)nnc42)C3(C)C)n1] | (1S,8R)-5-(2,6-difluorophenyl)-11,11-dimethyl-1-[6-(3-methyl-1H-pyrazol-4-yl)-2-pyridyl]-3,4-diazatricyclo[6.2.1.02,7]undeca-2(7),3,5-triene | 0.0027 |
| 155 | 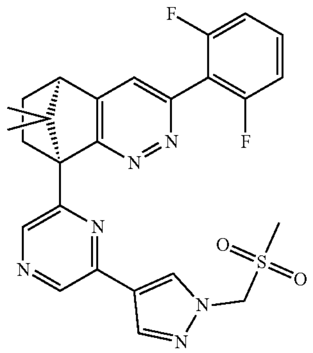 [SMILES: CC1(C)[C@H]2CC[C@]1(c1cncc(-c3cnn(CS(C)(=O)=O)c3)n1)c1nnc(-c3c(F)cccc3F)cc12] | (1S,8R)-5-(2,6-difluorophenyl)-11,11-dimethyl-1-[6-[1-(methylsulfonylmethyl)pyrazol-4-yl]pyrazin-2-yl]-3,4-diazatricyclo[6.2.1.02,7]undeca-2(7),3,5-triene | 0.0041 |

TABLE 1-continued

| | Structure | Name | $IC_{50}$ |
|---|---|---|---|
| 156 | 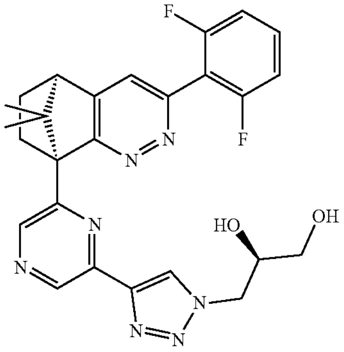 [SMILES: CC1(C)[C@H]2CC[C@]1(c1cncc(-c3cn(C[C@@H](O)CO)nn3)n1)c1nnc(-c3c(F)cccc3F)cc12] | (2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propane-1,2-diol | 0.013 |
| 157 | 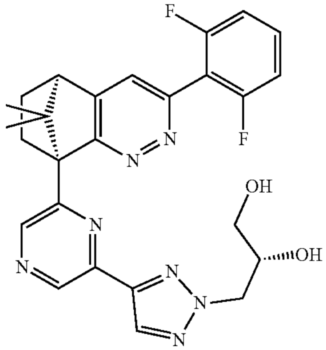 [SMILES: CC1(C)[C@H]2CC[C@]1(c1cncc(-c3cnn(C[C@@H](O)CO)n3)n1)c1nnc(-c3c(F)cccc3F)cc12] | (2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-2-yl]propane-1,2-diol | 0.0054 |
| 158 | 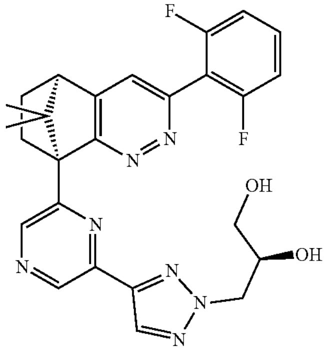 [SMILES: CC1(C)[C@H]2CC[C@]1(c1cncc(-c3cnn(C[C@H](O)CO)n3)n1)c1nnc(-c3c(F)cccc3F)cc12] | (2R)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-2-yl]propane-1,2-diol | 0.0067 |
| 159 | 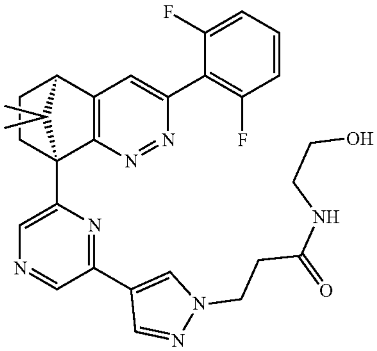 [SMILES: CC1(C)[C@H]2CC[C@]1(c1cncc(-c3cnn(CCC(=O)NCCO)c3)n1)c1nnc(-c3c(F)cccc3F)cc12] | N-(2-hydroxyethyl)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanamide | 0.0083 |

TABLE 1-continued

| | Structure | Name | $IC_{50}$ |
|---|---|---|---|
| 160 | 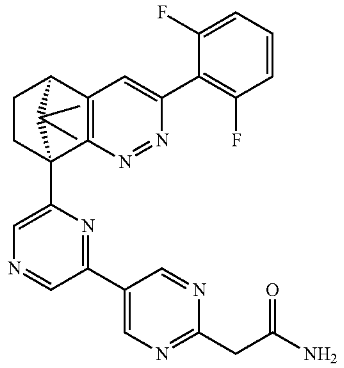 [SMILES: CC1(C)[C@H]2CC[C@]1(c1cncc(-c3cnc(CC(N)=O)nc3)n1)c1nnc(-c3c(F)cccc3F)cc12] | 2-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]acetamide | 0.0098 |
| 161 | 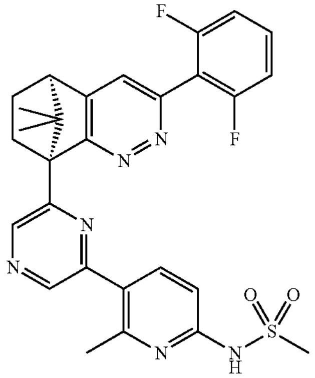 [SMILES: Cc1nc(NS(C)(=O)=O)ccc1-c1cncc([C@@]23CC[C@@H](c4cc(-c5c(F)cccc5F)nnc42)C3(C)C)n1] | N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-6-methyl-2-pyridyl]methanesulfonamide | 0.014 |
| 162 | 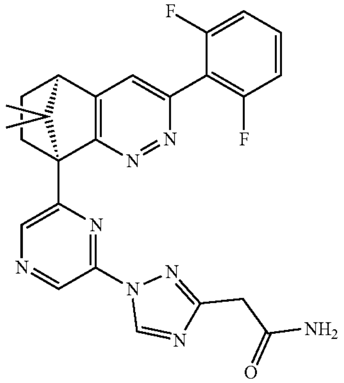 [SMILES: CC1(C)[C@H]2CC[C@]1(c1cncc(-n3cnc(CC(N)=O)n3)n1)c1nnc(-c3c(F)cccc3F)cc12] | 2-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]acetamide | 0.0080 |
| 163 | 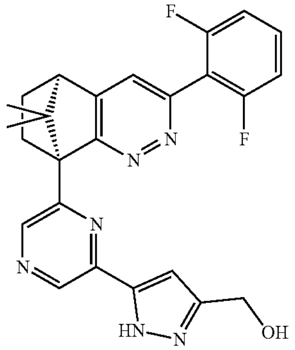 [SMILES: CC1(C)[C@H]2CC[C@]1(c1cncc(-c3cc(CO)n[nH]3)n1)c1nnc(-c3c(F)cccc3F)cc12] | [5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1H-pyrazol-3-yl]methanol | 0.015 |

TABLE 1-continued

| | Structure | Name | $IC_{50}$ |
|---|---|---|---|
| 164 | 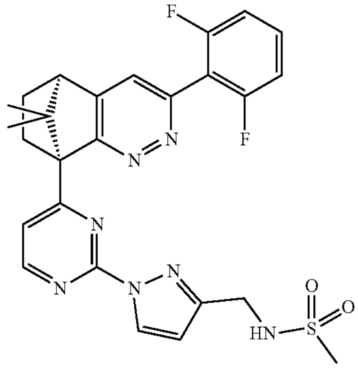 [SMILES: CC1(C)[C@H]2CC[C@]1(c1ccnc(-n3ccc(CNS(C)(=O)=O)n3)n1)c1nnc(-c3c(F)cccc3F)cc12] | N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-3-yl]methyl]methanesulfonamide | 0.016 |
| 165 | 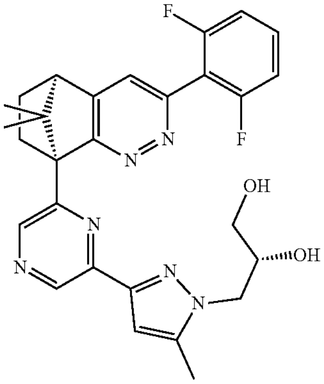 [SMILES: Cc1cc(-c2cncc([C@@]34CC[C@@H](c5cc(-c6c(F)cccc6F)nnc53)C4(C)C)n2)nn1C[C@@H](O)CO] | (2S)-3-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol | 0.023 |
| 166 | 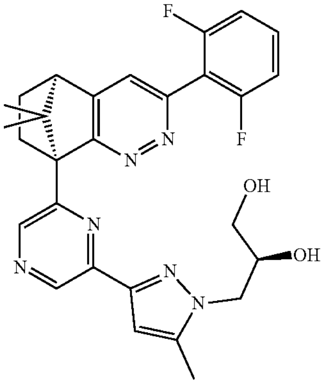 [SMILES: Cc1cc(-c2cncc([C@@]34CC[C@@H](c5cc(-c6c(F)cccc6F)nnc53)C4(C)C)n2)nn1C[C@H](O)CO] | (2R)-3-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol | 0.026 |
| 167 | 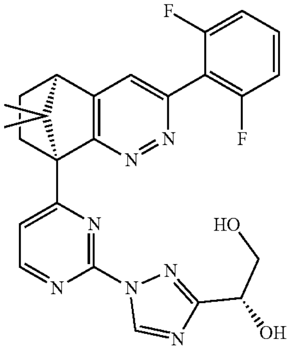 [SMILES: CC1(C)[C@H]2CC[C@]1(c1ccnc(-n3cnc([C@@H](O)CO)n3)n1)c1nnc(-c3c(F)cccc3F)cc12] | (1S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethane-1,2-diol | 0.037 |

TABLE 1-continued

| | Structure | Name | IC$_{50}$ |
|---|---|---|---|
| 168 | 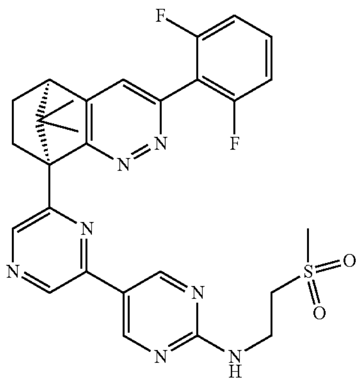 [SMILES: CC1(C)[C@H]2CC[C@]1(c1cncc(-c3cnc(NCCS(C)(=O)=O)nc3)n1)c1nnc(-c3c(F)cccc3F)cc12] | N-(2-methylsulfonylethyl)-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-amine | 0.015 |
| 169 | 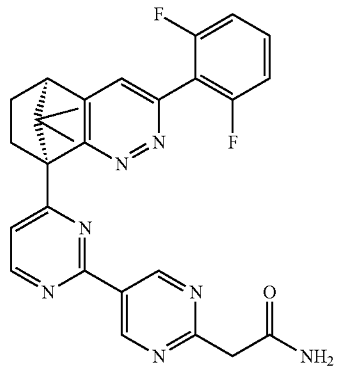 [SMILES: CC1(C)[C@H]2CC[C@]1(c1ccnc(-c3cnc(CC(N)=O)nc3)n1)c1nnc(-c3c(F)cccc3F)cc12] | 2-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]acetamide | 0.014 |
| 170 | 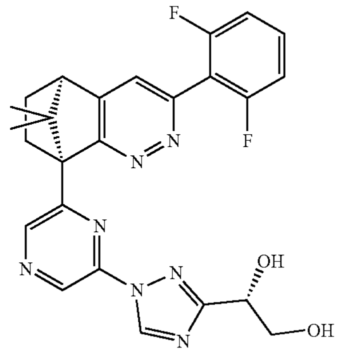 [SMILES: CC1(C)[C@H]2CC[C@]1(c1cncc(-n3cnc([C@H](O)CO)n3)n1)c1nnc(-c3c(F)cccc3F)cc12] | (1S)-1-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]ethane-1,2-diol | 0.014 |
| 171 | 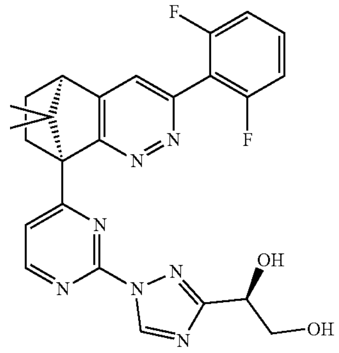 [SMILES: CC1(C)[C@H]2CC[C@]1(c1ccnc(-n3cnc([C@@H](O)CO)n3)n1)c1nnc(-c3c(F)cccc3F)cc12] | (1R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethane-1,2-diol | 0.024 |

TABLE 1-continued

| | Structure | Name | $IC_{50}$ |
|---|---|---|---|
| 172 | 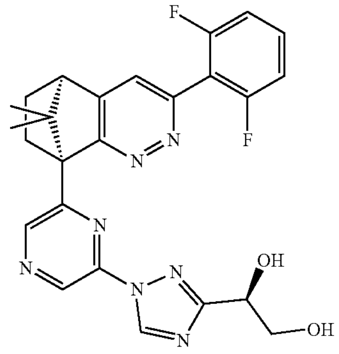 [SMILES: CC1(C)[C@H]2CC[C@]1(c1cncc(-n3cnc([C@@H](O)CO)n3)n1)c1nnc(-c3c(F)cccc3F)cc12] | (1R)-1-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]ethane-1,2-diol | 0.018 |
| 173 | 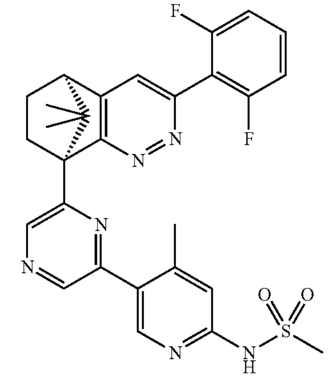 [SMILES: Cc1cc(NS(C)(=O)=O)ncc1-c1cncc([C@@]23CC[C@@H](c4cc(-c5c(F)cccc5F)nnc42)C3(C)C)n1] | N-[4-methyl-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide | 0.017 |
| 174 | 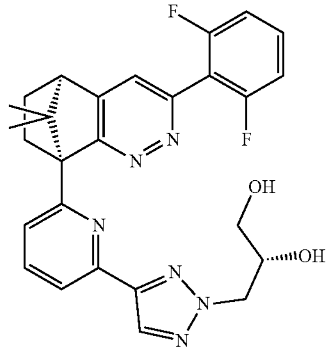 [SMILES: CC1(C)[C@H]2CC[C@]1(c1cccc(-c3cnn(C[C@@H](O)CO)n3)n1)c1nnc(-c3c(F)cccc3F)cc12] | (2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-2-yl]propane-1,2-diol | 0.0065 |
| 175 | 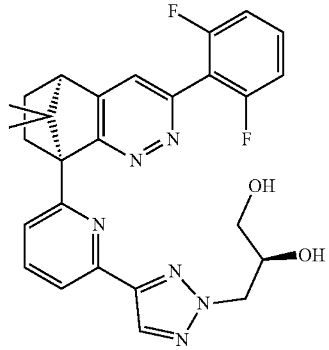 [SMILES: CC1(C)[C@H]2CC[C@]1(c1cccc(-c3cnn(C[C@H](O)CO)n3)n1)c1nnc(-c3c(F)cccc3F)cc12] | (2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-2-yl]propane-1,2-diol | 0.0066 |

TABLE 1-continued

| | Structure | Name | $IC_{50}$ |
|---|---|---|---|
| 176 | 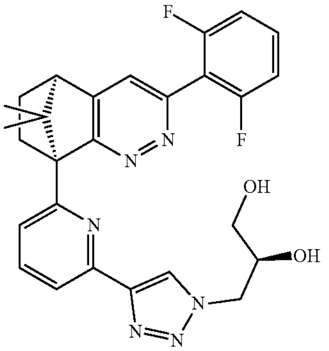 [SMILES: CC1(C)[C@H]2CC[C@]1(c1cccc(-c3cn(C[C@H](O)CO)nn3)n1)c1nnc(-c3c(F)cccc3F)cc12] | (2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-1-yl]propane-1,2-diol | 0.016 |
| 177 | 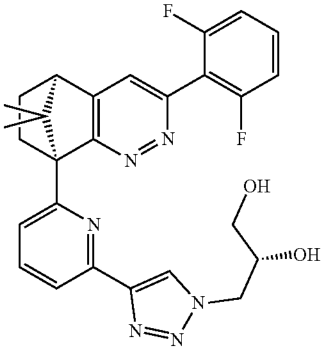 [SMILES: CC1(C)[C@H]2CC[C@]1(c1cccc(-c3cn(C[C@@H](O)CO)nn3)n1)c1nnc(-c3c(F)cccc3F)cc12] | (2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-1-yl]propane-1,2-diol | 0.014 |
| 178 | 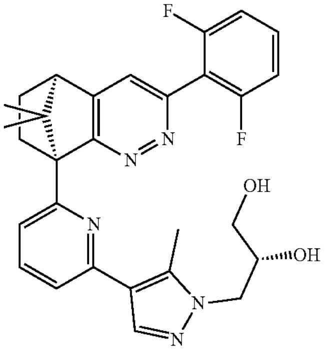 [SMILES: Cc1c(-c2cccc([C@@]34CC[C@@H](c5cc(-c6c(F)cccc6F)nnc53)C4(C)C)n2)cnn1C[C@@H](O)CO] | (2S)-3-[5-methyl-4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol | 0.0081 |
| 179 | 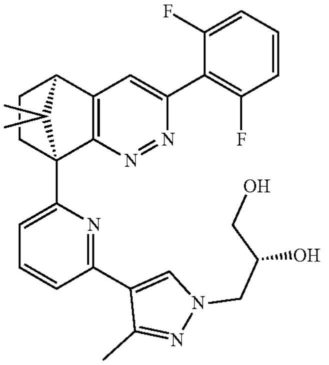 [SMILES: Cc1nn(C[C@@H](O)CO)cc1-c1cccc([C@@]23CC[C@@H](c4cc(-c5c(F)cccc5F)nnc42)C3(C)C)n1] | (2S)-3-[3-methyl-4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol | 0.0087 |

TABLE 1-continued

| | Structure | Name | $IC_{50}$ |
|---|---|---|---|
| 180 | 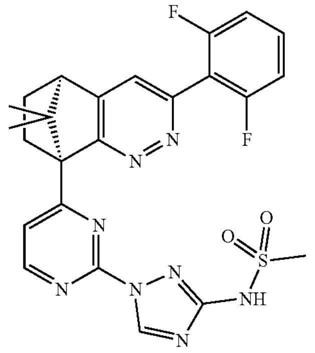 | N-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methanesulfonamide | 0.042 |
| 181 | 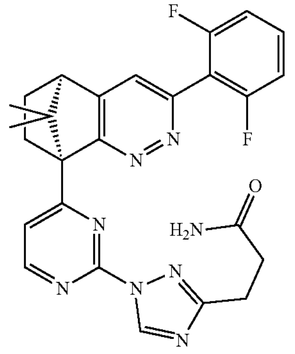 [SMILES: CC1(C)[C@H]2CC[C@]1(c1ccnc(-n3cnc(CCC(N)=O)n3)n1)c1nnc(-c3c(F)cccc3F)cc12] | 3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanamide | 0.024 |
| 182 | 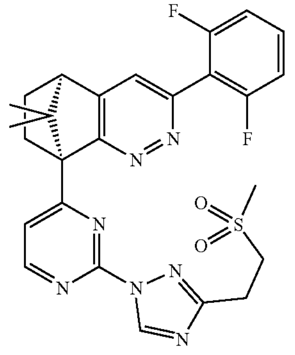 [SMILES: CC1(C)[C@H]2CC[C@]1(c1ccnc(-n3cnc(CCS(C)(=O)=O)n3)n1)c1nnc(-c3c(F)cccc3F)cc12] | (1S,8R)-5-(2,6-difluorophenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene | 0.032 |
| 183 | 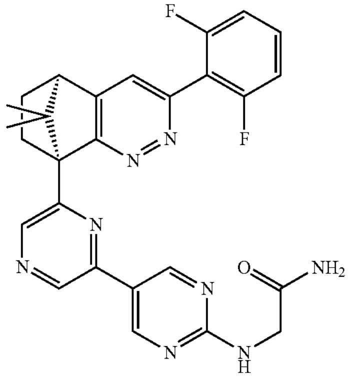 [SMILES: CC1(C)[C@H]2CC[C@]1(c1cncc(-c3cnc(NCC(N)=O)nc3)n1)c1nnc(-c3c(F)cccc3F)cc12] | 2-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]acetamide | 0.017 |

TABLE 1-continued

| | Structure | Name | $IC_{50}$ |
|---|---|---|---|
| 184 | 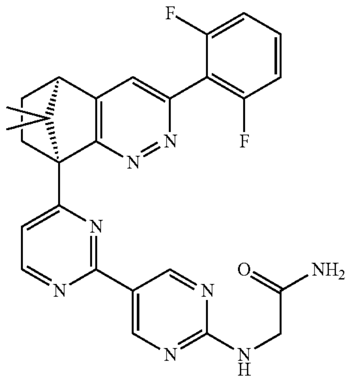 [SMILES: CC1(C)[C@H]2CC[C@]1(c1ccnc(-c3cnc(NCC(N)=O)nc3)n1)c1nnc(-c3c(F)cccc3F)cc12] | 2-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]acetamide | 0.017 |
| 185<br>186 | 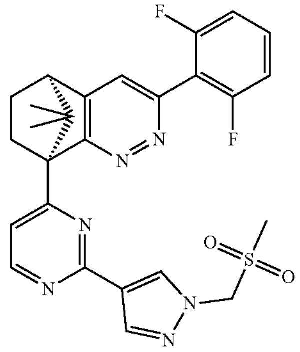 [SMILES: CC1(C)[C@H]2CC[C@]1(c1ccnc(-c3cnn(CS(C)(=O)=O)c3)n1)c1nnc(-c3c(F)cccc3F)cc12] | (1S,8R)-5-(2,6-difluorophenyl)-11,11-dimethyl-1-[2-[1-(methylsulfonylmethyl)pyrazol-4-yl]pyrimidin-4-yl]-3,4-diazatricyclo[6.2.1.02,7]undeca-2(7),3,5-triene | 0.0091 |
| 187 | 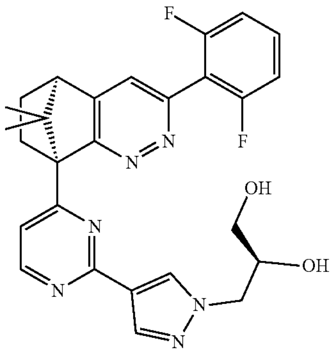 [SMILES: CC1(C)[C@H]2CC[C@]1(c1ccnc(-c3cnn(C[C@H](O)CO)c3)n1)c1nnc(-c3c(F)cccc3F)cc12] | (2S)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol | 0.010 |
| 188 | 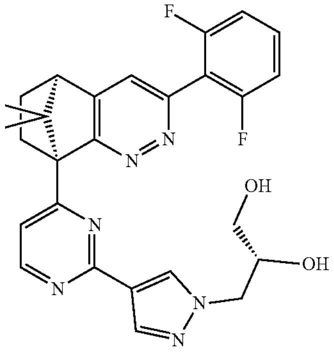 [SMILES: CC1(C)[C@H]2CC[C@]1(c1ccnc(-c3cnn(C[C@@H](O)CO)c3)n1)c1nnc(-c3c(F)cccc3F)cc12] | (2R)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol | 0.011 |

TABLE 1-continued

| | Structure | Name | $IC_{50}$ |
|---|---|---|---|
| 189 | 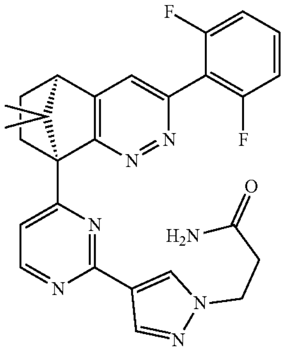 [SMILES: CC1(C)[C@H]2CC[C@]1(c1ccnc(-c3cnn(CCC(N)=O)c3)n1)c1nnc(-c3c(F)cccc3F)cc12] | 3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propanamide | 0.010 |
| 190 | 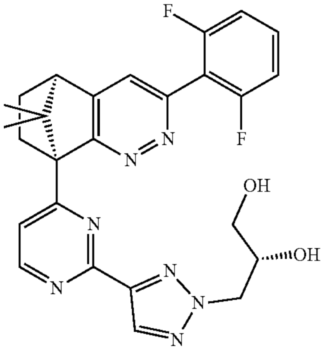 [SMILES: CC1(C)[C@H]2CC[C@]1(c1ccnc(-c3cnn(C[C@@H](O)CO)n3)n1)c1nnc(-c3c(F)cccc3F)cc12] | (2S)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-2-yl]propane-1,2-diol | 0.012 |
| 191 | 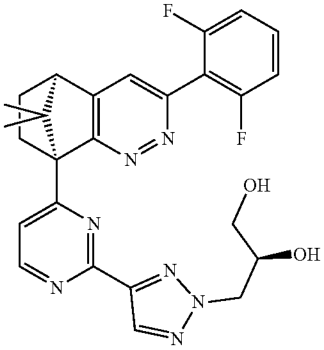 [SMILES: CC1(C)[C@H]2CC[C@]1(c1ccnc(-c3cnn(C[C@H](O)CO)n3)n1)c1nnc(-c3c(F)cccc3F)cc12] | (2R)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-2-yl]propane-1,2-diol | 0.012 |
| 192 | 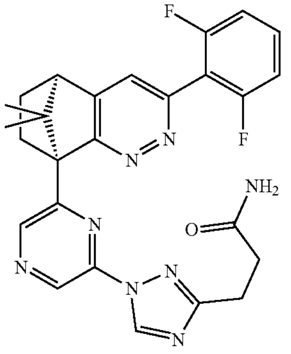 [SMILES: CC1(C)[C@H]2CC[C@]1(c1cncc(-n3cnc(CCC(N)=O)n3)n1)c1nnc(-c3c(F)cccc3F)cc12] | 3-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]propanamide | 0.0078 |

TABLE 1-continued

| | Structure | Name | $IC_{50}$ |
|---|---|---|---|
| 193 | 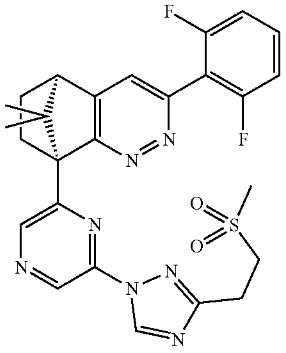 | (1S,8R)-5-(2,6-difluorophenyl)-11,11-dimethyl-1-[6-[3-(2-methylsulfonylethyl)-1,2,4-triazol-1-yl]pyrazin-2-yl]-3,4-diazatricyclo[6.2.1.02,7]undeca-2(7),3,5-triene | 0.0074 |
| 194 | 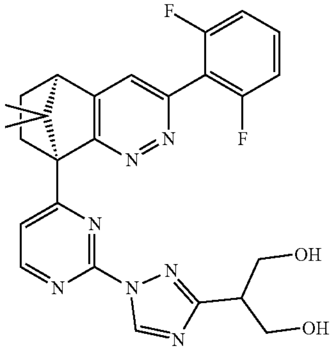 [SMILES: CC1(C)[C@H]2CC[C@]1(c1ccnc(-n3cnc(C(CO)CO)n3)n1)c1nnc(-c3c(F)cccc3F)cc12] | 2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol | 0.031 |
| 195 | 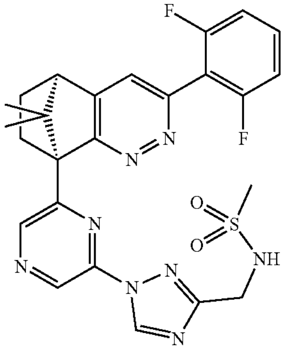 [SMILES: CC1(C)[C@H]2CC[C@]1(c1cncc(-n3cnc(CNS(C)(=O)=O)n3)n1)c1nnc(-c3c(F)cccc3F)cc12] | N-[[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]methyl]methanesulfonamide | 0.0077 |
| 196 | 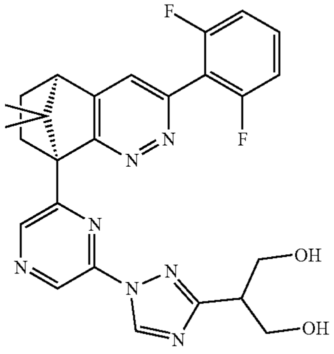 [SMILES: CC1(C)[C@H]2CC[C@]1(c1cncc(-n3cnc(C(CO)CO)n3)n1)c1nnc(-c3c(F)cccc3F)cc12] | 2-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]propane-1,3-diol | 0.023 |

TABLE 1-continued

| | Structure | Name | $IC_{50}$ |
| --- | --- | --- | --- |
| 197 | 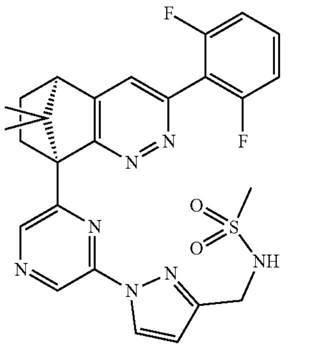 [SMILES: CC1(C)[C@H]2CC[C@]1(c1cncc(-n3ccc(CNS(C)(=O)=O)n3)n1)c1nnc(-c3c(F)cccc3F)cc12] | N-[[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-3-yl]methyl]methanesulfonamide | 0.0050 |
| 198 | 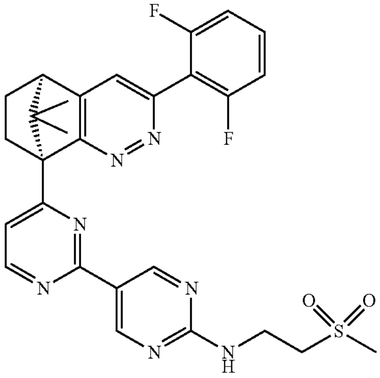 [SMILES: CC1(C)[C@H]2CC[C@]1(c1ccnc(-c3cnc(NCCS(C)(=O)=O)nc3)n1)c1nnc(-c3c(F)cccc3F)cc12] | N-(2-methylsulfonylethyl)-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-amine | 0.011 |
| 199 | 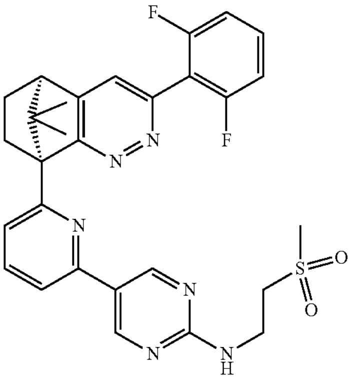 [SMILES: CC1(C)[C@H]2CC[C@]1(c1cccc(-c3cnc(NCCS(C)(=O)=O)nc3)n1)c1nnc(-c3c(F)cccc3F)cc12] | N-(2-methylsulfonylethyl)-5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-amine | 0.0068 |
| 200 | 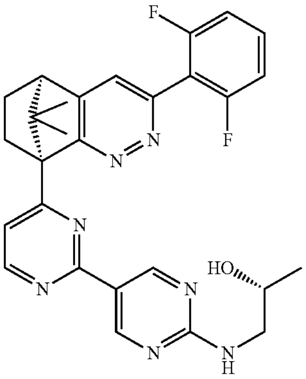 [SMILES: C[C@@H](O)CNc1ncc(-c2nccc([C@@]34CC[C@@H](c5cc(-c6c(F)cccc6F)nnc53)C4(C)C)n2)cn1] | (2S)-1-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]propan-2-ol | 0.012 |

TABLE 1-continued

| | Structure | Name | $IC_{50}$ |
|---|---|---|---|
| 201 | 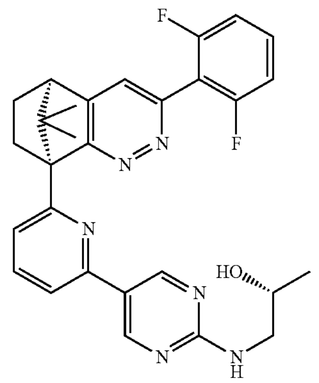 [SMILES: C[C@@H](O)CNc1ncc(-c2cccc([C@@]34CC[C@@H](c5cc(-c6c(F)cccc6F)nnc53)C4(C)C)n2)cn1] | (2S)-1-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propan-2-ol | 0.0058 |
| 202 | 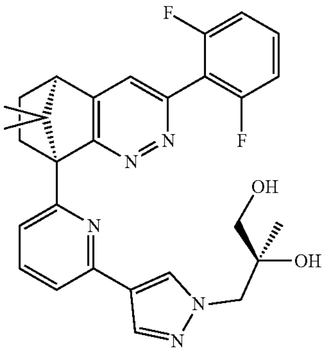 [SMILES: CC1(C)[C@H]2CC[C@]1(c1cccc(-c3cnn(C[C@](C)(O)CO)c3)n1)c1nnc(-c3c(F)cccc3F)cc12] | (2S)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol | 0.0062 |
| 203 | 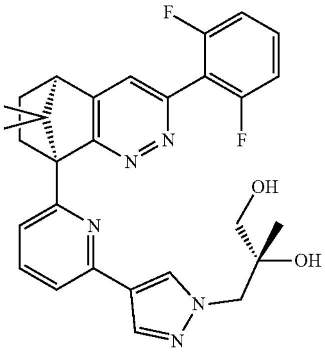 [SMILES: CC1(C)[C@H]2CC[C@]1(c1cccc(-c3cnn(C[C@@](C)(O)CO)c3)n1)c1nnc(-c3c(F)cccc3F)cc12] | (2R)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol | 0.0064 |
| 204 | 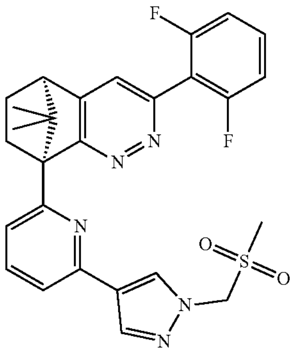 [SMILES: CC1(C)[C@H]2CC[C@]1(c1cccc(-c3cnn(CS(C)(=O)=O)c3)n1)c1nnc(-c3c(F)cccc3F)cc12] | (1S,8R)-5-(2,6-difluorophenyl)-11,11-dimethyl-1-[6-[1-(methylsulfonylmethyl)pyrazol-4-yl]-2-pyridyl]-3,4-diazatricyclo[6.2.1.02,7]undeca-2(7),3,5-triene | 0.0059 |

TABLE 1-continued

| | Structure | Name | $IC_{50}$ |
|---|---|---|---|
| 205 | 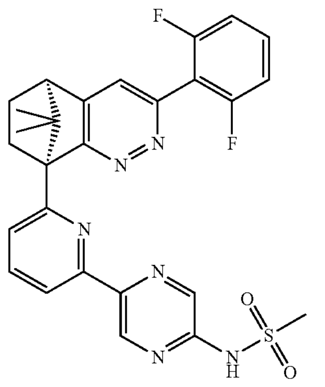 [SMILES: CC1(C)[C@H]2CC[C@]1(c1cccc(-c3cnc(NS(C)(=O)=O)cn3)n1)c1nnc(-c3c(F)cccc3F)cc12] | N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazin-2-yl]methanesulfonamide | 0.0088 |
| 206 | 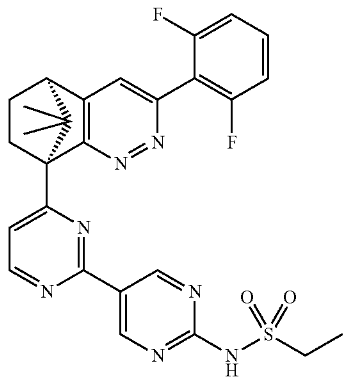 [SMILES: CCS(=O)(=O)Nc1ncc(-c2nccc([C@@]34CC[C@@H](c5cc(-c6c(F)cccc6F)nnc53)C4(C)C)n2)cn1] | N-[5-[4-[(1S,8R)-5-(2,6-difluorphenyl)-11,11-dimethyl-3,4-diazatricyclo[6.2.1.02,7]undeca-2(7),3,5-trien-1-yl]pyrimidin-2-yl]pyrimidin-2-yl]ethanesulfonamide | 0.010 |
| 207 | 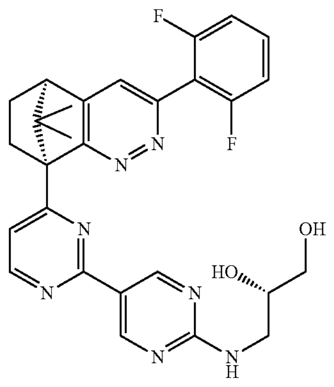 [SMILES: CC1(C)[C@H]2CC[C@]1(c1ccnc(-c3cnc(NC[C@H](O)CO)nc3)n1)c1nnc(-c3c(F)cccc3F)cc12] | (2R)-3-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]propane-1,2-diol | 0.014 |
| 208 | 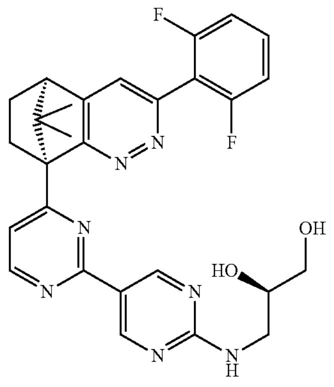 [SMILES: CC1(C)[C@H]2CC[C@]1(c1ccnc(-c3cnc(NC[C@@H](O)CO)nc3)n1)c1nnc(-c3c(F)cccc3F)cc12] | (2S)-3-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]propan-1,2-diol | 0.016 |

TABLE 1-continued

| | Structure | Name | $IC_{50}$ |
|---|---|---|---|
| 209 | 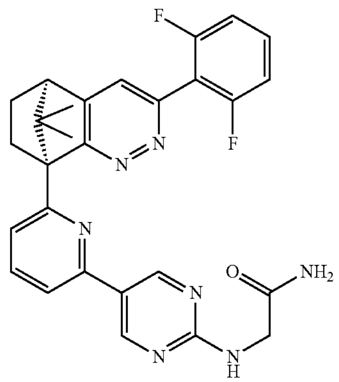 [SMILES: CC1(C)[C@H]2CC[C@]1(c1cccc(-c3cnc(NCC(N)=O)nc3)n1)c1nnc(-c3c(F)cccc3F)cc12] | 2-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]acetamide | 0.0054 |
| 210 | 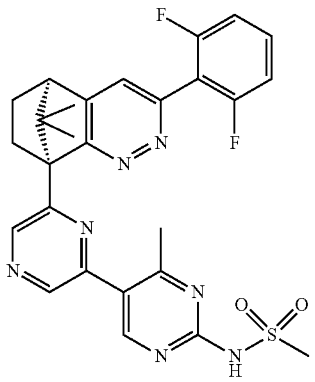 [SMILES: Cc1nc(NS(C)(=O)=O)ncc1-c1cncc([C@@]23CC[C@@H](c4cc(-c5c(F)cccc5F)nnc42)C3(C)C)n1] | N-[4-methyl-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]methanesulfonamide | 0.016 |
| 211 | 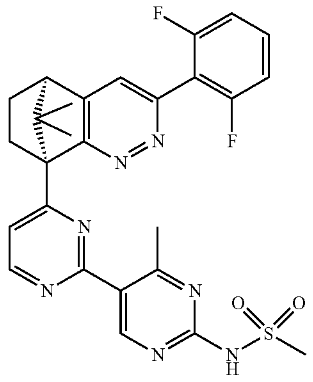 [SMILES: Cc1nc(NS(C)(=O)=O)ncc1-c1nccc([C@@]23CC[C@@H](c4cc(-c5c(F)cccc5F)nnc42)C3(C)C)n1] | N-[4-methyl-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]methanesulfonamide | 0.018 |
| 212 | 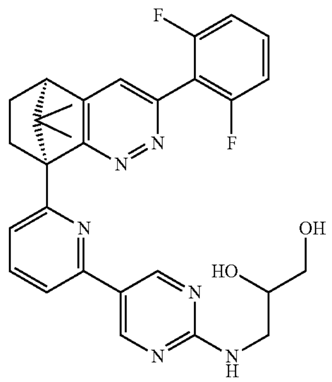 [SMILES: CC1(C)[C@H]2CC[C@]1(c1cccc(-c3cnc(NCC(O)CO)nc3)n1)c1nnc(-c3c(F)cccc3F)cc12] | 3-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propane-1,2-diol | 0.0064 |

TABLE 1-continued

| | Structure | Name | $IC_{50}$ |
|---|---|---|---|
| 213 | 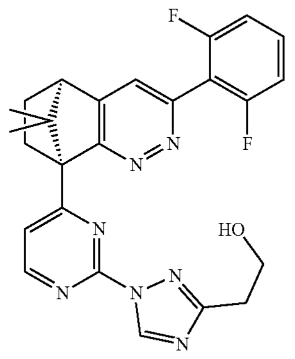 [SMILES: CC1(C)[C@H]2CC[C@]1(c1ccnc(-n3cnc(CCO)n3)n1)c1nnc(-c3c(F)cccc3F)cc12] | 2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethanol | 0.019 |
| 214 | 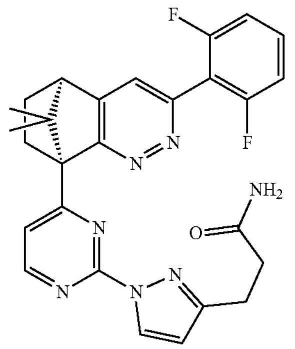 [SMILES: CC1(C)[C@H]2CC[C@]1(c1ccnc(-n3ccc(CCC(N)=O)n3)n1)c1nnc(-c3c(F)cccc3F)cc12] | 3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-3-yl]propanamide | 0.017 |
| 215 | 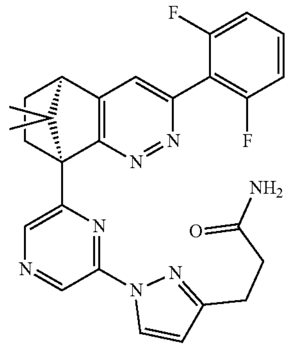 [SMILES: CC1(C)[C@H]2CC[C@]1(c1cncc(-n3ccc(CCC(N)=O)n3)n1)c1nnc(-c3c(F)cccc3F)cc12] | 3-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-3-yl]propanamide | 0.0098 |
| 216 | 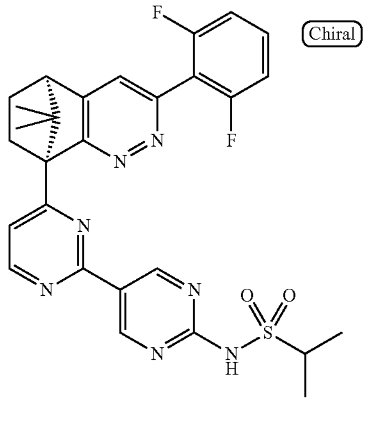 [SMILES: CC(C)S(=O)(=O)Nc1ncc(-c2nccc([C@@]34CC[C@@H](c5cc(-c6c(F)cccc6F)nnc53)C4(C)C)n2)cn1] | N-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]propane-2-sulfonamide | 0.012 |

TABLE 1-continued

| | Structure | Name | $IC_{50}$ |
|---|---|---|---|
| 217 | 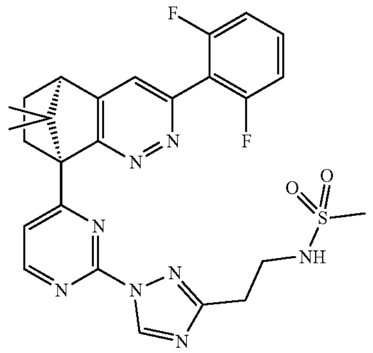 | N-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]methanesulfonamide | 0.014 |
| 218 | 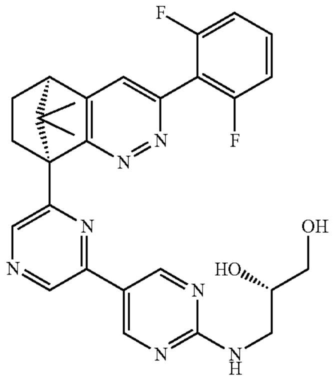 [SMILES: CC1(C)[C@H]2CC[C@]1(c1cncc(-c3cnc(NC[C@H](O)CO)nc3)n1)c1nnc(-c3c(F)cccc3F)cc12] | (2R)-3-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]propane-1,2-diol | 0.0098 |
| 219 | 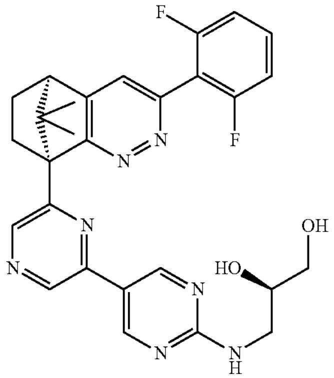 [SMILES: CC1(C)[C@H]2CC[C@]1(c1cncc(-c3cnc(NC[C@@H](O)CO)nc3)n1)c1nnc(-c3c(F)cccc3F)cc12] | (2S)-3-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]propane-1,2-diol | 0.0086 |
| 220 | 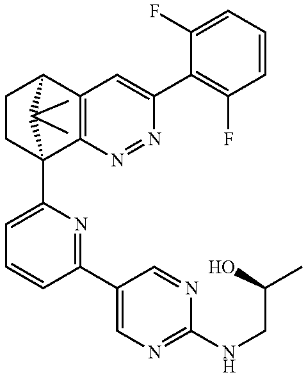 [SMILES: C[C@H](O)CNc1ncc(-c2cccc([C@@]34CC[C@@H](c5cc(-c6c(F)cccc6F)nnc53)C4(C)C)n2)cn1] | (2R)-1-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propan-2-ol | 0.0039 |

TABLE 1-continued

| | Structure | Name | $IC_{50}$ |
|---|---|---|---|
| 221 | 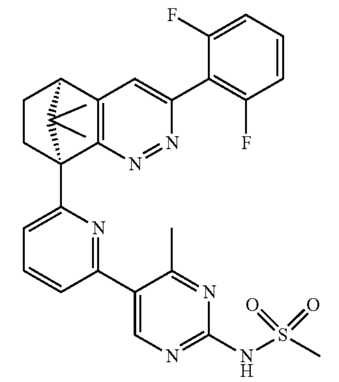 [SMILES: Cc1nc(NS(C)(=O)=O)ncc1-c1cccc([C@@]23CC[C@@H](c4cc(-c5c(F)cccc5F)nnc42)C3(C)C)n1] | N-[4-methyl-5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide | 0.0070 |
| 222 | 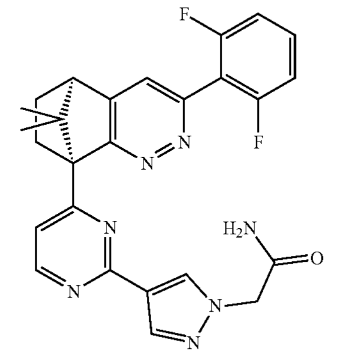 [SMILES: CC1(C)[C@H]2CC[C@]1(c1ccnc(-c3cnn(CC(N)=O)c3)n1)c1nnc(-c3c(F)cccc3F)cc12] | 2-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]acetamide | 0.0097 |
| 223 | 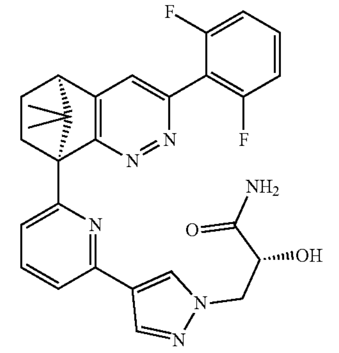 [SMILES: CC1(C)[C@H]2CC[C@]1(c1cccc(-c3cnn(C[C@@H](O)C(N)=O)c3)n1)c1nnc(-c3c(F)cccc3F)cc12] | (2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]-2-hydroxy-propanamide | 0.0052 |
| 224 | 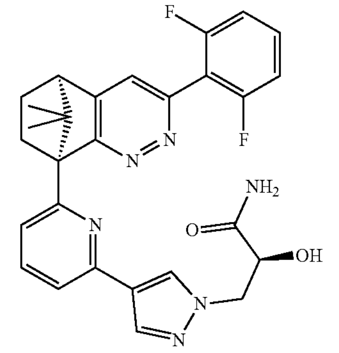 [SMILES: CC1(C)[C@H]2CC[C@]1(c1cccc(-c3cnn(C[C@H](O)C(N)=O)c3)n1)c1nnc(-c3c(F)cccc3F)cc12] | (2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]-2-hydroxy-propanamide | 0.0048 |

TABLE 1-continued

| | Structure | Name | $IC_{50}$ |
|---|---|---|---|
| 225 | 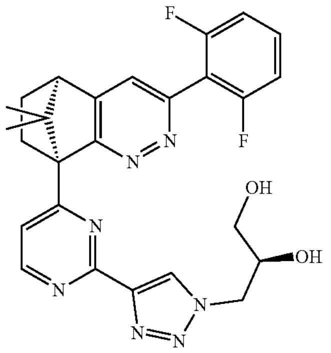 [SMILES: CC1(C)[C@H]2CC[C@]1(c1ccnc(-c3cn(C[C@H](O)CO)nn3)n1)c1nnc(-c3c(F)cccc3F)cc12] | (2S)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-1-yl]propane-1,2-diol | 0.028 |
| 226 | 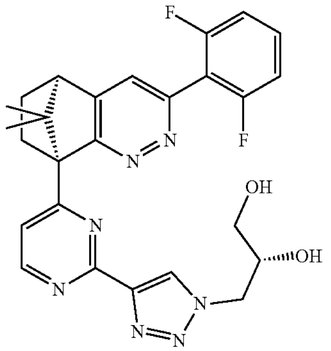 [SMILES: CC1(C)[C@H]2CC[C@]1(c1ccnc(-c3cn(C[C@@H](O)CO)nn3)n1)c1nnc(-c3c(F)cccc3F)cc12] | (2R)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-1-yl]propane-1,2-diol | 0.026 |
| 227 | 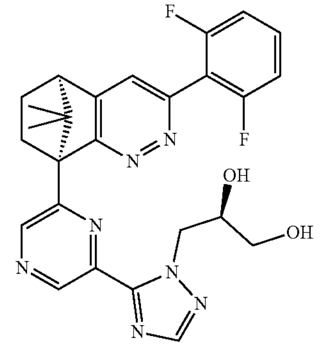 [SMILES: CC1(C)[C@H]2CC[C@]1(c1cncc(-c3ncnn3C[C@@H](O)CO)n1)c1nnc(-c3c(F)cccc3F)cc12] | (2R)-3-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-1-yl]propane-1,2-diol | 0.21 |
| 228 | 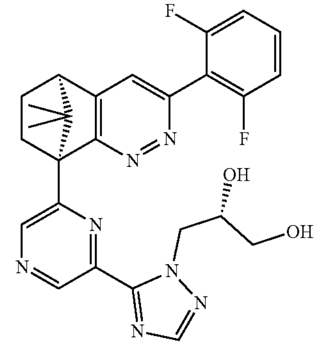 [SMILES: CC1(C)[C@H]2CC[C@]1(c1cncc(-c3ncnn3C[C@H](O)CO)n1)c1nnc(-c3c(F)cccc3F)cc12] | (2S)-3-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-1-yl]propane-1,2-diol | 0.19 |

TABLE 1-continued

| | Structure | Name | $IC_{50}$ |
|---|---|---|---|
| 229 | 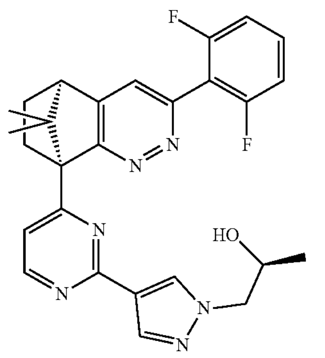 [SMILES: C[C@H](O)Cn1cc(-c2nccc([C@@]34CC[C@@H](c5cc(-c6c(F)cccc6F)nnc53)C4(C)C)n2)cn1] | (2R)-1-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propan-2-ol | 0.011 |
| 230 | 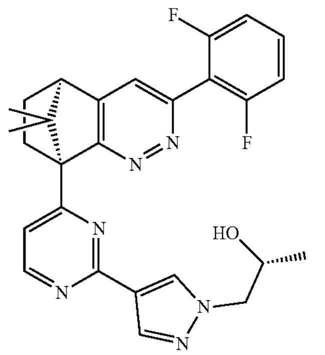 [SMILES: C[C@@H](O)Cn1cc(-c2nccc([C@@]34CC[C@@H](c5cc(-c6c(F)cccc6F)nnc53)C4(C)C)n2)cn1] | (2S)-1-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propan-2-ol | 0.0082 |
| 231 | 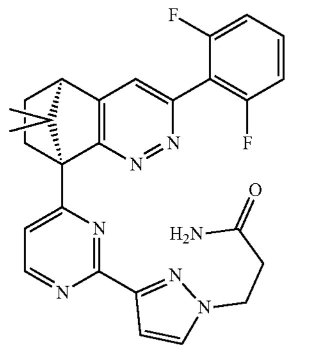 [SMILES: CC1(C)[C@H]2CC[C@]1(c1ccnc(-c3ccn(CCC(N)=O)n3)n1)c1nnc(-c3c(F)cccc3F)cc12] | 3-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propanamide | 0.034 |
| 232 | 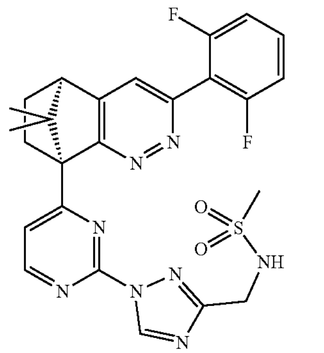 [SMILES: CC1(C)[C@H]2CC[C@]1(c1ccnc(-n3cnc(CNS(C)(=O)=O)n3)n1)c1nnc(-c3c(F)cccc3F)cc12] | N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]methanesulfonamide | 0.027 |

TABLE 1-continued

| | Structure | Name | $IC_{50}$ |
|---|---|---|---|
| 233 | 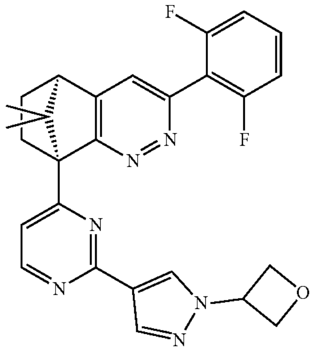 [SMILES: CC1(C)[C@H]2CC[C@]1(c1ccnc(-c3cnn(C4COC4)c3)n1)c1nnc(-c3c(F)cccc3F)cc12] | (1S,8R)-5-(2,6-difluorophenyl)-11,11-dimethyl-1-[2-[1-(oxetan-3-yl)pyrazol-4-yl]pyrimidin-4-yl]-3,4-diazatricyclo[6.2.1.02,7]undeca-2(7),3,5-triene | 0.0066 |
| 234 | 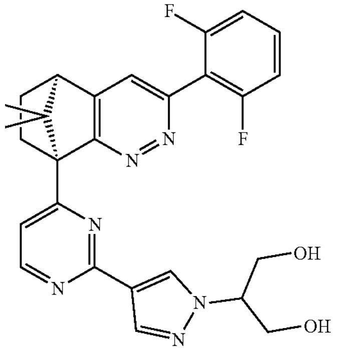 [SMILES: CC1(C)[C@H]2CC[C@]1(c1ccnc(-c3cnn(C(CO)CO)c3)n1)c1nnc(-c3c(F)cccc3F)cc12] | 2-[4-[4-[(2S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,3-diol | 0.011 |
| 235 | 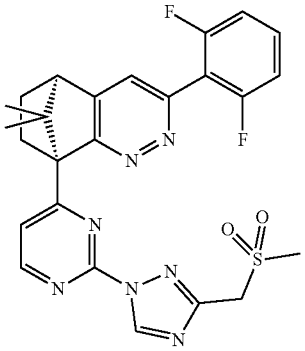 | (1S,8R)-5-(2,6-difluorophenyl)-11,11-dimethyl-1-[2-[3-(methylsulfonylmethyl)-1,2,4-triazol-1-yl]pyrimidin-4-yl]-3,4-diazatricyclo[6.2.1.02,7]undeca-2(7),3,5-triene | 0.028 |
| 236 | 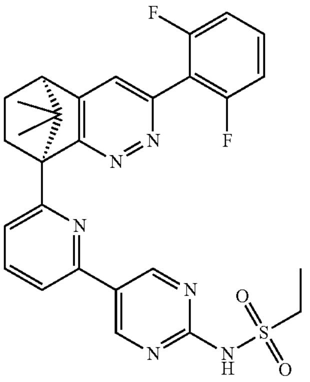 [SMILES: CCS(=O)(=O)Nc1ncc(-c2cccc([C@@]34CC[C@@H](c5cc(-c6c(F)cccc6F)nnc53)C4(C)C)n2)cn1] | N-[5-[6-[1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]ethanesulfonamide | 0.010 |

TABLE 1-continued

| | Structure | Name | $IC_{50}$ |
|---|---|---|---|
| 237 | 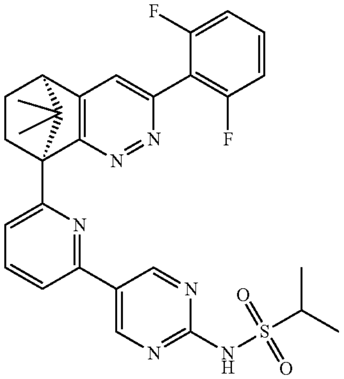 [SMILES: CC(C)S(=O)(=O)Nc1ncc(-c2cccc([C@@]34CC[C@@H](c5cc(-c6c(F)cccc6F)nnc53)C4(C)C)n2)cn1] | N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]propane-2-sulfonamide | 0.014 |
| 238 | 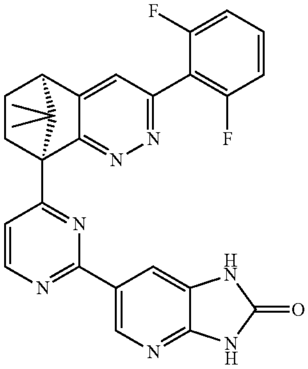 [SMILES: CC1(C)[C@H]2CC[C@]1(c1ccnc(-c3cnc4[nH]c(=O)[nH]c4c3)n1)c1nnc(-c3c(F)cccc3F)cc12] | 6-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,3-dihydroimidazo[4,5-b]pyridin-2-one | 0.014 |
| 239 | 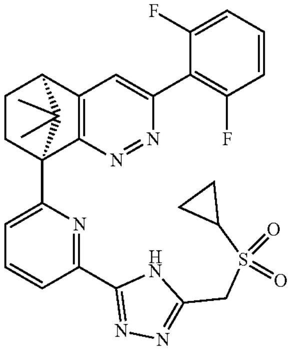 [SMILES: CC1(C)[C@H]2CC[C@]1(c1cccc(-c3nnc(CS(=O)(=O)C4CC4)[nH]3)n1)c1nnc(-c3c(F)cccc3F)cc12] | (1S,8R)-1-[6-[5-(cyclopropylsulfonylmethyl)-4H-1,2,4-triazol-3-yl]-2-pyridyl]-5-(2,6-difluorophenyl)-11,11-dimethyl-3,4-diazatricyclo[6.2.1.02,7]undeca-2(7),3,5-triene | 0.031 |
| 240 | 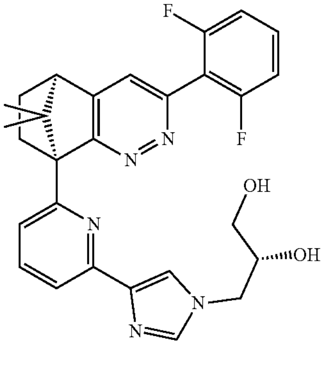 [SMILES: CC1(C)[C@H]2CC[C@]1(c1cccc(-c3cn(C[C@@H](O)CO)cn3)n1)c1nnc(-c3c(F)cccc3F)cc12] | (2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]imidazol-1-yl]propane-1,2-diol | 0.032 |

TABLE 1-continued

| | Structure | Name | $IC_{50}$ |
| --- | --- | --- | --- |
| 241 | 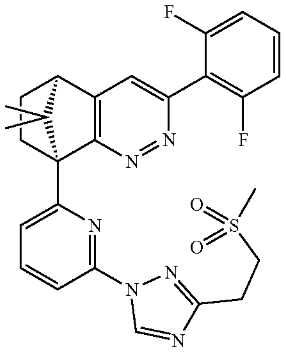 [SMILES: CC1(C)[C@H]2CC[C@]1(c1cccc(-n3cnc(CCS(C)(=O)=O)n3)n1)c1nnc(-c3c(F)cccc3F)cc12] | (1S,8R)-5-(2,6-difluorophenyl)-11,11-dimethyl-1-[6-[3-(2-methylsulfonylethyl)-1,2,4-triazol-1-yl]-2-pyridyl]-3,4-diazatricyclo[6.2.1.02,7]undeca-2(7),3,5-triene | 0.0071 |
| 242 | 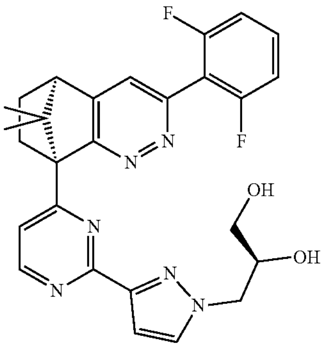 [SMILES: CC1(C)[C@H]2CC[C@]1(c1ccnc(-c3ccn(C[C@H](O)CO)n3)n1)c1nnc(-c3c(F)cccc3F)cc12] | (2S)-3-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol | 0.026 |
| 243 | 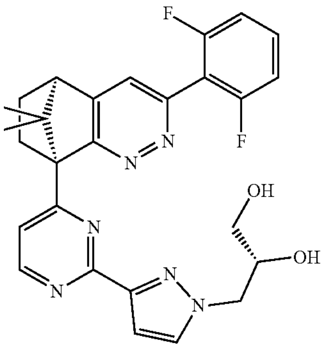 [SMILES: CC1(C)[C@H]2CC[C@]1(c1ccnc(-c3ccn(C[C@@H](O)CO)n3)n1)c1nnc(-c3c(F)cccc3F)cc12] | (2R)-3-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,2-diol | 0.033 |
| 244 | 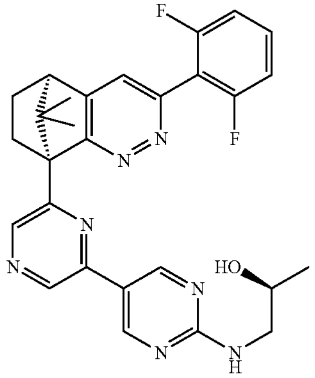 [SMILES: C[C@H](O)CNc1ncc(-c2cncc([C@@]34CC[C@@H](c5cc(-c6c(F)cccc6F)nnc53)C4(C)C)n2)cn1] | (2R)-1-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]propan-2-ol; 2,2,2-trifluoroacetic acid | 0.012 |

TABLE 1-continued

| | Structure | Name | $IC_{50}$ |
|---|---|---|---|
| 245 | 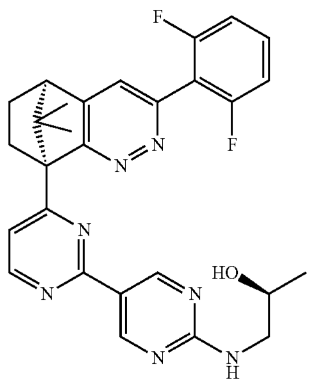 [SMILES: C[C@H](O)CNc1ncc(-c2nccc([C@@]34CC[C@@H](c5cc(-c6c(F)cccc6F)nnc53)C4(C)C)n2)cn1] | (2R)-1-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]propan-2-ol; 2,2,2-trifluoroacetic acid | 0.011 |
| 246 | 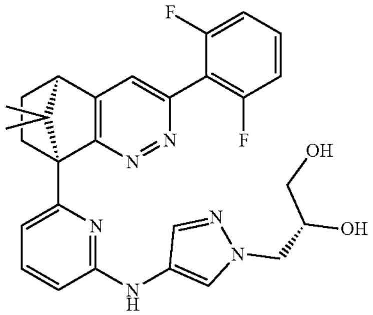 [SMILES: CC1(C)[C@H]2CC[C@]1(c1cccc(Nc3cnn(C[C@@H](O)CO)c3)n1)c1nnc(-c3c(F)cccc3F)cc12] | (2S)-3-[4-[[6-[(1S,8R)-5-(2,6-difluorophenyl)-11,11-dimethyl-3,4-diazatricyclo[6.2.1.02,7]undeca-2(7),3,5-trien-1-yl]-2-pyridyl]amino]pyrazol-1-yl]propane-1,2-diol | 0.026 |
| 247 | 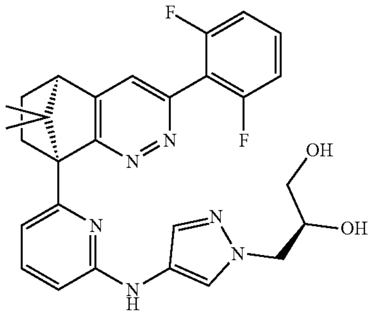 [SMILES: CC1(C)[C@H]2CC[C@]1(c1cccc(Nc3cnn(C[C@H](O)CO)c3)n1)c1nnc(-c3c(F)cccc3F)cc12] | (2R)-3-[4-[[6-[(1S,8R)-5-(2,6-difluorophenyl)-11,11-dimethyl-3,4-diazatricyclo[6.2.1.02,7]undeca-2(7),3,5-trien-1-yl]-2-pyridyl]amino]pyrazol-1-yl]propane-1,2-diol | 0.031 |
| 248 | 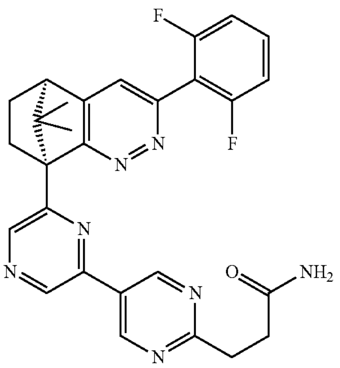 [SMILES: CC1(C)[C@H]2CC[C@]1(c1cncc(-c3cnc(CCC(N)=O)nc3)n1)c1nnc(-c3c(F)cccc3F)cc12] | 3-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]propanamide | 0.013 |

TABLE 1-continued

| | Structure | Name | IC50 |
|---|---|---|---|
| 249 | 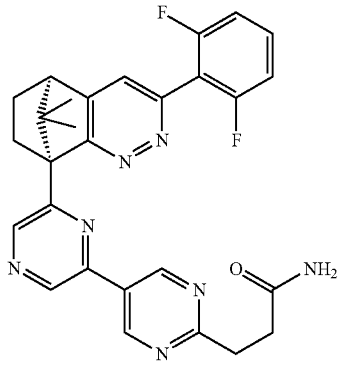 [SMILES: CC1(C)[C@H]2CC[C@]1(c1cncc(-c3cnc(CCC(N)=O)nc3)n1)c1nnc(-c3c(F)cccc3F)cc12] | 3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]propanamide | 0.013 |
| 250 | 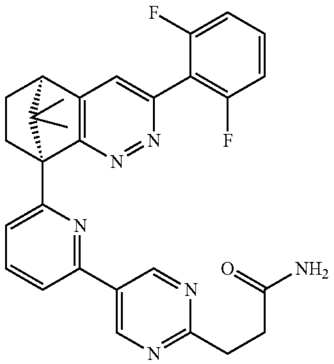 [SMILES: CC1(C)[C@H]2CC[C@]1(c1cccc(-c3cnc(CCC(N)=O)nc3)n1)c1nnc(-c3c(F)cccc3F)cc12] | 3-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]propanamide | 0.0089 |
| 251 | 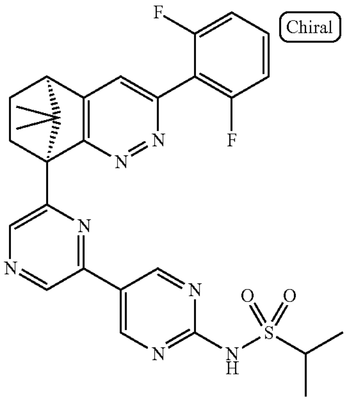 [SMILES: CC(C)S(=O)(=O)Nc1ncc(-c2cncc([C@@]34CC[C@@H](c5cc(-c6c(F)cccc6F)nnc53)C4(C)C)n2)cn1] | N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]propane-2-sulfonamide | 0.017 |
| 252 | 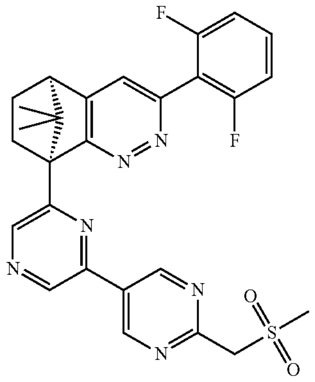 [SMILES: CC1(C)[C@H]2CC[C@]1(c1cncc(-c3cnc(CS(C)(=O)=O)nc3)n1)c1nnc(-c3c(F)cccc3F)cc12] | (1S,8R)-5-(2,6-difluorophenyl)-11,11-dimethyl-1-[6-[2-(methylsulfonylmethyl)pyrimidin-5-yl]pyrazin-2-yl]-3,4-diazatricyclo[6.2.1.02,7]undeca-2(7),3,5-triene | 0.010 |

TABLE 1-continued

| | Structure | Name | $IC_{50}$ |
|---|---|---|---|
| 253 | 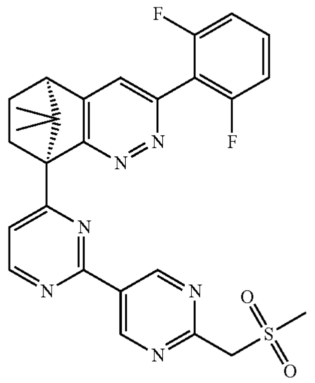 [SMILES: CC1(C)[C@H]2CC[C@]1(c1ccnc(-c3cnc(CS(C)(=O)=O)nc3)n1)c1nnc(-c3c(F)cccc3F)cc12] | (1S,8R)-5-(2,6-difluorophenyl)-11,11-dimethyl-1-[2-[2-(methylsulfonylmethyl)pyrimidin-5-yl]pyrimidin-4-yl]-3,4-diazatricyclo[6.2.1.02,7]undeca-2(7),3,5-triene | 0.012 |
| 254 | 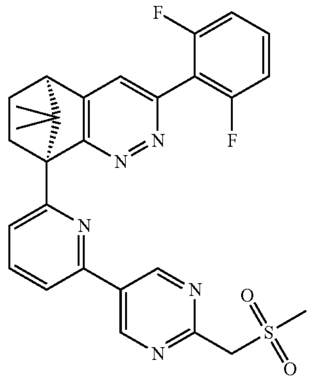 [SMILES: CC1(C)[C@H]2CC[C@]1(c1cccc(-c3cnc(CS(C)(=O)=O)nc3)n1)c1nnc(-c3c(F)cccc3F)cc12] | (1S,8R)-5-(2,6-difluorophenyl)-11,11-dimethyl-1-[6-[2-(methylsulfonylmethyl)pyrimidin-5-yl]-2-pyridyl]-3,4-diazatricyclo[6.2.1.02,7]undeca-2(7),3,5-triene | 0.0072 |
| 255 | 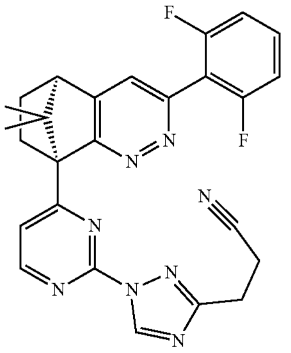 [SMILES: CC1(C)[C@H]2CC[C@]1(c1ccnc(-n3cnc(CCC#N)n3)n1)c1nnc(-c3c(F)cccc3F)cc12] | 3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanenitrile | 0.016 |
| 256 | 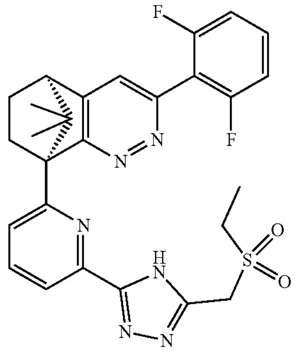 [SMILES: CCS(=O)(=O)Cc1nnc(-c2cccc([C@@]34CC[C@@H](c5cc(-c6c(F)cccc6F)nnc53)C4(C)C)n2)[nH]1] | (1S,8R)-5-(2,6-difluorophenyl)-1-[6-[5-(ethylsulfonylmethyl)-4H-1,2,4-triazol-3-yl]-2-pyridyl]-11,11-dimethyl-3,4-diazatricyclo[6.2.1.02,7]undeca-2(7),3,5-triene | 0.019 |

TABLE 1-continued

| | Structure | Name | $IC_{50}$ |
|---|---|---|---|
| 257 | 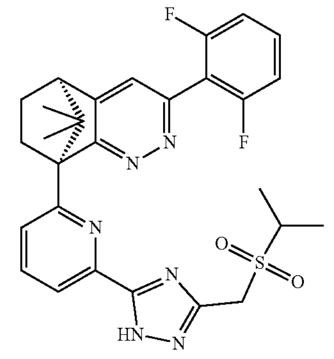 [SMILES: CC(C)S(=O)(=O)Cc1n[nH]c(-c2cccc([C@@]34CC[C@@H](c5cc(-c6c(F)cccc6F)nnc53)C4(C)C)n2)n1] | (1S,8R)-5-(2,6-difluorophenyl)-1-[6-[3-(isopropylsulfonylmethyl)-1H-1,2,4-triazol-5-yl]-2-pyridyl]-11,11-dimethyl-3,4-diazatricyclo[6.2.1.02,7]undeca-2,4,6-triene | 0.031 |
| 258 | 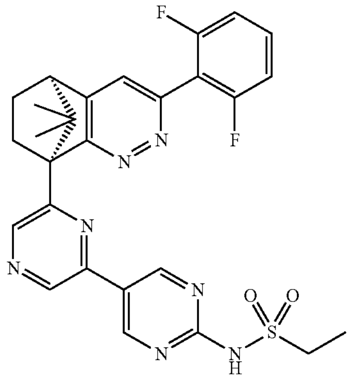 [SMILES: CCS(=O)(=O)Nc1ncc(-c2cncc([C@@]34CC[C@@H](c5cc(-c6c(F)cccc6F)nnc53)C4(C)C)n2)cn1] | N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethanesulfonamide | 0.0087 |
| 259 | 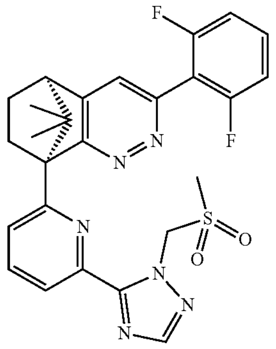 [SMILES: CC1(C)[C@H]2CC[C@]1(c1cccc(-c3ncnn3CS(C)(=O)=O)n1)c1nnc(-c3c(F)cccc3F)cc12] | (1S,8R)-5-(2,6-difluorophenyl)-11,11-dimethyl-1-[6-[2-(methylsulfonylmethyl)-1,2,4-triazol-3-yl]-2-pyridyl]-3,4-diazatricyclo[6.2.1.02,7]undeca-2(7),3,5-triene | 0.020 |
| 260 | 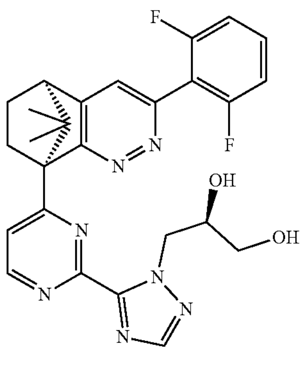 [SMILES: CC1(C)[C@H]2CC[C@]1(c1ccnc(-c3ncnn3C[C@@H](O)CO)n1)c1nnc(-c3c(F)cccc3F)cc12] | (2R)-3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-1-yl]propane-1,2-diol | 0.22 |

TABLE 1-continued

| | Structure | Name | $IC_{50}$ |
|---|---|---|---|
| 261 | 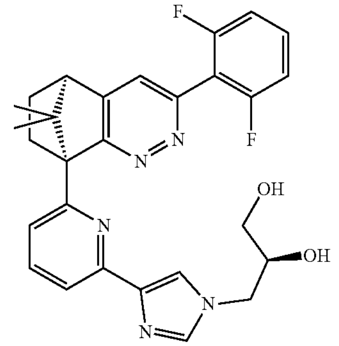 [SMILES: CC1(C)[C@H]2CC[C@]1(c1cccc(-c3cn(C[C@H](O)CO)cn3)n1)c1nnc(-c3c(F)cccc3F)cc12] | (2S)-3-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]imidazol-1-yl]propane-1,2-diol | 0.025 |
| 262 | 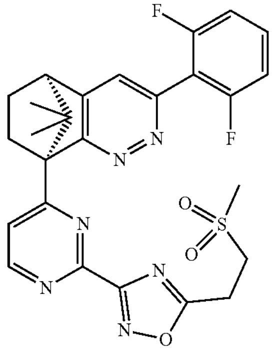 [SMILES: CC1(C)[C@H]2CC[C@]1(c1ccnc(-c3noc(CCS(C)(=O)=O)n3)n1)c1nnc(-c3c(F)cccc3F)cc12] | 5-(2-methylsulfonylethyl)-3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-oxadiazole | 0.028 |
| 263 | 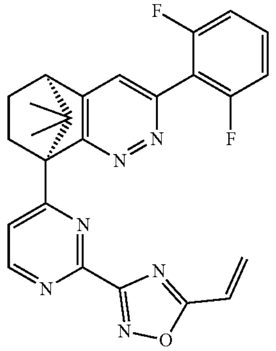 [SMILES: C=Cc1nc(-c2nccc([C@@]34CC[C@@H](c5cc(-c6c(F)cccc6F)nnc53)C4(C)C)n2)no1] | 3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-5-vinyl-1,2,4-oxadiazole | 0.030 |
| 264 | 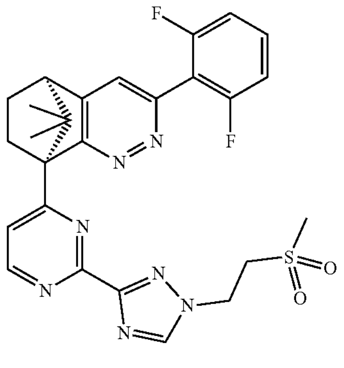 [SMILES: CC1(C)[C@H]2CC[C@]1(c1ccnc(-c3ncn(CCS(C)(=O)=O)n3)n1)c1nnc(-c3c(F)cccc3F)cc12] | (1S,8R)-5-(2,6-difluorophenyl)-11,11-dimethyl-1-[2-[1-(2-methylsulfonylethyl)-1,2,4-triazol-3-yl]pyrimidin-4-yl]-3,4-diazatricyclo[6.2.1.02,7]undeca-2(7),3,5-triene | 0.093 |

TABLE 1-continued

| | Structure | Name | $IC_{50}$ |
|---|---|---|---|
| 265 | 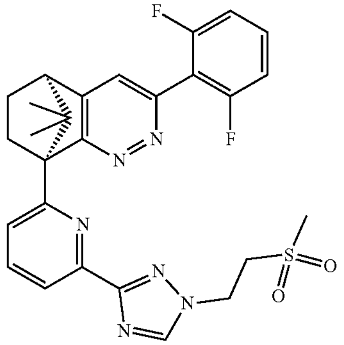 [SMILES: CC1(C)[C@H]2CC[C@]1(c1cccc(-c3ncn(CCS(C)(=O)=O)n3)n1)c1nnc(-c3c(F)cccc3F)cc12] | (1S,8R)-5-(2,6-difluorophenyl)-11,11-dimethyl-1-[6-[1-(2-methylsulfonylethyl)-1,2,4-triazol-3-yl]-2-pyridyl]-3,4-diazatricyclo[6.2.1.02,7]undeca-2(7),3,5-triene | 0.040 |
| 266 | 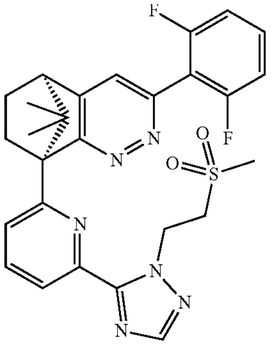 [SMILES: CC1(C)[C@H]2CC[C@]1(c1cccc(-c3ncnn3CCS(C)(=O)=O)n1)c1nnc(-c3c(F)cccc3F)cc12] | (1S,8R)-5-(2,6-difluorophenyl)-11,11-dimethyl-1-[6-[2-(2-methylsulfonylethyl)-1,2,4-triazol-3-yl]-2-pyridyl]-3,4-diazatricyclo[6.2.1.02,7]undeca-2(7),3,5-triene | 0.076 |
| 267 | 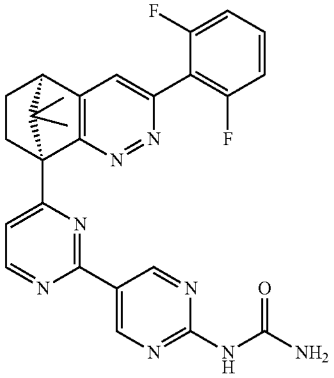 [SMILES: CC1(C)[C@H]2CC[C@]1(c1ccnc(-c3cnc(NC(N)=O)nc3)n1)c1nnc(-c3c(F)cccc3F)cc12] | [5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]urea | 0.023 |
| 268 | 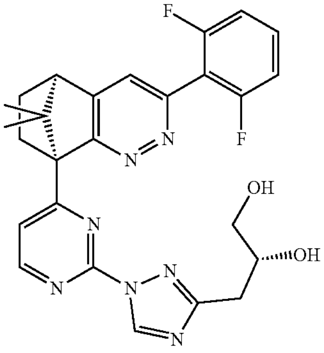 [SMILES: CC1(C)[C@H]2CC[C@]1(c1ccnc(-n3cnc(C[C@@H](O)CO)n3)n1)c1nnc(-c3c(F)cccc3F)cc12] | (2R)-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol | 0.041 |

TABLE 1-continued

| | Structure | Name | $IC_{50}$ |
|---|---|---|---|
| 269 | 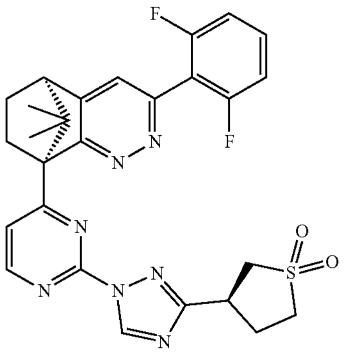 [SMILES: CC1(C)[C@H]2CC[C@]1(c1ccnc(-n3cnc([C@@H]4CCS(=O)(=O)C4)n3)n1)c1nnc(-c3c(F)cccc3F)cc12] | (3S)-3-[1-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,2,4-triazol-3-yl]thiolane 1,1-dioxide | 0.028 |
| 270 | 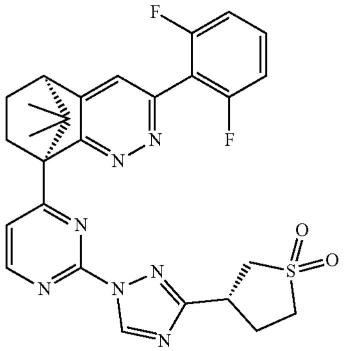 [SMILES: CC1(C)[C@H]2CC[C@]1(c1ccnc(-n3cnc([C@H]4CCS(=O)(=O)C4)n3)n1)c1nnc(-c3c(F)cccc3F)cc12] | (3R)-3-[1-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,2,4-triazol-3-yl]thiolane 1,1-dioxide | 0.029 |
| 271 | 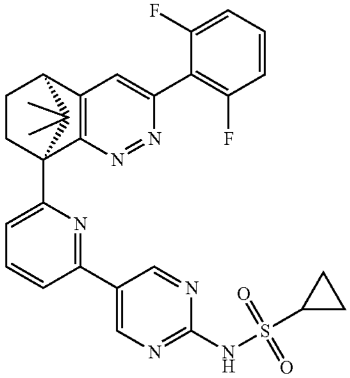 [SMILES: CC1(C)[C@H]2CC[C@]1(c1cccc(-c3cnc(NS(=O)(=O)C4CC4)nc3)n1)c1nnc(-c3c(F)cccc3F)cc12] | N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]cyclopropanesulfonamide | 0.0060 |
| 272 | 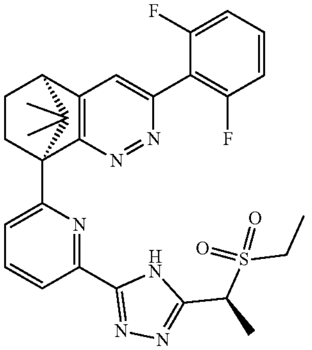 [SMILES: CCS(=O)(=O)[C@@H](C)c1nnc(-c2cccc([C@@]34CC[C@@H](c5cc(-c6c(F)cccc6F)nnc53)C4(C)C)n2)[nH]1] | (1S,8R)-5-(2,6-difluorophenyl)-11,11-dimethyl-1-[6-[5-[(1R)-1-ethylsulfonylethyl]-4H-1,2,4-triazol-3-yl]-2-pyridyl]-3,4-diazatricyclo[6.2.1.02,7]undeca-2(7),3,5-triene | 0.026 |

TABLE 1-continued

| | Structure | Name | IC50 |
|---|---|---|---|
| 273 | 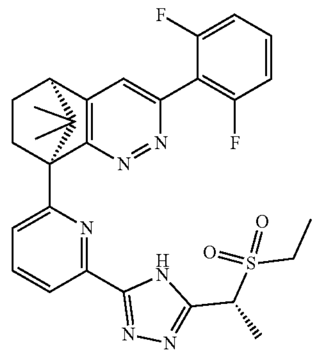 [SMILES: CCS(=O)(=O)[C@H](C)c1nnc(-c2cccc([C@@]34CC[C@@H](c5cc(-c6c(F)cccc6F)nnc53)C4(C)C)n2)[nH]1] | (1S,8R)-5-(2,6-difluorophenyl)-11,11-dimethyl-1-[6-[5-[(1S)-1-ethylsulfonylethyl]-4H-1,2,4-triazol-3-yl]-2-pyridyl]-3,4-diazatricyclo[6.2.1.02,7]undeca-2(7),3,5-triene | 0.021 |
| 274 | 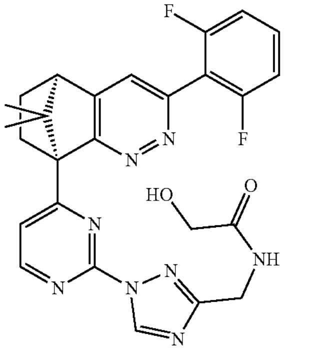 [SMILES: CC1(C)[C@H]2CC[C@]1(c1ccnc(-n3cnc(CNC(=O)CO)n3)n1)c1nnc(-c3c(F)cccc3F)cc12] | 2-hydroxy-N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]acetamide | 0.026 |
| 275 | 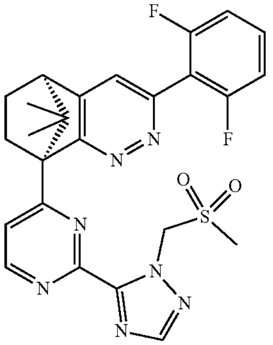 [SMILES: CC1(C)[C@H]2CC[C@]1(c1ccnc(-c3ncnn3CS(C)(=O)=O)n1)c1nnc(-c3c(F)cccc3F)cc12] | (1S,8R)-5-(2,6-difluorophenyl)-11,11-dimethyl-1-[2-[2-(methylsulfonylmethyl)-1,2,4-triazol-3-yl]pyrimidin-4-yl]-3,4-diazatricyclo[6.2.1.02,7]undeca-2(7),3,5-triene | 0.061 |
| 276 | 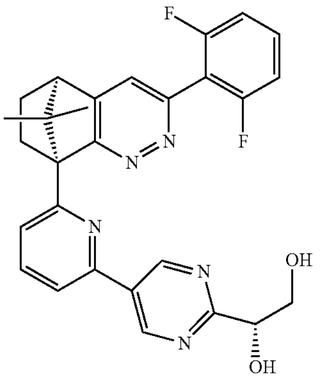 [SMILES: CC1(C)[C@H]2CC[C@]1(c1cccc(-c3cnc([C@@H](O)CO)nc3)n1)c1nnc(-c3c(F)cccc3F)cc12] | (1S)-1-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]ethane-1,2-diol | 0.0057 |

TABLE 1-continued

| | Structure | Name | $IC_{50}$ |
|---|---|---|---|
| 277 | 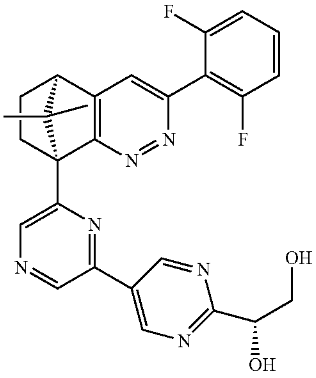 [SMILES: CC1(C)[C@H]2CC[C@]1(c1cncc(-c3cnc([C@@H](O)CO)nc3)n1)c1nnc(-c3c(F)cccc3F)cc12] | (1S)-1-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethane-1,2-diol | 0.012 |
| 278 | 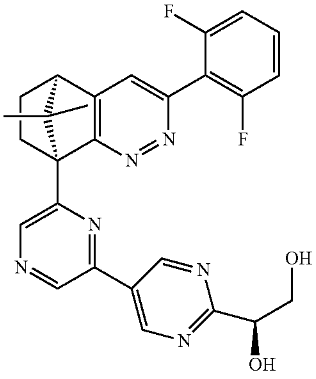 [SMILES: CC1(C)[C@H]2CC[C@]1(c1cncc(-c3cnc([C@H](O)CO)nc3)n1)c1nnc(-c3c(F)cccc3F)cc12] | (1R)-1-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethane-1,2-diol | 0.016 |
| 279 | 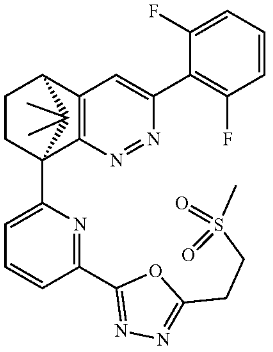 [SMILES: CC1(C)[C@H]2CC[C@]1(c1cccc(-c3nnc(CCS(C)(=O)=O)o3)n1)c1nnc(-c3c(F)cccc3F)cc12] | 2-(2-methylsulfonylethyl)-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,3,4-oxadiazole | 0.037 |
| 280 | 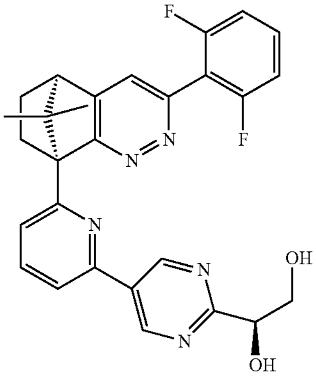 [SMILES: CC1(C)[C@H]2CC[C@]1(c1cccc(-c3cnc([C@H](O)CO)nc3)n1)c1nnc(-c3c(F)cccc3F)cc12] | (1R)-1-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]ethane-1,2-diol | 0.0061 |

TABLE 1-continued

| | Structure | Name | $IC_{50}$ |
|---|---|---|---|
| 281 | 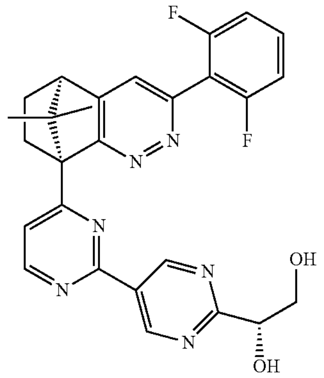 [SMILES: CC1(C)[C@H]2CC[C@]1(c1ccnc(-c3cnc([C@@H](O)CO)nc3)n1)c1nnc(-c3c(F)cccc3F)cc12] | (1S)-1-[5-[4-[1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]ethane-1,2-diol | 0.016 |
| 282 | 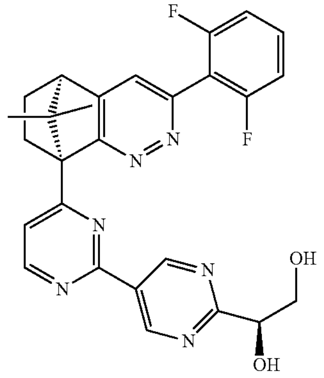 [SMILES: CC1(C)[C@H]2CC[C@]1(c1ccnc(-c3cnc([C@H](O)CO)nc3)n1)c1nnc(-c3c(F)cccc3F)cc12] | (1R)-1-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]ethane-1,2-diol | 0.015 |
| 283 | 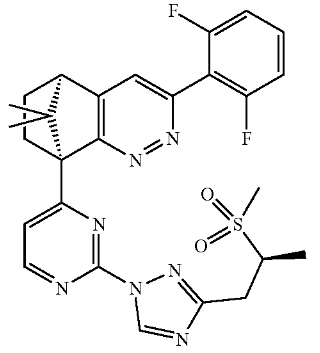 [SMILES: C[C@@H](Cc1ncn(-c2nccc([C@@]34CC[C@@H](c5cc(-c6c(F)cccc6F)nnc53)C4(C)C)n2)n1)S(C)(=O)=O] | (1S,8R)-5-(2,6-difluorophenyl)-11,11-dimethyl-1-[2-[3-[(2S)-methylsulfonylpropyl]-1,2,4-triazol-1-yl]pyrimidin-4-yl]-3,4-diazatricyclo[6.2.1.02,7]undeca-2(7),3,5-triene | 0.018 |
| 284 | 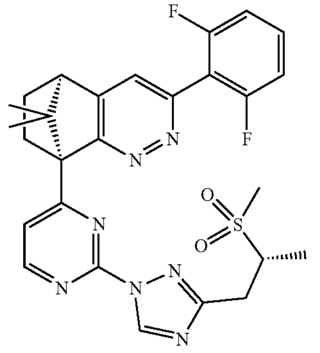 [SMILES: C[C@H](Cc1ncn(-c2nccc([C@@]34CC[C@@H](c5cc(-c6c(F)cccc6F)nnc53)C4(C)C)n2)n1)S(C)(=O)=O] | (1S,8R)-5-(2,6-difluorophenyl)-11,11-dimethyl-1-[2-[3-[(2R)-2-methylsulfonylpropyl]-1,2,4-triazol-1-yl]pyrimidin-4-yl]-3,4-diazatricyclo[6.2.1.02,7]undeca-2(7),3,5-triene | 0.021 |

TABLE 1-continued

| | Structure | Name | $IC_{50}$ |
|---|---|---|---|
| 285 | 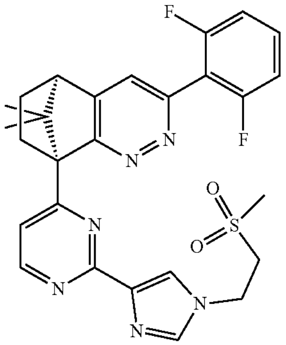 [SMILES: CC1(C)[C@H]2CC[C@]1(c1ccnc(-c3cn(CCS(C)(=O)=O)cn3)n1)c1nnc(-c3c(F)cccc3F)cc12] | (1S,8R)-5-(2,6-difluorophenyl)-11,11-dimethyl-1-[2-[1-(2-methylsulfonylethyl)imidazol-4-yl]pyrimidin-4-yl]-3,4-diazatricyclo[6.2.1.02,7]undeca-2(7),3,5-triene | 0.056 |
| 286 | 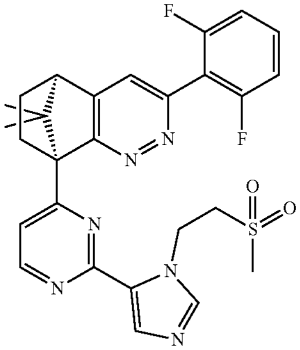 [SMILES: CC1(C)[C@H]2CC[C@]1(c1ccnc(-c3cncn3CCS(C)(=O)=O)n1)c1nnc(-c3c(F)cccc3F)cc12] | (1S,8R)-5-(2,6-difluorophenyl)-11,11-dimethyl-1-[2-[3-(2-methylsulfonylethyl)imidazol-4-yl]pyrimidin-4-yl]-3,4-diazatricyclo[6.2.1.02,7]undeca-2(7),3,5-triene | 0.045 |
| 287 | 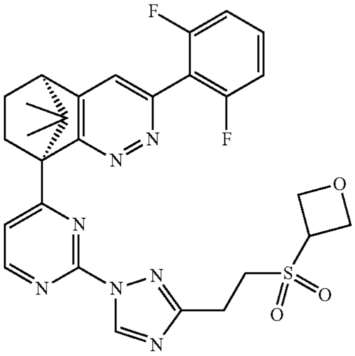 [SMILES: CC1(C)[C@H]2CC[C@]1(c1ccnc(-n3cnc(CCS(=O)(=O)C4COC4)n3)n1)c1nnc(-c3c(F)cccc3F)cc12] | (1S,8R)-5-(2,6-difluorophenyl)-11,11-dimethyl-1-[2-[3-(2-(oxetan-3-ylsulfonyl)ethyl]-1,2,4-triazol-1-yl]pyrimidin-4-yl]-3,4-diazatricyclo[6.2.1.02,7]undeca-2(7),3,5-triene | 0.039 |
| 288 | 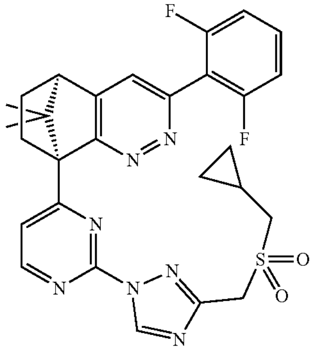 [SMILES: CC1(C)[C@H]2CC[C@]1(c1ccnc(-n3cnc(CS(=O)(=O)CC4CC4)n3)n1)c1nnc(-c3c(F)cccc3F)cc12] | (1S,8R)-1-[2-[3-(cyclopropylmethylsulfonylmethyl)-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene | 0.034 |

TABLE 1-continued

| | Structure | Name | $IC_{50}$ |
|---|---|---|---|
| 289 | 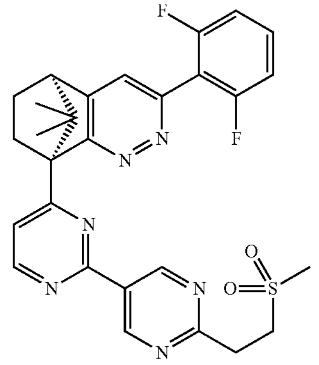 [SMILES: CC1(C)[C@H]2CC[C@]1(c1ccnc(-c3cnc(CCS(C)(=O)=O)nc3)n1)c1nnc(-c3c(F)cccc3F)cc12] | (1S,8R)-5-(2,6-difluorophenyl)-11,11-dimethyl-1-[2-[2-(2-methylsulfonylethyl)pyrimidin-5-yl]pyrimidin-4-yl]-3,4-diazatricyclo[6.2.1.02,7]undeca-2(7),3,5-triene | 0.018 |
| 290 | 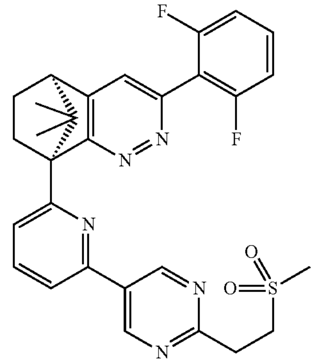 [SMILES: CC1(C)[C@H]2CC[C@]1(c1cccc(-c3cnc(CCS(C)(=O)=O)nc3)n1)c1nnc(-c3c(F)cccc3F)cc12] | (1S,8R)-5-(2,6-difluorophenyl)-11,11-dimethyl-1-[6-[2-(2-methylsulfonylethyl)pyrimidin-5-yl]-2-pyridyl]-3,4-diazatricyclo[6.2.1.02,7]undeca-2(7),3,5-triene | 0.011 |
| 291 | 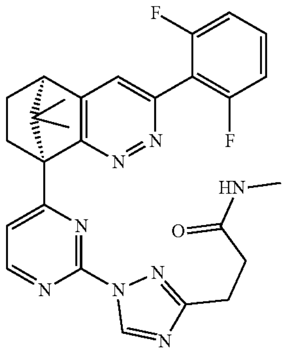 [SMILES: CNC(=O)CCc1ncn(-c2nccc([C@@]34CC[C@@H](c5cc(-c6c(F)cccc6F)nnc53)C4(C)C)n2)n1] | N-methyl-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanamide | 0.041 |
| 292 | 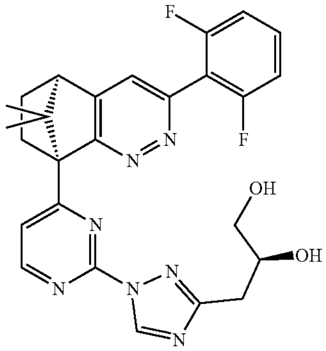 [SMILES: CC1(C)[C@H]2CC[C@]1(c1ccnc(-n3cnc(C[C@H](O)CO)n3)n1)c1nnc(-c3c(F)cccc3F)cc12] | (2S)-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol | 0.053 |

TABLE 1-continued

| | Structure | Name | IC$_{50}$ |
|---|---|---|---|
| 293 | 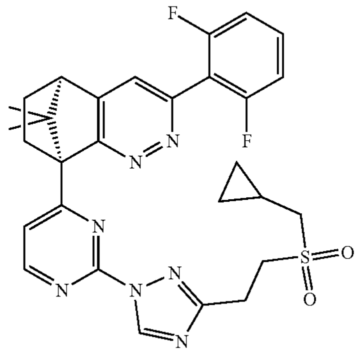 [SMILES: CC1(C)[C@H]2CC[C@]1(c1ccnc(-n3cnc(CCS(=O)(=O)CC4CC4)n3)n1)c1nnc(-c3c(F)cccc3F)cc12] | (1S,8R)-1-[2-[3-[2-(cyclopropylmethylsulfonyl)ethyl]-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene | 0.015 |
| 294 | 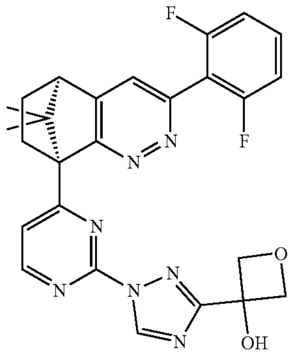 [SMILES: CC1(C)[C@H]2CC[C@]1(c1ccnc(-n3cnc(C4(O)COC4)n3)n1)c1nnc(-c3c(F)cccc3F)cc12] | 3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]oxetan-3-ol | 0.023 |
| 295 | 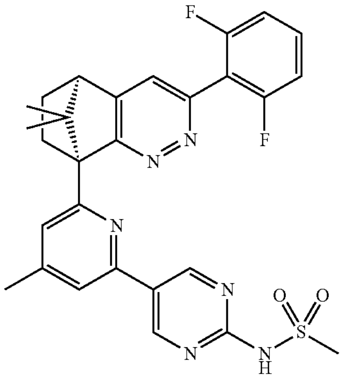 | N-[5-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide | 0.030 |
| 296 | 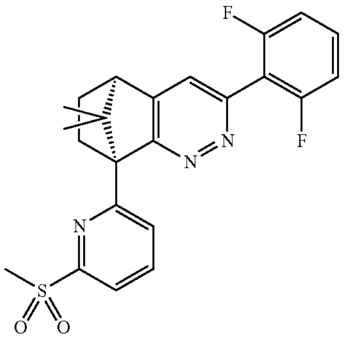 [SMILES: CC1(C)[C@H]2CC[C@]1(c1cccc(S(C)(=O)=O)n1)c1nnc(-c3c(F)cccc3F)cc12] | (1S,8R)-5-(2,6-difluorophenyl)-11,11-dimethyl-1-(6-methylsulfonyl-2-pyridyl)-3,4-diazatricyclo[6.2.1.02,7]undeca-2(7),3,5-triene | 0.010 |

TABLE 1-continued

| | Structure | Name | $IC_{50}$ |
|---|---|---|---|
| 297 | 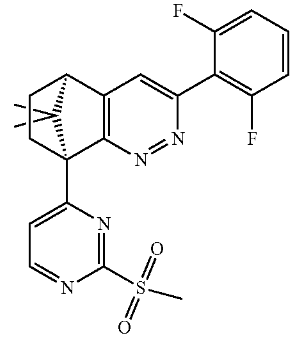 [SMILES: CC1(C)[C@H]2CC[C@]1(c1ccnc(S(C)(=O)=O)n1)c1nnc(-c3c(F)cccc3F)cc12] | (1S,8R)-5-(2,6-difluorophenyl)-11,11-dimethyl-1-(2-methylsulfonylpyrimidin-4-yl)-3,4-diazatricyclo[6.2.1.02,7]undeca-2(7),3,5-triene | |
| 298 | 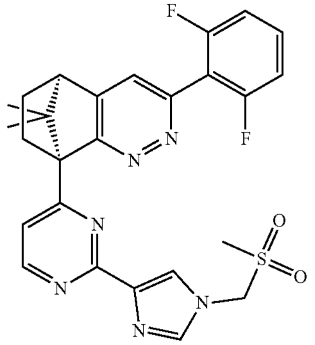 [SMILES: CC1(C)[C@H]2CC[C@]1(c1ccnc(-c3cn(CS(C)(=O)=O)cn3)n1)c1nnc(-c3c(F)cccc3F)cc12] | (1S,8R)-5-(2,6-difluorophenyl)-11,11-dimethyl-1-[2-[1-(methylsulfonylmethyl)imidazol-4-yl]pyrimidin-4-yl]-3,4-diazatricyclo[6.2.1.02,7]undeca-2(7),3,5-triene | 0.037 |
| 299 | 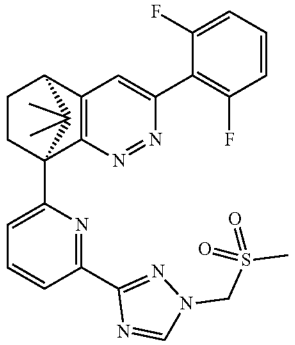 [SMILES: CC1(C)[C@H]2CC[C@]1(c1cccc(-c3ncn(CS(C)(=O)=O)n3)n1)c1nnc(-c3c(F)cccc3F)cc12] | (1S,8R)-5-(2,6-difluorophenyl)-11,11-dimethyl-1-[6-[1-(methylsulfonylmethyl)-1,2,4-triazol-3-yl]-2-pyridyl]-3,4-diazatricyclo[6.2.1.02,7]undeca-2(7),3,5-triene | 0.12 |
| 300 | 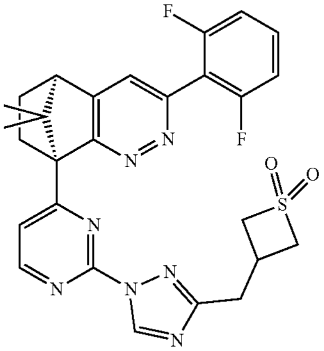 [SMILES: CC1(C)[C@H]2CC[C@]1(c1ccnc(-n3cnc(CC4CS(=O)(=O)C4)n3)n1)c1nnc(-c3c(F)cccc3F)cc12] | 3-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]thietane 1,1-dioxide | 0.11 |

TABLE 1-continued

| | Structure | Name | $IC_{50}$ |
|---|---|---|---|
| 301 | 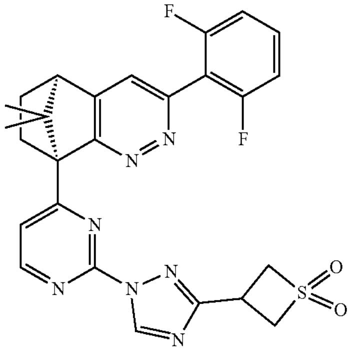 [SMILES: CC1(C)[C@H]2CC[C@]1(c1ccnc(-n3cnc(C4CS(=O)(=O)C4)n3)n1)c1nnc(-c3c(F)cccc3F)cc12] | 3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]thietane 1,1-dioxide | 0.043 |
| 301 | 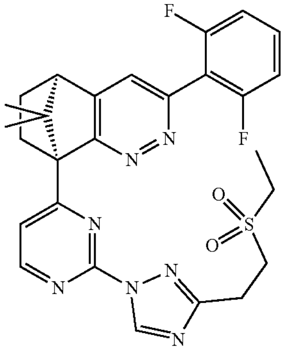 [SMILES: CCS(=O)(=O)CCc1ncn(-c2nccc([C@@]34CC[C@@H](c5cc(-c6c(F)cccc6F)nnc53)C4(C)C)n2)n1] | (1S,8R)-5-(2,6-difluorophenyl)-1-[2-[3-(2-ethylsulfonylethyl)-1,2,4-triazol-1-yl]pyrimidin-4-yl]-11,11-dimethyl-3,4-diazatricyclo[6.2.1.02,7]undeca-2(7),3,5-triene | 0.015 |
| 302 | 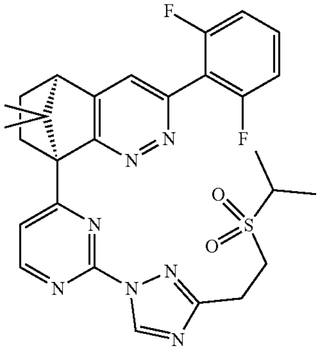 [SMILES: CC(C)S(=O)(=O)CCc1ncn(-c2nccc([C@@]34CC[C@@H](c5cc(-c6c(F)cccc6F)nnc53)C4(C)C)n2)n1] | (1S,8R)-5-(2,6-difluorophenyl)-1-[2-[3-(2-isopropylsulfonylethyl)-1,2,4-triazol-1-yl]pyrimidin-4-yl]-11,11-dimethyl-3,4-diazatricyclo[6.2.1.02,7]undeca-2(7),3,5-triene | 0.025 |
| 303 | 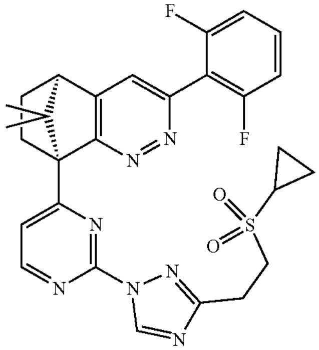 [SMILES: CC1(C)[C@H]2CC[C@]1(c1ccnc(-n3cnc(CCS(=O)(=O)C4CC4)n3)n1)c1nnc(-c3c(F)cccc3F)cc12] | (1S,8R)-1-[2-[3-(2-cyclopropylsulfonylethyl)-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene | 0.031 |

TABLE 1-continued

| | Structure | Name | $IC_{50}$ |
|---|---|---|---|
| 304 | 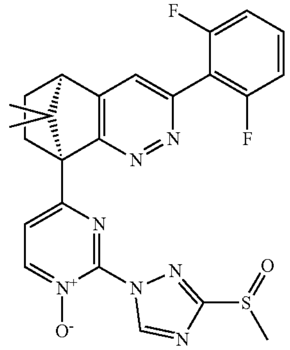 [SMILES: CS(=O)c1ncn(-c2nc([C@@]34CC[C@@H](c5cc(-c6c(F)cccc6F)nnc53)C4(C)C)cc[n+]2[O-])n1] | (1S,8R)-5-(2,6-difluorophenyl)-11,11-dimethyl-1-[2-(3-methylsulfinyl-1,2,4-triazol-1-yl)-1-oxido-pyrimidin-1-ium-4-yl]-3,4-diazatricyclo[6.2.1.02,7]undeca-2(7),3,5-triene | |
| 305 | 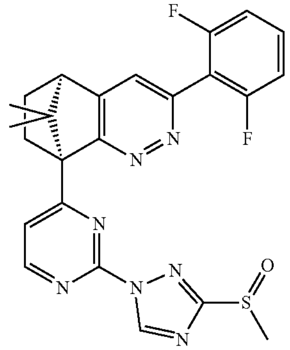 [SMILES: CS(=O)c1ncn(-c2nccc([C@@]34CC[C@@H](c5cc(-c6c(F)cccc6F)nnc53)C4(C)C)n2)n1] | (1S,8R)-5-(2,6-difluorophenyl)-11,11-dimethyl-1-[2-(3-methylsulfinyl-1,2,4-triazol-1-yl)pyrimidin-4-yl]-3,4-diazatricyclo[6.2.1.02,7]undeca-2(7),3,5-triene | 0.095 |
| 306 | 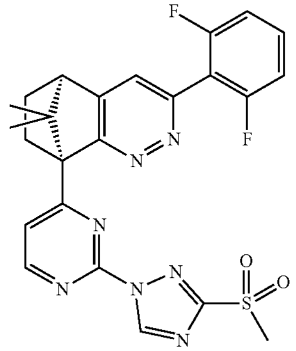 [SMILES: CC1(C)[C@H]2CC[C@]1(c1ccnc(-n3cnc(S(C)(=O)=O)n3)n1)c1nnc(-c3c(F)cccc3F)cc12] | (1S,8R)-5-(2,6-difluorophenyl)-11,11-dimethyl-1-[2-(3-methylsulfonyl-1,2,4-triazol-1-yl)pyrimidin-4-yl]-3,4-diazatricyclo[6.2.1.02,7]undeca-2(7),3,5-triene | 0.061 |
| 307 | 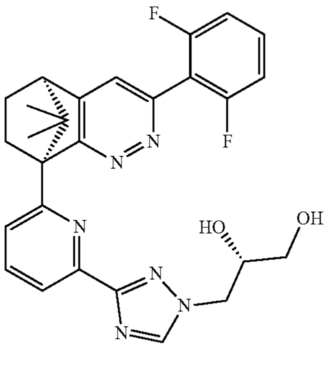 [SMILES: CC1(C)[C@H]2CC[C@]1(c1cccc(-c3ncn(C[C@H](O)CO)n3)n1)c1nnc(-c3c(F)cccc3F)cc12] | (2R)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-1-yl]propane-1,2-diol | 0.10 |

TABLE 1-continued

| | Structure | Name | $IC_{50}$ |
|---|---|---|---|
| 308 | 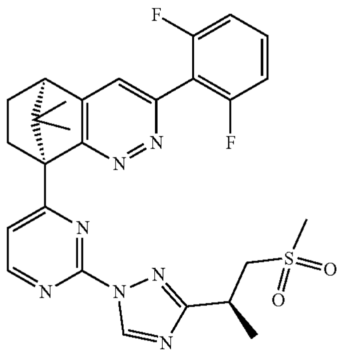 [SMILES: C[C@H](CS(C)(=O)=O)c1ncn(-c2nccc([C@@]34CC[C@@H](c5cc(-c6c(F)cccc6F)nnc53)C4(C)C)n2)n1] | (1S,8R)-5-(2,6-difluorophenyl)-11,11-dimethyl-1-[2-[3-[(1R)-1-methyl-2-methylsulfonyl-ethyl]-1,2,4-triazol-1-yl]pyrimidin-4-yl]-3,4-diazatricyclo[6.2.1.02,7]undeca-2(7),3,5-triene | 0.047 |
| 309 | 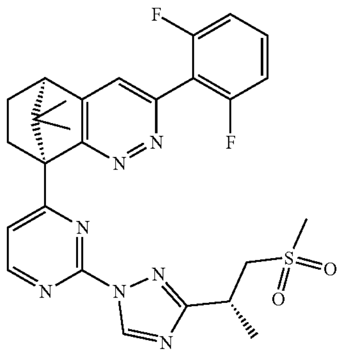 [SMILES: C[C@@H](CS(C)(=O)=O)c1ncn(-c2nccc([C@@]34CC[C@@H](c5cc(-c6c(F)cccc6F)nnc53)C4(C)C)n2)n1] | (1S,8R)-5-(2,6-difluorophenyl)-11,11-dimethyl-1-[2-[3-[(1S)-1-methyl-2-methylsulfonyl-ethyl]-1,2,4-triazol-1-yl]pyrimidin-4-yl]-3,4-diazatricyclo[6.2.1.02,7]undeca-2(7),3,5-triene | 0.063 |
| 310 | 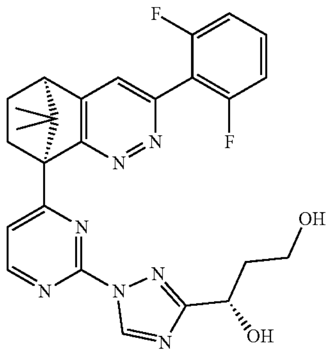 [SMILES: CC1(C)[C@H]2CC[C@]1(c1ccnc(-n3cnc([C@@H](O)CCO)n3)n1)c1nnc(-c3c(F)cccc3F)cc12] | (1R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol | 0.063 |
| 311 | 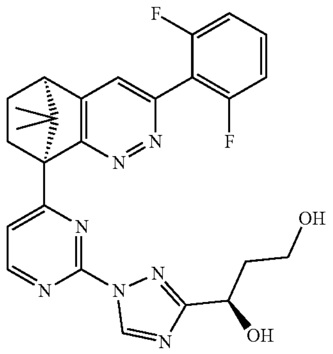 [SMILES: CC1(C)[C@H]2CC[C@]1(c1ccnc(-n3cnc([C@H](O)CCO)n3)n1)c1nnc(-c3c(F)cccc3F)cc12] | (1S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol | 0.054 |

TABLE 1-continued

| | Structure | Name | $IC_{50}$ |
|---|---|---|---|
| 312 | 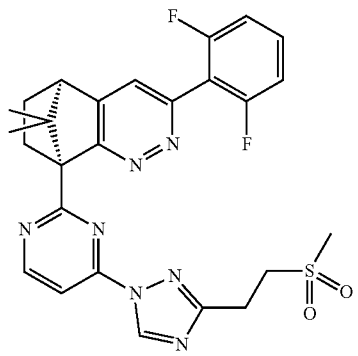 [SMILES: CC1(C)[C@H]2CC[C@]1(c1nccc(-n3cnc(CCS(C)(=O)=O)n3)n1)c1nnc(-c3c(F)cccc3F)cc12] | (5R,8R)-3-(2,6-difluorophenyl)-9,9-dimethyl-8-(4-(3-(2-(methylsulfonyl)ethyl)-1H-1,2,4-triazol-1-yl)pyrimidin-2-yl)-5,6,7,8-tetrahydro-5,8-methanocinnoline | 0.085 |
| 313 | 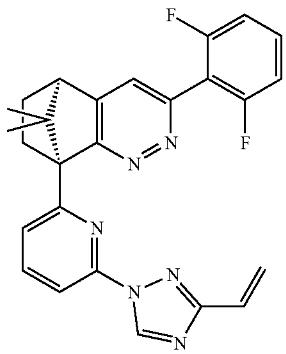 [SMILES: C=Cc1ncn(-c2cccc([C@@]34CC[C@@H](c5cc(-c6c(F)cccc6F)nnc53)C4(C)C)n2)n1] | (5R,8S)-3-(2,6-difluorophenyl)-9,9-dimethyl-8-(6-(3-vinyl-1H-1,2,4-triazol-1-yl)pyridin-2-yl)-5,6,7,8-tetrahydro-5,8-methanocinnoline | 0.0064 |
| 314 | 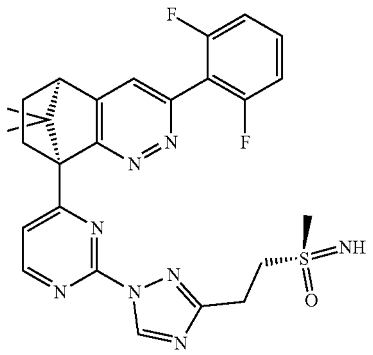 [SMILES: CC1(C)[C@H]2CC[C@]1(c1ccnc(-n3cnc(CC[S@](C)(=N)=O)n3)n1)c1nnc(-c3c(F)cccc3F)cc12] | imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane | 0.078 |
| 315 | 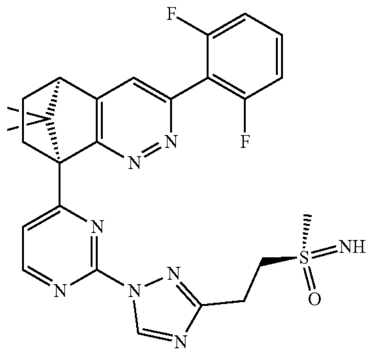 [SMILES: CC1(C)[C@H]2CC[C@]1(c1ccnc(-n3cnc(CC[S@@](C)(=N)=O)n3)n1)c1nnc(-c3c(F)cccc3F)cc12] | imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane | 0.062 |

TABLE 1-continued

| | Structure | Name | $IC_{50}$ |
|---|---|---|---|
| 316 | 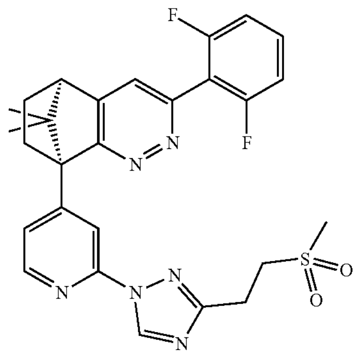 [SMILES: CC1(C)[C@H]2CC[C@]1(c1ccnc(-n3cnc(CCS(C)(=O)=O)n3)c1)c1nnc(-c3c(F)cccc3F)cc12] | (1S,8R)-5-(2,6-difluorophenyl)-11,11-dimethyl-1-[2-[3-(2-methylsulfonylethyl)-1,2,4-triazol-1-yl]-4-pyridyl]-3,4-diazatricyclo[6.2.1.02,7]undeca-2(7),3,5-triene | 0.032 |
| 317 | 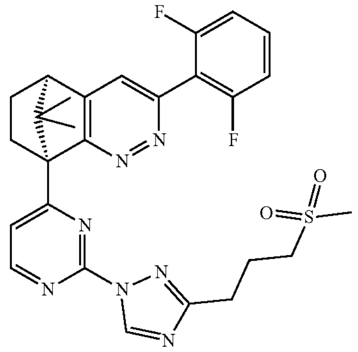 [SMILES: CC1(C)[C@H]2CC[C@]1(c1ccnc(-n3cnc(CCCS(C)(=O)=O)n3)n1)c1nnc(-c3c(F)cccc3F)cc12] | (1S,8R)-5-(2,6-difluorophenyl)-11,11-dimethyl-1-[2-[3-(3-methylsulfonylpropyl)-1,2,4-triazol-1-yl]pyrimidin-4-yl]-3,4-diazatricyclo[6.2.1.02,7]undeca-2(7),3,5-triene | 0.026 |
| 318 | 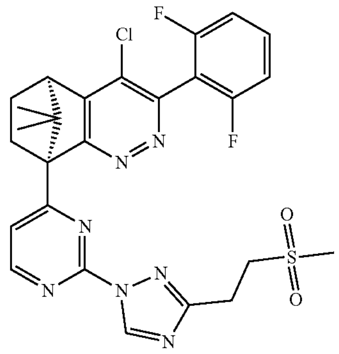 [SMILES: CC1(C)[C@H]2CC[C@]1(c1ccnc(-n3cnc(CCS(C)(=O)=O)n3)n1)c1nnc(-c3c(F)cccc3F)c(Cl)c12] | (1S,8R)-6-chloro-5-(2,6-difluorophenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene | 0.0074 |
| 319 | 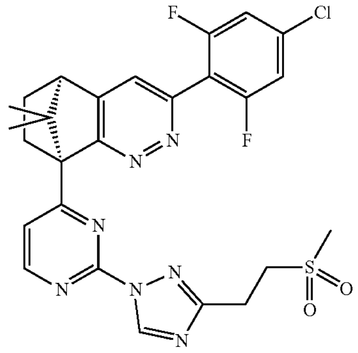 [SMILES: CC1(C)[C@H]2CC[C@]1(c1ccnc(-n3cnc(CCS(C)(=O)=O)n3)n1)c1nnc(-c3c(F)cc(Cl)cc3F)cc12] | (5R,8S)-3-(4-chloro-2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline | 0.0099 |

TABLE 1-continued

| | Structure | Name | $IC_{50}$ |
|---|---|---|---|
| 320 | 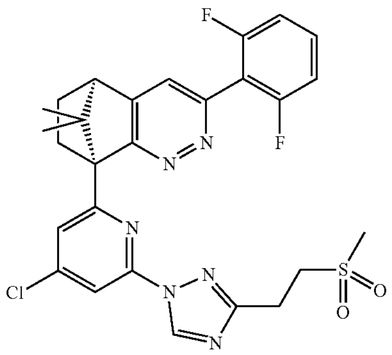 [SMILES: CC1(C)[C@H]2CC[C@]1(c1cc(Cl)cc(-n3cnc(CCS(C)(=O)=O)n3)n1)c1nnc(-c3c(F)cccc3F)cc12] | (1S,8R)-6-chloro-5-(2,6-difluorophenyl)-11,11-dimethyl-1-[6-[3-(2-methylsulfonylethyl)-1,2,4-triazol-1-yl]-2-pyridyl]-3,4-diazatricyclo[6.2.1.02,7]undeca-2(7),3,5-triene | 0.0063 |
| 321 | 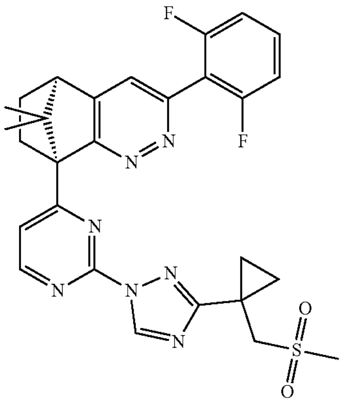 | (1S,8R)-5-(2,6-difluorophenyl)-11,11-dimethyl-1-[2-[3-[1-(methylsulfonylmethyl)cyclopropyl]-1,2,4-triazol-1-yl]pyrimidin-4-yl]-3,4-diazatricyclo[6.2.1.02,7]undeca-2(7),3,5-triene | 0.060 |
| 322 | 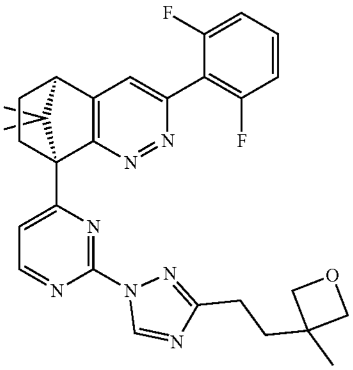 [SMILES: CC1(CCc2ncn(-c3nccc([C@@]45CC[C@@H](c6cc(-c7c(F)cccc7F)nnc64)C5(C)C)n3)n2)COC1] | (1S,8R)-5-(2,6-difluorophenyl)-11,11-dimethyl-1-[2-[3-[2-(3-methyloxetan-3-yl)ethyl]-1,2,4-triazol-1-yl]pyrimidin-4-yl]-3,4-diazatricyclo[6.2.1.02,7]undeca-2(7),3,5-triene | 0.17 |
| 323 | 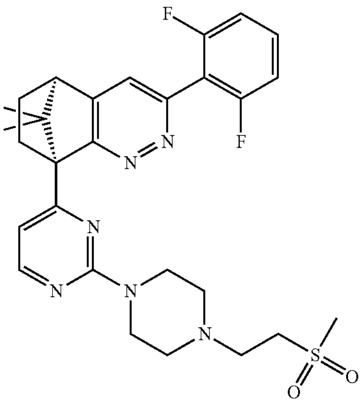 [SMILES: CC1(C)[C@H]2CC[C@]1(c1ccnc(N3CCN(CCS(C)(=O)=O)CC3)n1)c1nnc(-c3c(F)cccc3F)cc12] | (1S,8R)-5-(2,6-difluorophenyl)-11,11-dimethyl-1-[2-[4-(2-methylsulfonylethyl)piperazin-1-yl]pyrimidin-4-yl]-3,4-diazatricyclo[6.2.1.02,7]undeca-2(7),3,5-triene | 0.050 |

TABLE 1-continued

| | Structure | Name | IC$_{50}$ |
|---|---|---|---|
| 324 | 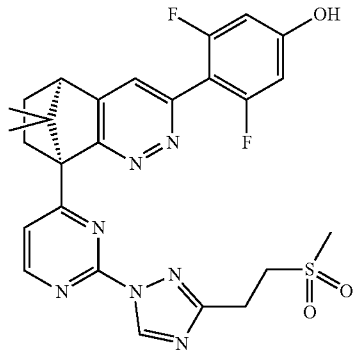 [SMILES: CC1(C)[C@H]2CC[C@]1(c1ccnc(-n3cnc(CCS(C)(=O)=O)n3)n1)c1nnc(-c3c(F)cc(O)cc3F)cc12] | 4-((5R,8S)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnolin-3-yl)-3,4-difluorophenol | 0.023 |
| 325 | 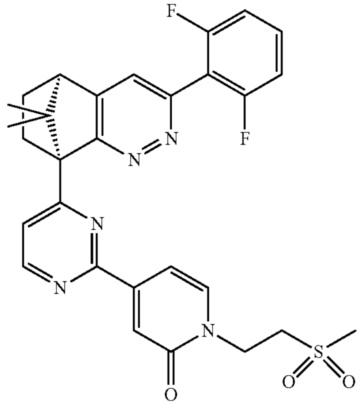 | 1-(2-methylsulfonylethyl)-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyridin-2-one | 0.012 |
| 326 | 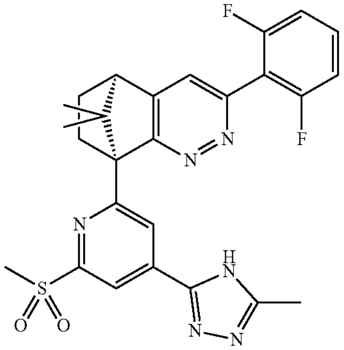 [SMILES: Cc1nnc(-c2cc([C@@]34CC[C@@H](c5cc(-c6c(F)cccc6F)nnc53)C4(C)C)nc(S(C)(=O)=O)c2)[nH]1] | (5R,8S)-3-(2,6-difluorophenyl)-9,9-dimethyl-8-(4-(5-methyl-4H-1,2,4-triazol-3-yl)-6-(methylsulfonyl)pyridin-2-yl)-5,6,7,8-tetrahydro-5,8-methanocinnoline | 0.18 |
| 327 | 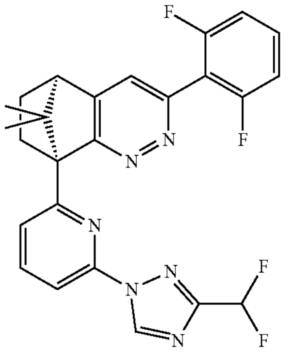 [SMILES: CC1(C)[C@H]2CC[C@]1(c1cccc(-n3cnc(C(F)F)n3)n1)c1nnc(-c3c(F)cccc3F)cc12] | (5R,8S)-8-(6-(3-(difluoromethyl)-1H-1,2,4-triazol-1-yl)pyridin-2-yl)-3-(2,6-difluorophenyl)-9,9-dimethyl-5,6,7,8-tetrahydro-5,8-methanocinnoline | 0.0031 |

TABLE 1-continued

| | Structure | Name | $IC_{50}$ |
|---|---|---|---|
| 328 | 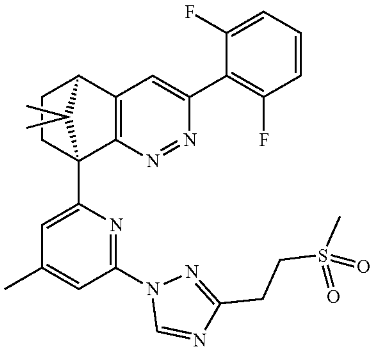 [SMILES: Cc1cc(-n2cnc(CCS(C)(=O)=O)n2)nc([C@@]23CC[C@@H](c4cc(-c5c(F)cccc5F)nnc42)C3(C)C)c1] | (1S,8R)-5-(2,6-difluorophenyl)-11,11-dimethyl-1-[4-methyl-6-[3-(2-methylsulfonylethyl)-1,2,4-triazol-1-yl]-2-pyridyl]-3,4-diazatricyclo[6.2.1.02,7]undeca-2(7),3,5-triene | 0.042 |
| 329 | 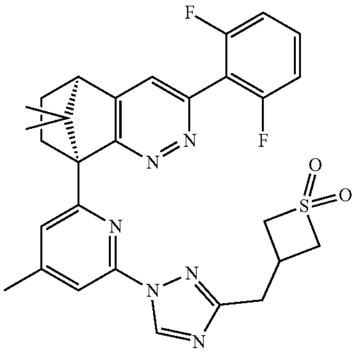 [SMILES: Cc1cc(-n2cnc(CC3CS(=O)(=O)C3)n2)nc([C@@]23CC[C@@H](c4cc(-c5c(F)cccc5F)nnc42)C3(C)C)c1] | 3-[[1-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methyl]thietane 1,1-dioxide | 0.036 |
| 330 | 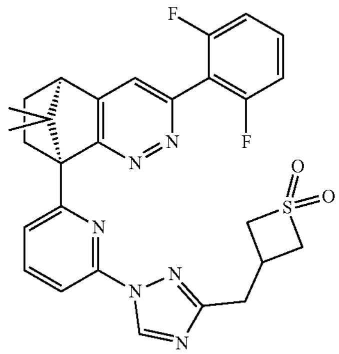 [SMILES: CC1(C)[C@H]2CC[C@]1(c1cccc(-n3cnc(CC4CS(=O)(=O)C4)n3)n1)c1nnc(-c3c(F)cccc3F)cc12] | 3-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methyl]thietane 1,1-dioxide | 0.018 |
| 331 | 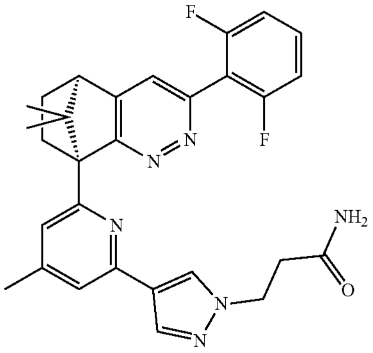 [SMILES: Cc1cc(-c2cnn(CCC(N)=O)c2)nc([C@@]23CC[C@@H](c4cc(-c5c(F)cccc5F)nnc42)C3(C)C)c1] | 3-[4-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide | 0.037 |

TABLE 1-continued

| | Structure | Name | $IC_{50}$ |
|---|---|---|---|
| 332 | 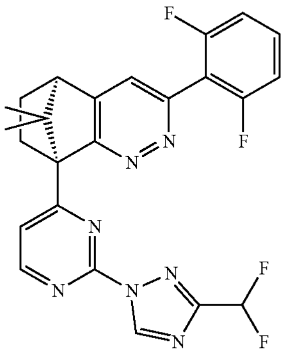 | (5R,8S)-8-(2-(3-(difluoromethyl)-1H-1,2,4-triazol-1-yl)pyrimidin-4-yl)-3-(2,6-difluorophenyl)-9,9-dimethyl-5,6,7,8-tetrahydro-5,8-methanocinnoline | 0.0084 |
| 333 | 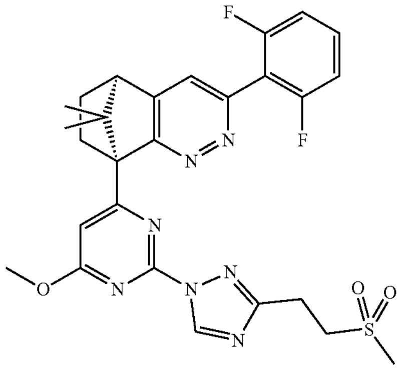 | (1S,8R)-5-(2,6-difluorophenyl)-1-[6-methoxy-2-[3-(2-methylsulfonylethyl)-1,2,4-triazol-1-yl]pyrimidin-4-yl]-11,11-dimethyl-3,4-diazatricyclo[6.2.1.02,7]undeca-2(7),3,5-triene | 0.033 |
| 334 | 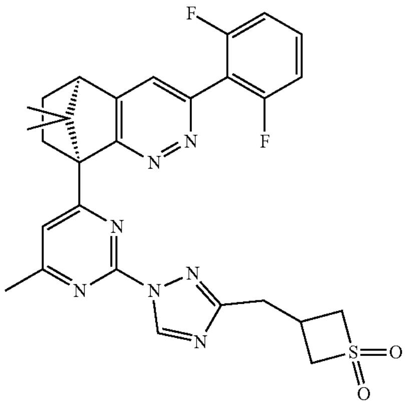 [SMILES: Cc1cc([C@@]23CC[C@@H](c4cc(-c5c(F)cccc5F)nnc42)C3(C)C)nc(-n2cnc(CC3CS(=O)(=O)C3)n2)n1] | 3-[[1-[4-methyl-6-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]thietane 1,1-dioxide | 0.062 |
| 335 | 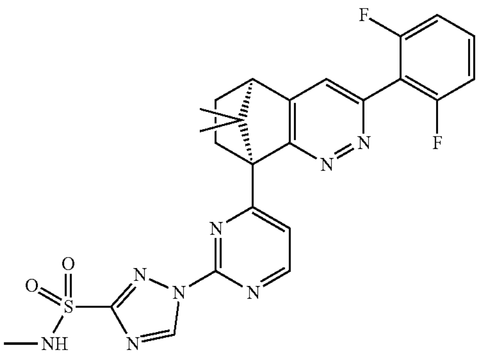 [SMILES: CNS(=O)(=O)c1ncn(-c2nccc([C@@]34CC[C@@H](c5cc(-c6c(F)cccc6F)nnc53)C4(C)C)n2)n1] | 1-(4-((5R,8S)-3-(2,6-difluorophenyl)-9,9-dimethyl-6,7-dihydro-5,8-methanocinnolin-8(5H)-yl)pyrimidin-2-yl)-N-methyl-1H-1,2,4-triazole-3-sulfonamide | 0.015 |

TABLE 1-continued

| | Structure | Name | $IC_{50}$ |
|---|---|---|---|
| 336 | 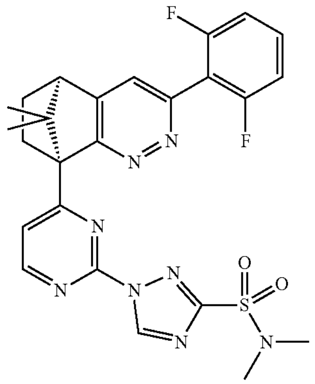 | N,N-dimethyl-1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazole-3-sulfonamide | |
| 337 | 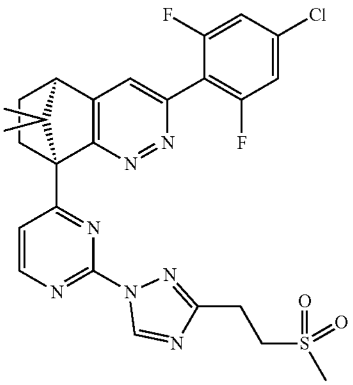 [SMILES: CC1(C)[C@H]2CC[C@]1(c1ccnc(-n3cnc(CCS(C)(=O)=O)n3)n1)c1nnc(-c3c(F)cc(Cl)cc3F)cc12] | (5R,8S)-3-(4-chloro-2,6-difluorophenyl)-9,9-dimethyl-8-(2-(3-(2-(methylsulfonyl)ethyl)-1H-1,2,4-triazol-1-yl)pyrimidin-4-yl)-5,6,7,8-tetrahydro-5,8-methanocinnoline | 0.0099 |
| 338 | 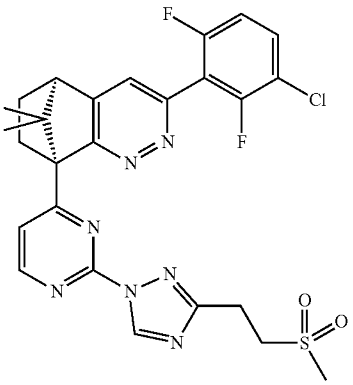 [SMILES: CC1(C)[C@H]2CC[C@]1(c1ccnc(-n3cnc(CCS(C)(=O)=O)n3)n1)c1nnc(-c3c(F)ccc(Cl)c3F)cc12] | (1R,8R)-5-(3-chloro-2,6-difluoro-phenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene | 0.0070 |
| 339 | 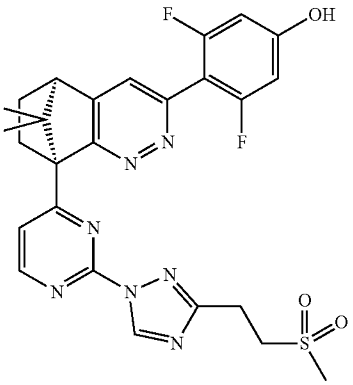 [SMILES: CC1(C)[C@H]2CC[C@]1(c1ccnc(-n3cnc(CCS(C)(=O)=O)n3)n1)c1nnc(-c3c(F)cc(O)cc3F)cc12] | | 0.023 |

TABLE 1-continued
| | Structure | Name | $IC_{50}$ |
|---|---|---|---|
| 340 | 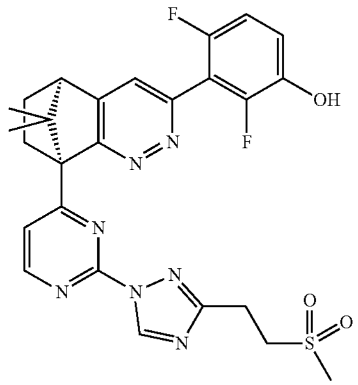 [SMILES: CC1(C)[C@H]2CC[C@]1(c1ccnc(-n3cnc(CCS(C)(=O)=O)n3)n1)c1nnc(-c3c(F)ccc(O)c3F)cc12] | | 0.044 |
| 341 | 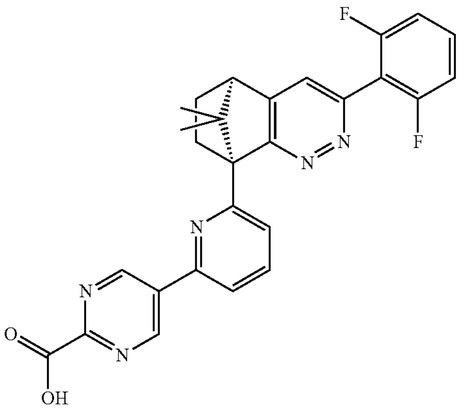 [SMILES: CC1(C)[C@H]2CC[C@]1(c1cccc(-c3cnc(C(=O)O)nc3)n1)c1nnc(-c3c(F)cccc3F)cc12] | 5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidine-2-carboxylic acid | 0.0049 |
| 342 | 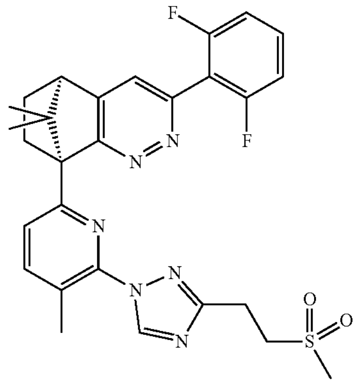 [SMILES: Cc1ccc([C@@]23CC[C@@H](c4cc(-c5c(F)cccc5F)nnc42)C3(C)C)nc1-n1cnc(CCS(C)(=O)=O)n1] | (1R,8R)-5-(2,6-difluorophenyl)-11,11-dimethyl-1-[5-methyl-6-[3-(2-methylsulfonylethyl)-1,2,4-triazol-1-yl]-2-pyridyl]-3,4-diazatricyclo[6.2.1.02,7]undeca-2(7),3,5-triene | 0.20 |
| 343 | 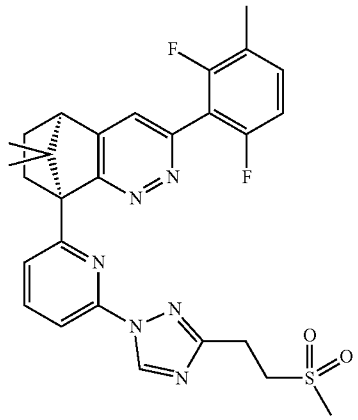 [SMILES: Cc1ccc(F)c(-c2cc3c(nn2)[C@@]2(c4cccc(-n5cnc(CCS(C)(=O)=O)n5)n4)CC[C@@H]3C2(C)C)c1F] | (1R,8R)-5-(2,6-difluoro-3-methyl-phenyl)-11,11-dimethyl-1-[6-[3-(2-methylsulfonylethyl)-1,2,4-triazol-1-yl]-2-pyridyl]-3,4-diazatricyclo[6.2.1.02,7]undeca-2(7),3,5-triene | 0.013 |

TABLE 1-continued

| | Structure | Name | $IC_{50}$ |
|---|---|---|---|
| 344 | 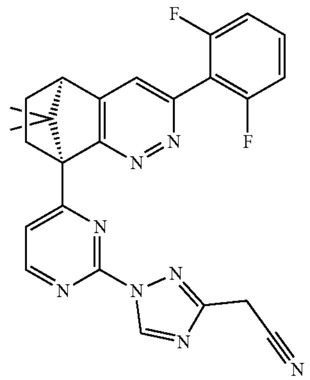 [SMILES: CC1(C)[C@H]2CC[C@]1(c1ccnc(-n3cnc(CC#N)n3)n1)c1nnc(-c3c(F)cccc3F)cc12] | 2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]acetonitrile | 0.0090 |
| 345 | 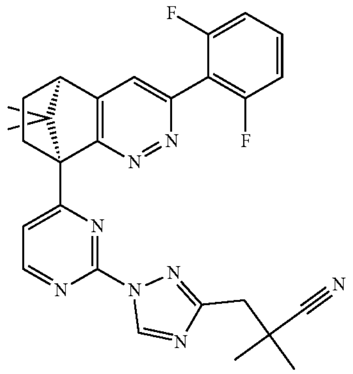 [SMILES: CC(C)(C#N)Cc1ncn(-c2nccc([C@@]34CC[C@@H](c5cc(-c6c(F)cccc6F)nnc53)C4(C)C)n2)n1] | 2,2-dimethyl-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanenitrile | 0.0080 |
| 346 | 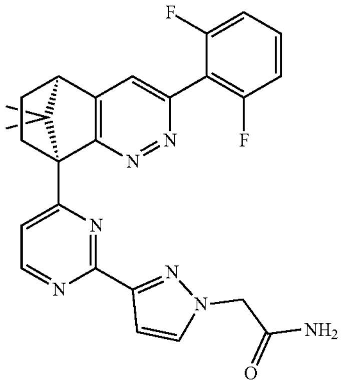 [SMILES: CC1(C)[C@H]2CC[C@]1(c1ccnc(-c3ccn(CC(N)=O)n3)n1)c1nnc(-c3c(F)cccc3F)cc12] | 2-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]acetamide | 0.013 |
| 347 | 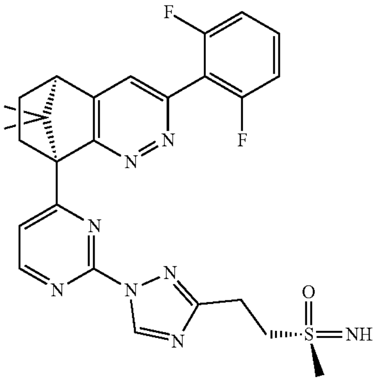 [SMILES: CC1(C)[C@H]2CC[C@]1(c1ccnc(-n3cnc(CC[S@@](C)(=N)=O)n3)n1)c1nnc(-c3c(F)cccc3F)cc12] | imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane | 0.078 |

TABLE 1-continued

| | Structure | Name | $IC_{50}$ |
|---|---|---|---|
| 348 | 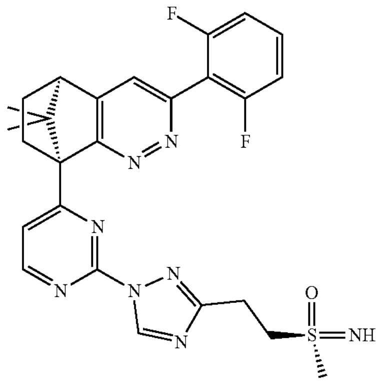 [SMILES: CC1(C)[C@H]2CC[C@]1(c1ccnc(-n3cnc(CC[S@](C)(=N)=O)n3)n1)c1nnc(-c3c(F)cccc3F)cc12] | imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane | 0.062 |
| 349 | 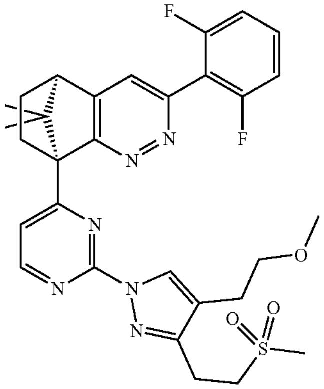 | (1S,8R)-5-(2,6-difluorophenyl)-1-[2-[4-(2-methoxyethyl)-3-(2-methylsulfonylethyl)pyrazol-1-yl]pyrimidin-4-yl]-11,11-dimethyl-3,4-diazatricyclo[6.2.1.02,7]undeca-2(7),3,5-triene | 0.044 |
| 350 | 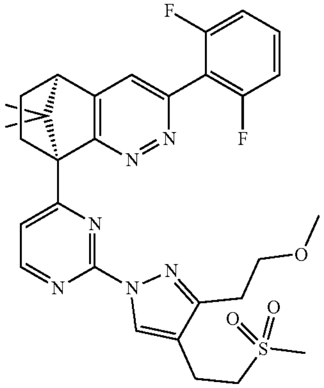 | (1S,8R)-5-(2,6-difluorophenyl)-1-[2-[3-(2-methoxyethyl)-4-(2-methylsulfonylethyl)pyrazol-1-yl]pyrimidin-4-yl]-11,11-dimethyl-3,4-diazatricyclo[6.2.1.02,7]undeca-2(7),3,5-triene | 0.060 |
| 351 | 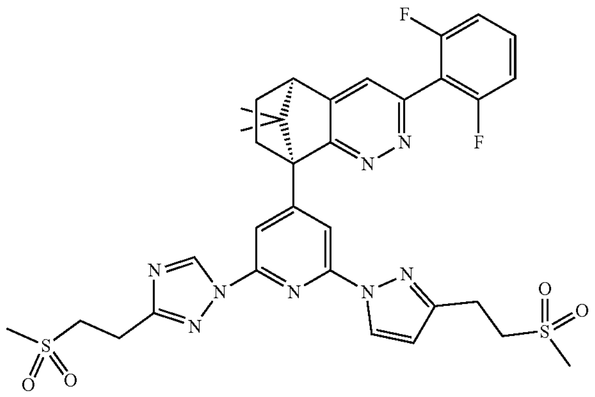 [SMILES: CC1(C)[C@H]2CC[C@]1(c1cc(-n3ccc(CCS(C)(=O)=O)n3)nc(-n3cnc(CCS(C)(=O)=O)n3)c1)c1nnc(-c3c(F)cccc3F)cc12] | (1S,8R)-1-[2,6-bis[3-(2-methylsulfonylethyl)-1,2,4-triazol-1-yl]-4-pyridyl]-5-(2,6-difluorophenyl)-11,11-dimethyl-3,4-diazatricyclo[6.2.1.02,7]undeca-2,4,6-triene | 0.57 |

TABLE 1-continued

| | Structure | Name | $IC_{50}$ |
|---|---|---|---|
| 352 | 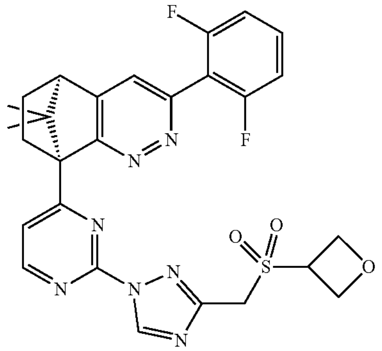 [SMILES: CC1(C)[C@H]2CC[C@]1(c1ccnc(-n3cnc(CS(=O)(=O)C4COC4)n3)n1)c1nnc(-c3c(F)cccc3F)cc12] | (1S,8R)-5-(2,6-difluorophenyl)-11,11-dimethyl-1-[2-[3-(oxetan-3-ylsulfonylmethyl)-1,2,4-triazol-1-yl]pyrimidin-4-yl]-3,4-diazatricyclo[6.2.1.02,7]undeca-2(7),3,5-triene | 0.018 |
| 353 | 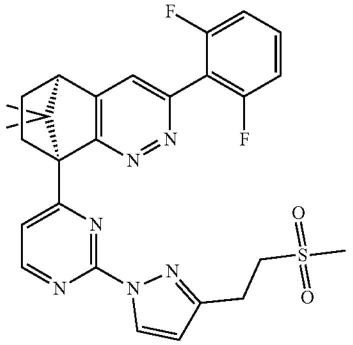 | (1S,8R)-5-(2,6-difluorophenyl)-11,11-dimethyl-1-[2-[3-(2-methylsulfonylethyl)pyrazol-1-yl]pyrimidin-4-yl]-3,4-diazatricyclo[6.2.1.02,7]undeca-2(7),3,5-triene | 0.013 |
| 354 | 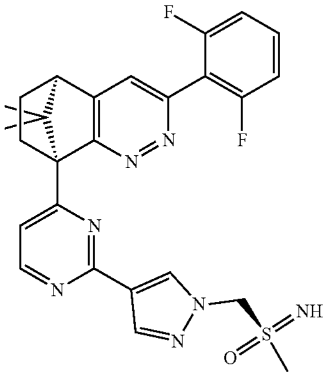 [SMILES: CC1(C)[C@H]2CC[C@]1(c1ccnc(-c3cnn(C[S@](C)(=N)=O)c3)n1)c1nnc(-c3c(F)cccc3F)cc12] | imino-methyl-oxo-[[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]methyl]-lambda6-sulfane | 0.0088 |
| 355 | 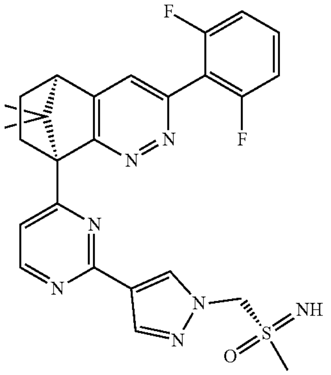 [SMILES: CC1(C)[C@H]2CC[C@]1(c1ccnc(-c3cnn(C[S@@](C)(=N)=O)c3)n1)c1nnc(-c3c(F)cccc3F)cc12] | imino-methyl-oxo-[[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]methyl]-lambda6-sulfane | 0.0091 |

TABLE 1-continued

| | Structure | Name | $IC_{50}$ |
|---|---|---|---|
| 356 | 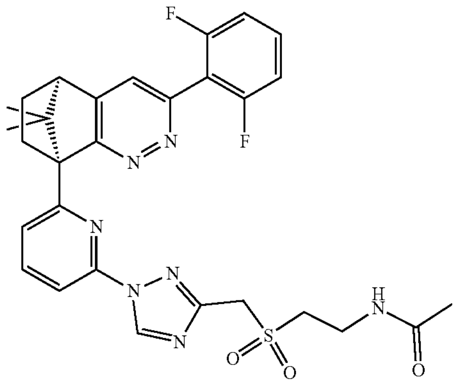 [SMILES: CC(=O)NCCS(=O)(=O)Cc1ncn(-c2cccc([C@@]34CC[C@@H](c5cc(-c6c(F)cccc6F)nnc53)C4(C)C)n2)n1] | N-[2-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonyl]ethyl]acetamide | 0.0081 |
| 357 | 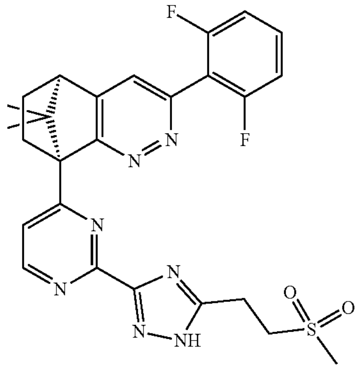 [SMILES: CC1(C)[C@H]2CC[C@]1(c1ccnc(-c3n[nH]c(CCS(C)(=O)=O)n3)n1)c1nnc(-c3c(F)cccc3F)cc12] | (1S,8R)-5-(2,6-difluorophenyl)-11,11-dimethyl-1-[2-[5-(2-methylsulfonylethyl)-1H-1,2,4-triazol-3-yl]pyrimidin-4-yl]-3,4-diazatricyclo[6.2.1.02,7]undeca-2(7),3,5-triene | 0.013 |
| 358 | 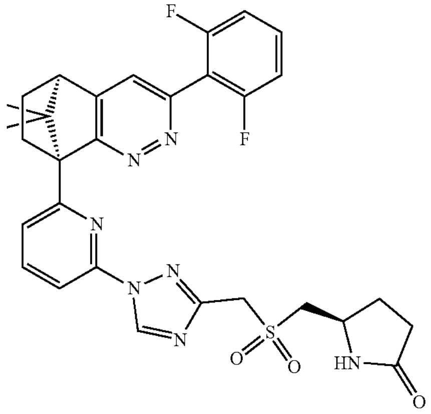 [SMILES: CC1(C)[C@H]2CC[C@]1(c1cccc(-n3cnc(CS(=O)(=O)C[C@H]4CCC(=O)N4)n3)n1)c1nnc(-c3c(F)cccc3F)cc12] | (5R)-5-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one | 0.0073 |
| 359 | 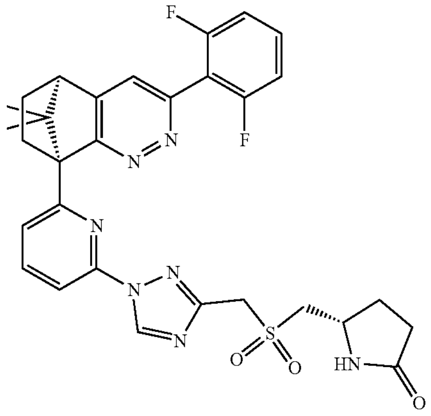 [SMILES: CC1(C)[C@H]2CC[C@]1(c1cccc(-n3cnc(CS(=O)(=O)C[C@@H]4CCC(=O)N4)n3)n1)c1nnc(-c3c(F)cccc3F)cc12] | (5S)-5-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one | 0.0091 |

TABLE 1-continued

| | Structure | Name | $IC_{50}$ |
|---|---|---|---|
| 360 | 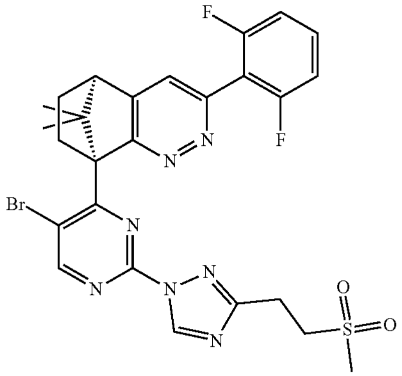 [SMILES: CC1(C)[C@H]2CC[C@]1(c1nc(-n3cnc(CCS(C)(=O)=O)n3)ncc1Br)c1nnc(-c3c(F)cccc3F)cc12] | (1S,8R)-1-[5-bromo-2-[3-(2-methylsulfonylethyl)-1,2,4-triazol-1-yl]pyrimidin-4-yl]-5-(2,6-difluorophenyl)-11,11-dimethyl-3,4-diazatricyclo[6.2.1.02,7]undeca-2(7),3,5-triene | 0.032 |
| 361 | 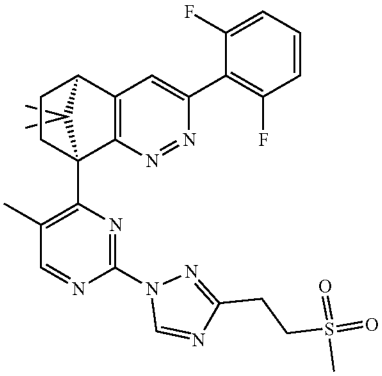 [SMILES: Cc1cnc(-n2cnc(CCS(C)(=O)=O)n2)nc1[C@@]12CC[C@@H](c3cc(-c4c(F)cccc4F)nnc31)C2(C)C] | (1S,8R)-5-(2,6-difluorophenyl)-11,11-dimethyl-1-[5-methyl-2-[3-(2-methylsulfonylethyl)-1,2,4-triazol-1-yl]pyrimidin-4-yl]-3,4-diazatricyclo[6.2.1.02,7]undeca-2(7),3,5-triene | 0.034 |
| 362 | 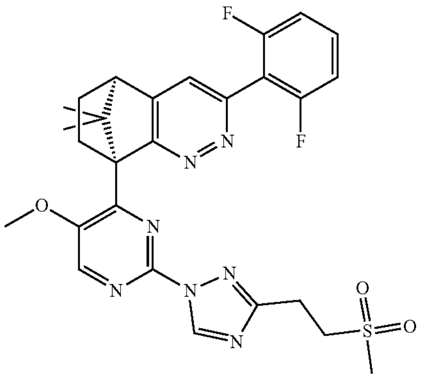 [SMILES: COc1cnc(-n2cnc(CCS(C)(=O)=O)n2)nc1[C@@]12CC[C@@H](c3cc(-c4c(F)cccc4F)nnc31)C2(C)C] | (1S,8R)-5-(2,6-difluorophenyl)-1-[5-methoxy-2-[3-(2-methylsulfonylethyl)-1,2,4-triazol-1-yl]pyrimidin-4-yl]-11,11-dimethyl-3,4-diazatricyclo[6.2.1.02,7]undeca-2(7),3,5-triene | 0.035 |
| 363 | 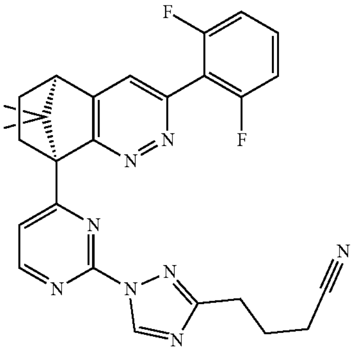 [SMILES: CC1(C)[C@H]2CC[C@]1(c1ccnc(-n3cnc(CCCC#N)n3)n1)c1nnc(-c3c(F)cccc3F)cc12] | 4-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]butanenitrile | 0.010 |

TABLE 1-continued

| | Structure | Name | $IC_{50}$ |
|---|---|---|---|
| 364 | 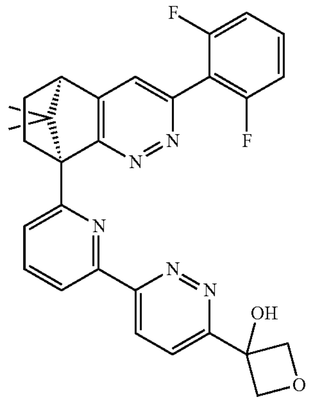 [SMILES: CC1(C)[C@H]2CC[C@]1(c1cccc(-c3ccc(C4(O)COC4)nn3)n1)c1nnc(-c3c(F)cccc3F)cc12] | 3-[6-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyridazin-3-yl]oxetan-3-ol | 0.024 |
| 365 | 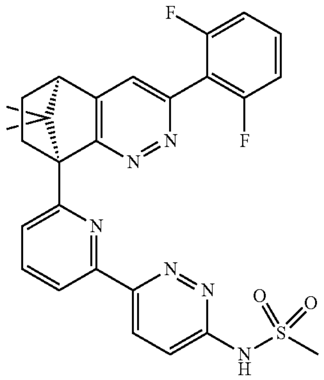 | N-[6-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyridazin-3-yl]methanesulfonamide | 0.0048 |
| 366 | 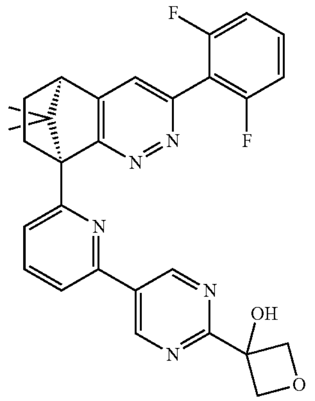 [SMILES: CC1(C)[C@H]2CC[C@]1(c1cccc(-c3cnc(C4(O)COC4)nc3)n1)c1nnc(-c3c(F)cccc3F)cc12] | 3-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]oxetan-3-ol | 0.0052 |
| 367 | 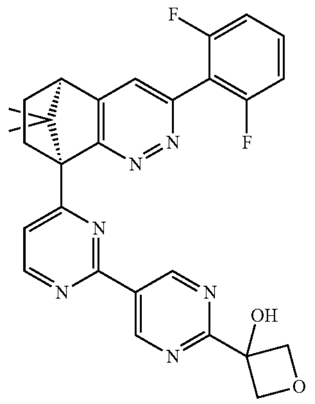 [SMILES: CC1(C)[C@H]2CC[C@]1(c1ccnc(-c3cnc(C4(O)COC4)nc3)n1)c1nnc(-c3c(F)cccc3F)cc12] | 3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]oxetan-3-ol | 0.0096 |

TABLE 1-continued

| | Structure | Name | $IC_{50}$ |
|---|---|---|---|
| 368 | 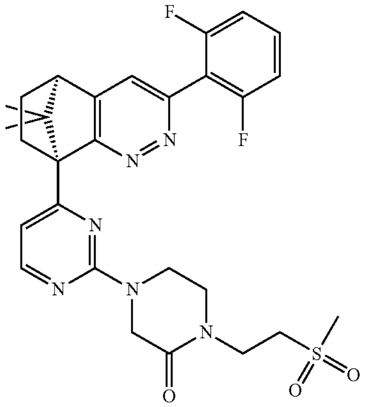 [SMILES: CC1(C)[C@H]2CC[C@]1(c1ccnc(N3CCN(CCS(C)(=O)=O)C(=O)C3)n1)c1nnc(-c3c(F)cccc3F)cc12] | 1-(2-methylsulfonylethyl)-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]piperazin-2-one | 0.011 |
| 369 | 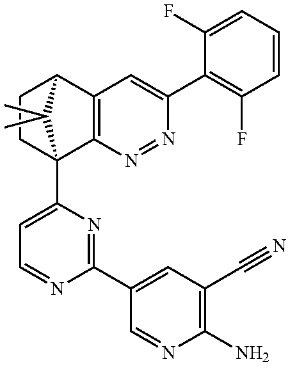 [SMILES: CC1(C)[C@H]2CC[C@]1(c1ccnc(-c3cnc(N)c(C#N)c3)n1)c1nnc(-c3c(F)cccc3F)cc12] | 2-amino-5-(4-((5R,8S)-3-(2,6-difluorophenyl)-9,9-dimethyl-6,7-dihydro-5,8-methanocinnolin-8(5H)-yl)pyrimidin-2-yl)nicotinonitrile | 0.0029 |
| 370 | 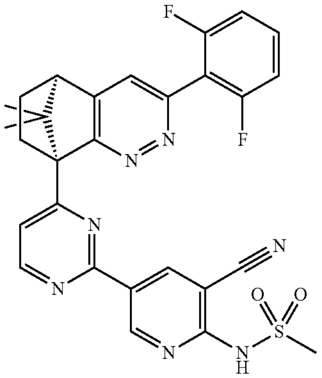 | N-(3-cyano-5-(4-((5R,8S)-3-(2,6-difluorophenyl)-9,9-dimethyl-6,7-dihydro-5,8-methanocinnolin-8(5H)-yl)pyrimidin-2-yl)pyridin-2-yl)methanesulfonamide | 0.022 |
| 371 | 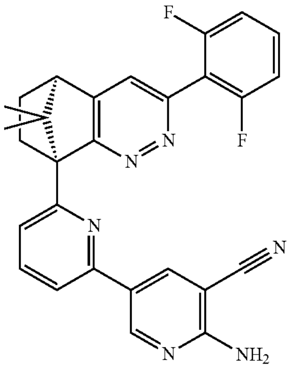 [SMILES: CC1(C)[C@H]2CC[C@]1(c1cccc(-c3cnc(N)c(C#N)c3)n1)c1nnc(-c3c(F)cccc3F)cc12] | 6'-amino-6-((5R,8S)-3-(2,6-difluorophenyl)-9,9-dimethyl-6,7-dihydro-5,8-methanocinnolin-8(5H)-yl)-[2,3'-bipyridin]-5'-carbonitrile | 0.0024 |

TABLE 1-continued

| | Structure | Name | $IC_{50}$ |
|---|---|---|---|
| 372 | 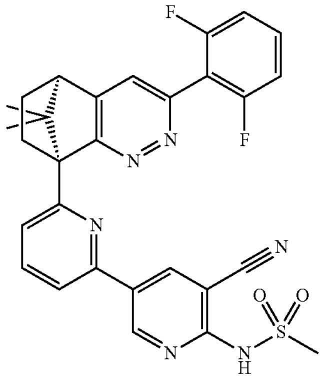 | N-(5'-cyano-6-((5R,8S)-3-(2,6-difluorophenyl)-9,9-dimethyl-6,7-dihydro-5,8-methanocinnolin-8(5H)-yl)-[2,3'-bipyridin]-6'-yl)methansulfonamide | 0.0081 |
| 373 | 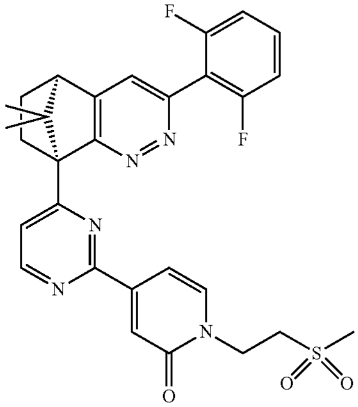 | 1-(2-methylsulfonylethyl)-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyridin-2-one | 0.012 |
| 374 | 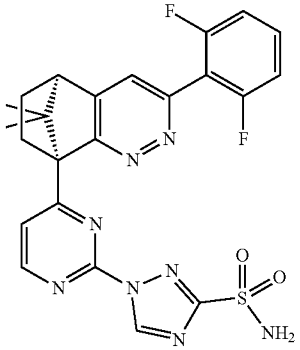 [SMILES: CC1(C)[C@H]2CC[C@]1(c1ccnc(-n3cnc(S(N)(=O)=O)n3)n1)c1nnc(-c3c(F)cccc3F)cc12] | 1-(4-((5R,8S)-3-(2,6-difluorophenyl)-9,9-dimethyl-6,7-dihydro-5,8-methanocinnolin-8(5H)-yl)pyrimidin-2-yl)-1H-1,2,4-triazole-3-sulfonamide | 0.28 |
| 375 | 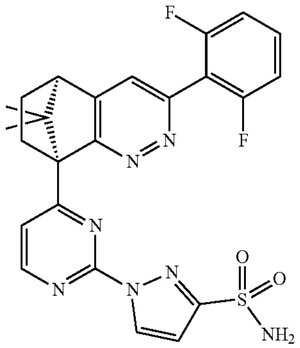 [SMILES: CC1(C)[C@H]2CC[C@]1(c1ccnc(-n3ccc(S(N)(=O)=O)n3)n1)c1nnc(-c3c(F)cccc3F)cc12] | 1-(4-((5R,8S)-3-(2,6-difluorophenyl)-9,9-dimethyl-6,7-dihydro-5,8-methanocinnolin-8(5H)-yl)pyrimidin-2-yl)-1H-pyrazole-3-sulfonamide | 0.011 |

TABLE 1-continued

| | Structure | Name | $IC_{50}$ |
|---|---|---|---|
| 376 | 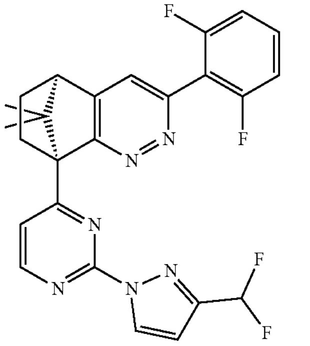 [SMILES: CC1(C)[C@H]2CC[C@]1(c1ccnc(-n3ccc(C(F)F)n3)n1)c1nnc(-c3c(F)cccc3F)cc12] | (5R,8S)-8-(2-(3-(difluorophenyl)-1H-pyrazol-1-yl)pyrimidin-4-yl)-3-(2,6-difluorophenyl)-9,9-dimethyl-5,6,7,8-tetrahydro-5,8-methanocinnoline | 0.0055 |
| 377 | 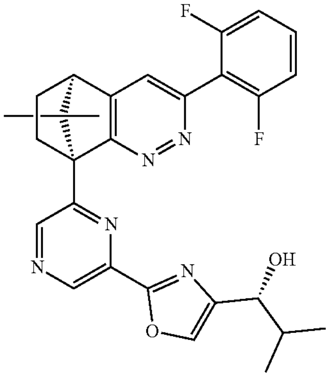 [SMILES: CC(C)[C@@H](O)c1coc(-c2cncc([C@@]34CC[C@@H](c5cc(-c6c(F)cccc6F)nnc53)C4(C)C)n2)n1] | (1R)-2-methyl-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-1-ol | |
| 378 | 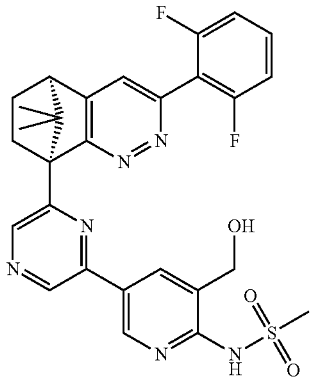 [SMILES: CC1(C)[C@H]2CC[C@]1(c1cncc(-c3cnc(NS(C)(=O)=O)c(CO)c3)n1)c1nnc(-c3c(F)cccc3F)cc12] | N-[3-(hydroxymethyl)-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide | |
| 379 | 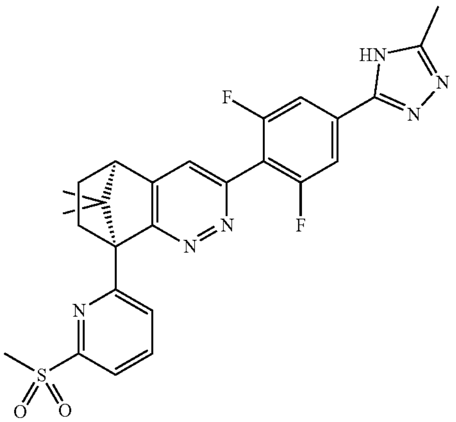 [SMILES: Cc1nnc(-c2cc(F)c(-c3cc4c(nn3)[C@@]3(c5cccc(S(C)(=O)=O)n5)CC[C@@H]4C3(C)C)c(F)c2)[nH]1] | (5R,8S)-3-(2,6-difluoro-4-(5-methyl-4H-1,2,4-triazol-3-yl)phenyl)-9,9-dimethyl-8-(6-(methylsulfonyl)pyridin-2-yl)-5,6,7,8-tetrahydro-5,8-methanocinnoline | |

TABLE 1-continued

| | Structure | Name | $IC_{50}$ |
|---|---|---|---|
| 380 | 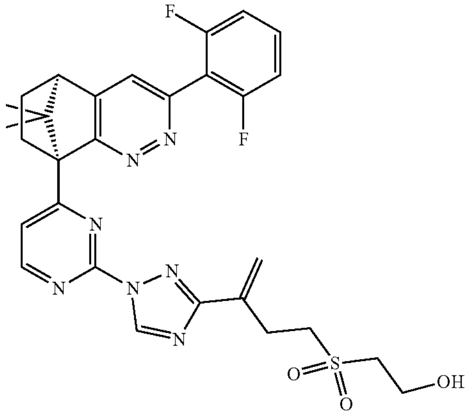 [SMILES: C=C(CCS(=O)(=O)CCO)c1ncn(-c2nccc([C@@]34CC[C@@H](c5cc(-c6c(F)cccc6F)nnc53)C4(C)C)n2)n1] | 2-[3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]but-3-enylsulfonyl]ethanol | |
| 381 | 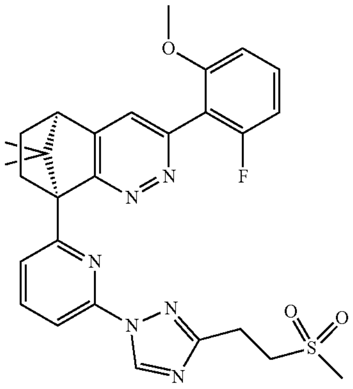 [SMILES: COc1cccc(F)c1-c1cc2c(nn1)[C@@]1(c3cccc(-n4cnc(CCS(C)(=O)=O)n4)n3)CC[C@@H]2C1(C)C] | (5R,8S)-3-(2-fluoro-6-methoxyphenyl)-9,9-dimethyl-8-(6-(3-(2-(methylsulfonyl)ethyl)-1H-1,2,4-triazol-1-yl)pyridin-2-yl)-5,6,7,8-tetrahydro-5,8-methanocinnoline | |
| 382 | 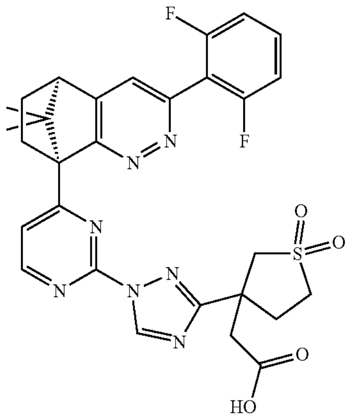 [SMILES: CC1(C)[C@H]2CC[C@]1(c1ccnc(-n3cnc(C4(CC(=O)O)CCS(=O)(=O)C4)n3)n1)c1nnc(-c3c(F)cccc3F)cc12] | 2-[1,1-dioxo-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]thiolan-3-yl]acetic acid | |

TABLE 1-continued

| | Structure | Name | IC50 |
|---|---|---|---|
| 383 | 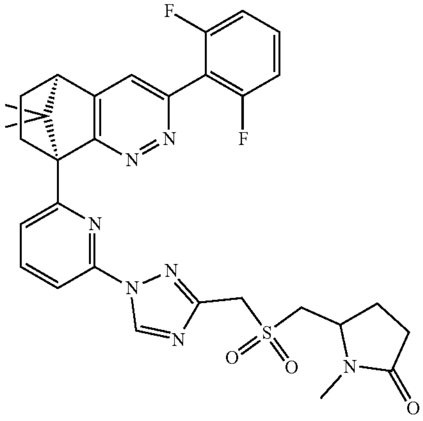 [SMILES: CN1C(=O)CCC1CS(=O)(=O)Cc1ncn(-c2cccc([C@@]34CC[C@@H](c5cc(-c6c(F)cccc6F)nnc53)C4(C)C)n2)n1] | 1-methyl-5-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one | |
| 384 | 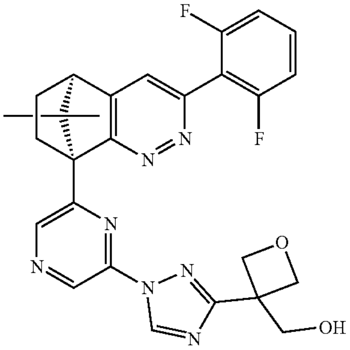 [SMILES: CC1(C)[C@H]2CC[C@]1(c1cncc(-n3cnc(C4(CO)COC4)n3)n1)c1nnc(-c3c(F)cccc3F)cc12] | [3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]oxetan-3-yl]methanol | |
| 385 | 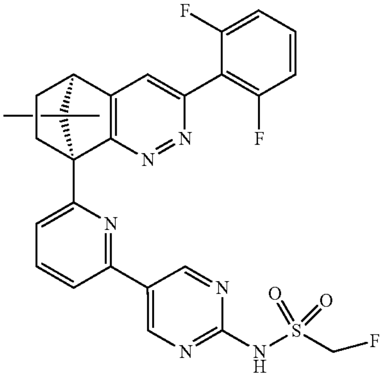 [SMILES: CC1(C)[C@H]2CC[C@]1(c1cccc(-c3cnc(NS(=O)(=O)CF)nc3)n1)c1nnc(-c3c(F)cccc3F)cc12] | 1-fluoro-N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide | |
| 386 | 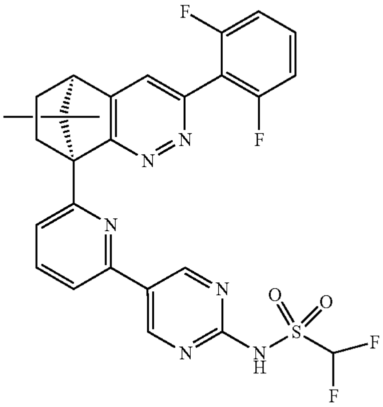 [SMILES: CC1(C)[C@H]2CC[C@]1(c1cccc(-c3cnc(NS(=O)(=O)C(F)F)nc3)n1)c1nnc(-c3c(F)cccc3F)cc12] | 1,1-difluoro-N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide | |

TABLE 1-continued

| | Structure | Name | $IC_{50}$ |
|---|---|---|---|
| 387 | 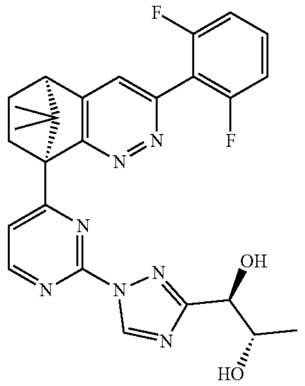 [SMILES: C[C@H](O)[C@H](O)c1ncn(-c2nccc([C@@]34CC[C@@H](c5cc(-c6c(F)cccc6F)nnc53)C4(C)C)n2)n1] | (1R,2S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol | |
| 388 | 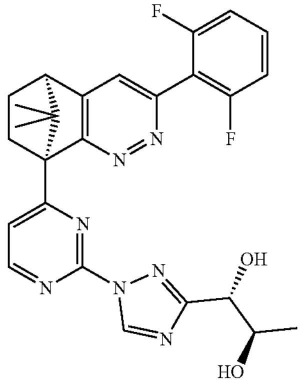 [SMILES: C[C@@H](O)[C@@H](O)c1ncn(-c2nccc([C@@]34CC[C@@H](c5cc(-c6c(F)cccc6F)nnc53)C4(C)C)n2)n1] | (1S,2R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol | |
| 389 | 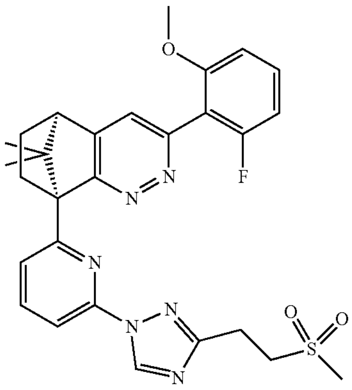 [SMILES: COc1cccc(F)c1-c1cc2c(nn1)[C@@]1(c3cccc(-n4cnc(CCS(C)(=O)=O)n4)n3)CC[C@@H]2C1(C)C] | (5R,8S)-3-(2-fluoro-6-methoxyphenyl)-9,9-dimethyl-8-(6-(3-(2-(methylsulfonyl)ethyl)-1H-1,2,4-triazol-1-yl)pyridin-2-yl)-5,6,7,8-tetrahydro-5,8-methanocinnoline | |

Additional proton NMR data for selected compounds is shown below, with the compound numbers below corresponding to the numbering in Table 1:

Compound 21, $^1H$ NMR ($CDCl_3$, 300 MHz): δ 8.92 (s, 1H), 8.72 (s, 1H), 8.11 (s, 1H), 8.04 (s, 1H), 7.49 (t, J=1.4 Hz, 1H), 7.42 (tt, J=8.4, 6.4 Hz, 1H), 7.07 (app. t, J=8.2 Hz, 2H), 4.23-4.34 (m, 2H), 4.09 (dd, J=13.7, 8.0 Hz, 1H), 3.29-3.38 (m, 2H), 3.18 (d, J=4.1 Hz, 1H), 2.48 (ddt, J=12.7, 10.7, 4.3 Hz, 1H), 1.75 (ddd, J=13.1, 9.1, 4.1 Hz, 1H), 1.39 (ddd, J=12.9, 9.3, 4.1 Hz, 1H), 1.29 (d, J=6.5 Hz, 3H), 1.15 (s, 3H), 0.82 (s, 3H)

Compound 300, $^1H$ NMR (400 MHz, $CDCl_3$) δ 9.18 (s, 1H), 8.86 (d, J=5.2 Hz, 1H), 8.01 (d, 5 J=5.2 Hz, 1H), 7.52 (t, J=1.3 Hz, 1H), 7.48-7.40 (m, 1H), 7.11-7.03 (m, 1H), 4.34-4.26 (m, 2H), 4.13-4.06 (m, 2H), 3.33-3.09 (m, 5H), 2.59-2.49 (m, 1H), 1.79 (ddd, J=4.1, 9.1, 13.1 Hz, 1H), 1.44 (ddd, J=3.9, 9.1, 12.9 Hz, 1H), 1.22 (s, 3H), 0.79 (s, 3H).

Compound 241: $^1H$ NMR (400 MHz, $CDCl_3$) δ 9.09 (s, 1H), 7.97-7.89 (m, 2H), 7.79 (dd, J=1.6, 7.4 Hz, 1H), 7.49 (t, J=1.3 Hz, 1H), 7.46-7.38 (m, 1H), 7.10-7.02 (m, 2H), 3.61 (t, J=7.8 Hz, 2H), 3.42 (t, J=7.7 Hz, 2H), 3.30 (ddd, J=4.0, 10.6, 13.1 Hz, 1H), 3.17 (d, J=4.0 Hz, 1H), 2.96 (s, 3H), 2.54-2.44 (m, 1H), 1.74 (ddd, J=4.1, 9.1, 13.1 Hz, 1H), 1.40 (ddd, J=3.9, 9.1, 12.8 Hz, 1H), 1.15 (s, 3H), 0.77 (s, 3H).

Compound 108: $^1H$ NMR (400 MHz, DMSO) δ 9.27 (s, 1H), 9.03-9.02 (m, 1H), 8.31 (s, 1H), 7.85 (s, 1H), 7.67-7.58 (m, 1H), 7.34-7.28 (m, 2H), 3.30-3.18 (m, 3H), 2.96-2.92 (m, 2H), 1.72-1.63 (m, 1H), 1.35 (d, J=7.0 Hz, 3H), 1.33-1.16 (m, 2H), 1.09 (s, 3H), 0.80 (s, 3H).

Compound 136: $^1H$ NMR (400 MHz, $CDCl_3$) δ 9.28 (s, 1H), 9.16-9.15 (m, 1H), 7.67-7.66 (m, 1H), 7.50-7.39 (m, 2H), 7.09-7.04 (m, 2H), 5.84-5.84 (m, 1H), 5.35-5.35 (m, 1H), 3.44-3.36 (m, 1H), 3.20 (d, J=4.0 Hz, 1H), 3.03-2.98 (m, 2H), 2.72-2.66 (m, 2H), 2.54-2.44 (m, 1H), 1.82-1.75 (m, 1H), 1.45-1.36 (m, 1H), 1.16 (s, 3H), 0.82 (s, 3H).

Compound 3: $^1$H NMR (400 MHz, DMSO) δ 9.28-9.27 (m, 1H), 9.03 (s, 1H), 8.31-8.30 (m, 1H), 7.86-7.84 (m, 1H), 7.65-7.60 (m, 2H), 7.34-7.28 (m, 2H), 4.22 (d, J=5.6 Hz, 2H), 3.23-3.17 (m, 1H), 2.99 (s, 3H), 2.48-2.43 (m, 1H), 1.72-1.64 (m, 1H), 1.36-1.22 (m, 2H), 1.09 (s, 3H), 0.81 (s, 3H).

Compound 223: $^1$H NMR (400 MHz, $CDCl_3$) δ 8.04 (s, 1H), 7.99 (s, 1H), 7.71-7.68 (m, 2H), 7.46-7.36 (m, 3H), 7.07-7.02 (m, 2H), 6.91 (d, J=1.7 Hz, 1H), 5.59-5.45 (m, 2H), 4.62-4.56 (m, 1H), 4.53-4.47 (m, 2H), 3.44-3.35 (m, 1H), 3.14 (d, J=4.0 Hz, 1H), 2.50-2.42 (m, 1H), 1.72-1.64 (m, 1H), 1.39-1.31 (m, 1H), 1.14 (s, 3H), 0.77 (s, 3H).

Compound 97: $^1$H NMR (400 MHz, $CDCl_3$) δ 8.03 (s, 1H), 7.94 (s, 1H), 7.68-7.65 (m, 2H), 7.47-7.33 (m, 3H), 7.08-7.02 (m, 2H), 4.31-4.27 (m, 2H), 4.14-4.09 (m, 1H), 3.91 (d, J=5.1 Hz, 1H), 3.66-3.61 (m, 2H), 3.45-3.36 (m, 1H), 3.14 (d, J=4.0 Hz, 1H), 2.89 (t, J=6.2 Hz, 1H), 2.51-2.41 (m, 1H), 1.74-1.65 (m, 1H), 1.40-1.32 (m, 1H), 1.15 (s, 3H), 0.77 (s, 3H).

Compound 19: $^1$H NMR (400 MHz, DMSO) δ 8.96 (s, 1H), 8.70 (s, 1H), 8.56 (s, 1H), 8.23-8.23 (m, 1H), 7.83 (s, 1H), 7.66-7.58 (m, 1H), 7.33-7.28 (m, 2H), 4.65 (t, J=6.9 Hz, 2H), 3.77 (t, J=6.9 Hz, 2H), 3.27-3.17 (m, 2H), 2.96-2.95 (m, 3H), 2.47-2.40 (m, 1H), 1.68-1.60 (m, 1H), 1.33-1.24 (m, 1H), 1.09 (s, 3H), 0.79 (s, 3H).

Compound 80: $^1$H NMR (400 MHz, CDCl3) δ 8.08 (s, 1H), 8.03 (s, 1H), 7.73-7.70 (m, 2H), 7.45-7.37 (m, 3H), 7.08-7.02 (m, 2H), 4.46 (t, J=6.8 Hz, 2H), 3.47-3.38 (m, 1H), 3.13 (d, J=4.0 Hz, 1H), 3.02 (t, J=6.8 Hz, 2H), 2.51-2.41 (m, 1H), 1.73-1.65 (m, 1H), 1.40-1.32 (m, 1H), 1.16 (s, 3H), 0.76 (s, 3H).

Compound 76: $^1$H NMR (400 MHz, CDCl3) δ 7.90 (dd, J=1.2, 7.5 Hz, 1H), 7.84-7.74 (m, 2H), 7.55-7.53 (m, 1H), 7.43 (ddd, J=9.6, 9.6, 9.6 Hz, 2H), 7.08-6.98 (m, 3H), 4.49-4.45 (m, 2H), 3.51-3.42 (m, 1H), 3.15-3.12 (m, 1H), 3.06-3.00 (m, 2H), 2.52-2.42 (m, 1H), 1.72 (ddd, J=3.9, 9.0, 12.9 Hz, 1H), 1.40-1.31 (m, 1H), 1.16 (s, 3H), 0.76 (s, 3H).

Compound 77: $^1$H NMR (400 MHz, CDCl3) δ 7.92-7.75 (m, 3H), 7.56 (d, J=2.3 Hz, 1H), 7.46-7.38 (m, 2H), 7.05 (t, J=7.8 Hz, 2H), 6.99 (d, J=2.6 Hz, 1H), 4.68 (t, J=6.0 Hz, 2H), 3.76-3.70 (m, 2H), 3.47-3.38 (m, 1H), 3.13 (d, J=4.0 Hz, 1H), 2.53 (s, 3H), 2.46 (tt, J=9.4, 8.5 Hz, 1H), 1.75-1.67 (m, 1H), 1.40-1.31 (m, 1H), 1.16 (s, 3H), 0.77 (s, 3H).

Compound 78: $^1$H NMR (400 MHz, CDCl3) δ 7.91 (dd, J=1.8, 7.8 Hz, 1H), 7.83 (dd, J=1.1, 7.4 Hz, 1H), 7.76 (t, J=7.8 Hz, 1H), 7.42 (ddd, J=16.7, 16.7, 6.3 Hz, 3H), 7.05 (qdt, J=5.7, 4.5, 4.4 Hz, 2H), 6.98 (d, J=2.5 Hz, 1H), 4.31-4.21 (m, 2H), 4.09-4.02 (m, 1H), 3.76-3.73 (m, 1H), 3.50-3.42 (m, 1H), 3.12 (d, J=4.0 Hz, 1H), 2.51-2.41 (m, 1H), 1.75-1.67 (m, 1H), 1.35 (ddd, J=3.9, 9.1, 12.4 Hz, 1H), 1.28 (d, J=6.5 Hz, 3H), 1.17 (s, 3H), 0.76 (s, 3H).

Compound 299: $^1$H NMR (400 MHz, CDCl3) δ8.44 (s, 1H), 8.09 (dd, J=1.0, 7.6 Hz, 1H), 7.95 (dd, J=1.0, 7.9 Hz, 1H), 7.86 (t, J=7.8 Hz, 1H), 7.43 (td, J=7.2, 26.0 Hz, 2H), 7.08-7.03 (m, 2H), 5.43-5.41 (m, 2H), 3.57-3.49 (m, 1H), 3.14 (d, J=4.0 Hz, 1H), 3.08-3.07 (m, 3H), 2.52-2.42 (m, 1H), 1.80-1.71 (m, 1H), 1.41-1.33 (m, 1H), 1.17 (s, 3H), 0.77 (s, 3H).

Compound 214: $^1$H NMR (400 MHz, DMSO) δ 8.88 (d, J=5.1 Hz, 1H), 8.58 (d, J=2.6 Hz, 1H), 7.84 (s, 1H), 7.70-7.60 (m, 2H), 7.38-7.28 (m, 3H), 6.83-6.78 (m, 1H), 6.46 (d, J=2.6 Hz, 1H), 3.23 (ddd, J=3.7, 10.0, 13.9 Hz, 2H), 2.91-2.86 (m, 2H), 2.45 (tt, J=6.6, 5.6 Hz, 3H), 1.66-1.58 (m, 1H), 1.33-1.23 (m, 1H), 1.11 (s, 3H), 0.76 (m, 3H).

Compound 215: $^1$H NMR (400 MHz, DMSO) δ 9.13 (s, 1H), 8.86 (s, 1H), 8.53 (d, J=2.6 Hz, 1H), 7.85 (s, 1H), 7.67-7.58 (m, 1H), 7.40-7.28 (m, 3H), 6.82 (s, 1H), 6.50 (d, J=2.6 Hz, 1H), 3.24 (ddd, J=3.7, 10.0, 13.5 Hz, 2H), 2.91 (t, J=7.5 Hz, 2H), 2.50-2.40 (ddd, J=4.1, 11.4, 15.5 Hz, 3H), 1.69-1.61 (m, 1H), 1.34-1.23 (m, 1H), 1.10 (s, 3H), 0.77 (s, 3H).

Compound 164: $^1$H NMR (400 MHz, CDCl3) δ 8.82 (d, J=5.2 Hz, 1H), 8.61 (d, J=2.6 Hz, 1H), 7.89 (d, J=5.2 Hz, 1H), 7.52-7.40 (m, 2H), 7.10-7.04 (m, 2H), 6.54 (d, J=2.6 Hz, 1H), 4.99-4.92 (m, 1H), 4.51 (d, J=6.2 Hz, 2H), 3.31 (dt, J=4.2, 9.0 Hz, 1H), 3.21 (d, J=3.9 Hz, 1H), 2.99 (s, 3H), 2.57-2.47 (m, 1H), 1.82-1.73 (m, 1H), 1.47-1.36 (m, 1H), 1.21 (s, 3H), 0.78 (s, 3H).

Compound 197: $^1$H NMR (400 MHz, CDCl3) δ9.21 (s, 1H), 9.03 (s, 1H), 8.49 (d, J=2.6 Hz, 1H), 7.50-7.50 (m, 1H), 7.47-7.38 (m, 1H), 7.09-7.04 (m, 2H), 6.50 (d, J=2.6 Hz, 1H), 4.97-4.90 (m, 1H), 4.49 (d, J=6.0 Hz, 2H), 3.28-3.19 (m, 2H), 3.03-3.02 (m, 3H), 2.54-2.45 (m, 1H), 1.84-1.76 (m, 1H), 1.46-1.38 (m, 1H), 1.15 (s, 3H), 0.83 (s, 3H).

Compound 177: $^1$H NMR (400 MHz, DMSO) δ 8.48 (s, 1H), 8.03-7.94 (m, 2H), 7.80 (s, 1H), 7.65-7.58 (m, 2H), 7.33-7.28 (m, 2H), 5.20 (d, J=5.5 Hz, 1H), 4.88 (t, J=5.5 Hz, 1H), 4.59 (dd, J=3.4, 13.8 Hz, 1H), 4.33 (dd, J=8.3, 13.9 Hz, 1H), 3.94-3.85 (m, 1H), 3.48-3.42 (m, 1H), 3.37 (ddd, J=5.5, 5.5, 5.5 Hz, 2H), 3.27 (d, J=3.4 Hz, 1H), 2.43-2.38 (m, 1H), 1.63-1.53 (m, 1H), 1.31-1.22 (m, 1H), 1.06 (s, 3H), 0.75 (s, 3H).

Compound 225: $^1$H NMR (400 MHz, DMSO) δ 9.00 (d, J=5.3 Hz, 1H), 8.36-8.35 (m, 1H), 7.86 (s, 1H), 7.74 (d, J=5.3 Hz, 1H), 7.67-7.59 (m, 1H), 7.34-7.29 (m, 2H), 5.10-5.00 (m, 2H), 4.90 (d, J=5.7 Hz, 1H), 4.75 (t, J=5.7 Hz, 1H), 3.99-3.90 (m, 1H), 3.44-3.35 (m, 3H), 3.31-3.25 (m, 1H), 2.48-2.41 (m, 5.0 Hz, 1H), 1.64-1.55 (m, 1H), 1.33-1.23 (m, 1H), 1.08 (s, 3H), 0.71 (s, 3H).

Compound 157: $^1$H NMR (400 MHz, DMSO) δ 9.12 (s, 1H), 8.90 (s, 1H), 8.36 (s, 1H), 7.85 (s, 1H), 7.67-7.58 (m, 1H), 7.34-7.28 (m, 2H), 5.09 (d, J=5.7 Hz, 1H), 4.85 (t, J=5.6 Hz, 1H), 4.64 (dd, J=3.9, 13.6 Hz, 1H), 4.42 (dd, J=8.4, 13.6 Hz, 1H), 4.13-4.06 (m, 1H), 3.46 (tdd, J=5.5, 17.1, 17.1 Hz, 2H), 3.26 (ddd, J=3.2, 10.0, 13.1 Hz, 2H), 2.48-2.41 (m, 1H), 1.71-1.62 (m, 1H), 1.34-1.22 (m, 1H), 1.09 (s, 3H), 0.79 (s, 3H).

Compound 109: $^1$H NMR (400 MHz, DMSO) δ 11.06 (s, 1H), 9.31 (s, 1H), 9.04 (s, 1H), 8.43 (d, J=5.2 Hz, 1H), 7.86 (s, 1H), 7.81-7.76 (m, 2H), 7.58-7.51 (m, 1H), 7.34-7.29 (m, 2H), 3.23 (ddd, J=3.6, 10.9, 13.7 Hz, 2H), 2.50 (s, 3H under DMSO signal), 2.49-2.42 (m, 1H), 1.76-1.68 (m, 1H), 1.37-1.28 (m, 1H), 1.13 (s, 3H), 0.82 (s, 3H).

Compound 149: $^1$H NMR (400 MHz, CDCl3) δ 10.70-10.60 (m, 1H), 9.38-9.37 (m, 2H), 7.94-7.84 (m, 2H), 7.71-7.69 (m, 1H), 7.49-7.39 (m, 2H), 7.09-7.03 (m, 2H), 3.54 (s, 3H), 3.48 (td, J=5.1, 18.0 Hz, 1H), 3.17 (d, J=4.0 Hz, 1H), 2.55-2.45 (m, 1H), 1.74 (dt, J=3.4, 10.7 Hz, 1H), 1.38 (dd, J=12.4, 15.8 Hz, 1H), 1.17 (s, 3H), 0.77 (s, 3H).

Compound 220: $^1$H NMR (400 MHz, DMSO) δ 9.02 (s, 2H), 7.89 (dt, J=10.1, 9.4 Hz, 2H), 7.80 (s, 1H), 7.65-7.56 (m, 2H), 7.40-7.28 (m, 3H), 4.73 (d, J=4.8 Hz, 1H), 3.87-3.79 (m, 1H), 3.30-3.26 (m, 4H), 2.47-2.40 (m, 1H), 1.62-1.53 (m, 1H), 1.30-1.23 (m, 1H), 1.10-1.07 (m, 6H), 0.73 (s, 3H).

Compound 142: $^1$H NMR (400 MHz, DMSO) δ 9.34-9.32 (m, 2H), 8.95 (s, 1H), 8.58 (dd, J=2.3, 8.2 Hz, 1H), 7.85 (s, 1H), 7.75 (t, J=6.3 Hz, 1H), 7.67-7.60 (m, 2H), 7.34-7.28 (m, 2H), 4.37 (d, J=6.2 Hz, 2H), 3.29-3.24 (m, 2H), 2.97 (s, 3H), 2.45 (ddd, J=5.4, 5.4, 5.4 Hz, 1H), 1.74-1.65 (m, 1H), 1.31 (ddd, J=4.1, 9.7, 13.1 Hz, 1H), 1.12 (s, 3H), 0.81 (s, 3H).

Compound 147: $^1$H NMR (400 MHz, CDCl3) δ 12.40 (s, 1H), 8.79-8.76 (m, 1H), 8.53-8.52 (m, 2H), 7.85 (d, J=5.2 Hz, 1H), 7.50 (s, 1H), 7.43 (ddd, J=5.9, 8.9, 14.9 Hz, 1H), 7.09-7.04 (m, 2H), 3.38-3.30 (m, 1H), 3.20 (d, J=6.3 Hz, 3H), 2.57-2.46 (m, 1H), 2.31 (s, 3H), 1.78-1.70 (m, 1H), 1.46-1.37 (m, 1H), 1.19 (s, 3H), 0.77 (s, 3H).

Compound 161: $^1$H NMR (400 MHz, CDCl3) δ 9.03 (s, 1H), 8.70 (s, 1H), 7.95-7.92 (m, 1H), 7.52 (s, 1H), 7.44 (ddd, J=7.0, 7.0, 7.0 Hz, 1H), 7.23 (d, J=8.4 Hz, 1H), 7.09-7.04 (m, 2H), 3.32 (ddd, J=7.9, 7.9, 13.2 Hz, 1H), 3.23 (s, 3H), 3.21 (d, J=4.8 Hz, 1H), 2.69 (s, 3H), 2.49 (ddt, J=4.2, 10.6, 11.2 Hz, 1H), 1.75 (ddd, J=4.0, 9.3, 12.8 Hz, 1H), 1.45-1.36 (m, 1H), 1.11 (s, 3H), 0.84 (s, 3H).

Compound 330: $^1$H NMR (400 MHz, CDCl3) δ 9.08 (s, 1H), 7.95-7.91 (m, 2H), 7.78 (dd, J=1.7, 7.2 Hz, 1H), 7.48 (s, 1H), 7.42 (ddd, J=7.9, 7.9, 15.4 Hz, 1H), 7.09-7.03 (m, 2H), 4.35-4.28 (m, 2H), 4.11-4.04 (m, 2H), 3.26-3.23 (m, 3H), 3.19-3.12 (m, 2H), 2.54-2.44 (m, 1H), 1.79-1.70 (m, 1H), 1.44-1.35 (m, 1H), 1.15 (s, 3H), 0.76 (s, 3H).

Compound 232: $^1$H NMR (400 MHz, CDCl3) δ9.22 (s, 1H), 8.86 (d, J=5.2 Hz, 1H), 8.01 (d, J=5.2 Hz, 1H), 7.52 (s, 1H), 7.44 (ddd, J=7.3, 7.3, 15.0 Hz, 1H), 7.10-7.05 (m, 2H), 5.15 (s, 1H), 4.64 (s, 2H), 3.33-3.21 (m, 2H), 3.05 (s, 3H), 2.62-2.49 (m, 1H), 1.83-1.75 (m, 1H), 1.48-1.40 (m, 1H), 1.23 (s, 3H), 0.79 (s, 3H).

Compound 301: $^1$H NMR (400 MHz, CDCl3) δ 9.22 (s, 1H), 8.87 (d, J=5.2 Hz, 1H), 8.03 (d, J=5.2 Hz, 1H), 7.52 (s, 1H), 7.44 (tt, J=7.1, 7.1 Hz, 1H), 7.10-7.05 (m, 2H), 4.75-4.68 (m, 2H), 4.59-4.51 (m, 2H), 4.14-4.03 (m, 1H), 3.27 (m, 2H), 2.62-2.49 (m, 1H), 1.84-1.75 (m, 1H), 1.49-1.40 (m, 1H), 1.22 (s, 3H), 0.79 (s, 3H).

Compound 255: $^1$H NMR (400 MHz, DMSO) δ 9.47 (s, 1H), 8.99 (d, J=5.3 Hz, 1H), 7.87-7.85 (m, 2H), 7.67-7.58 (m, 1H), 7.34-7.29 (m, 2H), 3.30-3.24 (m, 2H), 3.19-3.10 (m, 2H), 3.01-2.95 (m, 2H), 2.48-2.41 (m, 1H), 1.67-1.58 (m, 1H), 1.34-1.23 (m, 1H), 1.11 (s, 3H), 0.76 (s, 3H).

Compound 217: $^1$H NMR (400 MHz, CDCl3) δ 9.18-9.17 (m, 1H), 8.85 (d, J=5.2 Hz, 1H), 8.01 (d, J=5.2 Hz, 1H), 7.53-7.41 (m, 2H), 7.10-7.05 (m, 2H), 5.40 (t, J=5.8 Hz, 1H), 3.68-3.62 (m, 2H), 3.30-3.17 (m, 4H), 2.99-2.98 (m, 3H), 2.62-2.49 (m, 1H), 1.83-1.75 (m, 1H), 1.45 (ddd, J=3.8, 9.1, 13.0 Hz, 1H), 1.23 (s, 3H), 0.79 (s, 3H).

Compound 235: $^1$H NMR (400 MHz, CDCl3) δ 9.26 (s, 1H), 8.87 (d, J=5.2 Hz, 1H), 8.05 (d, J=5.2 Hz, 1H), 7.53 (s, 1H), 7.44 (tt, J=7.3, 7.2 Hz, 1H), 7.10-7.05 (m, 2H), 4.60 (s, 2H), 3.32-3.22 (m, 2H), 3.16 (s, 3H), 2.62-2.49 (m, 1H), 1.84-1.75 (m, 1H), 1.49-1.40 (m, 1H), 1.23 (s, 3H), 0.79 (s, 3H).

Compound 303: $^1$H NMR (400 MHz, CDCl3) δ 9.19-9.18 (m, 1H), 8.86 (d, J=5.3 Hz, 1H), 8.00 (d, J=7.8 Hz, 1H), 7.52 (s, 1H), 7.44 (tt, J=7.1, 7.3 Hz, 1H), 7.10-7.05 (m, 2H), 3.69-3.63 (m, 2H), 3.50-3.48 (m, 2H), 3.32-3.21 (m, 2H), 2.58-2.42 (m, 2H), 1.83-1.74 (m, 1H), 1.45 (ddd, J=4.1, 8.6, 12.4 Hz, 1H), 1.30 (td, J=4.9, 7.3 Hz, 2H), 1.21 (s, 3H), 1.08-1.03 (m, 2H), 0.78 (s, 3H).

Compound 374: $^1$H NMR (400 MHz, DMSO-d6) δ 9.65 (d, J=2.0 Hz, 1H), 9.04 (d, J=5.3 Hz, 1H), 7.98-7.90 (m, 1H), 7.86 (s, 1H), 7.79 (s, 1H), 7.68-7.57 (m, 1H), 7.37-7.26 (m, 2H), 3.42-3.21 (m, 2H), 2.89 (s, 1H), 2.73 (s, 1H), 1.69-1.59 (m, 1H), 1.37-1.28 (m, 1H), 1.12 (s, 3H), 0.74 (s, 3H).

Compound 375: $^1$H NMR (400 MHz, DMSO-d6) δ 8.99 (d, J=5.1 Hz, 1H), 8.82 (d, J=2.8 Hz, 1H), 7.88-7.81 (m, 2H), 7.73 (s, 2H), 7.63 (tt, J=8.5, 6.6 Hz, 1H), 7.37-7.26 (m, 2H), 6.93 (d, J=2.6 Hz, 1H), 3.41-3.17 (m, 2H), 2.50-2.41 (m, 1H), 1.69-1.58 (m, 1H), 1.36-1.25 (m, 1H), 1.12 (s, 3H), 0.76 (s, 3H).

Compound 376: $^1$H NMR (400 MHz, DMSO-d6) δ 8.97 (d, J=5.2 Hz, 1H), 8.82 (d, J=2.8 Hz, 1H), 7.88-7.80 (m, 2H), 7.63 (tt, J=8.5, 6.5 Hz, 1H), 7.36-7.27 (m, 2H), 7.22 (d, J=54.4 Hz, 1H), 6.90 (d, J=2.7 Hz, 1H), 3.38-3.20 (m, 2H), 2.50-2.41 (m, 1H), 1.70-1.59 (m, 1H), 1.35-1.25 (m, 1H), 1.12 (s, 3H), 0.76 (s, 3H).

Example 79 In Vitro RORc Ligand Binding Assay

This assay was used to determine a compound's potency in inhibiting activity of RORc by determining, $Ki_{app}$, $IC_{50}$, or percent inhibition values. Consumables used in this Example are shown in Table 2 below.

TABLE 2

Table2

| Consumable | Supplier and product code |
|---|---|
| GFB Unifilter plates | Perkin Elmer 6005177 |
| 3-[(3-Cholamidopropyl)dimethylammonio]-1-propanesulfonate (CHAPS) | Sigma C5070 |
| 96-well polypropylene U-bottom assay plate | Nunc 267245 |
| HEPES buffer, 1M | Sigma H3375 |
| Magnesium chloride ($MgCl_2$) | Sigma M8266 |
| D,L-Dithiothreitol (DTT) | Sigma D0632 |
| Sodium chloride (NaCl) | Sigma 71382 |
| Bovine serum albumin (BSA) | Sigma A7030 [lyophilized powder, ≥98% (agarose gel electrophoresis), Essentially fatty acid free, essentially globulin free] |
| 25-hydroxycholesterol | Sigma H1015 |
| 25-[26,27-$^3$H]hydroxycholesterol | Perkin Elmer NET674250UC American Radiolabeled Chemicals ART0766 |
| RORc ligand binding domain | Genentech (e.g., PUR 28048), expressed in *E. coli* |
| Plate seals | Perkin Elmer 6005185 |
| Microscint 0 | Perkin Elmer 6013611 |

Filter Plate Preparation

On day of the assay, 100 uL of 0.05% CHAPS (in deionized $H_2O$) was added to all wells of the GFB Unifilter plate and allowed soak for 1 h. A wash buffer of 50 mM HEPES (pH 7.4), 150 mM NaCl, and 5 mM $MgCl_2$ was prepared to wash the filter plate. To prepare an assay buffer, BSA was added to the wash buffer to reach 0.01% and DTT was added to reach 1 mM.

Compounds

For $IC_{50}$ mode, 10 mM compound stocks were serially diluted in DMSO with DMSO to give 20× required final concentration in DMSO (15 uL compound+30 uL DMSO). The 20× compound stocks were diluted in DMSO with Assay Buffer 4-fold to reach 5× the final test concentration in 25% DMSO (10 uL compound+30 uL Assay Buffer). Solutions were mixed by aspiration several times with a pipette set on 50 uL volume. For the assay, 10 uL of 5× compound stock solutions in 25% DMSO were added to the assay plate in duplicate.

For two point screening, 10 mM stock compound solutions were diluted in DMSO to obtain 200 uM (20× the high test concentration) and then diluted 10-fold further to reach 20 uM (20× the low test concentration). The 20× stocks were diluted 4-fold with Assay Buffer (10 uL compound+30 uL Assay Buffer) to reach 5× the test concentrations (50 uM and 5 uM) and 10 uL were added to two assay plates for the duplicate wells. With each concentration tested on 2 plates, each set of 80 compounds used 4 assay plates (1 uM and 10 uM, with n=2).

Nonspecific Binding (NSB) Samples, Total Binding (TB) Samples and No Receptor (No R) Samples 25-hydroxycholesterol (1 uM) was used to determine the level of NSB signal is prepared in DMSO as for compounds above, then diluted in Assay Buffer to give a final concentration of 5 uM. For 25-hydroxycholesterol in 25% DMSO/75% Assay Buffer; 10 uL per well was used for NSB samples. Wells for Total Binding and No Receptor sample determination contained 10 uL of 25% DMSO/75% Assay Buffer per well.

Radioligand (25-[$^3$H]hydroxycholesterol) Preparation

25-[$^3$H]hydroxycholesterol was diluted in Assay Buffer to obtain 15 nM and vortex to mix. Add 20 uL to all wells to reach 6 nM final concentration in the assay.

Receptor Preparation

The optimal concentration for RORc receptor was found to be 0.6 ug/mL. Stock receptor solution was diluted in assay buffer to obtain 1.5 ug/mL in Assay Buffer. 20 uL was added to all wells. For No Receptor samples, 20 uL Assay Buffer was substituted for receptor solution.

Sample Addition to Plates and Incubation

Assay plates were 96-well polypropylene V-bottom plates. 10 uL of 5× compound in 25% DMSO/75% Assay Buffer was added to Test wells. 10 uL of 25% DMSO/75% Assay Buffer was added to Total Binding or No Receptor wells. 10 uL of 5 uM 25-hydroxycholesterol in 25% DMSO/75% Assay Buffer was added to NSB wells. 20 uL of 15 nM 25-[$^3$H]hydroxycholesterol prepared in Assay Buffer was added to all wells. 20 uL of 1.5 ug/mL RORc receptor was added to wells (or 40 uL Assay Buffer to No R wells). Following addition to the wells, the plates were incubated 3 h at 25° C. Filtration Using a Packard Filtermate Harvester, the filter plate were washed 4 times following transfer of the incubated samples. Plates were dry-filtered completely (2 h at 50° C. or overnight at room temperature). 50 uL Microscint 0 was added to all wells and read on Topcount protocol Inverted.

Final Concentrations

Final concentrations were as follows: 50 mM HEPES buffer (pH 7.4); 150 mM NaCl; 1 mM DTT; 5 mM $MgCl_2$; 0.01% BSA; 5% DMSO; 0.6 ug/mL RORc receptor; 6 nM 25-[$^3$H]hydroxycholesterol. For NSB wells, 1 uM 25-hydroxycholesterol was also present.

Example 80: RORc Coactivator Peptide Binding Assay

Assays were carried out in 16-microL reaction volumes in black 384 Plus F Proxiplates (Perkin-Elmer 6008269). All assay components except test ligand were mixed in coregulator buffer D (Invitrogen PV4420) containing 5 mM DTT and added to the plate at twice their final concentrations in a volume of 8 microL. Test ligands at 2× the final concentration were then added to the wells in 8 μL of coregulator buffer D containing 5 mM DTT and 4% DMSO. Final incubations contained 1× coregulator buffer D, 5 mM DTT, test ligand, 2% DMSO, 50 nM biotinyl-CPSSHSSLTERKHKILHRLLQEGSPS (American Peptide Company; Vista, Calif.), 2 nM Europium anti-GST (Cisbio 61GSTKLB), 12.5 nM streptavidin-D2 (Cisbio 610SADAB), 50 mM KF, and 10 nM of bacterially-expressed human RORc ligand binding domain protein containing an N-terminal 6×His-GST-tag and residues 262-507 of Accession NP_005051. Ten test ligand concentrations were tested in duplicate. After the reaction plates were incubated for 3 h in the dark at room temperature (22-23° C.), the plate was read on an EnVision plate reader (PerkinElmer) following the Europium/D2 HTRF protocol (ex 320, em 615 and 665, 100 Ds lag time, 100 flashes, 500 s window). The time-resolved FRET signal at 665 nm was divided by that at 615 nm to generate the signal ratio of each well. The signal ratio of wells containing RORc and peptide but no test ligand were averaged and set to 0% Effect while the signal ratios of the blank wells containing coactivator peptide but no RORc were averaged and set to −100% Effect. RORc exhibits a basal (constitutive) signal in this assay and test ligands can increase or decrease the signal ratio relative to this basal signal level. RORc agonists increase the signal ratio in this assay and result in a positive % Effect value. Inverse agonists decrease the signal ratio, and result in a negative % Effect value. The $EC_{50}$ value is the concentration of test compound that provides half-maximal effect (increased or decreased assay signal) and is calculated by Genedata Screener® software (Genedata; Basel, Switzerland) using the following equation:

$$\%\ \text{Effect}=S_0+\{(S_{inf}-S_0)/[1+(10^{lgEC_{50}}/10^{c})^{n}]\}$$

where $S_0$ equals the activity level at zero concentration of test compound, $S_{inf}$ is the activity level at infinite concentration of test compound, $EC_{50}$ is the concentration at which the activity reaches 50% of the maximal effect, c is the concentration in logarithmic units corresponding to the values on the x-axis of the dose-response curve plot, and n is the Hill coefficient (the slope of the curve at the $EC_{50}$).

Example 81: Arthritis Mouse Model 8 to 10-week old male DBA/l (DBA/lOlaHsd, Harlan Laboratories) mice are housed in a specific pathogen free (SPF) animal facility. Arthritis is induced by two injections of collagen subcutaneously in the base of the tail. The initial injection (on day 0) uses bovine type II collagen (2 mg/ml from Chondrex, Redmond, Wash.) emulsified in equal volume of CFA containing 4 mg/ml of *M. tuberculosis* (Chondrex). The CII booster injection on Day 29 is emulsified in incomplete Freund's adjuvant (IFA). Each animal receives 0.1 ml of emulsion by subcutaneous/intradermal injection in the tail 2 to 3 cm from the body of the mouse. The booster injection site is in the vicinity of but different from the initial injection site and closer to the body of the animal. OR-1050 was formulated in HRC-6 as above. On weekdays, the animals receive two doses (a.m. and p.m.) of HRC-6 or 50 mg/kg OR-1050 p.o. (2.5 mls/kg). On weekends, a single dose of 100 mg/kg is administered (5 mls/kg).

The mice are observed daily for clinical symptoms of CIA based on the following qualitative scale. Each paw was examined individually and scored. Grade 0, normal; grade 1, mild but definite redness and swelling of the ankle or wrist, or apparent redness and swelling limited to individual digits, regardless of the number of affected digits; grade 2, moderate redness and swelling of ankle or wrist; grade 3, severe redness and swelling of the entire paw including digits; grade 4, maximally inflamed limb with involvement of multiple joints. To estimate cumulative disease severity for each animal, an area under the curve score is calculated for each animal by totaling the sum of the daily hind paw measurements between days 24 and 48.

Example 82: Muscular Sclerosis Mouse Model I

Experiments are conducted on female mice aged 4-6 weeks belong to the C57BL/6 strain weighing 17-20 g.

Experimental autoimmune encephalomyelitis (EAE) is actively induced using 95% pure synthetic myelin oligodendrocyte glycoprotein peptide 35-55 ($MOG_{35-55}$) (Invitrogen). Each mouse is anesthetized and receives 200 ug of $MOG_{35-55}$ peptide and 15 ug of Saponin extract from Quilija bark emulsified in 100 uL of phosphate-buffered saline. A 25 uL volume is injected subcutaneously over four flank areas. Mice are also intraperitoneally injected with 200 ng of pertussis toxin in 200 uL of PBS. A second, identical injection of pertussis toxin is given after 48 h.

A compound of the invention is administered at selected doses. Control animals receive 25 uL of DMSO. Daily treatment extends from day 26 to day 36 post-immunization. Clinical scores are obtained daily from day 0 post-immunization until day 60. Clinical signs are scored using the following protocol: 0, no detectable signs; 0.5, distal tail limpness, hunched appearance and quiet demeanor; 1, completely limp tail; 1.5, limp tail and hindlimb weakness (unsteady gait and poor grip with hind limbs); 2, unilateral partial hind limb paralysis; 2.5, bilateral hind limb paralysis; 3, complete bilateral hindlimb paralysis; 3.5, complete hindlimb paralysis and unilateral forelimb paralysis; 4, total paralysis of hind limbs and forelimbs (Eugster et al., Eur J Immunol 2001, 31, 2302-2312).

Inflammation and demyelination may be assessed by histology on sections from the CNS of EAE mice. Mice are sacrificed after 30 or 60 days and whole spinal cords are removed and placed in 0.32 M sucrose solution at 4° C. overnight. Tissues are prepared and sectioned. Luxol fast blue stain is used to observe areas of demyelination. Haematoxylin and eosin staining is used to highlight areas of inflammation by darkly staining the nuclei of mononuclear cells. Immune cells stained with H&E are counted in a blinded manner under a light microscope. Sections are separated into gray and white matter and each sector is counted manually before being combined to give a total for the section. T cells are immunolabeled with anti-CD3+ monoclonal antibody. After washing, sections are incubated with goat anti-rat HRP secondary antibody. Sections are then washed and counterstained with methyl green. Splenocytes isolated from mice at 30 and 60 days post-immunization are treated with lysis buffer to remove red blood cells. Cells are then re-suspended in PBS and counted. Cells at a density of about $3\times10^6$ cells/mL are incubated overnight with 20 ug/mL of MOG peptide. Supernatants from stimulated cells are assayed for IFNgamma protein levels using an appropriate mouse IFN-gamma immunoassay system.

Example 83: Muscular Sclerosis Mouse Model II

In this model, female rodents are anesthetized with isoflurane and injected with Freund's Incomplete Adjuvant containing 1 mg/mL neuronal antigen (e.g. myelin basic protein, myelin oligodendrocyte glycoprotein, proteolipid protein) and 4 mg/mL *Mycobacterium tuberculosis* at two sites on the back on day 0 of this study. A compound of interest is then dosed daily in a sub-cutaneous, intra-peritoneally, or oral manner from day 0 until the end of study at an efficacious dose. Daily observations of degree of paralysis are taken as measures of efficacy.

Example 84: Psoriasis Mouse Model I

The severe, combined immunodeficient (SCID) mouse model can be used to evaluate the efficacy of compounds for treating psoriasis in humans (Boehncke, Ernst Schering Res Found Workshop 2005, 50, 213-34; and Bhagavathula et al., J Pharmacol Expt'l Therapeutics 2008, 324(3), 938-947). Briefly, SCID mice are used as tissue recipients. One biopsy for each normal or psoriatic volunteer (human) is transplanted onto the dorsal surface of a recipient mouse. Treatment is initiated 1 to 2 weeks after transplantation. Animals with the human skin transplants are divided into treatment groups. Animals are treated twice daily for 14 days. At the end of treatment, animals are photographed and then euthanized. The transplanted human tissue along with the surrounding mouse skin is surgically removed and fixed in 10% formalin and samples obtained for microscopy. Epidermal thickness is measured. Tissue sections are stained with an antibody to the proliferation-associated antigen Ki-67 and with an anti-human CD3.sup.+ monoclonal antibody to detect human T lymphocytes in the transplanted tissue. Sections are also probed with antibodies to c-myc and beta-catenin. A positive response to treatment is reflected by a reduction in the average epiderma thickness of the psoriatic skin transplants. A positive response is also associated with reduced expression of Ki-67 in keratinocytes.

Example 85: Psoriasis Mouse Model II

Using the Imidquimod model of skin inflammation (Fits et al, Journal of Immunology, 2009, 182: 5836-5845), 10-12 week old BALB/c, Il17c+/+ or Il17c−/−, or Il17re+/+ or Il17re−/− mice were administered 50 mg Aldara cream (5% Imidquimod in Graceway, 3M) in the shaved back and right ear daily for 5 days. Clinical scoring and ear thickness measurements were performed daily. Scoring was based upon the manifestation of psoriatic symptoms, such as erythema, scaling and thickness: 0, No disease. 1, Very mild erythema with very mild thickening and scaling involving a small area. 2, Mild erythema with mild thickening and scaling involving a small area. 3, Moderate erythema with moderate thickening and scaling (irregular and patchy) involving a small area (<25%). 4, Severe erythema with marked thickening and scaling (irregular and patchy) involving a moderate area (25-50%). 5, Severe erythema with marked thickening and scaling (irregular and patchy) involving a large area (>50%). Ear and back tissue were harvested on day 5 for histological evaluation. Efficacy of compounds is compared in the imiquimod (IMQ) mouse model of psoriasis. Balb/c mice (10 males/group) received daily topical IMQ (5% cream) on shaved back and right ear for 5 days as described above. Animals received oral dose of a representative compound or DMF (45 or 90 mg-eq MMF/kg twice daily) or vehicle from Day −5 to Day+5. Erythema score is the primary outcome measure.

Example 86: Irritable Bowel Disease Mouse Model I

Effectiveness in treatment of inflammatory bowel disease may be evaluated as described by Jurjus et al., J Pharmaocol Toxicol Methods 2004, 50, 81-92; Villegas et al., Int'l Immunopharmacol 2003, 3, 1731-1741; and Murakami et al., Biochemical Pharmacol 2003, 66, 1253-1261. Briefly, female ICR mice are divided into treatment groups which are given either water (control), 5% DSS in tap water is given at the beginning of the experiment to induce colitis, or various concentrations of test compound. After administering test compound for 1 week, 5% DSS in tap water is also administered to the groups receiving test compound for 1 week. At the end of the experiment, all mice are sacrificed and the large intestine is removed. Colonic mucosa samples are obtained and homogenized. Proinflammatory mediators (e.g., IL-1alpha, IL-1beta, TNFalpha, PGE2, and PGF2alpha.) and protein concentrations are quantified. Each excised large intestine is histologically examined and the damage to the colon scored.

Example 87: Chronic Obstructive Pulmonary Disease Mouse Model

The cigarette smoke model of Martorana et al., Am J Respir Crit Care Med 2005, 172, 848-835; and Cavarra et al., Am J Respir Crit Care Med 2001, 164, 886-890 can be used for assessing efficacy in treating emphysema. Briefly, six-week old C57B1/6J male mice are exposed either to room air or to the smoke of five cigarettes for 20 minutes. For the acute study, mice are divided into three groups of 40 animals each. These groups are then divided into four subgroups of 10 mice each as follows: (1) no treatment/air-exposed; (2) no treatment/smoke-exposed; (3) a first dose of test compound plus smoke-exposed; and (4) a second dose of test compound. In the first group, trolox equivalent antioxidant capacity is assessed at the end of the exposure in bronchoalveolar lavage fluid. In the second group, cytokines and chemokines are determined in bronchoalveolar lavage fluid using a commercial cytokine panel at 4 hours; and in the third group bronchoalveolar lavage fluid cell count is assessed at 24 hours.

In a chronic study, the mice are exposed to either room air or to the smoke of three cigarettes/day, for 5 days/week, for 7 months. Five groups of animals are used: (1) no treatment/air-exposed; (2) a first dose of a test compound plus air-exposed; (3) no treatment/smoke-exposed; (4) a second dose of the test compound plus smoke-exposed; and (5) the first dose of the test compound plus smoke exposed. Seven months after chronic exposure to room air or cigarette smoke, 5 to 12 animals from each group are sacrificed and the lungs fixed intratracheally with formalin. Lung volume is measured by water displacement. Lungs are stained. Assessment of emphysema includes mean linear intercept and internal surface area. The volume density of macrophages, marked immunohistochemically with anti-mouse Mac-3 monoclonal antibodies is determined by point counting. A mouse is considered to have goblet cell metaplasia when at least one or more midsize bronchi/lung showed a positive periodic acid-Schiff staining for the determination of desmosine, fresh lungs are homogenized, processed, and analyzed by high-pressure liquid chromatography.

Example 88: Asthma Mouse Model

A single inhaled allergen challenge can induce an acute increase in airway responsiveness in some individuals and animal models. However, repeated allergen inhalations have demonstrated more pronounced, consistent, and prolonged increases in airway responsiveness. This mouse model of long-term repeated inhalations of allergen has been used to study the long term effect of allergic diseases in the lung, and to delineate the cells, mechanisms, molecules, and mediators involved in the induction of airway hyperresponsiveness of lung in humans.

Crystalline OVA is obtained from Pierce Chem. Co. (Rockford, Ill.) aluminum potassium sulfate (alum) from Sigma Chem. Co. (St. Louis, Mo.), pyrogen-free distilled water from Baxter, Healthcare Corporation (Deerfield, Ill.), 0.9% sodium chloride (normal saline) from Lymphomed (Deerfield, Ill.) and Trappsol™ HPB-L100 (aqueous hydroxypropylbeta cyclodextrin; 45 wt/vol % aqueous solution) from Cyclodextrin Technologies Development, Inc. (Gainesville, Fla.). The OVA (500 ug/ml in normal saline) is mixed with equal volumes of 10% (wt/vol) alum in distilled water. The mixture (pH 6.5 using 10 N NaOH) after incubation for 60 minutes at room temperature is centrifuged at 750 g for 5 minutes; the pellet resuspended to the original volume in distilled water and used within one hour. The selective 5-lipoxtgenase inhibitor, Zileuton (N-[1-benzo[b]thien-2-ylethyl]-N-hydroxyurea; J. Pharmacol Exp Ther. 1991; 256: 929-937) is dissolved in Trappsol™ Histatek, Inc. (Seattle, Wash.) to provide the mast cell degranulation inhibitor, f-Met-Leu-Phe-Phe ("HK-X").

Female BALB/c Once (6-8 wk of age) receive an i.p. injection of 0.2 ml (100 ug) of 30 OVA with alum (J. Exp Med. 1996; 184: 1483-1494). Mice are anesthetized with 0.2 ml i.p. of ketamine (0.44 mg/ml)/xylazine (6.3 mg/ml) in normal saline before receiving an intranasal (i.n.) dose of 100 ug OVA in 0.05 ml normal saline and an i.n. dose of 50 ug OVA in 0.05 ml normal saline separately on different days. Two control groups are used: the first group receives normal saline with alum i.p. and normal saline without alum i.n.; and the second group receives OVA with alum i.p., OVA without alum i.n., and normal saline, alone.

The trachea and left lung (the right lung may be used for bronchoalveolar lavage ("BAL") as described below) are obtained and fixed in 10% neutral formaldehyde solution at room temperature for about 15 h. After being embedded in paraffin, the tissues are cut into 5-um sections and processed with the different staining or immunolabling further. Discombe's eosinophil staining is used for counting the cell numbers with the counterstain of methylene blue. The eosinophil number per unit airway area (2,200 $um^2$) is determined by morphometry (J. Pathol. 1992; 166: 395-404; Am Rev Respir Dis. 1993; 147:448-456). Fibrosis is identified with the Masson's trichrome staining. Airway mucus iss identified by the following staining method: methylene blue, hematoxylin and eosin, mucicarmine, alcian blue, and alcian blue/periodic acid-Schiff (PAS) reaction (Troyer, H., "Carbohydrates" in Principles and Techniques of Histochemistry, Little, Brown and Company, Boston, Mass., 1980: 89-121; Sheehan, D. C., et al., "Carbohydrates" in Theory and Practice of Histotechnology, Battle Press, Columbus, Ohio, 1980: 159-179) Mucin is stained with mucicarmine solution; metanil yellow counterstain is employed. Acidic mucin and sulfated mucosubstances are stained with alcian blue, pH 2.5; nuclear fast red counterstain is used. Neutral and acidic mucosubstances are identified by alcian blue, pH 2.5, and PAS reaction. The degree of mucus plugging of the airways (0.5-0.8 mm in diameter) is also assessed by morphometry. The percent occlusion of airway diameter by mucus is classified on a semiquantitative scale from 0 to 4+. The histologic and morphometric analyses may be performed by individuals blinded to the protocol design.

On day 28, 24 hours after the last i.n. administration of either normal saline or OVA, pulmonary mechanics to intravenous infusion of methacholine may be determined in mice in vivo by a plethysmographic method as previously described (10, 1958; 192: 364-368; J. Appl. Physiol. 1988; 64: 2318-2323; J. Exp. Med. 1996; 184: 1483-1494).

After tying off the left lung at the mainstem bronchus, the right lung may be lavaged three times with 0.4 ml of normal saline. Bronchoalveolar lavage (BAL) fluid cells from a 0.05-ml aliquot of the pooled sample are counted using a hemocytometer and the remaining fluid centrifuged at 4° C. for 10 minutes at 200 g. The supernatant may be stored at 70.degree. C. until eicosanoid analysis is performed. After resuspension of the cell pellet in normal saline containing 10% bovine serum albumin ("BSA"), BAL cell smears are made on glass slides. To stain eosinophils, dried slides are stained with Discombe's diluting fluid (0.05% aqueous eosin and 5% acetone (vol/vol) in distilled water; J. Exp. Med. 1970; 131: 1271-1287) for 5-8 minutes, rinsed with water for 0.5 minutes, and counterstained with 0.07% methylene blue for 2 minutes.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I

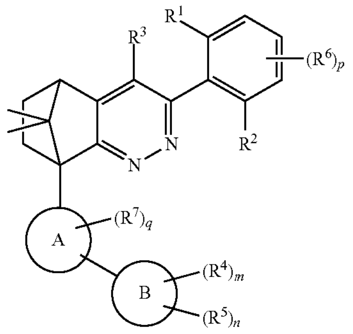

I or a pharmaceutical salt thereof,
wherein:
A is heteroaryl selected from:
  pyridinyl;
  pyrimidinyl;
  pyridazinyl; and
  pyrazinyl;

B is piperidinyl or heteroaryl wherein the heteroaryl selected from the group consisting of:
  oxazolyl;
  isoxazolyl;
  thiazolyl;
  isothiazolyl;
  pyrrolyl;
  imidazolyl;
  pyridazolyl;
  triazolyl;
  oxadiazolyl;
  thiadiazolyl;
  pyridinyl;
  pyrimidinyl;
  pyrazinyl;
  pyridazinyl; and
  2,3-dihydro-1H-imidazo[4,5-b]pyridinyl;

m is: 0; 1; or 2;
n is: 0; or 1;
p is: 0; or 1;
q is: 0; or 1;
$R^1$ is:
  halo;
$R^2$ is:
  hydrogen;
  halo; or
  methoxy;
$R^3$ is:
  hydrogen;
  cyano;
  $C_{1-6}$alkyl; or
  halo;
$R^4$ is:
  $C_{1-6}$alkyl which may be unsubstituted or substituted one or more times with halo;
  $C_{2-6}$alkenyl;
  cyano;
  hydroxyl-$C_{1-6}$alkyl wherein the $C_{1-6}$alkyl moiety may be unsubstituted or substituted one or more times with halo;
  $C_{1-6}$ alkoxy$C_{1-6}$alkyl wherein the $C_{1-6}$alkyl moieties may be unsubstituted or substituted one or more times with halo;

oxo;
hydroxy;
$C_{1-6}$alkylsulfinyl;
halo;

$R^5$ is:
$—(CR^{a1}R^{a2})_p—NR^bR^c$;
$—(CR^{a1}R^{a2})_p—SO_2—R^d$;
$—(CR^{a1}R^{a2})_p—C(O)—R^e$;
$—(CR^{a1}R^{a2})_p—NR^b—SO_2—R^d$;
$—(CR^{a1}R^{a2})_p—NR^b—C(O)—R^e$;
$—(CR^{a1}R^{a2})_p—NR^b—(CHR^c)_q—SO_2—R^d$;
$—(CR^{a1}R^{a2})_pNR^b—(CHR^c{}_q—C(O)—R^e$;
$—(CR^{a1}R^{a2})_p—CN$;
$—C_{2-6}$alkenyl-CN;
$—(CR^{a1}R^{a2})_p—Z$;
$—(CR^{a1}R^{a2})_p—SO_2—Z$;
$C_{1-6}$alkylsulfonimidamido; or
$C_{1-6}$alkylsulfonimidoyl$C_{1-6}$alkyl;

$R^6$ is:
$C_{1-6}$alkyl;
halo; or
hydroxyl;

$R^7$ is:
$C_{1-6}$alkyl;
$C_{1-6}$alkoxy;
halo; or
hydroxyl;

Z is:
$C_{3-6}$cycloalkyl which may be unsubstituted or substituted once or twice with $R^f$;
a four or five membered heterocyclyl selected from azetidinyl, oxetanyl, thietanyl or tetrahydrothiophenyl, each of which may be unsubstituted or substituted once or twice with $R^f$;
$C_{1-6}$alkyl-heterocyclyl wherein the heterocyclyl is a four or five membered heterocyclyl selected from azetidinyl, oxetanyl, thietanyl or tetrahydrothiophenyl, each of which may be unsubstituted or substituted once or twice with $R^f$; or
$C_{1-6}$alkylcarbonylamino$C_{1-6}$alkyl;

p is: 0; 1; 2; or 3
q is: 1; or 2;

$R^{a1}$ is:
hydrogen;
$C_{1-6}$alkyl which may be unsubstituted or substituted one or more times with halo;

$R^{a2}$ is:
hydrogen;
$C_{1-6}$alkyl which may be unsubstituted or substituted one or more times with halo; or
hydroxyl;
or $R^{a1}$ and $R^{a2}$ may together form a $=CH_2$ group;

$R^b$ is:
hydrogen;
$C_{1-6}$alkyl which may be unsubstituted or substituted one or more times with halo; or
hydroxyl-$C_{1-6}$alkyl wherein the $C_{1-6}$alkyl moiety may be unsubstituted or substituted one or more times with halo;

$R^c$ is:
hydrogen; or
$C_{1-6}$alkyl which may be unsubstituted or substituted one or more times with halo;

$R^d$ is:
$C_{1-6}$alky which may be unsubstituted or substituted one or more times with halo;
$C_{3-6}$cycloalkyl;
$C_{3-6}$cycloalkyl-$C_{1-6}$alkyl;
hydroxy$C_{1-6}$alkyl; or
$NR^bR^c$;

$R^e$ is:
$C_{1-6}$alkyl which may be unsubstituted or substituted one or more times with halo;
$C_{1-6}$alkoxy;
hydroxyl-$C_{3-6}$alkyl or
hydroxyl; or
$NR^bR^c$; and $R^f$ is: $C_{1-6}$alkyl which may be unsubstituted or substituted one or more times with halo;
halo;
oxo;
cyano$C_{1-6}$alkyl;
hydroxy;
$—CH_2COOH$;
hydroxy$C_{1-6}$alkyl; or
$C_{1-6}$alkylsulfonyl$C_{1-6}$alkyl;

and wherein the compound is selected from:
3-[2-[6[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]oxetan-3-ol;
[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanamine;
N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide;
2,2,2-trifluoro-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]ethanamine;
[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methylurea;
(2S)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,2-diol;
(S)-cyclopropyl-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;
(R)-cyclopropyl-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;
(1R)-2,2-difluoro-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol;
(1S)-2,2-difluoro-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol
(1S)-2-methyl-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-1-ol;
2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1R)-1-methylsulfonylethyl]oxazole;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1S)-1-methylsulfonylethyl]oxazole;

4-(isopropylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2S)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide;

(2R)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide;

N-(2-hydroxyethyl)-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanenitrile;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(1S,8R)-5-(2,6-difluorophenyl)-11,11-dimethyl-1-[6-[1-(2-methylsulfonylethyl)pyrazol-4-yl]pyrazin-2-yl]-3,4-diazatricyclo[6.2.1.02,7]undeca-2(7),3,5-triene;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

N-[(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]methanesulfonamide;

[5-methyl-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;

5-methyl-4-(methylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

ethyl N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]carbamate;

[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanesulfonamide;

2-methyl-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]-N-[(2S)-2-hydroxypropyl]acetamide;

2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]-N-[(2R)-2-hydroxypropyl]acetamide;

4-(1-methyl-1-methylsulfonyl-ethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2R)-1,1-difluoro-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(2S)-1,1-difluoro-2-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(2R)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol;

2-hydroxy-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]acetamide;

(1S)-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,3-diol;

(1R)-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propane-1,3-diol;

4-(1-ethylsulfonyl-1-methyl-ethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

4-(1-cyclopropylsulfonyl-1-methyl-ethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

N-[(1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]methanesulfonamide;

(2S)-2-hydroxy-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]propanamide;

N-methyl-N-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide;

(E)-3-[2-[6[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]prop-2-enenitrile;

3-[2-[6[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

2,2,2-trifluoro-N-[(1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]ethanamine;

(1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanamine;

(2R)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

(2S)-2-hydroxy-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]acetamide;

(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol;

(1S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethane-1,2-diol;

(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanamine;

2,2,2-trifluoro-N-[(1R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethyl]ethanamine;

2-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]amino]ethanol;

(1S,8R)-5-(2,6-difluorophenyl)-1-[6-[1-(2-ethylsulfonylethyl)pyrazol-4-yl]pyrazin-2-yl]-11,11-dimethyl-3,4-diazatricyclo[6.2.1.02,7]undeca-2(7),3,5-triene;

N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

ethyl N-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]carbamate;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(1S,8R)-5-(2,6-difluorophenyl)-11,11-dimethyl-1-[6-[1-(2-methylsulfonylethyl)pyrazol-3-yl]pyrazin-2-yl]-3,4-diazatricyclo[6.2.1.02,7]undeca-2(7),3,5-triene;

(1S,8R)-5-(2,6-difluorophenyl)-1-[6-[1-(2-ethylsulfonylethyl)pyrazol-3-yl]pyrazin-2-yl]-11,11-dimethyl-3,4-diazatricyclo[6.2.1.02,7]undeca-2(7),3,5-triene;

2-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methylamino]acetamide;

(1R)-2,2,2-trifluoro-1-[5-methyl-2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol;

(1S)-2,2,2-trifluoro-1-[5-methyl-2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]ethanol;

(2R)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(2S)-1-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-2-ol;

(1S,8R)-5-(2,6-difluorophenyl)-11,11-dimethyl-1-[2-[6-(methylsulfonylmethyl)-3-pyridyl]pyrimidin-4-yl]-3,4-diazatricyclo[6.2.1.02,7]undeca-2(7),3,5-triene;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(1S,8R)-5-(2,6-difluorophenyl)-11,11-dimethyl-1-[6-[1-(2-methylsulfonylethyl)pyrazol-4-yl]-2-pyridyl]-3,4-diazatricyclo[6.2.1.02,7]undeca-2(7),3,5-triene;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1R)-1-ethylsulfonylethyl]oxazole;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-[(1S)-1-ethylsulfonylethyl]oxazole;

4-[(1R)-1-cyclopropylsulfonylethyl]-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

4-[(1S)-1-cyclopropylsulfonylethyl]-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2R)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

(2S)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanenitrile;

(1S,8R)-5-(2,6-difluorophenyl)-11,11-dimethyl-1-[6-[1-(2-methylsulfonylethyl)pyrazol-3-yl]-2-pyridyl]-3,4-diazatricyclo[6.2.1.02,7]undeca-2(7),3,5-triene;

(2R)-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(2S)-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

2-methyl-1-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanenitrile;

2-[3-[4-[6(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]oxetan-3-yl]acetonitrile N-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide;

(1S,8R)-1-[2-[6-[(amino-methyl-oxo-lambda6-sulfanylidene)amino]-3-pyridyl]pyrimidin-4-yl]-5-(2,6- difluorophenyl)-11,11-dimethyl-3,4-diazatricyclo[6.2.1.02,7]undeca-2(7),3,5-triene;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]butan-2-ol;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]butan-2-ol;

2-methyl-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethanesulfonamide;

N-[2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethyl]methane sulfonamide 3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanesulfonamide;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethanol;

N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]methanesulfonamide;

5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyridine-2-sulfonamide;

2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-pyridyl]propan-2-ol;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanol;

N-[(1S)-1-methyl-2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]ethyl]methanesulfonamide;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

imino-methyl-oxo-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]-lambda6-sulfane;

imino-methyl-oxo-[[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]-lambda6-sulfane;

(1S,8R)-5-(2,6-difluorophenyl)-1-[6-[1-(2-methoxyethyl)pyrazol-4-yl]pyrazin-2-yl]-11,11-dimethyl-3,4-diazatricyclo[6.2.1.02,7]undeca-2(7),3,5-triene;

2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridine-4-sulfonamide;

5-chloro-4-(methylsulfonylmethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

4-(2-methylsulfonylethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

(2S)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

[5-(hydroxymethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methanol;

(2S)-2-methyl-3-[2-[6[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

(2R)-2-methyl-3-[2-[6[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

N-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

(2R)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

N-[2-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethyl]methanesulfonamide;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]ethanol;

(2R)-1-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(2S)-1-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

2-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]ethanol;

(2S)-1,1,1-trifluoro-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;

(2S)-1,1,1-trifluoro-3-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

N-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-4-pyridyl]methanesulfonamide;

(2R)-1,1,1-trifluoro-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;

5-chloro-4-(2-methylsulfonylethyl)-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazole;

N-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]methanesulfonamide;

(2R)-1,1,1-trifluoro-3-[3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

N-[[5-methyl-2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]methyl]methanesulfonamide;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propan-2-ol;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propan-2-ol;

N-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]methanesulfonamide;

N-[6-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

N-[6-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-3-pyridyl]methanesulfonamide;

(2R)-1-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(2S)-1-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]cyclobutanol;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,3-diol;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]cyclobutanol;

3-[2-[6[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanamide;

2-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]acetonitrile;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanamide;

N-(2-methylsulfonylethyl)-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridin-2-amine;

(2S)-2-hydroxy-N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]propanamide;

N-[[5-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methyl]methanesulfonamide;

1-[5-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]azetidin-3-ol;

N-[6-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyridazin-3-yl]methanesulfonamide;

N-[6-methyl-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide;

N-[6-methyl-4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

N-[3-methyl-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-2-pyridyl]methanesulfonamide;

N-[3-methyl-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

(2S)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;

(2R)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]acetamide;

N-(2-hydroxyethyl)-2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]acetamide;

(1S,8R)-5-(2,6-difluorophenyl)-11,11-dimethyl-1-[6-(3-methyl-1H-pyrazol-4-yl)-2-pyridyl]-3,4-diazatricyclo[6.2.1.02,7]undeca-2(7),3,5-triene;

(1S,8R)-5-(2,6-difluorophenyl)-11,11-dimethyl-1-[6-[1-(methylsulfonylmethyl)pyrazol-4-yl]pyrazin-2-yl]-3,4-diazatricyclo[6.2.1.02,7]undeca-2(7),3,5-triene;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-1-yl]propane-1,2-diol;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-2-yl]propane-1,2-diol;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-2-yl]propane-1,2-diol;

N-(2-hydroxyethyl)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanamide;

2-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]acetamide;

N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-6-methyl-2-pyridyl]methanesulfonamide;

2-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]acetamide;

[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1H-pyrazol-3-yl]methanol;

N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-3-yl]methyl]methanesulfonamide;

(2S)-3-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;

(2R)-3-[5-methyl-3-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;

(1S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethane-1,2-diol;

N-(2-methylsulfonylethyl)-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-amine;

2-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]acetamide;

(1S)-1[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]ethane-1,2-diol;

(1R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethane-1,2-diol;

(1R)-1[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]ethane-1,2-diol;

N-[4-methyl-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-2-yl]propane-1,2-diol;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-2-yl]propane-1,2-diol;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-1-yl]propane-1,2-diol;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]triazol-1-yl]propane-1,2-diol;

(2S)-3-[5-methyl-4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

(2S)-3-[3-methyl-4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

N-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methanesulfonamide;

3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanamide;

(1S,8R)-5-(2,6-difluorophenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene;

2-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino] acetamide;

2-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]acetamide;

(1S,8R)-5-(2,6-difluorophenyl)-11,11-dimethyl-1-[2-[1-(methylsulfonylmethyl)pyrazol-4-yl]pyrimidin-4-yl]-3,4-diazatricyclo[6.2.1.02,7]undeca-2(7),3,5-triene;

(2S)-3-[4-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]pyrazol-1-yl]propane-1,2-diol;

(2R)-3-[4-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]pyrazol-1-yl]propane-1,2-diol;

3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propanamide;

(2S)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-2-yl]propane-1,2-diol;

(2R)-3-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]triazol-2-yl]propane-1,2-diol;

3-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]propanamide;

(1S,8R)-5-(2,6-difluorophenyl)-11,11-dimethyl-1-[6-[3-(2-methylsulfonylethyl)-1,2,4-triazol-1-yl]pyrazin-2-yl]-3,4-diazatricyclo[6.2.1.02,7]undeca-2(7),3,5-triene;

2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol;

N-[[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]methyl]methanesulfonamide;

2-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-3-yl]propane-1,3-diol;

N-[[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-3-yl]methyl]methanesulfonamide;

N-(2-methylsulfonylethyl)-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-amine;

N-(2-methylsulfonylethyl)-5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-amine;

(2S)-1-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]propan-2-ol;

(2S)-1-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propan-2-ol;

(2S)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

(2R)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propane-1,2-diol;

(1S,8R)-5-(2,6-difluorophenyl)-11,11-dimethyl-1-[6-[1-(methylsulfonylmethyl)pyrazol-4-yl]-2-pyridyl]-3,4-diazatricyclo[6.2.1.02,7]undeca-2(7),3,5-triene;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazin-2-yl]methanesulfonamide;

N-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]ethanesulfonamide;

(2R)-3-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]amino]propane-1,2-diol;

(2S)-3-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl)pyrimidin-2-yl)amino]propane-1,2-diol;

2-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridl]pyrimidin-2-yl]amino]acetamide;

N-[4-methyl-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]methanesulfonamide;

N-[4-methyl-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]methanesulfonamide;

3-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propane-1,2-diol;

2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethanol;

3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-3-yl]propanamide;

3-[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-3-yl]propanamide;

N-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]propane-2-sulfonamide;

N-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]methanesulfonamide;

(2R)-3-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]propane-1,2-diol;

(2S)-3-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]propane-1,2-diol;

(2R)-1-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propan-2-ol;

N-[4-methyl-5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

2-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]acetamide;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]-2-hydroxypropanamide;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]-2-hydroxy-propanamide;

(2S)-3-[4-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]triazol-1-yl]propane-1,2-diol;

(2R)-3-[4-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]triazol-1-yl]propane-1,2-diol;

(2R)-3-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-1-yl]propane-1,2-diol;

(2S)-3-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-1,2,4-triazol-1-yl]propane-1,2-diol;

(2R)-1-[4-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]pyrazol-1-yl]propan-2-ol;

(2S)-1-[4-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]pyrazol-1-yl]propan-2-ol;

3-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propanamide;

N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]methanesulfonamide;

(1S,8R)-5-(2,6-difluorophenyl)-11,11-dimethyl-1-[2-[1-(oxetan-3-yl]pyrazol-4-yl]pyrimidin-4-yl]-3,4-diazatricyclo[6.2.1.02,7]undeca-2(7),3,5-triene;

2-[4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]propane-1,3-diol;

(1S,8R)-5-(2,6-difluorophenyl)-11,11-dimethyl-1-[2-[3-(methylsulfonylmethyl)-1,2,4-triazol-1-yl]pyrimidin-4-yl]-3,4-diazatricyclo[6.2.1.02,7]undeca-2(7),3,5-triene;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]ethanesulfonamide;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]propane-2-sulfonamide;

6-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,3-dihydroimidazo [4,5-b]pyridin-2-one;

(1S,8R)-1-[6-[5-(cyclopropylsulfonylmethyl)-4H-1,2,4-triazol-3-yl]-2-pyridyl]difluorophenyl)-11,11-dimethyl-3,4-diazatricyclo[6.2.1.02,7]undeca-2(7),3,5-triene;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]imidazol-1-yl]propane-1,2-diol;

(1S,8R)-5-(2,6-difluorophenyl)-11,11-dimethyl-1[6-[3-(2-methylsulfonylethyl)-1,2,4-triazol-1-yl]-2-pyridyl]-3,4-diazatricyclo[6.2.1.02,7]undeca-2(7),3,5-triene;

(2S)-3-[3-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]pyrazol-1-yl]propane-1,2-diol;

(2R)-3-[3-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]pyrazol-1-yl]propane-1,2-diol;

(2R)-1-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]amino]propan-2-ol;2,2,2-trifluoroacetic acid;

(2R)-1-[[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl)pyrimidin-2-yl)amino]propan-2-ol;2,2,2-trifluoroacetic acid;

(2S)-3-[4-[[6-[(1S,8R)-5-(2,6-difluorophenyl)-11,11-dimethyl-3,4-diazatricyclo[6.2.1.02,7]undeca-2(7),3,5-trien-1-yl]-2-pyridyl]amino]pyrazol-1-yl]propane-1,2-diol;

(2R)-3-[4-[[6-[(1S,8R)-5-(2,6-difluorophenyl)-11,11-dimethyl-3,4-diazatricyclo[6.2.1.02,7]undeca-2(7),3,5-trien-1-yl]-2-pyridyl]amino]pyrazol-1-yl]propane-1,2-diol;

3-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]propanamide;

3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]propanamide;

3-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]propanamide;

N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]propane-2-sulfonamide;

(1S,8R)-5-(2,6-difluorophenyl)-11,11-dimethyl-1-[6-[2-(methylsulfonylmethyl)pyrimidin-5-yl]pyrazin-2-yl]-3,4-diazatricyclo[6.2.1.02,7]undeca-2(7),3,5-triene;

(1S,8R)-5-(2,6-difluorophenyl)-11,11-dimethyl-1-[2-[2-(methylsulfonylmethyl)pyrimidin-5-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[6-[2-(methylsulfonylmethyl)pyrimidin-5-yl]-2-pyridyl]-3,4-diazatricyclo[6.2.1.02,7]undeca-2(7),3,5-triene;

3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanenitrile;

(1S,8R)-5-(2,6-difluorophenyl)-1-[6-[5-(ethylsulfonylmethyl)-4H-1,2,4-triazol-3-yl]-2-pyridyl]-11,11-dimethyl-3,4-diazatricyclo[6.2.1.02,7]undeca-2(7),3,5-triene;

(1S,8R)-5-(2,6-difluorophenyl)-1[6-[3-(isopropylsulfonylmethyl)-1H-1,2,4-triazol-5-yl]-2-pyridyl]-11,11-dimethyl-3,4-diazatricyclo[6.2.1.02,7]undeca-2,4,6-triene;

N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethanesulfonamide;

(1S,8R)-5-(2,6-difluorophenyl)-11,11-dimethyl-1-[6-[2-(methylsulfonylmethyl)-1,2,4-triazol-3-yl]-2-pyridyl]-3,4-diazatricyclo[6.2.1.02,7]undeca-2(7),3,5-triene;

(2R)-3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-1-yl]propane-1,2-diol;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]imidazol-1-yl]propane-1,2-diol;

5-(2-methylsulfonylethyl)-3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-oxadiazole;

3-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]-5-vinyl-1,2,4-oxadiazole;

(1S,8R)-5-(2,6-difluorophenyl)-11,11-dimethyl-1-[2-[1-(2-methylsulfonylethyl)-1,2,4-triazol-3-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[6-[1-(2-methylsulfonylethyl)-1,2,4-triazol-3-yl]-2-pyridyl]-3,4-diazatricyclo[6.2.1.02,7]undeca-2(7),3,5-triene;

(1S,8R)-5-(2,6-difluorophenyl)-11,11-dimethyl-1-[6-[2-(2-methylsulfonylethyl)-1,2,4-triazol-3-yl]-2-pyridyl]-3,4-diazatricyclo[6.2.1.02,7]undeca-2(7),3,5-triene;

[5-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]pyrimidin-2-yl]urea;

(2R)-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol;

(3S)-3-[1-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,2,4-triazol-3-yl]thiolane 1,1-dioxide;

(3R)-3-[1-[4-[(1S,8R)-5-(2,6-difluorophenyl)-11,11-dimethyl-3,4-diazatricyclo[6.2.1.02,7]undeca-2,4,6-trien-1-yl]pyrimidin-2-yl]-1,2,4-triazol-3-yl]thiolane 1,1-dioxide;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]cyclopropanesulfonamide;

(1S,8R)-5-(2,6-difluorophenyl)-11,11-dimethyl-1-[6-[5-[(1R)-1-ethylsulfonylethyl]-4H-1,2,4-triazol-3-yl]-2-pyridyl]-3,4-diazatricyclo[6.2.1.02,7]undeca-2(7),3,5-triene;

(1S,8R)-5-(2,6-difluorophenyl)-11,11-dimethyl-1-[6-[5-[(1S)-1-ethylsulfonylethyl]-4H-1,2,4-triazol-3-yl]-2-pyridyl]-3,4-diazatricyclo[6.2.1.02,7]undeca-2(7),3,5-triene;

2-hydroxy-N-[[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]methyl]acetamide;

(1S,8R)-5-(2,6-difluorophenyl)-11,11-dimethyl-1-[2-[2-(methylsulfonylmethyl)-1,2,4-triazol-3-yl]pyrimidin-4-yl]-3,4-diazatricyclo[6.2.1.02,7]undeca-2(7),3,5-triene;

(1S)-1-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]ethane-1,2-diol;

(1S)-1-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethane-1,2-diol;

(1R)-1-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrimidin-2-yl]ethane-1,2-diol;

2-(2-methylsulfonylethyl)-5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-A-1,3,4-oxadiazole;

(1R)-1-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]ethane-1,2-diol;

(1S)-1-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]ethane-1,2-diol;

(1R)-1-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]ethane-1,2-diol;

(1S,8R)-5-(2,6-difluorophenyl)-11,11-dimethyl-1-[2-[3-[(2S)-2-methylsulfonylpropyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-[(2R)-2-methylsulfonylpropyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[1-(2-methylsulfonylethyl)imidazo]-4-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-(2-methylsulfonylethyl)imidazo]-4-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-[2-(oxetan-3-ylsulfonyl)ethyl]-1,2,4-triazol-1-yl]pyrimidin-4-yl]-3,4-diazatricyclo[6.2.1.02,7]undeca-2(7),3,5-triene;

(1S,8R)-1-[2-[3-(cyclopropylmethylsulfonylmethyl)-1,2,4-triazol-1-yl]pyrimidin-4-yl]difluorophenyl)-11,11-dimethyl-3,4-diazatricyclo[6.2.1.02,7]undeca-2(7),3,5-triene;

(1S,8R)-5-(2,6-difluorophenyl)-11,11-dimethyl-1-[2-[2-(2-methylsulfonylethyl)pyrimidin-5-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[6-[2-(2-methylsulfonylethyl)pyrimidin-5-yl]-2-pyridyl]-3,4-diazatricyclo[6.2.1.02,7]undeca-2(7),3,5-triene;

N-methyl-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-A-1,2,4-triazol-3-yl]propanamide;

(2S)-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]propane-1,2-diol;

(1S,8R)-1-[2-[3-[2-(cyclopropylmethylsulfonyl)ethyl]-1,2,4-triazol-1-yl)pyrimidin-4-yl]difluorophenyl)-11,11-dimethyl-3,4-diazatricyclo[6.2.1.02,7]undeca-2(7),3,5-triene;

3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]oxetan-3-ol;

N-[5-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

(1S,8R)-5-(2,6-difluorophenyl)-11,11-dimethyl-1-(6-methylsulfonyl-2-pyridyl)-3,4-diazatricyclo[6.2.1.02,7]undeca-2(7),3,5-triene;

(1S,8R)-5-(2,6-difluorophenyl)-11,11-dimethyl-1-(2-methylsulfonylpyrimidin-4-yl)-3,4-diazatricyclo[6.2.1.02,7]undeca-2(7),3,5-triene;

(1S,8R)-5-(2,6-difluorophenyl)-11,11-dimethyl-1-[2-[1-(methylsulfonylmethyl)imidazol-4-yl]pyrimidin-4-yl]-3,4-diazatricyclo[6.2.1.02,7]undeca-2(7),3,5-triene (1S,8R)-5-(2,6-difluorophenyl)-11,11-dimethyl-1-[6-[1-(methylsulfonylmethyl)-1,2,4-triazol-3-yl]-2-pyridyl]-3,4-diazatricyclo[6.2.1.02,7]undeca-2(7),3,5-triene;

3-[[1-[4-[(1S,8R)-5-(2,6-difluorophenyl)-11,11-dimethyl-;3,4-diazatricyclo[6.2.1.02,7]undeca-2(7),3,5-trien-1-yl]pyrimidin-2-yl]-1,2,4-triazol-3-yl]methyl]thietane 1,1-dioxide;

3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]thietane 1,1-dioxide;

(1S,8R)-5-(2,6-difluorophenyl)-1-[2-[3-(2-ethylsulfonylethyl)-1,2,4-triazol-1-yl]pyrimidin-4-yl]-11,11-dimethyl-3,4-diazatricyclo[6.2.1.02,7]undeca-2(7),3,5-triene;

(1S,8R)-5-(2,6-difluorophenyl)-1-[2-[3-(2-isopropylsulfonylethyl)-1,2,4-triazol-1-yl]pyrimidin-4-yl]-11,11-dimethyl-3,4-diazatricyclo[6.2.1.02,7]undeca-2(7),3,5-triene;

(1S,8R)-1-[2-[3-(2-cyclopropylsulfonylethyl)-1,2,4-triazol-1-yl]pyrimidin-4-yl]difluorophenyl)-11,11-dimethyl-3,4-diazatricyclo[6.2.1.02,7]undeca-2(7),3,5-triene;

(1S,8R)-5-(2,6-difluorophenyl)-11,11-dimethyl-1-[2-(3-methylsulfinyl-1,2,4-triazol-1-yl)-1-oxido-pyrimidin-1-ium-4-yl]-3,4-diazatricyclo[6.2.1.02,7]undeca-2(7),3,5-triene;

(1S,8R)-5-(2,6-difluorophenyl)-11,11-dimethyl-1-[2-(3-methylsulfinyl-1,2,4-triazol-1-yl)pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-(3-methylsulfonyl-1,2,4-triazol-1-yl)pyrimidin-4-yl]-3,4-diazatricyclo[6.2.1.02,7]undeca-2(7),3,5-triene;

(2R)-3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-1-yl]propane-1,2-diol;

(1S,8R)-5-(2,6-difluorophenyl)-11,11-dimethyl-1-[2-[3-[(1R)-1-methyl-2-methylsulfonyl-ethyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-[(1S)-1-methyl-2-methylsulfonyl-ethyl]-1,2,4-triazol-1-yl]pyrimidin-4-yl]-3,4-diazatricyclo[6.2.1.02,7]undeca-2(7),3,5-triene;

(1R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol;

(1S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,3-diol;

(5R,8R)-3-(2,6-difluorophenyl)-9,9-dimethyl-8-(4-(3-(2-(methylsulfonyl)ethyl)-1H-1,2,4-triazol-1-yl]pyrimidin-2-yl)-5,6,7,8-tetrahydro-5,8-methanocinnoline;

(5R,8S)-3-(2,6-difluorophenyl)-9,9-dimethyl-8-(6-(3-vinyl-1H-1,2,4-triazol-1-yl]pyridin-2-yl)-5,6,7,8-tetrahydro-5,8-methanocinnoline;

imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;

imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;

(1S,8R)-5-(2,6-difluorophenyl)-11,11-dimethyl-1-[2-[3-(2-methylsulfonylethyl)-1,2,4-triazol-1-yl]-4-pyridyl]-3,4-diazatricyclo[6.2.1.02,7]undeca-2(7),3,5-triene;

(1S,8R)-5-(2,6-difluorophenyl)-11,11-dimethyl-1-[2-[3-(3-methylsulfonylpropyl)-1,2,4-triazol-1-yl]pyrimidin-4-yl]-3,4-diazatricyclo[6.2.1.02,7]undeca-2(7),3,5-triene;

(1S,8R)-6-chloro-5-(2,6-difluorophenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene;

(5R,8S)-3-(4-chloro-2,6-difluorophenyl)-9,9-dimethyl-8-(2-(3-(2-(methylsulfonyl)ethyl)-1H-1,2,4-triazol-1-yl]pyrimidin-4-yl)-5,6,7,8-tetrahydro-5,8-methanocinnoline;

(1S,8R)-6-chloro-5-(2,6-difluorophenyl)-11,11-dimethyl-1-[6-[3-(2-methylsulfonylethyl)-1,2,4-triazol-1-yl]-2-pyridyl]-3,4-diazatricyclo[6.2.1.02,7]undeca-2(7),3,5-triene;

(1S,8R)-5-(2,6-difluorophenyl)-11,11-dimethyl-1-[2-[3-[1-(methylsulfonylmethyl)cyclopropyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-[2-(3-methyloxetan-3-yl)ethyl]-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[4-(2-methylsulfonylethyl)piperazin-1-yl]pyrimidin-4-yl]-3,4-diazatricyclo[6.2.1.02,7]undeca-2(7),3,5-triene;

4-((5R,8S)-9,9-dimethyl-8-(2-(3-(2-(methylsulfonyl) ethyl)-1H-1,2,4-triazol-1-yl]pyrimidin-4-yl)-5,6,7,8-tetrahydro-5,8-methanocinnolin-3-yl)-3,5-difluorophenol;

1-(2-methylsulfonylethyl)-4-[4-[(1S,8R)-5-(2,6-difluorophenyl)-11,11-dimethyl-3,4-diazatricyclo [6.2.1.02,7]undeca-2(7),3,5-trien-1-yl]pyrimidin-2-yl]pyridin-2-one;

(5R,8S)-3-(2,6-difluorophenyl)-9,9-dimethyl-8-(4-(5-methyl-4H-1,2,4-triazol-3-yl)-6-(methylsulfonyl) pyridin-2-yl)-5,6,7,8-tetrahydro-5,8-methanocinnoline;

(5R,8S)-8-(6-(3-(difluoromethyl)-1H-1,2,4-triazol-1-yl]pyridin-2-yl)-3-(2,6-difluorophenyl)-9,9-dimethyl-5,6,7,8-tetrahydro-5,8-methanocinnoline;

(1S,8R)-5-(2,6-difluorophenyl)-11,11-dimethyl-1-[4-methyl-6-[3-(2-methylsulfonylethyl)-1,2,4-triazol-1-yl]-2-pyridyl]-3,4-diazatricyclo[6.2.1.02,7]undeca-2(7),3,5-triene;

3-[[1-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl] methyl]thietane 1,1-dioxide;

3-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methyl]thietane 1,1-dioxide;

3-[4-[4-methyl-6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide; and (5R,8S)-8-(2-(3-(difluoromethyl)-1H-1,2,4-triazol-1-yl]pyrimidin-4-yl)-3-(2,6-difluorophenyl)-9,9-dimethyl-5,6,7,8-tetrahydro-5,8-methanocinnoline;

(5R,8S)-8-(2-(3-(difluoromethyl)-1H-1,2,4-triazol-1-yl]pyrimidin-4-yl)-3-(2,6-difluorophenyl)-9,9-dimethyl-5,6,7,8-tetrahydro-5,8-methanocinnoline;

(1S,8R)-5-(2,6-difluorophenyl)-1-[6-methoxy-2-[3-(2-methylsulfonylethyl)-1,2,4-triazol-1-yl]pyrimidin-4-yl]-11,11-dimethyl-3,4-diazatricyclo[6.2.1.02,7]undeca-2(7),3,5-triene;

3-[[1-[4-methyl-6-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl] methyl]thietane 1,1-dioxide;

1-(4-((5R,8S)-3-(2,6-difluorophenyl)-9,9-dimethyl-6,7-dihydro-5,8-methanocinnolin-8(5H)-yl]pyrimidin-2-yl)-N-methyl-1H-1,2,4-triazole-3-sulfonamide;

N,N-dimethyl-1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazole-3-sulfonamide;

(5R,8S)-3-(4-chloro-2,6-difluorophenyl)-9,9-dimethyl-8-(2-(3-(2-(methylsulfonyl)ethyl)-1H-1,2,4-triazol-1-yl]pyrimidin-4-yl)-5,6,7,8-tetrahydro-5,8-methanocinnoline;

(1R,8R)-5-(3-chloro-2,6-difluoro-phenyl)-11,11-dimethyl-1-[2-[3-(2-methylsulfonylethyl)-1,2,4-triazol-1-yl]pyrimidin-4-yl]-3,4-diazatricyclo[6.2.1.02,7] undeca-2(7),3,5-triene;

5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidine-2-carboxylic acid;

(1R,8R)-5-(2,6-difluorophenyl)-11,11-dimethyl-1-[5-methyl-6-[3-(2-methylsulfonylethyl)-1,2,4-triazol-1-yl]-2-pyridyl]-3,4-diazatricyclo[6.2.1.02,7]undeca-2(7),3,5-triene;

(1R,8R)-5-(2,6-difluoro-3-methyl-phenyl)-11,11-dimethyl-1-[6-[3-(2-methylsulfonylethyl)-1,2,4-triazol-1-yl]-2-pyridyl]-3,4-diazatricyclo[6.2.1.02,7]undeca-2(7),3,5-triene;

2-[1-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]-1,2,4-triazol-3-yl]acetonitrile;

2,2-dimethyl-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propanenitrile;

2-[3-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrazol-1-yl]acetamide;

imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;

imino-methyl-oxo-[2-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]ethyl]-lambda6-sulfane;

(1S,8R)-5-(2,6-difluorophenyl)-1-[2-[4-(2-methoxyethyl)-3-(2-methylsulfonylethyl]pyrazol-1-yl]pyrimidin-4-yl]-11,11-dimethyl-3,4-diazatricyclo [6.2.1.02,7]undeca-2(7),3,5-triene;

(1S,8R)-5-(2,6-difluorophenyl)-1-[2-[3-(2-methoxyethyl)-4-(2-methylsulfonylethyl]pyrazol-1-yl]pyrimidin-4-yl]-11,11-dimethyl-3,4-diazatricyclo [6.2.1.02,7]undeca-2(7),3,5-triene;

(1S,8R)-5-(2,6-difluorophenyl)-11,11-dimethyl-1-[2-[3-(oxetan-3-ylsulfonylmethyl)-1,2,4-triazol-1-yl] pyrimidin-4-yl]-3,4-diazatricyclo[6.2.1.02,7]undeca-2(7),3,5-triene;

(1S,8R)-5-(2,6-difluorophenyl)-11,11-dimethyl-1-[2-[3-(2-methylsulfonylethyl)pyrazol-1-yl]pyrimidin-4-yl]-3,4-diazatricyclo[6.2.1.02,7]undeca-2(7),3,5-triene;

imino-methyl-oxo-[[4-[4-[(1S,8R)-5-(2,6-difluorophenyl)-11,11-dimethyl-3,4-diazatricyclo[6.2.1.02,7] undeca-2(7),3,5-trien-1-yl]pyrimidin-2-yl]pyrazol-1-yl]methyl]-lambda6-sulfane;

imino-methyl-oxo-[[4-[4-[(1S,8R)-5-(2,6-difluorophenyl)-11,11-dimethyl-3,4-diazatricyclo[6.2.1.02,7] undeca-2(7),3,5-trien-1-yl]pyrimidin-2-yl]pyrazol-1-yl]methyl]-lambda6-sulfane;

N-[2-[[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonyl]ethyl]acetamide;

(1S,8R)-5-(2,6-difluorophenyl)-11,11-dimethyl-1-[2-[5-(2-methylsulfonylethyl)-1H-1,2,4-triazol-3-yl] pyrimidin-4-yl]-3,4-diazatricyclo[6.2.1.02,7]undeca-2(7),3,5-triene;

(5R)-5-[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one;

(5S)-5-[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one;

bromo-2-[3-(2-methylsulfonylethyl)-1,2,4-triazol-1-yl]pyrimidin-4-yl]-5-(2,6-difluorophenyl)-11,11-dimethyl-3,4-diazatricycloazatricyclo[6.2.1.02,7]undeca-2(7),3,5-triene;

(1S,8R)-5-(2,6-difluorophenyl)-11,11-dimethyl-1-[5-methyl-2-[3-(2-methylsulfonylethyl)-1,2,4-triazol-1-yl]pyrimidin-4-yl]-3,4-diazatricyclo[6.2.1.02,7]undeca-2(7),3,5-triene;

(1S,8R)-5-(2,6-difluorophenyl)-1-[5-methoxy-2-[3-(2-methylsulfonylethyl)-1,2,4-triazol-1-yl]pyrimidin-4-yl]-11,11-dimethyl-3,4-diazatricyclo[6.2.1.02,7]undeca-2(7),3,5-triene;

4-[1-[4-[(1S,8R)-5-(2,6-difluorophenyl)-11,11-dimethyl-3,4-diazatricyclo[6.2.1.02,7]undeca-2(7),3,5-trien-1-yl)pyrimidin-2-yl]-1,2,4-triazol-3-yl]butanenitrile;

3-[6-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyridazin-3-yl]oxetan-3-ol;

N-[6-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyridazin-3-yl]methanesulfonamide;

3-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]oxetan-3-ol;

3-[5-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyrimidin-2-yl]oxetan-3-ol;

1-(2-methylsulfonylethyl)-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]piperazin-2-one;

2-amino-5-(4-((5R,8S)-3-(2,6-difluorophenyl)-9,9-dimethyl-6,7-dihydro-5,8-methanocinnolin-8(5H)-yl]pyrimidin-2-yl]nicotinonitrile;

N-(3-cyano-5-(4-((5R,8S)-3-(2,6-difluorophenyl)-9,9-dimethyl-6,7-dihydro-5,8-methanocinnolin-8(5H)-yl]pyrimidin-2-yl]pyridin-2-yl]methanesulfonamide;

6'-amino-6-((5R,8S)-3-(2,6-difluorophenyl)-9,9-dimethyl-6,7-dihydro-5,8-methanocinnolin-8(5H)-yl)-[2,3'-bipyridine]-5'-carbonitrile;

N-(5'-cyano-6-((5R,8S)-3-(2,6-difluorophenyl)-9,9-dimethyl-6,7-dihydro-5,8-methanocinnolin-8(5H)-yl)-[2,3'-bipyridin]-6'-yl)methanesulfonamide;

1-(2-methylsulfonylethyl)-4-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]pyridin-2-one;

1-(4-((5R,8S)-3-(2,6-difluorophenyl)-9,9-dimethyl-6,7-dihydro-5,8-methanocinnolin-8(5H)-yl]pyrimidin-2-yl)-1H-1,2,4-triazole-3-sulfonamide;

1-(4-((5R,8S)-3-(2,6-difluorophenyl)-9,9-dimethyl-6,7-dihydro-5,8-methanocinnolin-8(5H)-yl]pyrimidin-2-yl)-1H-pyrazole-3-sulfonamide;

(5R,8S)-8-(2-(3-(difluoromethyl)-1H-pyrazol-1-yl]pyrimidin-4-yl)-3-(2,6-difluorophenyl)-9,9-dimethyl-5,6,7,8-tetrahydro-5,8-methanocinnoline;

(1R)-2-methyl-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-1-ol;

N-[3-(hydroxymethyl)-5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

(5R,8S)-3-(2,6-difluoro-4-(5-methyl-4H-1,2,4-triazol-3-yl)phenyl)-9,9-dimethyl-8-(6-(methylsulfonyl)pyridin-2-yl)-5,6,7,8-tetrahydro-5,8-methanocinnoline;

2-[3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]but-3-enylsulfonyl]ethanol;

(5R,8S)-3-(2-fluoro-6-methoxyphenyl)-9,9-dimethyl-8-(6-(3-(2-(methylsulfonyl]ethyl)-1H-1,2,4-triazol-1-yl]pyridin-2-yl)-5,6,7,8-tetrahydro-5,8-methanocinnoline;

2-[1,1-dioxo-3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]thiolan-3-yl]acetic acid;

1-methyl-5-[1-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]-1,2,4-triazol-3-yl]methylsulfonylmethyl]pyrrolidin-2-one;

[3-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]oxetan-3-yl]methanol;

1-fluoro-N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

1,1-difluoro-N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

(1R,2S)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol;

(1S,2R)-1-[1-[4-[(1S,8R)-5-(2,6-difluorophenyl)-11,11-dimethyl-3,4-diazatricyclo[6.2.1.02,7]undeca-2(7),3,5-trien-1-yl]pyrimidin-2-yl]-1,2,4-triazol-3-yl]propane-1,2-diol; and (5R,8S)-3-(2-fluoro-6-methoxyphenyl)-9,9-dimethyl-8-(6-(3-(2-(methylsulfonyl]ethyl)-1H-1,2,4-triazol-1-yl]pyridin-2-yl)-5,6,7,8-tetrahydro-5,8-methanocinnoline.

2. The compound of claim 1, selected from:

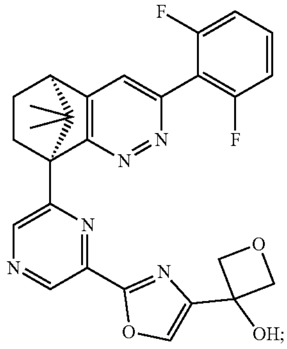
;

-continued
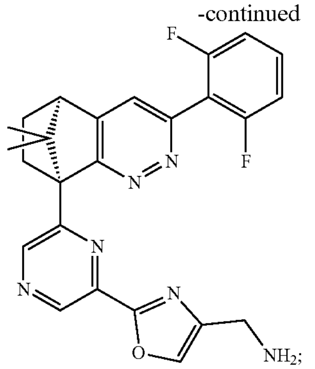
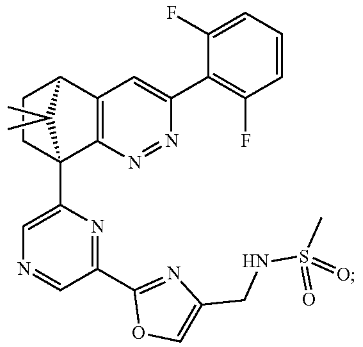
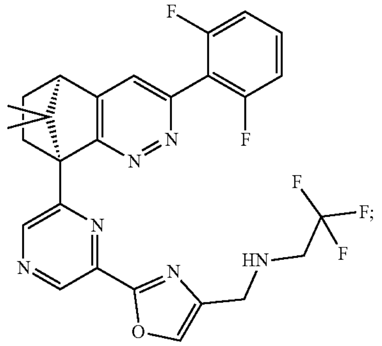
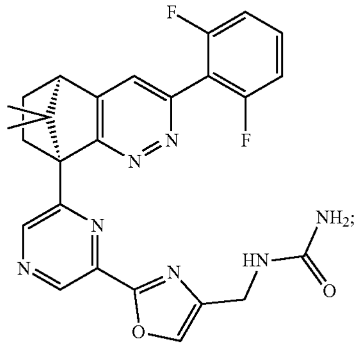
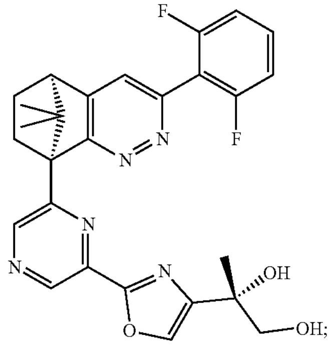
-continued
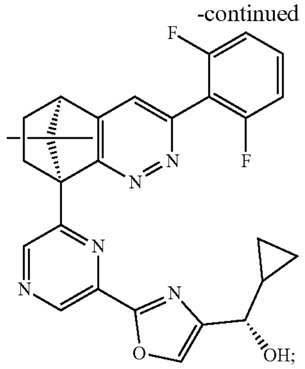
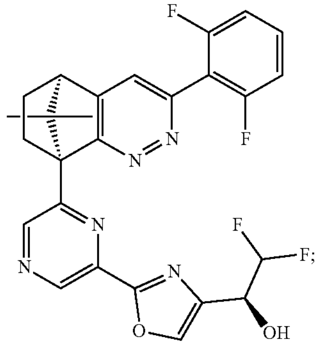
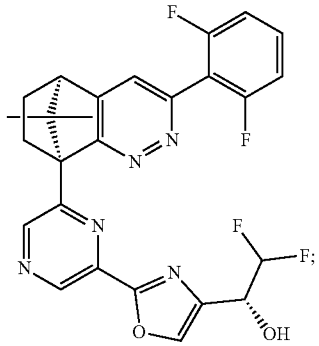
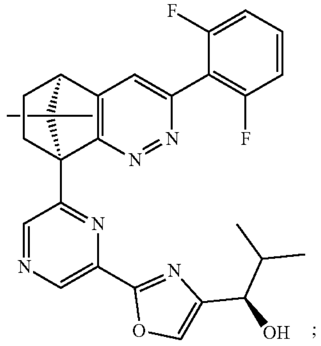
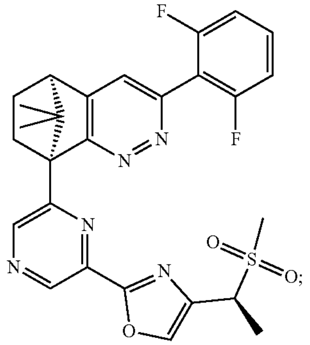

-continued
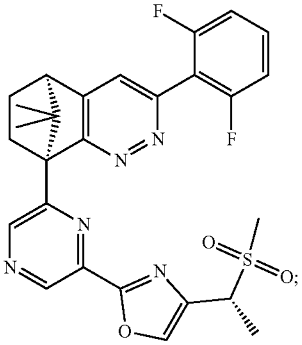
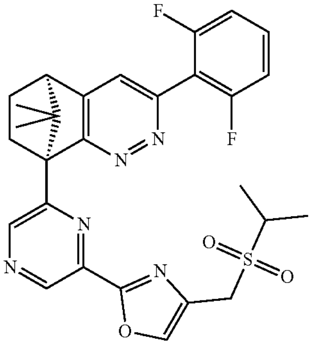
;
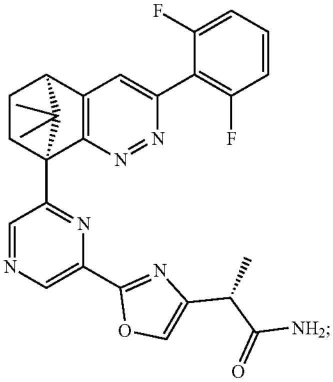
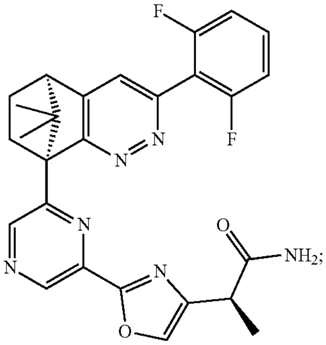
-continued
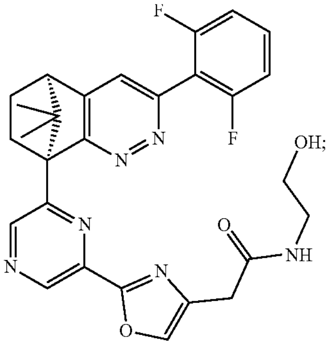
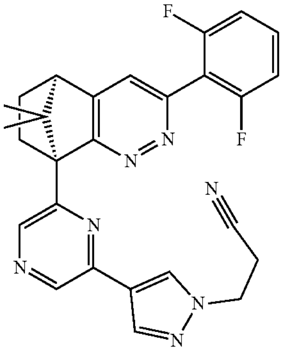
;
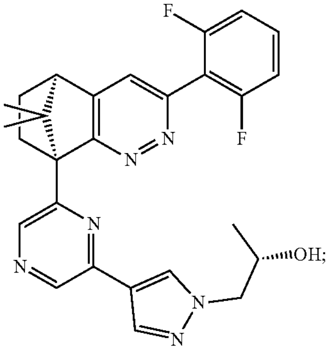
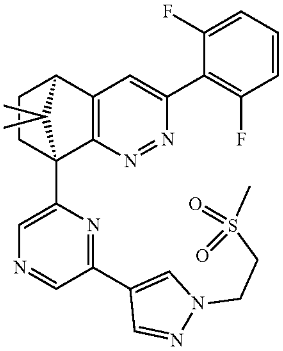
;

-continued
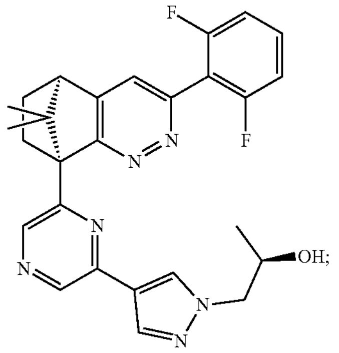
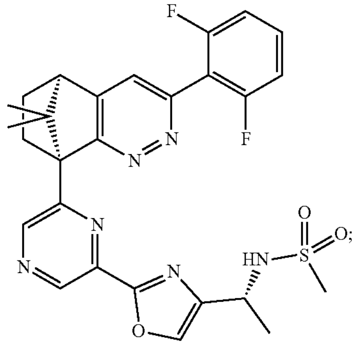
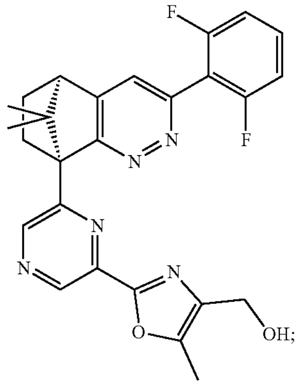
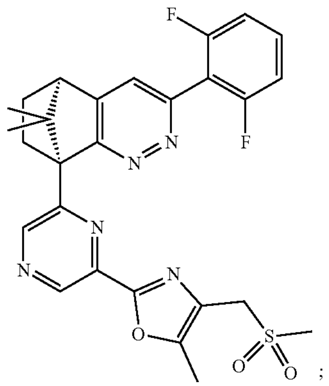
-continued
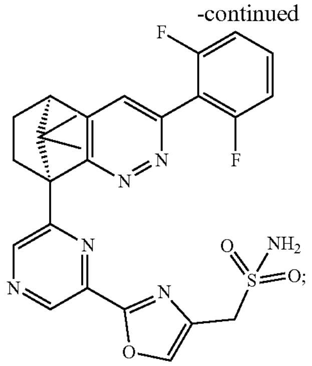
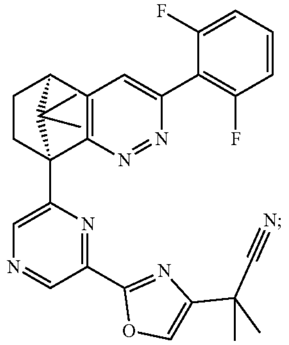
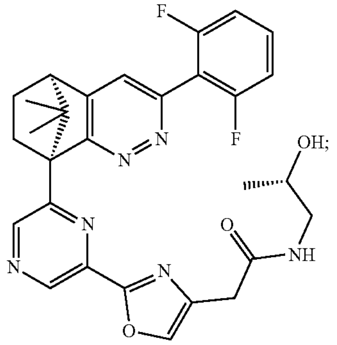
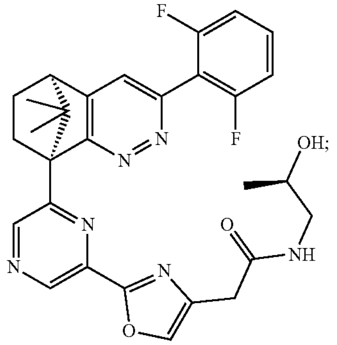
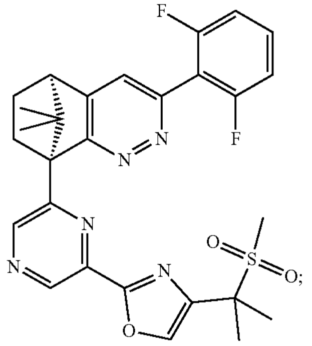

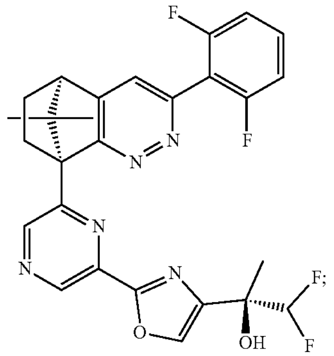
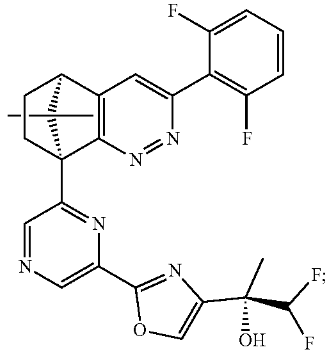
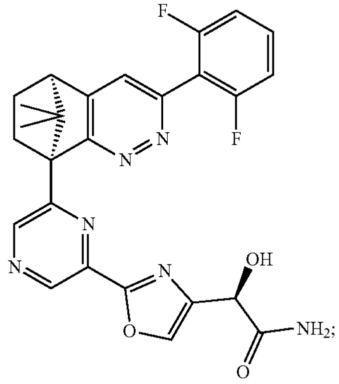
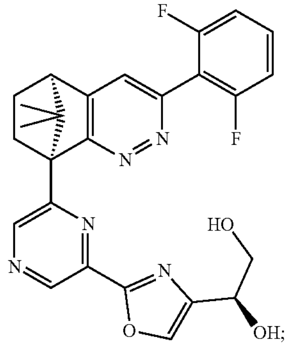
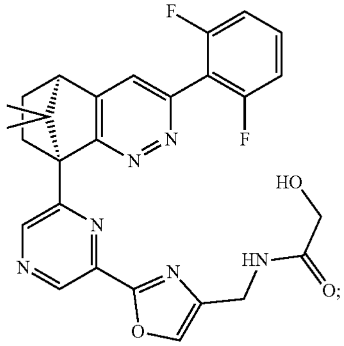
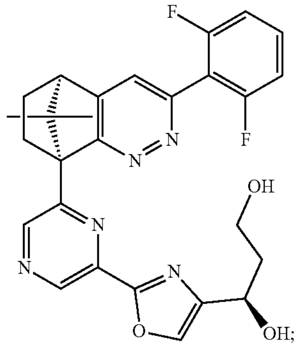
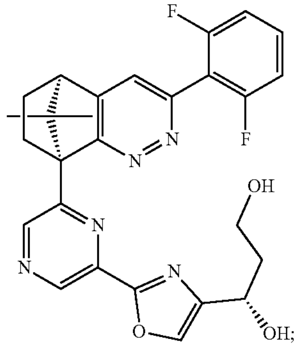
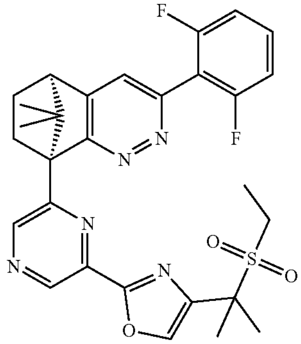
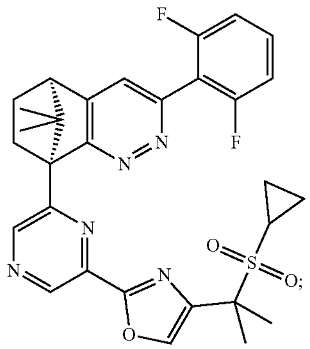

-continued
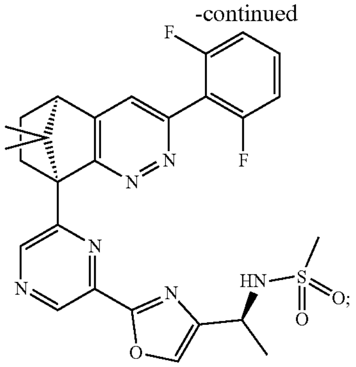
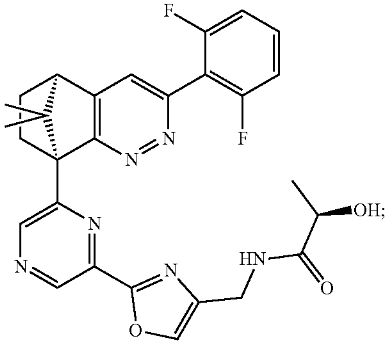
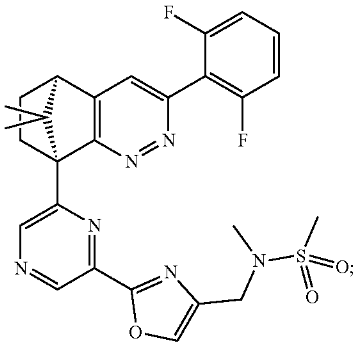
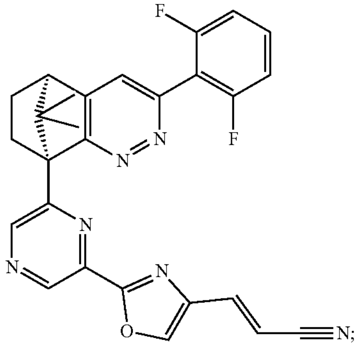
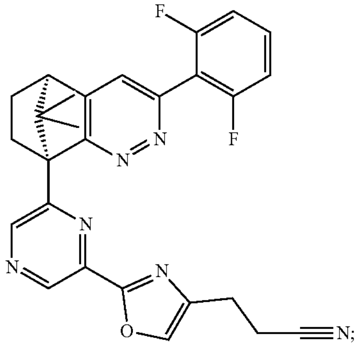
-continued
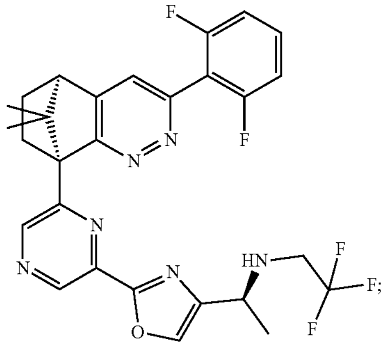
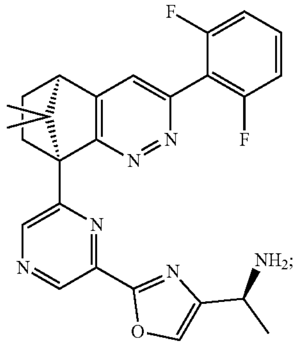
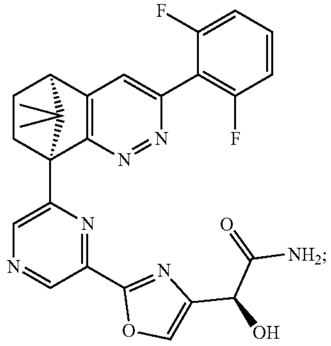
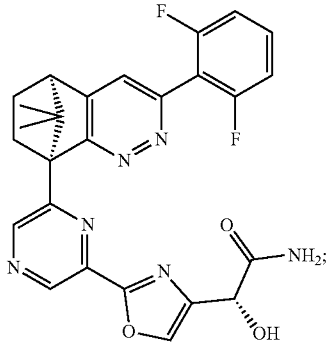
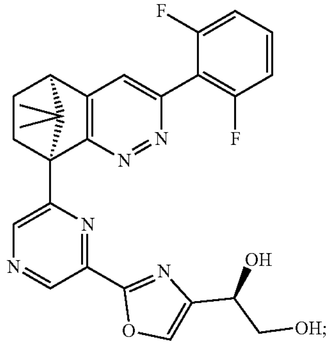

-continued
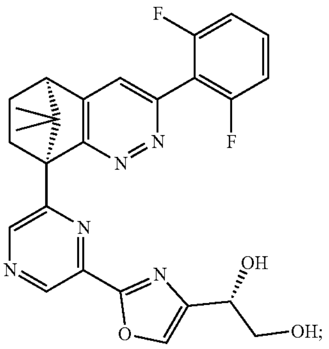
;
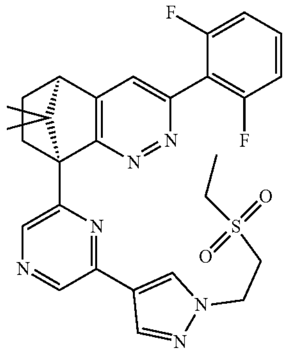
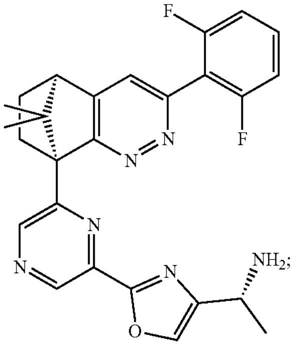
;
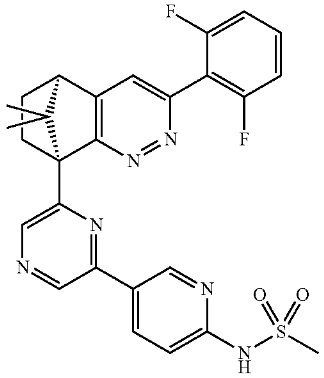
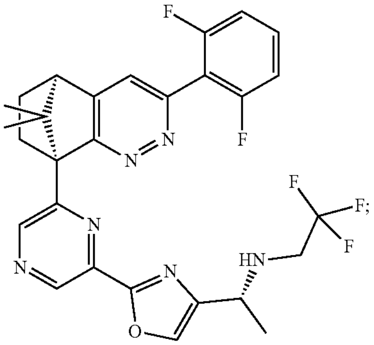
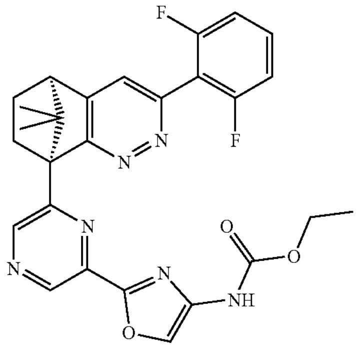
;
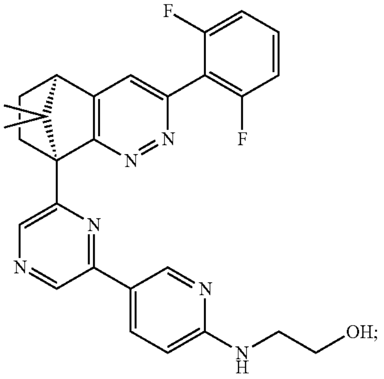
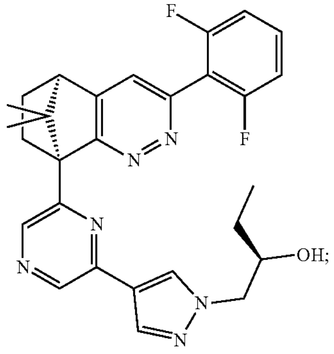

-continued
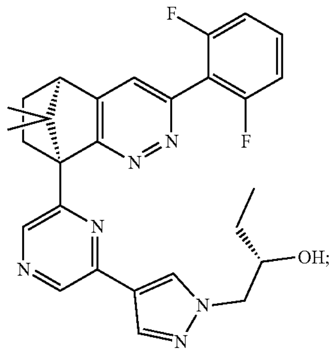
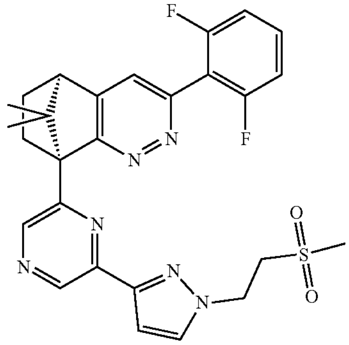
;
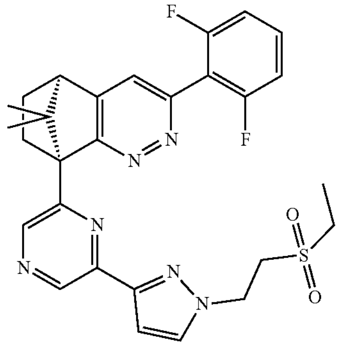
;
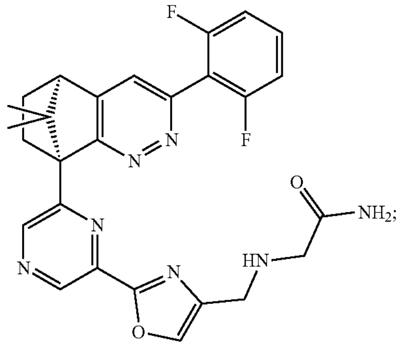
-continued
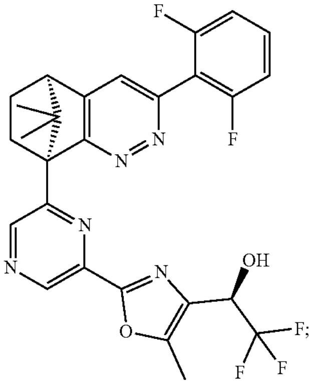
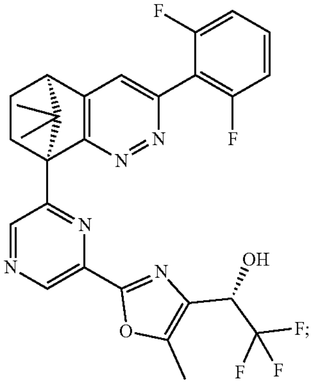
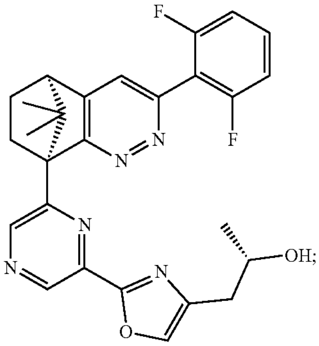
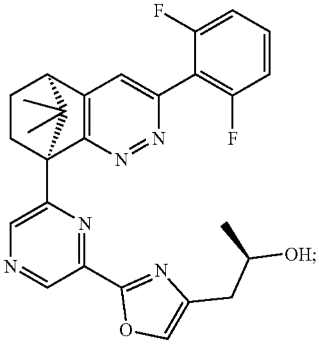

-continued
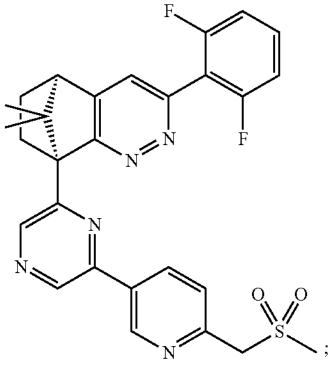
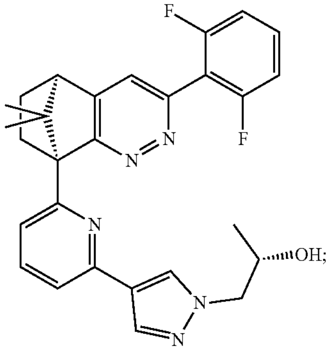
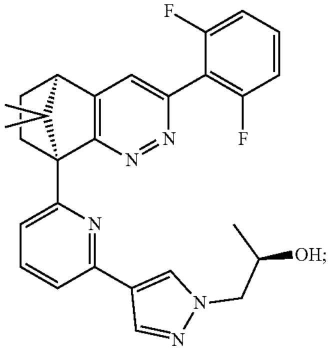
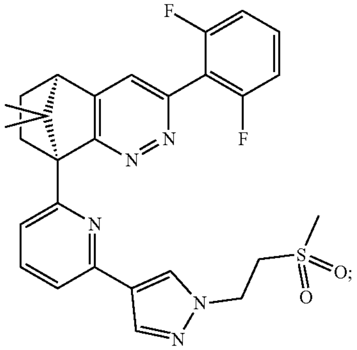
-continued
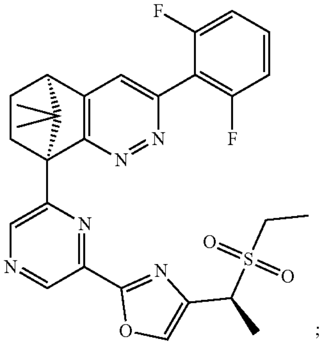
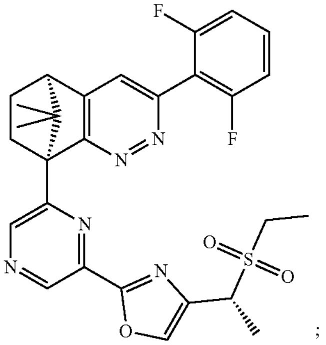
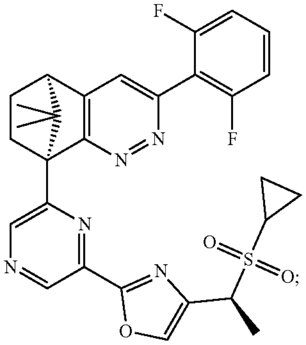
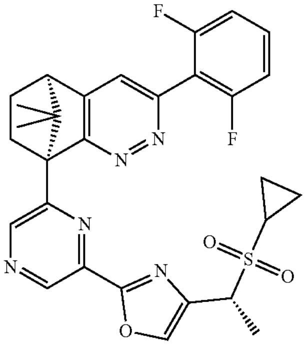
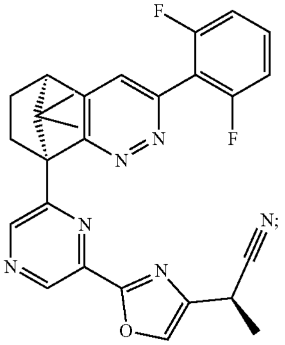

-continued
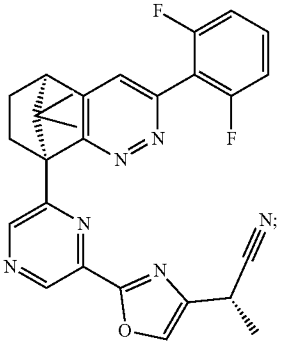
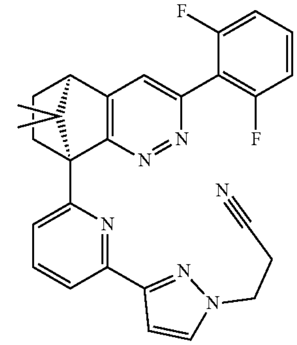
;
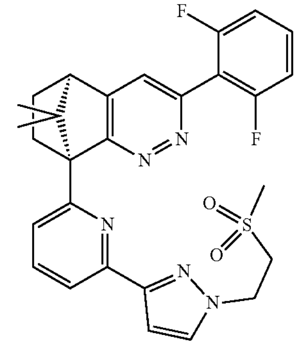
;
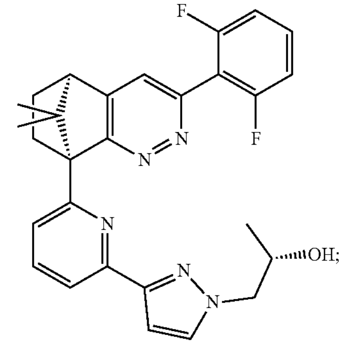
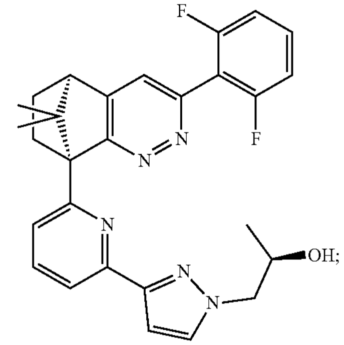
-continued
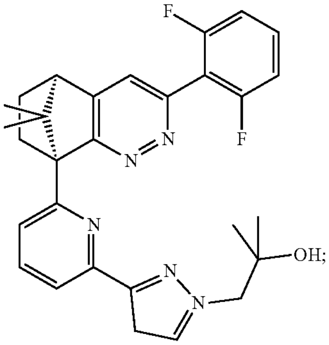
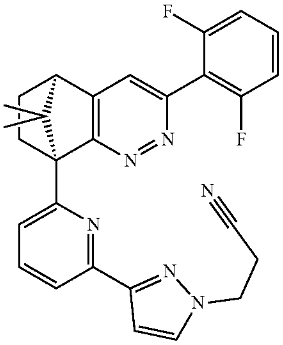
;
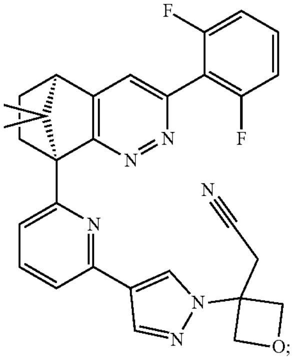
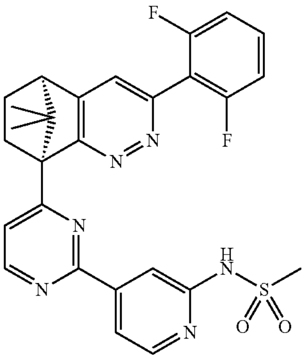
;

-continued
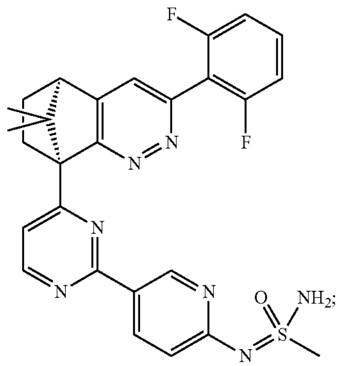
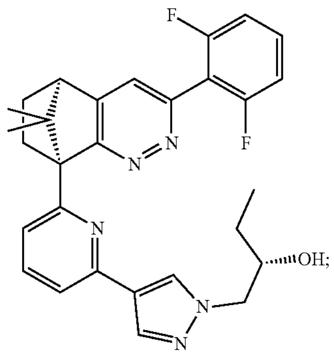
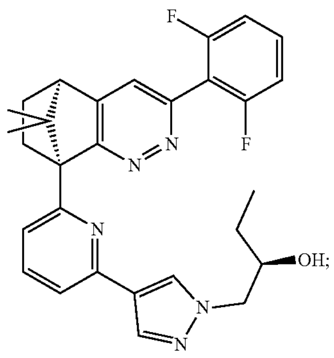
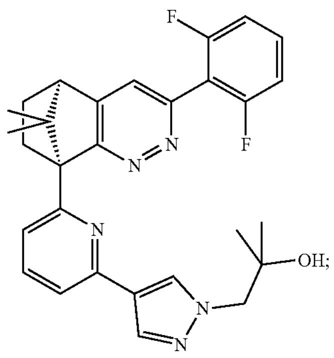
-continued
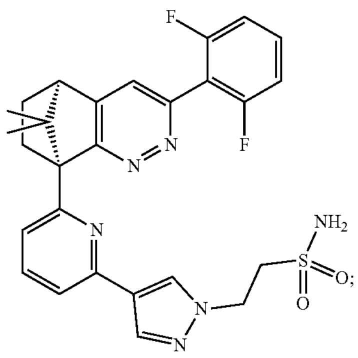
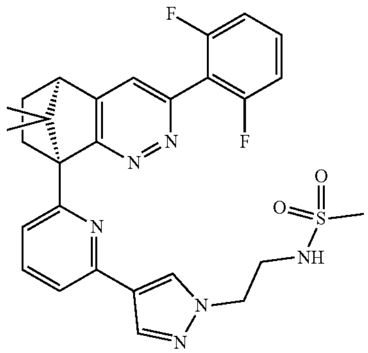
;
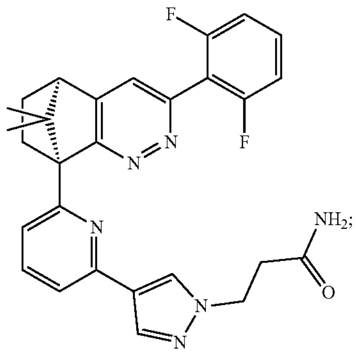
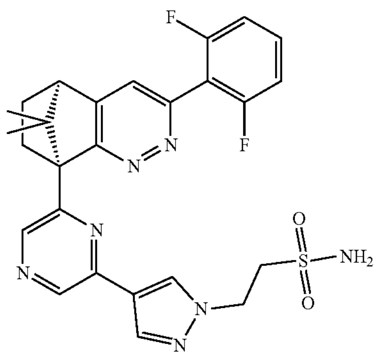

-continued
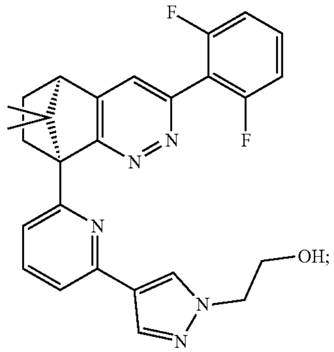
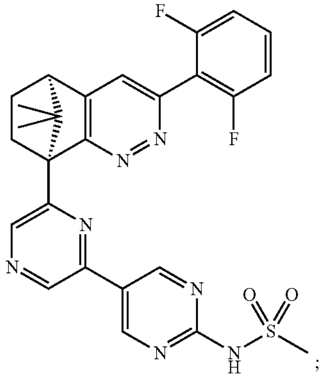
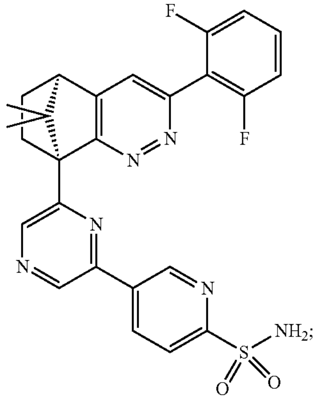
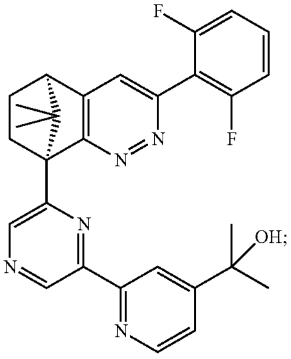
-continued
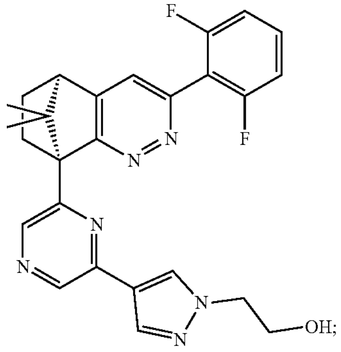
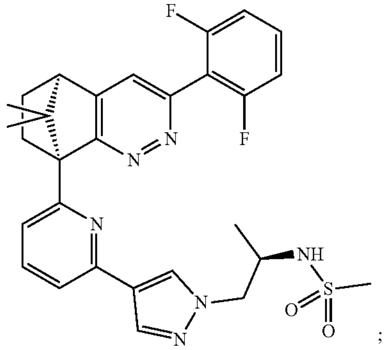
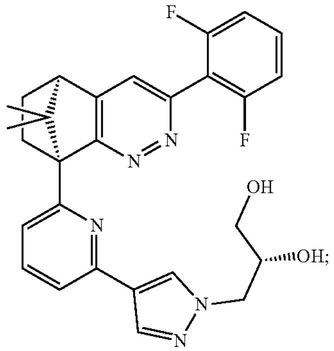
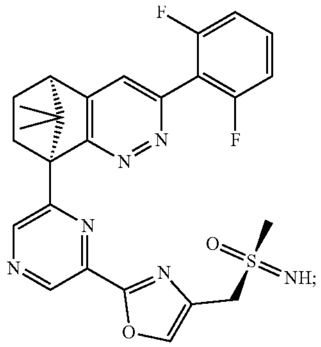

-continued
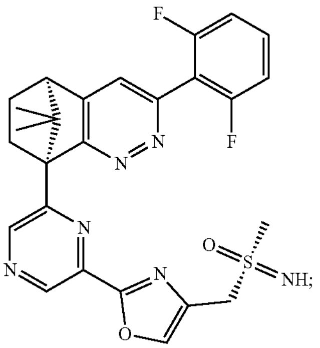
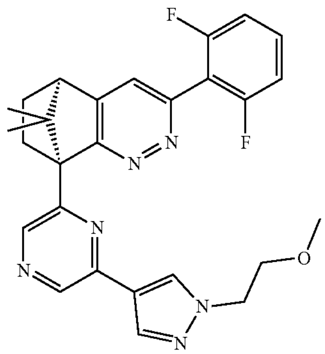
;
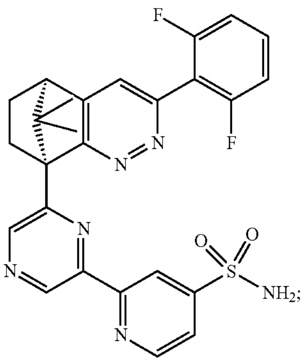
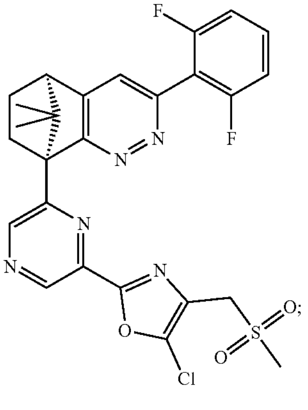
-continued
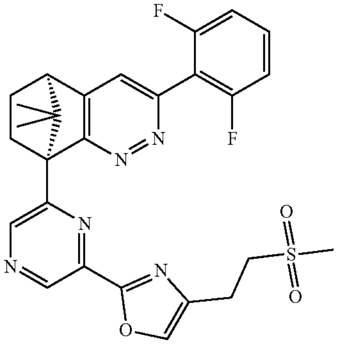
;
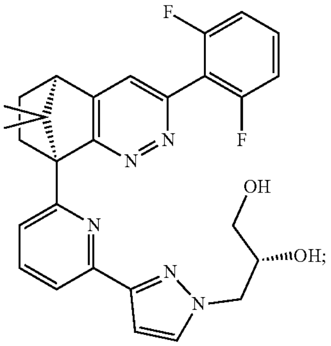
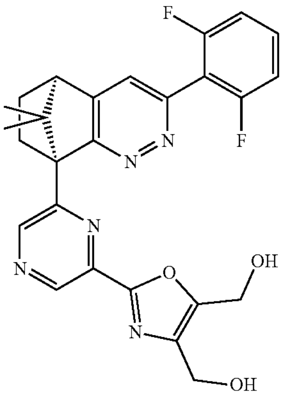
;
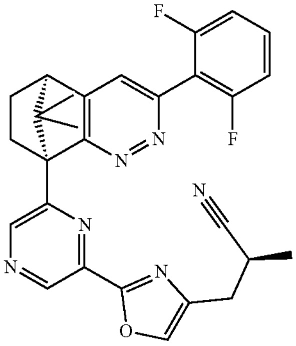
;

-continued
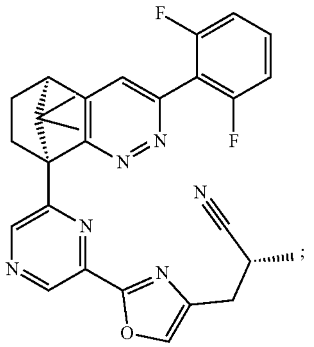
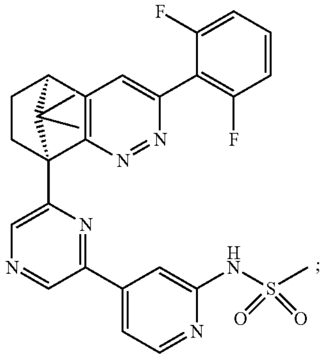
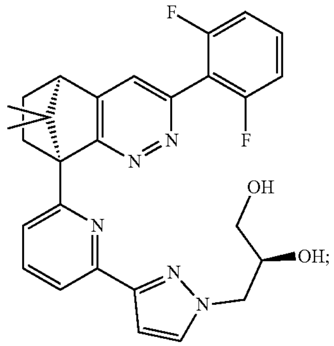
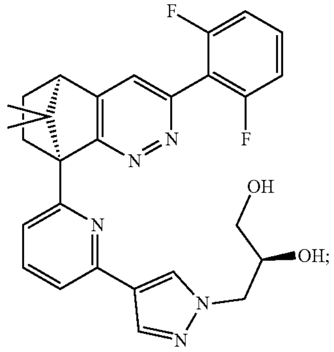
-continued
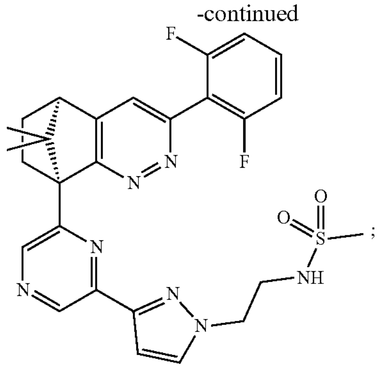
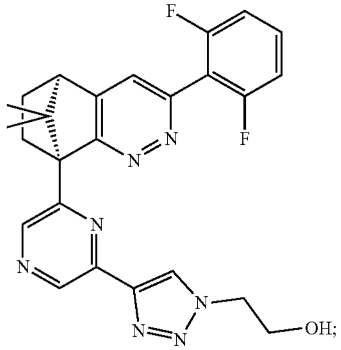
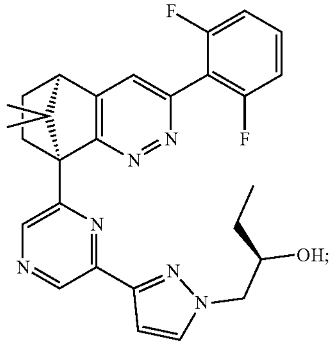
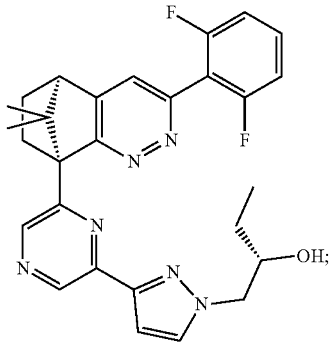
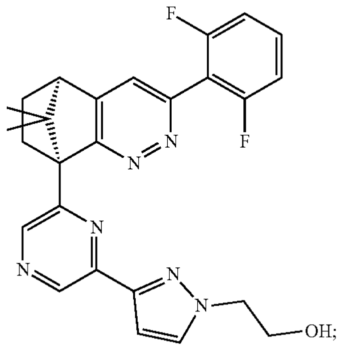

-continued
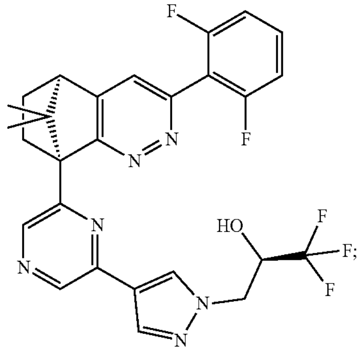
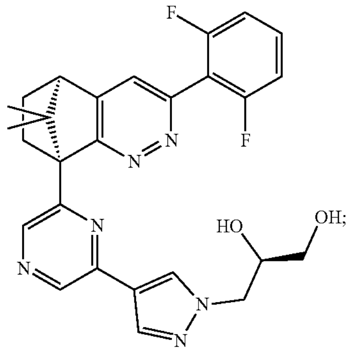
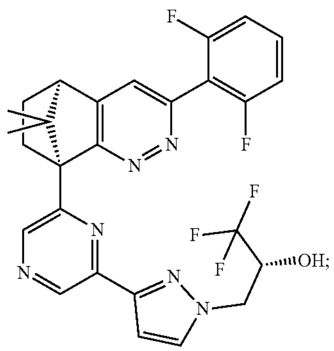
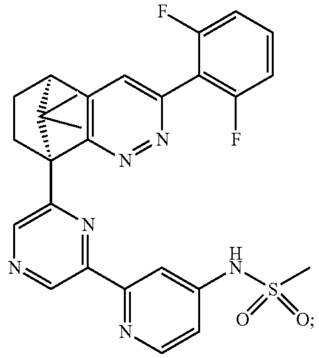
-continued
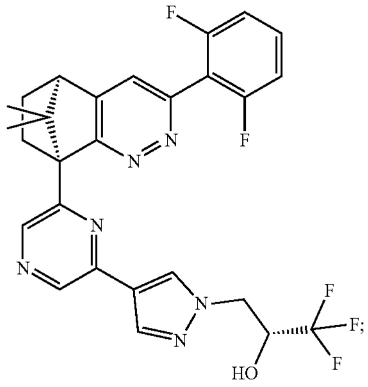
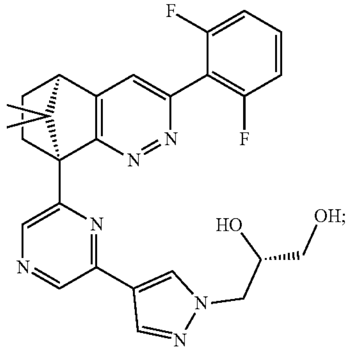
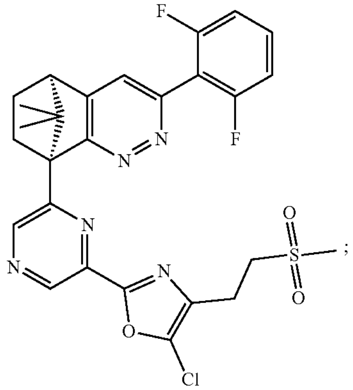
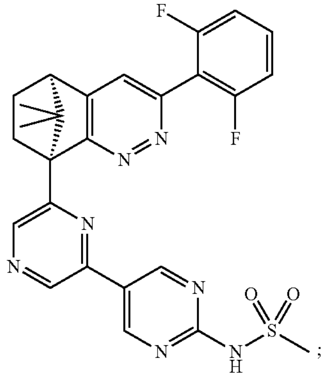

-continued
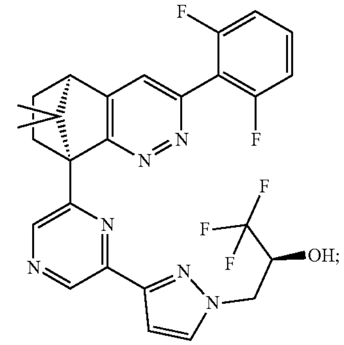
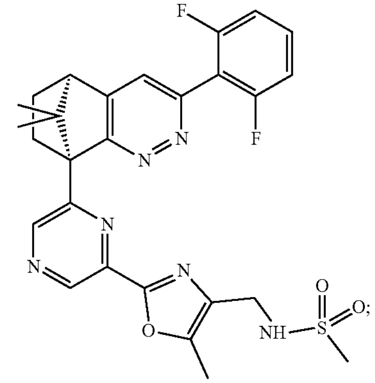
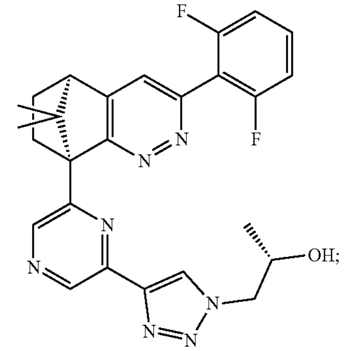
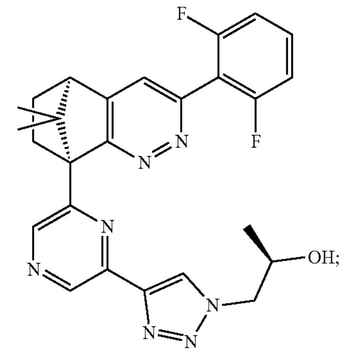
-continued
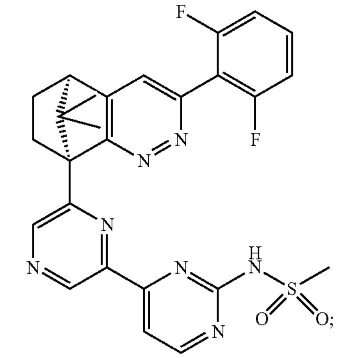
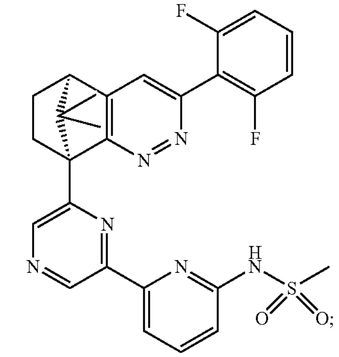
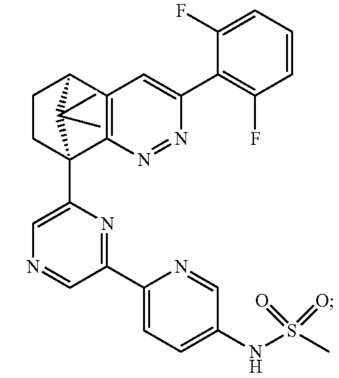
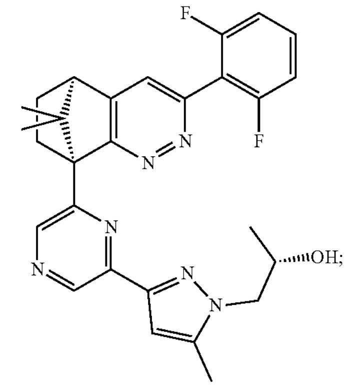

-continued
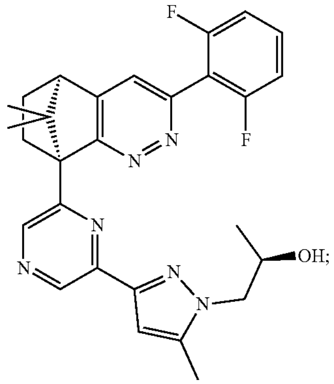
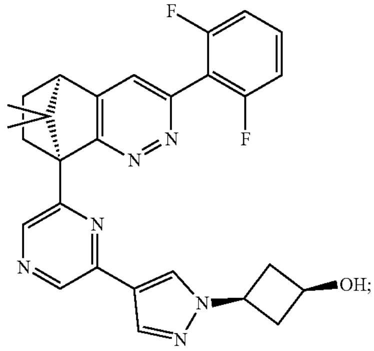
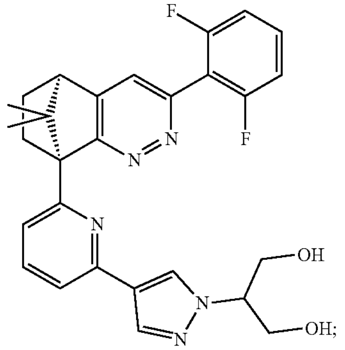
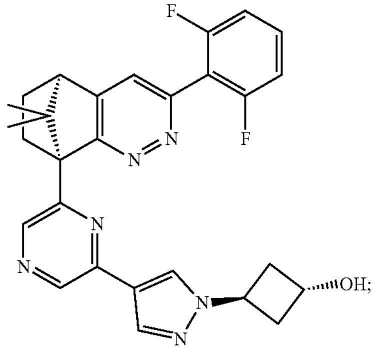
-continued
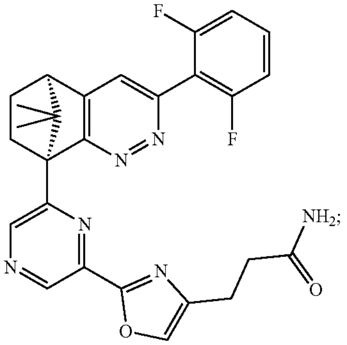
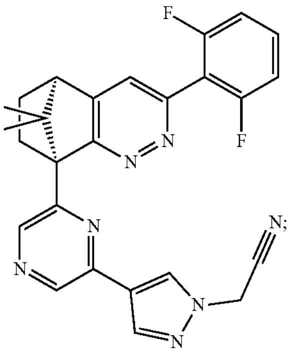
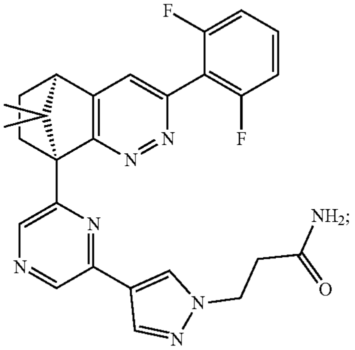
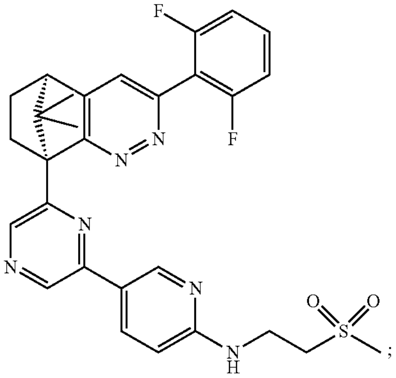

-continued
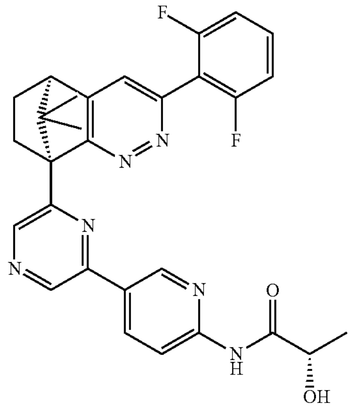
;
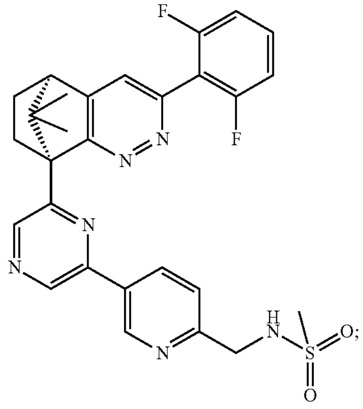
;
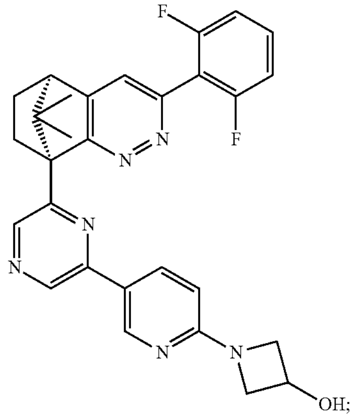
;
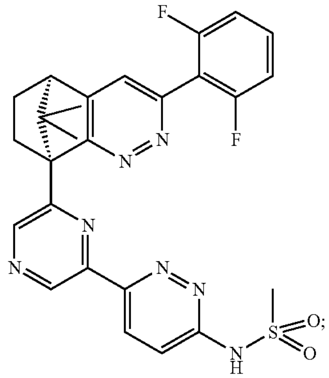
;
-continued
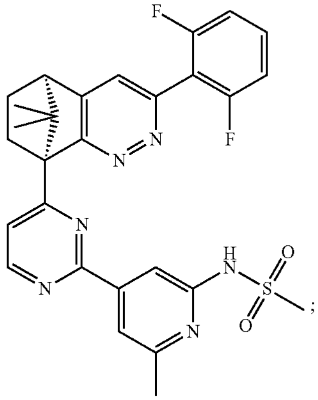
;
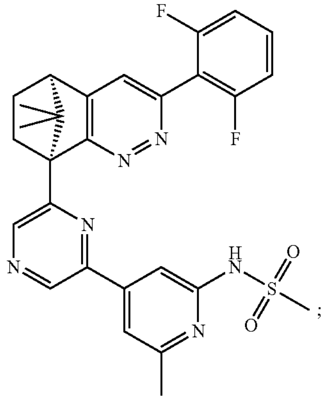
;
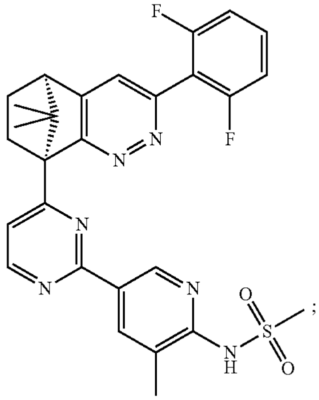
;
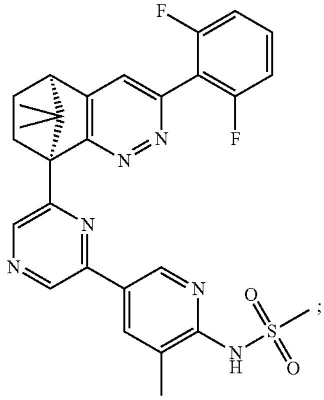
;

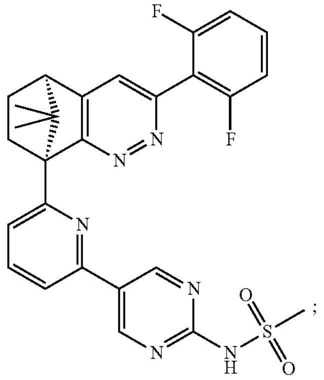
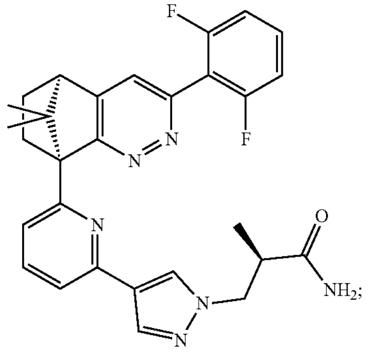
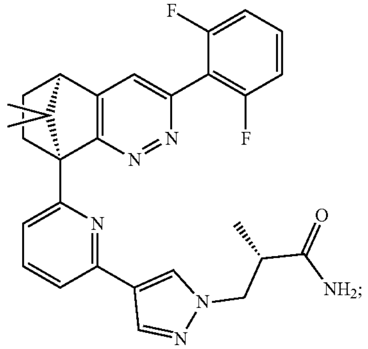
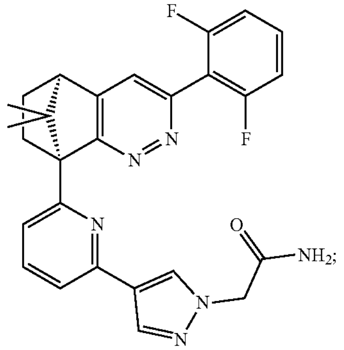
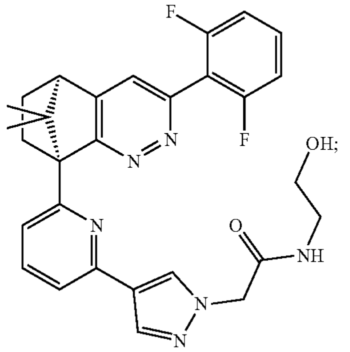
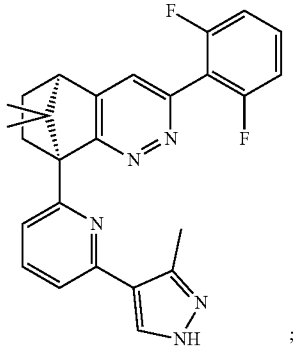
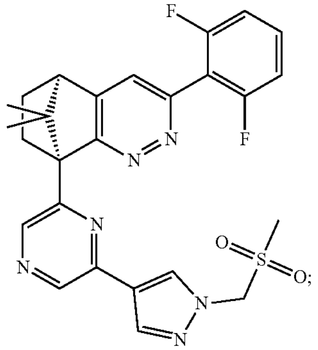
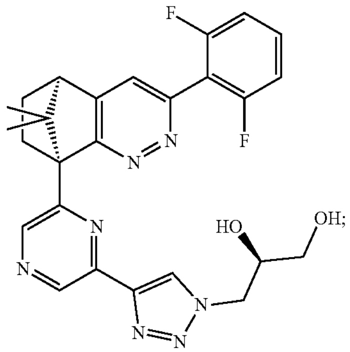

-continued
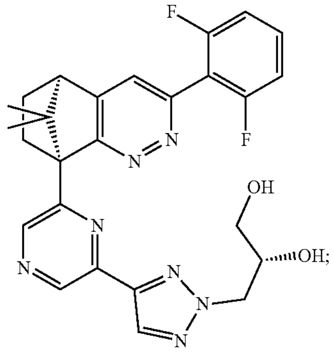
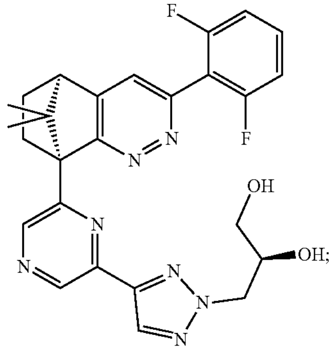
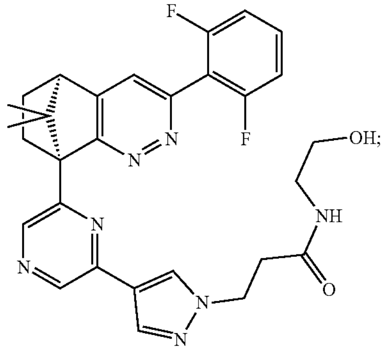
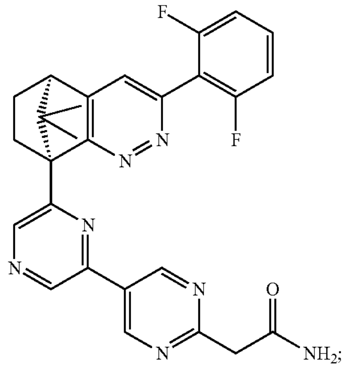
-continued
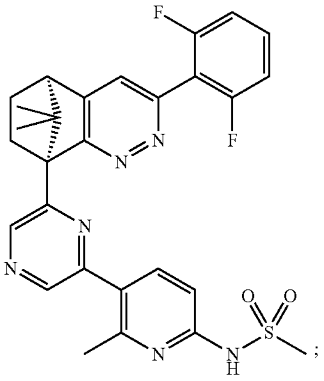
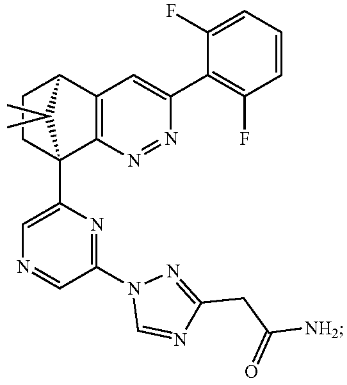
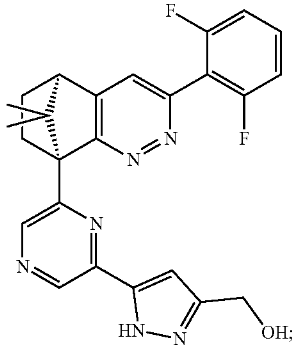
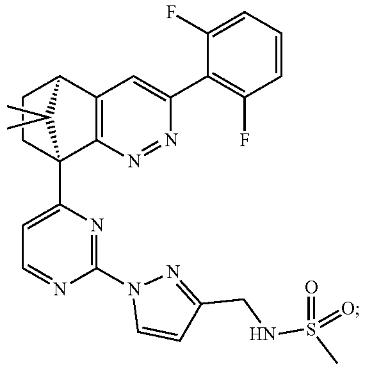

-continued
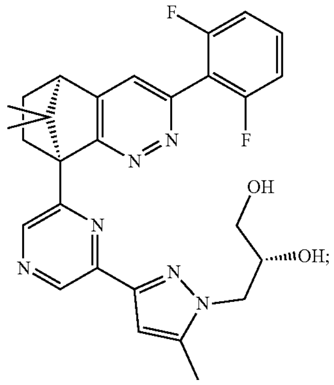
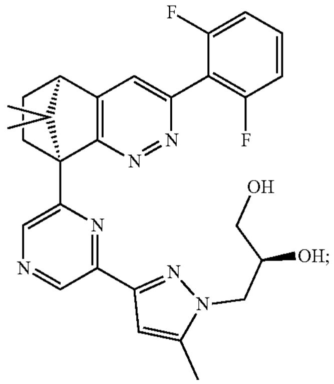
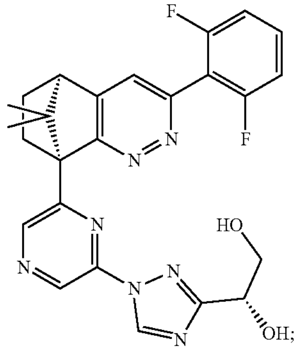
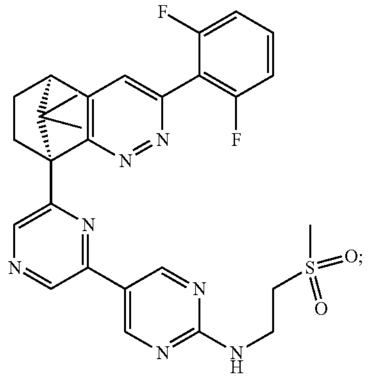
-continued
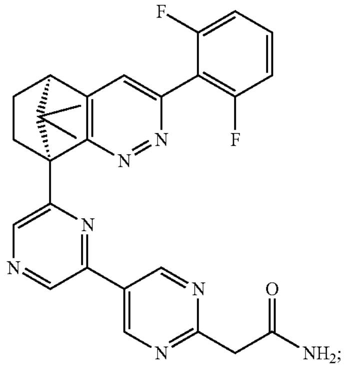
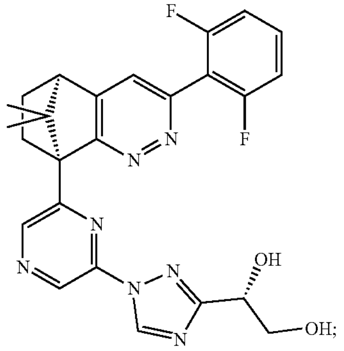
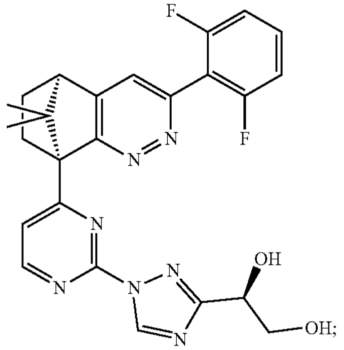
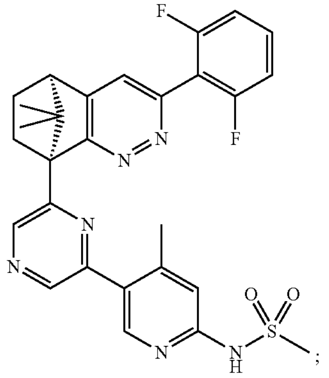

-continued
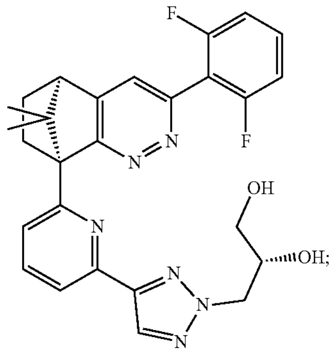
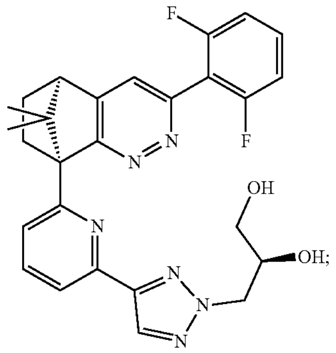
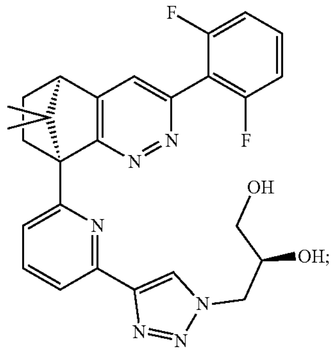
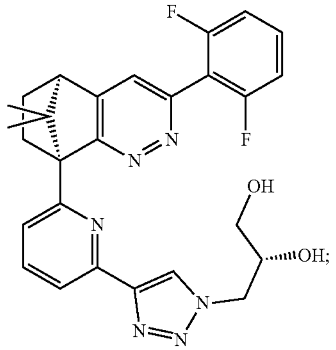
-continued
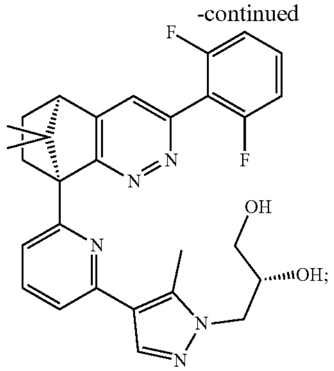
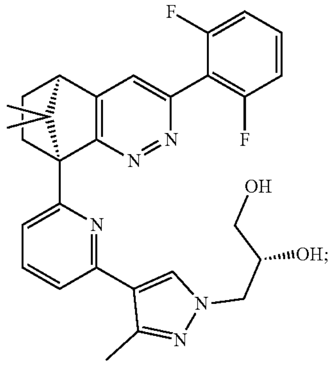
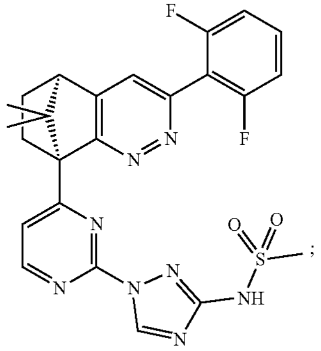
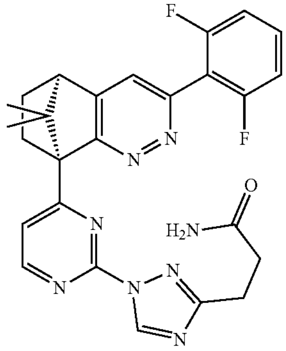
;

-continued
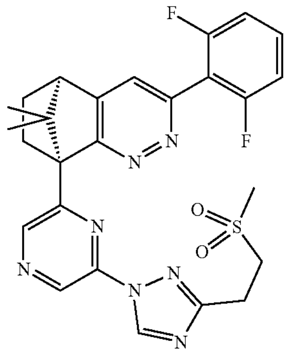
;
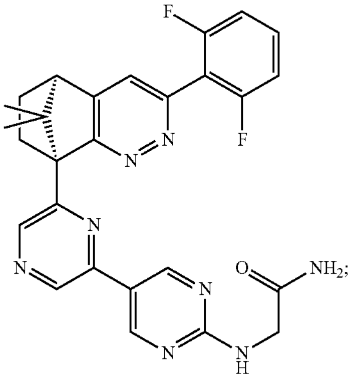
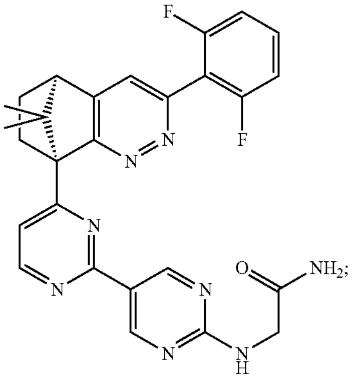
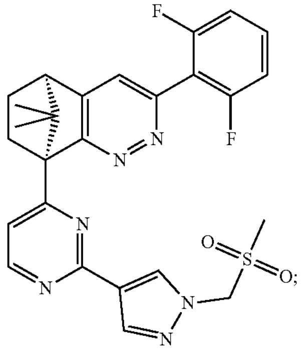
-continued
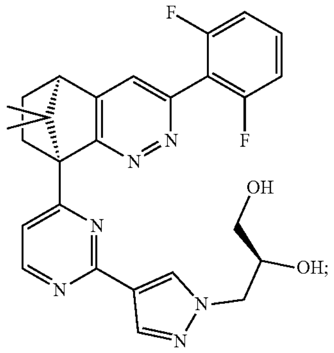
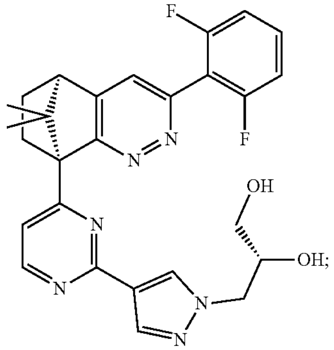
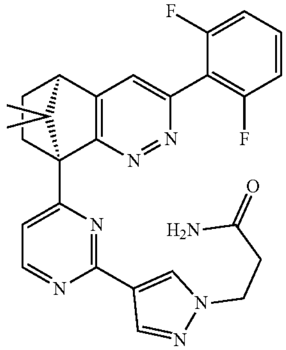
;
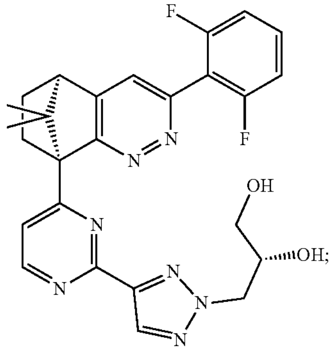

-continued
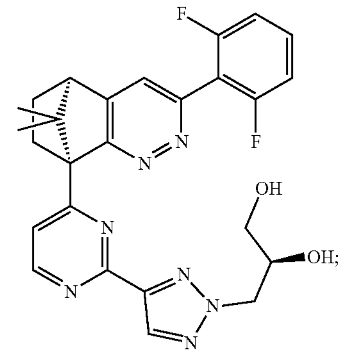
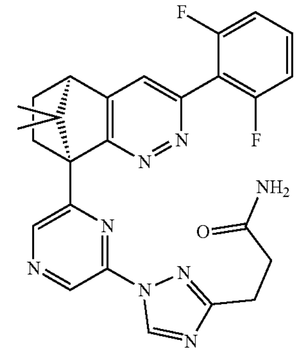
;
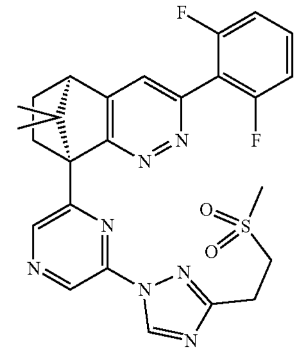
;
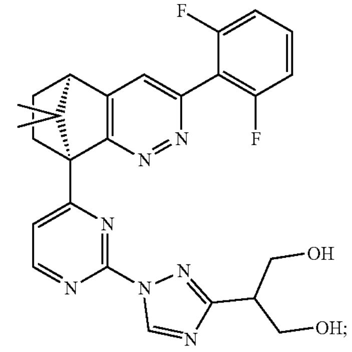
-continued
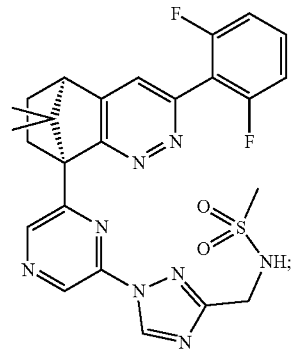
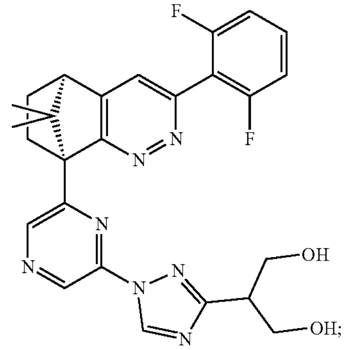
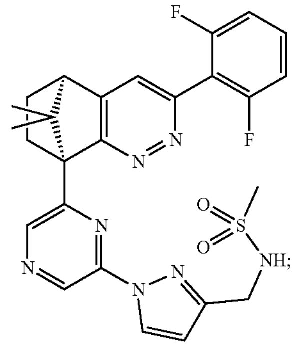
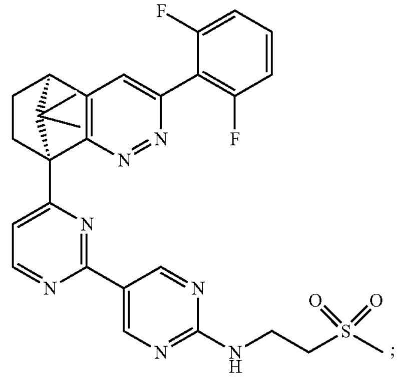

-continued
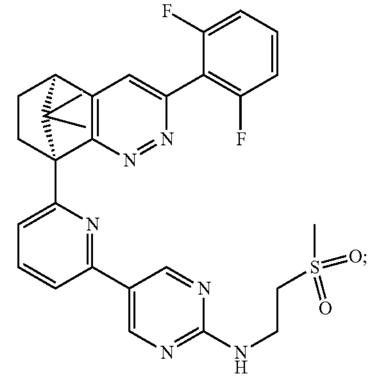
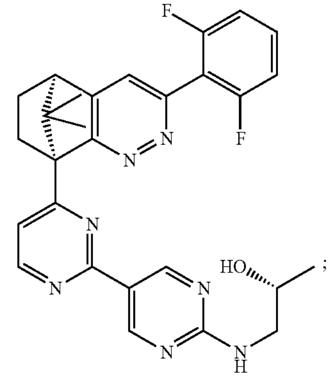
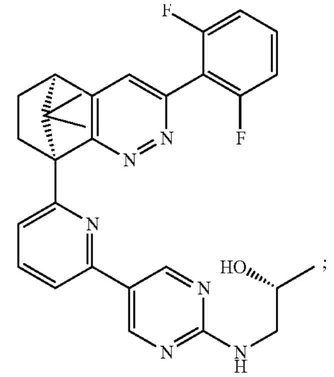
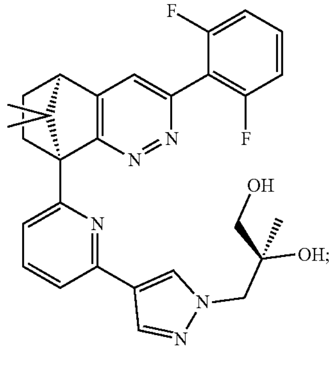
-continued
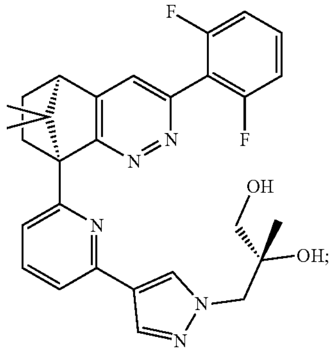
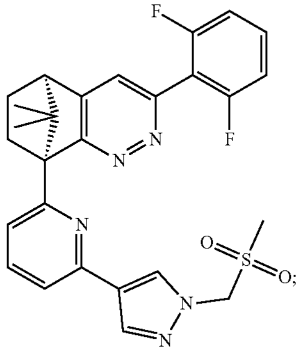
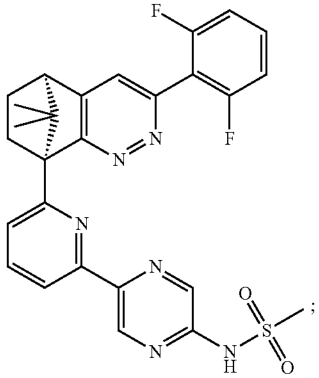
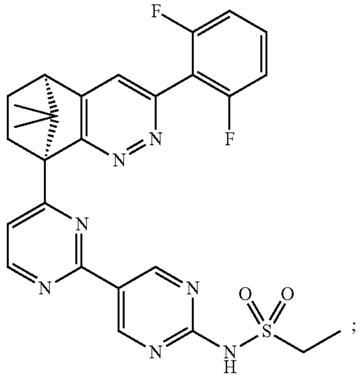

-continued
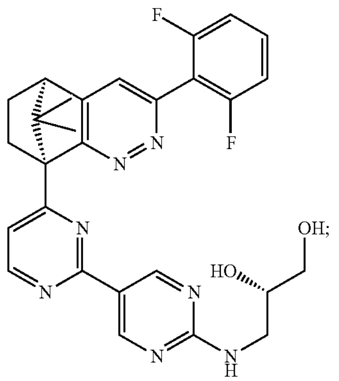
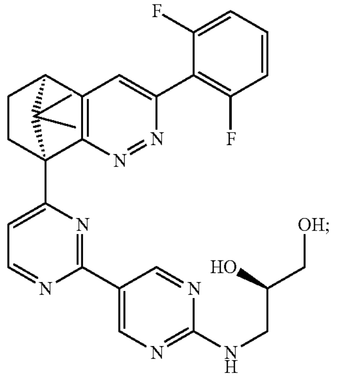
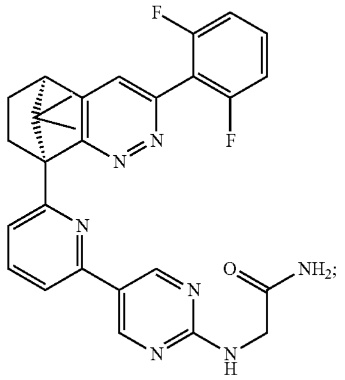
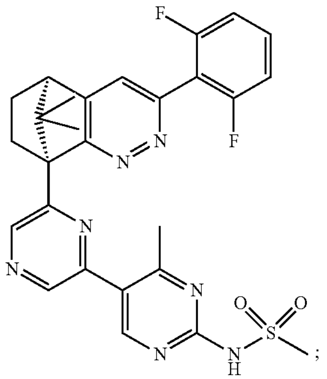
-continued
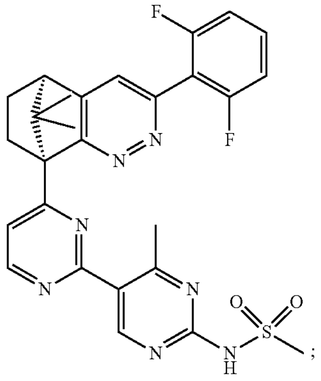
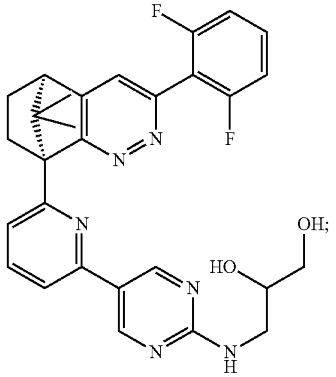
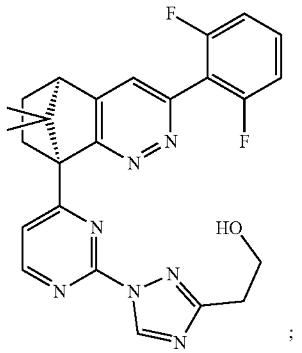
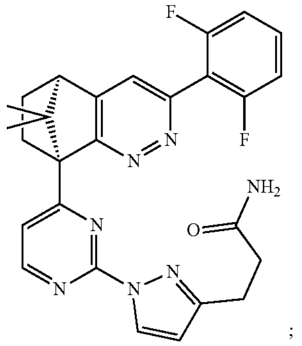

-continued
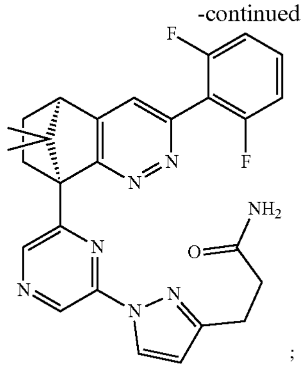
;
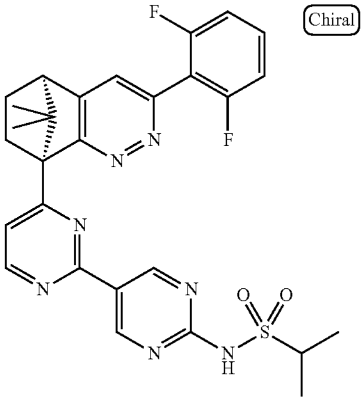
;
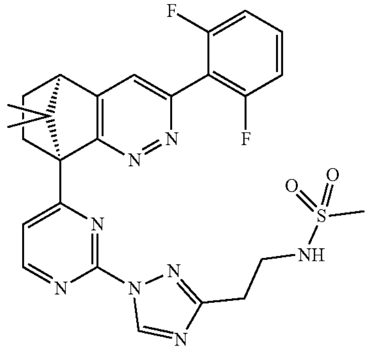
;
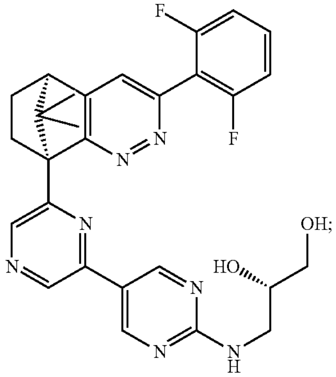
-continued
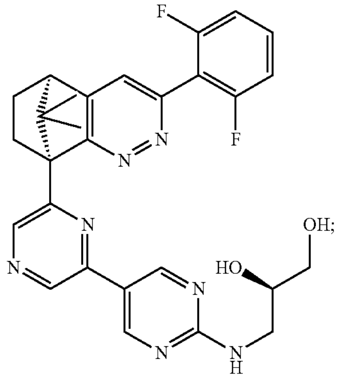
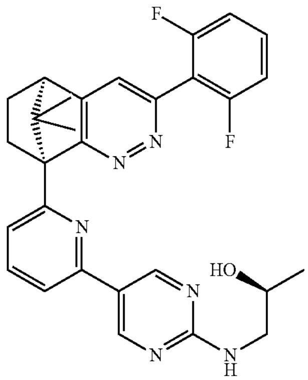
;
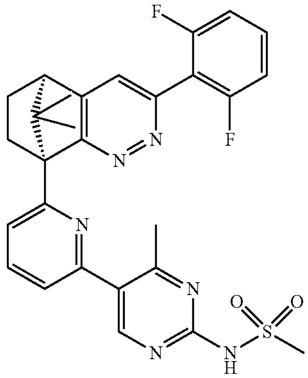
;
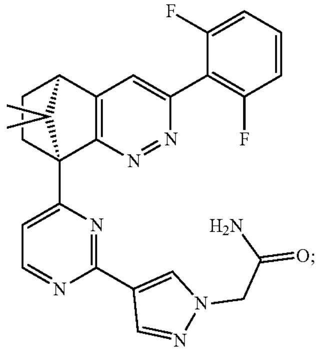

-continued
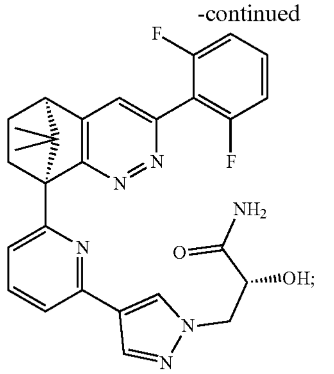
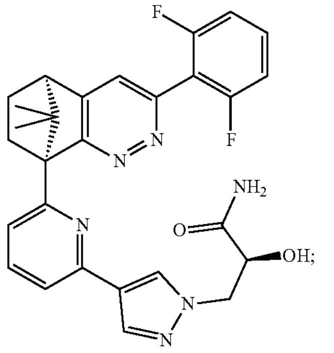
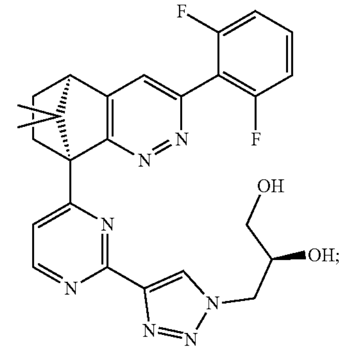
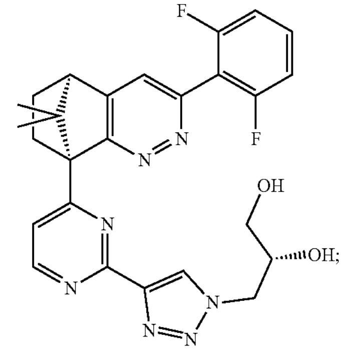
-continued
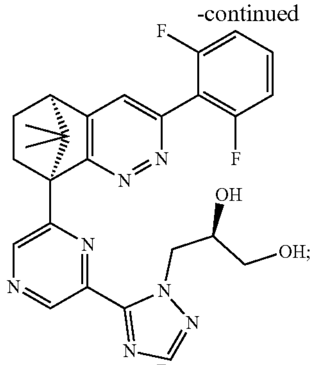
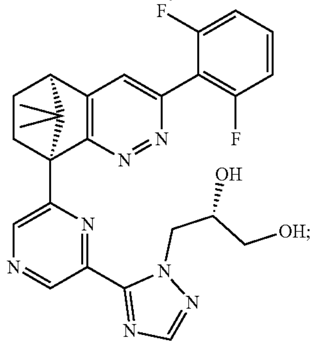
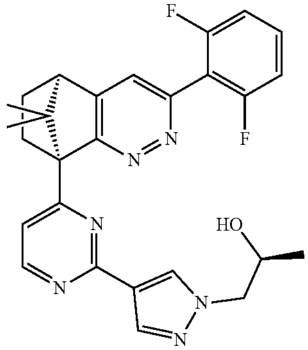
;
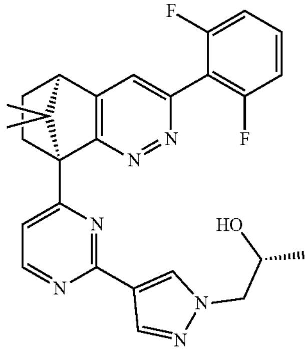
;
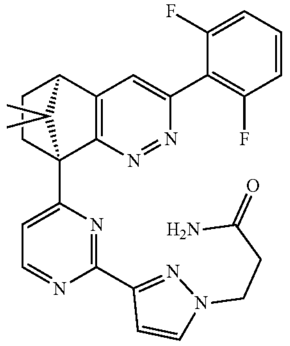
;

-continued
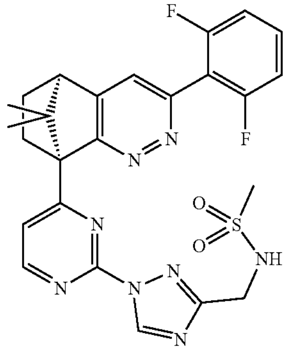
;
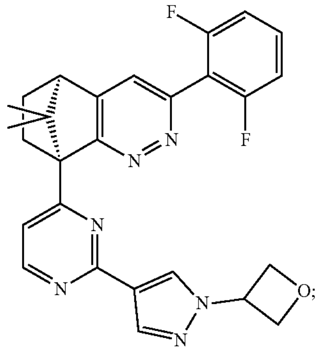
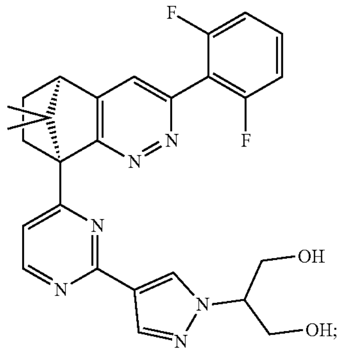
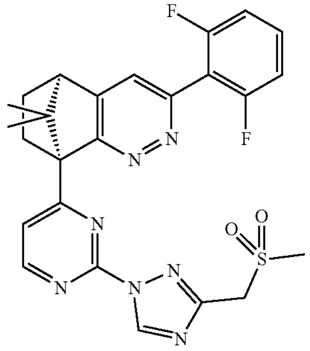
;
-continued
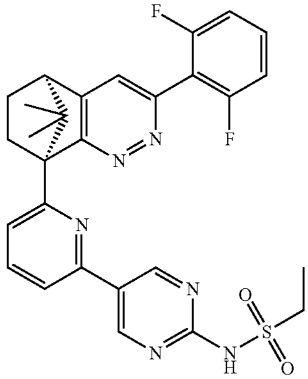
;
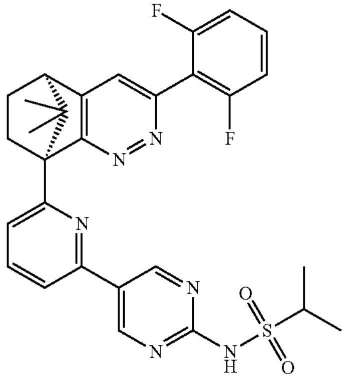
;
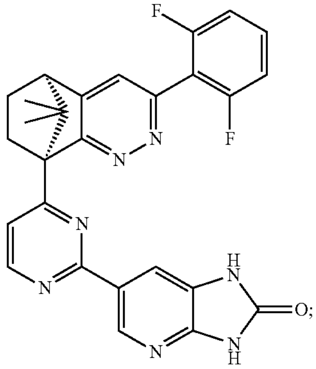
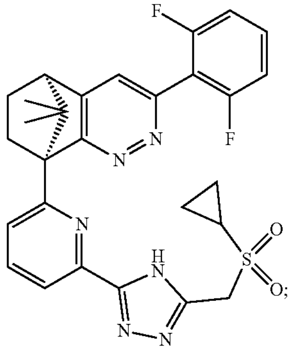

-continued
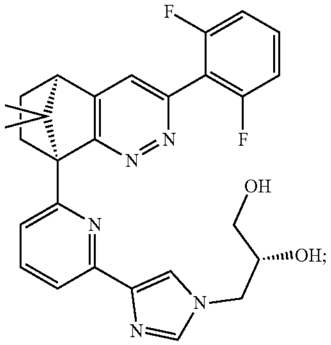
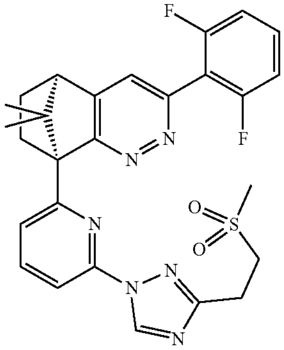
;
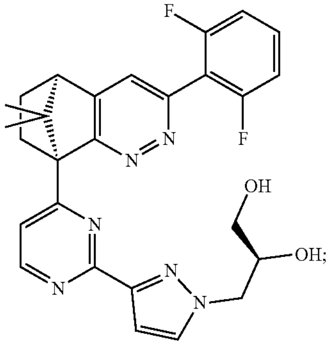
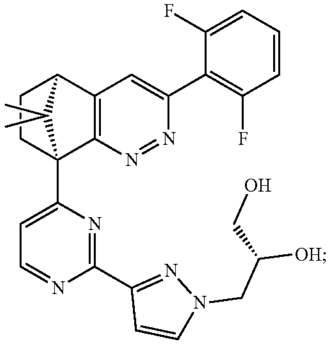
-continued
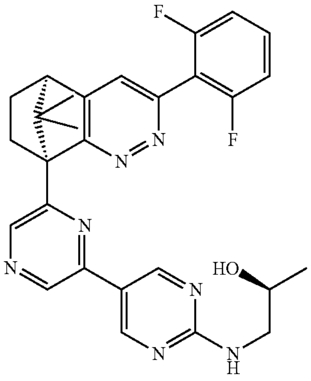
;
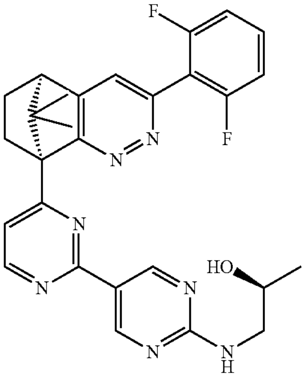
;
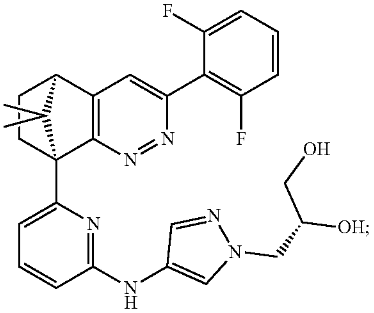
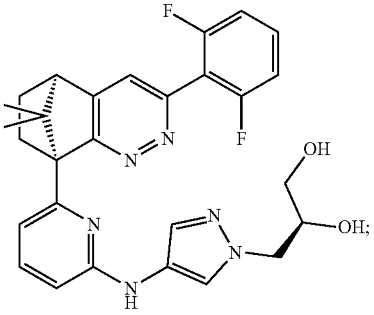

-continued
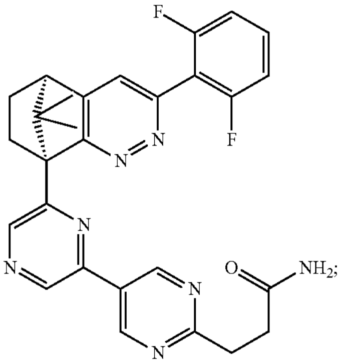
;
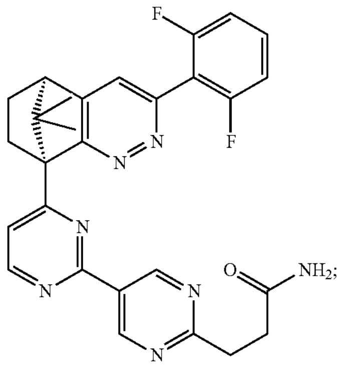
;
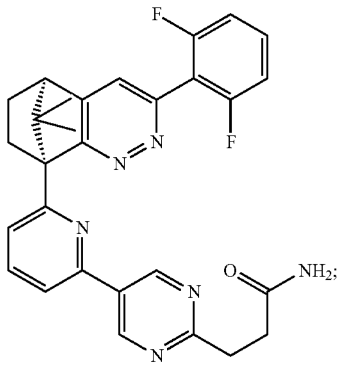
;
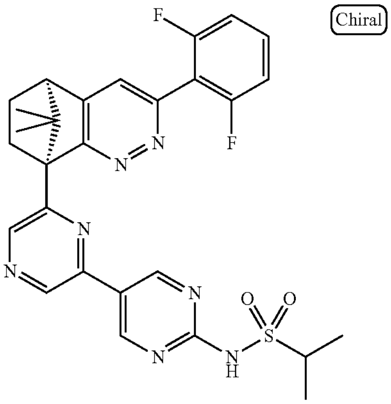
;
-continued
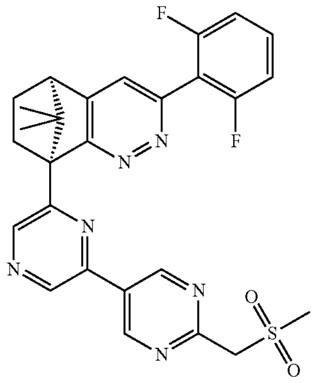
;
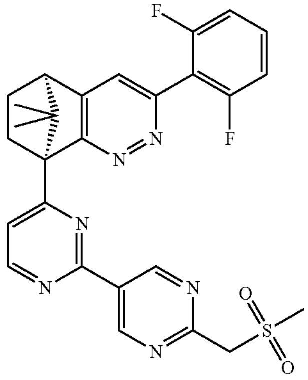
;
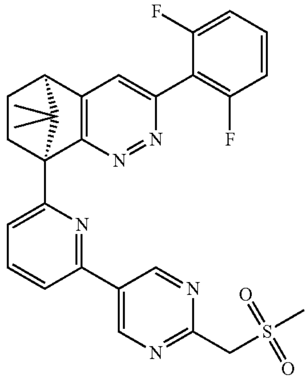
;
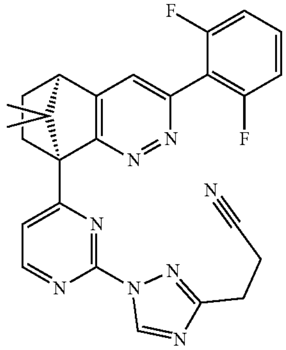
;

-continued
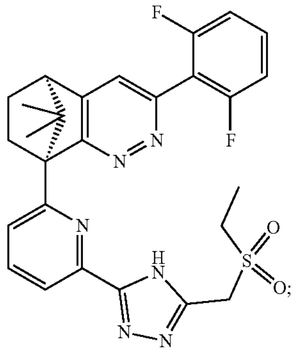
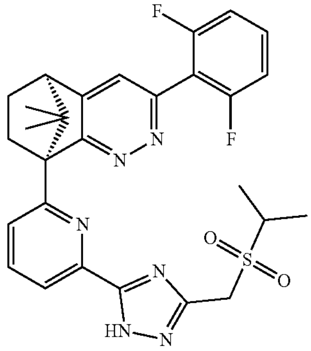
;
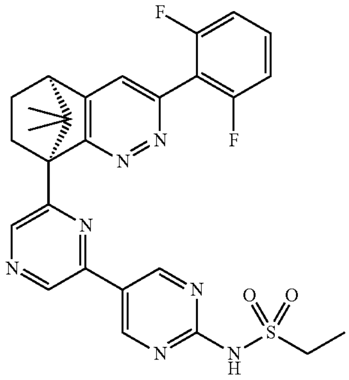
;
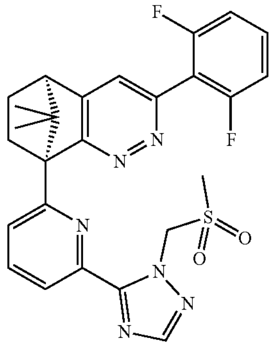
;
-continued
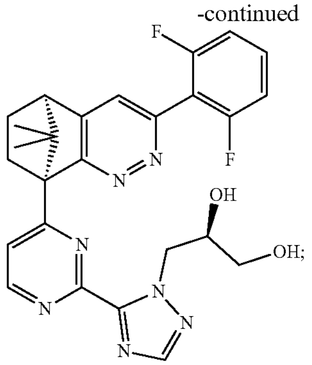
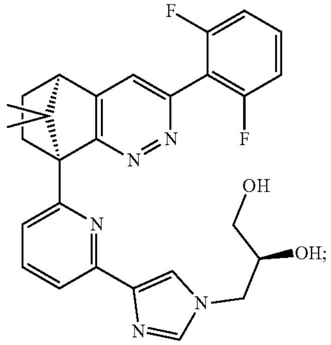
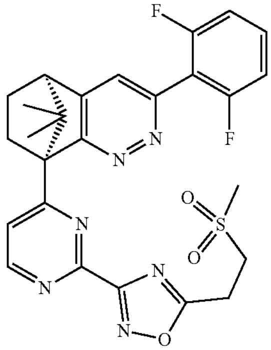
;
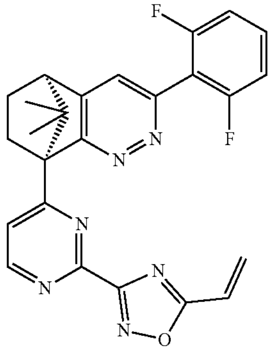
;
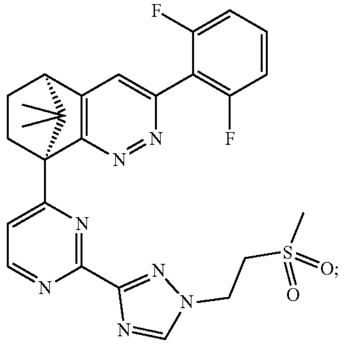

-continued
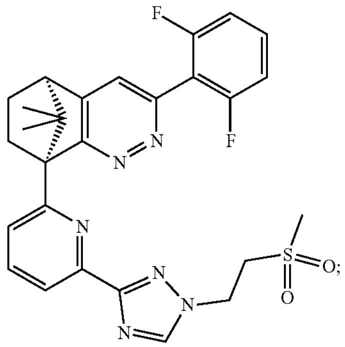
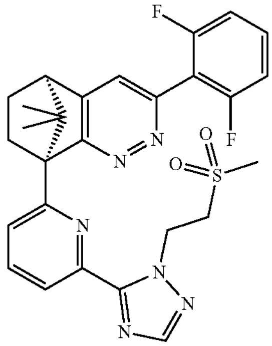
;
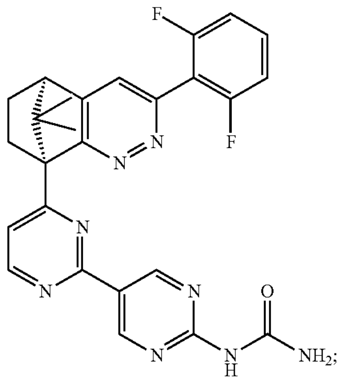
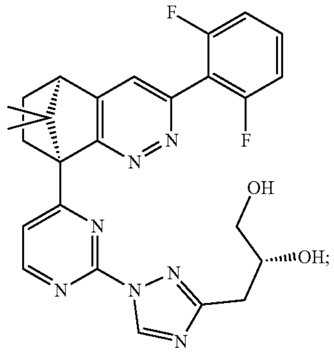
-continued
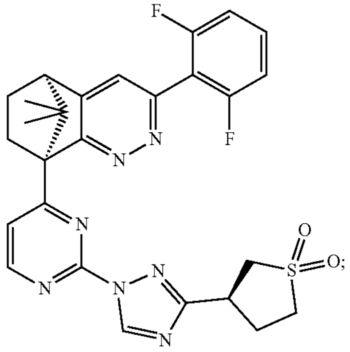
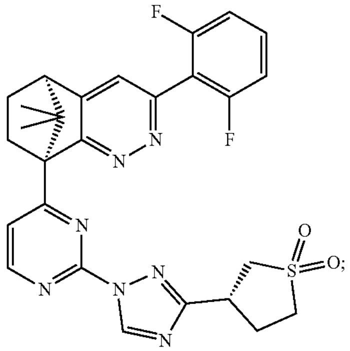
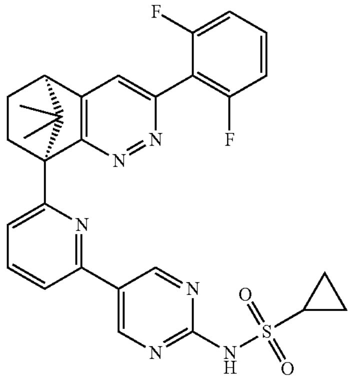
;
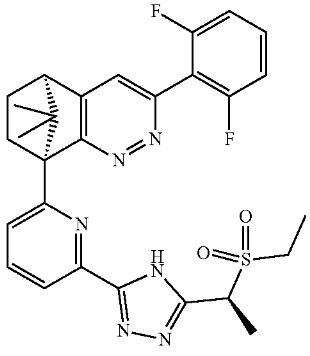
;

-continued
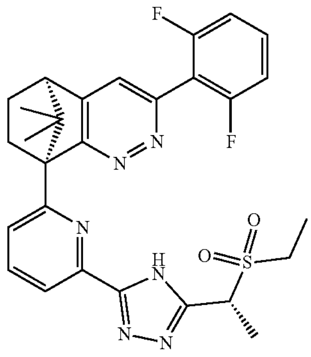
;
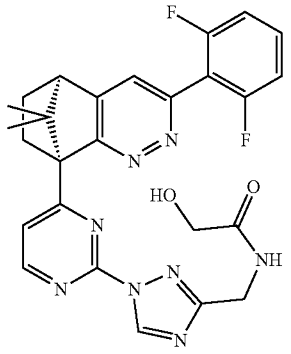
;
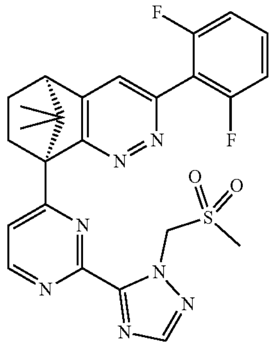
;
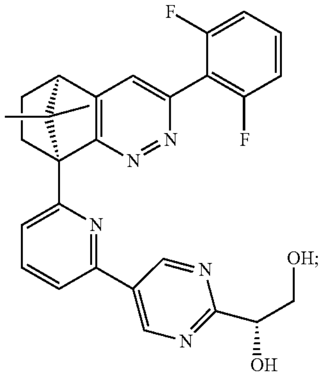
-continued
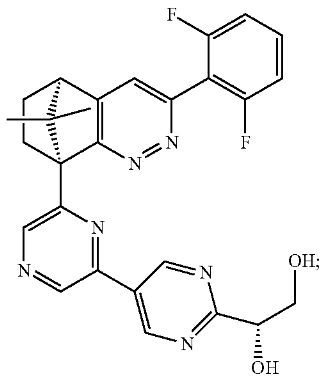
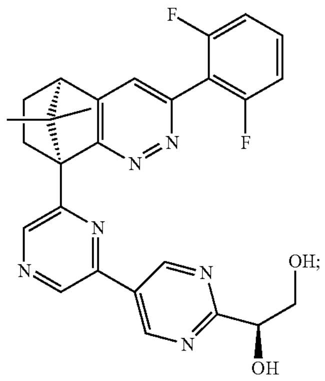
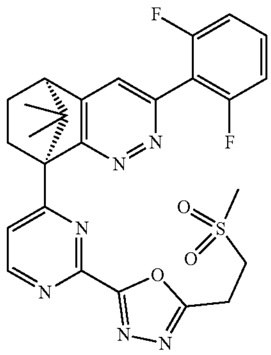
;
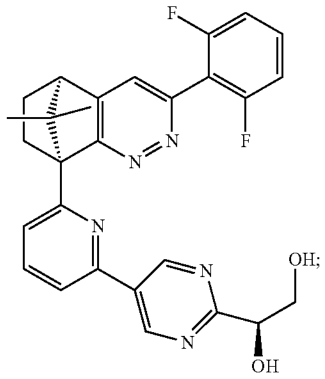

-continued
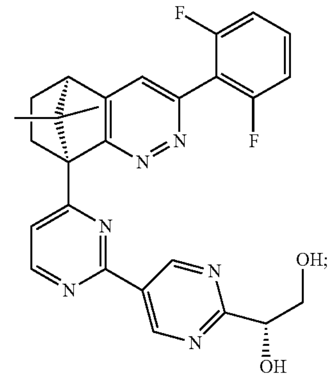
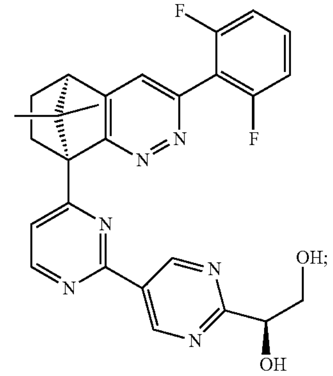
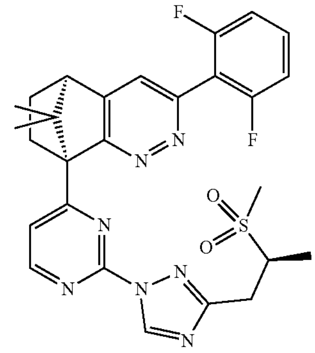
;
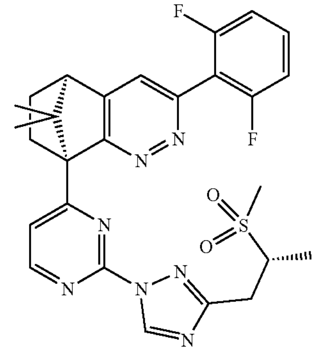
;
-continued
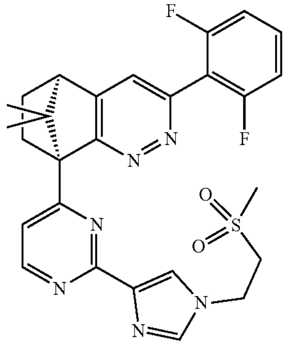
;
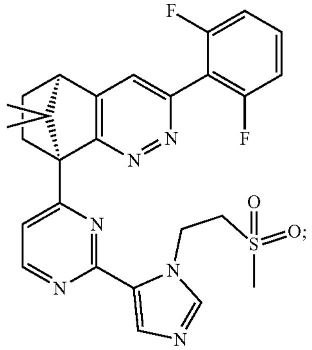
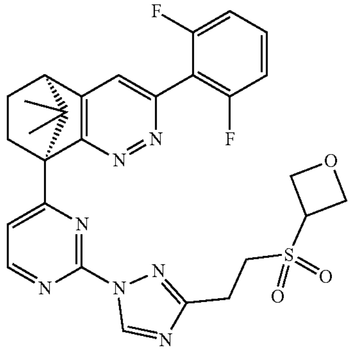
;
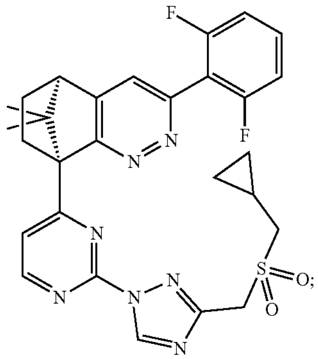

-continued
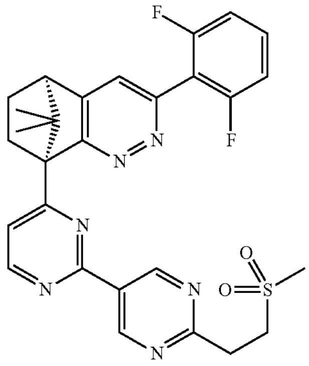
;
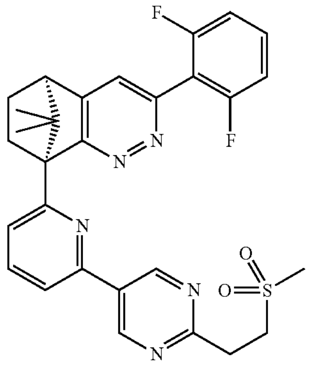
;
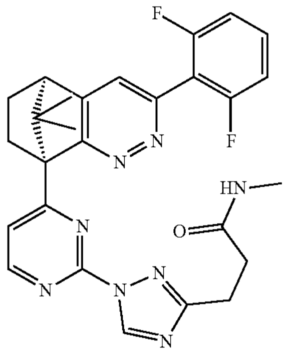
;
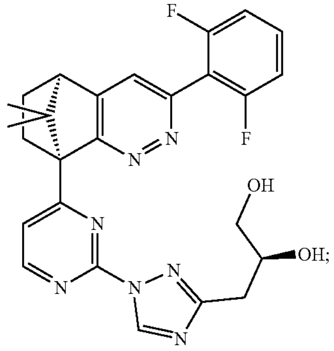
-continued
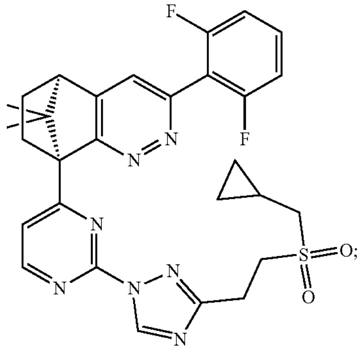
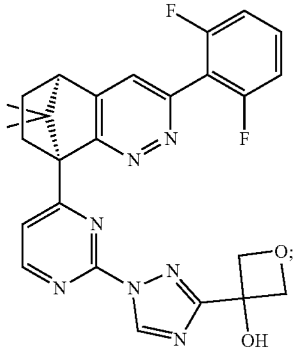
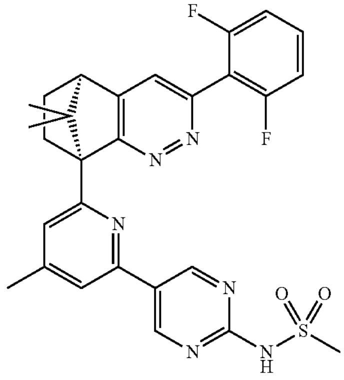
;
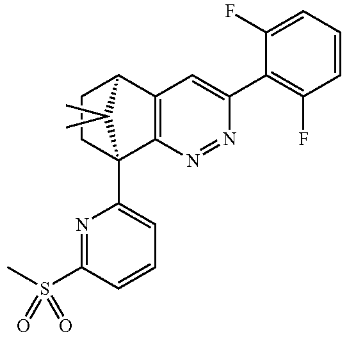
;

-continued
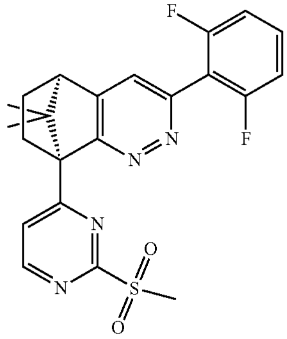
;
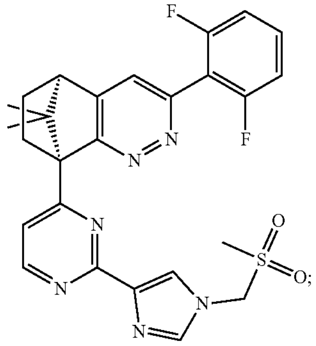
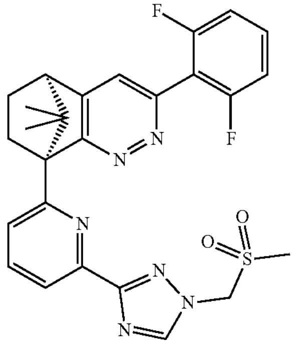
;
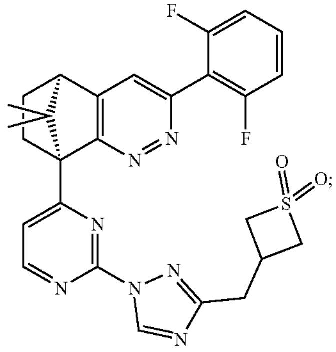
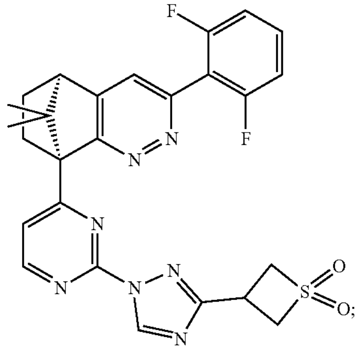
-continued
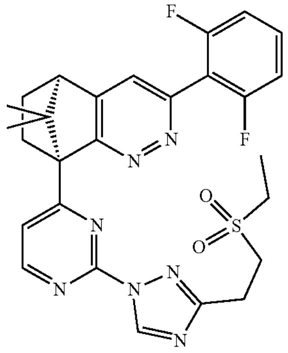
;
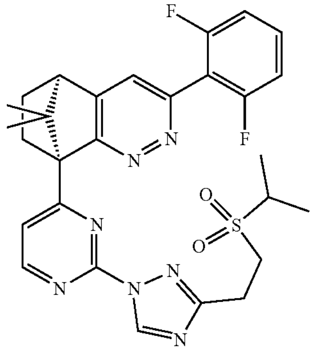
;
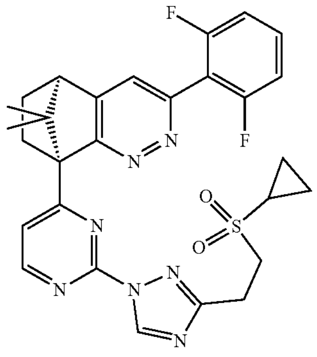
;
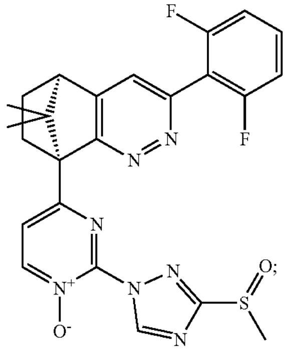

-continued
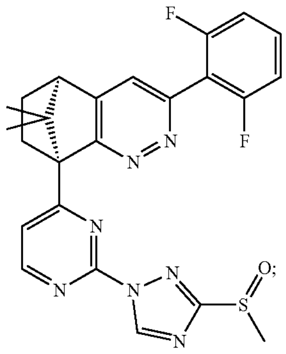
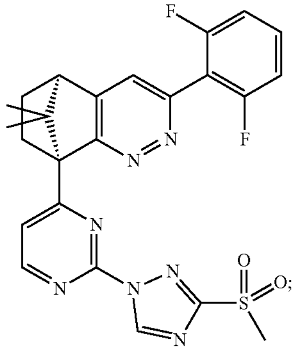
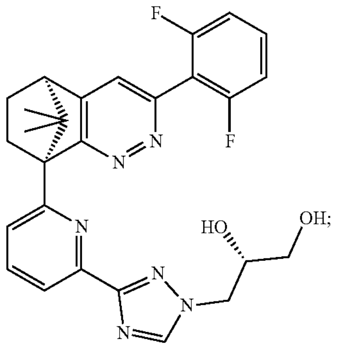
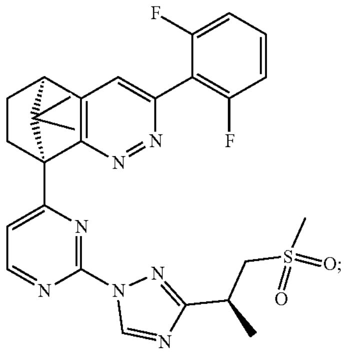
-continued
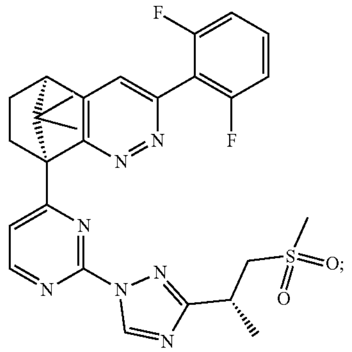
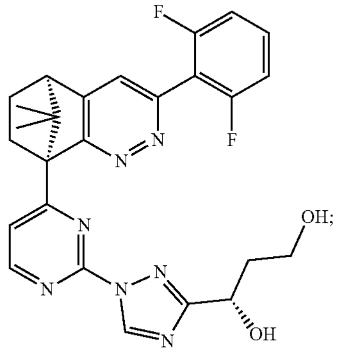
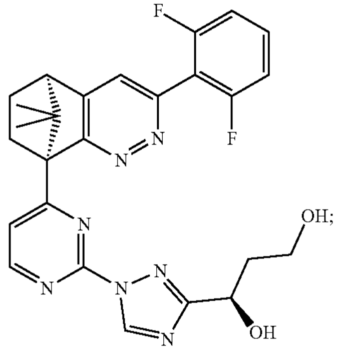
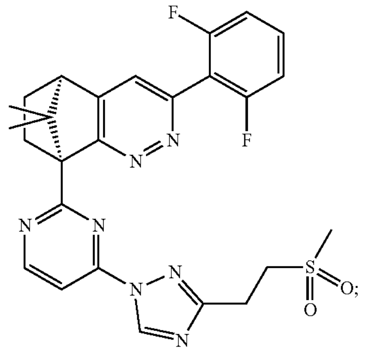

-continued
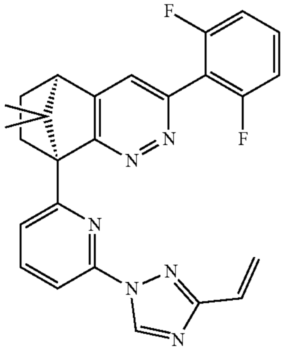
;
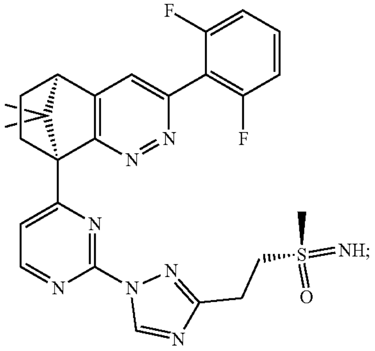
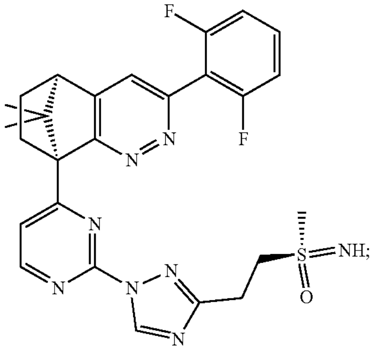
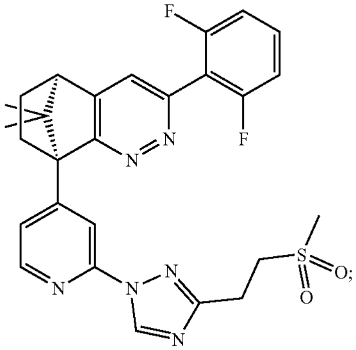
-continued
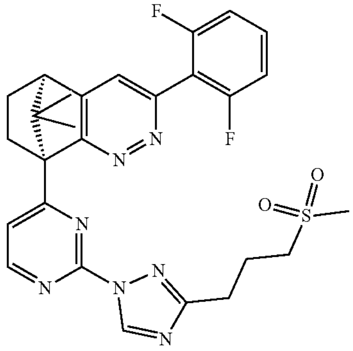
;
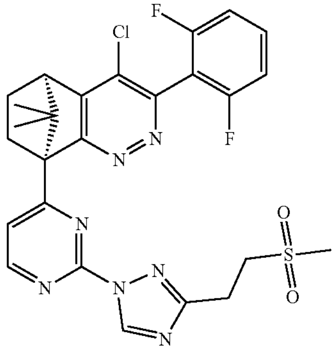
;
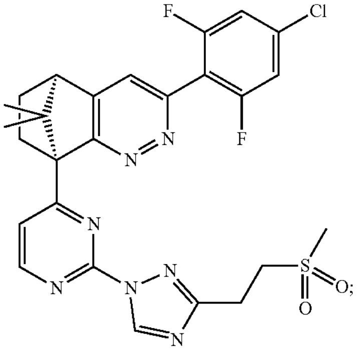
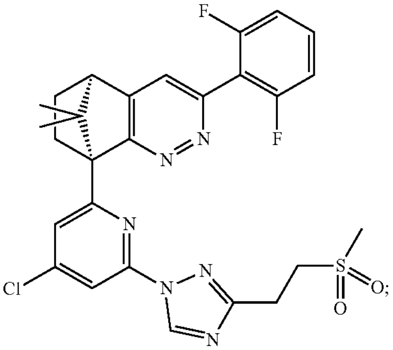

-continued
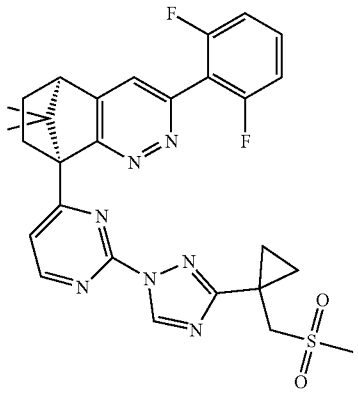
;
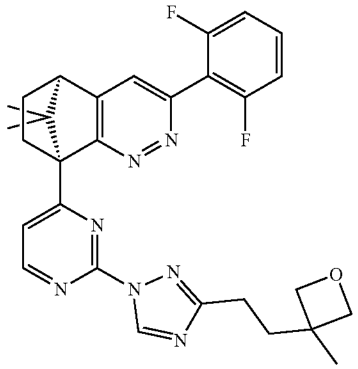
;
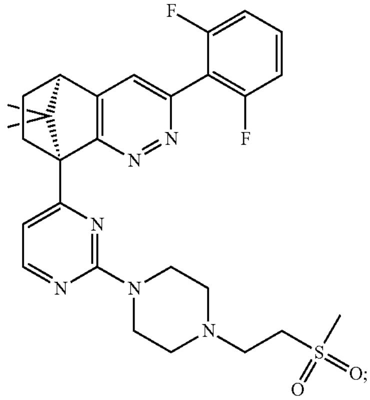
;
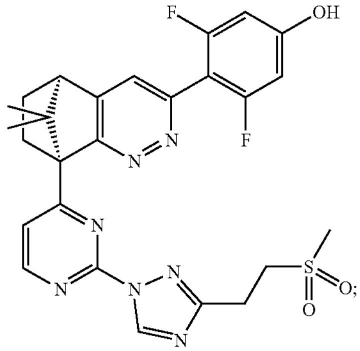
;
-continued
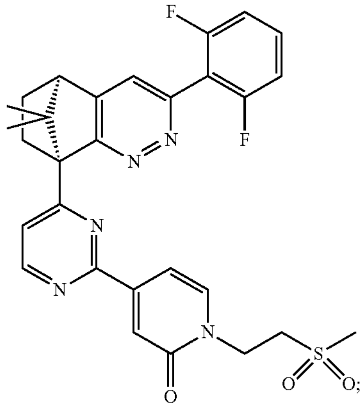
;
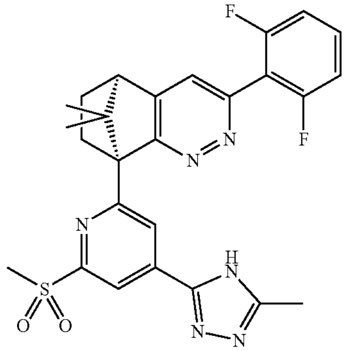
;
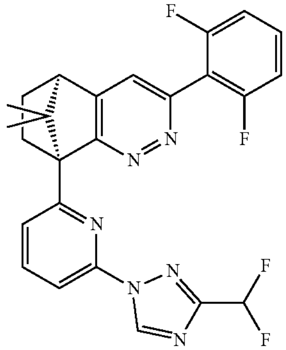
;
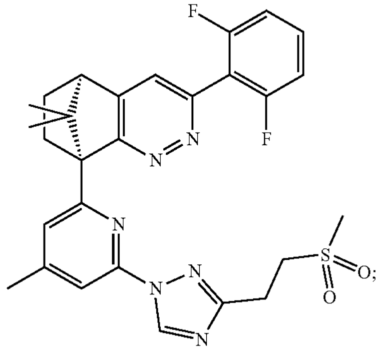
;

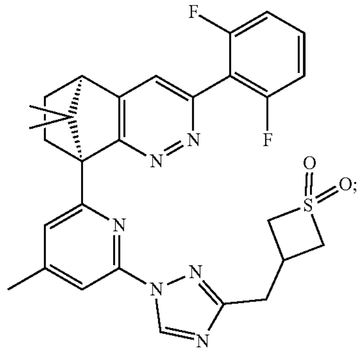
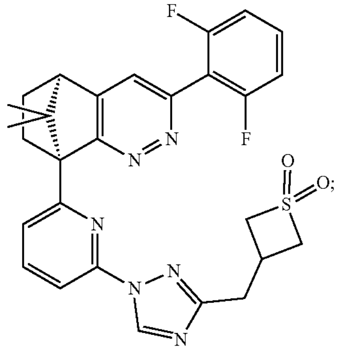
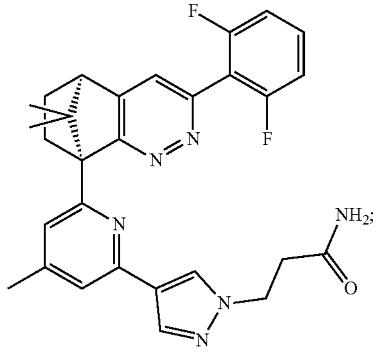
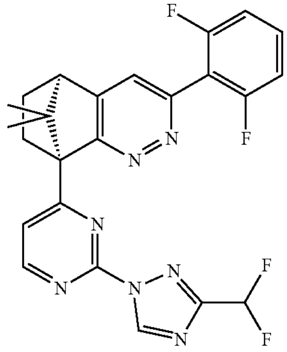
;
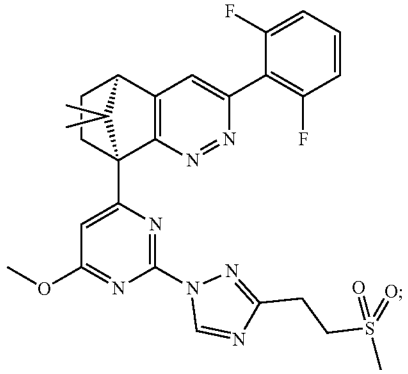
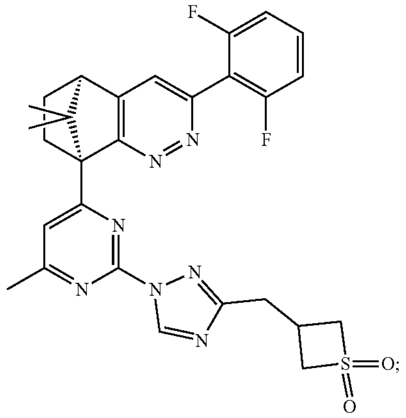
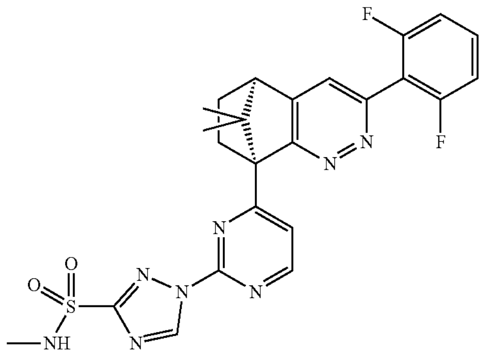
;
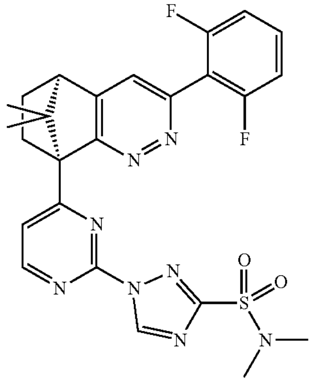
;

-continued
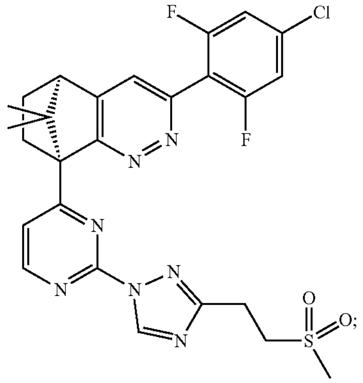
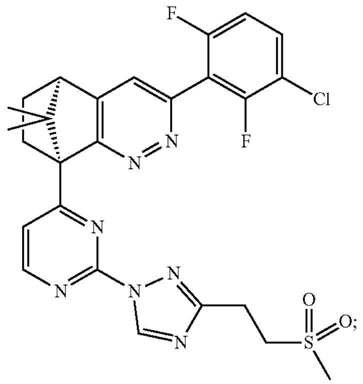
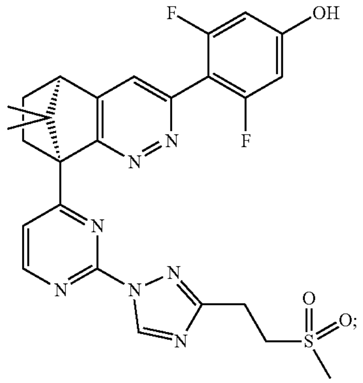
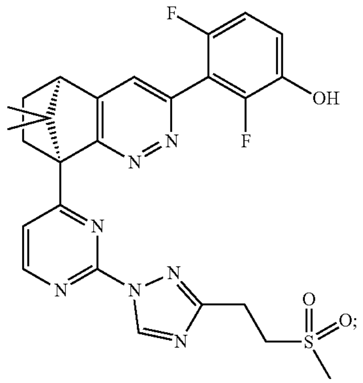
-continued
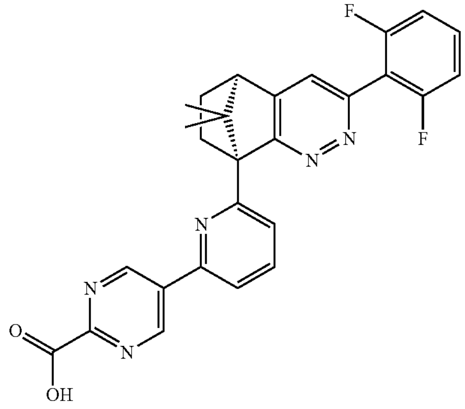
;
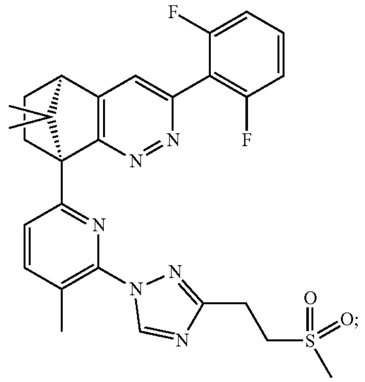
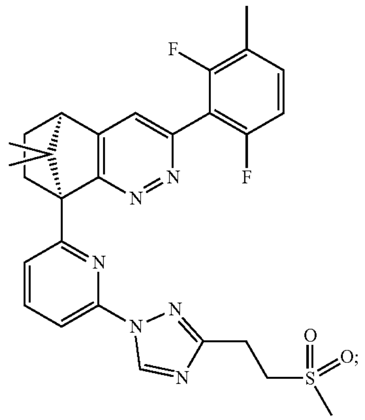
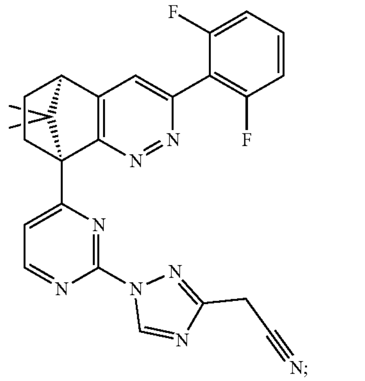

-continued
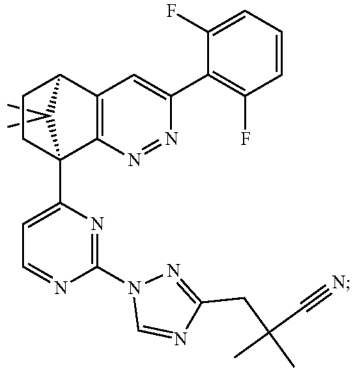
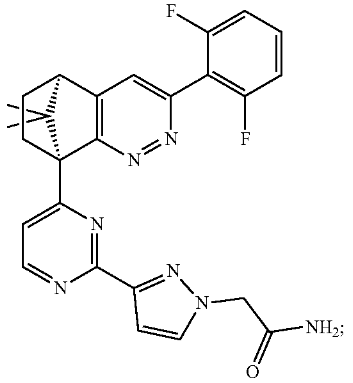
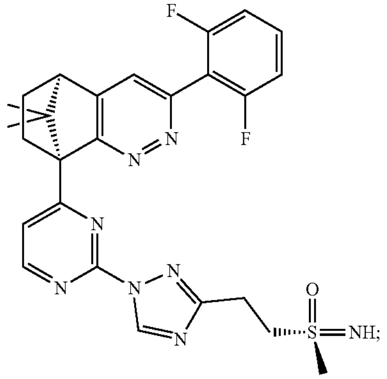
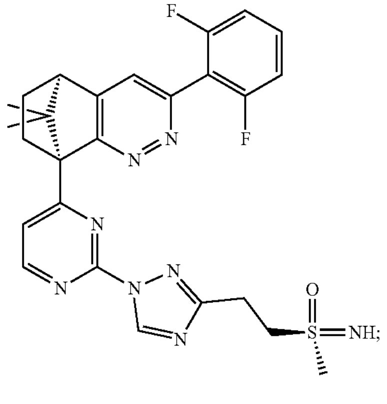
-continued
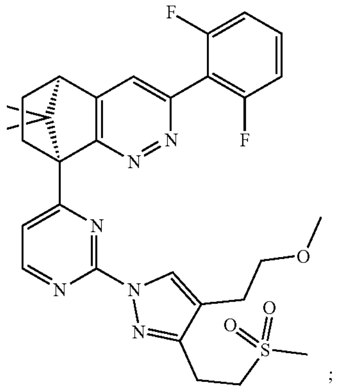
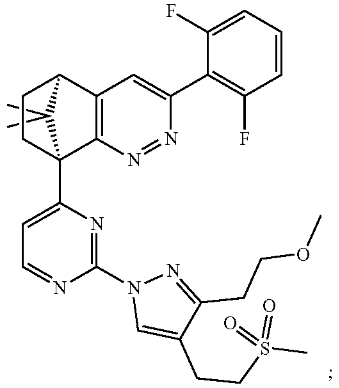
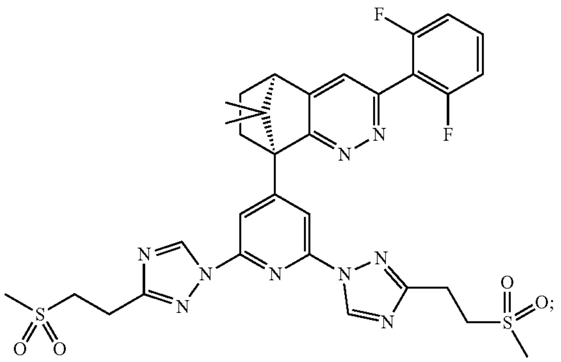
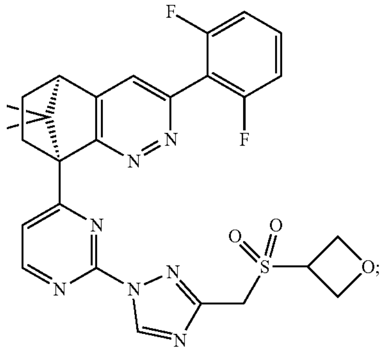

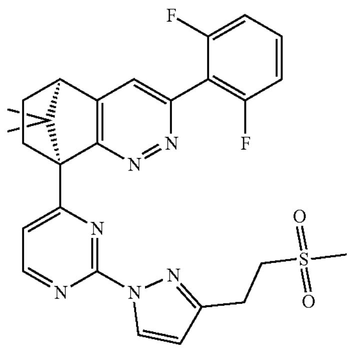
;
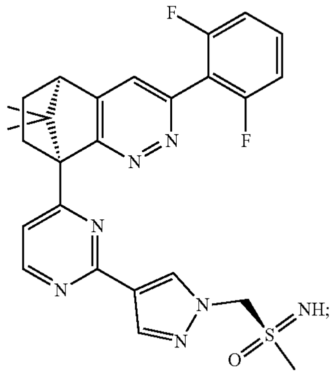
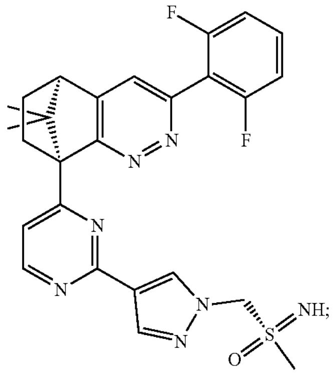
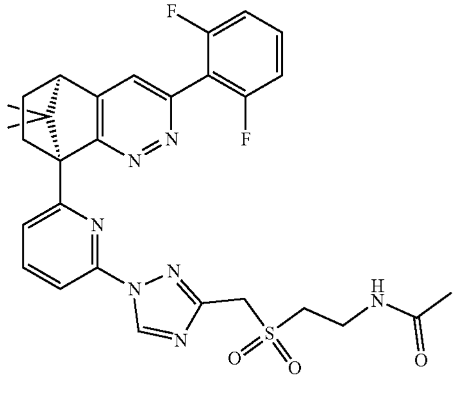
;
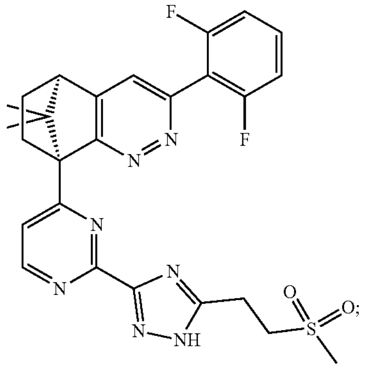
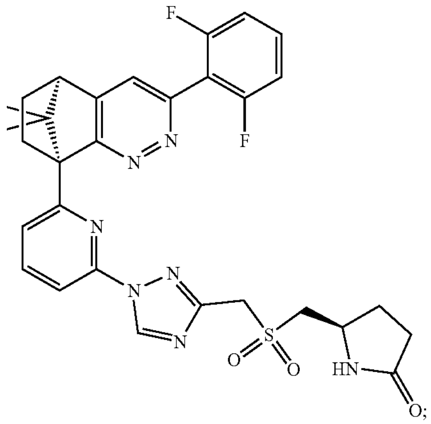
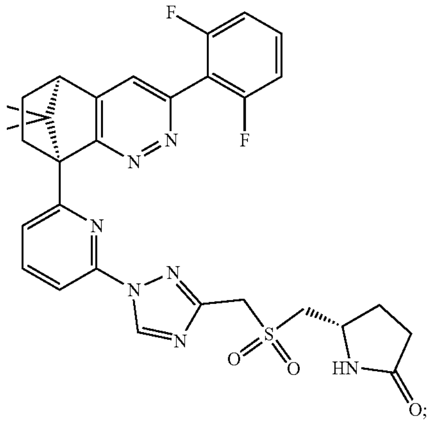
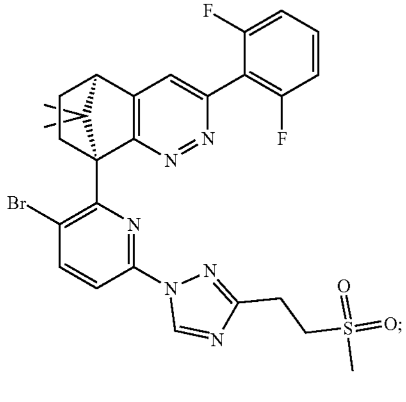

-continued
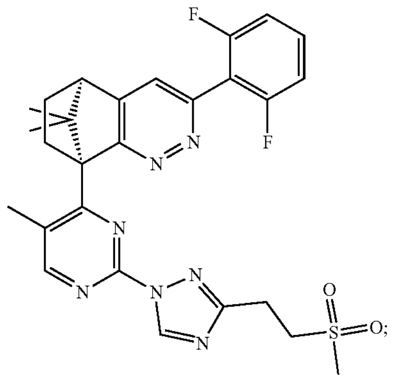
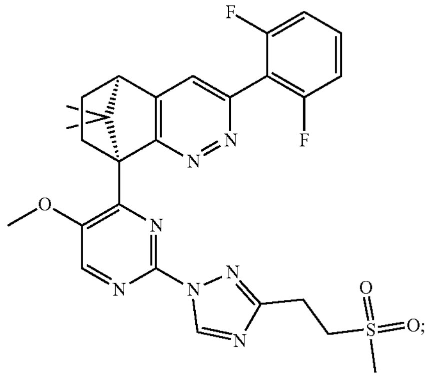
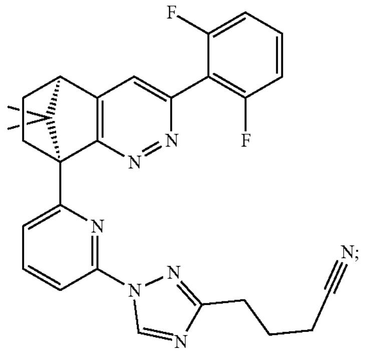
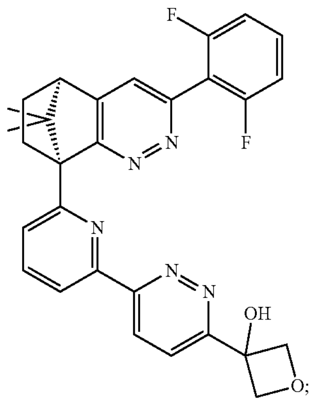
-continued
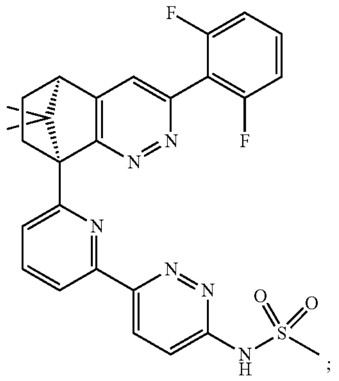
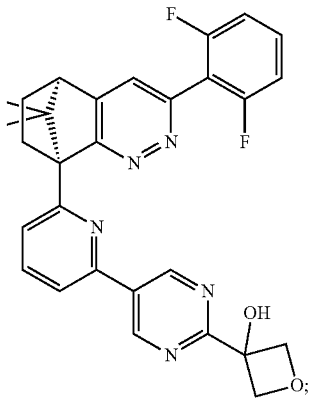
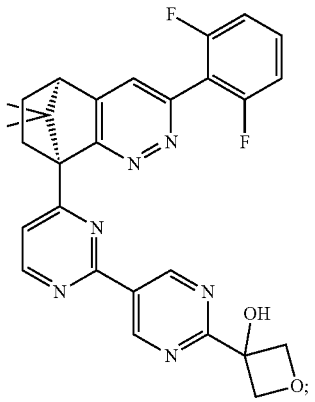
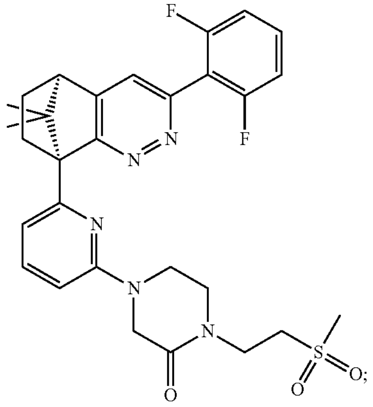

-continued
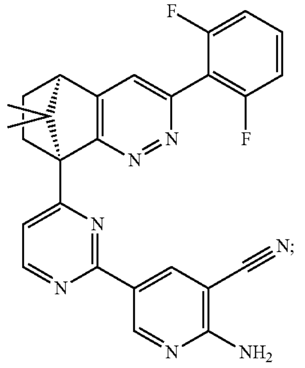
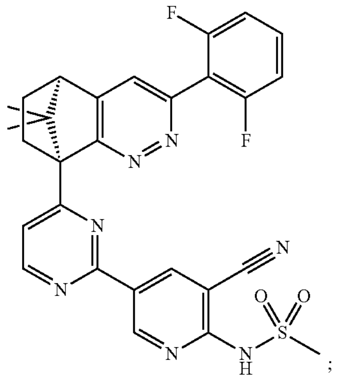
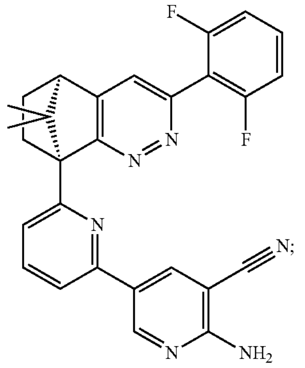
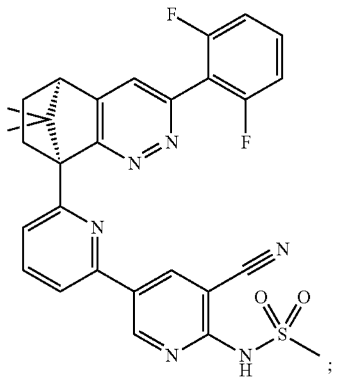
-continued
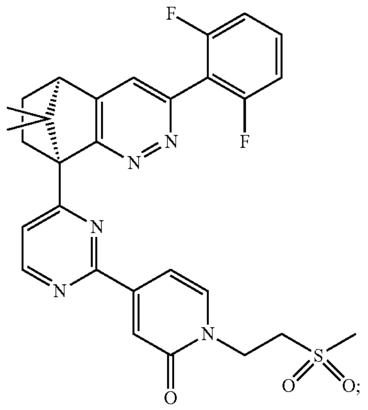
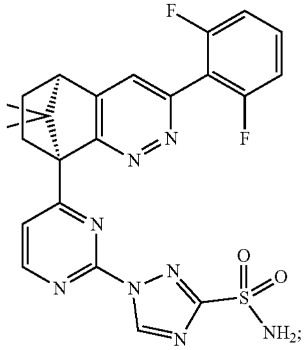
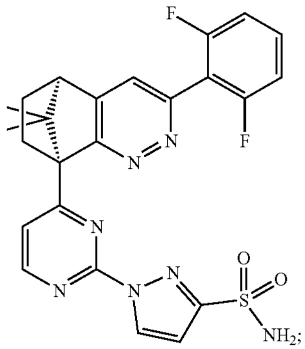
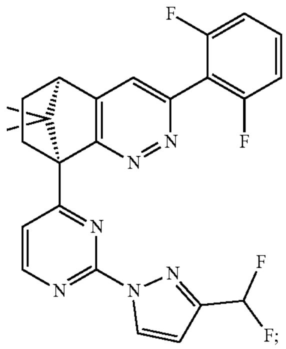

-continued
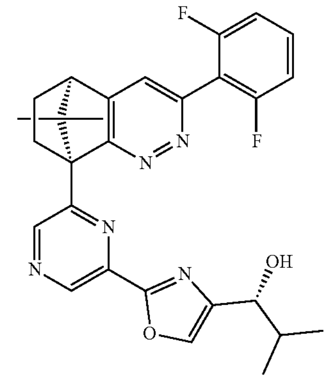
;
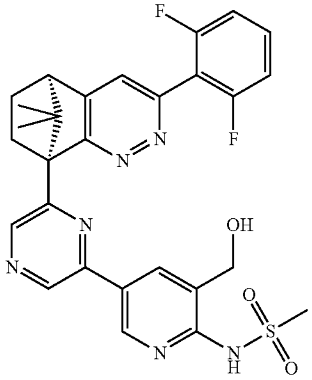
;
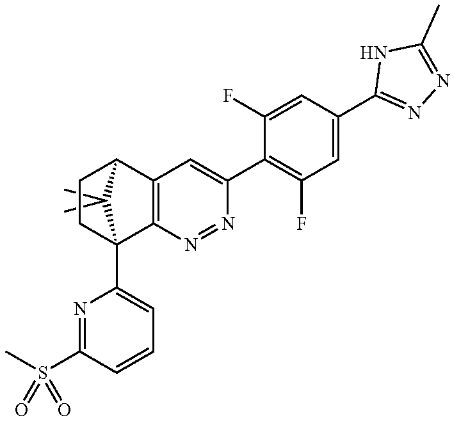
;
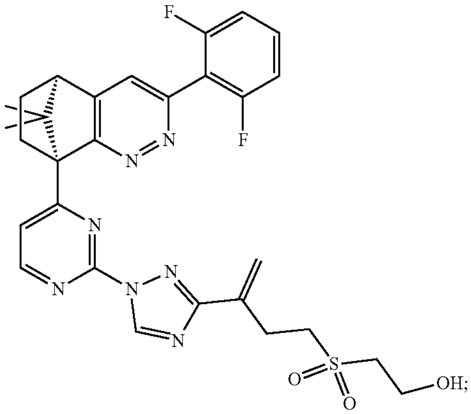
OH;
-continued
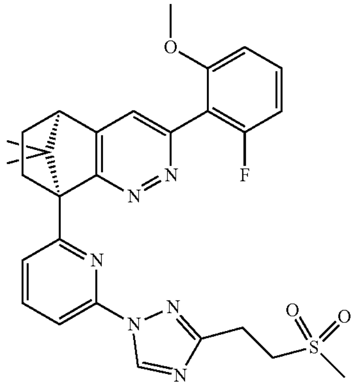
;
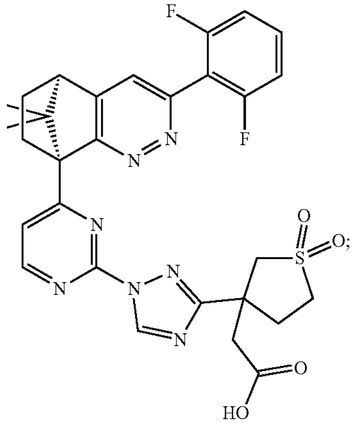
O;
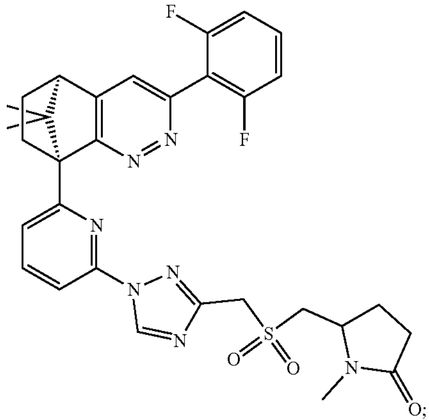
O;
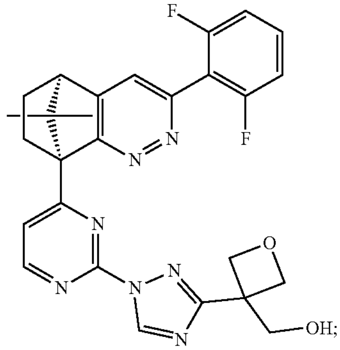
OH;

-continued

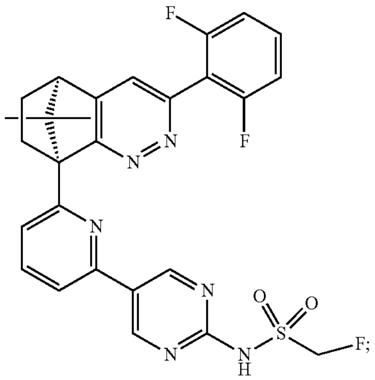

;

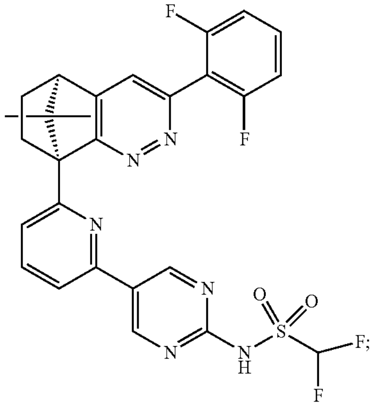

;

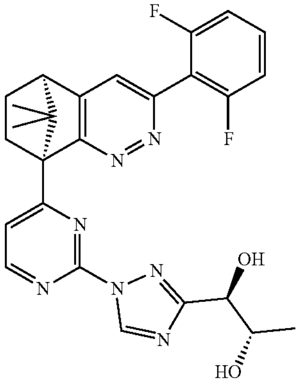

;

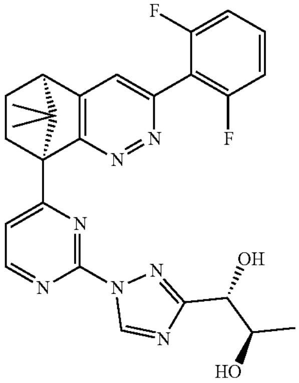

; and

-continued

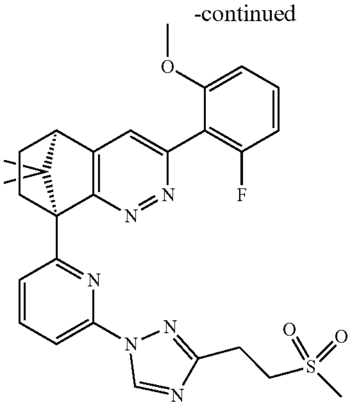

;

or a pharmaceutically acceptable salt thereof.

3. The compound of claim 1, selected from:

(1S)-2-methyl-1-[2-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propan-1-ol;

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanenitrile;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

(1S,8R)-5-(2,6-difluorophenyl)-11,11-dimethyl-1-[6-[1-(2-methylsulfonylethyl]pyrazol-4-yl]pyrazin-2-yl]-3,4-diazatricyclo[6.2.1.02,7]undeca-2(7),3,5-triene;

2-methyl-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

2-[[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]amino]ethanol;

(1S,8R)-5-(2,6-difluorophenyl)-1-[6-[1-(2-ethylsulfonylethyl]pyrazol-4-yl]pyrazin-2-yl]-11,11-dimethyl-3,4-diazatricyclo[6.2.1.02,7]undeca-2(7),3,5-triene;

N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methanesulfonamide;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(1S,8R)-5-(2,6-difluorophenyl)-11,11-dimethyl-1-[6-[1-(2-methylsulfonylethyl)pyrazol-3-yl]pyrazin-2-yl]-3,4-diazatricyclo[6.2.1.02,7]undeca-2(7),3,5-triene;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(1S,8R)-5-(2,6-difluorophenyl)-11,11-dimethyl-1-[6-[1-(2-methylsulfonylethyl)pyrazol-4-yl]-2-pyridyl]-3,4-diazatricyclo[6.2.1.02,7]undeca-2(7),3,5-triene;

(2R)-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

3-[3-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanenitrile;

3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanenitrile;

2-[3-[4-[4(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]oxetan-3-yl]acetonitrile;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propane-1,2-diol;

(2S)-2-hydroxy-N-[5-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]propanamide;

N-[5-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methyl]methanesulfonamide;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

(2S)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;

(2R)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]acetamide;

N-(2-hydroxyethyl)-2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]acetamide;

(1S,8R)-5-(2,6-difluorophenyl)-11,11-dimethyl-1-[6-(3-methyl-1H-pyrazol-4-yl)-2-pyridyl]-3,4-diazatricyclo[6.2.1.02,7]undeca-2(7),3,5-triene;

(1S,8R)-5-(2,6-difluorophenyl)-11,11-dimethyl-1-[6-[1-(methylsulfonylmethyl)pyrazol-4-yl]pyrazin-2-yl]-3,4-diazatricyclo[6.2.1.02,7]undeca-2(7),3,5-triene;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]triazol-2-yl]propane-1,2-diol;

(1S,8R)-5-(2,6-difluorophenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene;

N-[[1-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-3-yl]methyl]methanesulfonamide;

2-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]acetamide;

(2R)-1-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propan-2-ol;

(2R)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]-2-hydroxy-propanamide;

(2S)-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]-2-hydroxy-propanamide;

(1S)-1-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]ethane-1,2-diol;

(5R,8S)-8-(6-(3-(difluoromethyl)-1H-1,2,4-triazol-1-yl]pyridin-2-yl)-3-(2,6-difluorophenyl)-9,9-dimethyl-5,6,7,8-tetrahydro-5,8-methanocinnoline;

5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidine-2-carboxylic acid;

N-[6-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyridazin-3-yl]methanesulfonamide;

3-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]oxetan-3-ol;

2-amino-5-(4-((5R,8S)-3-(2,6-difluorophenyl)-9,9-dimethyl-6,7-dihydro-5,8-methanocinnolin-8(5H)-yl]pyrimidin-2-yl]nicotinonitrile;

6'-amino-6-((5R,8S)-3-(2,6-difluorophenyl)-9,9-dimethyl-6,7-dihydro-5,8-methanocinnolin-8(5H)-yl)-[2,3'-bipyridine]-5'-carbonitrile; and (5R,8S)-8-(2-(3-(difluoromethyl)-1H-pyrazol-1-yl]pyrimidin-4-yl)-3-(2,6-difluorophenyl)-9,9-dimethyl-5,6,7,8-tetrahydro-5,8-methanocinnoline;

or a pharmaceutically acceptable salt thereof.

4. The compound of claim 3, selected from:

3-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propanenitrile;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]propan-2-ol;

2-methyl-2-[2-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]oxazol-4-yl]propanenitrile;

(1S,8R)-5-(2,6-difluorophenyl)-1-[6-[1-(2-ethylsulfonylethyl)pyrazol-4-yl]pyrazin-2-yl]-11,11-dimethyl-3,4-diazatricyclo[6.2.1.02,7]undeca-2(7),3,5-triene;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]pyrazin-2-yl]pyrazol-1-yl]butan-2-ol;

(1S,8R)-5-(2,6-difluorophenyl)-11,11-dimethyl-1-[6-[1-(2-methylsulfonylethyl)pyrazol-3-yl]pyrazin-2-yl]-3,4-diazatricyclo[6.2.1.02,7]undeca-2(7),3,5-triene;

(2R)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(2S)-1-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propan-2-ol;

(1S,8R)-5-(2,6-difluorophenyl)-11,11-dimethyl-1-[6-[1-(2-methylsulfonylethyl)pyrazol-4-yl]-2-pyridyl]-3,4-diazatricyclo[6.2.1.02,7]undeca-2(7),3,5-triene;

3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanenitrile;

2-[3-[4-[4(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]oxetan-3-yl]acetonitrile;

N-[5-[6-[(1R,8R)-5-(2,6-difluorophenyl)-11,11-dimethyl-3,4-diazatricyclo[6.2.1.02,7]undeca-2(7),3,5-trien-1-yl]pyrazin-2-yl]-2-pyridyl]methyl]methanesulfonamide;

N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide;

(2S)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;

(2R)-2-methyl-3-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]propanamide;

2-[4-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrazol-1-yl]acetamide;

(1S,8R)-5-(2,6-difluorophenyl)-11,11-dimethyl-1-[6-(3-methyl-1H-pyrazol-4-yl)-2-pyridyl]-3,4-diazatricyclo[6.2.1.02,7]undeca-2(7),3,5-triene;

(1S,8R)-5-(2,6-difluorophenyl)-11,11-dimethyl-1-[6-[1-(methylsulfonylmethyl]pyrazol-4-yl]pyrazin-2-yl]-3,4-diazatricyclo[6.2.1.02,7]undeca-2(7),3,5-triene;

(1S,8R)-5-(2,6-difluorophenyl)-11,11-dimethyl-1-[2-[3-(2-methylsulfonylethyl)-1,2,4-triazol-1-yl]pyrimidin-4-yl]-3,4-diazatricyclo[6.2.1.02,7]undeca-2(7),3,5-triene;

(2R)-1-[[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]amino]propan-2-ol;

(5R,8S)-8-(6-(3-(difluoromethyl)-1H-1,2,4-triazol-1-yl]pyridin-2-yl)-3-(2,6-difluorophenyl)-9,9-dimethyl-5,6,7,8-tetrahydro-5,8-methanocinnoline;

2-amino-5-(4-((5R,8S)-3-(2,6-difluorophenyl)-9,9-dimethyl-6,7-dihydro-5,8-methanocinnolin-8(5H)-yl]pyrimidin-2-yl]nicotinonitrile; and 6'-amino-6-((5R,8S)-3-(2,6-difluorophenyl)-9,9-dimethyl-6,7-dihydro-5,8-methanocinnolin-8(5H)-yl)-[2,3'-bipyridine]-5'-carbonitrile;

or a pharmaceutically acceptable salt thereof.

5. The compound of claim 4, wherein the compound is (1S,8R)-5-(2,6-difluorophenyl)-11,11-dimethyl-1-[2-[3-(2-methylsulfonylethyl)-1,2,4-triazol-1-yl)pyrimidin-4-yl]-3,4-diazatricyclo[6.2.1.02,7]undeca-2(7),3,5-triene, or a pharmaceutically acceptable salt thereof.

6. The compound of claim 4, wherein the compound is N-[5-[6-[(1S,8R)-5-(2,6-difluorophenyl)-11,11-dimethyl-3,4-diazatricyclo[6.2.1.02,7]undeca-2(7),3,5-trien-1-yl]-2-pyridyl]pyrimidin-2-yl]methanesulfonamide, or a pharmaceutically acceptable salt thereof.

7. The compound of claim 2, wherein the compound is

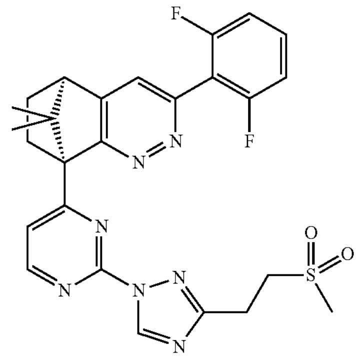 [SMILES: CC1(C)[C@H]2CC[C@]1(c1ccnc(-n3cnc(CCS(C)(=O)=O)n3)n1)c1nnc(-c3c(F)cccc3F)cc12]

or a pharmaceutically acceptable salt thereof.

8. The compound of claim 2, wherein the compound is

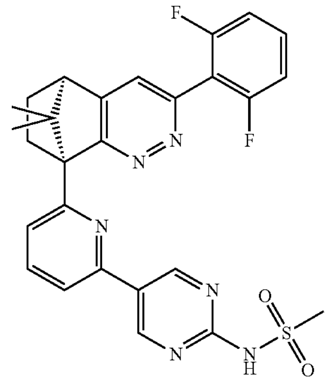

or a pharmaceutically acceptable salt thereof.

9. A pharmaceutical composition comprising a compound according to claim 1 and a therapeutically inert carrier.

* * * * *